US012612465B2

(12) United States Patent
Clogston et al.

(10) Patent No.: US 12,612,465 B2
(45) Date of Patent: Apr. 28, 2026

(54) FORMULATIONS COMPRISING PCSK9 SPECIFIC MONOCLONAL ANTIBODIES

(71) Applicant: Amgen Inc., Thousand Oaks, CA (US)

(72) Inventors: Christi L. Clogston, Camarillo, CA (US); Timothy David Osslund, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 1474 days.

(21) Appl. No.: 13/886,180

(22) Filed: May 2, 2013

(65) Prior Publication Data

US 2014/0030270 A1 Jan. 30, 2014

Related U.S. Application Data

(60) Provisional application No. 61/642,363, filed on May 3, 2012.

(51) Int. Cl.
| | |
|---|---|
| *C07K 16/40* | (2006.01) |
| *A61K 39/395* | (2006.01) |
| *A61K 39/00* | (2006.01) |

(52) U.S. Cl.
CPC .......... *C07K 16/40* (2013.01); *A61K 39/3955* (2013.01); *A61K 2039/505* (2013.01); *C07K 2317/21* (2013.01); *C07K 2317/33* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 3,983,140 A | 9/1976 | Endo et al. |
| 4,231,938 A | 11/1980 | Monaghan et al. |
| 4,444,784 A | 4/1984 | Hoffman et al. |
| 5,260,440 A | 11/1993 | Hirai et al. |
| 5,273,995 A | 12/1993 | Roth |
| 5,545,807 A | 8/1996 | Surani et al. |
| 5,766,886 A | 6/1998 | Studnicka et al. |
| 5,869,619 A | 2/1999 | Studnicka |
| 5,977,322 A | 11/1999 | Marks |
| 6,875,432 B2 | 4/2005 | Liu et al. |
| 7,029,895 B2 | 4/2006 | Glucksmann et al. |
| 7,261,893 B2 | 8/2007 | Veldman et al. |
| 7,300,754 B2 | 11/2007 | Abi Fadel et al. |
| 7,368,531 B2 | 5/2008 | Rosen et al. |
| 7,411,051 B2 | 8/2008 | Rosen et al. |
| 7,456,264 B2 | 11/2008 | Keler et al. |
| 7,482,147 B2 | 1/2009 | Glucksmann et al. |
| 7,572,618 B2 | 8/2009 | Mintier et al. |
| 7,737,266 B2 | 6/2010 | Soutschek et al. |
| 7,776,577 B2 | 8/2010 | Kapeller-Libermann et al. |
| 7,785,567 B2 | 8/2010 | Ong et al. |
| 7,803,374 B2 | 9/2010 | Lanza et al. |

| | | |
|---|---|---|
| 7,968,689 B2 | 6/2011 | Rosen et al. |
| 8,030,457 B2 | 10/2011 | Jackson et al. |
| 8,062,640 B2 | 11/2011 | Sleeman et al. |
| 8,080,243 B2 | 12/2011 | Liang et al. |
| 8,168,762 B2 | 5/2012 | Jackson et al. |
| 8,188,233 B2 | 5/2012 | Condra et al. |
| 8,188,234 B2 | 5/2012 | Condra et al. |
| 8,344,114 B2 | 1/2013 | Sparrow et al. |
| 8,357,371 B2 | 1/2013 | Sleeman et al. |
| 8,399,646 B2 | 3/2013 | Liang et al. |
| 8,420,098 B2 | 4/2013 | Camphausen et al. |
| 8,426,363 B2 | 4/2013 | Liang et al. |
| 8,501,184 B2 | 8/2013 | Sleeman et al. |
| 8,530,414 B2 | 9/2013 | Davies et al. |
| 8,563,528 B2 | 10/2013 | Straarup et al. |
| 8,563,698 B2 | 10/2013 | Jackson et al. |
| 8,598,320 B2 | 12/2013 | Hedrick et al. |
| 8,697,070 B2 | 4/2014 | Condra et al. |
| 8,697,633 B2 | 4/2014 | Zadini et al. |
| 8,710,192 B2 | 4/2014 | Rue et al. |
| 8,795,669 B2 | 8/2014 | Walsh et al. |
| 8,802,827 B2 | 8/2014 | Luo et al. |
| 8,829,165 B2 | 9/2014 | Jackson et al. |
| 8,859,741 B2 | 10/2014 | Jackson et al. |
| 8,871,913 B2 | 10/2014 | Jackson et al. |
| 8,871,914 B2 | 10/2014 | Jackson et al. |
| 8,877,900 B2 | 11/2014 | Luo et al. |
| 8,883,983 B2 | 11/2014 | Jackson et al. |
| 8,889,834 B2 | 11/2014 | Jackson et al. |
| 8,981,064 B2 | 3/2015 | Jackson et al. |
| 9,029,515 B2 | 5/2015 | Pons et al. |
| 9,045,547 B2 | 6/2015 | Jackson et al. |
| 9,056,915 B2 | 6/2015 | Jackson et al. |
| 9,078,904 B2 | 7/2015 | Mulligan-Kehoe |
| 9,084,777 B2 | 7/2015 | Morichika et al. |
| 9,175,093 B2 | 11/2015 | Liang et al. |
| 9,193,801 B2 | 11/2015 | Walsh et al. |
| 9,255,154 B2 | 2/2016 | Feldhaus et al. |
| 9,266,961 B2 | 2/2016 | Wu et al. |
| 9,493,576 B2 | 11/2016 | Jackson et al. |
| 9,550,837 B2 | 1/2017 | Sleeman et al. |
| 9,561,155 B2 | 2/2017 | Hanotin et al. |
| 9,682,013 B2 | 6/2017 | Hanotin et al. |
| 9,724,411 B2 | 8/2017 | Sleeman et al. |

(Continued)

FOREIGN PATENT DOCUMENTS

| | | |
|---|---|---|
| CL | 2011001435 | 2/2012 |
| CN | 1897918 | 1/2007 |

(Continued)

OTHER PUBLICATIONS

US 8,748,583 B2, 06/2014, Jackson et al. (withdrawn)

(Continued)

*Primary Examiner* — Sharon X Wen
(74) *Attorney, Agent, or Firm* — KNOBBE, MARTENS, OLSON & BEAR, LLP

(57) ABSTRACT

The present invention relates to methods of treating or preventing cholesterol related disorders, such as hypercholesterolemia, hyperlipidemia or dyslipidemia, using antibodies against proprotein convertase subtilisin/kexin type 9 (PCSK9). Formulations and methods of producing said formulations are also described.

47 Claims, 153 Drawing Sheets

Specification includes a Sequence Listing.

(56)     References Cited

U.S. PATENT DOCUMENTS

| | | |
|---|---|---|
| 9,920,134 B2 | 3/2018 | Jackson et al. |
| 9,994,923 B2 | 6/2018 | Jackson et al. |
| 10,023,654 B2 | 7/2018 | Sleeman et al. |
| 10,076,571 B2 | 9/2018 | Swergold |
| 10,259,885 B2 | 4/2019 | Feldhaus et al. |
| 10,472,425 B2 | 11/2019 | Walsh et al. |
| 10,611,850 B2 | 4/2020 | Christian et al. |
| 10,752,701 B2 | 8/2020 | Walsh et al. |
| 11,464,857 B2 | 10/2022 | Sloey et al. |
| 2002/0045571 A1 | 4/2002 | Liu et al. |
| 2002/0081679 A1 | 6/2002 | Chiang et al. |
| 2002/0086014 A1 | 7/2002 | Korman et al. |
| 2003/0119038 A1 | 6/2003 | Bingham et al. |
| 2004/0009178 A1 | 1/2004 | Bowdish et al. |
| 2004/0009553 A1 | 1/2004 | Glucksmann et al. |
| 2004/0023243 A1 | 2/2004 | Henry et al. |
| 2004/0038242 A1 | 2/2004 | Edmonds et al. |
| 2004/0248177 A1 | 12/2004 | Abi Fadel et al. |
| 2005/0101529 A1 | 5/2005 | Yue et al. |
| 2005/0118625 A1 | 6/2005 | Mounts |
| 2005/0147612 A1 | 7/2005 | Yayon et al. |
| 2005/0158303 A1 | 7/2005 | Liu et al. |
| 2005/0197285 A1 | 9/2005 | Rosen et al. |
| 2005/0282230 A1 | 12/2005 | Ashkenazi et al. |
| 2006/0116508 A1 | 6/2006 | Glucksmann et al. |
| 2006/0147945 A1 | 7/2006 | Edmonds et al. |
| 2006/0223088 A1 | 10/2006 | Rosen et al. |
| 2006/0223090 A1 | 10/2006 | Rosen et al. |
| 2006/0246483 A1 | 11/2006 | Rosen et al. |
| 2006/0286112 A1 | 12/2006 | Kellerman et al. |
| 2007/0015696 A1 | 1/2007 | Rosen et al. |
| 2007/0037206 A1 | 2/2007 | Rosen et al. |
| 2007/0041963 A1 | 2/2007 | Rosen |
| 2007/0055056 A1 | 3/2007 | Rosen et al. |
| 2007/0059312 A1 | 3/2007 | Baca et al. |
| 2007/0082345 A1 | 4/2007 | Ota et al. |
| 2007/0224663 A1 | 9/2007 | Rosen et al. |
| 2008/0008697 A1 | 1/2008 | Mintier et al. |
| 2008/0103090 A1 | 5/2008 | Rosen et al. |
| 2008/0113930 A1 | 5/2008 | Tan et al. |
| 2009/0142352 A1 | 6/2009 | Jackson et al. |
| 2009/0196880 A1 | 8/2009 | Gill et al. |
| 2009/0232795 A1 | 9/2009 | Condra et al. |
| 2009/0246192 A1 | 10/2009 | Condra et al. |
| 2009/0269350 A1 | 10/2009 | Glucksmann |
| 2009/0275053 A1 | 11/2009 | Horton et al. |
| 2009/0326202 A1 | 12/2009 | Jackson et al. |
| 2010/0015131 A1 | 1/2010 | Mi et al. |
| 2010/0040610 A1 | 2/2010 | Sitlani et al. |
| 2010/0040611 A1 | 2/2010 | Sparrow et al. |
| 2010/0041102 A1 | 2/2010 | Sitlani et al. |
| 2010/0068194 A1 | 3/2010 | Kim |
| 2010/0068199 A1 | 3/2010 | Liang et al. |
| 2010/0136028 A1 | 6/2010 | Sparrow et al. |
| 2010/0150937 A1 | 6/2010 | Sparrow et al. |
| 2010/0166768 A1 | 7/2010 | Sleeman et al. |
| 2010/0233177 A1 | 9/2010 | Yowe et al. |
| 2010/0291099 A1 | 11/2010 | Glucksmann |
| 2011/0027287 A1 | 2/2011 | Jackson et al. |
| 2011/0033465 A1 | 2/2011 | Hendrick et al. |
| 2011/0065902 A1 | 3/2011 | Sleeman et al. |
| 2011/0105726 A1 | 5/2011 | Rosen et al. |
| 2011/0111406 A1 | 5/2011 | Igawa et al. |
| 2011/0117011 A1 | 5/2011 | Jackson et al. |
| 2011/0142849 A1 | 6/2011 | Rue et al. |
| 2011/0207759 A1 | 8/2011 | Taylor |
| 2011/0229489 A1 | 9/2011 | Pons et al. |
| 2011/0230392 A1 | 9/2011 | Chiang et al. |
| 2011/0256148 A1 | 10/2011 | Sleeman et al. |
| 2012/0014951 A1 | 1/2012 | Liang et al. |
| 2012/0015435 A1 | 1/2012 | Liang et al. |
| 2012/0020975 A1 | 1/2012 | Jackson et al. |
| 2012/0020976 A1 | 1/2012 | Jackson et al. |
| 2012/0027765 A1 | 2/2012 | Jackson et al. |
| 2012/0076799 A1 | 3/2012 | Sparrow et al. |
| 2012/0077964 A1 | 3/2012 | Sparrow et al. |
| 2012/0082679 A1 | 4/2012 | Sparrow et al. |
| 2012/0082680 A1 | 4/2012 | Sitlani et al. |
| 2012/0093818 A1 | 4/2012 | Jackson et al. |
| 2012/0195910 A1 | 8/2012 | Wu et al. |
| 2012/0208208 A1 | 8/2012 | Ni et al. |
| 2012/0208209 A1 | 8/2012 | Ichetovkin et al. |
| 2012/0213794 A1 | 8/2012 | Luo et al. |
| 2012/0213797 A1 | 8/2012 | Jackson et al. |
| 2012/0219558 A1 | 8/2012 | Ni et al. |
| 2012/0231005 A1 | 9/2012 | Luo et al. |
| 2012/0251544 A1 | 10/2012 | Jackson et al. |
| 2012/0301461 A1 | 11/2012 | Condra et al. |
| 2013/0052201 A1 | 2/2013 | Jackson et al. |
| 2013/0058944 A1 | 3/2013 | Jackson et al. |
| 2013/0064825 A1 | 3/2013 | Chan et al. |
| 2013/0064834 A1 | 3/2013 | Sleeman et al. |
| 2013/0071379 A1 | 3/2013 | Condra et al. |
| 2013/0071405 A1 | 3/2013 | Davies et al. |
| 2013/0072665 A1 | 3/2013 | Jackson et al. |
| 2013/0079501 A1 | 3/2013 | Jackson et al. |
| 2013/0079502 A1 | 3/2013 | Jackson et al. |
| 2013/0085265 A1 | 4/2013 | Jackson et al. |
| 2013/0085266 A1 | 4/2013 | Sleeman et al. |
| 2013/0115223 A1 | 5/2013 | Sparrow et al. |
| 2013/0171128 A1 | 7/2013 | Huang et al. |
| 2013/0189277 A1 | 7/2013 | Walsh et al. |
| 2013/0189278 A1 | 7/2013 | Sitlani et al. |
| 2013/0197055 A1 | 8/2013 | Kamens et al. |
| 2013/0243784 A1 | 9/2013 | Swergold et al. |
| 2013/0273069 A1 | 10/2013 | Liang et al. |
| 2013/0302399 A1 | 11/2013 | Feldhaus et al. |
| 2013/0315927 A1 | 11/2013 | Goldstein et al. |
| 2013/0344085 A1 | 12/2013 | Wu et al. |
| 2014/0004122 A1 | 1/2014 | Chan et al. |
| 2014/0099312 A1 | 4/2014 | Sleeman et al. |
| 2014/0154262 A1 | 6/2014 | Hanotin et al. |
| 2014/0161808 A1 | 6/2014 | Mintier et al. |
| 2014/0178402 A1 | 6/2014 | Hanotin et al. |
| 2014/0228545 A1 | 8/2014 | Jackson et al. |
| 2014/0228547 A1 | 8/2014 | Jackson et al. |
| 2014/0228557 A1 | 8/2014 | Jackson et al. |
| 2014/0235830 A1 | 8/2014 | Jackson et al. |
| 2014/0235831 A1 | 8/2014 | Jackson et al. |
| 2014/0341928 A1 | 11/2014 | Walsh et al. |
| 2014/0357850 A1 | 12/2014 | Jackson et al. |
| 2014/0357854 A1 | 12/2014 | Jackson et al. |
| 2015/0004174 A1 | 1/2015 | Wasserman et al. |
| 2015/0031870 A1 | 1/2015 | Jackson et al. |
| 2015/0087819 A1 | 3/2015 | Jackson et al. |
| 2015/0266974 A1 | 9/2015 | Pons et al. |
| 2016/0032015 A1 | 2/2016 | Walsh et al. |
| 2016/0096898 A1 | 4/2016 | Liang et al. |
| 2016/0137745 A1 | 5/2016 | Baccara-Dinet et al. |
| 2016/0152734 A1 | 6/2016 | Udata |
| 2016/0194408 A1 | 7/2016 | Feldhaus et al. |
| 2016/0202239 A1 | 7/2016 | Voros et al. |
| 2016/0355606 A1 | 12/2016 | Wu et al. |
| 2017/0049886 A1 | 2/2017 | Pordy et al. |
| 2017/0266079 A1 | 9/2017 | Hanotin et al. |
| 2017/0296657 A1 | 10/2017 | Sleeman et al. |
| 2017/0306051 A1 | 10/2017 | Pfizer |
| 2017/0340515 A1 | 11/2017 | Hanotin et al. |
| 2018/0044436 A1 | 2/2018 | Walsh et al. |
| 2018/0265592 A1 | 9/2018 | Sitlani et al. |
| 2018/0333490 A1 | 11/2018 | Swergold |
| 2019/0284301 A1 | 9/2019 | Walsh et al. |
| 2019/0343719 A1 | 11/2019 | Hanotin et al. |
| 2019/0389968 A1 | 12/2019 | Feldhaus et al. |
| 2020/0024366 A1 | 1/2020 | Pons et al. |
| 2020/0368350 A1 | 11/2020 | Somaratne et al. |
| 2021/0047434 A1 | 2/2021 | Chan et al. |
| 2021/0054100 A1 | 2/2021 | Walsh et al. |
| 2023/0235085 A1 | 7/2023 | Hamer et al. |

FOREIGN PATENT DOCUMENTS

| | | | |
|---|---|---|---|
| DE | 2524355 | A1 | 12/1975 |
| EP | 0033538 | A2 | 8/1981 |

(56) References Cited

FOREIGN PATENT DOCUMENTS

| | | |
|---|---|---|
| EP | 409281 A1 | 1/1991 |
| EP | 521471 A1 | 1/1993 |
| EP | 11305513.1 | 4/2011 |
| EP | 11305514.9 | 4/2011 |
| EP | 11306039.6 | 8/2011 |
| EP | 11306040.4 | 8/2011 |
| EP | 11306201.2 | 9/2011 |
| EP | 11306202.0 | 9/2011 |
| EP | 11306449.7 | 11/2011 |
| EP | 11306450.5 | 11/2011 |
| EP | 2481758 | 8/2012 |
| EP | 2615114 A2 | 7/2013 |
| EP | 2 650 016 | 10/2013 |
| EP | 2703009 | 3/2014 |
| EP | 2706070 | 3/2014 |
| EP | 2862877 | 4/2015 |
| EP | 2215124 B1 | 2/2016 |
| EP | 2358756 B1 | 1/2017 |
| EP | 2215214 B1 | 5/2018 |
| EP | 2707029 B1 | 1/2020 |
| EP | 2641917 | 5/2020 |
| EP | 2615114 B1 | 4/2022 |
| JP | 2005-130764 | 5/2005 |
| WO | WO 93/12227 | 6/1993 |
| WO | WO 97/45140 | 12/1997 |
| WO | WO 98/01100 | 1/1998 |
| WO | WO 98/22136 | 5/1998 |
| WO | WO 98/24893 | 6/1998 |
| WO | WO 00/76310 | 12/2000 |
| WO | WO 01/031007 | 5/2001 |
| WO | WO 01/57081 | 8/2001 |
| WO | WO 01/98468 | 12/2001 |
| WO | WO 02/14358 | 2/2002 |
| WO | WO 02/32936 | 4/2002 |
| WO | WO 2002/046383 | 6/2002 |
| WO | WO 2002/090526 | 11/2002 |
| WO | WO 2002/102993 | 12/2002 |
| WO | WO 2002/102994 | 12/2002 |
| WO | WO 2004/018649 | 3/2004 |
| WO | WO 2004/022718 | 3/2004 |
| WO | WO 2004/055164 | 7/2004 |
| WO | WO 2004/097047 | 11/2004 |
| WO | WO 06/020676 | 2/2006 |
| WO | WO 2006/081171 | 8/2006 |
| WO | WO-2006138181 A2 * | 12/2006 ........... A61K 39/395 |
| WO | WO 2007/074880 | 7/2007 |
| WO | WO 2007/089753 | 8/2007 |
| WO | WO 2007/128121 | 11/2007 |
| WO | WO 08/057457 | 5/2008 |
| WO | WO 08/057458 | 5/2008 |
| WO | WO 08/057459 | 5/2008 |
| WO | WO 08/063382 | 5/2008 |
| WO | WO 2008/062063 | 5/2008 |
| WO | WO 2008/063382 | 5/2008 |
| WO | WO 2008/086395 | 5/2008 |
| WO | WO 2008/105797 A2 | 9/2008 |
| WO | WO 2008/109871 A2 | 9/2008 |
| WO | WO 08/125623 | 10/2008 |
| WO | WO 2008/121615 | 10/2008 |
| WO | WO 08/133647 | 11/2008 |
| WO | WO 09/026558 | 2/2009 |
| WO | WO 2008/109871 A3 | 2/2009 |
| WO | WO 09/055783 | 4/2009 |
| WO | WO 2008/109871 A8 | 7/2009 |
| WO | WO 09/100297 | 8/2009 |
| WO | WO 09/100318 | 8/2009 |
| WO | WO 2009/100324 | 8/2009 |
| WO | WO 2009/125825 | 10/2009 |
| WO | WO 2009/131740 A2 | 10/2009 |
| WO | WO 10/029513 | 3/2010 |
| WO | WO 2010/029513 A3 | 3/2010 |
| WO | WO 2010/068526 | 6/2010 |
| WO | WO 10/077854 | 7/2010 |
| WO | WO 2010/077422 | 7/2010 |
| WO | WO 2010/102241 | 9/2010 |
| WO | WO 11/028938 | 3/2011 |
| WO | WO 11/037791 | 3/2011 |
| WO | WO 11/053665 | 5/2011 |
| WO | WO 11/053743 | 5/2011 |
| WO | WO 11/053759 | 5/2011 |
| WO | WO 11/053783 | 5/2011 |
| WO | WO 2011/061712 | 5/2011 |
| WO | WO 11/072263 | 6/2011 |
| WO | WO 2011/088120 A1 | 7/2011 |
| WO | WO 11/111007 | 9/2011 |
| WO | WO 2011/130354 A1 | 10/2011 |
| WO | WO 12/054438 | 4/2012 |
| WO | WO 2012/06792 | 5/2012 |
| WO | WO 12/088313 | 6/2012 |
| WO | WO 12/101251 | 8/2012 |
| WO | WO 12/101252 | 8/2012 |
| WO | WO 12/101253 | 8/2012 |
| WO | WO 12/109530 | 8/2012 |
| WO | WO 2012/154999 | 11/2012 |
| WO | WO 12/168491 | 12/2012 |
| WO | WO 12/170607 | 12/2012 |
| WO | WO 12/177741 | 12/2012 |
| WO | WO 13/008185 | 1/2013 |
| WO | WO 13/016648 | 1/2013 |
| WO | WO 13/039958 | 3/2013 |
| WO | WO 13/039969 | 3/2013 |
| WO | WO 2013/091103 | 6/2013 |
| WO | WO 2013/148284 | 10/2013 |
| WO | WO 2013/169886 | 11/2013 |
| WO | WO 2013/188855 | 12/2013 |
| WO | WO 2014/079886 | 5/2014 |
| WO | WO 2014/150983 | 9/2014 |
| WO | WO 2014/209384 | 12/2014 |
| WO | WO 2015/142668 A1 | 9/2015 |
| WO | WO2016/046684 | 3/2016 |
| WO | WO 2016/202415 | 12/2016 |
| WO | WO 2018/089912 A2 | 5/2018 |
| WO | WO 2021/243002 | 12/2021 |

OTHER PUBLICATIONS

Lagace Ta et al., Secreted PCSK 9 decreases the number of LDL receptors in hepatocytes and in livers of parabiotic mice. J Clin Invest. Nov. 2006;116(11): pp. 2995-3005 The whole text.

Search Report for corresponding Taiwanese Patent Application No. 101116742, dated Jan. 20, 2014.

U.S. Appl. No. 09/499,235 (parent of U.S. Pub. No. 2003/0119038), filed Feb. 7, 2000, Chiang et al.

U.S. Appl. No. 09/517,906 (parent of U.S. Pub. No. 2003/0119038), filed Mar. 3, 2000, Chiang et al.

U.S. Appl. No. 09/692,785 (parent of U.S. Pub. No. 2002/0081679), filed Oct. 20, 2000, Chiang et al.

U.S. Appl. No. 09/775,009 (Published as U.S. Publication No. 2002-0081679), filed Feb. 1, 2001, Chiang et al.

U.S. Appl. No. 10/287,290 (Published as U.S. Publication No. 2003-0119038), filed Nov. 1, 2002, Bingham et al.

U.S. Appl. No. 10/426,776 (Published as U.S. Publication No. 2004-0009553), filed Apr. 30, 2003, Glucksmann et al.

U.S. Appl. No. 11/313,836 (Published as U.S. Publication No. 2006-0116508), filed Dec. 21, 2005, Glucksmann et al.

U.S. Appl. No. 12/198,817 (Published as U.S. Pub. No. 2011/0105726), filed Aug. 26, 2008, Rosen et al.

U.S. Appl. No. 12/312,383 (Published as U.S. Publication No. 2010-0040610), filed May 7, 2009, Sitlani et al.

U.S. Appl. No. 12/312,397 (Published as U.S. Publication No. 2010-0136028), filed May 7, 2009, Sparrow et al.

U.S. Appl. No. 12/312,398 (Published as U.S. Publication No. 2010-040611), filed May 7, 2009, Sparrow et al.

U.S. Appl. No. 12/312,399 (Published as U.S. Publication No. 2010-150937), filed May 7, 2009, Sparrow et al.

U.S. Appl. No. 12/312,401 (Published as U.S. Publication No. 2010-0041102), filed May 7, 2009, Sitlani et al.

U.S. Appl. No. 12/316,681 (Published as U.S. Publication No. 2009-0269350), filed Dec. 16, 2008, Kapeller-Libermann et al.

(56) References Cited

OTHER PUBLICATIONS

U.S. Appl. No. 12/316,797, filed Dec. 16, 2008, Glucksmann et al.
U.S. Appl. No. 12/322,861 (Published as U.S. Publication No. 2009-0232795), filed Feb. 6, 2009, Condra et al.
U.S. Appl. No. 12/322,867 (Published as U.S. Publication No. 2009-0246192), filed Feb. 6, 2009, Condra et al.
U.S. Appl. No. 12/474,176 (Published as U.S. Publication No. 2009-0326202), filed Dec. 31, 2009, Jackson et al.
U.S. Appl. No. 12/558,312 (Published as U.S. Publication No. 2010-0068199), filed Sep. 11, 2009, Liang et al.
U.S. Appl. No. 12/595,538 (Published as U.S. Publication No. 2010-0233177), filed Oct. 12, 2009, Yowe et al.
U.S. Appl. No. 12/637,942 (Published as U.S. Publication No. 2010-0166768), filed Dec. 15, 2009, Sleeman et al.
U.S. Appl. No. 12/739,761 (Published as U.S. Publication No. 2011-0033465), filed Oct. 6, 2010, Hedrick.
U.S. Appl. No. 12/817,236 (Published as U.S. Publication No. 2010-0231099), filed Nov. 18, 2010, Glucksmann et al.
U.S. Appl. No. 12/903,084 (Published as U.S. Publication No. 2011-0027287), filed Feb. 3, 2011, Jackson et al.
U.S. Appl. No. 12/949,846 (Published as U.S. Publication No. 2011-0065902), filed Nov. 19, 2010, Sleeman et al.
U.S. Appl. No. 12/965,743 (Published as U.S. Publication No. 2011-0142849), filed Dec. 10, 2010, Rue.
U.S. Appl. No. 13/045,345 (Published as U.S. Publication No. 2011-0229489), filed Mar. 10, 2011, Pons et al.
U.S. Appl. No. 13/071,809 (Published as U.S. Publication No. 2011-0230392), filed Sep. 22, 2011, Chiang et al.
U.S. Appl. No. 13/095,234 (Published as U.S. Publication No. 2011-0256148), filed Apr. 27, 2011, Sleeman et al.
U.S. Appl. No. 13/174,423 (Published as U.S. Pub. No. 2012/0093818), filed Jun. 30, 2011, Jackson et al.
U.S. Appl. No. 13/225,265 (Published as U.S. Publication No. 2012-0014951), filed Sep. 2, 2011, Liang et al.
U.S. Appl. No. 13/225,119 (Published as U.S. Publication No. 2012-0015435), filed Sep. 2, 2011, Liang et al.
U.S. Appl. No. 13/242,744 (Published as U.S. Publication No. 2012-0082679), filed Sep. 23, 2011, Sparrow et al.
U.S. Appl. No. 13/242,809 (Published as U.S. Publication No. 2012-0076799), filed Sep. 23, 2011, Sparrow et al.
U.S. Appl. No. 13/242,831 (Published as U.S. Publication No. 2012-0082680), filed Sep. 23, 2011, Sitlani et al.
U.S. Appl. No. 13/246,219 (Published as U.S. Publication No. 2012-0077964), filed Sep. 27, 2011, Sparrow et al.
U.S. Appl. No. 13/251,909 (Published as U.S. Publication No. 2012/0020975), filed Jan. 26, 2012, Jackson et al.
U.S. Appl. No. 13/251,955 (Published as U.S. Publication No. 2012/0020976), filed Jan. 26, 2012, Jackson et al.
U.S. Appl. No. 13/252,016 (Published as U.S. Publication No. 2012/0027765), filed Feb. 2, 2012, Jackson et al.
U.S. Appl. No. 13/333,315 (Published as U.S. Publication No. 2012-0195910), filed Dec. 21, 2011, Wu et al.
U.S. Appl. No. 13/422,887 (Published as U.S. Publication No. 2013-0085265), filed Mar. 16, 2012, Jackson et al.
U.S. Appl. No. 13/422,904 (Published as U.S. Publication No. 2013-0079501), filed Mar. 16, 2012, Jackson et al.
U.S. Appl. No. 13/463,751 (Published as U.S. Publication No. 2012-0213797), filed May 3, 2012, Jackson et al.
U.S. Appl. No. 13/466,433 (Published as U.S. Publication No. 2013-0071379), filed May 8, 2012, Condra et al.
U.S. Appl. No. 13/466,439 (Published as U.S. Publication No. 2012-0301461), filed May 8, 2012, Condra et al.
U.S. Appl. No. 13/469,032 (Published as U.S. Publication No. 2013-0064825), filed Mar. 14, 2013, Chan et al.
U.S. Appl. No. 13/494,912 (Published as U.S. Publication No. 2012/025154), filed Jun. 12, 2012, Jackson et al.
U.S. Appl. No. 13/497,663 (Published as U.S. Publication No. 2012-0219558), filed Sep. 15, 2010, Ni et al.
U.S. Appl. No. 13/503,708 (Published as U.S. Publication No. 2012-0208208), filed Aug. 16, 2012, Ni et al.
U.S. Appl. No. 13/503,726 (Published as U.S. Publication No. 2012-0231005), filed Apr. 24, 2012, Luo et al.
U.S. Appl. No. 13/503,729 (Published as U.S. Publication No. 2012-0213794, filed Aug. 23, 2012, Luo et al.
U.S. Appl. No. 13/503,732 (Published as U.S. Publication No. 2012-0208209), filed Aug. 16, 2012, Ichetovkin et al.
U.S. Appl. No. 13/611,196 (Published as U.S. Publication No. 2013-0071405), filed Mar. 21, 2013, Davies et al.
U.S. Appl. No. 13/619,555 (Published as U.S. Publication No. 2013/0072665), filed Mar. 21, 2013, Jackson et al.
U.S. Appl. No. 13/655,984 (Published as U.S. Publication No. 2013-0058944), filed Mar. 7, 2013, Jackson et al.
U.S. Appl. No. 13/656,392 (Published as U.S. Publication No. 2013/0052201), filed May 28, 2013, Jackson et al.
U.S. Appl. No. 13/672,792 (Published as U.S. Publication No. 2013-0064834), filed Mar. 14, 2013, Sleeman, et al.
U.S. Appl. No. 13/682,698 (Published as U.S. Publication No. 2013/0079502), filed Mar. 28, 2013, Jackson et al.
U.S. Appl. No. 13/690,585 (published as U.S. Pub. No. 2013/0085266), filed Apr. 4, 2013, Sleeman, et al.
U.S. Appl. No. 13/724,447 (published as U.S. Pub. No. 2013/0115223), filed May 9, 2013, Sparrow et al.
U.S. Appl. No. 13/742,205 (child of 2010/0041102), filed Jan. 15, 2013, Merck.
U.S. Appl. No. 13/918,755 (published as U.S. Pub. No. 2013/0344085), filed Dec. 26, 2013, Wu et al.
U.S. Appl. No. 14/316,587, filed Jun. 26, 2014, Wasserman et al.
U.S. Appl. No. 60/857,248, filed Nov. 7, 2006, Merck & Co., Inc.
U.S. Appl. No. 60/857,293, filed Nov. 7, 2006, Merck & Co., Inc.
U.S. Appl. No. 12/474,176 (Claims), filed May 28, 2009, Jackson et al.
U.S. Appl. No. 12/903,084 (Claims), filed Feb. 3, 2011, Jackson et al.
U.S. Appl. No. 13/174,423 (Claims), filed Apr. 19, 2012, Jackson et al.
U.S. Appl. No. 13/251,909 (Claims), filed Jan. 26, 2012, Jackson et al.
U.S. Appl. No. 13/251,955 (Claims), filed Jan. 26, 2012, Jackson et al.
U.S. Appl. No. 13/252,016 (Claims), filed Feb. 2, 2012, Jackson et al.
U.S. Appl. No. 13/422,887 (Claims), filed Mar. 16, 2012, Jackson et al.
U.S. Appl. No. 13/422,904 (Claims), filed Mar. 16, 2012, Jackson, et al.
U.S. Appl. No. 13/463,751 (Claims), filed Aug. 23, 2012, Jackson et al.
U.S. Appl. No. 13/494,912 (Claims), filed Oct. 4, 2012, Jackson et al.
U.S. Appl. No. 13/619,555 (Claims), filed Sep. 14, 2012, Jackson et al.
U.S. Appl. No. 13/655,984 (Claims), filed Oct. 19, 2012, Jackson et al.
U.S. Appl. No. 13/656,392 (Claims), filed Oct. 19, 2012, Jackson, et al.
U.S. Appl. No. 13/682,698 (Claims), filed Nov. 20, 2012, Jackson, et al.
U.S. Appl. No. 13/860,016 (Claims), filed Apr. 10, 2013, Jackson, et al.
U.S. Appl. No. 14/261,087 (Claims), filed Apr. 24, 2014, Jackson et al.
U.S. Appl. No. 14/260,975 (Claims), filed Apr. 24, 2014, Jackson et al.
U.S. Appl. No. 14/261,063 (Claims), filed Apr. 24, 2014, Jackson et al.
U.S. Appl. No. 14/261,065 (Claims), filed Apr. 24, 2014, Jackson et al.
U.S. Appl. No. 14/260,985 (Claims), filed Apr. 24, 2014, Jackson et al.
U.S. Appl. No. 14/459,777 (Claims), filed Aug. 14, 2014, Jackson et al.
U.S. Appl. No. 14/459,743 (Claims), filed Aug. 14, 2014, Jackson et al.

(56)                    References Cited

OTHER PUBLICATIONS

U.S. Appl. No. 14/459,768 (Claims), filed Aug. 14, 2014, Jackson et al.

U.S. Appl. No. 14/459,787 (Claims), filed Aug. 14, 2014, Jackson et al.

U.S. Appl. No. 14/459,844 (Claims), filed Aug. 14, 2014, Jackson et al.

U.S. Appl. No. 14/487,932 (Claims), filed Sep. 16, 2014, Jackson et al.

Abboud et al., "Proprotein Convertase Subtilisin/Kexin Type 9 (PCSK9) Gene is a Risk Factor of Large-Vessel Atherosclerosis Stroke," PLoS One, 2(10): e1043, Oct. 2007.

Abifadel et al., "Mutations in PCSK9 cause autosomal dominant hypercholesterolemia," Nature Genetics 34, 154-156 (2003).

Advisory Action received in U.S. Appl. No. 12/312,401, dated Nov. 2, 2012, filed May 7, 2009 (Merck).

Akers et al., "Formulation Development of Protein Dosage Forms," Pharmaceutical Biotechnology, Kluwer, Dordrecht, NL, vol. 14, Jan. 1, 2002, pp. 47-127.

Alborn et al., "Serum proprotein convertase subtilisin kexin type 9 is correlated directly with serum LDL cholesterol," Clin Chem, 53(10): 1814-1819, (2007).

Allard et al., "Genetic heterogeneity of autosomal dominant hypercholesterolemia: PCSK9, a third genet involved in the disease," Current Topics in Genetics, 1, pp. 103-112, 2005.

Allard et al., "Novel mutations of the PCSK9 gene cause variable phenotype of autosomal dominant hypercholesterolemia," Human mutation, 26(5), pp. 497, Nov. 2005.

Allard et al., "PC9, a new actor in autosomal dominant hypercholesterolemia," Current Genomics, 6(7), pp. 535-543, Nov. 2005.

Amended Claims in 15 pages for European Application No. 09808999.8 filed Sep. 11, 2009 (WO 2010/029513).

Anderson et al., "Activation of the furin endoprotease is a multiple-step process: requirements for acidification and internal propeptide cleavage," EMBO J. 16, 1508-1518, 1997.

Attie et al., "Dual regulation of the LDL receptor—some clarity and new questions," Cell Metab., 1(5): 290-292, (2005).

Attie et al., "The mystery of PCSK9," Aterioscler Thromb Vasc Biol., 24(8): 1337-1339, (2004).

Austin et al., "Genetic causes of monogenic heterozygous familial hypercholesterolemia: a HuGE prevalence review," American Journal of Epidemiology, 160(5): 407-420, 2004.

Barrios et al., "Length of the Antibody Heavy Chain Complementarity Determining Region 3 as a Specificity-Determining Factor," J. Mol. Recognit., vol. 17, 2004, pp. 332-338.

Bansal et al., "Cord blood lipoproteins and prenatal influences," Current Opinion in Lipidology, 16(4): 400-408, Aug. 2005.

Basak, "Inhibitors of Proprotein Convertases," J Mol Med 83: pp. 844-855, 2005.

Bedi et al., "Inhibition of squalene synthase upregulates PCSK9 expression in rat liver," Arch Biochem Biophys., 470(2): 116-119, (2008).

Benjannet et al., "NARC-1/PCSK9 and its natural mutants: zymogen cleavage and effects on the low density lipoprotein (LDL) receptor and LDL cholesterol," J Biol Chem, 2004, 279(47): 48865-48875.

Benjannet et al., "The Proprotein Convertase (PC) PCSK9 Is Inactivated by Furin and/or PC5/6A," J Biol Chem, Oct. 13, 2006, 281(41): 30561-30572.

Berge et al., Missense mutations in the PCSK9 gene are associated with hypocholesterolemia and possibly increased response to statin therapy. Arterioscler. Thromb. Vasc. Biol. (2006) 26, 1094-1100.

Bingham et al., "Proapoptotic Effects of NARC 1 (= PCSK9), the Gene Encoding a Novel Serine Proteinase," Cytometry Part A, 2006, 69A: 1123-1131.

Bottomley et al., "Structural and biochemical characterization of the wild type PCSK9/EGF-AB complex and natural FH mutants," J Biol. Chem., Nov. 2008.

Brown et al., "Lowering LDL—not only how low, but how long?" Science 311, 1721-1723, (2006).

Brunger et al., "Crystallography & NMR System: A new software suite for macromolecular structure determination," Acta Crystallogr D Biol Crystallogr 54: 905-921 (1998).

Burnett et al., "New therapies for familial hypercholesterolemia," Expert Opin. Ther. Patents 16(3): 349-361, 2006.

Cameron et al., "Effect of mutations in the PCSK9 gene on the cell surface LDL receptors," Hum. Mol. Genet. 15: 1551-1558 (2006).

Cameron et al., "Berberine decreases PCSK9 expression in HepG2 cells," Atherosclerosis, 201(2): 266-273, (2008).

Cameron et al., "Characterization of novel mutations in the catalytic domain of the PCSK9 gene," J Intern Med., 263(4): 420-431, (2008).

Cameron et al., "Investigations on the evolutionary conservation of PCSK9 reveal a functionally important protrusion," The FEBS Journal, pp. 1-13, 2008.

Campbell, Chapter 1, Monoclonal Antibody Technology, 1984, pp. 1-32, Elsevier Science Publishers B.V., The Netherlands.

Careskey et al., "Atorvastatin increases human serum levels of proprotein convertase subtilisin/kexin type 9," J Lipid Res., 49(2): 394-398, (2008).

Casset et al., "A Peptide Mimetic of an Anti-CD4 Monoclonal Antibody by Rational Design," Biochemical and Biophysical Research Communications, 2003, vol. 307, pp. 198-205.

Cayman Chemical Company, "Material Safety Data Sheet PCSK9 (human) Polyclonal Antibody," Jul. 26, 2007, pp. 1-3.

Cayman Chemical Company, "Material Safety Data Sheet PCSK9 (murine) Polyclonal Antibody," Sep. 5, 2007, pp. 1-4.

Cayman Chemical Company, "Product information PCSK9 (murine) Polyclonal Antibody," Sep. 5, 2007, pp. 1-2.

Cayman Chemical Company, "Product information PCSK9 Polyclonal Antibody Catalog No. 10007185," Dec. 10, 2007, pp. 1-2.

"PCSK9 (mouse) Polyclonal Antibody Cayman Chemical"; Quartzy PCSK9 (mouse) Polyclonal Antibody; Website: https://www.quartzy.com/reagent-detail/1464130/1/PCSK9--mouse--Polyclonal-Antibody-Cayman; Cayman Chemical Company: "Product information Proprotein Convertase Subtilisin Kexin 9; NARC-1 antigen." The reference is a webpage, and no date of publication is immediately apparent in the document. Applicants note that the webpage was printed on Nov. 7, 2013, and has a copyright date of 2013 to Quartzy; however, the webpage may have been available, in some form, prior to this date. It is noted that the document includes an "introduction date" of Jan. 22, 2007. pp. 1-4.

CCP4. The CCP4 suite: programs for protein crystallography. Acta Crystallogr D. Biol Crystallogr 50, 760-763 (1994).

Chamow et al., TIBTECH 14: 52-60, 1996 (entitled "Antibody Engineering at the Millennium").

Chan Joyce C Y et al. "A Proprotein convertase subtilisin/kexin type 9 neutralizing antibody reduces serum cholesterol in mice and nonhuman primates," Proc Nat Acad Sci, Jun. 16, 2009, vol. 106, No. 24, pp. 9820-9825.

Chen et al., "Influence of histidine on the stability and physical properties of a fully human antibody in aqueous and solid forms" Pharmaceutical Research, Kluwer Academic Publishers, New York, NY vol. 20, No. 12, Dec. 1, 2003, pp. 1952-1960.

Chen et al., "A common PCSK9 haplotype, encompassing the E670G coding single nucleotide polymorphism, is a novel genetic marker for plasma low-density lipoprotein cholesterol levels and severity of coronary atherosclerosis," J Am Coll Cardiol. 45(10): 1611-1619, (2005).

Chen et al., "A common PCSK9 haplotype, encompassing the E670G cSNP, is associated with plasma low-density lipoprotein levels and severity of coronary atherosclerosis," Circulation 110 (17, Suppl. S), Oct. 26, 2004.

Chen et al., "Selection and Analysis of an Optimized Anti-VEGF Antibody: Crystal Structure of an Affinity Matured Fab in Complex with Antigen," J. Mol. Biol., 1999, vol. 293, pp. 865-881.

Cohen et al., "Sequence variations in PCSK9, low LDL, and protection against coronary heart disease," N. Engl. J. Med. 354, 1264-1272 (2006).

Cohen et al., "Erratum: Low LDL cholesterol in African Americans resulting from frequent nonsense mutations in PCSK9," Nature Genetics, 37(3), pp. 328, 2005.

(56)　　　　　References Cited

OTHER PUBLICATIONS

Cohen et al., "Low LDL cholesterol in individuals of African descent resulting from frequent nonsense mutations in PCSK9," Nature Genetics, 37(2): 161-165, (2005).

Colman, "Effects of amino acid sequence changes on antibody-antigen interactions," Research in Immunology, vol. 145, pp. 33-36, 1994.

Comments to Communications filed Mar. 26, 2013 in European Patent Application No. 08798550.3.

Costet et al., "Hepatic PCSK9 Expression Is Regulated by Nutritional Status via Insulin and Sterol Regulatory Element-binding Protein 1c," Journal of Biological Chemistry, Mar. 2006, 281(10): pp. 6211-6218.

Costet et al., "PCSK9 and LDL cholesterol: unraveling the target to design the bullet," Trends Biochem Sci., 33(9): 426-434, (2008).

Costet et al., "Proprotein Convertase Subtilisin Kexin type 9 is repressed by the peroxisome proliferator activated receptor alpha ligand fenofibric acid," Circulation, 114, 18, Suppl. S., Oct. 31, 2006.

Cunningham et al., "Structural and biophysical studies of PCSK9 and its mutants linked to familiar hypercholesterolemia," Nature Structural & Molecular Biology, vol. 14, No. 5, pp. 413-419 (May 2007).

Damgaard et al., "No genetic linkage or molecular evidence for involvement of the PCSK9, ARH or CYP7A1 genes in the Familial Hypercholesterolemia phenotype in a sample of Danish families without pathogenic mutations in the LDL receptor and apoB genes," Atherosclerosis 177(2): 415-422, 2004.

Davignon et al., "Erratum to NARC-1: A potential new target for drug therapy of hypercholesterolemia," Atherosclerosis, 176, pp. 429, 2004.

Davignon et al., "Narc-1: A Potential New Target for Drug Therapy of Hypercholesterolemia," XIIIth International Symposium on Atherosclerosis, Sep. 28-Oct. 2, 2003, Kyoto, Japan, 182-183.

Dedoussis et al., "LDL-receptor mutations in Europe," *Human Mutation*, 24(6): 443-459, 2004.

De Pascalis et al., "Grafting of 'Abbreviated' Complementarity Determining Regions Containing Specificity Determining Residues Essential for Ligand Contact to Engineer a Less Immunogenic Humanized Monoclonal Antibody," J. Immunol, 2002, vol. 169, pp. 3076-3084.

Ding et al., "Molecular population genetics of PCSK9: a signature of recent positive selection," Pharmacogenet Genomics. 18(3): 169-179, (2008).

Dubuc et al., "Statins upregulate PCSK9, the gene encoding the proprotein convertase neural apoptosis-regulated convertase-1 implicated in familial hypercholesterolemia," Arterioscler. Thromb. Vasc. Biol. 24: 1454-1459 (2004).

Duff et al., "Antibody-mediated disruption of the interaction between PCSK9 and the low-density lipoprotein receptor," Biochemical Journal, published online Feb. 5, 2009 as Manuscript BJ20082407.

EB 06682 Goat Anti-PCSK9 Antibody, Everest Biotech Online Catalogue, © 2007, auto-generated Sep. 7, 2007.

Ellis et al., "Engineered Anti-CD38 Monoclonal Antibodies for Immunotherapy of Multiple Myeloma," The Journal of Immunology 155: 925-937, 1995.

English Translation of Office Action dated Jul. 1, 2013 in Ukrainian Patent Application No. 201003346.

Evans et al., "The E670G SNP in the PCSK9 gene is associated with polygenic hypercholesterolemia in men but not in women," BMC Med Genet., 7: 66, (2006).

European Patent Office Communication dated Jul. 24, 2014 in European Pat. App. No. 08798550.3.

European Search Report and Opinion dated Jan. 8, 2014 in European Application No. 13151352.5.

Ex Parte Quayle action received in U.S. Appl. No. 13/095,234, dated Jul. 3, 2012 (Regeneron).

Extended European Search Report dated Oct. 14, 2013 in European Application No. 13151343.4.

Extended European Search Report dated Feb. 5, 2014 in European Application No. 13151381.4.

Fan et al., "Self-Association of Human PCSK9 Correlates with its LDLR-Degrading Activity," Biochemistry, 2008, 47: 1631-1639.

File History of European Appl. No. 07861680.2, filed Nov. 2, 2007. (WO 2008/057457 and EP 2083859).

File History of European Appl. No. 07861681.0, filed Nov. 2, 2007. (WO 2008/057458 and EP 2083860).

File History of European Appl. No. 07870839.3, filed Nov. 2, 2007. (WO 2008/063382 and EP 2083864).

File History of European Appl. No. 07874101.4, filed Nov. 2, 2007. (WO 2008/133647 and EP 2106261).

File History of European Appl. No. 08736129.1, filed Apr. 11, 2008. (WO 2008/125623 and EP 2137218).

File History of European Appl. No. 08841231.7, filed Oct. 27, 2008. (WO 2009/055783 and EP 2205639).

File History of European Appl. No. 09707156.7, filed Feb. 6, 2009. (WO 2009/100318 and EP 2245070).

File History of European Appl. No. 09808999.8, filed Sep. 11, 2009. (WO 2010/029513).

File History of PCT Appl. No. PCT/EP2008/054417, filed Apr. 11, 2008, 130 pages (Novartis).

File History of PCT Appl. No. PCT/IB2009/053990, filed Sep. 11, 2009, 362 pages.

File History of PCT Appl. No. PCT/US2007/023169, filed Nov. 2, 2007, 116 pages.

File History of PCT Appl. No. PCT/US2007/023212, filed Nov. 2, 2007, 114 pages.

File History of PCT Appl. No. PCT/US2007/023213, filed Nov. 2, 2007, 113 pages.

File History of PCT Appl. No. PCT/US2007/023214, filed Nov. 2, 2007, 114 pages.

File History of PCT Appl. No. PCT/US2007/023223, filed Nov. 2, 2007, 115 pages.

File History of PCT Appl. No. PCT/US2008/081311, filed Oct. 27, 2008, 154 pages.

File History of PCT Appl. No. PCT/US2009/033341, filed Feb. 6, 2009, 304 pages.

File History of PCT Appl. No. PCT/US2009/033369, filed Feb. 6, 2009, 310 pages.

File History of PCT Appl. No. PCT/US2009/068013, filed Dec. 15, 2009, 388 pages.

File History of U.S. Appl. No. 10/877,773, filed Jun. 25, 2004.

File History of U.S. Appl. No. 10/877,774, filed Jun. 25, 2004.

File History of U.S. Appl. No. 12/197,093, filed Aug. 22, 2008.

File History of U.S. Appl. No. 12/268,363, filed Nov. 10, 2008.

File History of U.S. Appl. No. 12/312,383, filed May 7, 2009.

File History of U.S. Appl. No. 12/312,397, filed May 7, 2009.

File History of U.S. Appl. No. 12/312,398, filed May 7, 2009.

File History of U.S. Appl. No. 12/312,399, filed May 7, 2009.

File History of U.S. Appl. No. 12/312,401, filed May 7, 2009.

File History of U.S. Appl. No. 12/322,861, filed Feb. 6, 2009.

File History of U.S. Appl. No. 12/322,867, filed Feb. 6, 2009.

File History of U.S. Appl. No. 12/396,313, filed Mar. 2, 2009.

File History of U.S. Appl. No. 12/474,176, filed May 28, 2009.

File History of U.S. Appl. No. 12/558,312, filed Sep. 11, 2009.

File History of U.S. Appl. No. 12/595,538, filed Oct. 12, 2009.

File History of U.S. Appl. No. 12/637,942, filed Dec. 15, 2009.

File History of U.S. Appl. No. 12/649,179, filed Dec. 29, 2009.

File History of U.S. Appl. No. 12/903,084, filed Oct. 12, 2010.

File History of U.S. Appl. No. 13/095,234, filed Apr. 27, 2011 (Regeneron).

File History of U.S. Appl. No. 13/225,265, filed Sep. 2, 2011 (Rinat/Pfizer).

File History of U.S. Appl. No. 13/242,809, filed Sep. 23, 2011 (Merck).

File History of U.S. Appl. No. 13/422,887, filed Mar. 16, 2012.

File History of U.S. Appl. No. 13/174,423, filed Jun. 30, 2011.

File History of U.S. Appl. No. 13/251,909, filed Oct. 3, 2011.

File History of U.S. Appl. No. 13/251,955, filed Oct. 3, 2011.

File History of U.S. Appl. No. 13/252,016, filed Oct. 3, 2011.

File History of U.S. Appl. No. 13/463,751, filed May 3, 2012.

File History of U.S. Appl. No. 13/422,904, filed Mar. 16, 2012.

(56)　　　　　References Cited

OTHER PUBLICATIONS

File History of U.S. Appl. No. 13/494,912, filed Jun. 12, 2012.
File History of U.S. Appl. No. 13/619,555, filed Sep. 14, 2012.
File History of U.S. Appl. No. 13/655,984, filed Oct. 19, 2012.
File History of U.S. Appl. No. 13/656,392, filed Oct. 19, 2012.
File History of U.S. Appl. No. 13/682,698, filed Nov. 20, 2012.
File History of U.S. Appl. No. 13/860,016, filed Apr. 10, 2012.
File History of U.S. Appl. No. 14/261,087, filed Apr. 24, 2014.
File History of U.S. Appl. No. 14/260,975, filed Apr. 24, 2014.
File History of U.S. Appl. No. 14/261,063, filed Apr. 24, 2014.
File History of U.S. Appl. No. 14/261,065, filed Apr. 24, 2014.
File History of U.S. Appl. No. 14/260,985, filed Apr. 24, 2014.
File History of U.S. Appl. No. 14/459,777, filed Aug. 14, 2014.
File History of U.S. Appl. No. 14/459,743, filed Aug. 14, 2014.
File History of U.S. Appl. No. 14/459,768, filed Aug. 14, 2014.
File History of U.S. Appl. No. 14/459,787, filed Aug. 14, 2014.
File History of U.S. Appl. No. 14/459,844, filed Aug. 14, 2014.
File History of U.S. Appl. No. 14/487,932, filed Sep. 16, 2014.
File History of U.S. Appl. No. 14/316,587, filed Jun. 26, 2014.
File History of U.S. Appl. No. 13/469,032, filed May 10, 2012.
File History of U.S. Appl. No. 13/931,716, filed Jun. 28, 2013.
Fisher et al., "Effects of pH and low density lipoprotein (LDL) on PCSK9-dependent LDL receptor regulation," J Biol. Chem., 282(28): 20502-20512, (2007).
Folsom et al., "Variation in PCSK9, low LDL cholesterol, and risk of peripheral arterial disease," Atherosclerosis, 202(1): 211-215, (2009).
Fouchier et al., "PCSK9 mutations found in patients diagnosed with autosomal dominant hypercholesterolemia in the Netherlands," Circulation, 110 (17 Suppl. S) Oct. 26, 2004.
Fouchier et al., "Update of the molecular basis of familial hypercholesterolemia in The Netherlands," Human Mutation, 26(6), pp. 550-556, Dec. 2005.
Frank-Kamenetsky et al., "Therapeutic RNAi targeting PCSK9 acutely lowers plasma cholesterol in rodents and LDL cholesterol in nonhuman primates," Proc. Natl. Acad. Sci. USA, 105(33): 11915-11920, 2008.
Fu et al., "Folding pathway mediated by an intramolecular chaperone: The inhibitory and chaperone functions of the subtilisin propeptide are not obligatorily linked," J. Biol. Chem. 275: 16871-16878, 2000.
GenomeNet Database: PIR, Entry T1824D, Barrell et al., Nov. 1998.
GenomeNet Database: UniProt, Entry: A0E922, Parte, Aury et al., 2006.
Goldstein et al., "Familial hypercholesterolemia" in The Metabolic & Molecular Bases of Inherited Disease (eds. Scriver, C.S. et al.) 2863-2913 (McGraw-Hill, New York, 2001).
Goldstein et al., "The cholesterol quartet," Science 292, 1310-1312 (2001).
Graadt Van Roggen et al., "FH Afrikaner-3 LDL receptor mutation results in defective LDL receptors and causes a mild form of familial hypercholesterolemia," Arteriosclerosis, Thrombosis, and Vascular Biology, 15(6), pp. 765-772, Jun. 1995.
Graadt Van Roggen et al., "Low density lipoprotein receptor founder mutations in Afrikaner familial hypercholesterolaemic patients: A comparison of two geographical areas," Human Genetics, 88(2), pp. 204-208, 1991.
Graham et al., "Antisense inhibition of proprotein convertase subtilisin/kexin type 9 reduces serum LDL in hyperlipidemic mice," J Lipid Research, 48: 763-767, 2007.
Graham et al., "Genetic screening protocol for familial hypercholesterolemia which includes splicing defects gives an improved mutation detection rate," Atherosclerosis, 182(2), pp. 331-340, Oct. 2005.
Grefhorst et al., "Plasma PCSK9 preferentially reduces liver LDL receptors in mice," J Lipid Res., 49(6):1303-1311, (2008).
Grozdanov et al., "Expression and localization of PCSK9 in rat hepatic cells" Biochemistry and Cell Biology, Feb. 2006, 84(1): 80-92.

Grozdanov et al., "Expression of Pcsk9 in rat hepatic cells," FASEB Journal 19 (4 Suppl. S, Part 1, Mar. 4, 2005.
Hallman et al., "Relation of PCSK9 mutations to serum low-density lipoprotein cholesterol in childhood and adulthood (from the Bogalusa Heart Study)," Am J Cardiol., 100(1): 69-72, (2007).
Hampton et al., "The self-inhibited structure of full-length PCSK9 at 1.9 Å reveals structural homology with resistin within the C-terminal domain," Proc. Nat. Acad. Sci. USA, Sep. 2007, 104(37): 14604-14609.
Henrich et al., "The crystal structure of the proprotein processing proteinase furin explains its stringent specificity," Nat. Struct. Biol. 10: 520-526, 2003.
Henrich et al., "Proprotein convertase models based on the crystal structures of furin and kexin: Explanation of their specificity," J. Mol. Biol. 345: 211-227, 2005.
Holla et al., "Degradation of the LDL receptors by PCSK9 is not mediated by a secreted protein acted upon by PCSK9 extracelluarly," BMC Cell Biol., 8: 9, (2007).
Holla et al., "Low-density lipoprotein receptor activity in Epstein-Barr virus-transformed lymphocytes from heterozygotes for the D374Y mutation in the PCSK9 gene," Scand J Clin Lab., 66(4): 317-328, (2006).
Hooper et al., "The C679X mutation in PCSK9 is present and lowers blood cholesterol in a Southern African population," Atherosclerosis, 193(2): 445-448, (2007).
Horton et al., "Molecular biology of PCSK9: its role in LDL metabolism," Trends in Biochemical Sciences, 3(2): 71-77, 2006.
Houghten et al., "Relative Importance of Position and Individual Amino Acid Residues in Peptide Antigen-Antibody Interactions: Implications in the Mechanism of Antigenic Drift and Antigenic Shift," New Approaches to Immunization, Vaccines 86, Cold Spring Harbor Laboratory, p. 21-25, 1986.
Human Proprotein Convertase 9/PCSK9 Antibody, Antigen Affinity-purified Polyclonal Sheep IgG, Catalog No. AF3888. R & D Systems: Tools for Cell Biology Research™ Rev: Oct. 21, 2010 p. 1 of 1.
Human/Mouse Proprotein Convertase 9/PCSK9 Antibody, Monoclonal Rat IgG, Clone # 407119, Catalog No. MAB3888. R & D Systems: Tools for Cell Biology Research™ Rev. Oct. 12, 2010 p. 1 of 1. Available for sale since Jun. 2007.
Human/Mouse Proprotein Convertase 9/PCSK9 Antibody, Monoclonal Rat IgG, Clone # 407119, Catalog No. MAB38881. R & D Systems: Tools for Cell Biology Research™ Rev. Oct. 12, 2010 p. 1 of 1. Available for sale since Apr. 2008.
Human/Mouse Proprotein Convertase 9/PCSK9 Antibody, Monoclonal Rat IgG, Clone # 407119, Catalog No. MAB38882. R & D Systems: Tools for Cell Biology Research™ Rev. Oct. 12, 2010 p. 1 of 1. Available for sale since Feb. 2009.
Ikemura et al., "Requirement of pro-sequence for the production of active subtilisin E in Escherichia coli," J. Biol. Chem. 262: 7859-7864, 1987.
International Preliminary Examination Report dated Mar. 4, 2010, received in Int'l Appl. No. PCT/US2008/074097 filed Aug. 22, 2008, 10 pages.
International Search Report and Written Opinion dated Dec. 19, 2008, received in Int'l Appl. No. PCT/US2008/073927.
International Search Report and Written Opinion dated Dec. 19, 2008, received in Int'l Appl. No. PCT/US2008/074097.
International Search Report dated Dec. 9, 2008, from Int'l Appl. No. PCT/EP2008/054417 (WO 2008/125623).
International Search Report dated Jan. 9, 2009, from Int'l Appl. No. PCT/US2007/023169 (WO 2008/133647).
International Search Report dated Jul. 31, 2009, from Int'l Appl. No. PCT/US2008/081311 (WO 2009/055783).
International Search Report dated Jun. 1, 2010, from Int'l Appl. No. PCT/IB2009/053990 (WO 2010/029513).
International Search Report dated Jun. 25, 2009, from Int'l Appl. No. PCT/US2009/033369 (WO 2009/100318).
International Search Report dated Oct. 1, 2008, from Int'l Appl. No. PCT/US2007/023213 (WO 2008/057458).
International Search Report dated Oct. 1, 2008, from Int'l Appl. No. PCT/US2007/023223 (WO 2008/063382).

(56) References Cited

OTHER PUBLICATIONS

International Search Report dated Oct. 15, 2008, from Int'l Appl. No. PCT/US2007/023212 (WO 2008/057457).

International Search Report published Feb. 5, 2009, in Int'l Appl. No. PCT/EP2008/054417.

International Search Report received in PCT Appl. No. PCT/US2008/074097, dated Dec. 5, 2008.

Issue Fee payment dated Aug. 12, 2011, in U.S. Appl. No. 12/197,093.

Jeon et al., "Structure and physiologic function of the low-density lipoprotein receptor," Annu. Rev. Biochem. 74: 535-562 (2005).

Jirholt et al., "How does mutant proprotein convertase neural apoptosis-regulated convertase 1 induce autosomal dominant hypercholersterolemia," *Arteriosclerosis, Thrombosis and Vascular Biology*, 24(8): 1334-1336, 2004.

Kala et al., "Phage Displayed Antibodies to Heat Stable Alkaline Phosphatase: Framework Region as a Determinant of Specificity," J. Biochem., vol. 132, 2002, pp. 535-541.

Kastelein et al., "What promise does PCSK9 hold?" J Am Coll Cardiol., 45(10): 1620-1621, (2005).

Kathiresan et al., "A PCSK9 missense variant associated with a reduced risk of early-onset myocardial infarction," N Engl J Med., 358(21): 2299-2300, (2008).

Kim et al., "Long-distance PCR-based screening for large rearrangements of the LDL receptor gene in Korean patients with familial hypercholesterolemia," Clinical Chemistry, 45(9), p. 1424-1430, 1999.

Knappik et al., "Fully Synthetic Human Combinatorial Antibody Libraries (HuCAL) Based on Modular Consensus Frameworks and CDRs Randomized with Trinucleotides." J Mol. Biol. 296 (2000): 57-86.

Kotowski et al., "A spectrum of PCSK9 alleles contributes to plasma levels of low-density lipoprotein cholesterol," Am. J. Hum. Genet. 78: 410-422, 2006.

Kotowski et al., "Multiple sequence variations in PCSK9 contribute to decreased plasma levels of LDL cholesterol," Circulation, 112 (17, Suppl. S), Oct. 25, 2005.

Kotze et al., "Familial hypercholesterolemia: Potential diagnostic value of mutation screening in a pediatric population of South Africa," Clinical Genetics, 54(1), pp. 74-78, Jul. 1998.

Kourimate et al.,"Dual mechanisms for the fibrate-mediated repression of proprotein convertase subtilisin/kexin type 9," J Biol. Chem., 283(15): 9666-9673, (2008).

Kwon et al., "Molecular basis for LDL receptor recognition by PSK9," Proc. Natl. Acad. Sci. USA, Feb. 12, 2008, 105(6): 1820-1825.

Lalanne et al., "Wild-type PCSK9 inhibits LDL clearance but does not affect apoB-containing lipoprotein production in mouse and cultured cells," J Lipid Res., 46(6): 1312-1319, (2005).

Lambert et al., "PCSK9: a promising therapeutic target for dyslipidemias?" Trends Endocrinol. Metab. 17, 79-81 (2006).

Lambert et al., "Fasting induces hyperlipidemia in mice overexpressing proprotein convertase subtilisin kexin type 9: lack of modulation of very-low density lipoprotein hepatic output by the low-density lipoprotein receptor," Endocrinology, 147(10): 4985-4995, (2006).

Lambert et al., "Molecular basis of PCSK9 function," Atherosclerosis, 203(1): 1-7, (2009).

Lambert et al., "Plasma PCSK9 concentrations correlate with LDL and total cholesterol in diabetic patients and are decreased by fenofibrate treatment," Clin Chem., 54(6): 1038-1045, (2008).

Lambert et al., "Unravelling the functional significance of PCSK9," Curr Opin Lipidol., 18(3): 304-309, (2007).

Lamminmaki et al., "Crystal Structure of a Recombinant Anti-estradiol Fab Fragment in Complex with 17β-Estradiol," The Journal of Biological Chemistry, 276(39): 36687-36694, Sep. 28, 2001.

Langhi et al., "Activation of the farnesoid X receptor represses PCSK9 expression in human hepatocytes," FEBS Lett., 582(6): 949-955, (2008).

Lederman et al., "A Single Amino Acid Substitution in a Common African Allele of the CD4 Molecule Ablates Binding of the Monoclonal Antibody, OKT4," Molecular Immunology 28: 1171-1181, 1991.

Leren et al., "Mutations in the PCSK9 gene in Norwegian subjects with autosomal dominant hypercholesterolemia," Clin. Genet., 65(5): 419-422, (2004).

Li et al., "β-Endorphin omission analogs: Dissociation of immunoreactivity from other biological activities," Proc. Natl. Acad. Sci. USA, 77(6): 3211-3214, Jun. 1980.

Li et al.,"Secreted PCSK9 promotes LDL receptor degradation independently of proteolytic activity," Biochem J. 406, 203-207 (2007).

Li Hai et al. "Recent patents on PCSK9: a new target for treating hypercholesterolemia," Recent Patents on DNA & Gene Sequences, Nov. 1, 2009, vol. 3, No. 3, pp. 201-212.

Lopez et al., "Inhibition of PCSK9 as a novel strategy for the treatment of hypercholesterolemia," Drug News Perspect., 21(6): 323-330, (2008).

Lopez et al., "PCSK9: an enigmatic process," Biochem Biophys Acta., 1781(4): 184-191, (2008).

Ma et al., "Functional Characterization of Novel Genes Regulated in a Cell Culture Model of Neuronal Apoptosis," Neuroscience 2002 Abstract, Nov. 5, 2002, p. 1.

MacCallum et al., "Antibody-antigen Interactions: Contact Analysis and Binding Site Topography," Journal of Molecular Biology, 1996, vol. 262, pp. 732-745.

Marais et al., "The diagnosis and management of familial hypercholesterolaemia," *European Review for Medical and Pharmacological Sciences*, 9(3), pp. 141-149, May 2005.

Maxwell et al., "Adenoviral-mediated expression of PCSK9 in mice results in a low-density lipoprotein receptor knockout phenotype," Proc Natl Acad Sci USA, May 2004, 101(18): 7100-7105.

Maxwell et al., "Novel putative SREBP and LXR target genes identified by microarray analysis in liver of cholesterol-fed mice," Journal of Lipid Research, vol. 14, 2109-2119, 2003.

Maxwell et al., "Overexpression of PCSK9 accelerates the degradation of the LDLR in a post-endoplasmic reticulum compartment," Proc. Natl. Acad. Sci. USA (2005) 102, 2069-2074.

Maxwell et al., "Overexpression of Pcsk9 leads to the formation of an LDLR-Pcsk9 complex and acceleration of LDLR degradation," Circulation, 110 (17 Suppl. S) Oct. 26, 2004.

Maxwell et al., "Proprotein convertase subtilisin kexin 9: The third locus implicated in autosomal dominant hypercholesterolemia," *Current Opinion in Lipidology*, 16(2), pp. 167-172, Apr. 2005.

Mayne et al., "Plasma PCSK9 levels are significantly modified by statins and fibrates in humans," Lipids Health Dis., 7: 22, (2008).

Mayne et al., "Plasma PCSK9 Levels Correlate with Cholesterol in Men but not in Women," Biochemical and Biophysical Research Communications (BBRC) 361: 451-456, 2007.

Mbikay et al., "Of PCSK9, cholesterol homeostasis and parasitic infections: possible survival benefits of loss-of-function PCSK9 genetic polymorphisms," Med Hypotheses, 69(5): 1010-1017, (2007).

McNutt et al., "Catalytic Activity Is Not Required for Secreted PCSK9 to Reduce Low Density Lipoprotein Receptors in HepG2 Cells," Journal of Biological Chemistry, 282(29): 20799-20803, Jul. 20, 2007.

McNutt et al., "Antagonism of secreted PCSK9 increases low density lipoprotein receptor expression in HepG2 cells," Journal of Biological Chemistry, 284(16): 10561-10570, Apr. 17, 2009.

Mendez et al., "Functional transplant of megabase human immunoglobulin loci recapitulates human antibody response in mice," Nature Genetics, 15: 146-156, Feb. 1997.

Naoumova et al., "Severe hypercholesterolemia in four British families with the D374Y mutation in the PCSK9 gene: Long-term follow-up and treatment response," *Arteriosclerosis, Thrombosis, and Vascular Biology*, 25(12): 2654-2660, Dec. 2005.

Nassoury et al., "The cellular trafficking of the secretory proprotein convertase PCSK9 and its dependence on the LDLR," Traffic, 8(6): 718-722, (2007).

Naureckiene et al., "Functional Characterization of Narc1, a Novel Proteinase Related to Proteinase K," Arch Biochem Biophys, Dec. 1, 2003; 420(1): 55-67.

(56)          References Cited

OTHER PUBLICATIONS

New England Bio Labs, "Furin" Jan. 2006.
Ngo et al., "The Protein Folding Problem and Tertiary Structure Prediction," 1994, pp. 492-495.
Ni et al., "A PCSK9 C-terminal Domain Binding Fab Inhibits PCSK9 Internalization and Restores LDL-uptake," *Circulation*, vol. 120 No. 18 Suppl 2, Nov. 2009, p. S477.
Ni Yan G et al. "A PCSK9-binding antibody that structurally mimics the EGF(A) domain of LDL-receptor reduces LDL cholesterol in vivo," J Lipid Research, Jan. 2011, vol. 52, No. 1, pp. 78-86.
Ni Yan G et al. "A proprotein convertase subtilisin-like/kexin type 9 (PCSK9) C-terminal domain antibody antigen-binding fragment inhibits PCSK9 internalization and restores low density lipoprotein uptake," J Biol Chem, Apr. 23, 2010, vol. 285, No. 17, Apr. 23, 2010, pp. 12882-12891.
Notice of Allowance dated Jun. 26, 2014 in U.S. Appl. No. 14/261,087.
Notice of Allowance dated Jun. 30, 2014 in U.S. Appl. No. 14/260,975.
Notice of Allowance dated Jun. 20, 2014 in U.S. Appl. No. 14/261,063.
Notice of Allowance dated Jun. 24, 2014 in U.S. Appl. No. 14/261,065.
Notice of Allowance dated Jun. 20, 2014 in U.S. Appl. No. 14/260,985.
Notice of Allowance dated Feb. 11, 2014, received in U.S. Appl. No. 13/860,016.
Notice of Allowance dated Jun. 14, 2013, received in U.S. Appl. No. 13/252,016.
Notice of Allowance dated Jun. 17, 2013, received in U.S. Appl. No. 12/474,176.
Notice of Allowance dated Jun. 19, 2013, received in U.S. Appl. No. 12/474,176.
Notice of Allowance dated Jun. 27, 2011, received in U.S. Appl. No. 12/197,093.
Notice of Allowance dated Oct. 11, 2011, received in U.S. Appl. No. 12/322,861.
Notice of Allowance dated Oct. 13, 2011, received in U.S. Appl. No. 12/322,867.
Notice of Allowance dated Dec. 22, 2011, received in U.S. Appl. No. 13/251,955.
Notice of Allowance dated Mar. 5, 2012, received in U.S. Appl. No. 13/252,016.
Notice of Allowance dated Mar. 6, 2013, received in U.S. Appl. No. 13/252,016.
Notice of Allowance dated Mar. 25, 2014, received in U.S. Appl. No. 13/252,016.
Notice of Allowance dated Mar. 31, 2014 received in U.S. Appl. No. 13/174,423.
Notice of Allowance dated Jun. 21, 2012, received in U.S. Appl. No. 13/252,016.
Notice of Allowance dated Nov. 5, 2012, received in U.S. Appl. No. 13/252,016.
Notice of Allowance dated Oct. 9, 2013, received in U.S. Appl. No. 13/252,016.
Notice of Allowance dated Sep. 5, 2013 received in U.S. Appl. No. 13/174,423.
Notice of Allowance and Examiner Interview Summary dated Sep. 21, 2012, received in U.S. Appl. No. 13/095,234 (Regeneron).
Office Action dated Jul. 17, 2014 in U.S. Appl. No. 12/903,084.
Notice of Opposition received in Colombian Patent Application No. 10 033833, dated Jun. 24, 2011 (with English translation).
Notice of Publication received in U.S. Appl. No. 13/251,955, filed Oct. 3, 2011.
Office Action and Search Report dated Jul. 4, 2013 for R.O.C. Taiwan Patent Application 097132236 (with English translation).
Office Action dated Jun. 27, 2013 for Chinese Patent Application 200880113475.4 (with English translation).
Office Action dated Apr. 9, 2013 received in Colombian Patent Appl. No. 10 033833 (with English translation).

Office Action dated May 7, 2014 in Japanese Application No. 2013-195240 with English Translation.
Office Action dated Apr. 17, 2013 received in Philippines Patent Appl. No. 1/2010/500421.
Office Action dated May 21, 2013 received in Japanese Patent Appl. No. 2010-52208 (with English translation).
Office Action dated Aug. 8, 2013 received in U.S. Appl. No. 13/422,904.
Office Action dated Aug. 12, 2013, received in U.S. Appl. No. 13/494,912.
Office Action dated Aug. 16, 2013, received in U.S. Appl. No. 13/860,016.
Office Action dated Aug. 24, 2010, received in U.S. Appl. No. 12/322,867.
Office Action dated Aug. 25, 2010, received in U.S. Appl. No. 12/322,861.
Office Action dated Dec. 2, 2013 in Vietnamese Application No. 1-2010-00689 (with English Translation).
Office Action dated Dec. 16, 2013 in New Zealand Patent Application No. 618641.
Office Action dated Feb. 1, 2013, received in Australian Patent Application No. 2008288791.
Office Action dated Feb. 11, 2011, received in U.S. Appl. No. 12/322,867 (Merck).
Office Action dated Feb. 4, 2011, received in U.S. Appl. No. 12/558,312 (Pfizer).
Office Action dated Feb. 5, 2014 received in European Patent Appl. No. 08798550.3.
Office Action dated Mar. 27, 2012, received in U.S. Appl. No. 13/242,809 (Merck).
Office Action dated Nov. 6, 2013 in Israeli Patent Application No. 204013 (with English translation).
Office Action dated Jan. 18, 2011, received in U.S. Appl. No. 12/637,942 (Regeneron).
Office Action dated Jan. 20, 2012, received in U.S. Appl. No. 12/312,401 (Merck).
Office Action dated Jan. 26, 2011, received in U.S. Appl. No. 12/322,861 (Merck).
Office Action dated Jan. 5, 2011, received in European Application No. 08798550.3.
Office Action dated Jan. 15, 2014 in Malaysian Application No. PI2010000750.
Office Action dated Jan. 28, 2014 in U.S. Appl. No. 13/494,912.
Office Action dated Jan. 30, 2014 in U.S. Appl. No. 13/422,904.
Office Action dated Jul. 11, 2007, received in U.S. Appl. No. 11/439,325.
Office Action dated Jul. 13, 2012, received in New Zealand Patent Application No. 584101.
Office Action dated Jun. 12, 2012, received in New Zealand Patent Application No. 584101.
Office Action dated Jul. 31, 2012, received in Chinese Patent Application No. 200880113475.4 (with English Translation).
Office Action dated Oct. 15, 2013, received in Korean Patent Application No. 10-2010-7006252 (with English translation).
Office Action dated May 28, 2014 in Korean Pat. App. No. 10-2010-7006252 (with English translation).
Office Action dated Oct. 21, 2013 in Colombian Application No. 13 202843 (with English Translation).
Office Action dated Oct. 29, 2012 in Peruvian Patent Application No. 001426-2008 (with English translation).
Office Action dated Sep. 24, 2012, received in U.S. Appl. No. 13/225,265 (Pfizer).
Office Action dated Sep. 26, 2011, received in U.S. Appl. No. 12/474,176.
Office Action received in Eurasian Patent Application No. 201000356, filed Aug. 22, 2008 (with English translation).
Office Action received in European Patent Application No. 08798550.3, dated Jun. 15, 2012.
Office Action dated Feb. 13, 2012 in Israeli Patent Application No. 204013 (with English Translation).
English Translation of Office Action received in Mexican Patent Application No. MX/a/2010/001921, dated Oct. 20, 2011.

(56) References Cited

OTHER PUBLICATIONS

Office Action received in New Zealand Patent Application No. 584101, dated Nov. 30, 2010.
Office Action received in U.S. Appl. No. 12/312,401, dated Jul. 17, 2012 (Merck).
Office Action received in U.S. Appl. No. 12/474,176, dated May 22, 2012.
Office Action received in U.S. Appl. No. 12/949,846, dated Jul. 11, 2012 (Regeneron).
Office Action received in U.S. Appl. No. 12/474,176, dated Jan. 10, 2013.
Otwinowski et al., "Multiparametric scaling of diffraction intensities," Acta Crystallogr A 59: 228-234 (2003).
Ouguerram et al., "Apolipoprotein B100 metabolism in autosomal-dominant hypercholesterolemia related to mutations in PCSK9," Arterioscler thromb Vasc Biol. 24: 1448-1453, 2004.
Padlan et al., "Structure of an Antibody-Antigen Complex: Crystal Structure of the HyHEL 10 Fab Lysozyme Complex," Proc. Natl. Acad. Sci., vol. 86, Aug. 1989, pp. 5938-5942.
Pandit et al., "Functional analysis of sites within PCSK9 responsible for hypercholesterolemia," J Lipid Res., 49(6): 1333-1343, (2008).
Parhofer et al., "What we have learned about VLDL and LDL metabolism from human kinetics studies," *Journal of Lipid Research*, 47(8), pp. 1620-1630, 2006.
Parhofer, Klaus. "Lipoprotein(a): Medical treatment options for an elusive molecule." Current Pharmaceutical Design, 2011, vol. 17, 871-876.
Park et al., "Post-transcriptional regulation of low density lipoprotein receptor protein by proprotein convertase subtilisin/kexin type 9a in mouse liver," J. Biol. Chem. 279, pp. 50630-50638, 2004.
Paul, Fundamental Immunology, 3rd Edition, 1993, pp. 292-295, under the heading "Fv Structure and Diversity in Three Dimensions".
Peterson et al., "PCSK9 function and physiology," J Lipid Res., 49(7): 1595-1599, (2008).
Petition for Extension of Time to Respond dated Jan. 15, 2013 in U.S. Appl. No. 12/312,401 (Merck).
Piatesi et al., "Immunological Optimization of a Generic Hydrophobic Pocket for High Affinity Hapten Binding and Diels-Alder Activity," Chem Bio Chem, vol. 5(4), Apr. 2004, pp. 460-466.
Piper et al., "The Crystal Structure of PCSK9: A Regulator of Plasma LDL-Cholesterol," Structure, 15, 1-8, pp. 545-552 (May 2007).
Pisciotta et al., "Additive effect of mutations in LDLR and PCSK9 genes on the phenotype of familial hypercholesterolemia," *Atherosclerosis* 186(2), pp. 433-440, Jun. 2006.
Poirier et al., "Implication of the proprotein convertase NARC-1/PCSK9 in the development of the nervous system," J Neurochem, 98(3): 838-850, (2006).
Poirier et al., "The proprotein convertase PCSK9 induces the degradation of low density lipoprotein receptor (LDLR) and its closest family members VLDLR and ApoER2," J Biol Chem., 283(4): 2363-2372, (2008).
Polisecki et al., "Genetic variation a the PCSK9 locus moderately lowers low-density lipoprotein cholesterol levels, but does not significantly lower vascular disease risk in an elderly population," Atherosclerosis, 200(1): 95-101, (2008).
Preliminary Amendment for U.S. Appl. No. 13/422,887, filed Mar. 16, 2012.
Preliminary Amendment for U.S. Appl. No. 13/422,904, filed Mar. 16, 2012.
Preliminary Amendment for U.S. Appl. No. 13/463,751, filed May 3, 2012.
Preliminary Amendment for U.S. Appl. No. 13/494,912, filed Jun. 15, 2012.
Preliminary Amendment for U.S. Appl. No. 13/619,555, filed Sep. 14, 2012.
Preliminary Amendment dated Oct. 19, 2012 for U.S. Appl. No. 13/655,984, filed Oct. 19, 2012.
Preliminary Amendment dated Oct. 19, 2012 for U.S. Appl. No. 13/656,392, filed Oct. 19, 2012.
Preliminary Amendment dated Apr. 15, 2013 for U.S. Appl. No. 13/860,016.
Preliminary Amendment dated May 7, 2014 in U.S. Appl. No. 14/261,087.
Preliminary Amendment dated May 7, 2014 in U.S. Appl. No. 14/260,975.
Preliminary Amendment dated May 7, 2014 in U.S. Appl. No. 14/261,063.
Preliminary Amendment dated May 7, 2014 in U.S. Appl. No. 14/261,065.
Preliminary Amendment dated May 7, 2014 in U.S. Appl. No. 14/260,985.
Preliminary Amendment dated Sep. 17, 2014 in U.S. Appl. No. 14/459,777.
Preliminary Amendment dated Sep. 17, 2014 in U.S. Appl. No. 14/459,743.
Preliminary Amendment dated Sep. 16, 2014 in U.S. Appl. No. 14/459,768.
Preliminary Amendment dated Sep. 16, 2014 in U.S. Appl. No. 14/459,787.
Preliminary Amendment dated Sep. 16, 2014 in U.S. Appl. No. 14/459,844.
Preliminary Amendment dated Oct. 3, 2014 in U.S. Appl. No. 14/487,932.
Qian et al., "Secreted PCSK9 downregulates low density lipoprotein receptor through receptor-mediated endocytosis," J Lipid Res., 48(7): 1488-1498, (2007).
Rader et al., "Monogenic hypercholesterolemia: New insights in pathogenesis and treatment," *Journal of Clinical Investigation*, 111 (12), pp. 1795-1803, 2003.
Rashid et al., "Decreased plasma cholesterol and hypersensitivity to statins in mice lacking Pcsk9," PNAS, vol. 102, No. 15, 5374-5379 (Apr. 12, 2005).
Ratliff et al., "Transgenic Expression of CYP7A1 in LDL Receptor-Deficient Mice Blocks Diet-Induced Hypercholesterolemia," Journal of Lipid Research, 47, 2006, 1513-1520.
Rawlings et al., "MEROPS: the peptidase database," Nucleic Acids Res. 34, D270-D272, 2006.
RCSB Protein Data Bank: An Information Portal to Biological Macromolecular Structures. Search Results for keyword "pcsk9" search conducted Jan. 10, 2008. Website accessed at http://www. rcsb.org/pdb/home/home.do• Piper et al. "The Crystal Structure of Proprotein convertase subtilisin kexin type 9 (PCSK9)" (Released May 8, 2007)• Cunningham et al. "Crystal Structure of PCSK9" (Deposited Mar. 12, 2007, released Apr. 10, 2007)• Hampton et al. "The Crystal Structure of PCSK9 at 1.9 Angstroms Resolution Reveals Structure Homology to Resistin within the C-Terminal Domain" (Released Sep. 18, 2007)• Kwon, H.J. "PCSK9: EGF-A complex" (Deposited Dec. 19, 2007, released Feb. 12, 2008).
Response in 52 pages to EP Office Action received in EP Appl. No. 08736129.1, filed Apr. 11, 2008 (WO 2008/125623 and EP 2137218).
Response to Office Action dated Jan. 5, 2011 received in European Application No. 08798550.3.
Response to Office Action filed Apr. 10, 2013 in U.S. Appl. No. 12/474,176.
Response to Office Action filed Apr. 30, 2012 received in U.S. Appl. No. 12/312,401 (Merck).
Response to Office Action filed Mar. 23, 2012 in U.S. Appl. No. 12/474,176.
Response to Final Office Action filed Oct. 25, 2012 in U.S. Appl. No. 12/312,401 (Merck).
Response to Office Action filed Nov. 20, 2012 in U.S. Appl. No. 12/474,176.
Response to Office Action filed Aug. 23, 2013 in U.S. Appl. No. 12/989,404.
Response to Office Action filed on Dec. 21, 2012 in European Application No. 08798550.3.
Restriction Requirement dated Dec. 14, 2012 received in U.S. Appl. No. 13/494,912.
Restriction Requirement dated Feb. 24, 2014 received in U.S. Appl. No. 12/903,084.

(56)                    References Cited

OTHER PUBLICATIONS

Rudenko et al., "Structure of the LDL Receptor Extracellular Domain at Endosomal pH," Science 298, 2353-2358 (2002).

Rudikoff et al., "Single Amino Acid Substitution Altering Antigen Binding Specificity," Proc. Natl. Acad. Sci. 79: 1979-1983, 1982.

Saint-Jore et al., "Autosomal dominant type IIa hypercholesterolemia: Evaluation of the respective contributions of LDLR and APOB gene defects as well as a third major group of defects," *European Journal of Human Genetics*, 8(8), pp. 621-630, 2000.

Sakai et al., "Molecular identification of the sterol-regulated luminal protease that cleaves SREBPs and controls lipid composition of animal cells," Mol. Cell 2: 505-514, 1998.

"Sanofi and Regeneron Report Positive Preliminary Phase 2 Program Results for Anti-PCSK9 Antibody in Hypercholesterolemia," http://www.prnewswire.com/news-releases/sanofi-and-regeneron-report-positive-preliminary-phase-2-program-results-for-anti-pcsk9-antibody-in-hypercholesterolemia-133590188.html, PR Newswire, Nov. 10, 2011, pp. 1.

Schmidt et al., "A Novel Splicing Variant of Proprotein Convertase Subtilisin/Kexin Type 9," DNA Cell Biol, Apr. 2008, 27(4): 183-189.

Schmidt et al., "A 15-ketosterol is a liver X receptor ligand that suppresses sterol-responsive element binding protein-2 activity," *Journal of Lipid Research*, 47(5), May 2006, 1037-1044.

Schmidt et al., "Secreted proprotein convertase subtilisin/kexin type 9 reduces both hepatic and extrahepatic low-density lipoprotein receptors in vivo," Biochem Biophys Res Commun., 370(4): 634-640, (2008).

Search Report dated May 16, 2012 received in Chinese Patent Application No. 200880113475.4 (with English Translation).

Search Report dated Sep. 9, 2013 received in Korean Patent Application No. 10-2010-7006252 (with English Translation).

Search Report and Written Opinion received in Singaporean Patent Application No. 201001062-7 filed Aug. 22, 2008.

Seidah et al., "Mammalian subtilisin/kexin isozyme SKI-1: a widely expressed proprotein convertase with a unique cleavage specificity and cellular localization," Proc. Natl. Acad. Sci. USA 96: 1321-1326, 1999.

Seidah et al., "The proprotein convertases and their implication in sterol and/or lipid metabolism," Biological Chemistry, 387(7): 871-877, 2006.

Seidah et al., "The proprotein convertases in health and disease," Molecular & Cellular Proteomics, 2(9), Sep. 2003.

Seidah et al., "The secretory proprotein convertase neural apoptosis-regulated convertase 1 (NARC-1): Liver regeneration and neuronal differentiation," PNAS 100: 928-933, 2003.

Seidah et al., "The proprotein convertases are potential targets in the treatment of dyslipidemia," J. Mol. Med., 95: 685-696, Mar. 10, 2007.

Shan et al., "PCSK9 binds to multiple receptors and can be functionally inhibited by an EGF-A peptide," Biochem. Biophys. Res. Commun., pp. 1-5 (2008).

Shen et al., "The molecular genetics of coronary artery disease and myocardial infarction," *Acute Coronary Syndromes*, 6(4), pp. 129-141, 2004.

Shibata et al., "No genetic association between PCSK9 polymorphisms and Alzheimer's disease and plasma cholesterol level in Japanese patients," *Psychiatric Genetics*, 15(4), pp. 239, Dec. 2005.

Shioji et al., "Genetic variants in PCSK9 affect the cholesterol level in Japanese," Journal of Human Genetics, 49(2) pp. 109-114, 2004.

Soutar, Anne K. "Unexpected roles for PCSK9 in lipid metabolism," Current Opinion in Lipidology, Jun. 2011, vol. 22, No. 3, pp. 192-196.

Stahl, "Regeneron: Investor Day Early Clinical Development #1 REGN727: anti-PCSK9," Jul. 15, 2010: pp. 1-21.

Sun et al., Evidence for effect of mutant PCSK9 on apoliprotein B secretion as the cause of unusually severe dominant hypercholesterolemia, Human Molecular Genetics 14: 1161-1169, 2005.

Tall, "Protease variants, LDL, and coronary heart disease," *New England Journal of Medicine*, 354(12), pp. 1310-1312, Mar. 23, 2006.

Tangrea et al., "Solution structure of the pro-hormone convertase 1 pro-domain from Mus musculus," J. Mol. Biol. 320: 801-812, 2002.

Third Party Observations for Application No. EP20080798550 dated Jan. 2013 by Anonymous.

Third Party Observations for Application No. EP20080798550 dated Jan. 2013 by Carpmaels & Ransford.

Third Party Observations for Application No. EP20080798550 submitted Dec. 22, 2012 by third party.

Timms et al., "A mutation in PCSK9 causing autosomal-dominant hypercholesterolemia in a Utah pedigree," Hum Genet., 114(4): 349-353, (2004).

Topol, "Cholesterol, racial variation and targeted medicines," Nature Medicine, 11(2), pp. 122-123, Feb. 2005.

Topol et al., "Genetic susceptibility to myocardial infarction and coronary artery disease," *Human Molecular Genetics*, 15 (Rev. Issue 2), R117-R123, 2006.

Transmittal page from Information Disclosure Statement dated May 28, 2009 in U.S. Appl. No. 12/474,176.

Tuakli-Wosornu et al., "Genetic deficiency of proprotein convertase Subtilisin/Kexin 9: identification of a compound heterozygote with no PCSK9," *Circulation*, 114 (18, Suppl. S). Oct. 31, 2006.

Vajdos et al., "Comprehensive Functional Maps of the Antigen Binding Site of an Anti ErbB2 Antibody Obtained with Shotgun Scanning Mutagenesis," J. Mol. Biol., 2002, vol. 320, pp. 415-428.

Van Regenmortel et al., "Mapping Epitope Structure and Activity: From One-Dimensional Prediction to Four-Dimensional Description of Antigenic Specificity," Methods: A Companion to Methods in Enzymology 9: 465-472, 1996.

Varret et al., "A Third Major Locus for Autosomal Dominant Hypercholesterolema Maps to 1p34.1-p32," *American Journal of Human Genetics*, 64: 1378-1387, 1999.

Varret et al., "ARH and HCHOLA3: Two different genes at 1p both implicated in familial hypercholesterolemia," *American Journal of Human Genetics*, 71 (4 Supplement), Oct. 2002.

Varret et al., "Familial autosomal dominant hypercholesterolemia: Highly skewed contribution of mutations in the LDLR, APOB, FH3 and FH4 genes," *Circulation*, 106 (19 Supplement) Nov. 5, 2002.

Villeger et al., "Familial hypercholesterolemia: 30 years after Brown and Goldstein," *Recent Research Developments in Human Genetics*, 1(pt.1), pp. 35-51, 2002.

Wells, "Additivity of mutational effects in proteins," Biochemistry 29(37): 8509-8517, 1990.

Wu et al., "Humanization of a Murine Monoclonal Antibody by Simultaneous Optimization of Framework and CDR Residues," J. Mol. Biol., vol. 294: 151-162, 1999.

Yende et al., "Genetic polymorphisms that predict outcome and need for treatment in cardiovascular disease," *Current Opinion in Critical Care* 12(5), pp. 420-425, Oct. 2006.

Yue et al., "The c.43_44insCTG variation in PCSK9 is associated with low plasma LDL-cholesterol in a Caucasian population," *Human Mutation*, 27(5), pp. 460-466, May 2006.

Zaid et al., "Proprotein convertase subtilisin/kexin type 9 (PCSK9): hepatocyte-specific low-density lipoprotein receptor degradation and critical role in mouse liver regeneration," Hepatology, 48(2): 646-654, (2008).

Zhang et al., "Binding of PCSK9 to EGF-A Repeat of LDL Receptor Decreases Receptor Recycling and Increases Degradation," Journal of Biological Chemistry, Apr. 23, 2007.

Zhang et al., "Structural requirements for PCSK9-mediated degradation of the low-density lipoprotein receptor," PNAS, Sep. 2, 2008, 105(35): 13045-13050.

Zhang et al., "Binding of Proprotein Convertase Subtilisin/Kexin Type 9 to Epidermal Growth Factor-like Repeat A of Low Density Lipoprotein Receptor Decreases Receptor Recycling and Increases Degradation," Journal of Biological Chemistry, 282(25), pp. 18602-18612, Jun. 22, 2007.

Zhao et al., "Molecular characterization of loss-of-function mutations in PCSK9 and identification of a compound heterozygote," *American Journal of Human Genetics*, 79: 514-523, 2006.

(56)            References Cited

OTHER PUBLICATIONS

Zhao et al., "Functional characterization of sequence variations in PCSK9," *Circulation*, 112 (17, Suppl. S.), Oct. 25, 2005.
Office Action dated Nov. 4, 2014 in U.S. Appl. No. 13/469,032.
Extended European Search Report dated Oct. 17, 2013, received in European Appl. No. 13151375.6.
U.S. Appl. No. 14/562,546 (Claims), filed Dec. 5, 2014, Jackson et al.
File History of U.S. Appl. No. 14/562,546, filed Dec. 5, 2014.
Green, et al. "Antibody engineering via genetic engineering of the mouse: XenoMouse strains are a vehicle for the facile generation of therapeutic human monoclonal antibodies". Journal of Immunological Methods 1999, pp. 11-23, vol. 231.
Notice of Allowance dated Jan. 29, 2015, received in U.S. Appl. No. 13/252,016.
Notice of Allowance dated Nov. 4, 2014 in U.S. Appl. No. 13/251,909.
Notice of Allowance dated Nov. 5, 2014 in U.S. Appl. No. 13/251,909.
Office Action dated Dec. 5, 2014 in Canadian Application No. 2,792,740.
Office Action dated Jan. 14, 2015, received in EP Appl. No. 08798550.3.
Office Action dated Jan. 14, 2015, received in EP Appl. No. 13151343.4.
Office Action dated Jan. 14, 2015, received in EP Appl. No. 13151352.5.
Office Action dated Jan. 14, 2015, received in EP Appl. No. 13151375.6.
Office Action dated Jan. 27, 2015 in U.S. Appl. No. 12/903,084.
Office Action dated Jan. 29, 2015 in U.S. Appl. No. 13/422,904.
Office Action dated Jun. 21, 2013 in European Patent Application No. 08798550.3.
Office Action dated Nov. 2014 in Egyptian Patent Application PCT 302/2010 (with English translation).
Owens et al., "The genetic engineering of monoclonal antibodies". Journal of Immunological Methods 1994, pp. 149-165, vol. 168.
Search Report dated Apr. 28, 2014 in Panama Patent App. No. 89691-01 (with English Translation).
Email from USPTO, transmitted Mar. 7, 2015 in U.S. Appl. No. 14/459,844.
International Search Report and Written Opinion dated Jul. 19, 2013, from Int'l Appl. No. PCT/US2013/039561.
Notice of Allowance dated Feb. 18, 2015 received in U.S. Appl. No. 13/174,423.
Notice of Allowance dated Mar. 13, 2015 received in U.S. Appl. No. 14/459,768.
Notice of Allowance dated Mar. 16, 2015 received in U.S. Appl. No. 14/459,844.
Notice of Allowance dated Mar. 18, 2015 received in U.S. Appl. No. 14/459,787.
Office Action dated Feb. 13, 2015 in U.S. Appl. No. 13/494,912.
Office Action dated Dec. 24, 2014, received in Israeli Patent Application No. 70292 (with English Translation).
Replacing Written Opinion dated Jan. 21, 2015 in Singapore Patent App. No. 2013082854.
Notice of Allowance dated Mar. 24, 2015 in U.S. Appl. No. 13/251,909.
Office Action dated Mar. 30, 2015 in Algerian Application No. 130776 (with English Translation).
Cleland et al. "A Specific Molar Ratio of Stabilizer to Protein is Required for Storage Stability of a Lyophilized Monoclonal Antibody". Journal of Pharmaceutical sciences. vol. 90, No. 3, 2001, pp. 310-321.
Office Action dated Mar. 10, 2015 in Colombian Application No. 13-286712 (with summary English translation).
Advisory Action dated May 7, 2015 in U.S. Appl. No. 12/903,084.
Advisory Action dated May 19, 2015 in U.S. Appl. No. 13/422,904.
Amendment dated Jan. 19, 2015 in U.S. Appl. No. 14/459,787.
Amendment dated Jan. 19, 2015 in U.S. Appl. No. 14/459,844.
"Human nicotine specific antibody related protein, SEQ ID 85", Database Geneseq, identified in Search Report as "[Online] Jul. 23, 2009", XP002727665 retrieved from EBI accession No. GSP:AXB70134; Additional dates are provided in the document.
"Human angiopoietin-2 (Ang-2) antibody heavy chain variable region SEQ: 45.", Database Geneseq, identified in Search Report as "[Online] Feb. 2, 2012", XP002727666 retrieved from EBI accession No. GSP:AZQ43949; Additional dates are provided in the document.
International Search Report and Written Opinion dated Oct. 23, 2014 in PCT App. No. PCT/US2014/024702.
Issue Notification dated May 13, 2015 in U.S. Appl. No. 13/251,909.
Issue Notification dated May 27, 2015 in U.S. Appl. No. 14/459,768.
Notice of Allowance dated Jun. 16, 2015, received in U.S. Appl. No. 14/562,546.
Office Action dated Apr. 9, 2015 in Canadian Patent App. No. 2,696,252.
Office Action dated Apr. 27, 2015 in Costa Rican App. No. 11328 (with summary English translation).
Office Action dated May 12, 2015 in U.S. Appl. No. 13/469,032.
Office Action dated May 20, 2015 in U.S. Appl. No. 14/459,777.
Office Action dated Jun. 2, 2015 in U.S. Appl. No. 14/487,932.
Office Action dated Jun. 3, 2015 in U.S. Appl. No. 13/422,887.
Office Action dated Jun. 3, 2015 in U.S. Appl. No. 13/463,751.
Defendants' Preliminary Invalidity Contentions, dated May 8, 2015 in *Amgen Inc.*, v. *Sanofi*, in the United States District Court for the District of Delaware, C.A. No. 14-CV-1317, 108 pages.
Defendants' First Amended Preliminary Invalidity Contentions, dated Jun. 22, 2015 in *Amgen Inc.*, v. *Sanofi*, in the United States District Court for the District of Delaware, C.A. No. 14-CV-1317, 71 pages.
Joint Claim Construction Statement filed Jun. 24, 2015 in *Amgen Inc.*, v. *Sanofi*, in the United States District Court for the District of Delaware, C.A. No. 14-CV-1317, 13 pages.
Expert Declaration of Gregory A. Petsko, D.Phil. Regarding the Proper Construction of the Disputed Claim Elements from the Patents-at-Issue, filed Jul. 10, 2015 in *Amgen Inc.*, v. *Sanofi*, in the United States District Court for the District of Delaware, C.A. No. 14-CV-1317, 75 pages.
Plaintiff's Opening Claim Construction Brief, filed Jul. 10, 2015 in *Amgen Inc.*, v. *Sanofi*, in the United States District Court for the District of Delaware, C.A. No. 14-CV-1317, 37 pages.
Defendants' Answering Claim Construction Brief, filed Jul. 31, 2015 in *Amgen Inc.*, v. *Sanofi*, in the United States District Court for the District of Delaware, C.A. No. 14-CV-1317, 34 pages.
Plaintiff's Reply Claim Construction Brief, filed Aug. 14, 2015 in *Amgen Inc.*, v. *Sanofi*, in the United States District Court for the District of Delaware, C.A. No. 14-CV-1317, 21 pages.
Defendants' Surreply Claim Construction Brief, dated Aug. 28, 2015 in *Amgen Inc.*, v. *Sanofi*, in the United States District Court for the District of Delaware, C.A. No. 14-CV-1317, 19 pages.
Barbas et al., Assembly of combinatorial antibody libraries on phage surfaces: The gene III site, PNAS, 1991, vol. 88: pp. 7978-7982.
Barbas et al., Selection and evolution of highaffinity human antiviral antibodies, Trends Biotechnol., 1996, vol. 14: pp. 230-234.
Boulianne et al., Production of functional chimaeric mouse/human antibody, Nature, 1984, vol. 312: pp. 643-646.
Bradbury et al., Use of Living Columns to Select Specific Phage Antibodies, Nature Bio/Technology, 1993, vol. 11: pp. 1565-1569.
Brams et al., Antigen-Specific IgG Responses from Naive Human Splenocytes: In Vitro Priming Followed by Antigen Boost in the SCID Mouse, J. Immunol., 1998, vol. 160: pp. 2051-2058.
Bruggemann et al., Production of human antibody repertoires in transgenic mice, Curr. Op. Biotechnol., 1997, vol. 8: pp. 455-458.
Bruggemann et al., Strategies for expressing human antibody repertoires in transgenic mice, Immunol. Today, 1996, vol. 17: pp. 391-397.
Burton et al., Human Antibodies from Combinatorial Libraries, Adv. Immunol.,1994, vol. 57: pp. 191-280.
Carballido et al., Generation of primary antigen-specific human T- and B-cell responses in immunocompetent SCID-hu mice , Nat. Med., 2000, vol. 6: pp. 103-106.

(56) References Cited

OTHER PUBLICATIONS

Casali et al., Human monoclonals from antigen-specific selection of B lymphocytes and transformation by EBV , Science, 1986, vol. 234: pp. 476-479.

Chiorazzi et al., Use of Epstein-Barr virus-transformed B cell lines for the generation of immunoglobulin-producing human B cell hybridomas, J. Exp. Med., 1982, vol. 156: pp. 930-935.

Chowdhury et al., Improving antibody affinity by mimicking somatic hypermutation in vitro, Nature Biotech., 1999, vol. 17: pp. 568-572.

Clackson, et al., Making antibody fragments using phage display libraries, Nature, 1991, vol. 352: pp. 624-628.

Co et al., Genetically Engineered Deglycosylation of the Variable Domain Increases the Affinity of an Anti-CD33 Monoclonal Antibody, Mol. Immunol., 1993, vol. 30: pp. 1361-1367.

Croce et al., Production of human hybridomas secreting antibodies to measles virus, Nature, 1980, vol. 288: pp. 488-489.

Fishwild et al., High-avidity human IgGkappa monoclonal antibodies from a novel strain of minilocus transgenic mice, Nature Biotechnology, 1996, vol. 14: pp. 845-851.

Foung et al., Rescue of human monoclonal antibody production from an EBV-transformed B cell line by fusion to a human-mouse hybridoma, J. Immunol. Methods, 1984, vol. 70: pp. 83-90.

Georgiou et al., Display of heterologous proteins on the surface of microorganisms: From the screening of combinatorial libraries to live recombinant vaccines, Nature Biotech., 1997, vol. 15: pp. 29-34.

Gilliland et al., Elimination of the Immunogenicity of Therapeutic Antibodies, J. Immunol., 1999, vol. 62(6): pp. 3663-3671.

Goding et al., Antibody production by hybridomas Review, J. Immunol. Meth., 1980, vol. 39: pp. 285-308.

Green et al., Antigen-specific human monoclonal antibodies from mice engineered with human Ig heavy and light chain YACs, Nature Genetics, 1994, vol. 7: pp. 12-21.

Griffiths et al., Human anti-self antibodies with high specificity from phage display libraries, EMBO J., 1993, vol. 12: pp. 725-734.

Griffiths et al., Isolation of high affinity human antibodies directly from large synthetic repertoires, EMBO J., 1994, vol. 13: pp. 3245-3260.

Hanes et al., In vitro selection and evolution of functional proteins by using ribosome display, PNAS, 1997, vol. 94: pp. 4937-4942.

Harding et al., Class Switching in Human Immunoglobulin Transgenic Mice, Ann. NY Acad. Sci., 1995, vol. 764: pp. 536-546.

Hawkins et al., Selection of Phage Antibodies by Binding Affinity: Mimicking Affinity Maturation, J. Mol. Biol., 1992, vol. 226: pp. 889-896.

Hoogenboom et al., By-passing Immunisation: Human Antibodies from Synthetic Repertoires of Germline V H Gene Segments Rearranged in Vitro, J. Mol. Biol. 1992, vol. 227: pp. 381-388.

Hoogenboom, Designing and optimizing library selection strategies for generating high-affinity antibodies, Trends Biotechnol., 1997, vol. 15: pp. 62-70.

Horton et al., Molecular biology of PCSK9: its role in LDL metabolism, Trends Biochem. Sci., 2007, vol. 32(2): pp. 71-77.

Ifversen et al., SCID-hu-PBL: a model for making human antibodies?, Sem. Immunol. 1996, vol. 8: pp. 243-248.

Ishida et al., Review: Production of Human Monoclonal and Polyclonal Antibodies in TransChromo Animals, Cloning Stem Cells, 2002, vol. 4: pp. 91-102.

Issandou, Pharmacological regulation of low density lipoprotein receptor expression: Current status and future developments, Pharmacol. & Therapeutics, 2006, vol. 111: pp. 424-433.

Jakobovits, Production of fully human antibodies by transgenic mice, Curr. Op. Biotechnol., 1995, vol. 6: pp. 561.

Jespers et al., Guiding the Selection of Human Antibodies from Phage Display Repertoires to a Single Epitope of an AntigenNature Biotechnology, 1994, vol. 12: pp. 899-903.

Jones et al., Replacing the complementarity-determining regions in a human antibody with those from a mouse , Nature, 1986, vol. 321: pp. 522-525.

Kang et al., Antibody redesign by chain shuffling from random combinatorial immunoglobulin libraries, PNAS, 1991, vol. 88: pp. 11120-11123.

Karpas et al., human myeloma cell line suitable for the generation of human monoclonal antibodies, PNAS, 2001, vol. 98: pp. 1799-1804.

Kaufman et al., Growth-Dependent Expression of Dihydrofolate Reductase mRNA from Modular cDNA Genes, Mol. Bio., 1982, vol. 159: pp. 601-621.

Kellerman et al., Antibody discovery: the use of transgenic mice to generate human monoclonal antibodies for therapeutics, Curr. Opinion in Biotechnology, 2002, vol. 13: pp. 593-597.

Kieke et al., Isolation of anti-T cell receptor scFv mutants by yeast surface display, Protein Engineering, 1997, vol. 10: pp. 1303-1310.

Kim et al., Crystal Structure of Fervidolysin from Fervidobacterium pennivorans, a Keratinolytic Enzyme Related to Subtilisin, J. Mol. Biol., 2004, vol. 335: pp. 787-797.

Kohler et al., Continuous cultures of fused cells secreting antibody of predefined specificity, Nature, 1975, vol. 256: pp. 495-497.

Kozbor et al., Human Anti-Tetanus Toxoid Monoclonal Antibody Secreted by EBV-Transformed Human B Cells Fused with Murine Myeloma, Hybridoma, 1982, vol. 1: pp. 323-328.

Lonberg et al., Antigen-specific human antibodies from mice comprising four distinct genetic modifications, Nature 1994, vol. 368: pp. 856-859.

Lonberg et al., Human Antibodies from Transgenic Mice, Int. Rev. Immunol. 1995, vol. 13: pp. 65-93.

Lo, Antibody Engineering Methods and Protocols, Methods in Molecular Biology, 2004, pp. 3-555, vol. 248, Humana Press, Totowa, New Jersey.

Marks et al., By-Passing Immunization: Building High Affinity Human Antibodies by Chain Shuffling, Bio/Technology, 1992, vol. 10: pp. 779.

Marks et al., Human Antibody Fragments Specific for Human Blood Group Antigens from a Phage Display Library, Bio/Technology, 1993, vol. 11: pp. 1145.

Marks et al., Molecular Evolution of Proteins on Filamentous Phage, J. Biol. Chem., 1992, vol. 267: pp. 16007.

Marks et al., By-passing Immunization: Human Antibodies from V-gene Libraries Displayed on Phage, J. Mol. Biol., 1991, vol. 222: pp. 581.

Martensson et al., Antigen-specific human immunoglobulin production in SCID mice transplanted with human peripheral lymphocytes is dependent on CD4+ CD45RO+ T cells, Immunol., 1994, vol. 83: pp. 1271-179.

Martensson et al., Enhancement of specific immunoglobulin production in SCID-hu-PBL mice after in vitro priming of human B cells with superantigen, Immunol., 1995, vol. 84: pp. 224-230.

McCafferty et al., Phage antibodies: filamentous phage displaying antibody variable domains, Nature, 1990, vol. 348: pp. 552-554.

McCune et al., The SCID-hu Mouse: Murine Model for the Analysis of Human Hematolymphoid Differentiation and Function, Science, 1988, vol. 241: pp. 1632-1639.

Morrison et al., Chimeric human antibody molecules: Mouse antigen-binding domains with human constant region domains, PNAS, 1984, vol. 82: pp. 6851-6855.

Mosier et al., Transfer of a functional human immune system to mice with severe combined immunodeficiency, Nature, 1988, vol. 335: pp. 256-259.

Mullinax et al., Identification of human antibody fragment clones specific for tetanus toxoid in a bacteriophage A immunoexpression library, PNAS, 1990, vol. 87: pp. 8095-8099.

Murphy et al., Antibodies to CD40 Prevent Epstein-Barr Virus-Mediated Human B-Cell Lymphomagenesis in Severe Combined Immune Deficient Mice Given Human Peripheral Blood Lymphocytes, Blood, 1995, vol. 86: pp. 1946-1953.

Neuberger et al., Mice perform a human repertoire, Nature, 1997, vol. 386: pp. 25.

Olsson et al., Human-human hybridomas producing monoclonal antibodies of predefined antigenic specificity, PNAS, 1980, vol. 77: pp. 5429-5431.

Rader et al., Phage display of combinatorial antibody libraries, Curr. Op. Biotechnol., 1997, vol. 8: pp. 503-508.

(56)                    References Cited

OTHER PUBLICATIONS

Riechmann et al., Reshaping human antibodies for therapy, Nature, 1988, vol. 332: pp. 323-327.
Roguska et al., A comparison of two murine monoclonal antibodies humanized by CDR-grafting and variable domain resurfacing, Prot. Engineer., 1996, vol. 9: pp. 895-904.
Saldanha et al., A single backmutatlon in the human kIV framework of a previously unsuccessfully humanized antibody restores the binding activity and increases the secretion in cos cells, Mol. Immunol., 1999, vol. 36: pp. 709-719.
Sambrook et al., Molecular Cloning: A Laboratory Manual 2d ed., Cold Spring Harbor Laboratory Press, Cold Spring Harbor, N.Y. (1989).
Schier et al., Isolation of Picomolar Affinity Anti-c-erbB-2 Single-chain Fv by Molecular Evolution of the Complementarity Determining Regions in the Center of the Antibody Binding Site, J. Mol. Biol., 1996, vol. 263: pp. 551-567.
Sheets et al., Efficient construction of a large nonimmune phage antibody library: The production of high-affinity human single-chain antibodies to protein antigens, PNAS, 1998, vol. 95: pp. 6157-6162.
Soutar et al., Mechanisms of Disease: genetic causes of familial hypercholesterolemia, Nat. Clin. Pract., 2007, vol. 4(4): pp. 214-225.
Taylor et al., Human immunoglobulin transgenes undergo rearrangement, somatic mutation and class switching in mice that lack endogenous IgM, Int. Immunol., 1994, vol. 6: pp. 579-591.
Teng et al., Construction and testing of-mouse-human heteromyelomas for human monoclonal antibody production, PNAS, 1983, vol. 80: pp. 7308-7312.
Thompson et al., Affinity Maturation of a High-affinity Human Monoclonal Antibody Against the Third Hypervariable Loop of Human Immunodeficiency Virus: Use of Phage Display to Improve Affinity and Broaden Strain Reactivity, J. Mol. Biol., 1996, vol. 256: pp. 77-88.
Tomlinson et al., The Imprint of Somatic Hypermutation on the Repertoire of Human Germline V Genes, J. Mol. Biol., 1996, vol. 256: pp. 813-817 (1996).
Urlaub et al., Isolation of Chinese hamster cell mutants deficient in dihydrofolate reductase activity, Proc. Natl. Acad. Sci. USA, 1980, vol. 77: pp. 4216-4220).
Vaswami et al., Humanized antibodies as potential therapeutic drugs, Annals of Allergy, Asthma, & Immunol., 1998, vol. 81: pp. 105-119.
Vaughan et al., Human Antibodies with Sub-nanomolar Affinities Isolated from a Large Non-immunized Phage Display Library, Nature Biotechnology, 1996, vol. 14: pp. 309-314.
Verhoeyen et al., Reshaping Human Antibodies: Grafting an Antilysozyme Activity, Science, 1988, vol. 239: pp. 1534-1536.
Wagner et al., The diversity of antigen-specific monoclonal antibodies from transgenic mice bearing human immunoglobulin gene miniloci, Eur. J. Immunol., 1994, vol. 24: pp. 2672-2681.
Wagner et al., Antibodies generated from human immunoglobulin miniloci in transgenic mice, Nucl. Acids Res., 1994, vol. 22: pp. 1389-1393.
Winter et al., Making Antibodies by Phage Display Technology, Annu. Rev. Immunol., 1994, vol. 12: pp. 433-455.
Winter et al., Synthetic human antibodies and a strategy for protein engineering, FEBS Letts, 1998, vol. 430: pp. 92-94.
Zou et al., Dominant expression of a 1.3 Mb human IgK locus replacing mouse light chain production, FASEB J. 1996, vol. 10: pp. 1227-1232.
American Heart Association, Good vs. Bad Cholesterol, content last reviewed Apr. 21, 2014, updated Jan. 12, 2015, copyright 2015, accessed on the world wide web at www.heart.org/HEARTORG/Conditions/Cholesterol/AboutCholesterol/Good-vs-Bad-Cholesterol_UCM_305561_Article.jsp.
Amgen Press Release entitled "Journal of the American Medical Association Publishes Phase 3 LAPLACE-2 Study Showing Evolocumab Significantly Reduced LDL Cholesterol in Patients on Statins Regardless of Statin Dose" dated May 13, 2014, accessed on the world wide web at wwwext.amgen.com/media/media_pr_detail.jsp?Year=2014&releaseID=1930510.
Amgen Press Release entitled "Amgen Announces Positive Top-Line Results From Phase 3 YUKAWA-2 Trial of Evolocumab in Combination With Statins in Japanese Patients With High Cardiovascular Risk and High Cholesterol" dated Aug. 28, 2014, accessed on the world wide web at wwwext.amgen.com/media/media_pr_detail.jsp?year=2014&releaseID=1961803.
Amendment Accompanying Request for Continued Examination dated Jul. 2, 2015 in U.S. Appl. No. 14/562,546.
Amgen Press Release entitled "FDA Approves Amgen's New Cholesterol-Lowering Medication Repatha™ (Evolocumab)" dated Aug. 27, 2015, accessed on the world wide web at www.multivu.com/players/English/7414054-amgen-repatha-fda-approval/.
FDA News Release: "FDA approves Repatha to treat certain patients with high cholesterol", release date Aug. 27, 2015, accessed on the world wide web at www.fda.gov/NewEvents/Newsroom/PressAnnouncements/ucm.460082.htm.
Herper "Wall Street Gets It Backward on Amgen Cholesterol Drug" dated Apr. 29, 2013, webpage copyright 2015, accessed on the world wide web at www.forbes.com/sites#/sites/matthewherper/2013/04/29/wall-street-gets-it-backward-on-amgen-cholesterol-drug.
Issue Notification dated Jul. 22, 2015 in U.S. Appl. No. 14/459,787.
Ito et al., "The His-probe method: effects of histidine residues introduced into the complementarity-determining regions of antibodies on antigen-antibody interactions at different pH values", Federation of European Biochemical Societies 309: 85-88, 1992.
Office Action dated Apr. 22, 2015 in Taiwanese Patent App. No. 103110948 (with English translation).
Office Action dated Apr. 22, 2015 in Taiwanese Patent App. No. 103110947 (with English translation).
Office Action dated Aug. 13, 2015, received in U.S. Appl. No. 13/619,555.
Office Action dated Aug. 18, 2015, received in U.S. Appl. No. 13/494,912.
Office Action dated Jul. 3, 2015, received in Korean Patent Application No. 10-2014-7010033 (with English translation).
Advisory Action dated Jan. 9, 2013 in U.S. Appl. No. 12/649,179.
Office Action dated Jan. 29, 2014, received in U.S. Appl. No. 12/649,179.
Office Action dated Mar. 12, 2015, received in U.S. Appl. No. 12/649,179.
Office Action dated May 3, 2011, received in U.S. Appl. No. 12/649,179.
Office Action dated Oct. 29, 2010, received in U.S. Appl. No. 12/649,179.
Office Action dated Sep. 6, 2013, received in U.S. Appl. No. 12/649,179.
Office Action dated Sep. 30, 2014 in U.S. Appl. No. 12/649,179.
Notice of Allowance dated Oct. 1, 2015 received in U.S. Appl. No. 14/459,787.
Notice of Allowance dated Oct. 2, 2015 received in U.S. Appl. No. 14/459,844.
Perez De La Lastra, et al., "Epitope mapping of 10 monoclonal antibodies against the pig analogue of human membrane cofactor protein (MCP)" Immunology 96: 663-670 (1999).
Third Party Observations for Application No. EP20080798550 dated Sep. 25, 2015 by Anonymous.
Third Party Observations for Application No. 08798550.3 dated Oct. 1, 2015 by Carpmaels & Ransford.
Third Party Observations for Application No. 08798550.3 dated Oct. 19, 2015 by Carpmaels & Ransford.
Memorandum dated Oct. 20, 2015 in *Amgen Inc.*, v. *Sanofi*, in the United States District Court for the District of Delaware, C.A. No. 14-CV-1317, 8 pages.
Clackson, J.A. Wells, "A Hot Spot of Binding Energy in a Hormone-Receptor Interface" Science (1995) vol. 267: pp. 383-386.
Lambert, G., et al., "The PCSK9 Decade," J. Lipid Research (2012) vol. 53, pp. 2515-2524.
Lodish, H., et al., Molecular Cell Biology (1999) 4th ed., pp. 14-49, W.H. Freeman and Company, New York.

(56) References Cited

OTHER PUBLICATIONS

Janeway, C.A. et al., Immunobiology: The Immune System in Health and Disease (2001) 5th ed., pp. 93-122, Garland Publishing, New York.
Janeway, C.A. et al., Immunobiology: The Immune System in Health and Disease (2001) 5th ed., pp. 683-707. Garland Publishing, New York.
Third Party Observations for Application No. 08798550.3 dated Nov. 1, 2015 by Carpmaels & Ransford.
Regeneron and Sanofi Announce New Praluent®. . . Heading Date Nov. 10, 2015 copyright date 2015, in 3 pages.
U.S. Appl. No. 60/911,654, filed Apr. 13, 2007, Yowe et al.
Office Action dated Nov. 19, 2015 in U.S. Appl. No. 12/903,084.
Communication under rule 71(3) dated Dec. 15, 2015 in European Patent Application No. 08 798 550.3.
Office Action dated Dec. 17, 2015 in U.S. Appl. No. 13/422,904.
Provision of the Minutes in Accordance with Rule 124(4) EPC dated Dec. 10, 2015 in European Application No. 08 798 550.3 (including Annex I, Annex II, and Annex III).
Submission to European Patent Office in Preparation for Oral Proceedings dated Nov. 25, 2015 in European Patent App. No. 07 798 550.3 (includes Declaration by Dr. Chadwick King; Auxiliary Requests 1*, 1**, 9A, and 9B; Decision to revoke EP 1 528 933; and CV of Dr. Tobias Raum).
Office Action dated Dec. 18, 2015 in U.S. Appl. No. 13/174,423.
Examiner's Answer dated Dec. 11, 2015 in U.S. Appl. No. 12/649,179.
Office Action dated Dec. 17, 2015 in U.S. Appl. No. 13/742,205 (Merck).
Decision of Opposition dated Dec. 24, 2015 in Japanese Patent No. 5705288 (with English translation).
Office Action dated Aug. 3, 2015 in U.S. Appl. No. 13/982,381 (Sanofi).
Office Action dated Aug. 4, 2015 in U.S. Appl. No. 13/982,373 (Sanofi).
Office Action dated Feb. 8, 2016 in U.S. Appl. No. 14/459,777.
Response to Office Action filed Nov. 11, 2015 in U.S. Appl. No. 13/611,405 (Regeneron).
Response to Office Action filed Jun. 12, 2015 in U.S. Appl. No. 13/982,373 (Sanofi).
Response to Office Action filed Jun. 26, 2015 in U.S. Appl. No. 13/982,381 (Sanofi).
Written Opposition dated Oct. 22, 2015 in Japanese Pat. No. 5705288 (with English translation).
U.S. Appl. No. 14/777,371, filed Sep. 15, 2015, Amgen Inc.
U.S. Appl. No. 14/777,401, filed Sep. 15, 2015, Amgen Inc.
Office Action dated Feb. 24, 2016 in U.S. Appl. No. 13/463,751.
Office Action dated Feb. 24, 2016 in U.S. Appl. No. 14/487,932.
Office Action dated Feb. 26, 2016 in U.S. Appl. No. 13/422,887.
Office Action dated Mar. 1, 2016 in U.S. Appl. No. 13/682,698.
Opposition in European Patent App. No. 08798550.3, submitted by Sanofi on Feb. 24, 2016, and Communicated by European Patent Office dated Mar. 3, 2016, including submitted documents D13, D14a, D15-19, D20, D21a, D21b, D22a, P1a, P2a, P2b, P3a, P3b, and P4a, in 85 pages.
Yang, et al. "CDR Walking Mutagenesis for the Affintiy Maturation of a Potent Human Anti-HIV-1 Antibody into the Picomolar Range" J. Mol. Biol., vol. 254, pp. 392-403, 1995.
Harlow, Ed. et al., "Antibodies, a Laboratory Manual" New York, Cold Spring Harbor, 1988, pp. 55-95.
Text Intended for Grant for European Patent No. 2215124 (issuing from European App. No. 08798550.3), in 787 pages.
Trial Brief dated Jan. 18, 2018 in Invalidation Trial against Japanese Patent No. 5705288 (with English translation).
U.S. Appl. No. 61/063,949, filed Feb. 7, 2008, Merck & Co., Inc.
U.S. Appl. No. 61/066,577, filed Feb. 21, 2008, Merck & Co., Inc.
Office Action dated Apr. 4, 2016 in U.S. Appl. No. 13/619,555.
Dubé et al. Lipoprotein(a): more interesting than ever after 50 years, Curr. Opin. Lipidol. 23:133-140 (2012).
International Preliminary Report on Patentability dated Sep. 15, 2015 in PCT App. No. PCT/US2014/028339.

International Preliminary Report on Patentability dated Sep. 15, 2015 in PCT App. No. PCT/US2014/024702.
International Search Report dated Oct. 17, 2014, from Int'l Appl. No. PCT/US2014/028339.
Kochinsky, et al., Lipoprotein(a) An Important Cardiovascular Risk Factor and a Clinical Conundrum, Endocrinol. Metab. Clin. N. Am. 43: 949-962 (2014).
Lamon-Fava et al., Lipoprotein(a) levels, apo(a) isoform size, and coronary heart disease risk in the Framingham Offspring Study, J. Lipid Res., 52: 1181-1187 (2011).
Office Action dated Apr. 22, 2016 in European Patent App. No. 12 701 015.5 (Sanofi).
Office Action dated Apr. 26, 2016 in European Patent App. No. 12 701 742.4 (Sanofi).
Office Action dated Feb. 23, 2016 in Japanese Patent Application 2014-510478 (with English translation).
Pfizer v. Amgen in the High Court of Justice, Chancery Division, Patents Court, United Kingdom, Claim No. HP-2016-000017, Submissions dated Mar. 24, 2016. The references identified in this document are not being submitted because they are already of record.
Pokala et al., Energy Functions for Protein Design: Adjustment with Protein-Protein Complex Affinities, Models for the Unfolded State, and Negative Design of Solubility and Specificity, J. Mol. Biol. 347: pp. 203-227 (2004).
Response to Office Action, including Declaration filed under 37 C.F.R. §1.131, dated Apr. 18, 2016 in U.S. Appl. No. 13/742,205 (Merck).
Third Party Observations filed Feb. 24, 2016 regarding European Patent Application No. EP20120761864.
Tsimikas, Antisense therapy targeting apolipoprotein(a): a randomized double-blind, placebo-controlled phase 1 study. Lancet. 386: 1472-1483 (2015).
Written Answer for Invalidation Trial dated Jun. 2, 2016 in Japanese Invalidation Trial 2016-800004 (Invalidation Trial against U.S. Pat. No. 5,705,288), including Exhibits A2 and A6.
Written Demand for Correction dated Jun. 2, 2016 in Japanese Invalidation Trial 2016-800004 (Invalidation Trial against U.S. Pat. No. 5,705,288).
Letter to Judge Sue L. Robinson Dated Jan. 28, 2016, including Kwon et al. "Molecular basis for LDL receptor recognition by PCSK9". PNAS Feb. 12, 2008, 105(6):1820-1825, in 7 Pages total {Document 0182}.
Supplemental and Second Amended Complaint for Patent Infringement and Declaratory Judgement of Patent Infringement Filed Jan. 29, 2016 in Amgen Inc., v. Sanofi, in the United States District Court for the District of Delaware, C.A. No. 14-CV-1317, 31 Pages {Document 0184}.
Memorandum in Support of Amgen's Daubert Motion to Exclude Testimony on (1) Post-Priority Date Embodiments/Antibodies of the Selected Claims and (2) Defendants Expert Opinions as to the Patent's Disclosure of Representative Species, Dated Feb. 2, 2016, Filed Feb. 8, 2016 in Amgen Inc., v. Sanofi, in the United States District Court for the District of Delaware, C.A. No. 14-CV-1317, 27 Pages {Document 0195}.
Opening Brief in Support of Defendant's Motion to Exclude Certain Expert Testimony From Plaintiffs on Written Description and Reasonable Royalties Redacted Public Version, Dated Feb. 2, 2016, Filed Feb. 9, 2016 in Amgen Inc., v. Sanofi, in the United States District Court for the District of Delaware, C.A. No. 14-CV-1317, 25 pages {Document 0199}.
Redacted Public Version of Exhibits, Dated and Filed Feb. 9, 2016 in Amgen Inc., v. Sanofi, in the United States District Court for the District of Delaware, C.A. No. 14-CV-1317, 164 Pages {Document 0200-1}.
Memorandum in Opposition Defendant's Daubert Motion to Exclude Certain Expert Testimony to Exclude Certain Expert Testimony from Amgen on Written Description and Reasonable Royalties Redacted Public Version, Dated Feb. 9, 2016, Filed Feb. 16, 2016 in Amgen Inc., v. Sanofi, in the United States District Court for the District of Delaware, C.A. No. 14-CV-1317, 25 Pages {Document 0214}.

(56) References Cited

OTHER PUBLICATIONS

Defendants' Brief in Opposition to Amgen's Daubert Motion to Exclude Testimony on (1) Post-Priority Date Embodiments/ Antibodies of the Selected Claims and (2) Defendants' Expert Opinions as to the Patent's Disclosure of Representative Species, Redacted Public Version, Dated Feb. 9, 2013 Filed Feb. 16, 2016 in *Amgen Inc.*, v. *Sanofi*, in the United States District Court for the District of Delaware, C.A. No. 14-CV-1317, 16 pages {Document 0218}.

Reply Brief in Support of Defendant's Motion to Exclude Certain Expert Testimony From Certain Expert Testimony From Plaintiffs on Written Description and Reasonable Royalties Public Redacted Version, Dated Feb. 12, 2016, Filed Feb. 16, 2016 in *Amgen Inc.*, v. *Sanofi*, in the United States District Court for the District of Delaware, C.A. No. 14-CV-1317, 15 pages {Document 0227}.

Defendant's Motion for Reargument of the Feb. 18 Memorandum Order Granting Amgen's Daubert Motion Regarding Post-Priority Date Evidence, Public Redacted Version, Dated Feb. 19, 2016, Filed Feb. 26, 2016 in *Amgen Inc.*, v. *Sanofi*, in the United States District Court for the District of Delaware, C.A. No. 14-CV-1317, 14 Pages {Document 0243}.

Plaintiff's Response to Defendant's Evidentiary Issues 10 and 11, Public Redacted Version Dated and Filed Mar. 7, 2016 in *Amgen Inc.*, v. *Sanofi*, in the United States District Court for the District of Delaware, C.A. No. 14-CV-1317, 3 Pages {Document 0259}.

Opposition for Defendant's Motion for Reargument of the Feb. 18 Memorandum Order Granting Amgen's Daubert Motion Regarding Post-Priority Date Evidence, Public Redacted Version, Dated Feb. 22, 2016, Filed Mar. 13, 2016 in *Amgen Inc.*, v. *Sanofi*, in the United States District Court for the District of Delaware, C.A. No. 14-CV-1317, 15 Pages {Document 0287}.

Declaration of Shane G. Smith in Support of Plaintiffs' Opposition to Defendants' Motion for Reargument of the Feb. 18 Memorandum Order Granting Amgen's Daubert Motion Regarding Post-Priority Date Evidence, Public Redacted Version, Dated Feb. 22, 2016, Filed Mar. 13, 2016 in *Amgen Inc.*, v. *Sanofi*, in the United States District Court for the District of Delaware, C.A. No. 14-CV-1317, 18 Pages {Document 0288}.

Plaintiff's Memoranda on Evidentiary Issues 10 and 14, Public Redacted Version, Dated Mar. 4, 2016, Filed Mar. 13, 2016 in *Amgen Inc.*, v. *Sanofi*, in the United States District Court for the District of Delaware, C.A. No. 14-CV-1317, 10 Pages {Document 0289}.

Plaintiff's One Page Memoranda on Evidentiary Issues 4 and 13, Dated Mar. 4, 2016, Filed Mar. 13, 2016 in *Amgen Inc.*, v. *Sanofi*, in the United States District Court for the District of Delaware, C.A. No. 14-CV-1317, 5 Pages {Document 0290}.

Verdict Sheet, Dated and Filed Mar. 16, 2016 in *Amgen Inc.*, v. *Sanofi*, in the United States District Court for the District of Delaware, C.A. No. 14-CV-1317, 3 Pages {Document 0304 }.

Defendant's Bench Memorandum on the Relevance of Post-Priority Date Documents to Show 2008 State of the Art, Public Redacted Version, Dated Mar. 10, 2016, Filed Mar. 22, 2016 in *Amgen Inc.*, v. *Sanofi*, in the United States District Court for the District of Delaware, C.A. No. 14-CV-1317, 9 Pages {Document 0310}.

Proffer of Michael J. Eck, M.D.., Ph.D. Public Redacted Version, Dated Mar. 10, 2016, Filed Mar. 22, 2016 in *Amgen Inc.*, v. *Sanofi*, in the United States District Court for the District of Delaware, C.A. No. 14-CV-1317, 63 Pages {Document 0311}.

Proffer of Donald Siegel, M.D., Ph.D. Dated Mar. 10, 2016, Filed Mar. 22, 2016 in *Amgen Inc.*, v. *Sanofi*, in the United States District Court for the District of Delaware, C.A. No. 14-CV-1317, 115 Pages {Document 0312}.

Defendant's Rule 50(a) Motion for Judgment as a Matter of Law of Now Willful Infringement Public Redacted Version, Dated Mar. 14, 2016, Filed Mar. 22, 2016 in *Amgen Inc.*, v. *Sanofi*, in the United States District Court for the District of Delaware, C.A. No. 14-CV-1317, 26 Pages {Document 0314}.

Defendant's Opposition to Plaintiff's One Page Memoranda Regarding Plaintiffs' Evidentiary Issues 10 and 14 Public Redacted Version, Dated Mar. 7, 2016, Filed Mar. 22, 2016 in *Amgen Inc.*, v. *Sanofi*, in the United States District Court for the District of Delaware, C.A. No. 14-CV-1317, 4 Pages {Document 0315}.

Declaration of Jenna M. Pelleccha in Support of Defendants' One Page Memoranda Regarding Plaintiffs' Evidentiary Issues 10 and 14 Public Redacted Version, Dated Mar. 7, 2016, Filed Mar. 22, 2016 in *Amgen Inc.*, v. *Sanofi*, in the United States District Court for the District of Delaware, C.A. No. 14-CV-1317, 46 Pages {Document 0316}.

Defendants' Opposition to Plaintiffs' One Page Memoranda Regarding Plaintiffs' Evidentiary Issues 4 and 13 Public Redacted Version, Dated Mar. 7, 2016, Filed Mar. 22, 2016 in *Amgen Inc.*, v. *Sanofi*, in the United States District Court for the District of Delaware, C.A. No. 14-CV-1317, 4 Pages {Document 0318}.

Amgen's Motion to Exclude Supplemental Expert Report, Exclude Non-Prior Art References from Evidence and Exclude Evidence of Obviousness, Dated Mar. 7, 2016, Filed Mar. 22, 2016 in *Amgen Inc.*, v. *Sanofi*, in the United States District Court for the District of Delaware, C.A. No. 14-CV-1317, 13 Pages {Document 0320}.

Plaintiffs' Proffer Concerning Post-Priority Crystal Structure Evidence From Dr. Gregory Petsko, Public Redacted Version, Dated Mar. 14, 2016, Filed Mar. 22, 2016 in *Amgen Inc.*, v. *Sanofi*, in the United States District Court for the District of Delaware, C.A. No. 14-CV-1317, 7 Pages {Document 0322}.

Response to Defendant's Request for Admission of Evidence Related to Amgen's Post-Priority Date Efforts, Public Redacted Version, Dated Mar. 14, 2016, Filed Mar. 22, 2016 in *Amgen Inc.*, v. *Sanofi*, in the United States District Court for the District of Delaware, C.A. No. 14-CV-1317, 11 Pages {Document 0323}.

Plaintiff's Opposition to Defendant's Rule 50(a) Motion for Judgment as a Matter of Law of no Willful Infringement, Public Redacted Version, Dated Mar. 15, 2016, Filed Mar. 22, 2016 in *Amgen Inc.*, v. *Sanofi*, in the United States District Court for the District of Delaware, C.A. No. 14-CV-1317, 23 Pages {Document 0324}.

Docket Public Redacted Version Dated Mar. 24, 2016 in *Amgen Inc.*, v. *Sanofi*, in the United States District Court for the District of Delaware, C.A. No. 14-CV-1317, 3 Pages {Document 0328}.

Plaintiff's Answering Brief in Opposition to Defendants' Motion for Judgment as a Matter of Law on Written Description and Enablement, Dated and Filed May 2, 2016 in *Amgen Inc.*, v. *Sanofi*, in the United States District Court for the District of Delaware, C.A. No. 14-CV-1317, 24 Pages {Document 0352}.

Opening Brief in Support of Defendants' Motion for a New Trial, Redacted Public Version, Dated Apr. 22, 2016, Filed May 5, 2016 in *Amgen Inc.*, v. *Sanofi*, in the United States District Court for the District of Delaware, C.A. No. 14-CV-1317, 37 Pages {Document 0355}.

Amgen's Motion for Judgment as a Matter of Law, Dated and Filed Mar. 11, 2016 in *Amgen Inc.*, v. *Sanofi*, in the United States District Court for the District of Delaware, C.A. No. 14-CV-1317, 14 Pages {Document 0282}.

Amgen's Daubert Motion to Exclude Testimony on (1) Post-Priority Date Embodiments/Antibodies of the Selected Claims and (2) Defendants' Expert Opinions as to the Patent's Disclosure of Representative Species, Dated and Filed Feb. 2, 2016 in *Amgen Inc.*, v. *Sanofi*, in the United States District Court for the District of Delaware, C.A. No. 14-CV-1317, 2 Pages {Document 0191}.

Corrected Version of Transcript of Status Conference of Jan. 27, 2016, Dated Feb. 3, 2016 in *Amgen Inc.*, v. *Sanofi*, in the United States District Court for the District of Delaware, C.A. No. 14-CV-1317, 29 Pages.

Volume 1 Mini-Trial Transcript Dated Mar. 8, 2016 in *Amgen Inc.*, v. *Sanofi*, in the United States District Court for the District of Delaware, C.A. No. 14-CV-1317, 52 Pages.

Volume 2 Mini-Trial Transcript Dated Mar. 9, 2016 in *Amgen Inc.*, v. *Sanofi*, in the United States District Court for the District of Delaware, C.A. No. 14-CV-1317, 72 Pages.

Volume 3 Mini-Trial Transcript Dated Mar. 10, 2016 in *Amgen Inc.*, v. *Sanofi*, in the United States District Court for the District of Delaware, C.A. No. 14-CV-1317, 116 Pages.

(56)            References Cited

OTHER PUBLICATIONS

Volume 4 Mini-Trial Transcript Dated Mar. 11, 2016 in *Amgen Inc.*, v. *Sanofi*, in the United States District Court for the District of Delaware, C.A. No. 14-CV-1317, 75 Pages.
Volume 5 Mini-Trial Transcript Dated Mar. 14, 2016 in *Amgen Inc.*, v. *Sanofi*, in the United States District Court for the District of Delaware, C.A. No. 14-CV-1317, 43 Pages.
Defendant's Answer to Supplemental and Second Complaint for Patent Infringement and Declaratory Judgment of Patent Infringement Dated and Filed Feb. 16, 2016 in *Amgen Inc.*, v. *Sanofi*, in the United States District Court for the District of Delaware, C.A. No. 14-CV-1317, 25 Pages {Document 0220}.
Defendant's Memo Regarding Disputed Jury Instructions Dated and Filed Mar. 13, 2016 in *Amgen Inc.*, v. *Sanofi*, in the United States District Court for the District of Delaware, C.A. No. 14-CV-1317, 55 Pages {Document 0291}.
Defendants' Notice Pursuant to 35 USC 282 Dated and Filed Feb. 5, 2016 in *Amgen Inc.*, v. *Sanofi*, in the United States District Court for the District of Delaware, C.A. No. 14-CV-1317, 23 Pages {Document 0194}.
Defendants' Responses to Plaintiffs' Evidentiary Issues 1 and 2 and 5 Dated and Filed Feb. 26, 2016 in *Amgen Inc.*, v. *Sanofi*, in the United States District Court for the District of Delaware, C.A. No. 14-CV-1317, 4 Pages {Document 0241}.
Final Jury Instructions Dated and Filed Mar. 14, 2016 in *Amgen Inc.*, v. *Sanofi*, in the United States District Court for the District of Delaware, C.A. No. 14-CV-1317, 31 Pages {Document 0299}.
Judgment Following a Jury Verdict Pursuant to Fed. R. Civ. P. 58(b) Dated and Filed Mar. 18, 2016 in *Amgen Inc.*, v. *Sanofi*, in the United States District Court for the District of Delaware, C.A. No. 14-CV-1317, 1 Page {Document 0308}.
Letter to Judge Robinson re 09/18 Claim Dated and Filed Sep. 29, 2015 in *Amgen Inc.*, v. *Sanofi*, in the United States District Court for the District of Delaware, C.A. No. 14-CV-1317, 2 Pages {Document 0128}.
Letter to Judge Robinson re Amgen's 09/29 Claim Dated and Filed Oct. 5, 2015 in *Amgen Inc.*, v. *Sanofi*, in the United States District Court for the District of Delaware, C.A. No. 14-CV-1317, 1 Page {Document 0134}.
Letter to Judge Robinson re: One Page Memoranda on Evidentiary Issues Dated and Filed Feb. 24, 2016 in *Amgen Inc.*, v. *Sanofi*, in the United States District Court for the District of Delaware, C.A. No. 14-CV-1317, 5 Pages {Document 0240}.
Letter to Judge Robinson re Jury Instructions Dated and Filed Mar. 13, 2016 in *Amgen Inc.*, v. *Sanofi*, in the United States District Court for the District of Delaware, C.A. No. 14-CV-1317, 3 Pages {Document 0292}.
Letter to Judge Robinson re Court's Directive Dated and Filed Mar. 14, 2016 in *Amgen Inc.*, v. *Sanofi*, in the United States District Court for the District of Delaware, C.A. No. 14-CV-1317, 51 Pages {Document 0297}.
Memorandum Order Dated and Filed Feb. 18, 2016 in *Amgen Inc.*, v. *Sanofi*, in the United States District Court for the District of Delaware, C.A. No. 14-CV-1317, 5 Pages {Document 0226}.
Memorandum Order Dated and Filed Mar. 2, 2016 in *Amgen Inc.*, v. *Sanofi*, in the United States District Court for the District of Delaware, C.A. No. 14-CV-1317, 4 Pages {Document 0249}.
Memorandum Order Dated and Filed Mar. 2, 2016 in *Amgen Inc.*, v. *Sanofi*, in the United States District Court for the District of Delaware, C.A. No. 14-CV-1317, 10 Pages {Document 0250}.
Memorandum Order Dated and Filed Mar. 7, 2016 in *Amgen Inc.*, v. *Sanofi*, in the United States District Court for the District of Delaware, C.A. No. 14-CV-1317, 3 Pages {Document 0264}.
Memorandum Order Dated and Filed Mar. 7, 2016 in *Amgen Inc.*, v. *Sanofi*, in the United States District Court for the District of Delaware, C.A. No. 14-CV-1317, 2 Pages {Document 0269}.
Memorandum Order Dated and Filed Mar. 16, 2016 in *Amgen Inc.*, v. *Sanofi*, in the United States District Court for the District of Delaware, C.A. No. 14-CV-1317, 3 Pages {Document 0302}.

Opening Brief in Support of Motion for Summary Judgment as a Matter of Law on Written Description and Enablement Dated and Filed Apr. 15, 2016 in *Amgen Inc.*, v. *Sanofi*, in the United States District Court for the District of Delaware, C.A. No. 14-CV-1317, 26 Pages {Document 0333}.
Proposed Final Jury Instructions Dated and Filed Feb. 17, 2016 in *Amgen Inc.*, v. *Sanofi*, in the United States District Court for the District of Delaware, C.A. No. 14-CV-1317, 97 Pages {Document 0224}.
Proposed Preliminary Jury Instructions Filed Feb. 17, 2016 in *Amgen Inc.*, v. *Sanofi*, in the United States District Court for the District of Delaware, C.A. No. 14-CV-1317, 11 Page {Document 0223}.
Reply Memorandum in Support of Amgen's Daubert Motion to Exclude Testimony on (1) Post-Priority Date Embodiments/Antibodies of the Selected Claims and (2) Defendants' Expert Opinions as to the Patent's Disclosure of Representative Species, Dated Feb. 12, 2016 in *Amgen Inc.*, v. *Sanofi*, in the United States District Court for the District of Delaware, C.A. No. 14-CV-1317, 15 Pages {Document 0208}.
Sanofi Regeneron's Final Invalidity Contentions Dated Nov. 2, 2015 in *Amgen Inc.*, v. *Sanofi*, in the United States District Court for the District of Delaware, C.A. No. 14-CV-1317, 60 Pages.
Transcript of Pre-Trial Conference Dated Feb. 22, 2016 in *Amgen Inc.*, v. *Sanofi*, in the United States District Court for the District of Delaware, C.A. No. 14-CV-1317, 49 Pages.
Trial Transcript Verdict Mar. 16, 2016, *Amgen v. Sanofi* CA No. 14-1317-SLR, Minuscript Dated Mar. 16, 2016 in *Amgen Inc.*, v. *Sanofi*, in the United States District Court for the District of Delaware, C.A. No. 14-CV-1317, 18 Pages.
Declaration of Shane G. Smith in Support of Amgen's Daubert Motion to Exclude Testimony on (1) Post-Priority Date Embodiments/Antibodies of the Selected Claims and (2) Defendants' Expert Opinions as to the Patent's Disclosure of Representative Species, Redacted Public Version Dated Feb. 8, 2016 in *Amgen Inc.*, v. *Sanofi*, in the United States District Court for the District of Delaware, C.A. No. 14-CV-1317, 45 Pages {Document 0196}.
Declaration of Jonathan J. Underwood in Support of Defendants' Motion to Exclude Certain Expert Testimony from Plaintiff on Written Description and Reasonable Royalties Dated Feb. 9, 2016 in *Amgen Inc.*, v. *Sanofi*, in the United States District Court for the District of Delaware, C.A. No. 14-CV-1317, 4 Pages {Document 0200}.
Plaintiffs' Response to Defendant's Evidentiary Issues 12 and 13, Redacted Public Version Dated Mar. 22, 2016 in *Amgen Inc.*, v. *Sanofi*, in the United States District Court for the District of Delaware, C.A. No. 14-CV-1317, 5 Pages {Document 0319}.
Amgen's Response to Defendants' Evidentiary Issue 14 Dated Feb. 26, 2016 in *Amgen Inc.*, v. *Sanofi*, in the United States District Court for the District of Delaware, C.A. No. 14-CV-1317, 1 Page {Document 0242-2}.
Office Action dated Jun. 23, 2016 in U.S. Appl. No. 13/494,912.
Office Action dated Jun. 27, 2016 in U.S. Appl. No. 14/459,844.
Office Action dated Jun. 29, 2016 in U.S. Appl. No. 14/562,546.
Notice of Allowance dated Jun. 30, 2016 received in U.S. Appl. No. 14/459,787.
Office Action dated Aug. 1, 2016 in U.S. Appl. No. 13/931,716.
Office Action dated Jul. 28, 2016 in U.S. Appl. No. 13/742,205 (Merck).
U.S. Appl. No. 13/469,032, filed May 10, 2012, Chan et al.
U.S. Appl. No. 13/931,716, filed Jun. 28, 2013, Chan et al.
U.S. Appl. No. 13/422,904, filed Mar. 16, 2012, Jackson et al.
U.S. Appl. No. 13/656,392, filed Oct. 19, 2012, Jackson et al.
U.S. Appl. No. 13/682,698, filed Nov. 20, 2012, Jackson et al.
U.S. Appl. No. 13/860,016, filed Apr. 10, 2013, Jackson et al.
International Search Report for corresponding PCT Application No. PCT/US2012/037394, dated Jul. 5, 2012.
Written Opinion for corresponding PCT Application No. PCT/US2012/037394, dated Jul. 5, 2012.
Brunner et al., "Expression and prognostic significance of Tetranectin in invasive and non-invasive bladder cancer", Virchows Archiv, vol. 450, No. 6, pp. 659-664 (Apr. 13, 2007).

(56) References Cited

OTHER PUBLICATIONS

Davignon, et al. "Statins and Ezetimibe Modulate Plasma Proprotein Convertase Subtilisin Kexin-9 (PCSK9) Levels". Transactions of The American Clinical and Climatological Association, vol. 120, pp. 163-173 (2009).

Office Action dated Sep. 30, 2016, 2016 in U.S. Appl. No. 13/682,698.

Office Action dated Oct. 5, 2016, 2016 in U.S. Appl. No. 14/459,777.

Examiner's Answer dated Jun. 1, 2017 in U.S. Appl. No. 13/422,904.

Office Action dated Jun. 5, 2017 in U.S. Appl. No. 14/316,587.

Office Action dated May 15, 2017 in U.S. Appl. No. 13/931,716.

The 1$^{st}$ Oral Hearing Record dated Feb. 24, 2017 in the Invalidation Trial against JP 5705288 (with English Translation).

The 1$^{st}$ Oral Hearing Record dated Feb. 24, 2017 in the Invalidation Trial against JP 5906333 (with English Translation).

Petition Regarding Oral Hearing Brief by Demandee dated Feb. 21, 2017 in the Invalidation Trial against JP 5906333 (with English Translation).

Petition Regarding Oral Hearing Brief by Demandee dated Feb. 21, 2017 in the Invalidation Trial against JP 5705288 (with English Translation).

Advance Notice of Trial Decision dated Mar. 9, 2017 in the Invalidation Trial against JP 5705288 (with English Translation).

Advance Notice of Trial Decision dated Mar. 9, 2017 in the Invalidation Trial against JP 5906333 (with English Translation).

Stipulated Order dated Feb. 22, 2016 in in *Amgen Inc.*, v. *Sanofi*, in the United States District Court for the District of Delaware, C.A. No. 14-CV-1317, 3 Pages {Document 0235}.

Memorandum Opinion dated Jan. 3, 2017 in in *Amgen Inc.*, v. *Sanofi*, in the United States District Court for the District of Delaware, C.A. No. 14-CV-1317, 29 Pages {Document 0389}.

Final Judgment dated Jan. 3, 2017 in in *Amgen Inc.*, v. *Sanofi*, in the United States District Court for the District of Delaware, C.A. No. 14-CV-1317, 1 Page {Document 0391}.

Memorandum Order dated Jan. 5, 2017 in in *Amgen Inc.*, v. *Sanofi*, in the United States District Court for the District of Delaware, C.A. No. 14-CV-1317, 7 Pages {Document 0392}.

Attwood, The Babel of Bioinformatics, Science 290: 471-473, 2000.

Carter, Potent antibody therapeutics by design, Nature Reviews Immunology, vol. 6, pp. 343-357, May 2006.

Cohen, et al., Combination Therapy Enhances the Inhibition of Tumor Growth with the Fully Human Anti-Type 1 Insulin-Like Growth Factor Receptor Monoclonal Antibody CP-751, 871, Clinical Cancer Research, vol. 11, pp. 2063-2073, Mar. 1, 2005.

English translation of Refutation 1 filed by Sanofi on Sep. 5, 2016 in the Invalidation Trial against JP 5705288.

English translation of Refutation 2 filed by Sanofi on Sep. 5, 2016 in the Invalidation Trial against JP 5705288.

English translation of Written Answer filed by Amgen on Sep. 15, 2016 in the Invalidation Trial against JP 5906333.

U.S. Appl. No. 60/982,922, filed Oct. 26, 2007, Schering Corporation.

English translation of Written Demand for Correction filed by Amgen on Sep. 15, 2016 in the Invalidation Trial against JP 5906333.

Hoogenboom, Selecting and screening recombinant antibody libraries, Nature Biotechnology, vol. 23, No. 9, pp. 1105-1116, Sep. 2005.

McCafferty, et al., Construction and Screening of Antibody Display Libraries, Chapter 6, pp. 79-111, Phage Display of Peptides and Proteins, Kay et al. (Eds), Academic Press Inc., 1996.

Office Action dated Aug. 1, 2016 in Chinese Patent Application No. 201410219429.X (with English Translation).

Office Action dated Aug. 1, 2016 in Chinese Patent Application No. 201410218704.6 (with English Translation).

Office Action dated Jul. 25, 2016 and listing of pending claims in European Patent Application No. 07 870 839.3 (Merck).

Opposition in European Patent App. No. 08798550.3, submitted Nov. 24, 2016 (Sanofi), including listed documents D33 and D34, and a summary translation of D33, in 64 pages. References D12 and D14 in this document are not submitted because they are already of record.

Opposition in European Patent App. No. 08798550.3, submitted Nov. 24, 2016 (Sanofi-Aventis Deutschland GmbH, Sanofi-Aventis Groupe S.A., Sanofi Winthrop Industries S.A.), including listed documents D33 and D34, and a summary translation of D33, in 114 pages. References D1-D14, D14a, D15-D21, D21a, D21b, D22, D22a, D23-D32, PA and PB in this document are not submitted because they are already of record.

Opposition in European Patent App. No. 08798550.3, submitted Nov. 24, 2016 (Regeneron Pharmaceutical, Inc.), including listed document D22 in 70 pages. References D1-D10, D10a, D11-D19, D19a, D19b, D20, D21, D23-D26, D29 and D34 in this document are not submitted because they are already of record.

Opposition in European Patent App. No. 08798550.3, submitted Nov. 24, 2016 (Eli Lilly and Company), including listed documents D34-D38, in 72 pages. References D1-D14, D14a, D15-D21, D21a, D21b, D22, D22a, D23-D33 and PA in this document are not submitted because they are already of record.

Opposition in European Patent App. No. 08798550.3, submitted Nov. 22, 2016 (Strawman Limited), in 34 pages. References D1-D14, D14a, D15-D21, D21a, D22-D32, PA and PB in this document are not submitted because they are already of record.

Response to Office Action and Amendment dated Jul. 25, 2016 in U.S. Appl. No. 14/100,992 (Regeneron).

Search Report dated Jul. 18, 2016 in Chinese Patent App. 201410219429.X (with English translation).

Search Report dated Jul. 18, 2016 in Chinese Patent App. 201410218704.6 (with English translation).

Skolnick, From genes to protein structure and function: novel applications to computational approaches in the genomic era, Tibtech 18: 34-39, 2000.

Third Party Observations filed Oct. 10, 2016 regarding European Patent Application No. EP20070870839.

Trial Brief dated May 31, 2016 in Invalidation Trial against Japanese Patent No. 5906333 (with English translation).

Yang, et al., Fully human anti-interleukin-8 monoclonal antibodies: potential therapeutics for the treatment of inflammatory disease states, Journal of Leukocyte Biology, vol. 66, pp. 401-410, Sep. 1999.

Appellants' Opening Brief, Dated Feb. 17, 2017 in *Amgen Inc.*, v. *Sanofi*, in the United States Court of Appeals for the Federal Circuit C.A. No. 17-1480, On Appeal from the United States District of Delaware C.A. No. 14-CV-1317, 118 Pages {Document 062}.

Office Action dated Jan. 9, 2018 in Japanese Patent Application No. 2017-065349 (with English translation).

Office Action dated Jan. 25, 2018 in U.S. Appl. No. 14/316,587.

Office Action dated Feb. 7, 2018 in U.S. Appl. No. 13/494,912.

Office Action dated Feb. 8, 2018 in U.S. Appl. No. 13/619,555.

Office Action dated Feb. 12, 2018 in U.S. Appl. No. 13/682,698.

Office Action dated Nov. 6, 2017 in Israeli Application No. 229276 (with English Translation).

Supplemental Declaration of Jonathan J. Underwood in Support of Defendants Reply Brief in Support of Motion to Exclude Certain Expert Testimony From Plaintiff on Written Description and Reasonable Roy, Filed Feb. 19, 2016 in *Amgen Inc.*, v. *Sanofi*, in the United States District Court for the District of Delaware, C.A. No. 14-CV-1317, 22 Pages {Document 0228}.

Second Declaration of James L. Higgins in Support of Amgen's Motion to Exclude Expert Testimony of Ashley J. Stevens, Filed Feb. 19, 2016 in *Amgen Inc.*, v. *Sanofi*, in the United States District Court for the District of Delaware, C.A. No. 14-CV-1317, 26 Pages {Document 0230}.

Plaintiffs' One Page Memorandum Regarding Offer of Proof of Dr. Leonard Schleifer, Filed Mar. 2, 2016 in *Amgen Inc.*, v. *Sanofi*, in the United States District Court for the District of Delaware, C.A. No. 14-CV-1317, 8 Pages {Document 0248}.

Defendants Opening Submission Regarding Evidentiary Issues 10-13, Filed Mar. 4, 2016 in *Amgen Inc.*, v. *Sanofi*, in the United States District Court for the District of Delaware, C.A. No. 14-CV-1317, 40 Pages {Document 0254}.

(56)　　　　　References Cited

OTHER PUBLICATIONS

Defendants Responses to Plaintiffs Evidentiary Issues 1 and 2, and 5; Filed Mar. 7, 2016 in *Amgen Inc.*, v. *Sanofi*, in the United States District Court for the District of Delaware, C.A. No. 14-CV-1317, 4 Pages {Document 0262}.

Letter to Judge Robinson Re Prior Art Issue, Filed Mar. 13, 2016 in *Amgen Inc.*, v. *Sanofi*, in the United States District Court for the District of Delaware, C.A. No. 14-CV-1317; 5 Pages {Document 0284}.

Reply Brief in Support of Defendants Motion for Judgment as a Matter of Law on Written Description and Enablement, Filed May 12, 2016 in *Amgen Inc.*, v. *Sanofi*, in the United States District Court for the District of Delaware, C.A. No. 14-CV-1317, 16 Pages {Document 0361}.

Defendant's Brief in Opposition to Plaintiffs' Motion for a Permanent Injunction, Filed May 18, 2016 in *Amgen Inc.*, v. *Sanofi*, in the United States District Court for the District of Delaware, C.A. No. 14-CV-1317, 39 Pages {Document 0363}.

Plaintiffs' Answering Brief in Opposition to Defendants' Motion for a New Trial, Filed May 18, 2016 in *Amgen Inc.*, v. *Sanofi*, in the United States District Court for the District of Delaware, C.A. No. 14-CV-1317, 37 Pages {Document 0364}.

Appendix to Plaintiffs' Answering Brief in Opposition to Defendants' Motion for a New Trial, Filed May 18, 2016 in *Amgen Inc.*, v. *Sanofi*, in the United States District Court for the District of Delaware, C.A. No. 14-CV-1317, 20 Pages {Document 0365}.

Corrected Opening Brief in Support of Defendants Motion for Judgment as a Matter of Law On, Filed May 23, 2016 in *Amgen Inc.*, v. *Sanofi*, in the United States District Court for the District of Delaware, C.A. No. 14-CV-1317, 26 Pages {Document 0367}.

Corrected Reply Brief in Support of Defendants Motion for Judgment as a Matter of Law on Written Description and Enablement, Filed May 23, 2016 in *Amgen Inc.*, v. *Sanofi*, in the United States District Court for the District of Delaware, C.A. No. 14-CV-1317, 16 Pages {Document 0370}.

Corrected Opening Brief in Support of Defendants' Motion for a New Trial, Filed May 24, 2016 in *Amgen Inc.*, v. *Sanofi*, in the United States District Court for the District of Delaware, C.A. No. 14-CV-1317, 37 Pages {Document 0372}.

Corrected Defendants' Brief in Opposition to Plaintiffs' Motion for a Permanent Injunction, Filed May 24, 2016 in *Amgen Inc.*, v. *Sanofi*, in the United States District Court for the District of Delaware, C.A. No. 14-CV-1317, 38 Pages {Document 0373}.

Plaintiffs' Corrected Opening Brief in Support of Motion for Permanent Injunctive Relief, Filed Jun. 6, 2016 in *Amgen Inc.*, v. *Sanofi*, in the United States District Court for the District of Delaware, C.A. No. 14-CV-1317, 36 Pages {Document 0382}.

Joint Exhibit List, Filed Jun. 15, 2016 in *Amgen Inc.*, v. *Sanofi*, in the United States District Court for the District of Delaware, C.A. No. 14-CV-1317, 9 Pages {Document 0384}.

Order, Filed Jan. 3, 2017 in *Amgen Inc.*, v. *Sanofi*, in the United States District Court for the District of Delaware, C.A. No. 14-CV-1317, 1 Page {Document 0390}.

Transcript Markman Hearing, Filed Feb. 8, 2017 in *Amgen Inc.*, v. *Sanofi*, in the United States District Court for the District of Delaware, C.A. No. 14-CV-1317, 112 Pages {Document 0411}.

Status Conference, Filed Feb. 8, 2017 in *Amgen Inc.*, v. *Sanofi*, in the United States District Court for the District of Delaware, C.A. No. 14-CV-1317, 68 Pages {Document 0413}.

Defendants Brief in Support of Their Motion to Stay the Permanent Injunction Pending Appeal, Filed Feb. 20, 2017 in *Amgen Inc.*, v. *Sanofi*, in the United States District Court for the District of Delaware, C.A. No. 14-CV-1317, 26 Pages {Document 0417}.

Declaration of Robert H. Eckel, M.D., Filed Feb. 20, 2017 in *Amgen Inc.*, v. *Sanofi*, in the United States District Court for the District of Delaware, C.A. No. 14-CV-1317, 10 Pages {Document 0418}.

Declaration of James L. Higgins in Support of Amgen's Motion to Amend Final Rule 54(b) Judgment (D.I. 391) Under Fed. R. Civ. P. 59(e) and 35 U.S.C. § 284 to Include an Accounting and Enhancement Determination Following Appeal, Filed Feb. 24, 2017 in

*Amgen Inc.*, v. *Sanofi*, in the United States District Court for the District of Delaware, C.A. No. 14-CV-1317, 51 Pages {Document 0426}.

Brief of Amicus Curiae, Eli Lilly and Company, Supporting Defendants-Appellants, Filed Feb. 23, 2017 in *Amgen Inc.*, v. *Sanofi*, in the United States Court of Appeals for the Federal Circuit, C.A. No. 17-1480, 36 Pages {Document 0073}.

Brief for Amici Curiae AARP and AARP Foundation in Support of Defendants-Appellants and Arguing for Reversal of Permanent Injunction, Filed Feb. 23, 2017 in *Amgen Inc.*, v. *Sanofi*, in the United States Court of Appeals for the Federal Circuit, C.A. No. 17-1480, 19 Pages {Document 0078}.

Motion of Amici Curiae Dr. Luis Aparicio, MD; Dr. W. Ross Davis, MD; Dr. Avichai Eres, MD; Dr. Norman Lepor, MD; Dr. Mary McGowan, MD; Dr. Narendra Singh, MD; Dr. Paul Thompson, MD; Rosa Debernardo; and Alina Wilson for Leave to File Amicus Curiae Brief, Filed Feb. 24, 2017 in *Amgen Inc.*, v. *Sanofi*, in the United States Court of Appeals for the Federal Circuit, C.A. No. 17-1480, 43 Pages {Document 0086}.

Brief of Amici Curiae Pfizer Inc. and Ipsen Pharma S.A.S. in Support of Defendants-Appellants and Reversal of the District Court's Decision on Written Description, Filed Feb. 24, 2017 in *Amgen Inc.*, v. *Sanofi*, in the United States Court of Appeals for the Federal Circuit, C.A. No. 17-1480, 34 Pages {Document 0092}.

Notice of Correction, Filed Mar. 3, 2017 in *Amgen Inc.*, v. *Sanofi*, in the United States Court of Appeals for the Federal Circuit, C.A. No. 17-1480, 9 Pages {Document 0104}.

Amgen's Opposition to Proposed Amici Providers' and Patients' Motion for Leave to File Amicus Curiae, Filed Mar. 6, 2017 in *Amgen Inc.*, v. *Sanofi*, in the United States Court of Appeals for the Federal Circuit, C.A. No. 17-1480, 120 Pages {Document 0108-1 through 108-8}.

Reply Memorandum in Further Support of Motion for Leave to File Amici Curiae Brief, Filed Mar. 9, 2017 in *Amgen Inc.*, v. *Sanofi*, in the United States Court of Appeals for the Federal Circuit, C.A. No. 17-1480, 19 Pages {Document 0113}.

Brief for Amici Curiae Dr. Luis Aparicio, MD; Dr. W. Ross Davis, MD; Dr. Avichai Eres, MD; Dr. Norman Lepor, MD; Dr. Mary Mcgowan, MD; Dr. Narendra Singh, MD; Dr. Paul Thompson, MD; Rosa Debernardo; and Alina Wilson in Support of Defendants-Appellants and Arguing to Vacate the Permanent Injunction, Filed Mar. 22, 2017 in *Amgen Inc.*, v. *Sanofi*, in the United States Court of Appeals for the Federal Circuit, C.A. No. 17-1480, 32 Pages {Document 0116}.

Brief of Plaintiffs-Appellees, Filed Mar. 24, 2017 in *Amgen Inc.*, v. *Sanofi*, in the United States Court of Appeals for the Federal Circuit, C.A. No. 17-1480, 98 Pages {Document 0119}.

Brief of Amicus Curiae in Support of Appellees, Filed Mar. 30, 2017 in *Amgen Inc.*, v. *Sanofi*, in the United States Court of Appeals for the Federal Circuit, C.A. No. 17-1480, 35 Pages {Document 0125}.

Reply Brief for Defendants-Appellants, Filed Mar. 31, 2017 in *Amgen Inc.*, v. *Sanofi*, in the United States Court of Appeals for the Federal Circuit, C.A. No. 17-1480, 43 Pages {Document 0130}.

Amgen's Petition for Rehearing En Banc, Filed Dec. 6, 2017 in *Amgen Inc.*, v. *Sanofi*, in the United States Court of Appeals for the Federal Circuit, C.A. No. 17-1480, 55 Pages {Document 0163}.

Office Action dated Apr. 13, 2018 in U.S. Appl. No. 13/469,032.

Office Action dated Apr. 20, 2018 in U.S. Appl. No. 14/459,777.

U.S. Appl. No. 61/096,716, filed Sep. 12, 2008, Rinat Neuroscience Corp./Pfizer.

U.S. Appl. No. 61/122,482, filed Dec. 15, 2008, Regeneron.

U.S. Appl. No. 61/210,566, filed Mar. 18, 2009, Regeneron.

U.S. Appl. No. 61/168,753, filed Apr. 13, 2009, Regeneron.

U.S. Appl. No. 61/218,136, filed Jun. 18, 2009, Regeneron.

U.S. Appl. No. 61/232,161, filed Aug. 7, 2009, Rinat Neuroscience Corp./Pfizer.

U.S. Appl. No. 61/235,643, filed Aug. 20, 2009, Rinat Neuroscience Corp./Pfizer.

U.S. Appl. No. 61/245,691, filed Sep. 25, 2009, Merck.

U.S. Appl. No. 61/249,135, filed Oct. 6, 2009, Regeneron.

U.S. Appl. No. 61/256,720, filed Oct. 30, 2009, Merck.

U.S. Appl. No. 61/256,732, filed Oct. 30, 2009, Merck.

U.S. Appl. No. 61/261,776, filed Nov. 17, 2009, Regeneron.

(56)　　　　　References Cited

OTHER PUBLICATIONS

U.S. Appl. No. 61/285,942, filed Dec. 11, 2009, Novartis.
U.S. Appl. No. 61/323,117, filed Apr. 12, 2010, Merck.
U.S. Appl. No. 61/323,148, filed Apr. 12, 2010, Merck.
U.S. Appl. No. 61/405,938, filed Oct. 22, 2010, Schering.
U.S. Appl. No. 61/426,343, filed Dec. 22, 2010, Genentech, Inc.
U.S. Appl. No. 61/477,788, filed Apr. 21, 2011, Genentech, Inc.
U.S. Appl. No. 61/495,548, filed Jun. 10, 2011, Novartis.
U.S. Appl. No. 61/507,865, filed Jul. 14, 2011, Pfizer, Inc.
U.S. Appl. No. 61/512,666, filed Jul. 28, 2011, Regeneron.
U.S. Appl. No. 61/535,625, filed Sep. 16, 2011, Eli Lilly.
U.S. Appl. No. 61/535,392, filed Sep. 16, 2011, Regeneron.
U.S. Appl. No. 61/559,162, filed Nov. 14, 2011, Regeneron.
U.S. Appl. No. 61/614,312, filed Mar. 22, 2012, Pfizer, Inc.
U.S. Appl. No. 61/617,615, filed Mar. 29, 2012, Genentech, Inc.
U.S. Appl. No. 61/641,321, filed May 2, 2012, Regeneron.
U.S. Appl. No. 61/643,063, filed May 4, 2012, Pfizer, Inc.
U.S. Appl. No. 61/642,972, filed May 4, 2012, Genentech, Inc.
Daugherty et al., Formulation and delivery issues for monoclonal antibody therapeutics. Advanced Drug Delivery Reviews 58, pp. 686-706, 2006.
Evidence Explanatory filed Sep. 25, 2017 by Sanofi K.K. in Japanese Case No. 2017 (Wa) No. 16468: Case of seeking injunction of patent infringement (with English translation).
Evidence Explanatory filed Nov. 6, 2017 by Sanofi K.K. in Japanese Case No. 2017 (Wa) No. 16468: Case of seeking injunction of patent infringement (with English translation).
Defendant's First Brief filed Sep. 25, 2017 by Sanofi K.K. in Japanese Case No. 2017 (Wa) No. 16468: Case of seeking injunction of patent infringement (with English translation).
Defendant's Second Brief filed Sep. 25, 2017 by Sanofi K.K. in Japanese Case No. 2017 (Wa) No. 16468: Case of seeking injunction of patent infringement (with English translation).
Defendant's Third Brief filed Nov. 6, 2017 by Sanofi K.K. in Japanese Case No. 2017 (Wa) No. 16468: Case of seeking injunction of patent infringement (with English translation).
U.S. Appl. No. 61/644,065, filed May 8, 2012, Alder Bio.
U.S. Appl. No. 61/654,481, filed Jun. 1, 2012, Alder Bio.
Further Submissions Against EP 2215124 dated Oct. 9, 2017 by Regeneron Pharmaceuticals, in Opposition against European Patent No. EP 2215124.
Kamerzell et al., Increasing IgG Concentration Modulates the Conformational Heterogeneity and Bonding Network that Influence Solution Properties. J. Phys. Chem. B 113, pp. 6109-6118, 2009.
Notice of Allowance dated Sep. 29, 2017 received in U.S. Appl. No. 13/174,423.
Office Action dated Apr. 4, 2017 in U.S. Appl. No. 13/422,887.
Office Action dated Apr. 4, 2017 in U.S. Appl. No. 13/463,751.
Office Action dated Apr. 7, 2017 in U.S. Appl. No. 14/487,932.
Office Action dated Apr. 13, 2017 in U.S. Appl. No. 14/459,844.
Office Action dated Apr. 14, 2017 in U.S. Appl. No. 14/562,546.
Office Action dated Aug. 24, 2017 in U.S. Appl. No. 12/903,084.
Office Action dated Aug. 30, 2017 in Malaysian Patent App. No. PI 2013004036.
Office Action dated Jun. 29, 2017 in U.S. Appl. No. 13/494,912.
Office Action dated Jun. 29, 2017, received in U.S. Appl. No. 13/619,555.
Office Action dated Jun. 30, 2017 in U.S. Appl. No. 13/469,032.
Office Action dated Sep. 22, 2017 in U.S. Appl. No. 13/655,984.
Brief of Sanofi Dated Aug. 21, 2017 in Litigation of *Amgen Inc.* vs. *Sanofi-Aventis Deutschland GmbH, et al.* in Regional Court of Dusseldorf.
Submissions Dated Aug. 21, 2017 Filed in Litigation of *Amgen Inc.* vs. *Sanofi-Aventis Deutschland GmbH, et al.* in Regional Court of Dusseldorf as item HE 24 including submitted documents D102-D116.
Item HE 25 dated Aug. 21, 2017 in Litigation of *Amgen Inc.* vs. *Sanofi-Aventis Deutschland GmbH, et al.* in Regional Court of Dusseldorf.

The 1st Brief Dated Jun. 29, 2017 in Case No. 2017 (Wa) No. 16468 The Case Seeking Injunction of Patent Right *Amgen Inc.* v. *Sanofi K.K*, (in Japan).
Trial Decision Dated Aug. 10, 2017 Filed as Exhibit 12-1 in Case No. 2017 (Wa) No. 16468 The Case Seeking Injunction of Patent Right *Amgen Inc.* v. *Sanofi K.K* (in Japan).
Trial Decision Dated Aug. 10, 2017 Filed as Exhibit Exhibit 12-2 in Case No. 2017 (Wa) No. 16468 The Case Seeking Injunction of Patent Right *Amgen Inc.* v. *Sanofi K.K* (in Japan).
Declaration of Thomas U. Schwartz Dated Nov. 5, 2017 Filed as Exhibit B No. 4 in Case No. 2017 (Wa) No. 16468 The Case Seeking Injunction of Patent Right *Amgen Inc.* v. *Sanofi K.K* (in Japan.
Declaration of Chadwick King Dated Jan. 30, 2017 Filed as Exhibit Exhibit 13 in Case No. 2017 (Wa) No. 16468 The Case Seeking Injunction of Patent Right *Amgen Inc.* v. *Sanofi K.K* (in Japan).
Evidence Explanatory Dated Feb. 10, 2017 in Case No. 2017 (Wa) No. 16468 The Case Seeking Injunction of Patent Right *Amgen Inc.* v. *Sanofi K.K*, (in Japan).
Decision to Stay Dated Jul. 20, 2017 in Australian Patent Opposition of Australian Application No. 2013203748 (to Applicant).
Decision to Stay Dated Jul. 20, 2017 in Australian Patent Opposition of Australian Application No. 2013203748 (to Opponent).
Direction Proposal Dated Jul. 6, 2017 in Australian Patent Opposition of Australian Application No. 2013203748 (to Applicant).
Direction Proposal Dated Jul. 6, 2017 in Australian Patent Opposition of Australian Application No. 2013203748 (to Opponent).
Opponent's Response Dated Jun. 14, 2017 in Australian Patent Opposition of Australian Application No. 2013203748.
Allowed Claims Dated Dec. 1, 2016 in Australian Patent Application No. 2013203748.
Notice of Opposition Dated Apr. 3, 2017 in Australian Patent Application No. 2013203748.
Applicant's Request to Stay in the Opposition Proceedings Dated Dec. 1, 2016 in Australian Patent Application No. 2013203748.
Applicant's Voluntary Amendments of the Specification Dated Dec. 1, 2016 in Australian Patent Application No. 2013203748.
Declaration of Stephen Michael Mahler Dated Oct. 24, 2016 in Australian Patent Opposition of Australian Application No. 2013203748.
Statement of Grounds and Particulars Dated Aug. 2, 2016 in Australian Application No. 2013203748.
Notice of Opposition Dated May 2, 2016 in Australian Application No. 2013203748.
Office Action dated Dec. 5, 2014 in Australian Application No. 2013203748.
Office Action dated Dec. 19, 2014 in Australian Application No. 2013203748.
Opponent Letter Dated Aug. 1, 2017 in Opposition to Australian Application No. 2013203689.
Declaration of Stephen Michael Mahler Dated May 12, 2017 in Australian Patent Opposition of Australian Application No. 2013203689.
Declaration of Michael Parker Dated May 15, 2017 in Australian Patent Opposition of Australian Application No. 2013203689.
Notice of Opposition Dated Nov. 11, 2016 in Australian Application No. 2013203689.
Office Action dated Nov. 24, 2014 in Australian Application No. 2013203689.
Office Action dated Jul. 8, 2016 in Australian Application No. 2013203689.
Opponent Letter Dated Aug. 1, 2017 in Opposition to Australian Application No. 2013203751.
Declaration of Stephen Michael Mahler Dated Jun. 22, 2017 in Australian Patent Opposition of Australian Application No. 2013203751.
Declaration of Michael Parker Dated Jun. 22, 2017 in Australian Patent Opposition of Australian Application No. 2013203751.
Notice of Opposition Dated Dec. 22, 2016 in Australian Application No. 2013203751.
Office Action dated Dec. 9, 2014 in Australian Application No. 2013203751.
Declaration of Stephen Michael Mahler Dated May 12, 2017 in Australian Patent Opposition of Australian Application No. 2013203685.
Statement of Grounds and Particulars Dated Feb. 13, 2017 in Australian Application No. 2013203685.

(56) References Cited

OTHER PUBLICATIONS

Notice of Opposition Dated Nov. 11, 2016 in Australian Application No. 2013203685.
Office Action dated Nov. 17, 2014 in Australian Application No. 2013203685.
Office Action dated Jan. 15, 2015 in Australian Application No. 2013203685.
Office Action dated Jul. 6, 2016 in Australian Application No. 2013203685.
Opponent Letter Dated Aug. 1, 2017 in Opposition to Australian Application No. 2013203677.
Direction Proposal Dated Jul. 6, 2017 in Australian Patent Opposition of Australian Application No. 2013203677 (to Applicant).
Direction Proposal Dated Jul. 6, 2017 in Australian Patent Opposition of Australian Application No. 2013203677 (to Opponent).
Opponent's Response Dated Aug. 10, 2017 in Australian Patent Opposition of Australian Application No. 2013203677.
Declaration of Stephen Michael Mahler Dated Oct. 14, 2016 in Australian Patent Opposition of Australian Application No. 2013203677.
Statement of Grounds and Particulars Dated Jul. 18, 2016 in Australian Application No. 2013203677.
Notice of Opposition Dated Apr. 14, 2016 in Australian Application No. 2013203677.
Office Action dated Jan. 15, 2015 in Australian Application No. 2013203677.
Office Action dated Dec. 8, 2014 in Australian Application No. 2013203677.
Statement of Grounds and Particulars Dated Feb. 13, 2017 in Australian Application No. 2013203689.
Proprietor's Observations regarding the Notice of Opposition, dated May 2, 2017 in Opposition against European Patent No. EP 2215124.
Further Submissions Against EP 2215124 by Regeneron Pharmaceuticals, dated May 19, 2017 in Opposition against European Patent No. EP 2215124.
Further Objections by Sanofi-Aventis Group, dated May 26, 2017 in Opposition against European Patent No. EP 2215124.
Proprietor's Response to Submissions of Opponent 4 and Opponent 5, dated Aug. 1, 2017 in Opposition against European Patent No. EP 2215124.
Expert Declaration by Prof. Edward A. Fisher, MD, Mph, PhD, dated Apr. 26, 2017, in Opposition against European Patent No. EP 2215124 (Document D90).
Declaration of Chi-Chien "Oscar" Pan, dated May 29, 2017 in Opposition against European Patent No. EP 2215124 (Document D91).
Declaration by Prof. Anthony R. Rees, D.Phil., dated Apr. 26, 2017 in Opposition against European Patent No. EP 2215124, including Figures 1, 2 & 4 (Document D89).
Declaration by Prof. Anthony R. Rees, D.Phil., dated Aug. 1, 2017 in Opposition against European Patent No. EP 2215124 (Document D101).
Excerpt of German Complaint Dated Jul. 26, 2016 in Litigation of *Amgen Inc.* vs. *Sanofi-Aventis Deutschland GmbH, et al.* in Regional Court of Dusseldorf (Cited as Document D33 in Opposition against European Patent No. EP 2215124).
Deposit PBD accession code "2xtj" and Amino Acid Sequences from the Protein Data Bank Accessed Jun. 30, 2015 on the world wide web at www.rcsb.org/pdb/explore/explore.do?structureId=2xtj (Document D22a in Opposition against European Patent No. Ep 2215124).
World Health Organization, Cardiovascular diseases (CVDs) accessible on the world wide web at www.who.int/mediacentre/factsheets/fs317/en/ (Document D75 in Opposition against European Patent No. EP 2215124). This item lists a date of "Reviewed Sep. 2016." However, as the listed item refers to a web page, it may have been available, in some form, at an earlier point in time.
Stroes et al., "Statin-Associated Muscle Symptoms: Impact on Statin Therapy—European Atherosclerosis Society Consensus Panel Statement on Assessment, Aetiology and Management," European Heart Journal, 36, 1012-1022 (2015), (Document D76 in Opposition against European Patent No. EP 2215124).
Stein, "Other Therapies for Reducing Low-Density Lipoprotein Cholesterol: Medications in Development," Endocrinol Metab Clin N Am, 38, 99-119 (2009), (Document D77 in Opposition against European Patent No. EP 2215124).
Blom et al, "A 52-Week Placebo-Controlled Trial of Evolocumab in Hyperlipidemia," N Eng J Med, 370; 19, 1809-1819, (May 8, 2014), (Document D78 in Opposition against European Patent No. EP 2215124 ).
Stein, "Management of Dysilipidemia in the High-Risk Patient," American Heart Journal, vol. 144, No. 6, S43-S50, (Dec. 2002), (Document D79 in Opposition against European Patent No. EP 2215124).
Ito, et al., "Challenges in the Diagnosis and Treatment of Homozygous Familial Hypercholesterolemia," Drugs, 75, 1715-1724, (2015), (Document D80 in Opposition against European Patent No. EP 2215124).
Sando, et al., "Nonstatin Therapies for Management of Dyslipidemia: A Review," Clinical Therapeutics, vol. 37, No. 10, 2153-2179, (Oct. 2015), (Document D81 in Opposition against European Patent No. EP 2215124).
Selvarajah, et al, "Comparing Antigenicity and Immunogenicity of Engineered gp120," Journal of Virology, vol. 79, No. 19, p. 12148-12163, (Oct. 2005), (Document D83 in Opposition against European Patent No. EP 2215124).
Excerpt from Pharmacology/Toxicology NDA/BLA Review and Evaluation of Alirocumab (Praluent®); FDA BLA Appl. No. 125559; Executive Summary, p. 5, electronically signed Jan. 7, 2015. Accessible on the world wide web at www.accessdata.fda.gov/drugsatfda_docs/nda/2015/125559Orig1s000PharmR.pdf, (Document D84 in Opposition against European Patent No. EP 2215124 ).
Laver, et al, "Epitopes on Protein Antigens: Misconceptions and Realities," Cell Press, vol. 61, 553-556, (May 18, 1990), (Document D85 in Opposition against European Patent No. EP 2215124).
Pepscan, HiSense Linear Epitopes, accessible on the world wide web at pepscan.com/products-services/linear-epitopes/, capture from Apr. 26, 2014, as accessed on the world wide web at web.archive.org/web/20140426103616/http://pepscan.com/products-services/linear-epitopes (Document D86 in Opposition against European Patent No. EP 2215124).
Case Report—Precision Epitope Mapping of Human anti-SIRPα, accessible on the world wide web at www.pepscan.com/wp-cont4ent/uploads/2015/06/SIRPA_case-report-PDF.pdf. Submitted with Proprietor's Observations on May 2, 2017 in Opposition against European Patent No. EP 2215124. However, as this item is accessible on the world wide web, it may have been available in some form at an earlier point in time. (Document D87).
Baerga-Ortiz, et al., "Epitope Mapping of a Monoclonal Antibody Against Human Thrombin by H/D-Exchange Mass Spectrometry Reveals Selection of a Diverse Sequence in a Highly Conserved Protein," Protein Science, 11: 1300-1308, (2002), (Document D88 in Opposition against European Patent No. EP 2215124).
Twisk, et al, "The Role of the LDL Receptor in Apolipoprotein B. Secretion," The Journal of Clinical Investigation, vol. 105, No. 4, 521-532, (Feb. 2000), (Document D65 in Opposition against European Patent No. EP 2215124).
Gillian-Daniel, et al., "Endoplasmic Reticulum Localization of the Low Density Lipoprotein Receptor Mediates Presecretory Degradation of Apolipoprotein B," PNAS, vol. 99, No. 7, 4337-4342, (Apr. 2, 2002), (Document D66 in Opposition against European Patent No. EP 2215124).
Ouguerram, et al., "Apolipoprotein B100 Metabolism in Autosomal-Dominant Hypercholesterolemia Related to Mutations in PCSK9," Arterioscler Thromb Vasc Biol. 1448-1453 (Aug. 2004), (Document D68 in Opposition against European Patent No. EP 2215124).
Seidah, et al., "A Key Modulator of Cardiovascular Health," Circulation Research, 114: 1022-1036, (Mar. 14, 2014), (Document D73 in Opposition against European Patent No. EP 2215124).
PDB Statistics Search for Date Range Mar. 2007 to May 2007, Worldwide PDB Protein Data Bank, submitted with Proprietor's Observations on May 2, 2017 in Opposition against European

(56) References Cited

OTHER PUBLICATIONS

Patent No. EP 2215124. However, as this item refers to a web page, it may have been available in some form at an earlier point in time. (Document D97).

Strong et al Hepatic Sortilin Regulates Both Apolipoprotein B Secretion and LDL Catabolism;. J. Clin. Invest. 122(8): 2807-2816, (2012).

Amgen Press Release entitled "FDA Approves Amgen's Repatha® (evolocumab) to Prevent Heart Attack and Stroke" dated Dec. 1, 2017 accessed on the World Wide Web at www.prnewswire.com/news-releases/fda-approves-amgens-repatha-evolocumab-to-prevent-heart-attack-and-stroke-300565428.html; as this item refers to a webpage, it may have been available in some form at an earlier date.

Prescribing Information for Repatha® (evolocumab) injection, for subcutaneous use, dated Dec. 2017.

Office Action dated Feb. 27, 2018 in Peruvian Patent Application No. 002471-2013/DIN.

Decision dated Oct. 5, 2017 in *Amgen Inc.*, v. *Sanofi*, in the United States Court of Appeals for the Federal Circuit, C.A. No. 17-1480, 24 pages.

Office Action dated Nov. 8, 2018 in Costa Rican Patent Application No. 2013-0000640 (with English Translation).

Office Action dated Jan. 25, 2019 in U.S. Appl. No. 13/463,751.

Office Action dated Jan. 28, 2019 in U.S. Appl. No. 14/562,546.

Office Action dated May 2, 2019 in U.S. Appl. No. 14/316,587.

Examination Reported dated Jun. 12, 2019 in Indian Patent Application No. 10476/DELNP/2013.

Office Action dated Apr. 30, 2019 in Eurasian Application No. EA 201792336 (With English Translation).

First Examination Report dated Jan. 15, 2019 in New Zealand Patent Application No. 734570.

First Examination Report dated Jan. 16, 2019 in New Zealand Patent Application No. 717550.

Examination Report dated Nov. 21, 2018 in Gulf Coast Application No. GC 2012-22147.

Office Action dated Mar. 8, 2019 in U.S. Appl. No. 13/931,716.

Order Denying Amgen's Petition for Rehearing En Banc, Dated Feb. 23, 2018 in *Amgen Inc.*, v. *Sanofi*, in the United States Court of Appeals for the Federal Circuit, C.A. No. 17-1480, 2 Pages {Document 0178}.

Amgen's Petition for a Writ of Certiorari Dated Jul. 2018 in *Amgen Inc.*, v. *Sanofi* in the Supreme Court of the United States, 123 Pages.

Summons to Attend Oral Proceedings Pursuant to Rule 115 (1) EPC in European Patent Application No. 12722044.0 Dated Nov. 15, 2018; 7 pages.

Examination Report received in Australian Patent Application No. 2017232084 dated Nov. 22, 2018; 3 pages.

Office Action dated Jun. 18, 2018 in U.S. Appl. No. 14/562,546.

Office Action dated Jun. 21, 2018 in U.S. Appl. No. 13/422,887.

Summons to Attend Oral Proceedings Pursuant to Rule 115 (1) EPC in European Patent Application No. 08798550.3 Dated Dec. 13, 2017.

Reply Brief of Sanofi Dated Jan. 18, 2018 in Litigation of *Amgen Inc.* vs. *Sanofi-Aventis Deutschland GmbH, et al.* in Regional Court of Dusseldorf. (with English translation).

Reply Brief of Amgen Dated Jan. 31, 2018 in Litigation of *Amgen Inc.* vs. *Sanofi-Aventis Deutschland GmbH, et al.* in Regional Court of Dusseldorf (with English translation).

Defendant's Fourth Brief filed Dec. 14, 2017 by Sanofi K.K. in Japanese Case No. 2017 (Wa) No. 16468: Case of seeking injunction of patent infringement (with English translation).

Description of Evidence (3) filed Dec. 14, 2017 by Sanofi K.K. in Japanese Case No. 2017 (Wa) No. 16468: Case of seeking injunction of patent infringement (with English translation).

Written Opinion of Katsuya Tamai dated Dec. 14, 2017 in Case No. 2017 (Wa) No. 16468 The Case Seeking Injunction of Patent Right *Amgen Inc.* v. *Sanofi K.K*, (in Japan) (Exhibit B6).

Written Opinion of Takeshi Maedai dated Dec. 14, 2017 in Case No. 2017 (Wa) No. 16468 The Case Seeking Injunction of Patent Right *Amgen Inc.* v. *Sanofi K.K*, (in Japan) (Exhibit B7).

Written Opinion of Yoshiyuki Tamura dated Dec. 14, 2017 in Case No. 2017 (Wa) No. 16468 The Case Seeking Injunction of Patent Right *Amgen Inc.* v. *Sanofi K.K*, (in Japan) (Exhibit B8).

Office Action dated Sep. 21, 2017 in Chilean Application No. 201303214 (With English Translation).

Communication Pursuant to Article 94(3) EPC in European Application No. 16204336.8 dated Mar. 28, 2018.

Office Action dated Jan. 17, 2018 in Mexican Patent Application Np. MX/a/2013/013187.

Office Action dated Apr. 4, 2018 in Argentinian Application No. P 08 01 03668 (with English Translation).

Office Action dated Mar. 19, 2018 in Canadian Patent Application No. 2,835,294.

Office Action dated Apr. 25, 2018 in Chinese Patent Application No. 201280034417.9 (with English translation).

Office Action dated Mar. 3, 2018 in Brazilian Patent Application No. PI0816117-8 (with English translation).

Office Action dated Apr. 10, 2018 in Israeli Patent Application No. 252616 (with English translation).

Office Action dated May 3, 2018 in Chinese Patent Application No. 201410218672.X (with English translation).

Sabatine, M., et al. Evolocumab and Clincial Outcomes in Patients with Caridovascular Disease, New England Journal of Medicine, vol. 376, No. 18, pp. 1713-1722, (2017).

Stein, E, et al. Effect of the Proprotein Convertase Subtilisin.Kexin 9 Monocloan Antibody, AMG 145 in Momozygous Familial Hyperchloesterolemia, Circulation, 128, pp. 2113-2120, (2013).

Lloyd, C. et al. Modelling the Human Immune Response: Perforamce of a 1011 Human Antibody Repertoire Against a Broad Panel of Therapeutically Relevant Antigens, Protein Engieering, Design & Selection vol. 2, No. 3, pp. 159-168, (2009).

Weaver, J. Animal Stuides Paint Mislaeading Picture, Published online on Mar. 30, 2010; Accessible on the world wide web at <https://www.nature.com/news/2010/100330/full/news.2010.158.html>.

Office Action dated May 29, 2018 in Philippines Patent Application No. 1/2010/500421.

Office Action dated May 11, 2018 in Mexican Patent Application No. MX/a/2015/005275 (with English Translation).

Office Action dated Nov. 19, 2015 in U.S. Appl. No. 13/655,984.

Office Action dated Aug. 10, 2018 in Chinese Application No. 201410219429.X (With English Translation).

Office Action dated Aug. 10, 2018 in Chinese Application No. 201410218704.6 (With English Translation).

Raal, F. et al. PCSK9 inhibition with evolocumab (AMG 145) in heterozygous familial hypercholesterolaemia (RUTHERFORD-2): a randomised, double-blind, placebo-controlled trial, Lancet, vol. 85, pp. 331-340, (2015).

International Search Report and Written Opinion dated May 23, 2018 in International Patent Application No. PCT/US2017/061346.

Sabatine, M., et al. Efficacy and Safety of Evolovumab in Reducing Lipids and Cardiovascular Events, New England Journal of Medicine, vol. 372, No. 16, pp. 1500-1509, (2015).

Robinson, J et al al., Efficacy and safety of alirocumab in reducing lipids and cardiovascular events, New England Journal of Medicine, vol. 372, No. 16, pp. 1489-1499, (2015).

Navarese, E. et al. Effects of Proprotein Convertase Subtilsin/Kexin Type 9 Antibodies in Adults With Hypercholesterolemia, Annals of Internal Medicine, vol. 163, No. 1, pp. 40-78, (2015).

Puri, R. et al. Impact of PCSK9 inhibition on coronary atheroma progression: Rationale and design of Global Assessment of Plaque Regression with a PCSK9 Antibody as Measured by Intravascular Ultrasound (GLAGOV). American Heart Journal, vol. 176, pp. 83-92, (2016).

Nicholls,, S. et al. , Effect of Two Intensive Statin Regimens on Progression of Coronary Disease, New England Journal of Medicine, vol. 365 No. 22, pp. 2079-2087, (2011).

Nicholls,, S. et al. ,Effect of Evolocumab on Progression of Coronary Disease in Statin-Treated Patients The GLAGOV Randomized Clinical Trial, JAMA The Journal of the American Medical Association, vol. 316 No. 22, pp. 2373, (2016).

Ray, K. , et al., Reductions in Atherogenic Lipids and Major Cardiovascular Events Clinical Perspective: Pooled Analysis of 10

(56)         References Cited

OTHER PUBLICATIONS

Odyssey Trials Comparing Alirocumab With Control, Circulation, vol. 134, No. 24, pp. 1931-1943, (2016).

Silverman, M. et al, Association Between Lowering LDL-C and Cardiovascular Risk Reduction Among Different Therapeutic Interventions : A Systematic Review and Meta-analysis, JAMA The Journal of the American Medical Association, vol. 316 No. 22, pp. 1289 (2016).

Gugliano, R. et al., Clinical efficacy and safety of achieving very low LDL-cholesterol concentrations with the PCSK9 inhibitor evolocumab: a prespecified secondary analysis of the FOURIER trial, The Lancet, vol. 390, No. 10106, pp. 1962-1971, (2017).

Office Action dated May 14, 2018 in Eurasian Application No. 201000356 (with English Translation).

Office Action dated Mar. 7, 2018 in Gulf Coast Application No. GCC/P/2008/11573.

Office Action dated Jul. 13, 2018 in Malaysian Application No. PI 2014001682.

Office Action dated Jul. 13, 2018 in Malaysian Application No. PI 2014001683.

Office Action dated Aug. 14, 2018 in Korean Application No. 10-2013-7032805 (with English Translation).

Office Action dated Aug. 30, 2018 in New Zealand Application No. 717550.

Office Action dated Aug. 28, 2018 in Japanese Application No. 2017-244758 (with English Translation).

Filing of Opposition Dated Apr. 27, 2018 in Chilean Patent Application No. 3288-2017 (with English Translation).

Office Action dated Apr. 8, 2019 in Korean Patent Applicant No. 10-2013-7032805 (With English Translation.

Office Action dated Feb. 27, 2019 in Israeli Patent Application No. 2554770 (with English translation).

Office Action dated Mar. 1, 2019 in Canadian Patent Application No. 2,835,294.

Wang et al. Potential aggregation prone regions in biotherapeutics: a survey of commercial monoclonal antibodies in MAbs (vol. 1, No. 3, pp. 254-267), (2009).

Office Action dated Aug. 31, 2016 in U.S. Appl. No. 12/903,084.

Office Action dated Aug. 31, 2016 in U.S. Appl. No. 13/469,032.

Office Action dated Sep. 1, 2016 in U.S. Appl. No. 13/655,984.

Office Action dated Sep. 7, 2016 in U.S. Appl. No. 13/174,423.

Alekseychyk et al., High-Throughput Screening and Stability Optimization of Anti-Streptavidin IgG1 and IgG2 Formulations. J. Biomolecular Screening. 19(9):1290-1301, (2014).

Bolli, R. et al., L-Proline reduces IgG dimer content and enhances the stability of intravenous immunoglobulin (IVIG) solutions, Biologicals, vol. 38, pp. 150-157, (2010).

Falconer, R. et al. Stabilization of a monoclonal antibody during purification and formulation by addition of basic amino acid excipients, J Chem Technol Biotechnol, 86, pp. 942-948, (2011).

Wang et al., Viscosity-Lowering Effect of Amino Acids and Salts on Highly Concentrated Solutions of Two IgG1 Monoclonal Antibodies. Molecular Pharmaceutics. 12:4478-4487, (2015).

Office Action Dated Sep. 1, 2019 in Gulf Coast Application No. 2012-21247.

Office Action Dated Oct. 16, 2019 in Australian Application No. 2017232084.

Office Action Dated Sep. 13, 2018 in Peruvian Patent Application No. 02471-2013/DIN (with English Translation).

Office Action Dated Aug. 9, 2018 in Peruvian Patent Application No. 02471-2013/DIN (with English Translation).

Office Action Dated Jul. 23, 2018 in Peruvian Patent Application No. 02471-2013/DIN (with English Translation).

Examination Report received in Australian Patent Application No. 2013396206 Dated Oct. 19, 2018.

Office Action Dated Sep. 3, 2018 in Brazilian Patent Application No. BR122018012430-0 (With English Translation).

Office Action Dated Nov. 26, 2018 in Ukrainian Patent Application No. 28439/3A/18 (With English Translation).

Office Action Dated Oct. 26, 2018 in Taiwanese Patent App. No. 103110948 (With English Translation).

Office Action Dated Oct. 26, 2018 in Taiwanese Patent App. No. 103110949 (With English Translation).

Office Action Dated Dec. 5, 2018 in Philippines Patent Application No. Jan. 2013/502287.

Office Action dated Oct. 18, 2018 in Vietnamese Application No. 1-2013-03886 (with English Translation).

Office Action Dated Oct. 18, 2018 in Mexican Patent Application No. MX/a/2013/01318 (with English Translation).

Office Action Dated Oct. 26, 2018 in Taiwanese Patent App. No. 103110947 (With English Translation).

Examination Report Dated Feb. 4, 2019 in Philippines Patent Application No. Jan. 2010/500421.

Summons to Attend Oral Proceedings Dated Feb. 11, 2019 in European Patent Application No. 16204336.8.

The Merck Manual of Diagnosis of Therapy, Seventeenth Edition, Merck Research Laboratories, Whitehouse Station, NJ pp. 206-211 (1999).

Communication Pursuant to Article 94(3) EPC in European Application No. 13151352.5 Dated Feb. 21, 2019.

Communication Pursuant to Article 94(3) EPC in European Application No. 13737090.4 Dated Mar. 19, 2019.

Summons to Attend Oral Proceedings Dated Jan. 4, 2019 in European Patent Application No. 13724077.6.

Office Action Dated Jan. 9, 2019 in Brazilian Patent Application No. BR122018012430-0 (With English Translation).

Office Action Dated Feb. 8, 2019 in Mexican Patent Application No. in Mexican Patent Application No. MX/a/2015/005275 (with English Translation).

Office Action Dated Feb. 27, 2019 in Israeli Patent Application No. 252616 (with English translation).

Office Action Dated Mar. 19, 2019 in Japanese Patent Application No. 2018-031718 (With English translation).

Proprotein convertase subtillisin/kexin type 9 precursor, UniProtKB, Ver. 55, Q8NBP7 (Aug. 21, 2007). (Search Date Feb. 17, 2017).

Office Action Dated Apr. 23, 2019 in Korean Patent Application No. 10-2018-7009055 (With English Translation).

Office Action Dated May 3, 2019 in Canadian Patent Application No. 2,916,259.

Examination Report Dated May 15, 2019 in Philippines Patent Application No. Jan. 2010/500421.

Office Action Dated Oct. 28, 2016 in African Patent Application No. AP/P/2013/007303.

Technical Examination Report Dated Jun. 10, 2019 in Brazilian Patent Application No. BR122018012430-0 (With English Translation).

Office Action Dated Jun. 25, 2019 in Japanese Patent Application No., 2017-244758 (With English Translation).

Search Report and Written Opinion dated Apr. 12, 2019 in Brazilian Patent Application No. BR112013028819 (With English Translation).

Office Action dated Aug. 20, 2019 in U.S. Appl. No. 12/903,084.

Notice of Allowability Dated Jul. 1, 2019 in U.S. Appl. No. 15/510,600.

Response to Office Action Dated Jun. 3, 2019 in U.S. Appl. No. 15/510,600.

Office Action Dated Jan. 15, 2019 in U.S. Appl. No. 15/510,600.

Response to Office Action Dated Jun. 11, 2019 in European Patent Application No. 12753240.6.

Communication Pursuant to Article 94(3) EPC Dated Aug. 24, 2018 in European Patent Application No. 12753240.6.

Office Action dated Sep. 16, 2019 in U.S. Appl. No. 13/469,032.

Office Action dated Sep. 18, 2019 in U.S. Appl. No. 13/494,912.

Office Action dated Sep. 18, 2019 in U.S. Appl. No. 13/422,904.

Office Action dated Sep. 19, 2019 in U.S. Appl. No. 13/682,698.

Office Action dated Sep. 26, 2019 in U.S. Appl. No. 13/463,751.

Office Action Dated Aug. 26, 2019 in Costa Rican Patent Application No. 2015-0295 (with English translation).

Office Action Dated Sep. 13, 2019 in European Patent Application No. 13151343.4.

Office Action dated Nov. 12, 2019 in U.S. Appl. No. 13/619,555.

(56) References Cited

OTHER PUBLICATIONS

Office Action dated Jul. 23, 2019 in Korean Patent Application No. 10-2013-7032805 (with English translation).
Examination Report dated Aug. 13, 2019 in Philippines Patent Application No. Jan. 2013/502287.
Office Action dated Jul. 22, 2019 in Argentinian Patent Application No. 20120101655 (with English translation).
Office Action Dated Nov. 1, 2019 in Chinese Patent Application No. 201280034417.9 (with English translation).
Communication Pursuant to Article 94(3) EPC Dated Sep. 13, 2019 in European Patent Application No. 13151375.6.
Petition under 37 CFR 1.181 dated Aug. 28, 2018 in U.S. Appl. No. 61/010,630.
Petition Decision dated May 22, 2019 in U.S. Appl. No. 61/010,630.
Office Action dated Dec. 19, 2019 in U.S. Appl. No. 14/316,587.
Office Action dated Dec. 12, 2019 in U.S. Appl. No. 13/422,887.
Office Action dated Dec. 20, 2019 in U.S. Appl. No. 14/459,777.
Office Action dated Oct. 22, 2019 in Chinese Patent Application No. 201380035382.5 (with English Translation).
Office Action dated Nov. 1, 2019 in Taiwanese Patent Application No. 106130882 (with English Translation).
Office Action dated Oct. 16, 2019 in Mexican Patent Application No. MX/a/2015/005275 (with English Translation).
Koren et al., "Long-term Low-Density Lipoprotein Cholesterol-Lowering Efficacy, Persistence, and Safety of Evolocumab in Treatment of Hypercholesterolemia, Results Up to 4 Years From the Open-Label OSLER-1 Extension Study", JAMA Cardiology, pages E1 - E10, Mar. 14, 2017.
"Cleveland Clinic-Led Study Shows Reversal of Coronary Plaque Buildup With Injectable Cholesterol Drug", Nov. 15, 2016, News Releases, Cleveland Clinic, 7 pages.
Philippine Substantive Examination Report mailed Dec. 10, 2019 for Philippine Patent Application No. PH12013502285, which corresponds to subject U.S. Appl. No. 14/562,546, 5 pages.
Philippine Substantive Examination Report mailed Dec. 12, 2019 for Philippine Patent Application No. PH12013502286, which corresponds to subject U.S. Appl. No. 14/562,546, 5 pages.
Office Action dated Dec. 3, 2019 for Egyptian Patent Application No. 2010020302 which was filed Feb. 23, 2010.
Extended European Search Report dated Dec. 18, 2019, received in European Appl. No. 19175489.4.
Notice of Allowance dated Feb. 21, 2020, received in U.S. Appl. No. 14/562,546.
Office Action dated Dec. 16, 2019 in ROC (Taiwan) Application No. 107117443 (with English Translation).
Opposition Notice dated Jan. 29, 2020 in Colombian Application No. NC2019/0004814 (with English Translation).
Defendant's Memorandum in Support of Their Motion for Summary Judgment of Patent Invalidity, Filed Nov. 26, 2018 in *Amgen Inc., v. Sanofi*, in the United States District Court for the District of Delaware, C.A. No. 14-CV-1317, 31 Pages {Document 0652}.
Opening Brief in Support of Plaintiffs' Motion for Partial Summary Judgment to Estop Defendants From Asserting Written Description and Enablement Defenses that Contradict Defendants' Own PTO Filings, Filed Nov. 26, 2018 in *Amgen Inc., v. Sanofi*, in the United States District Court for the District of Delaware, C.A. No. 14-1317 RGA, 31 pages {Document 0662}.
Declaration of Victoria L. Reines in Support of Defendants' Motion for Summary Judgment of Patent Invalidity, Filed Nov. 26, 2018 in *Amgen Inc., v. Sanofi*, in the United State District Court for the District of Delaware, C.A. No. 1:14-01317-RGA, 6 pages {Document 0653-Main}.
Volume I of VIII Exhibits 1 through 6 to Declaration of Victoira L. Reines in Support of Defendants' Motion for Summary Judgment of Patent Invalidity, Filed Nov. 26, 2018 in *Amgen Inc., v. Sanofi*, in the United States District Court for the District of Delaware, C.A. No. 14-1317 RGA, in 25 pages {Document 0653-1}.
Volume II of VIII Exhibits 7 to Declaration of Victoira L. Reines in Support of Defendants' Motion for Summary Judgement of Patent Invalidity, Filed Nov. 26, 2018 in *Amgen Inc., v. Sanofi*, in the United States District Court for the District of Delaware, C.A. No. 14-1317 RGA, in 395 pages {Document 0654}.
Volume III of VIII Exhibit 8—Part 1 of 2 to Declaration of Victoira L. Reines in Support of Defendants' Motion for Summary Judgement of Patent Invalidity, Filed Nov. 26, 2018 in *Amgen Inc., v. Sanofi*, in the United States District Court for the District of Delaware, C.A. No. 14-1317 RGA, in 336 pages {Document 0655}.
Volume IV of VIII Exhibit 8—Part 2 of 2 and Exhibit 9 to Declaration of Victoira L. Reines in Support of Defendants' Motion for Summary Judgment of Patent Invalidity, Filed Nov. 26, 2018 in *Amgen Inc., v. Sanofi*, in the United States District Court for the District of Delaware, C.A. No. 14-1317 RGA, in 416 pages {Document 0656}.
Volume V of VIII Exhibit 10 to Declaration of Victoira L. Reines in Support of Defendants' Motion for Summary Judgement of Patent Invalidity, Filed Nov. 26, 2018 in *Amgen Inc., v. Sanofi*, in the United States District Court for the District of Delaware, C.A. No. 14-1317 RGA, in 379 pages {Document 0657}.
Volume VI of VIII Exhibit 11 through 13 to Declaration of Victoira L. Reines in Support of Defendants' Motion for Summary Judgement of Patent Invalidity, Filed Nov. 26, 2018 in *Amgen Inc., v. Sanofi*, in the United States District Court for the District of Delaware, C.A. No. 14-1317 RGA, in 477 pages {Document 0658}.
Volume VII of VIII Exhibits 14 through 15 to Declaration of Victoira L. Reines in Support of Defendants' Motion for Summary Judgement of Patent Invalidity, Filed Nov. 26, 2018 in *Amgen Inc., v. Sanofi*, in the United States District Court for the District of Delaware, C.A. No. 14-1317 RGA, in 380 pages {Document 0659}.
Declaration of Michelle M. Ovanesian in Support of Plaintiffs' motion for Partial Summary Judgment to Estop Defendants from Asserting Written Description and Enablement Defenses that Contradict Defendants' Own PTO Filings, Filed Nov. 26, 2018 in *Amgen Inc., v. Sanofi*, in the United States District Court for the District of Delaware, C.A. No. 14-1317-RGA, in 457 pages {Document 0663}.
Declaration of Michelle M. Ovanesian in Support of Plaintiffs' motion for Partial Summary Judgment to Estop Defendants from Asserting Written Description and Enablement Defenses that Contradict Defendants' Own PTO Filings, vol. 2—Exhibits 14 through 18, Filed Nov. 26, 2018 in *Amgen Inc., v. Sanofi*, in the United States District Court for the District of Delaware, C.A. No. 14-1317-RGA, in 525 pages {Document 0664}.
Declaration of Michelle M. Ovanesian in Support of Plaintiffs' motion for Partial Summary Judgment to Estop Defendants from Asserting Written Description and Enablement Defenses that Contradict Defendants' Own PTO Filings, vol. 3—Exhibits 19 through 20, Filed Nov. 26, 2018 in *Amgen Inc., v. Sanofi*, in the United States District Court for the District of Delaware, C.A. No. 14-1317-RGA, in 528 pages {Document 0665}.
Declaration of Michelle M. Ovanesian in Support of Plaintiffs' motion for Partial Summary Judgment to Estop Defendants from Asserting Written Description and Enablement Defenses that Contradict Defendants' Own PTO Filings, vol. 4—Exhibits 21 through 23, Filed Nov. 26, 2018 in *Amgen Inc., v. Sanofi*, in the United States District Court for the District of Delaware, C.A. No. 14-1317-RGA, in 437 pages {Document 0666}.
Declaration of Michelle M. Ovanesian in Support of Plaintiffs' motion for Partial Summary Judgment to Estop Defendants from Asserting Written Description and Enablement Defenses that Contradict Defendants' Own PTO Filings, vol. 5—Exhibits 24 through 27, Filed Nov. 26, 2018 in *Amgen Inc., v. Sanofi*, in the United States District Court for the District of Delaware, C.A. No. 14-1317-RGA, in 487 pages {Document 0667}.
Declaration of Michelle M. Ovanesian in Support of Plaintiffs' motion for Partial Summary Judgment to Estop Defendants from Asserting Written Description and Enablement Defenses that Contradict Defendants' Own PTO Filings, vol. 6—Exhibits 29 through 30, Filed Nov. 26, 2018 in *Amgen Inc., v. Sanofi*, in the United States District Court for the District of Delaware, C.A. No. 14-1317-RGA, in 251 pages {Document 0668}.
Defendants' Memorandum in Opposition to Amgen's Motion for Partial Summary Judgment and in Support of Defendants' Cross Motion for Summary Judgment on Estoppel, Filed Dec. 11, 2018 in

(56)                    References Cited

OTHER PUBLICATIONS

*Amgen Inc.,* v. *Sanofi,* in the United States District Court for the District of Delaware, C.A. No. 1:14- 01317-RGA, in 28 pages {Document 0686}.

Declaration of Anne W. Pearlman in Support of Defendants' Opposition to Amgen's Motion for Partial Summary Judgment and in Support of Defendants' Cross Motion for Summary Judgment on Estoppel, Filed Dec. 4, 2018 in *Amgen Inc.,* v. *Sanofi,* in the United States District Court for the District of Delaware, C.A. No. 1:14-01317-RGA, in 4 pages {Document 0675 Main}.

Exhibit 1 to Declaration of Anne W. Pearlman in Support of Defendants' Opposition to Amgen's Motion for Partial Summary and in Support of Defendants' Cross Motion for Judgement on Estoppel, Filed Dec. 4, 2018, in *Amgen Inc.,* v. *Sanofi,* in the United States District Court for the District of Delaware, C.A. No. 1:14-01317-RGA, in 385 pages {Document 0675-1}.

Volume II of V Exhibits 2 Through 4 to Declaration of Anne W. Pearlman in Support of Defendants' Opposition to Amgen's Motion for Partial Summary an in Support of Defendants' Cross Motion for Judgment on Estoppel, Filed Dec. 4, 2018, in *Amgen Inc.,* v. *Sanofi,* in the United States District Court for the District of Delaware, C.A. No. 1:14-01317-RGA, in 406 pages {Document 0677}.

Volume III of V Exhibits 5 Through 13 to Declaration of Anne W. Pearlman in Support of Defendants' Opposition to Amgen's Motion for Partial Summary an in Support of Defendants' Cross Motion for Judgment on Estoppel, Filed Dec. 4, 2018, in *Amgen Inc.,* v. *Sanofi,* in the United States District Court for the District of Delaware, C.A. No. 1:14-01317-RGA, in 587 pages {Document 0679}.

Volume IV of V Exhibit 14 to Declaration of Anne W. Pearlman in Support of Defendants' Opposition to Amgen's Motion for Partial Summary an in Support of Defendants' Cross Motion for Judgment on Estoppel, Filed Dec. 11, 2018, in *Amgen Inc.,* v. *Sanofi,* in the United States District Court for the District of Delaware, C.A. No. 1:14-01317-RGA, in 2 pages {Document 0687}.

Volume V of V Exhibits 15 Through 20 to Declaration of Anne W. Pearlman in Support of Defendants' Opposition to Amgen's Motion for Partial Summary an in Support of Defendants' Cross Motion for Judgment on Estoppel, Filed Dec. 4, 2018, in *Amgen Inc.,* v. *Sanofi,* in the United States District Court for the District of Delaware, C.A. No. 1:14-01317-RGA, in 570 pages {Document 0681}.

Plaintiffs' Answering Brief in Opposition to Defendants' Motion for Summary Judgment of Patent Invalidity, Filed Dec. 11, 2018, in *Amgen Inc.,* v. *Sanofi,* in the United States District Court for the District of Delaware, C.A. No. 1:14-01317 RGA, in 33 pages {Document 0688}.

Declaration of Michelle M. Ovanesian in Support of Plaintiffs' Answering Brief to Defendants' Motion for Summary Judgment of Patent Invalidity, Filed Dec. 11, 2018, in Amgen Inc., v. Sanofi, in the United States District Court for the District of Delaware, C.A. No .: 14-1317-RGA, in 46 pages {Document 0689}.

Declaration Michelle M. Ovanesian in Support of Plaintiffs' Answering Brief to Defendants' Motion for Summary Judgment of Patent Invialidity, vol. 2: Exhibit F—Exhibit V, Filed Dec. 11, 2018, in Amgen Inc., v. Sanofi, in the United States District Court for the District of Delaware, C.A. No. 1:14-01317 RGA, in 40 pages {Document 0690}.

Defendants' Reply Memorandum in Support of Their Motion for Summary Judgment of Patent Invalidity, Filed Dec. 13, 2018, in *Amgen Inc.,* v. *Sanofi,* in the United States District Court for the District of Delaware, C.A. No. 1:14-01317-RGA, in 16 pages {Document 0695}.

Declaration of Victoria L. Reines in Support of Defendants' Reply Memorandum in Support of Their Motion for Summary Judgment of Patent Invalidity, Filed Dec. 13, 2018, in *Amgen Inc.,* v. *Sanofi,* in the United States District Court for the District of Delaware, C.A. No. 1:14-01317-RGA, in 2 pages {Document 0696 Main}.

Declaration of Victoria L. Reines in Support of Defendants' Reply Memorandum in Support of Their Motion for Summary Judgment of Patent Invalidity, Exhibit 44 through 46, Filed Dec. 13, 2018 in *Amgen Inc.,* v. *Sanofi,* in the United States District Court for the District of Delaware, C.A. No. 1:14-01317-RGA, in 3 pages {Document 0696-1}.

Supplemental Declaration of Michelle M. Ovanesian in Support of Plaintiffs' Motion for Partial Summary Judgment to Estop Defendants from Asserting Written Description and Enablement Defenses that Contradict Defendants' Own PTO Filings, Filed Dec. 18, 2018, in *Amgen Inc.,* v. *Sanofi,* in the United States District Court for the District of Delaware, C.A. No. 14-1317-RGA, in 100 pages {Document 0697 Main}.

Supplemental Declaration of Michelle M. Ovanesian in Support of Plaintiffs' Motion for Partial Summary Judgment to Estop Defendants from Asserting Written Description and Enablement Defenses that Contradict Defendants' Own PTO Filings, Filed Dec. 18, 2018, in *Amgen Inc.,* v. *Sanofi,* in the United States District Court for the District of Delaware, C.A. No. 14-1317-RGA, in 100 pages {Document 0697-1}.

Supplemental Declaration of Michelle M. Ovanesian in Support of Plaintiffs' Motion for Partial Summary Judgment to Estop Defendants from Asserting Written Description and Enablement Defenses that Contradict Defendants' Own PTO Filings, Filed Dec. 18, 2018, in *Amgen Inc.,* v. *Sanofi,* in the United States District Court for the District of Delaware, C.A. No. 14-1317-RGA, in 87 pages {Document 0697-2}.

Proffer of Leonard Schleifer, Filed Feb. 26, 2019, in *Amgen Inc.,* v. *Sanofi,* in the United States District Court for the District of Delaware, C.A. No. 1:14-01317-RGA, in 5 pages {Document 0820 Main}.

Proffer of Leonard Schleifer, Exhibit A, Filed Feb. 26, 2019, in *Amgen Inc.,* v. *Sanofi,* in the United States District Court for the District of Delaware, C.A. No. 1:14-01317-RGA, in 5 pages {Document 0820-1}.

Proffer of Leonard Schleifer, Exhibit B, Filed Feb. 26, 2019, in *Amgen Inc.,* v. *Sanofi,* in the United States District Court for the District of Delaware, C.A. No. 1:14-01317-RGA, in 1 pages {Document 0820-2}.

Proffer of Leonard Schleifer, Exhibit E, Filed Feb. 26, 2019, in *Amgen Inc.,* v. *Sanofi,* in the United States District Court for the District of Delaware, C.A. No. 1:14-01317-RGA, in 1 pages {Document 0820-3}.

Proffer of Leonard Schleifer, Exhibit F, Filed Feb. 26, 2019, in *Amgen Inc.,* v. *Sanofi,* in the United States District Court for the District of Delaware, C.A. No. 1:14-01317-RGA, in 1 pages {Document 0820-4}.

Proffer of Scott Boyd, M.D., Ph.D., Filed Feb. 28, 2019, in *Amgen Inc.,* v. *Sanofi,* in the United States District Court for the District of Delaware, C.A. No. 1:14-01317-RGA, in 40 pages {Document 0824}.

Defendants' Bench Memorandum Regarding Amgen's Improper Reliance on Antibodies that were not Disclosed in the '630 Provisional, Filed Mar. 4, 2019, in *Amgen Inc.,* v. *Sanofi,* in the United States District Court for the District of Delaware, C.A. No. 1:14-01317-RGA, in 4 pages {Document 0847}.

Defendants' Bench Memorandum Regarding Amgen's Attempts to Use Evidence for Enablement Purposes, Filed Mar. 4, 2019, in *Amgen Inc.,* v. *Sanofi,* in the United States District Court for the District of Delaware, C.A. No. 1:14-01317-RGA, in 3 pages {Document 0848 Main}.

Defendants' Bench Memorandum Regarding Amgen's Attempts to Use Evidence for Enablement Purposes, Exhibit A, Filed Mar. 4, 2019, in *Amgen Inc.,* v. *Sanofi,* in the United States District Court for the District of Delaware, C.A. No. 1:14-01317-RGA, in 1 pages {Document 0848-1}.

Defendants' Bench Memorandum Regarding Amgen's Attempts to Use Evidence for Enablement Purposes, Exhibit A, Filed Mar. 4, 2019, in *Amgen Inc.,* v. *Sanofi,* in the United States District Court for the District of Delaware, C.A. No. 1:14-01317-RGA, in 1 pages {Document 0848-2}.

Amgen's Motion for Judgment as a Matter of Law, Filed Mar. 1, 2019, in *Amgen Inc.,* v. *Sanofi,* in the United States District Court for the District of Delaware, C.A. No. 14-1317-RGA, in 15 pages {Document 08421.

(56) References Cited

OTHER PUBLICATIONS

Plaintiffs' Initial Objections to Proffer of Michael J. Eck, M.D., Ph.D., Filed Mar. 1, 2019, in *Amgen Inc., v. Sanofi*, in the United States District Court for the District of Delaware, C.A. No. 14-1317-RGA, in 9 pages {Document 0843}.
Plaintiffs' Initial Objections to Proffer of Scot Boyd, M.D., Ph.D., Filed Mar. 1, 2019, in *Amgen Inc., v. Sanofi*, in the United States District Court for the District of Delaware, C.A. No. 14-1317-RGA, in 14 pages {Document 0844}.
Plaintiffs' Objections to Second Proffer of Leonard Schleifer, Filed Mar. 1, 2019, in *Amgen Inc., v. Sanofi*, in the United States District Court for the District of Delaware, C.A. No. 14-1317-RGA, in 6 pages {Document 0845}.
Plaintiffs' Objections and Counter-Proffer to Second Remand Proffer of Dr. Leonard Schleifer, Filed Mar. 4, 2019, in *Amgen Inc., v. Sanofi*, in the United States District Court for the District of Delaware, C.A. No. 14-1317-RGA, in 13 pages {Document 0849}.
Plaintiffs' Objections and Counter-Proffer to Proffers of Scott Boyd, M.D., Ph.D and Michael J. Eck, M.D., Ph.D., Filed Mar. 4, 2019, in *Amgen Inc., v. Sanofi*, in the United States District Court for the District of Delaware, C.A. No. 14-1317-RGA, in 34 pages {Document 0850}.
Defendants' Motion Under Fed. R. Civ. P. 50 (A) For Judgment as a Matter of Law, Filed Feb. 28, 2019, in *Amgen Inc., v. Sanofi*, in the United States District Court for the District of Delaware, C.A. No. 1:14-01317-RGA, in 12 pages {Document 0838}.
Cross-Proffers of Anthony Rees and Gregory Petsko, Filed Mar. 6, 2019, in *Amgen Inc., v. Sanofi*, in the United States District Court for the District of Delaware, C.A. No. 1:14-01317-RGA, in 5 pages {Document 0860 Main}.
Cross-Proffers of Anthony Rees and Gregory Petsko, Exhibit 1-16, Filed Mar. 6, 2019, in *Amgen Inc., v. Sanofi*, in the United States District Court for the District of Delaware, C.A. No. 1:14-01317-RGA, in 1 pages {Document 0860-1}.
Cross-Proffers of Simon Jackson, Filed Mar. 6, 2019, in *Amgen Inc., v. Sanofi*, in the United States District Court for the District of Delaware, C.A. No. 1:14-01317-RGA, in 6 pages {Document 0861 Main}.
Cross-Proffers of Simon Jackson, Exhibit 1-16, Filed Mar. 6, 2019, in *Amgen Inc., v. Sanofi*, in the United States District Court for the District of Delaware, C.A. No. 1:14-01317-RGA, in 1 pages {Document 0861-1}.
Defendants' Opening Brief in Support of Motion Under Fed. R. Civ. P. 59 for New Trial, Filed Mar. 25, 2019, in *Amgen Inc., v. Sanofi*, in the United States District Court for the District of Delaware, C.A. No. 1:14-01317-RGA, in 27 pages {Document 0904 Main}.
Defendants' Opening Brief in Support of Motion Under Fed. R. Civ. P. 59 for New Trial, Exhibits 1-24, Filed Mar. 25, 2019, in *Amgen Inc., v. Sanofi*, in the United States District Court for the District of Delaware, C.A. No. 1:14-01317-RGA, in 1 pages {Document 0904-1}.
Defendants' Opening Brief in Support of Motion Under Fed. R. Civ. P. 50 (B) for Judgment as a Matter of Law, Filed Mar. 25, 2019, in *Amgen Inc., v. Sanofi*, in the United States District Court for the District of Delaware, C.A. No. 1:14-01317-RGA, in 28 pages {Document 0905 Main}.
Defendants' Opening Brief in Support of Motion Under Fed. R. Civ. P. 50 (B) for Judgment as a Matter of Law, Exhibit 1-4, Filed Mar. 25, 2019, in *Amgen Inc., v. Sanofi*, in the United States District Court for the District of Delaware, C.A. No. 1:14-01317-RGA, in 10 pages {Document 0905-1}.
Reply Brief in Support of Defendants' Motion Under Fed. R. Civ. P. 59 for New Trial, Filed Apr. 29, 2019, in *Amgen Inc., v. Sanofi*, in the United States District Court for the District of Delaware, C.A. No. 1:14-01317-RGA, in 16 pages {Document 0992}.
Corrected Brief for Defendants-Appellants, Filed Mar. 3, 2017, in *Amgen Inc., v. Sanofi*, in the United States Court of Appeals for the Federal Circuit, No. 17-1480, in 118 pages {Document FC1 106}.

Citation of Supplemental Authority, Filed May 3, 2017, in *Amgen Inc., v. Sanofi*, in the United States Court of Appeals for the Federal Circuit, No. 17-1480, in 29 pages {Document FC1 151}.
Response to Defendants' Rule 28 (j) Letter, Filed May 5, 2017, in *Amgen Inc., v. Sanofi*, in the United States Court of Appeals for the Federal Circuit, No. 17-1480, in 3 pages {Document FC1 152}.
Brief for Plaintiffs-Appellants Amgen Inc., Amgen Manufacturing, Limited, and Amgen USA, Inc. filed Feb. 21, 2020, in *Amgen Inc., v. Sanofi*, in the United States Court of Appeals for the Federal Circuit, Case: 20-1074, Document: 55, in 124 pages.
Notice of Allowance dated Aug. 19, 2020 in U.S. Appl. No. 14/562,546.
Office Action dated Aug. 12, 2020 in U.S. Appl. No. 13/931,716.
U.S. Appl. No. 16/348,653, filed May 9, 2019, Somaratne et al.
U.S. Appl. No. 17/011,433, filed Sep. 3, 2020, Chan et al.
Evidence Explanatory dated Feb. 12, 2020 for Case of trial for invalidation of Japanese Patent No. 5705288 (with English Translation).
Written Demand dated Feb. 12, 2020 Case of trial for invalidation of Japanese Patent No. 5705288 (with English Translation).
Evidence Explanatory dated Feb. 12, 2020 for Case of trial for invalidation of Japanese Patent No. 5906333 (with English Translation).
Written Demand dated Feb. 12, 2020 for Case of trial for invalidation of Japanese Patent No. 5906333 (with English Translation).
Notice of Reexamination dated Mar. 17, 2020 in Chinese Application No. 201410218672.X (with English Translation).
Search Report and Written Opinion received in Singaporean Patent Application No. 10201603700T, dated Feb. 13, 2020.
Expert Report of Professor Jay D. Horton filed by Sanofi in an Opposition filed in Israeli Patent Application No. 204013, received Apr. 28, 2020.
Expert Report of Professor Michael J. Eck filed by Sanofi in an Opposition filed in Israeli Patent Application No. 204013, received Apr. 28, 2020.
Office Action dated Feb. 26, 2020 in Vietnamese Application No. 1-2017-04226.
Office Action dated Mar. 5, 2020 in Canadian Application No. 2,835,294.
Office Action dated Feb. 6, 2020 in Israeli Application No. 229276.
Tamura et al., Structural Correlates of an Anticarcinoma Antibody: Identification of Specificity-Determining Residues (SDRs) and Development of a Minimally Immunogenic Antibody Variant by Retention of SDRs Only. J Immunol Feb. 1, 2000, 164 (3) 1432-1441.
Stroes et al., Consistent LDL-C Response With Evolocumab Among Patient Subgroups in Proficio: A Pooled Analysis of 3146 Patients From Phase 3 Studies. Clin Cardiol. Oct. 2018;41(10):1328-1335.
Statement of Defense and Counterclaim filed by Sanofi-Aventis in District Court of The Hague, in *Amgen Inc et al. v. Sanofi-Aventis Netherlands B.V et al.*, Docket No. C/09/589942, dated May 27, 2020.
Expert Report of Dr. Scott Boyd (Exhibits SB-1-SB-2), in *Amgen Inc et al. v. Sanofi-Aventis Netherlands B.V et al.*, Docket No. C/09/589942, dated May 25, 2020.
Expert Report of Professor Michael J. Eck (Exhibits ME-1-ME-5), in *Amgen Inc et al. v. Sanofi-Aventis Netherlands B.V et al.*, Docket No. C/09/589942, dated May 25, 2020.
Office Action Dated Dec. 26, 2019 in U.S. Appl. No. 15/902,775.
Office Action Dated Apr. 14, 2020 in Canadian Patent Application No. 2,916,259.
Office Action and Written Opinion dated Apr. 18, 2020 in Brazilian Patent Application No. BR112013028819 (With English Translation).
Written Opinion dated Apr. 18, 2020 in Brazilian Application No. BR122019021784-0 (with English Translation).
Extended European Search Report dated Apr. 29, 2020, received in European Appl. No. 19207796.4.
Horton et al., PCSK9: a convertase that coordinates LDL catabolismipid Res. Apr. 2009;50 Suppl(Suppl):S172-7.
Office Action dated Mar. 27, 2020 in Indonesian Application No. P00201701904 (with English Translation).
Notice of Reexamination Dated Jun. 18, 2020 In Chinese Application No. 201410219429.X (With English Translation).

(56) References Cited

OTHER PUBLICATIONS

Minutes of Oral Proceedings dated Mar. 8, 2019 in European Application No. 08 798 550.3.
Written Decision of Opposition Division dated Mar. 8, 2019 in European Application No. 08 798 550.3.
Trial Decision dated Dec. 27, 2018, Action for Invalidity 2016-800004, Demandant Sanofi, 4th Division, Intellectual Property High Court (with English Translation).
Office Action dated Jun. 19, 2020 in Chinese Application No. 201710556773.1 (with English Translation).
Office Action Dated Mar. 3, 2020 in U.S. Appl. No. 16/182,279.
Office Action Dated Jun. 22, 2020 in African Patent Application No. AP/P/2019/011828.
Office Action dated Jul. 15, 2020 in Chinese Patent Application No. 201280034417.9 (with English translation).
Notice of Reexamination Dated Jun. 18, 2020 In Chinese Application No. 201410218704.6 (With English Translation).
Office Action dated Sep. 25, 2020 in U.S. Appl. No. 14/316,587.
Office Action dated Jul. 31, 2020 in Brazilian Application No. BR112013028819-1 (with English Translation).
Office Action dated Jul. 31, 2020 in Brazilian Application No. BR122019021784-0 (with English Translation).
Office Action dated Aug. 18, 2020 in Argentinian Patent Application No. 20120101655 (with English translation).
Office Action dated Jun. 16, 2020 in Gulf Coast Application No. GCC 2012-38764.
Office Action Dated Sep. 22, 2020 in Korean Patent Applicant No. 10-2020-7019200 (With English Translation).
Office Action dated Oct. 13, 2020 in Chilean Application No. 201901304 (With English Translation).
Supplemental Data to D9 (Lagace T.A et al. (2006) J. Clin. Invest., 116(11): 2995) filed in European Opposition to Ep 2215124B1.
Calculation of IC50 of the antibodies of D14 to PCSK9, filed in European Opposition to Ep 2215124B1, dated Oct. 2015.
Declaration by Dr. Darren Kamikura and CV dated Nov. 21, 2016, filed in European Opposition to Ep 2215124B1.
Declaration by Dr. Malgorzata Gonciarz and CV dated Nov. 21, 2016, filed in European Opposition to Ep 2215124B1.
Declaration by Dr. Riechmann Dated May 26, 2017, filed in European Opposition to Ep 2215124B1.
Declaration by Prof. Schwartz Dated May 23, 2017, filed in European Opposition to Ep 2215124B1.
Declaration by Prof. J. Horton Dated May 23, 2017, filed in European Opposition to EP 2215124B1.
Pdb file 2P4E Crystal Structure of PCSK9 Structural and biophysical studies of PCSK9 and its mutants linked to familial hypercholesterolemia, Nature Structural & Molecular Biology, vol. 14, pp. 413-419, 2007.
2P4E Statistics Search, filed in European Opposition to Ep 2215124B1. No date of publication is immediately apparent in this document. It is noted that the search date in the document itself is between Mar. 2007 and May 2007 for p. 1. For p. 2, it is noted that the search date is between Jun. 2007 and Jun. 2017.
Exhibit I Cell Assay Screening: Dose Response Against PCSK9 (D37aY) by LDL Uptake Assay (Feb. 24, 2015) filed in European Opposition to Ep 2215124B1.
Declaration by Dr. Edward A. Fisher Dated Jul. 20, 2018, filed in European Opposition to EP 2215124B1.
Declaration by Dr. Anthony R. Rees Dated Aug. 27, 2018, filed in European Opposition to EP 2215124B1.
Colored Figure of Tony Rees Third Declaration filed in European Opposition to Ep 2215124B1 Dated Aug. 27, 2018.
Weider et al. Proprotein Convertase Subtilisin/Kexin Type 9 (PCSK9) Single Domain Antibodies Are Potent Inhibitors of Low Density Lipoprotein Receptor Degradation, The Journal Of biological chemistry, vol. 291, No. S2, p. 16659-16671, 2016.
Declaration by Kelly Berry Dated Jan. 2017, filed in European Opposition to EP 2215124B1.
Declaration by Wei Wang Dated Jan. 25, 2017, filed in European Opposition to EP 2215124B1.

Appendix A to D143_Laboratory Notebook No. 96691 Researcher's Name: Wei Wang Imaged Date Sep. 30, 2009.
Appendix B to D143_Laboratory Notebook No. 107157 Researcher's Name: Wei Wang Imaged Date Sep. 14, 2011.
Declaration by Joyce Chi Yee Chan Dated Jan. 30, 2017, filed in European Opposition to EP 2215124B1.
Immunobiology: The Immune system in health and disease, 6th Edition, Editor: C.A. Janeway, Jr. (2005) Garland Science Publishing, New York, NY 10001, 2299.
Declaration by Dr. Peter Hudson of Sep. 25, 2017 (filed by Amgen in defense of the Australian counterpart), filed in European Opposition to Ep 2215124B1.
Declaration by Prof. Thomas Schwartz of Sep. 27, 2018, filed in European Opposition to EP 2215124B1.
Declaration by Dr. Jay Horton of Sep. 27, 2018 (D147), filed in European Opposition to Ep 2215124B1.
Guo et al. Evaluation of Power Strength for Hepatic Gene Expression in Vivo Following Adenovirus- mediated gene transfer, Gene Therapy, vol. 3, pp. 802-810, 1996.
Shimano et al. Isoform 1c of Sterol Regulatory element Bindng Protein is less active than isoform 1a in livers of transgenic mice and in cultured cells, J. Clinical Inves. Vol. 99, No. 5, pp. 846, 1997.
Declaration by Prof. Thomas Schwartz of Sep. 27, 2018 (D151) filed in European Opposition to Ep 2215124B1.
Declaration by Fabian Strohschein of 3D Activation GmbH (Sep. 27, 2018) filed in European Opposition to Ep 2215124B1.
EPO communication Pursuant to Article 94(3) EPC dated Mar. 3, 2018 in European U.S. Appl. No. 16/204,336.
Declaration by John Whealan Dated Sep. 19, 2018, filed in European Opposition to EP 2215124B1.
Release German Federal Patent Court Dated Sep. 7, 2018 with English Translation, filed in European Opposition to Ep 2215124B1.
Declaration by Mark O'Leavey Dated Nov. 7, 2018, filed in European Opposition to EP 2215124B1.
Bhat et al. Molecular Surface Generation Using a Variable-Radius Solvent Probe, Proteins (62):244-261 (Annex 1 of D158), 2006.
Prior Art Timeline for EP 2 215 124 (Overview) (D161), filed in European Opposition to EP 2215124B1, filed on Nov. 18, 2018.
Prior Art Timeline from D9 to Priority Date (D162), filed in European Opposition to EP 2215124B1, filed on Nov. 18, 2018.
Declaration by Prof. Schwartz filed in European Opposition to EP 2215124B1, dated Nov. 19, 2018.
2nd Declaration by John Whealan Dated Nov. 22, 2018, filed in European Opposition to EP 2215124B1.
Abdiche et al., Antibodies Targeting Closely Adjacent or Minimally Overlapping Epitopes Can Displace One Another, (2017), Plos One 12(1): e0169535.
Patentee's internal Research Plan: Human Proprotein Convertase Subtilisin/Kexin Type 9a (PCSK9) (Jun. 2006) filed in European Opposition to EP 2215124B1.
Horton, Internal Medicine Grand Rounds handout: PCSK9: A New Regulatory of Plasma LDL Cholesterol, Dated Dec. 21, 2007.
Evidence for public availability (PCSK9_record_no 23210) filed in European Opposition to Ep 2215124B1, dated Jun. 28, 2019.
Additional evidence for public availability of D169 Additional evidence for public availability of D169 filed in European Opposition to EP 2215124B1, dated Feb. 2010.
20160127_Transcript of Status Conference-Excerpt (excluding Handout) filed in European Opposition to Ep 2215124B1, dated Jan. 27, 2016.
Court Order Excluding UTSW Handout filed Feb. 18, 2016 in European Opposition to EP 2215124B1.
2nd Declaration of Dr. Lutz Riechmann, Dated Jul. 7, 2019, filed in European Opposition to EP 2215124B1.
Declaration of Dr Andre Frenzel of Yumab, including annexed declarations of Dr Markus Hildinger of Evitria, Dr Markus Hildinger of Evitria and Dr Tammy Huang of Regeneron, Dated Jul. 6, 2019, filed in European Opposition to Ep 2215124B1.
3rd Declaration of Dr. Lutz Riechmann Dated Jul. 7, 2019, filed in European Opposition to EP 2215124B1.
2nd Declaration of Bastian Zimmermann (Biaffin) Dated Jan. 17, 2017, filed in European Opposition to EP 2215124B1.

(56)                    References Cited

OTHER PUBLICATIONS

Declaration of S. Jackson (2019), filed in European Opposition to EP 2215124B1.
Declaration of T. Rees (2020), filed in European Opposition to EP 2215124B1.
EPO submission—Sanofi, dated Jul. 25, 2019, filed in European Opposition to EP 2215124B1.
Regeneron's Grounds of Appeal dated Jul. 8, 2019, filed in European Opposition to EP 2215124B1.
Regeneron's (AO5) Reply to Grounds of Appeal - Dec. 3, 2019, filed in European Opposition to EP 2215124B1.
Sanofi's Grounds of Appeal dated Jul. 18, 2019 filed in European Opposition to EP 2215124B1.
Sanofi-Aventis Statement of grounds of appeal—Sanofi, dated Jul. 18, 2019, filed in European Opposition to EP 2215124B1.
Further Submissions of Sanofi, dated Oct. 22, 2019, filed in European Opposition to EP 2215124B1.
Sanofi's (AO1) Reply to Grounds of Appeal, dated Dec. 3, 2019, filed in European Opposition to EP 2215124B1.
Regeneron's Submission—Declaration of Ashique Rafique, dated Aug. 28, 2020, filed in European Opposition to EP 2215124B1.
Expert Declaration of Anthony R. Rees, D. Phil, Dated Jul. 26, 2016 (D56), filed in European Opposition to EP 2215124B1.
Minutes of The Oral Proceedings Dated Nov. 24, 2020 filed in European Opposition to EP 2215124B1.
Verdict filed Feb. 26, 2019, in *Amgen Inc., v. Sanofi,* in the United States District Court for the District of Delaware, Case 1:14-cv-01317-RGA, Document 818, 4 pages.
Memorandum Opinion filed on Aug. 28, 2019 in *Amgen Inc., v. Sanofi,* in the United States District Court for the District of Delaware, Case 1:14-cv-01317-RGA, Document 1050, 34 pages.
Final Office Action Dated Nov. 19, 2020 in U.S. Appl. No. 13/469,032.
Decision dated Feb. 11, 2021 in *Amgen Inc., v. Sanofi,* in the United States Court of Appeals for the Federal Circuit, No. 20-1074, {Document 132} 14 pages.
Appellants' Petition for Rehearing en Banc filed on Apr. 14, 2021 in *Amgen Inc., v. Sanofi,* in the United States Court of Appeals for the Federal Circuit, No. 20-1074, {Document 136} 49 pages.
On Petition for Rehearing en Banc filed on Jun. 21, 2021 in *Amgen Inc., v. Sanofi,* in the United States Court of Appeals for the Federal Circuit, No. 20-1074, {Document 159} 11 pages.
Beglova, N. et al., "The LDL receptor: How acid pulls the trigger", Trends Biochem. Sci., 2005, vol. 30:309-317.
Beglova, N. et al., "Cooperation between Fixed and Low pH-Inducible Interfaces Controls Lipoprotein Release by the LDL Receptor", Mol. Cell, 2004, vol. 16:281-92.
Supplemental Data related to article NI, Yan G et al., "A PCSK9-binding antibody that structurally mimics the EGF(A) domain of LDL-receptor reduces LDL cholesterol in vivo," J Lipid Research, Jan. 2011, in 10 pages.
Restriction Requirement dated Dec. 4, 2020 received in U.S. Appl. No. 16/348,653 (APMOL.018NP).
Winkler et al., "Changing the Antigen Binding Specificity by Single Point Mutations of an Anti-p24 (HIV-1) Antibody", The Journal of Immunology, 2000, vol. 165:4505-4514.
Office Action dated Aug. 27, 2018 in U.S. Appl. No. 13/655,984.
Notice of Allowance dated May 28, 2020, received in U.S. Appl. No. 14/562,546.
Office Action dated Feb. 3, 2021 in Korean Patent Application No. 10-2020-7019200 (with English translation).
Decision of Reexamination with English Translation dated Oct. 22, 2020 in Chinese Application No. 201410218672.X.
Declaration by Prof. Thomas Schwartz of Sep. 27, 2018 (D147) filed in European Opposition to Ep 2215124B1.
Declaration by Dr. Jay Horton of Sep. 27, 2018 (D148), filed in European Opposition to Ep 2215124B1.
Office Action dated Oct. 20, 2020 in Ukrainian Patent Application No. a201401217 with English Translation.
Search Report and Written Opinion received in Singaporean Patent Application No. 11201904266Q, dated Sep. 29, 2020.

1st Brief of the Defendant (invalidity argument regarding the present patent 1) in Damages Case against JP 5705288 (with English Translation) Dated Oct. 16, 2020.
2nd Brief of the Defendant (invalidity argument regarding the present patent 2) in Damages Case against JP 5705288 (with English Translation) Dated Oct. 16, 2020.
3rd Brief of the Defendant in Damages Case against JP 5705288 (with English Translation) Dated Oct. 23, 2020.
Description of Evidences (1) in Damages Case against JP 5705288 (with English Translation) Dated Oct. 16, 2020.
4th Brief of the Defendant in Damages Case against JP 5705288 (with English Translation) Dated Oct. 30, 2020.
Exhibit B2-1 in Damages Case against JP 5705288 (Declaration of Dr. Andre Frenzel in Dated Dec. 13, 2019).
Exhibit B2-2 in Damages Case against JP 5705288 (Declaration of Dr. Lutz Riechmann in Dated Dec. 16, 2019).
Exhibit B3 in Damages Case against JP 5705288 (Decision of Aug. 28, 2019 by U.S. District Court of Delaware, for civil case 14-1317-RGA).
Exhibit B4-1 in Damages Case against JP 5705288 (Decision of Sep. 11, 2019 by U.S. District Court of Delaware, for civil case 14-1317-RGA).
Exhibit B4-2 in Damages Case against JP 5705288 (Document referred to as "DTX.3221,2" in the decision of Aug. 28, 2019 by U.S. District Court of Delaware, for civil case 14-1317-RGA).
Exhibit B5-1 in Damages Case against JP 5705288 (Declaration of Dr. Andre Frenzel Dated Dec. 15, 2019).
Exhibit B5-2 in Damages Case against JP 5705288 (Declaration of Dr. Lutz Riechmann Dated Dec. 17, 2019).
KIPOS Notice of Preliminary Rejection dated Sep. 4, 2020 in Korean Application 10-2020- 7017279 (With English Translation).
Examination Report dated Nov. 2, 2020 in Gulf Coast Application No. GC 2012-38764.
Notice of Allowability dated Sep. 23, 2020 in U.S. Appl. No. 14/562,546.
Datasheet for the decision of Oct. 29, 2020, filed in European Patent Appeal to EP 2215124, in 8 pages.
Office Action dated Oct. 16, 2020 in Indonesian Patent Application No. P00201701905, in 6 pages (with English translation).
Office Action dated Jan. 14, 2021 in Chinese Patent Application No. 201410218704.6 in 19 pages (with English translation).
Office Action dated Nov. 29, 2020 in Argentinian Patent Application No. 20120101655 in 5 pages (with English translation).
Office Action dated Jan. 27, 2021 in U.S. Appl. No. 12/903,084.
Office Action dated Jan. 29, 2021 in U.S. Appl. No. 13/931,716.
Office Action dated Feb. 8, 2021 in U.S. Appl. No. 13/422,904.
Office Action dated Jan. 21, 2021 in Australian Patent Application No. 2020201012 in 5 pages.
Office Action dated Mar. 9, 2021 in U.S. Appl. No. 13/494,912.
Notice of Opposition dated Feb. 5, 2021 filed in European Patent Application No. 13151352.5 (European Patent No. 2641917B1), in 72 pages.
Witness Declaration by Dr. Jork Zwicker on the Oral Proceedings held in the matter T 845/19 of Nov. 3, 2020, in 23 pages.
Identification of Nucleic Acid Sequences considering Code Degeneracy, as filed in the Opposition of European Patent No. 2641917, in 7 pages, submitted Feb. 5, 2021.
Request for Grant of the Divisional European Patent Application 13151352.5 as filed on Jan. 15, 2013, in 5 pages.
5th Brief of the Defendant Sanofi K.K. in Damages Case against JP 5705288 (with English Translation) dated Jan. 8, 2021, in 15 pages.
6th Brief of the Defendant Sanofi K.K. in Damages Case against JP 5705288 (with English Translation) dated Jan. 8, 2021, in 23 pages.
Exhibit B13 filed in Damages Case against JP 5705288 (Report on oral hearing before the Technical Boards of Appeal e-mailed Oct. 29, 2020 by IPD Analytics), in 2 pages.
Exhibit B15 filed in Damages Case against JP 5705288 (Report on cancellation of injunction by German court e-mailed Nov. 5, 2020 by IPD Analytics), in 2 pages.
Exhibit B16 filed in Damages Case against JP 5705288 (Witness Statement of Dr. Jork Zwicker dated Nov. 3, 2020), in 23 pages.
Exhibit B19 filed in Damages Case against JP 5705288 (Report by IPD Analytics: PCSK9 Antibodies Update [Amgn, Regn, Sny]:

(56)            References Cited

OTHER PUBLICATIONS

Appeals Court Affirms Delaware Court Decision Invalidating Amgen's Patents), in 1 page, dated Feb. 11, 2021.
Declaration by Prof. Thomas Schwartz of Aug. 15, 2017 (D115) filed in European Opposition to Ep 2215124B1.
Office Action dated Mar. 24, 2021 in U.S. Appl. No. 13/682,698.
Office Action dated Oct. 14, 2020 in African Patent Application No. AP/P/2019/011613, in 5 pages.
Notice of Reexamination dated Jan. 27, 2021 in Chinese Application No. 201410219429.X (with English Translation), in 20 pages.
Office Action dated Mar. 5, 2020 in U.S. Appl. No. 13/655,984.
Office Action dated Mar. 3, 2021 in Israeli Patent Application No. 273353, in 7 pages.
Office Action dated Mar. 2, 2021 in Japanese Patent Application No. 2019-231236, in 7 pages.
Office Action dated Mar. 29, 2021 in U.S. Appl. No. 13/463,751, in 27 pages.
Prescribing Information for LIPITOR® (atorvastatin calcium) Tablets, for oral administration, dated Jun. 2009, in 23 pages.
Notice of Allowance dated Apr. 21, 2021 in U.S. Appl. No. 14/562,546.
Office Action dated Nov. 27, 2020 in Gulf Coast Patent Application No. GCC/P/2008/38365, in 4 pages.
Opposition Notice dated Jul. 31, 2019 in Colombian Application No. NC2019/0004814 (with English Translation).
Office Action dated May 20, 2021 in U.S. Appl. No. 13/619,555, in 29 pages.
Office Action dated Jun. 17, 2021 in U.S. Appl. No. 14/316,587, in 26 pages.
Office Action dated Jun. 24, 2021 in U.S. Appl. No. 13/422,887 in 31 pages.
Office Action dated Jun. 28, 2021 in U.S. Appl. No. 14/459,777 in 28 pages.
Office Action issued for Uruguayan Patent Application No. 034063 dated May 11, 2021 in 11 pages (with English translation).
Office Action issued for Singaporean Patent Application No. 10201603700T dated May 21, 2021 in 10 pages (with English translation).
Office Action issued for Chinese Patent Application No. 201710556773.1 dated May 8, 2021 in 14 pages (with English translation).
Office Action issued for Korean Patent Application No. 10-2020-7019200 dated Jun. 11, 2021 in 7 pages (with English translation).
"Guidance for Industry—Estimating the Maximum Safe Starting Dose in Initial Clinical Trials for Therapeutics in Adult Healthy Volunteers", U.S. Department of Health and Human Services Food and Drug Administration, Jul. 2005, in 30 pages. URL: https://www.fda.gov/media/72309/download.
Wang, W et al., "Antibody Structure, Instability, and Formulation", Journal of Pharmaceutical Sciences, Jan. 2007, vol. 96(1), pp. 1-26, XP009084505, Issn: 0022-3549, Doi: 10.1002/JPS.20727.
Office Action for Australian Application No. 2020201219 in 4 pages, dated Apr. 30, 2021.
Office Action for Egyptian Application No. PCT 302/2010 (2010020302) with English translation in 10 pages. No date for this document is immediately apparent. Applicant notes that the document recognizes a paper submitted on Mar. 2, 2020, and that this document was received on Jun. 29, 2021.
Office Action for Chilean Application No. 201703288 with English translation in 76 pages, dated Apr. 9, 2021.
Office Action in U.S. Appl. No. 13/469,032, dated Jul. 27, 2021.
Office Action dated Sep. 24, 2021 in U.S. Appl. No. 12/903,084.
Office Action dated Sep. 14, 2021 in U.S. Appl. No. 13/655,984.
Office Action dated Sep. 27, 2021 in U.S. Appl. No. 16/348,653.
Notice of Allowability for U.S. Appl. No. 14/562,546 in 3 pages, dated Oct. 27, 2021.
Certified Copy of Priority Document for U.S. Appl. No. 60/911,654, filed in European Opposition for EP 2215124 in 83 pages on Feb. 24, 2016.

Declaration of Dr. Andre Frenzel (3) (Exhibit B21) dated Aug. 13, 2021, filed by Sanofi K.K. in Japanese Case Number: 2020 (Wa) No. 8642: Case of Claim for Damages (with English translation).
Declaration of Professor Jay Horton (Exhibit B22), filed Aug. 18, 2021, filed by Sanofi K.K. in Japanese Case Number: 2020 (Wa) No. 8642: Case of Claim for Damages (with English translation).
Defendant's Eighth Brief filed Aug. 20, 2021, by Sanofi K.K. in Japanese Case Number: 2020 (Wa) No. 8642: Case of Claim for Damages (with English translation).
Defendant's Eleventh Brief filed Aug. 20, 2021, by Sanofi K.K. in Japanese Case Number: 2020 (Wa) No. 8642: Case of Claim for Damages (with English translation).
Defendant's Ninth Brief filed Aug. 20, 2021, by Sanofi K.K. in Japanese Case Number: 2020 (Wa) No. 8642: Case of Claim for Damages (with English translation).
Defendant's Seventh Brief filed Aug. 20, 2021, by Sanofi K.K. in Japanese Case Number: 2020 (Wa) No. 8642: Case of Claim for Damages (with English translation).
Defendant's Tenth Brief filed Aug. 20, 2021, by Sanofi K.K. in Japanese Case Number: 2020 (Wa) No. 8642: Case of Claim for Damages (with English translation).
Defendant's Twelfth Brief filed Aug. 20, 2021, by Sanofi K.K. in Japanese Case Number: 2020 (Wa) No. 8642: Case of Claim for Damages (with English translation).
Duff, C et al., "Antibody-mediated disruption of the interaction between PCSK9 and the low-density lipoprotein receptor", Biochemical Journal, May 2009, vol. 419(3), pp. 577-584.
Hoogenboom, H et al. "Designing and Optimizing library selection strategies for generating high-affinity antibodies", TIBTECH, Feb. 1997, vol. 15, pp. 62-70.
House, D., "Alnylam and The Medicines Company's inclisiran shows significant treatment effect in mid-stage study", Seeking Alphaa, Aug. 2017, in 1 page. URL: https://seekingalpha.com/news3/292152-alnylam-medicines-companys-inclisiranshows-significant-treatment-effect-mld-stage-study.
Lagace, T., "PCSK9 and LDLR degradation: regulatory mechanisms in circulation and in cells", Current Opinion, 2014, vol. 25, No. 5, pp. 387-393.
Notice of Allowance in U.S. Appl. No. 14/562,546 in 15 pages, dated Aug. 4, 2021.
Office Action dated Apr. 28, 2021 in U.S. Appl. No. 16/348,653, in 111 pages.
Office Action dated Aug. 23, 2020 in Chilean Application No. 201901304 (with English Translation).
Office Action dated Oct. 22, 2021 in U.S. Appl. No. 13/931,716.
Office Action for Colombian Application No. NC2019/0004814 in 12 pages, dated Jul. 9, 2021.
Office Action for European Application No. EP 19207796.4 in 11 pages, dated Oct. 25, 2021.
Office Action in Chilean Application No. 201901304 with English translation in 31 pages, dated May 17, 2021.
Patentee's (Amgen Inc.) Reply to the Appellant-Opponent's Grounds of Appeal (T8045/19) regarding Opposition against European Patent No. EP 2215124, in 192 pages, dated Dec. 3, 2019.
Poirier, S et al., "Dissection of the Endogenous Cellular Pathways of PCSK9-induced Low Density Lipoprotein Receptor Degradation—Evidence for an Intracellular Route", The Journal of Biological Chemistry, Oct. 2009, vol. 284(42), pp. 28856-28864.
Protocol for Competition Assay (Exhibit A18-Exhibit 3), filed Aug. 20, 2021 by Sanofi K.K. in Japanese Case Number: 2020 (Wa) No. 8642: Case of Claim for Damages (with English translation).
Summons to Attend Oral Proceedings Pursuant to Rule 115 (1) EPC in European Patent Application No. 13151352.5 in 31 pages, dated Oct. 12, 2021.
Final Office Action Dated Jan. 27, 2022, in U.S. Appl. No. 13/682,698 in 26 pages.
Final Office Action Dated Jan. 11, 2022, in U.S. Appl. No. 13/494,912 in 22 pages.
Office Action Dated Jan. 12, 2022, in U.S. Appl. No. 14/316,587 in 22 pages.
Notice of Allowance Dated Feb. 8, 2022, in U.S. Appl. No. 14/562,546 in 11 pages.
U.S. Appl. No. 60/957,668, filed Aug. 23, 2007, Jackson et al.

(56) References Cited

OTHER PUBLICATIONS

U.S. Appl. No. 61/008,965, filed Dec. 21, 2007, Jackson et al.
U.S. Appl. No. 61/010,630, filed Jan. 9, 2008, Jackson et al.
U.S. Appl. No. 61/484,610, filed May 10, 2011, Gibbs.
"Trial Evaluating PCSK9 Antibody in Subjects with LDL Receptor Abnormalities (TESLA)", ClinicalTrials.gov, first posted May 1, 2012, identifier: NCT01588496, in 7 pages.
Catapano, A et al., "2016 ESC/EAS Guidelines for the Management of Dyslipidemias", European Heart Journal, Aug. 2016, vol. 37, pp. 2999-3058. URL: doi:10.1093/eurheartj/ehw272.
Final Office Action for U.S. Appl. No. 13/463,751 in 23 pages, dated Feb. 11, 2022.
Gogas, B. et al., "Assessment of coronary atherosclerosis by IVUS and IVUS-based imaging modalities: progression and regression studies, tissue composition and beyond", The International Journal of Cardiovascular Imaging, Mar. 2011, vol. 27(2), pp. 225-237.
Goldberg, A. et al., "Familial hypercholesterolemia: screening, diagnosis and management of pediatric and adult patients: clinical guidance from the National Lipid Association Expert Panel on Familial Hypercholesterolemia", Journal of Clinical Lipidology, Jun. 2011, vol. 5, pp. 133-140.
Latimer, J. et al., "PCSK9 inhibitors in the prevention of cardiovascular disease", Journal of Thrombosis and Thrombolysis, Oct. 2016, vol. 42(3), pp. 405-419.
Notice of Allowability for U.S. Appl. No. 14/562,546 in 3 pages, dated Feb. 25, 2022.
Office Action for Chinese Application No. CN 201710556773.1 with English translation in 14 pages, dated Dec. 2, 2021.
Office Action for Egyptian Application No. EG 1716/2013 with English translation in 8 pages, dated Jul. 26, 2021.
Office Action for Japanese Application No. JP 2019-231236 in 11 pages, dated Jan. 11, 2022.
Office Action for Japanese Application No. JP 2019-525021 with English translation in 7 pages, dated Nov. 30, 2021.
Office Action for Saudi Arabian Application No. SA 519401782 with English translation in 10 pages, mailed Sep. 29, 2021.
Office Action for Singaporean Application No. Sg 11201904266Q in 8 pages, dated Jan. 14, 2022. .
Office Action for Taiwanese Application No. TW 109115264 with English translation in 17 pages, dated Dec. 29, 2021.
Office Action for U.S. Appl. No. 13/469,032 in 21 pages, dated Mar. 21, 2022.
Office Action for U.S. Appl. No. 13/422,904 in 22 pages, dated Dec. 22, 2021.
Office Action for Uruguayan Application No. UY 034063 with English translation in 8 pages, dated Dec. 30, 2021.
Schroeder, H. et al., "Structure and function of immunoglobulins", The Journal of Allergy and Clinical Immunology, Feb. 2010, vol. 125, pp. S41-S52.
Waters, D. et al., "PCSK9 Inhibitors for Statin Intolerance?", The Journal of the American Medical Association, Apr. 2016, vol. 315(15), pp. 1571-1572 (author's manuscript).
Office Action for Egyptian Application No. EG 1716/2013 with English translation in 9 pages, received Mar. 14, 2022.
Amgen's Petition for a Writ of Certiorari filed in Nov. 2021 in Amgen Inc., v. Sanofi, in the Supreme Court of the United States, 118 pages.
Office Action dated May 16, 2022 in U.S. Appl. No. 16/348,653 in 24 pages.
Office Action dated May 19, 2022 in U.S. Appl. No. 14/316,587 in 11 pages.
Notice of Allowance dated May 25, 2022 in U.S. Appl. No. 14/562,546 in 17 pages.
Final Office Action for U.S. Appl. No. 13/655,984 in 24 pages, dated Jul. 28, 2022.
U.S. Appl. No. 61/562,303, filed Nov. 21, 2011, Gibbs.
U.S. Appl. No. 61/595,526, filed Feb. 6, 2012, Dias et al.
U.S. Appl. No. 61/614,417, filed Mar. 22, 2012, Dias et al.
U.S. Appl. No. 61/642,363, filed May 3, 2012, Chan et al.

"History of Changes for Study: NCT01588496, Trial Evaluating PCSK9 Antibody in Subjects with LDL Receptor Abnormalities (TESLA)", ClinicalTrials.gov, first posted May 1, 2012, last update posted Sep. 20, 2012, identifier: NCT01588496, available at https://clinicaltrials.gov/ct2/history/NCT01588496?V_4=View#StudyPageTop. The reference is a webpage, and the dates apparent in the document are listed herewith. However, the webpage may have been available, in some form, prior to this date.
"PCSK9 inhibition: A game changer in cholesterol management", Mayo Clinic, Nov. 2015, in 5 pages. URL: https://www.mayoclinic.org/medical-professionals/cardiovascular-diseases/news/pcsk9-inhibition-a-game-changer-in-cholesterol-management/mac-20430713. The reference is a webpage, and the date apparent in the document is listed herewith. However, the webpage may have been available, in some form, prior to this date.
"Sanofi finalizes Praluent® (alirocumab) restructuring with Regeneron", Press Release by Sanofi dated Apr. 6, 2020, in 3 pages.
13th Brief of the Defendant (Counterarguments against "I" alone in 7th Brief of the Plaintiff) in Damages Case against JP 5705288, with English Translation in 65 pages, dated Dec. 21, 2021.
7th Brief of the Plaintiff (Counterargument to Defendant's 7th, 9th and 10th Briefs) in Damages Case against JP 5705288, with English Translation in 109 pages, dated Dec. 7, 2021.
8th Brief of the Plaintiff (Counterargument to Defendant's 12th Brief) in Damages Case against JP 5705288, with English Translation in 10 pages, dated Dec. 7, 2021.
9th Brief of the Plaintiff (Counterargument to Defendant's 8th Brief) in Damages Case against JP 5705288, with English Translation in 100 pages, dated Dec. 10, 2021.
Bahadur, R. P. et al., "The interface of protein-protein complexes: Analysis of contacts and prediction of interactions", Cellular and Molecular Life Sciences, Dec. 2008, vol. 65, pp. 1059-1072.
Briand, J. P., et al., "Synthetic Peptides as Antigens: Pitfalls of Conjugation Methods", Journal of Immunological Methods, Apr. 1985, vol. 78, pp. 59-69.
Chames, P. et al., "Chapter 10—Selection of Antibodies Against Biotinylated Antigens", *Methods in Molecular Biology—Antibody Phage Display Methods and Protocols,* ed., Philippa M. O'Brien et al., 2002, vol. 178, pp. 147-157.
Cohen, S. et al., "Immunogenicity risk assessment for biotherapeutics through in vitro detection of CD134 and CD137 on T helper cells", MABS, Mar. 2021, vol. 13(1), in 12 pages.
Corrected Notice of Allowability for U.S. Appl. No. 14/562,546 in 3 pages, dated Jun. 15, 2022.
Curriculum Vitae of Gregory A. Petsko filed in Damages Case against JP 5705288 dated Jun. 2020, in 28 pages.
Davis, G. et al., "Production of Human Antibodies from Transgenic Mice", *Methods in Molecular Biology—Antibody Engineering Methods and Protocols,* ed., Benny K. C. Lo, 2004, vol. 248, pp. 191-200.
Decision from Düsseldorf Higher Regional Court, 2 U 35/19 (Oberlandesgericht Düsseldorf, 2 U 35/19) filed in Damages Case against JP 5705288 with English translation dated Aug. 5, 2019, in 14 pages.
Declaration of Chi-Chien "Oscar" Pan filed in Damages Case against JP 5705288 dated Dec. 12, 2017, in 34 pages.
Declaration of Dr. Andre Frenzel (4) filed in Damages Case against JP 5705288 dated Mar. 17, 2022, in 20 pages.
Declaration of Evan A. Stein, M.D., Ph.D. filed in Damages Case against JP 5705288 dated Aug. 1, 2019, in 21 pages.
Declaration of Prof. Heike Zeitler filed in Damages Case against JP 5705288 with English translation dated Oct. 21, 2019, in 5 pages.
Declaration of Prof. Jay Horton filed in Damages Case against JP 5705288 dated Mar. 18, 2022, in 20 pages.
Declaration of Prof. Thomas U. Schwartz filed in Damages Case against JP 5705288 dated Apr. 22, 2018, in 6 pages.
Email correspondence from Ulrike Schatz to Dr. Ehrlich filed in Damages Case against JP 5705288 with English translation dated Jul. 23, 2019, in 3 pages.
Expert Declaration by Prof. Anthony R. Rees filed in Damages Case against JP 5705288 dated Apr. 19, 2021, in 42 pages.
Expert Declaration by Professor Anthony R. Rees filed in Damages Case against JP 5705288 dated Dec. 2, 2021, in 37 pages.

(56) References Cited

OTHER PUBLICATIONS

Expert Declaration by Professor Dr. Gregory A. Petsko filed in Damages Case against JP 5705288 dated Jul. 20, 2020, in 50 pages.

Expert Report of Dr. Rex Parker filed in Damages Case against JP 5705288 dated Dec. 8, 2021, in 33 pages.

Expert Report of Dr. Rex Parker filed in Damages Case against JP 5705288 dated Mar. 19, 2021, 99 pages.

Final Office Action for U.S. Appl. No. 12/903,084 in 23 pages, dated Aug. 8, 2022.

Final Office Action for U.S. Appl. No. 13/931,716 in 27 pages, dated Jul. 5, 2022.

Goubau, S. et al., "Immunization of Sheep Against Modified Peptides of Gonadotropin Releasing Hormone Conjugated to Carriers", Domestic Animal Endocrinology, Oct. 1989, vol. 6(4), pp. 339-347.

Hoge, S., "Peptide Antigen Design for Antibody Production", Sigma-Aldrich.com, 2003, in 2 pages.

Huang, L. et al., "Discovery of human antibodies against the C5aR target using phage display technology," Journal of Molecular Recognition, 2005, vol. 18, pp. 327-333.

Hust, M. et al., "Selection Strategies II: Antibody Phage Display", Handbook of Therapeutic Antibodies, ed., Stefan Dubel, Jan. 2007, vol. 1, pp. 45-68.

International Search Report and Written Opinion for Application No. PCT/US2021/034489 in 20 pages, dated Sep. 29, 2021.

Jones, S. et al., "Principles of protein-protein interactions", Proceedings of the National Academy of Sciences, Jan. 1996, vol. 93, pp. 13-20.

Lateef, S. et al., "An Improved Protocol for Coupling Synthetic Peptides to Carrier Proteins for Antibody Production Using DMF to Solubilize Peptides", Journal of Biomolecular Techniques, Jul. 2007, vol. 18, pp. 173-176.

Letter from Dr. Ursula Kassner to Prof. Dr. W. Dieter Paar filed in Damages Case against JP 5705288 with English translation dated Jul. 25, 2019, in 5 pages.

Letter from Steven P. Caltrider to Intellectual Property High Court of Japan filed in Damages Case against JP 5705288 dated Jun. 21, 2019, in 16 pages.

Lins, L. et al., "Analysis of accessible surface of residues in proteins", Protein Science, Jul. 2003, vol. 12(7), pp. 1406-1417.

Office Action for Canadian Application No. CA 2835294 in 3 pages, dated Mar. 24, 2022.

Office Action for Chilean Application No. CL 201703288 with English translation in 58 pages, dated May 4, 2022.

Office Action for Chilean Application No. CL 202002993 with English translation in 38 pages, dated Feb. 10, 2022.

Office Action for Israeli Application No. IL 273353 with English translation in 8 pages, dated Jan. 19, 2022.

Office Action for Peruvian Application No. PE 2386-2017 with English Summary in 9 pages, dated Feb. 14, 2022.

Office Action for Taiwanese Application No. TW 107117443 with English translation in 14 pages, dated Apr. 6, 2022.

Office Action for U.S. Appl. No. 13/619,555 in 22 pages, dated Apr. 5, 2022.

Office Action for U.S. Appl. No. 14/459,777 in 22 pages, dated May 4, 2022.

Pedersen, J. et al., "Comparison of Surface Accessible Residues in Human and Murine Immunoglobulin Fv Domains: Implication for Humanization of Murine Antibodies", Journal of Molecular Biology, Jan. 1994, vol. 235, pp. 959-973.

Piche-Nicholas, N. et al., "Changes in complementarity-determining regions significantly alter IgG binding to the neonatal Fc receptor (FcRn) and pharmacokinetics", MABS, Jan. 2018, vol. 10, pp. 81-94.

Ramaraj, T. et al., "Antigen-antibody interface properties: Composition, residue interactions, and features of 53 non-redundant structures", Biochimica et Biophysica Acta, Mar. 2012, vol. 1824(3), pp. 520-532.

Schaaper, W. M. M. et al., "Manipulation of antipeptide immune response by varying the coupling of the peptide with the carrier protein", Molecular Immunology, 1989, vol. 26(1), pp. 81-85.

Schwartz, "Alirocumab and Cardiovascular Outcomes after Acute Coronary Syndrome", The New England Journal of Medicine, Nov. 2019, vol. 379(22), pp. 2097-2107.

Second Expert Report of Professor Michael J. Eck filed in Damages Case against JP 5705288 dated Sep. 1, 2020, in 33 pages.

Spitthover, R. et al., "Real-world study: Escalating targeted lipid-lowering treatment with PCSK9- inhibitors and lipoprotein apheresis", Journal of Clinical Apheresis, Aug. 2019, vol. 34(4), pp. 423-433.

Timmerman, P., "Report of Binding Studies in ELISA for a Series of Anti-PCSK9 Monoclonal Antibodies", Pepscan, May 2021, Version 1.0, in 9 pages.

Verdict in the Proceedings for the Issuance of an Injunction (Bundesgerichtshof Im namen des volkes Urteil in dem Verfahren auf Erlass einer einstweiligen Verfugung) filed in Damages Case against JP 5705288 dated Jun. 4, 2019, in 52 pages.

Brief Communication—Letter from Sanofi in the Opposition for European Patent Application No. 13151352.5 (European Patent No. 2641917B1) in 73 pages, dated Jan. 3, 2023.

Brief Communication regarding Oral Proceedings in the Opposition for European Patent Application No. 13151352.5 (European Patent No. 2641917B1) in 1 page, dated Nov. 28, 2022.

Cen, J. et al., "Progress in the study of statins in relation to coronary atheroma progression and retraction", South China Journal of Cardiovascular Diseases, Jun. 2010, vol. 16, No. 3, with English machine translation in 15 pages.

Decision regarding the Oppositions for Australian Patent Application Nos. AU 2013203677, AU 2013203685, AU 2013203689, AU 2013203748, and AU 2013203751 in 57 pages, dated Sep. 26, 2022.

Declaration of Professor Dr. Samuel I. Gunderson (D51) filed in the Opposition for European Patent Application No. 13151352.5 (European Patent No. 2641917B1) in 35 pages, dated Nov. 22, 2022.

Final Office Action for U.S. Appl. No. 13/422,904 in 25 pages, dated Sep. 14, 2022.

Final Office Action for U.S. Appl. No. 13/463,751 in 22 pages, dated Dec. 8, 2022.

Final Office Action for U.S. Appl. No. 14/316,587 in 23 pages, dated Nov. 4, 2022.

Final Office Action for U.S. Appl. No. 16/348,653 in 12 pages, dated Oct. 13, 2022.

Hirayama, A. et al., "Effects of Evolocumab (AMG 145), a Monoclonal Antibody to PCSK9, in Hypercholesterolemic, Statin-Treated Japanese Patients at High Cardiovascular Risk—Primary Results From the Phase 2 YUKAWA Study", Circulation Journal, May 2014, vol. 78, pp. 1073-1082.

International Preliminary Report on Patentability for Application No. PCT/US2012/037394 in 10 pages, dated Nov. 21, 2013.

International Preliminary Report on Patentability for Application No. PCT/US2021/034489 in 14 pages, dated Dec. 8, 2022.

Notice of Allowability for U.S. Appl. No. 14/562,546 in 12 pages, dated Oct. 4, 2022.

O'Donoghue, M. et al., "Long-Term Evolocumab in Patients with Established Atherosclerotic Cardiovascular Disease", Circulation, Oct. 2022, vol. 146, pp. 1109-1119.

Office Action for Argentine Application No. AR P180100333 with English translation in 7 pages, dated Feb. 18, 2022.

Office Action for Chinese Application No. CN 201780083280.9 with English translation in 28 pages, dated Sep. 28, 2022.

Office Action for Eurasian Application No. EA 201991160 with English translation in 12 pages, dated Jun. 18, 2021.

Office Action for Eurasian Application No. EA 201991160 with English translation in 8 pages, dated Jun. 10, 2022.

Office Action for European Application No. EP 19175489.4 in 6 pages, dated Sep. 14, 2022.

Office Action for European Application No. EP 19207796.4 in 13 pages, dated Sep. 9, 2022.

Office Action for Indonesian Application No. Id P00201708121 with English translation in 6 pages, dated Dec. 13, 2022.

Office Action for Israeli Application No. IL 266579 in 6 pages, dated Jun. 22, 2022.

(56)                   References Cited

OTHER PUBLICATIONS

Office Action for Israeli Application No. IL 288048 in 6 pages, dated Jul. 24, 2022.
Office Action for Korean Application No. KR 10-2021-7027670 with English translation in 9 pages, dated Aug. 12, 2022.
Office Action for Korean Application No. KR 10-2022-7006200 with English translation in 4 pages, dated Apr. 12, 2022.
Office Action for Malaysian Application No. MY PI 2014001682 in 3 pages, dated Dec. 13, 2022.
Office Action for Peruvian Application No. PE 001494-2018/DIN with English Summary in 14 pages, dated Dec. 7, 2022.
Office Action for Philippines Application No. PH 1/2013/502285 in 4 pages, dated Aug. 4, 2022.
Office Action for Taiwanese Application No. TW 109115264 with English translation in 23 pages, dated Sep. 5, 2022.
Office Action for U.S. Appl. No. 13/469,032 in 19 pages, dated Sep. 15, 2022.
Office Action for Vietnamese Application No. VN 1-2019-01647 with English translation in 4 pages, dated Oct. 31, 2022.
Restriction Requirement for U.S. Appl. No. 17/011,433 in 5 pages, dated Nov. 25, 2022.
Sanofi's Written Submission in the Opposition for European Patent Application No. 13151352.5 (European Patent No. 2641917B1) in 17 pages, dated Nov. 30, 2022.
Stroes, E. et al., "Anti-PCSK9 Antibody Effectively Lowers Cholesterol in Patients with Statin Intolerance: the GAUSS-2 Randomized, Placebo-Controlled Phase 3 Clinical Trial of Evolocumab", Journal of the American College of Cardiology, Jun. 2014, vol. 63, pp. 2541-2548.
Third Report of the National Cholesterol Education Program (NCEP) Expert Panel on Detection, Evaluation, and Treatment of the High Blood Cholesterol in Adults (Adult Treatment Panel III) Final Report, National Institutes of Health, NIH Publication No. 02-5215, Sep. 2002, in 284 pages.
Zhang, X. et al., "Clinical Application Progress of Statin Drugs", Medical Recapitulate, Jun. 2013, vol. 19, No. 11, pp. 2051-2054.
Zhou, Y., "Intensive lipid lowering and reversing plaque to further improve cardiovascular disease prognosis", Chinese Journal of Arteriosclerosis, Nov. 2008, vol. 16, No. 11., with English machine translation in 9 pages.
On Writ of Certiorari to the United States Court of Appeals for the Federal Circuit filed in Dec. 2022 in *Amgen Inc.*, v. *Sanofi*, in the Supreme Court of the United States, 64 pages.
Final Office Action for U.S. Appl. No. 13/931,716 in 27 pages, dated Jan. 3, 2023.
Cicero, A. FG et al., "Profile of evolocumab and its potential in the treatment of hyperlipidemia", Drug Design, Development and Therapy, Jun. 2015, vol. 9, pp. 3073-3082.
Civil Verdict from Beijing Intellectual Property Court for Chinese Application No. CN 201410218704.6 with partial English translation in 41 pages, dated May 24, 2023.
Daugherty, A. et al., "Chapter 8: Formulation and delivery issues for monoclonal antibody therapeutics", Current Trends in Monoclonal Antibody Development and Manufacturing, Jan. 2010, pp. 103-129.
Expert Declaration of Wayne A. Marasco, M.D., Ph.D., with Curriculum Vitae, filed in the Appeal of the Rejection of CN 201410218704.6 in 11 pages, dated Aug. 3, 2021.
Final Office Action for U.S. Appl. No. 12/903,084 in 25 pages, dated May 18, 2023.
Final Office Action for U.S. Appl. No. 13/655,984 in 26 pages, dated May 18, 2022.
Final Office Action for U.S. Appl. No. 14/316,587 in 17 pages, dated May 5, 2023.
Final Office Action for U.S. Appl. No. 16/348,653 in 12 pages, dated Apr. 4, 2023.
IP High Court Decision with English translations, of the Japanese IP High Court regarding JP pat No. 5705288 rendered on Jan. 26, 2023 in 215 pages (10093).

IP High Court Decision with English translations, of the Japanese IP High Court regarding JP pat No. 5906333 rendered on Jan. 26, 2023 in 214 pages (10094).
Janeway, C. A. et al., "Chapter 4: The Generation of Lymphocyte Antigen Receptors", *Immunobiology: The Immune System in Health and Disease*, 2001, 5th edition, in 11 pages.
Kunik, V. et al., "The indistinguishability of epitopes from protein surface is explained by the distinct binding preferences of each of the six antigen-binding loops", Protein Engineering, Design & Selection, 2013, vol. 26, No. 10, pp. 599-609.
Liu, L. et al., "IGH V3-23*01 and its allele V3-23*03 differ in their capacity to form the canonical human antibody combining site specific for the capsular polysaccharide of *Haemophilus influenzae* type b", Immunogenetics, 2003, vol. 55, pp. 336-338.
Malby, S. et al., "The First Epidermal Growth Factor-like Domain of the Low-Density Lipoprotein Receptor Contains a Noncanonical Calcium Binding Site", Biochemistry, Feb. 2001, vol. 40, No. 8, pp. 2555-2563.
Non-Final Office Action for U.S. Appl. No. 17/011,433 in 119 pages, dated Mar. 24, 2023.
Notice of Allowability for U.S. Appl. No. 14/562,546 in 11 pages, dated Mar. 1, 2023.
Observations by Third-Party in the name of Carpmaels & Ransford LLP for European Application No. EP 19207796.4 in 11 pages, dated Mar. 5, 2023.
Office Action for Brazilian Application No. BR 112019009726-0 with English translation in 12 pages, dated Dec. 9, 2022.
Office Action for Chilean Application No. CL 202002993 with English Summary in 12 pages, dated Feb. 2, 2023.
Office Action for Egyptian Application No. EG 1716/2013 with English translation in 8 pages. No date for this document is immediately apparent. Applicant notes that this document was received Feb. 22, 2023.
Office Action for European Application No. EP 19203125.0 in 7 pages, dated Mar. 29, 2023.
Office Action for Indian Application No. IN 10476/DELNP/2013 in 3 pages, dated Feb. 10, 2023.
Office Action for Japanese Application No. JP 2019-231236 with English translations in 10 pages, dated Nov. 1, 2022.
Office Action for Korean Application No. KR 10-2019-7016872 with English translation in 16 pages, dated Mar. 3, 2023.
Office Action for Malaysian Application No. MY PI 2014001683 in 4 pages, dated Dec. 14, 2022.
Office Action for Malaysian Application No. MY PI 2018000605 in 3 pages, dated Apr. 14, 2023.
Office Action for Mexican Application No. MX/a/2019/004264 with English Summary in 8 pages, dated Jan. 25, 2023.
Office Action for Peruvian Application No. PE 001494-2018/DIN with English translation in 15 pages, dated Apr. 27, 2023.
Office Action for U.S. Appl. No. 13/469,032 in 12 pages, dated Feb. 8, 2023.
Office Action for U.S. Appl. No. 13/619,555 in 25 pages, dated Jan. 26, 2023.
Office Action for U.S. Appl. No. 14/459,777 in 20 pages, dated Mar. 2, 2023.
Office Action for Ukrainian Application No. UA a201906329 with English translation in 18 pages, dated May 8, 2023.
Result of Consultation for European Application No. EP 19207796.4 in 19 pages, dated Mar. 1, 2023.
Result of Consultation for European Application No. EP 19207796.4 in 8 pages, dated Mar. 15, 2023.
Sarkar, S. K. et al., "A transient amphipathic helix in the prodomain of PCSK9 facilitates binding to low-density lipoprotein particles", Journal of Biological Chemistry, Feb. 2020, vol. 295(8), pp. 2285-2298.
Seidah, N. et al., "The Multifaceted Biology of PCSK9", Endocrine Reviews, Jun. 2022, vol. 43, No. 3, pp. 558-582.
Swinney, D. C., "Chapter 18—Molecular Mechanism of Action (MMoA) in Drug Discovery", Annual Reports in Medicinal Chemistry, ed., John E. Macor, 2011, vol. 46, pp. 301-316.
Third-Party Observations for European Application No. EP 19207796.4 in 9 pages, dated Mar. 26, 2023.

(56)            References Cited

OTHER PUBLICATIONS

Amici Curiae Brief of Alliance of U.S. Startups and Inventors for Jobs ("USIJ") and Innovation Alliance ("IA") in Support of Petitioner—On Writ of Certiorari to the United States Court of Appeals for the Federal Circuit dated Jan. 3, 2023 in *Amgen Inc.,* v. *Sanofi,* in the Supreme Court of the United States, No. 21-757, 31 pages.

Brief for Amicus Curiae, Fresenius Kabi USA, LLC, in Support of Respondents—On Writ of Certiorari to the United States Court of Appeals for the Federal Circuit dated Feb. 10, 2023 in *Amgen Inc.,* v. *Sanofi,* in the Supreme Court of the United States, No. 21-757, 18 pages.

Brief for High Tech Inventors Alliance and the Computer & Communications Industry Association as Amici Curiae in Support of Neither Party—On Writ of Certiorari to the United States Court of Appeals for the Federal Circuit dated Jan. 3, 2023 in *Amgen Inc.,* v. *Sanofi,* in the Supreme Court of the United States, No. 21-757, 40 pages.

Brief for Respondents—On Writ of Certiorari to the United States Court of Appeals for the Federal Circuit dated Feb. 3, 2023 in *Amgen Inc.,* v. *Sanofi,* in the Supreme Court of the United States, No. 21-757, 65 pages.

Brief for Small and Medium Biotechnology Companies as Amici Curiae in Support of Respondents—On Writ of Certiorari to the United States Court of Appeals for the Federal Circuit dated Feb. 2023 in *Amgen Inc.,* v. *Sanofi,* in the Supreme Court of the United States, No. 21-757, 36 pages.

Brief for the American Intellectual Property Law Association as Amicus Curiae Suggesting Affirmance—On Writ of Certiorari to the United States Court of Appeals for the Federal Circuit dated Feb. 10, 2023 in *Amgen Inc.,* v. *Sanofi,* in the Supreme Court of the United States, No. 21-757, 25 pages.

Brief for Viatris Inc. as Amicus Curiae in Support of Respondents—On Writ of Certiorari to the United States Court of Appeals for the Federal Circuit dated Feb. 2023 in *Amgen Inc.,* v. *Sanofi,* in the Supreme Court of the United States, No. 21-757, 34 pages.

Brief of Abbvie Inc. as Amicus Curiae in Support of Petitioners—On Writ of Certiorari to the United States Court of Appeals for the Federal Circuit dated Jan. 3, 2023 in *Amgen Inc.,* v. *Sanofi,* in the Supreme Court of the United States, No. 21-757, 24 pages.

Brief of Amici Curiae Association of University Technology Managers, Inc., Biogen Inc., Bristol-Myers Squibb Company, Corning Incorporated, Merck Sharp & Dohme Corp., and St. Jude Children's Research Hospital, Inc. in Support of Petitioners—On Writ of Certiorari to the United States Court of Appeals for the Federal Circuit dated Dec. 22, 2021 in *Amgen Inc.,* v. *Sanofi,* in the Supreme Court of the United States, No. 21-757, 24 pages.

Brief of Amici Curiae Eli Lilly and Company, Ipsen Bioscience, Inc. and Innovent Biologics, Inc. in Support of Respondents - On Writ of Certiorari to the United States Court of Appeals for the Federal Circuit dated Feb. 10, 2023 in *Amgen Inc.,* v. *Sanofi,* in the Supreme Court of the United States, No. 21-757, 40 pages.

Brief of Amici Curiae Regenxbio Inc., IGM Biosciences, Inc., and Adaptive Phage Therapeutics, Inc. in Support of Neither Party—On Writ of Certiorari to the United States Court of Appeals for the Federal Circuit dated Jan. 3, 2023 in *Amgen Inc.,* v. *Sanofi,* in the Supreme Court of the United States, No. 21-757, 30 pages.

Brief of Amicus Curiae Glaxosmithkline PLC in Support of Petitioners—On Writ of Certiorari to the United States Court of Appeals for the Federal Circuit dated Dec. 22, 2021 in *Amgen Inc.,* v. *Sanofi,* in the Supreme Court of the United States, No. 21-757, 20 pages.

Brief of Amicus Curiae GSK PLC in Support of Petitioners—On Writ of Certiorari to the United States Court of Appeals for the Federal Circuit dated Jan. 3, 2023 in *Amgen Inc.,* v. *Sanofi,* in the Supreme Court of the United States, No. 21-757, 25 pages.

Brief of Amicus Curiae Intellectual Property Owners Association in Support of Neither Party—On Writ of Certiorari to the United States Court of Appeals for the Federal Circuit dated Jan. 3, 2023 in *Amgen Inc.,* v. *Sanofi,* in the Supreme Court of the United States, No. 21-757, 23 pages.

Brief of Amicus Curiae New York Intellectual Property Law Association in Support of Neither Party—On Writ of Certiorari to the United States Court of Appeals for the Federal Circuit dated Dec. 28, 2022 in *Amgen Inc.,* v. *Sanofi,* in the Supreme Court of the United States, No. 21-757, 29 pages.

Brief of Amicus Curiae Pfizer Inc. in Support of Respondents—On Writ of Certiorari to the United States Court of Appeals for the Federal Circuit dated Feb. 10, 2023 in *Amgen Inc.,* v. *Sanofi,* in the Supreme Court of the United States, No. 21-757, 25 pages.

Brief of Amicus Curiae Professor Robin Feldman in Support of Respondents—On Writ of Certiorari to the United States Court of Appeals for the Federal Circuit dated Feb. 9, 2023 in *Amgen Inc.,* v. *Sanofi,* in the Supreme Court of the United States, No. 21-757, 43 pages.

Brief of Amicus Curiae Public Interest Patent Law Institute in Support of Respondents—On Writ of Certiorari to the United States Court of Appeals for the Federal Circuit dated Feb. 2023 in *Amgen Inc.,* v. *Sanofi,* in the Supreme Court of the United States, No. 21-757, 23 pages.

Brief of Chemistry and the Law Division of the American Chemical Society as Amicus Curiae in Support of Petitioners—On Writ of Certiorari to the United States Court of Appeals for the Federal Circuit dated Jan. 3, 2023 in *Amgen Inc.,* v. *Sanofi,* in the Supreme Court of the United States, No. 21-757, 34 pages.

Brief of Diversified Researchers and Innovators in Support of Petitioners—On Writ of Certiorari to the United States Court of Appeals for the Federal Circuit dated Jan. 3, 2023 in *Amgen Inc.,* v. *Sanofi,* in the Supreme Court of the United States, No. 21-757, 35 pages.

Brief of Genentech, Inc., Astrazeneca Pharmaceuticals LP, Bayer AG, Gilead Sciences, Inc., and Johnson & Johnson as Amici Curiae in Support of Respondents—On Writ of Certiorari to the United States Court of Appeals for the Federal Circuit dated Feb. 10, 2023 in *Amgen Inc.,* v. *Sanofi,* in the Supreme Court of the United States, No. 21-757, 39 pages.

Brief of Instil Bio, Inc. as Amicus Curiae in Support of Petitioners—On Writ of Certiorari to the United States Court of Appeals for the Federal Circuit dated Jan. 3, 2023 in *Amgen Inc.,* v. *Sanofi,* in the Supreme Court of the United States, No. 21-757, 14 pages.

Brief of Intellectual Property Law Professors and Scholars as Amici Curiae in Support of the Respondents—On Writ of Certiorari to the United States Court of Appeals for the Federal Circuit dated Feb. 10, 2023 in *Amgen Inc.,* v. *Sanofi,* in the Supreme Court of the United States, No. 21-757, 42 pages.

Brief of Intellectual Property Professors as Amici Curiae in Support of Petitioners—On Writ of Certiorari to the United States Court of Appeals for the Federal Circuit dated Dec. 22, 2021 in *Amgen Inc.,* v. *Sanofi,* in the Supreme Court of the United States, No. 21-757, 17 pages.

Brief of Intellectual Property Professors as Amici Curiae in Support of Petitioners—On Writ of Certiorari to the United States Court of Appeals for the Federal Circuit dated Jan. 3, 2023 in *Amgen Inc.,* v. *Sanofi,* in the Supreme Court of the United States, No. 21-757, 26 pages.

Brief of Law Professors Joshua D. Sarnoff, Sharon K. Sandeen, and Ana Santos Rutschman as Amici Curiae in Support of Respondents—On Writ of Certiorari to the United States Court of Appeals for the Federal Circuit dated Feb. 10, 2023 in *Amgen Inc.,* v. *Sanofi,* in the Supreme Court of the United States, No. 21-757, 44 pages.

Brief of National Association of Patent Practitioners, Inc. as Amicus Curiae in Support of Petitioner—On Writ of Certiorari to the United States Court of Appeals for the Federal Circuit dated Jan. 3, 2023 in *Amgen Inc.,* v. *Sanofi,* in the Supreme Court of the United States, No. 21-757, 28 pages.

Brief of Sir Gregory Paul Winter and Interested Scientists as Amici Curiae in Support of Respondents—On Writ of Certiorari to the United States Court of Appeals for the Federal Circuit dated Feb. 10, 2023 in *Amgen Inc.,* v. *Sanofi,* in the Supreme Court of the United States, No. 21-757, 38 pages.

Brief of the Association for Accessible Medicines as Amicus Curiae in Support of Respondents—On Writ of Certiorari to the United

(56) References Cited

OTHER PUBLICATIONS

States Court of Appeals for the Federal Circuit dated Feb. 10, 2023 in *Amgen Inc.,* v. *Sanofi,* in the Supreme Court of the United States, No. 21-757, 36 pages.

Brief of the Fynder Group, Inc. d/b/a Nature's Fynd as Amicus Curiae in Support of Petitioners—On Writ of Certiorari to the United States Court of Appeals for the Federal Circuit dated Jan. 3, 2023 in *Amgen Inc.,* v. *Sanofi,* in the Supreme Court of the United States, No. 21-757, 35 pages.

Brief of the Intellectual Property Law Association of Chicago as Amicus Curiae in Support of No Party—On Writ of Certiorari to the United States Court of Appeals for the Federal Circuit dated Jan. 3, 2023 in *Amgen Inc.,* v. *Sanofi,* in the Supreme Court of the United States, No. 21-757, 42 pages.

Brief of Unified Patents, LLC as Amicus Curiae in Support of Respondents—On Writ of Certiorari to the United States Court of Appeals for the Federal Circuit dated Feb. 2023 in *Amgen Inc.,* v. *Sanofi,* in the Supreme Court of the United States, No. 21-757, 38 pages.

Letter from Jeffrey P. Kushan from Sidley to Solicitor General Prelogar and Undersecretary Vidal dated Jun. 6, 2022, regarding Writ of Certiorari to the United States Court of Appeals for the Federal Circuit in *Amgen Inc.,* v. *Sanofi,* in the Supreme Court of the United States, No. 21-757, 3 pages.

Letter from Michael G. Penn from Instil Bio to Mr. Krause and Ms. Rasheed (the USPTO) dated Apr. 29, 2022, regarding Writ of Certiorari to the United States Court of Appeals for the Federal Circuit in *Amgen Inc.,* v. *Sanofi,* in the Supreme Court of the United States, No. 21-757, 2 pages.

Letter from Thomas D. Smith from GSK to Mr. Krause and Ms. Rasheed (the USPTO) dated May 13, 2022, regarding Writ of Certiorari to the United States Court of Appeals for the Federal Circuit in *Amgen Inc.,* v. *Sanofi,* in the Supreme Court of the United States, No. 21-757, 2 pages.

Reply Brief for Petitioners—On Writ of Certiorari to the United States Court of Appeals for the Federal Circuit dated Mar. 2023 in *Amgen Inc.,* v. *Sanofi,* in the Supreme Court of the United States, No. 21-757, 32 pages.

Syllabus and Opinion of the Court—On Writ of Certiorari to the United States Court of Appeals for the Federal Circuit dated May 18, 2023 in *Amgen Inc.,* v. *Sanofi,* in the Supreme Court of the United States, No. 21-757, 23 pages.

U.S. Appl. No. 61/063,980, filed Feb. 7, 2008, Merck & Co., Inc.

"7.3 Anti-Atherosclerotic Drugs", Basics of Physiology and Pharmacology, edited by Yushu Wang, Jan. 2016, pp. 113-115.

"A Study to Evaluate the Effect of Rosuvastatin On Intravascular Ultrasound-Derived Coronary Atheroma Burden (ASTEROID)", ClinicalTrials.gov, post last updated Nov. 19, 2010 (accessed Aug. 3, 2023), ClinicalTrials.gov Identifier: NCT00240318, in 4 pages. URL: https://classic.clinicaltrials.gov/ct2/show/NCT00240318 [This refers to a webpage and the dates apparent in the document are listed herewith. However, the webpage may have been publicly available in some form at a date earlier than those listed].

"Antibody therapeutics approved or in regulatory review in the EU or US", The Antibody Society, webpage accessed Oct. 30, 2023, in 9 pages. URL: https://www.antibodysociety.org/resources/approved-antibodies/ [This refers to a webpage and a date is not immediately apparent on the webpage. The webpage may have been publicly available in some form before the noted date].

"ClinicalTrials.gov Glossary Terms", ClinicalTrials.gov, webpage accessed Oct. 22, 2023, in 19 pages. URL: https://clinicaltrials.gov/study-basics/glossary. This refers to a web page, and a date is not immediately apparent on the web page. This web page may have been publicly available in some form before the noted date.

"CT-322 in Treating Patients with Advanced Solid Tumors and Non-Hodgkin's Lymphoma", ClinicalTrials.gov, post last updated Feb. 24, 2009, ClinicalTrials.gov Identifier: NCT00374179, in 8 pages. URL: https://clinicaltrials.gov/study/NCT00374179 [This refers to a webpage and the dates apparent in the document are listed herewith. However, the webpage may have been publicly available in some form at a date earlier than those listed].

"Journal of Lipid Research Impact Factor & Key Scientometrics", SCI Journal, accessed Sep. 11, 2023, in 22 pages. URL: https://www.scijournal.org/impact-factor-of-j-lipid-res.shtml. This refers to a web page, and a date is not immediately apparent on the web page. The webpage may have been publicly available in some form before the noted date.

"Mechanism of Action", Amgen, accessed Aug. 17, 2017, in 2 pages. URL: https://www.repathahcp.com/what-is-repatha/#about-moa [This refers to a webpage and No. date of publication is immediately apparent in the document itself. The webpage may have been publicly available in some form at a date earlier than those listed here].

"Simvastatin", Wikipedia, webpage last edited on Feb. 19, 2023 (accessed Aug. 22, 2023), in 6 pages. URL: https://en.wikipedia.org/wiki/Simvastatin#:~:text=Simvastatin%2C%20sold%20under%20the%20brand,i n%20those%20at%20high%20risk. [This refers to a webpage and the dates apparent in the document are listed herewith. However, the webpage may have been publicly available in some form at a date earlier than those listed].

"Simvastatin", Wikipedia, webpage last edited on Jun. 11, 2007 (accessed May 23, 2023), in 4 pages. URL: https://en.wikipedia.org/w/index.php?title=Simvastatin&oldId=137568170 [This refers to a webpage and the dates apparent in the document are listed herewith. However, the webpage may have been publicly available in some form at a date earlier than those listed].

"Single Ascending Dose Safety Study of BMS-962476 in Healthy Subjects and Patients With Elevated Cholesterol on Statins", ClinicalTrials.gov, post last updated Sep. 4, 2013, ClinicalTrials.gov Identifier: NCT01587365, in 11 pages. URL: https://clinicaltrials.gov/study/NCT01587365 [This refers to a webpage and the dates apparent in the document are listed herewith. However, the webpage may have been publicly available in some form at a date earlier than those listed].

"Study of Coronary Atheroma by Intravascular Ultrasound: Effect of Rosuvastatin Versus Atorvastatin (SATURN)", ClinicalTrials.gov, post last updated Jul. 16, 2012 (accessed Aug. 3, 2023), ClinicalTrials.gov Identifier: NCT00620542, in 6 pages. URL: https://classic.clinicaltrials.gov/ct2/show/NCT00620542 [This refers to a webpage and the dates apparent in the document are listed herewith. However, the webpage may have been publicly available in some form at a date earlier than those listed].

2002 Clontech Information Sheet for the pIRES2-EGFP construct filed in Revocation of European Patent No. EP 3666797 B1 in 3 pages, dated Oct. 3, 2002.

Abdiche, Y. N. et al., "Antibodies Targeting Closely Adjacent or Minimally Overlapping Epitopes Can Displace One Another", PloS One, Jan. 2017, vol. 12(1): e0169535, in 22 pages.

Alberts, B. et al., Molecular Biology of the Cell, Garland Science, Mar. 2002, 4th ed., pp. 1376-1377 (textbook excerpt only).

Annex 1—Summary of Product Characteristics (Xolaris SmPC (2005)) filed in Revocation of European Patent No. EP 3666797 B1 in 60 pages, 2005.

Annex: Detailed Reply to Section IV 6.2 "Case Law Summary" of the Defence filed in Revocation of European Patent No. EP 3666797 B1 in 14 pages, dated Nov. 13, 2023.

Bottomley, M. et al., "Structural and biochemical characterization of the wild type PCSK9-EGF(AB) complex and natural familial hypercholesterolemia mutants", The Journal of Biological Chemistry, Jan. 2009, vol. 284, pp. 1313-1323.

Bregenholt, S. et al., "Recombinant Human Polyclonal Antibodies: A New Class of Therapeutic Antibodies Against Viral Infections", Current Pharmaceutical Design, 2006, vol. 12, pp. 2007-2015.

Brown, M. et al., "Tolerance to Single, but not Multiple, Amino Acid Replacements in Antibody VH CDR2", The Journal of Immunology May 1996, vol. 156, pp. 3285-3291.

Coleman, D. L., "Effects of Parabiosis of Obese with Diabetes and Normal Mice", Diabetologia, 1993, vol. 9, pp. 294-298.

Communication of the Board of Appeal pursuant to Article 15(1) of the Rules of Procedure of the Boards of Appeal (T 845/19 Preliminary Opinion) for European Patent No. EP 2215124 in 70 pages, dated Feb. 5, 2020.

(56)    References Cited

OTHER PUBLICATIONS

Csala, M. et al., "Transport and transporters in the endoplasmic reticulum", Biochimica et Biophysica Acta 1768, 2007, pp. 1325-1341.

Dall'Acqua, W. et al., "A Mutational Analysis of Binding Interactions in an Antigen-Antibody Protein-Protein Complex", Biochemistry, 1998, vol. 37, pp. 7981-7991.

Decision of the Enlarged Board of Appeal for G 0001/22 and G 0002/22 in 59 pages, dated Oct. 10, 2023.

Declaration of Dr. Sally Redshaw filed in Revocation of European Patent No. EP 3666797 B1 in 20 pages, dated Nov. 10, 2023.

Declaration of Professor Jay Horton filed in Opposition against EP 3666797 B1 in 45 pages, dated Nov. 9, 2023.

Declaration of Professor Jay Horton filed in UPC Revocation Action against EP 3666797 B1 in 45 pages, dated May 31, 2023.

Declaration of Professor Scott Boyd, M.D., Ph.D filed in Opposition against EP 3666797 B1 in 21 pages on Nov. 13, 2023.

Declaration of Professor Scott Boyd, M.D., Ph.D filed in Revocation of European Patent No. EP 3666797 B1 in 12 pages, dated Nov. 10, 2023.

Declaration of Professor Scott Boyd, M.D., Ph.D filed in UPC Revocation Action against EP 3666797 B1 in 62 pages, dated May 31, 2023.

Declaration of Professor Thomas U. Schwartz filed in Opposition against EP 3666797 B1 in 24 pages, dated Nov. 9, 2023.

Declaration of Professor Thomas U. Schwartz filed in Revocation of European Patent No. EP 3666797 B1 in 13 pages, dated Nov. 12, 2023.

Declaration of Professor Thomas U. Schwartz filed in UPC Revocation Action against EP 3666797 B1 in 25 pages, dated May 31, 2023.

Deng, X. et al., "Enhancing antibody patent protection using epitope mapping information", MABS, 2018, vol. 10, No. 2, pp. 204-209.

Dimasi, J. A. et al., "The price of innovation: new estimates of drug development costs", Journal of Health Economics, 2003, vol. 22, pp. 151-185.

Dincer, A. et al., "Reducing Peptide Sequence Bias in Quantitative Mass Spectrometry Data with Machine Learning", J. Proteome Res. 2022, vol. 21, pp. 1771-1782.

Dixon, E. P. et al., "Chapter 58: Rapid Development of Monoclonal Antibodies Using Repetitive Immunizations, Multiple Sites", Cell Biology: A Laboratory Handbook, edited by J. E. Celis et al., 2006, 3rd edition, vol. 1, pp. 483-490.

Dondelinger, M. et al., "Understanding the significance and implications of antibody numbering and antigen-binding surface/residue definition", Frontiers in Immunology, Oct. 2018, vol. 9, Article 2278, in 15 pages.

Dong, Y. et al., "Heterogeneous Immunosensing Using Antigen and Antibody Monolayers on Gold Surfaces with Electrochemical and Scanning Probe Detection", Anal. Chem., Jun. 2000, vol. 72, pp. 2371-2376.

Erviti, J. et al., "Restoring mortality data in the FOURIER cardiovascular outcomes trial of evolocumab in patients with cardiovascular disease: a reanalysis based on regulatory data", BMJ Open, 2022, vol. 12 (e060172), in 12 pages.

Evidence of Date of Amgen's Research Plan filed in Revocation of European Patent No. EP 3666797 B1, dated Feb. 21, 2019, in 3 pages.

Excerpt from Deposition of Nicholas J. Papadopoulos in the Matter of *Amgen* v. *Sanofi*, filed in Revocation of European Patent No. EP 3666797 B1 in 4 pages, dated Sep. 10, 2015.

Extract from Brief for Respondents in *Amgen* v. Sanofi (U.S. Supreme Court) filed in Revocation of European Patent No. EP 3666797 B1 in 1 page, dated Feb. 3, 2023.

Extract from the Trial Transcript for U.S. District Court Case of *Amgen* v. *Sanofi* filed in Revocation of European Patent No. EP 3666797 B1 in 8 pages, dated Feb. 19, 2019.

Final Office Action for U.S. Appl. No. 13/422,904 in 21 pages, dated Jul. 5, 2023.

Final Office Action for U.S. Appl. No. 13/469,032 in 19 pages, dated Aug. 29, 2023.

Final Office Action for U.S. Appl. No. 13/619,555 in 27 pages, dated Nov. 24, 2023.

Final Office Action for U.S. Appl. No. 13/931,716 in 26 pages, dated Aug. 17, 2023.

Final Office Action for U.S. Appl. No. 17/011,433 in 17 pages, dated Sep. 13, 2023.

Gao, F. et al., "A common polymorphism in the LDL receptor gene has multiple effects on LDL receptor function", Human Molecular Genetics, Apr. 2013, vol. 22, pp. 1424-1431.

Glennie, M. et al., "Clinical Trials of Antibody Therapy", Immunology Today, 2000, vol. 21, pp. 403-410.

Goldstein, J. et al., "Familial Hypercholesterolemia—A Genetic Regulatory Defect in Cholesterol Metabolism", The American Journal of Medicine, Feb. 1975, vol. 58, pp. 147-150.

Greenspan, N. et al., "Defining epitopes: It's not as easy as it seems", Nature Biotechnology, Oct. 1999, vol. 17, pp. 936-937.

Hoogenboom, H. et al., "Natural and Designer Binding Sites Made by Phage Display Technology", Immunology Today, 2000, vol. 21, pp. 371-378.

Hughes, J.P. et al., "Principles of early drug discovery", British Journal of Pharmacology, 2011, vol. 162, pp. 1239-1249.

Kilpatrick, K. et al., "Rapid Development of Affinity Matured Monoclonal Antibodies Using RIMMS", Hybridoma, 1997, vol. 16(4), pp. 381-389.

Kola, I. et al., "Can the pharmaceutical industry reduce attrition rates?", Nature Reviews, Aug. 2004, vol. 3, pp. 711-715.

Kuroda, D. et al., "Computer-aided Antibody Design", Protein Engineering, Design and Selection, 2012, vol. 25, pp. 507-521.

Lipsky, M. et al., "From Idea to Market: The Drug Approval Process", Journal of the American Board of Family Practice, September-Oct. 2001, vol. 14(5), pp. 362-367.

Lo Conte, L. et al., "The Atomic Structure of Protein-Protein Recognition Sites", J. Mol. Biol, 1999, vol. 285, pp. 2177-2198.

Maggon, K., "Monoclonal Antibody Gold Rush", Current Medicinal Chemistry, 2007, vol. 14, pp. 1978-1987.

Malo, J. et al., "PCSK9: from molecular biology to clinical applications", Annals of Clinical Biochemistry, 2020, vol. 57(1), pp. 7-25.

McMaster, M. C., "Chapter 12: Drug Discovery and Benchtops LC/MS", LC/MS: A Practical User's Guide, 2005, John Wiley & Sons, Inc., pp. 111-118.

McPherson, A. et al., "Introduction to protein crystallization", Acta Crystallographica, 2014, vol. F70, pp. 2-20.

McPherson, A., "Introduction to protein crystallization", Methods, 2004, vol. 34, pp. 254-265.

Minutes of the Oral Proceedings (T 845/19) for European Patent No. EP 2215124 in 6 pages, dated Oct. 28 and 29, 2020.

Nissen, S. et al., "Effect of Very High-Intensity Statin Therapy on Regression of Coronary Atherosclerosis—The ASTEROID Trial", JAMA, Apr. 2006, pp. 1556-1565.

Notice of Allowability for U.S. Appl. No. 14/562,546 in 15 pages, dated Sep. 13, 2023.

Notice of Opposition by Sanofi with Consolidated List of Documents for European Patent No. EP 3666797 dated Nov. 10, 2023, in 65 pages.

Notice of Termination of Reconsideration by Examiners before Appeal Proceedings for Japanese Application No. JP 2019-231236 (Appeal No. JP 2023-003462) with English translation in 2 pages, dated May 9, 2023.

Notice of Transfer of a Case for Reconsideration by Examiners before Appeal for Japanese Application No. JP 2019-231236 (Appeal No. JP 2023-003462) with English translation in 2 pages, dated Apr. 18, 2023.

Office Action for Bahraini Application No. BH 20190124 in 13 pages, dated Oct. 25, 2023.

Office Action for Canadian Application No. CA 3043700 in 5 pages, dated Sep. 12, 2023.

Office Action for Chinese Application No. CN 201780083280.9 with English translation in 21 pages, dated Sep. 14, 2023.

Office Action for Chinese Application No. CN 201780083280.9 with English translation in 26 pages, dated Jun. 2, 2023.

(56)          References Cited

OTHER PUBLICATIONS

Office Action for Chinese Application No. CN 202010703260.0 with English translation in 28 pages, dated Aug. 3, 2023.
Office Action for Chinese Application No. CN 202011304952.4 with English translation in 9 pages, dated Aug. 12, 2023.
Office Action for Chinese Application No. CN 202011305148.8 with English translation in 26 pages, dated Jul. 1, 2023.
Office Action for Chinese Application No. CN 202011305376.5 with English translation in 18 pages, dated Jun. 10, 2023.
Office Action for Chinese Application No. CN 202110835168.4 with English translation in 34 pages, dated Aug. 3, 2023.
Office Action for Eurasian Application No. EA 201991160/28 with English translation in 9 pages, dated Sep. 11, 2023.
Office Action for Israeli Application No. IL 288048 in 9 pages, dated Jul. 6, 2023.
Office Action for Korean Application No. KR 10-2019-7016872 with English translation in 13 pages, dated Aug. 2, 2023.
Office Action for Korean Application No. KR 10-2023-7017950 with English translation in 4 pages, dated Jul. 4, 2023.
Office Action for Malaysian Application No. MY PI2019002686 in 6 pages, dated Jul. 28, 2023.
Office Action for Mexican Application No. MX/a/2019/005627 with English translation in 9 pages, dated Oct. 9, 2023.
Office Action for Peruvian Application No. PE 001494-2018/DIN with English summary in 15 pages, dated Sep. 27, 2023.
Office Action for Philippines Application No. PH Jan. 2013/502285 in 4 pages, mailed May 3, 2023.
Office Action for Philippines Application No. PH Jan. 2013/502286 in 4 pages, mailed May 31, 2023.
Office Action for U.S. Appl. No. 16/348,653 in 25 pages, dated Nov. 9, 2023.
Office Action for United Arab Emirates Application No. AE P6000679/2019 in 11 pages. No date for this document is immediately apparent. Applicant notes that this document was received Aug. 8, 2023.
Office Action for Vietnamese Application No. VN 1-2019-01647 with English translation in 4 pages, dated Oct. 30, 2023.
PCT Request Form for International Application No. PCT/US2009/033341 filed Feb. 6, 2009, in 10 pages.
PCT Request Form for International Application No. PCT/US2009/033369 filed Feb. 6, 2009, in 9 pages.
Pirrone, G et al., "Applications of Hydrogen/Deuterium Exchange MS from 2012 to 2014", Analytical Chemistry, 2015, vol. 87, pp. 99-118.
Ramasamy, I., "Recent Advances in Physiological Lipoprotein Metabolism", Clin. Chem. Lab. Med., 2014, vol. 52, pp. 1695-1727.
Re-Examination Report for Japanese Application No. JP 2019-231236 (Appeal No. JP 2023-003462) with English translation in 4 pages, dated Apr. 27, 2023.
Reichert, J. et al., "Monoclonal antibody successes in the clinic", Nature Biotechnology, Sep. 2005, vol. 23, pp. 1073-1078.
Reply to Defence to Revocation and Defence to the Application to Amend the Patent for European Patent No. EP 3666797 dated Nov. 13, 2023, in 140 pages.
Roguin, L. P. et al., "Monoclonal Antibodies Inducing Conformational Changes on the Antigen Molecule", Scandinavian Journal of Immunology, 2003, vol. 58, pp. 387-394.
Sacks, F. et al., "Low-Density Lipoprotein Size and Cardiovascular Disease: A Reappraisal", The Journal of Clinical Endocrinology and Metabolism, 2003, vol. 88(10), pp. 4525-4532.
Saldanha, J., "Chapter 6: Molecular Engineering I: Humanization", Handbook of Therapeutic Antibodies, ed., Stefan Dubel, Jan. 2007, vol. 1, pp. 119-144.
Scott, D. E. et al., "Small molecules, big targets: drug discovery faces the protein-protein interaction challenge", Nature Reviews, Aug. 2016, vol. 15, pp. 533-550.
Second Declaration of Professor Jay Horton filed in Revocation of European Patent No. EP 3666797 B1 in 86 pages, dated Nov. 11, 2023.
Statement of Defence and Counterclaim for Revocation filed for European Patent No. EP 3666797 in 173 pages, dated Nov. 10, 2023.
Statement of Revocation of Patent for European Application No. EP 19207796.4 in 85 pages, dated Jun. 1, 2023.
Sweeney, C. J. et al., "Phase I study of CT-322, first Adnectin protein therapeutic and potent inhibitor of VEGFR-2, in patients (pts) with advanced solid tumors (ST)", Journal of Clinical Oncology, May 2008, vol. 26, pp. 3523-3523 (abstract only).
Tsutsumi, Y. et al., "Chemical Modification of Natural Human Tumor Necrosis Factor-a with Polyethylene Glycol Increases its Anti-tumor Potency", Jpn. J. Cancer Res., vol. 85, Jan. 1994, pp. 9-12.
Turk, B., "Targeting proteases: successes, failures and future prospects", Nature Reviews, Sep. 2006, vol. 5, pp. 785-799.
Weiner, L., "Fully Human Therapeutic Monoclonal Antibodies", J. Immunother, January/Feb. 2006, vol. 29, pp. 1-9.
Weinstein, J. et al., "The Macroscopic and Microscopic Pharmacology of Monoclonal Antibodies", International Society for Immunopharmacology, 1992, vol. 14(3), pp. 457-463.
Wilchek, M. et al., "Chapter 4: Avidin-Biotin Immobilisation Systems", Immobilised Marcomolecules: Application Potentials, edited by U.B. Sleytr, 1993, pp. 51-60.
Yang, Q., "4.2 Interaction between antigen and antibody" Molecular Biology, Jun. 2004, Zhejiang University Press, pp. 112-117.
Final Office Action for U.S. Appl. No. 14/316,587 in 20 pages, dated Dec. 21, 2023.
Declaration of Professor Thomas U. Schwartz filed in Opposition against EP 3666797 B1 in 11 pages, dated Feb. 12, 2023.
Final Office Action for U.S. Appl. No. 13/469,032 in 19 pages, dated Mar. 14, 2024.
Final Office Action for U.S. Appl. No. 13/931,716 in 27 pages, dated Feb. 27, 2024.
Final Office Action for U.S. Appl. No. 16/348,653 in 19 pages, dated Mar. 14, 2024.
Notice of Allowability for U.S. Appl. No. 14/562,546 in 19 pages, dated Mar. 14, 2024.
Notice of Opposition by Regeneron Pharmaceuticals Inc. filed in Opposition for European Patent No. EP 3666797 in 103 pages, dated Feb. 19, 2024.
Office Action for Australian Application No. AU 2017356219 in 7 pages, dated Dec. 8, 2023.
Office Action for Chinese Application No. CN 202011305148.8 with English translation in 14 pages, dated Feb. 2, 2024.
Office Action for Chinese Application No. CN 202011305376.5 with English translation in 16 pages, dated Dec. 15, 2023.
Office Action for European Application No. EP 23173456.7 in 21 pages, Mar. 12, 2024.
Office Action for Japanese Application No. JP 2023-030747 with English translation in 9 pages, dated Feb. 20, 2024.
Office Action for Korean Application No. KR 10-2019-7016872 with English translation in 10 pages, dated Dec. 29, 2023.
Office Action for Korean Application No. KR 10-2023-7014430 with English summary in 7 pages, dated Jan. 10, 2024.
Office Action for Peruvian Application No. Pe 001349-2022/DIN with English translation in 12 pages, dated Feb. 27, 2024.
Office Action for Singaporean Application No. SG 11201904266Q in 7 pages, dated Jan. 5, 2024.
Reply to Amgen's Defence to the Counterclaim to Invalidity filed for European Patent No. EP 3666797 in 12 pages, dated Mar. 7, 2024.
Request to Remove Dr. Galli as Member of the Opposition Division Panel filed in Opposition against EP 3666797 B1 in 4 pages, dated Feb. 19, 2024.
Second Declaration of Professor Anthony R. Rees filed in Opposition against EP 3666797 B1 in 20 pages, dated Dec. 12, 2023.
Non-Final Office Action for U.S. Appl. No. 17/011,433 in 24 pages, dated Mar. 27, 2024.
Office Action in Peruvian Application No. PE 001494-2018/DIN with English Translation in 17 pages, dated Jul. 9, 2024.
"Bristol-Myers Squibb Enters Cardiovascular Disease Collaboration with Isis Pharmaceuticals" [press release], PRNewswire-FirstCall via COMTEX News Network, May 9, 2007, in 2 pages.

(56)  References Cited

OTHER PUBLICATIONS

Appendix A of Declaration by Wei Wang Dated Jan. 25, 2017, filed in European Opposition to EP 2215124B1.
Appendix B of Declaration by Wei Wang Dated Jan. 25, 2017, filed in European Opposition to EP 2215124B1.
Baran, D. et al., "Principles for computational design of binding antibodies", PNAS, Oct. 2017, vol. 114, No. 41, pp. 10900-10905.
Berzofsky, J., "Chapter 4—Antigen-Antibody Interactions and Monoclonal Antibodies", in *Fundamental Immunology*, William E., Md. Paul (ed.), Aug. 2003, 5th ed., in 68 pages.
Brown, M. et al., "Receptor-mediated endocytosis: Insights from the lipoprotein receptor system", Proc. Natl. Acad. Sci., Jul. 1979, vol. 76, No. 7, pp. 3330-3337.
Brown, M. S. et al., "A Receptor-Mediated Pathway for Cholesterol Homeostasis", Science, Apr. 1986, vol. 232, pp. 34-47.
Chowdhury, P. S. et al., "Improving antibody affinity by mimicking somatic hypermutation in vitro", Nature Biotechnology, Jun. 1999, vol. 17(6), pp. 568-572.
Communication pursuant to Rule 114(2) EPC (Observations by a Third Party) for European Application No. EP 23173456.7 in 138 pages, dated Sep. 10, 2024.
Curriculum Vitae of Dr. Rex Arnold Parker filed in Opposition against EP 3666797 B1 in 12 pages, dated Jun. 2023.
Curriculum Vitae of Professor Anthony R. Rees filed in Opposition against EP 3666797 B1 in 5 pages, dated Jul. 2023.
Decision of the Unified Patent Court (UPC) Central Division (Munich) in the Revocation Action for EP Patent No. 3666797 in 53 pages, dated Jul. 16, 2024.
Declaration of Dr. Rex Arnold Parker filed in Opposition against EP 3666797 B1 in 76 pages, dated Jun. 28, 2024.
Declaration of Professor Anthony R. Rees filed in Opposition against EP 3666797 B1 in 62 pages, dated Jun. 27, 2024.
Edwards, B. M. et al., "The Remarkable Flexibility of the Human Antibody Repertoire; Isolation of Over One Thousand Different Antibodies to a Single Protein, BLyS", J. Mol. Biol., 2003, vol. 334, pp. 103-118.
Esteve, E. et al., "Dyslipidemia and inflammation: an evolutionary conserved mechanism", Clinical Nutrition, 2005, vol. 24, pp. 16-31.
Final Decision filed in Opposition against IL 204013 with English translation in 91 pages, dated Jul. 10, 2024.
Final Office Action for U.S. Appl. No. 13/469,032 in 20 pages, dated Aug. 1, 2024.
Final Office Action for U.S. Appl. No. 14/316,587 in 21 pages, dated Jul. 18, 2024.
Fraser, R. et al., "Lipoproteins and the Liver Sieve: The Role of the Fenestrated Sinusoidal Endothelium in Lipoprotein Metabolism, Atherosclerosis, and Cirrhosis", Hepatology, Mar. 1995, pp. 863-874.
Glaser, R. W. et al., "Antigen-Specific Enrichment of Peripheral Blood Lymphocytes with Magnetic Beads Combined with Electrofusion enables Efficient Production of Human Mabs", Acta Biotechnol., 1992, vol. 12, pp. 259-268.
Havel, R. J. et al., "Hepatic Catabolismof Remnant Lipoproteins: Where the Action is", Arterioscler Thromb Vasc Biol, Feb. 2004, in 4 pages.
Homer, V. M. et al., "Identification and characterization of two non-secreted PCSK9 mutants associated with familial hypercholesterolemia in cohorts from New Zealand and South Africa", Atherosclerosis, 2008, vol. 196, pp. 659-666.
Horton, J. D. et al., "Combined analysis of oligonucleotide microarray data from transgenic and knockout mice identifies direct SREBP target genes", PNAS, Oct. 2003, vol. 100, No. 21, pp. 12027-12032.
Ioannidis, J. P. A., "Why Most Published Research Findings are False", PLoS Medicine, Aug. 2005, vol. 2, pp. 0696-0701.
Jia, X.-C. et al., "A novel method of Multiplexed Competitive Antibody Binning for the characterization of monoclonal antibodies", Journal of Immunological Methods, 2004, vol. 288, pp. 91-98.
Kondrashov, D. A. et al., "Sampling of the native conformational ensemble of myoglobin via structures in different crystalline environments", Proteins, 2008, vol. 70, pp. 353-362.

Kruth, H. S., "Lipoprotein Cholesterol and Atherosclerosis", Current Molecular Medicine, 2001, vol. 1, pp. 633-653.
Ladner, R. C., "Mapping the Epitopes of Antibodies", Biotechnology and Genetic Engineering Reviews, 2007, vol. 24(1), in 31 pages.
Lo Surdo, P. et al., "Mechanistic implications for LDL receptor degradation from the PCSK9/LDLR structure at neutral pH", EMBO reports, 2011, vol. 12, No. 12, pp. 1300-1305.
McCuskey, R. S. et al., "The Hepatic Microvascular System in Health and Its Response to Toxicants", The Anatomical Record, 2008, vol. 291, pp. 661-671.
Miller, S. et al., "Interior Surface of Monomeric Proteins", J. Mol. Biol., 1987, vol. 196, pp. 641-656.
Notice of Allowability for U.S. Appl. No. 14/562,546 in 10 pages, dated Aug. 5, 2024.
Office Action for Chilean Application No. CL 201901304 with English translation in 6 pages, dated May 7, 2024.
Office Action for Chinese Application No. CN 202011304952.4 with English translation in 12 pages, dated Jun. 28, 2024.
Office Action for Chinese Application No. CN 202011304952.4 with English translation in 14 pages, dated Apr. 4, 2024.
Office Action for Chinese Application No. CN 202011305376.5 with English translation in 12 pages, dated May 9, 2024.
Office Action for Chinese Application No. CN 202110464822.5 with English translation in 33 pages, dated Apr. 25, 2024.
Office Action for Eurasian Application No. EA 201991160/28 with English translation in 7 pages, dated Apr. 25, 2024.
Office Action for Israeli Application No. IL 266579 in 8 pages, dated Mar. 21, 2024.
Office Action for Israeli Application No. IL 304868 in 3 pages, dated Jun. 20, 2024.
Office Action for Israeli Application No. IL 304868 in 4 pages, dated Feb. 8, 2024.
Office Action for Japanese Application No. JP 2023-019926 with English translation in 9 pages, dated Mar. 12, 2024.
Office Action for Korean Application No. KR 10-2023-7014430 with English translation in 7 pages, dated Jul. 3, 2024.
Office Action for Mexican Application No. MX/a/2019/005627 with English translation in 12 pages, dated Apr. 16, 2024.
Office Action for Russian Application No. EA 202192450/28 with English translation in 9 pages, dated Mar. 15, 2024.
Office Action for Taiwanese Application No. TW 111138485 with English translation in 9 pages, dated May 27, 2024.
Office Action in Argentinian Application No. AR 20200100189 with English translation in 14 pages, dated Aug. 23, 2024.
Office Action in Indonesian Application No. ID P00201708121 with English translation in 8 pages, dated Sep. 4, 2024.
Prescribing Information for LOVENOX (Enoxaparin Sodium) injection, for subcutaneous and intravenous use, Reference ID: 4907820, dated Dec. 2021, in 48 pages.
Prescribing Information for NETSPOT (kit for the preparation of gallium Ga 68 dotatate injection), for intravenous use, Reference ID: 3939719, dated Jun. 2016, in 13 pages.
Rees, A. R., "Understanding the human antibody repertoire", MABS, 2020, vol. 12, No. 1, e1729683, in 17 pages.
Rudenko, G. et al., "Full wwPDB X-ray Structure Validation Report—Extracellular Domain of the LDL Receptor", Worldwide PDB, Oct. 2021, in 69 pages.
Spencer, D. I. R. et al., "A strategy for mapping and neutralizing conformational immunogenic sites on protein therapeutics", Proteomics, 2002, vol. 2, pp. 271-279.
Summons to Attend Oral Proceedings pursuant to Rule 115(1) filed in Opposition against EP 3666797 B1 in 87 pages, dated Aug. 8, 2024.
Tucker, T. J. et al., "A Series of Novel, Highly Potent, and Orally Bioavailable Next-Generation Tricyclic Peptide PCSK9 Inhibitors", Journal of Medicinal Chemistry, 2021, vol. 64, pp. 16770-16800.
U.S. Appl. No. 61/486,610, filed May 16, 2011, Goel et al.
"A Phase 1, Randomized, Double-Blind, Placebo-Controlled, Ascending Multiple Dose Study to Evaluate the Safety, Tolerability, Pharmacokinetics and Pharmacodynamics of Evolocumab AMG 145 in Subjects with Hyperlipidemia on Stable Doses of a Statin", DialogSolutions, May 27, 2010, post last updated Nov. 2, 2018,

(56) References Cited

OTHER PUBLICATIONS

Accession No. NCT01133522, in 14 pages. URL: https://dialog.proquest.com/professional/docview/2516940217?accountid=131444. [This refers to a webpage and the dates apparent in the document are listed herewith. However, the webpage may have been publicly available in some form at a date earlier than those listed].

"Ascending Multiple Dose Study to Evaluate the Safety, Tolerability, Pharmacokinetics and Pharmacodynamics of Evolocumab (AMG 145) in Adults With Hyperlipidemia on Stable Doses of a Statin—Record History Tab", ClinicalTrials.gov, last updated Nov. 2, 2018 (dated Sep. 11, 2015), Version 22, identifier: NCT01133522, in 12 pages.

"Ascending Multiple Dose Study to Evaluate the Safety, Tolerability, Pharmacokinetics and Pharmacodynamics of Evolocumab (AMG 145) in Adults With Hyperlipidemia on Stable Doses of a Statin—Record History Tab", ClinicalTrials.gov, last updated Nov. 2, 2018 (dated May 27, 2010), Version 1, identifier: NCT01133522, in 11 pages.

"Trial Evaluating PCSK9 Antibody in Subjects with LDL Receptor Abnormalities (TESLA)—Record History Tab", ClinicalTrials.gov, last updated Nov. 29, 2018 (dated Jun. 22, 2012), Version 2, identifier: NCT01588496 (Tesla), in 11 pages.

Communication Pursuant to Rule 114(2) EPC (Observations by a Third Party) for European Application No. EP 23173456.7 in 12 pages, dated Nov. 7, 2024.

Decision to Dismiss the Amendment for Japanese Application No. JP 2023-019926 with English translation in 5 pages, dated Nov. 5, 2024.

Declaration of Professor Thomas U. Schwartz for European Application No. 23173456.7 in 13 pages, dated Oct. 23, 2024.

Dias, C. et al., "Effects of AMG 145 on Low-Density Lipoprotein Cholestrol Levels", Journal of American College of Cardiology, 2012, vol. 60, No. 19, pp. 1888-1898.

Final Office Action for U.S. Appl. No. 13/931,716 in 16 pages, dated Apr. 24, 2025.

Final Office Action for U.S. Appl. No. 16/348,653 in 13 pages, dated May 19, 2025.

Final Office Action for U.S. Appl. No. 17/011,433 in 15 pages, dated Apr. 16, 2025.

International Preliminary Report on Patentability for PCT Application No. PCT/US2013/048714 in 7 pages, mailed Jan. 7, 2016.

International Preliminary Report on Patentability for PCT Application No. PCT/US2017/061346 in 15 pages, mailed May 23, 2019.

International Search Report and Written Opinion for PCT Application No. PCT/US2013/048714 in 10 pages, mailed Nov. 5, 2013.

Judgement from the Federal Court of Australia concerning the Oppositions for Australian Patent Application Nos. AU 2013203677, AU 2013203685, AU 2013203689, AU 2013203748, and AU 2013203751 in 136 pages, dated Apr. 23, 2025.

Non-Final Office Action for U.S. Appl. No. 13/931,716 in 31 pages, dated Nov. 7, 2024.

Non-Final Office Action for U.S. Appl. No. 17/011,433 in 16 pages, dated Nov. 7, 2024.

Office Action for African Application No. AP/P/2021/013268 in 4 pages, dated Apr. 3, 2025.

Office Action for Australian Application No. AU 2017356219 in 6 pages, dated Nov. 6, 2024.

Office Action for Australian Application No. AU 2022215259 in 3 pages, dated Sep. 17, 2024.

Office Action for Australian Application No. AU 2022241573 in 6 pages, dated Nov. 7, 2024.

Office Action for Brazilian Application No. BR 112013028819-1 with English translation in 11 pages, dated Dec. 26, 2024.

Office Action for Brazilian Application No. BR 122019021784-0 with English translation in 12 pages, dated Dec. 26, 2024.

Office Action for Canadian Application No. CA 3043700 in 4 pages, dated Nov. 12, 2024.

Office Action for Chilean Application No. CL 202002993 with English Summary in 8 pages, dated Jan. 2, 2025.

Office Action for Chinese Application No. CN202110835168.4 with English translation in 14 pages, dated Nov. 2, 2024.

Office Action for Chinese Application No. CN 202010703260.0 with English translation in 13 pages, dated Oct. 25, 2024.

Office Action for Chinese Application No. CN 202011305376.5 with English translation in 17 pages, dated Sep. 25, 2024.

Office Action for Chinese Application No. CN 202110464822.5 with English translation in 14 pages, dated Jan. 1, 2025.

Office Action for Eurasian Application No. EA 202192450 with English translation in 4 pages, dated Oct. 22, 2024.

Office Action for European Application No. EP 19203125.0 in 6 pages, dated Mar. 21, 2025.

Office Action for European Application No. EP 23173456.7 in 5 pages, dated Jan. 14, 2025.

Office Action for Gulf Coast Application No. GCC/P/2008/41481 in 3 pages, dated May 30, 2024.

Office Action for Israeli Application No. IL 266579 in 7 pages, dated Mar. 20, 2025.

Office Action for Japanese Application No. JP 2019-231236 with English translation in 31 pages, dated Dec. 3, 2024.

Office Action for Japanese Application No. JP 2023-019926 with English translation in 3 pages, dated Nov. 5, 2024.

Office Action for Japanese Application No. JP 2023-030747 with English translation in 9 pages, dated Dec. 3, 2024.

Office Action for Korean Application No. KR 10-2023-7014430 with English translation in 7 pages, dated Mar. 19, 2025.

Office Action for Korean Application No. KR 10-2024-7018411 with English translation in 4 pages, dated Aug. 30, 2024.

Office Action for Mexican Application No. MX/a/2019/005627 with English translation in 10 pages, dated Dec. 4, 2024.

Office Action for Mexican Application No. MX/a/2020/008898 with English translation in 12 pages, dated Feb. 21, 2025.

Office Action for New Zealand Application No. NZ 816863 in 1 page, dated Dec. 23, 2024.

Office Action for Thailand Application No. TH 1301006357 with English translation in 18 pages, dated Mar. 12, 2025.

Office Action for U.S. Appl. No. 13/469,032 in 18 pages, dated Feb. 7, 2025.

Office Action for U.S. Appl. No. 13/619,555 in 26 pages, dated Oct. 23, 2024.

Office Action for U.S. Appl. No. 14/316,587 in 19 pages, dated Feb. 27, 2025.

Office Action for U.S. Appl. No. 14/562,546 in 12 pages, dated Mar. 19, 2025.

Office Action for U.S. Appl. No. 16/348,653 in 21 pages, dated Dec. 4, 2024.

Office Action for United Arab Emirates Application No. AE P6000679/2019 in 6 pages, dated Dec. 22, 2024.

Raal, F. J. et al., "Inhibition of PCSK9 with evolocumab in homozygous familial hypercholesterolaemia (TESLA Part B): a randomised, double-blind, placebo-controlled trial", Lancet, Jan. 2015, vol. 385, pp. 341-350.

Robinson, J. G. et al., "Effect of Evolocumab or Ezetimibe Added to Moderate- or High-Intensity Statin Therapy on LDL-C Lowering in Patients With Hypercholesterolemia: the LAPLACE-2 randomized clinical trial", JAMA, May 2014, vol. 311, No. 18, pp. 1870-1882.

Office Action for Eurasian Application No. EA 202590696 in 4 pages, dated May 7, 2025.

Summons to Attend Oral Proceedings pursuant to Rule 115(1) EPC for European Application No. EP 19175489.4 in 7 pages, dated May 20, 2025.

Notice of Allowance for U.S. Appl. No. 13/469,032 in 10 pages, dated Jul. 9, 2025.

Final Office Action for U.S. Appl. No. 13/619,555 in 20 pages, dated Jul. 9, 2025.

Office Action for Egyptian Application No. EG 3022010 with English Summary in 8 pages, dated May 19, 2025.

Appeal Decision for Japanese Application No. JP 2019-525021 with English translation in 73 pages, dated May 20, 2025.

Giugliano, R. P. et al., "Efficacy, safety, and tolerability of a monoclonal antibody to proprotein convertase subtilisin/kexin type 9 in combination with a statin in patients with hypercholesterolaemia

(56) References Cited

OTHER PUBLICATIONS (LAPLACE-TIMI 57): a randomised, placebo-controlled, dose-ranging, phase 2 study", The Lancet, 2012, vol. 380, pp. 2007-2017.

Decision of the Supreme People's Court of China for Chinese Application No. CN 201410218704.6 with partial English translation in 26 pages, dated Jun. 30, 2025.

Final Office Action for U.S. Appl. No. 17/011,433 in 17 pages, dated Aug. 25, 2025.

Office Action for Indonesian Application No. ID P00201708121 with English translation in 6 pages, dated Jun. 3, 2025.

Office Action for New Zealand Application No. NZ 753201 in 5 pages, dated Jul. 1, 2025.

Office Action for New Zealand Application No. NZ 794398 in 5 pages, dated Jul. 1, 2025.

Office Action for Vietnamese Application No. VN 1-2017-04224 with English translation in 5 pages, dated May 30, 2025.

The Supreme People's Court of the People's Republic of China Administrative Judgement for Chinese Application No. CN 201410219429.X with English translation in 30 pages, dated Jun. 30, 2025.

Final Office Action for U.S. Appl. No. 13/931,716 in 25 pages, dated Sep. 18, 2025.

Final Office Action for U.S. Appl. No. 14/562,546 in 12 pages, dated Sep. 25, 2025.

Notice of Allowance for U.S. APpl. No. 13/469,032 in 4 pages, dated Sep. 2, 2025.

Office Action for Argentinian Application No. AR P200100189 with English translation in 10 pages, dated Aug. 29, 2025.

Office Action for Australian Application No. AU 2022241573 in 3 pages, dated Oct. 27, 2025.

Office Action for Eurasian Application No. EA 202590696 with English translation in 6 pages, dated Sep. 16, 2025.

Office Action for Japanese Application No. JP 2023-030747 with English translation in 10 pages, dated Aug. 19, 2025.

Office Action for Korean Application No. KR 10-2019-7016872 with English translation in 52 pages, dated Aug. 22, 2025.

Office Action for Korean Application No. KR 10-2024-7018411 with English translation in 7 pages, dated Sep. 30, 2025.

Office Action for U.S. Appl. No. 14/316,587 in 17 pages, dated Sep. 26, 2025.

Offce Action for U.S. Appl. No. 16/348,653 in 10 pages, dated Oct. 17, 2025.

* cited by examiner

QEDEDGDYEELVLALRSEEDGLAEAPEHGTTATFHRCAKDPWRLPGTYVVVLKEETHL
SQSERTARRLQAQAARRGYLTKILHVFHGLLPGFLVKMSGDLLELALKLPHVDYIEEDS
SVFAQSIPWNLERITPPRYRADEYQPPDGGSLVEVYLLDTSIQSDHREIEGRVMVTDFEN
VPEEDGTRFHRQASKCDSHGTHLAGVVSGRDAGVAKGASMRSLRVLNCQGKGTVSGT
LIGLEFIRKSQLVQPVGPLVVLLPLAGGYSRVLNAACQRLARAGVVLVTAAGNFRDDAC
LYSPASAPEVITVGATNAQDQPVTLGTLGTNFGRCVDLFAPGEDIIGASSDCSTCFVSQS
GTSQAAAHVAGIAAMMLSAEPELTLAELRQRLIHFSAKDVINEAWFPEDQRVLTPNLVA
ALPPSTHGAGWQLFCRTVWSAHSGPTRMATAIARCAPDEELLSCSSFSRSGKRRGERME
AQGGKLVCRAHNAFGGEGVYAIARCCLLPQANCSVHTAPPAEASMGTRVHCHQQGHV
LTGCSSHWEVEDLGTHKPPVLRPRGQPNQCVGHREASIHASCCHAPGLECKVKEHGIPA
PQGQVTVACEEGWTLTGCSALPGTSHVLGAYAVDNTCVVRSRDVSTTGSTSEEAVTAV
AICCRSRHLAQASQELQ

SEQ ID NO:1

FIG. 1A

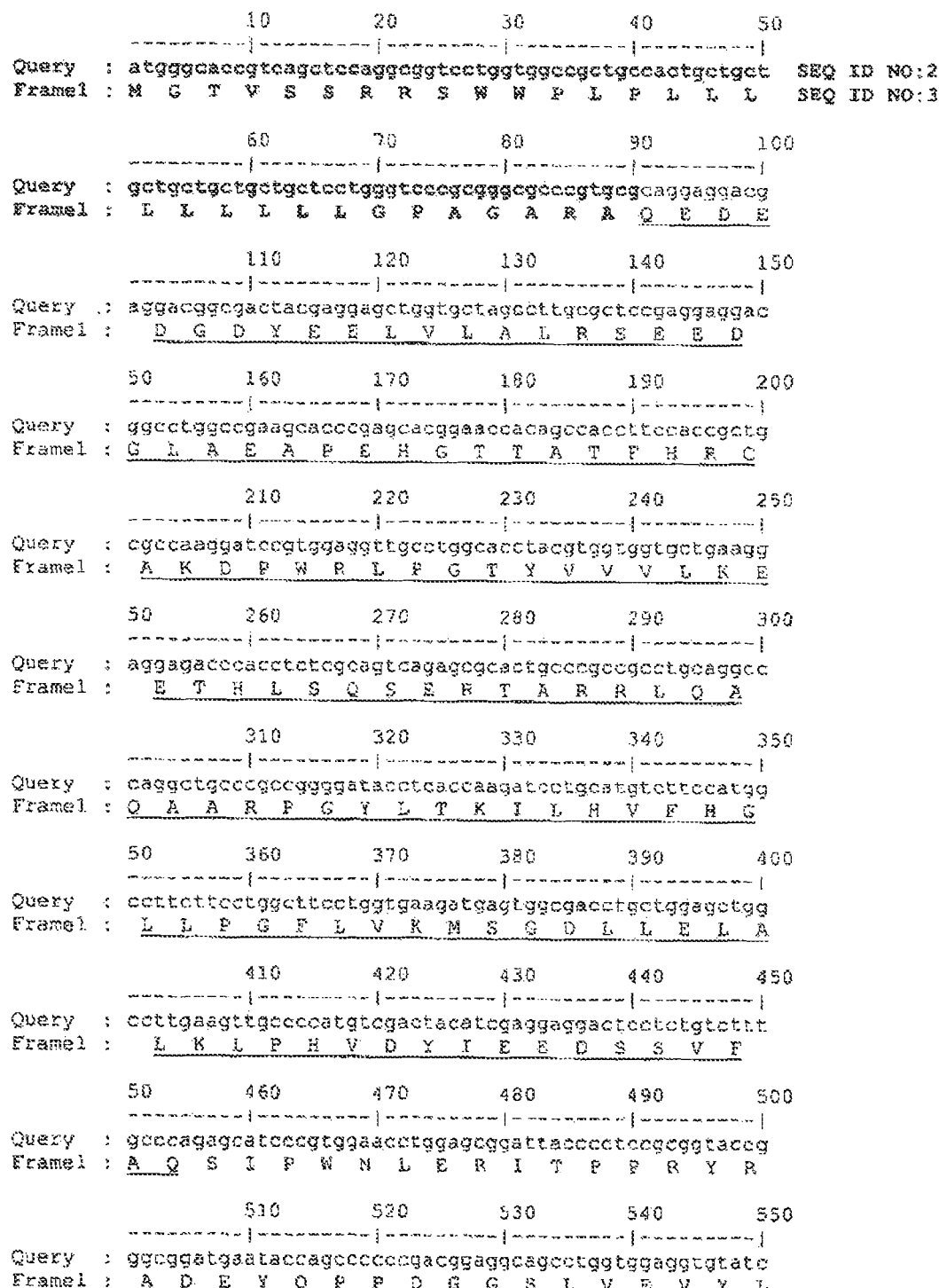
FIG. 1B₁

```
          50        560        570        580        590        600
       ----------|----------|----------|----------|----------|
Query  : tcctagacaccagcatacagagtgaccaccgggaaatcgagggcagggtc
Frame1 :   L  D  T  S  I  Q  S  D  H  R  E  I  E  G  R  V 610        620        630        640        650
       ----------|----------|----------|----------|----------|
Query  : atggtcaccgacttcgagaatgtgcccgaggaggacgggacccgcttcca
Frame1 :   M  V  T  D  F  E  N  V  P  E  D  G  T  R  F  H 50        660        670        680        690        700
       ----------|----------|----------|----------|----------|
Query  : cagacaggccagcaagtgtgacagtcatggcacccacctggcaggggtgg
Frame1 :   R  Q  A  S  K  C  D  S  H  G  T  H  L  A  G  V  V 710        720        730        740        750
       ----------|----------|----------|----------|----------|
Query  : tcagcggccgggatgccggcgtggccaagggtgccagcatgcgcagcctg
Frame1 :   S  G  R  D  A  G  V  A  K  G  A  S  M  R  S  L 50        760        770        780        790        800
       ----------|----------|----------|----------|----------|
Query  : cgcgtgctcaactgccaagggaagggcacggttagcggcaccctcatagg
Frame1 :   R  V  L  N  C  Q  G  K  G  T  V  S  G  T  L  I  G 810        820        830        840        850
       ----------|----------|----------|----------|----------|
Query  : cctggagtttattcggaaaagccagctggtccagcctgtggggccactgg
Frame1 :   L  E  F  I  R  K  S  Q  L  V  Q  P  V  G  P  L  V 50        860        870        880        890        900
       ----------|----------|----------|----------|----------|
Query  : tggtgctgctgcccctggcgggtgggtacagccgcgtcctcaacgccgcc
Frame1 :   V  L  L  P  L  A  G  G  Y  S  R  V  L  N  A  A 910        920        930        940        950
       ----------|----------|----------|----------|----------|
Query  : tgccagcgcctggcgagggctggggtcgtgctggtcaccgctgccggcaa
Frame1 :   C  Q  R  L  A  R  A  G  V  V  L  V  T  A  A  G  N 50        960        970        980        990       1000
       ----------|----------|----------|----------|----------|
Query  : cttccgggacgatgcctgcctctactccccagcctcagctcccgaggtca
Frame1 :   F  R  D  D  A  C  L  Y  S  P  A  S  A  P  E  V  I 1010       1020       1030       1040       1050
       ----------|----------|----------|----------|----------|
Query  : tcacagttggggccaccaatgcccaggaccagccggtgaccctggggact
Frame1 :   T  V  G  A  T  N  A  Q  D  Q  P  V  T  L  G  T 50       1060       1070       1080       1090       1100
       ----------|----------|----------|----------|----------|
Query  : ttggggaccaactttggccgctgtgtggacctctttgccccagggggagga
Frame1 :   L  G  T  N  F  G  R  C  V  D  L  F  A  P  G  E  D
```

FIG. 1B₂

```
        100      1110      1120      1130      1140      1150
        ---------|---------|---------|---------|---------|
Query : catcattggtgcctccagcgactgcagcacctgctttgtgtcacagagtg
Frame1 :  I  I  G  A  S  S  D  C  S  T  C  F  V  S  Q  S  G 150      1160      1170      1180      1190      1200
        ---------|---------|---------|---------|---------|
Query : ggacatcacaggctgctgccacgtggctggcattgcagccatgatgctg
Frame1 :  T  S  Q  A  A  A  H  V  A  G  I  A  A  M  M  L 200      1210      1220      1230      1240      1250
        ---------|---------|---------|---------|---------|
Query : tctgccgagccggagctcaccctggccgagttgaggcagagactgatcca
Frame1 :  S  A  E  P  E  L  T  L  A  E  L  R  Q  R  L  I  H 250      1260      1270      1280      1290      1300
        ---------|---------|---------|---------|---------|
Query : cttctctgccaaagatgtcatcaatgaggcctggttccctgaggaccagc
Frame1 :  F  S  A  K  D  V  I  N  E  A  W  F  P  E  D  Q  R 300      1310      1320      1330      1340      1350
        ---------|---------|---------|---------|---------|
Query : gggtactgacccccaacctggtggccgccctgccccccagcacccatggg
Frame1 :  V  L  T  P  N  L  V  A  A  L  P  P  S  T  H  G 350      1360      1370      1380      1390      1400
        ---------|---------|---------|---------|---------|
Query : gcaggttggcagctgttttgcaggactgtgtggtcagcacactcggggcc
Frame1 :  A  G  W  Q  L  F  C  R  T  V  W  S  A  H  S  G  P 400      1410      1420      1430      1440      1450
        ---------|---------|---------|---------|---------|
Query : tacacggatggccacagccatcgccgctgcgccccagatgaggagctgc
Frame1 :  T  R  M  A  T  A  I  A  R  C  A  P  D  E  E  L  L 450      1460      1470      1480      1490      1500
        ---------|---------|---------|---------|---------|
Query : tgagctgctccagtttctccaggagtgggaagcggcggggcgagcgcatg
Frame1 :  S  C  S  S  F  S  R  S  G  K  R  R  G  E  R  M 500      1510      1520      1530      1540      1550
        ---------|---------|---------|---------|---------|
Query : gaggcccaaggggggcaagctggtctgccgggcccacaacgcttttggggg
Frame1 :  E  A  Q  G  G  K  L  V  C  R  A  H  N  A  F  G  G 550      1560      1570      1580      1590      1600
        ---------|---------|---------|---------|---------|
Query : tgagggtgtctacgccattgccaggtgctgcctgctaccccaggccaact
Frame1 :  E  G  V  Y  A  I  A  R  C  C  L  L  P  Q  A  N  C 600      1610      1620      1630      1640      1650
        ---------|---------|---------|---------|---------|
Query : gcagcgtccacacagctccaccagctgaggccagcatggggacccgtgtc
Frame1 :  S  V  H  T  A  P  P  A  E  A  S  M  G  T  R  V
```

FIG. 1B₃

```
            650        1660        1670        1680        1690        1700
          ------|---------|---------|---------|---------|---------|
Query   : cactgccaccaacagggccacgtcctcaggctgcagctcccactggga
Frame1  :  H  C  H  Q  Q  G  H  V  L  T  G  C  S  S  H  W  E 700        1710        1720        1730        1740        1750
          --------|---------|---------|---------|---------|---------|
Query   : ggtggaggaccttggcacccacaagccgcctgtgctgaggccacgaggtc
Frame1  :  V  E  D  L  G  T  H  K  P  P  V  L  R  P  R  G  Q 750        1760        1770        1780        1790        1800
          --------|---------|---------|---------|---------|---------|
Query   : agcccaaccagtgcgtgggccacaggggaggccagcatccacgcttcctgc
Frame1  :   P  N  Q  C  V  G  H  R  E  A  S  I  H  A  S  C 800        1810        1820        1830        1840        1850
          --------|---------|---------|---------|---------|---------|
Query   : tgccatgccccaggtctggaatgcaaagtcaaggagcatggaatcccggc
Frame1  :  C  H  A  P  G  L  E  C  K  V  K  E  H  G  I  P  A 850        1860        1870        1880        1890        1900
          --------|---------|---------|---------|---------|---------|
Query   : ccctcaggggcaggtgaccgtggcctgcgaggagggctggaccctgactg
Frame1  :  P  Q  G  Q  V  T  V  A  C  E  E  G  W  T  L  T  G 900        1910        1920        1930        1940        1950
          --------|---------|---------|---------|---------|---------|
Query   : gctgcagcgccctccctgggacctcccacgtcctggggggcctacgcgta
Frame1  :   C  S  A  L  P  G  T  S  H  V  L  G  A  Y  A  V 950        1960        1970        1980        1990        2000
          --------|---------|---------|---------|---------|---------|
Query   : gacaacacgtgtgtagtcaggagccgggacgtcagcactacaggcagcac
Frame1  :  D  N  T  C  V  V  R  S  R  D  V  S  T  T  G  S  T 2010        2020        2030        2040        2050
          --------|---------|---------|---------|---------|---------|
Query   : cagcgaagaggccgtgacagccgttgccatctgctgccggagccggcacc
Frame1  :  S  E  E  A  V  T  A  V  A  I  C  C  R  S  R  H  L 50         2060        2070        2080        2090        2100
          --------|---------|---------|---------|---------|---------|
Query   : tggcgcaggcctcccaggagctccag
Frame1  :  A  Q  A  S  Q  E  L  Q
```

FIG. 1B₄

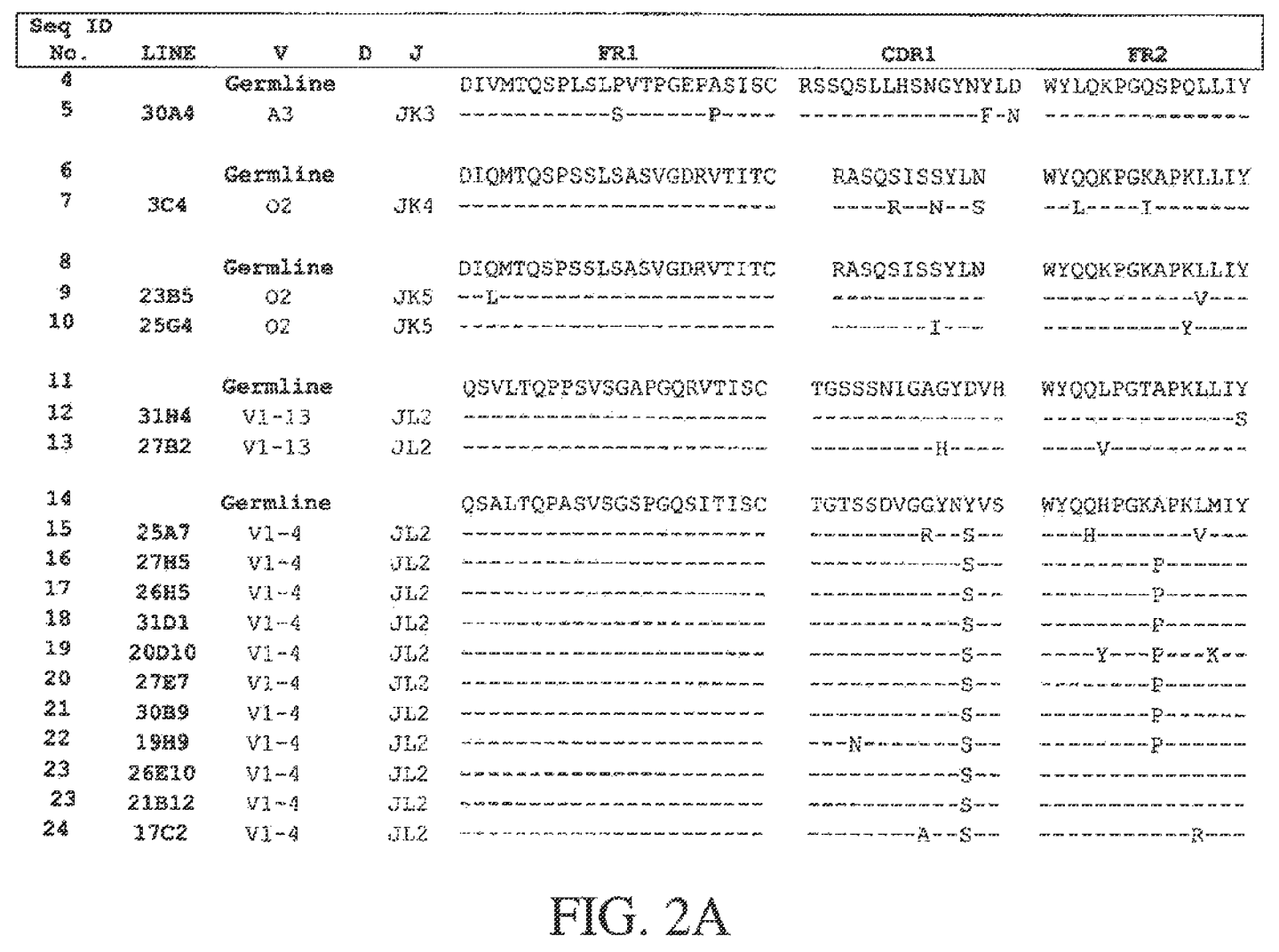

| Seq ID No. | LINE | V | D | J | FR1 | CDR1 | FR2 |
|---|---|---|---|---|---|---|---|
| 4 | | Germline | | | DIVMTQSPLSLPVTPGEPASISC | RSSQSLLHSWGYNYLD | WYLQKPGQSPQLLIY |
| 5 | 30A4 | A3 | | JK3 | --------S------P----- | ----------F-N | ------------- |
| 6 | | Germline | | | DIQMTQSPSSLSASVGDRVTITC | RASQSISSYLN | WYQQKPGKAPKLLIY |
| 7 | 3C4 | O2 | | JK4 | | ----R--N--S | ---L---I----- |
| 8 | | Germline | | | DIQMTQSPSSLSASVGDRVTITC | RASQSISSYLN | WYQQKPGKAPKLLIY |
| 9 | 23B5 | O2 | | JK5 | ---L------------------ | | -----------V-- |
| 10 | 25G4 | O2 | | JK5 | | ------I----- | ----------Y--- |
| 11 | | Germline | | | QSVLTQPPSVSGAPGQRVTISC | TGSSSNIGAGYDVR | WYQQLPGTAPKLLIY |
| 12 | 31B4 | V1-13 | | JL2 | | | ----------S |
| 13 | 27B2 | V1-13 | | JL2 | | ------H----- | -----V-------- |
| 14 | | Germline | | | QSALTQPASVSGSPGQSITISC | TGTSSDVGGYNYVS | WYQQHPGKAPKLMIY |
| 15 | 25A7 | V1-4 | | JL2 | | ----R---S--- | -----H-------V--- |
| 16 | 27H5 | V1-4 | | JL2 | | -----------S--- | -----------P--- |
| 17 | 26H5 | V1-4 | | JL2 | | -----------S--- | -----------P--- |
| 18 | 31D1 | V1-4 | | JL2 | | -----------S--- | -----------P--- |
| 19 | 20D10 | V1-4 | | JL2 | | -----------S--- | ----Y---P---K--- |
| 20 | 27E7 | V1-4 | | JL2 | | -----------S--- | -----------P--- |
| 21 | 30B9 | V1-4 | | JL2 | | -----------S--- | -----------P--- |
| 22 | 19H9 | V1-4 | | JL2 | | ---N-------S--- | -----------P--- |
| 23 | 26E10 | V1-4 | | JL2 | | -----------S--- | |
| 23 | 21B12 | V1-4 | | JL2 | | -----------S--- | |
| 24 | 17C2 | V1-4 | | JL2 | | ----A--S--- | -----------R--- |

FIG. 2A

| Seq ID No. | LINE | V | D | J | FR1 | CDR1 | FR2 |
|---|---|---|---|---|---|---|---|
| 25 | Germline | | | | QSALTQPASVSGSPGQSITISC | TGTSSDVGGYNYVS | WYQQHPGKAPKLMIY |
| 26 | 23G1 | V1-4 | | JL3 | ---------------------- | -------S------ | --------------- |
| 27 | Germline | | | | QSALTQPASVSGSPGQSITISC | TGTSSDVGSYNLVS | WYQQHPGKAPKLMIY |
| 28 | 13B1 | V1-7 | | JL3 | L--------------------- | -------N------ | --YS----------- |
| 29 | Germline | | | | QSVLTQPPSASGTPGQRVTISC | SGSSSNIGSNTVN | WYQQLPGTAPKLLIY |
| 30 | 9C9 | V1-16 | | JL3 | ---------------------- | ------K------ | --V------------ |
| 31 | 9B6 | V1-16 | | JL3 | ---------P------------ | ------------- | --------------- |
| 32 | 31A4 | V1-16 | | JL3 | ---------------------- | ------------- | --------------- |
| 33 | 1A12 | V1-16 | | JL3 | ---------------------- | ------K------ | --F------------ |
| 34 | Germline | | | | QSVLTQPPSVSAAPGQKVTISC | SGSSSNIGNNYVS | WYQQLPGTAPKLLIY |
| 35 | 16F12 | V1-19 | | JL1 | ---------------------- | ---------F--- | --------------- |
| 36 | 22E2 | V1-19 | | JL1 | ---------------------- | ---------F--- | --F------------ |
| 37 | 27A6 | V1-19 | | JL1 | ---------------------- | ---------F--- | --F------------ |
| 38 | 28B12 | V1-19 | | JL1 | ---------------------- | ---------F--- | --------------- |
| 39 | 28D8 | V1-19 | | JL1 | -------T-------------- | ---------F--- | --------------- |
| 40 | 31G11 | V1-19 | | JL1 | ---------------------- | ---------F--- | --------------- |
| 41 | Germline | | | | QSVLTQPPSVSAAPGQKVTISC | SGSSSNIGNNYVS | WYQQLPGTAPKLLIY |
| 42 | 13B5 | V1-19 | | JL2 | ---------------------- | ----N-------- | --------------- |
| 43 | Germline | | | | SYELTQPPSVSVSPGQTASITC | SGDKLGDKYAC | WYQQKPGQSPVLVIY |
| 44 | 31B12 | V2-1 | | JL2 | ---------------R------ | ----------- | --------------- |
| 45 | Germline | | | | QPVLTQPPSASASLGASVTLTC | TLSSGYSNYKVD | WYQQRPGKGPRFVMR |
| 46 | 3B6 | V5-2 | | JL2 | -----------LF--------- | ----S-E----- | --------------- |

| Seq ID No. | LINE | CDR2 | FR3 | CDR3 | FR4 |
|---|---|---|---|---|---|
| 4 | 30A4 | LGSNRAS | GVPDRFSGSGSGTDFTLKISRVEAEDVGVYYC | MQALQTPFT | FGPGTKVDIK |
| 5 | | ---H--- | ------------------------------- | ---V--- | ---------- |
| 6 | 3C4 | AASSLQS | GVPSRFSGSGSGTDFTLT·SSLQPEDFATYYC | QQSYSTPLT | FGGGTKVEIK |
| 7 | | --------- | ----------------S--------------- | --------I | ---------- |
| 8 | 23B5 | AASSLQS | GVPSRFSGSGSGTDFTLT·SSLQPEDFATYYC | QQSYSTPIT | FGGGTKLEIK |
| 9 | | --------- | -------------M------------------ | -----S--- | ---------- |
| 10 | 25G4 | --A----- | -------------------------------- | -----A--- | ---------- |
| 11 | 31B4 | GNSNRPS | GVPDRFSGSKSGTSASLAITGLQAEDEADYYC | QSYDSSLSGSV | FGGGTKLTVL |
| 12 | 27B2 | --------- | -------------------------------- | ---N---V- | ---------- |
| 13 | | --TY---- | -------------------------------- | --------- | ---------- |
| 14 | 25A7 | EVSNRPS | GVSNRFSGSRSGNTASLTISGLQAEDEADYYC | SSYTSSSVV | FGGGTKLTVL |
| 15 | 25A7v1 | --------- | --------T----------------------- | -----T-M- | ---------- |
| 286 | 27B5 | --------- | --------I----------------------- | -----T-M- | ---------- |
| 16 | 27B5v1 | --------- | ------I-T----------------------- | -----T-X- | ---------- |
| 287 | 26B5 | --------- | --------I----------------------A | -----T-M- | ---------- |
| 17 | 31D1 | --------- | --------------------------------A | -----T-M- | ---------- |
| 18 | 20D10 | --------- | --------------------------------T | -----T-M- | ---------- |
| 19 | 27E7 | --------- | --------------------------------A | -----T-M- | ---------- |
| 20 | 30B9 | --------- | --------------------------------T | -----T-M- | ----A----- |
| 21 | 19B9 | --------- | -I------------------------------T | -----T-M- | ---------- |
| 22 | 19B9v1 | --------- | -I------------------------------T | -----T-M- | ---------- |
| 38 | 26B10 | --------- | -------------------------------- | N----T-M- | ---------- |
| 23 | 21B12 | --------- | -------------------------------- | N----T-M- | ---------- |
| 23 | 17C2 | --------- | -------------------------------- | -----T-M- | ---------- |

| Seq ID NO. | LINE | CDR2 | FR3 | CDR3 | FR4 |
|---|---|---|---|---|---|
| 25 | | EVSNRPS | GVSNRFSGSKSGNTASLTISGLQAEDEADYYC | SSYTSSS V | FGGGTKLTVL |
| 26 | 23G1 | --T---- | ------------------- | N----T-M- | ---------- |
| 27 | | EGSKRPS | GVSNRFSGSKSGNTASLTISGLQAEDEADYYC | CSYAGSST | FGGGTKLTVL |
| 28 | 13H1 | -V----- | ------------------- | -------LV | ---------- |
| 29 | | SNNQRPS | GVPDRFSGSKSGTSASLAISGLQSEDEADYYC | AAWDDSLN V | FGGGTKLTVL |
| 30 | 9C9 | R------L | ------------------- | -----W--- | ---------- |
| 31 | 9B6 | ---R--- | ------------------- | -----W--- | ---------- |
| 32 | 31A4 | | ------------------- | -V------GMV | ---------- |
| 33 | 1A12 | ---R--- | ------------------- | ------W | ------A--- |
| 34 | | DNNKRPS | GIPDRFSGSKSGTSATLGITGLQTGDEADYYC | GTWDSSLSAYV | FGTGTKVTVL |
| 35 | 16F12 | -Y----- | ------------------- | | ----R---- |
| 36 | 22E2 | -Y----- | ------------------- | -----G--- | ----R---- |
| 37 | 27A6 | -Y----- | ------------------- | -----S--- | ----R---- |
| 38 | 28B12 | -Y----- | ------------------- | -----G--- | ----R---- |
| 39 | 28D6 | -Y----- | ------------------- | -----G--- | ----R---- |
| 40 | 31G11 | -S----- | --------D- | | ---------- |
| 41 | | DNNKRPS | GIPDRFSGSKSGTSATLGITGLQTGDEADYYC | GTWDSSLSAVV | FGGGTKLTVL |
| 42 | 13B5 | ------- | ------M--- | | ---------- |
| 43 | | QDSKRPS | GIPERFSGSMSGNTALLTISGTQAMDEADYYC | QAWDSSTAVV | FGGGTKLTVL |
| 44 | 31B12 | -NT-W-L | -----K---V- | -----V- | ---------- |
| 45 | | VGTGGIVGSKGD | GIPDRFSVLGSGLNRYLTIKNIQEEDESDYHC | GADHGSGSNFVVV | FGGGTKLTVL |
| 46 | 3B6 | -D-------E | | ------T---- | ---------- |
| 45 | | VGTGGIV | GSKGDGIPDRFSVLGSGLNRYLTIKNIQEEDE | SDYHCGADHGSGSNFVVV | FGGGTKLTVL |
| 46 | 3B6v1 | -D------- | ----R---- | ------T---- | ---------- |

FIG. 2D

| Seq ID No. | LINE | V | D | J | FR1 | CDR1 | FR2 |
|---|---|---|---|---|---|---|---|
| 47 | Germline | | | | QVQLVQSGAEVKKPGASVKVSCKAS | GYTFTSYGIS | WVRQAPGQGLEWMG |
| 48 | 20D10 | VH1-18 | | JH6B | --I---------------------- | ---PL----- | ------------- |
| 49 | 26E10 | VH1-18 | | JH6B | ------------------------- | ----L----- | ------------- |
| 49 | 21B12 | VH1-18 | | JH6B | ------------------------- | ----L----- | ------------- |
| 50 | 23G1 | VH1-18 | | JH6B | ------------------------- | ----L----- | ------------- |
| 51 | 26H5 | VH1-18 | | JH6B | ------------------------- | ----L----- | ------------- |
| 52 | 27H5 | VH1-18 | | JH6B | -------R----------------- | ----L----- | ------------- |
| 53 | 31D1 | VH1-18 | | JH6B | --I---------------------- | ----L----- | ------------- |
| 54 | 27E7 | VH1-18 | | JH6B | -----------L------------- | ---SL----- | ------------- |
| 55 | 30B9 | VH1-18 | | JH6B | ------------------------- | ---PL----- | ------------- |
| 56 | 19H9 | VH1-18 | | JH6B | ------------------------- | ---AL----- | ------------- |
| 57 | 17C2 | VH1-18 | | JH6B | ------------------------- | ----S----- | ------------- |
| 58 | 25A7 | VH1-18 | | JH6B | ------------------------- | ----P----- | ------------- |
| 59 | Germline | | | | QVQLVQSGAEVKKPGASVKVSCKAS | GYTFTSYGIS | WVRQAPGQGLEWMG |
| 60 | 3B6 | VH1-18 | | JH4B | ------------------------- | GFTFSSYWMS | WVRQAPGKGLEWVA |
| 61 | Germline | | | | EVQLVESGGGLVQPGGSLRLSCAAS | ---------- | ------------- |
| 62 | 9H6 | VH3-7 | D7-27 | JH3A | ------------------------- | -----R---- | WVRQAPGKGLEWVA |
| 63 | Germline | | | | EVQLVESGGGLVQPGGSLRLSCAAS | GFTFSSYYMS | ------------- |
| 64 | 9C9 | VH3-7 | D7-27 | JH3B | -------------------VV-- | ---------- | ------------- |
| 65 | 1A12 | VH3-7 | D7-27 | JH3B | ------------------------- | ---------- | ------------- |
| 66 | Germline | | | | EVQLVESGGGLVKPGGSLRLSCAAS | GFTFSSYSMN | WVRQAPGKGLEWVS |
| 67 | 31H4 | VH3-21 | D3-3 | JH3A | ------------------------- | --L---NF-- | ------------- |
| 68 | Germline | | | | EVQLLESGGGLVQPGGSLRLSCAAS | GFTFSSYAMS | WVRQAPGKGLEWVS |
| 69 | 13B5 | VH3-23 | | JH4B | ------------------------- | ---------- | ------------- |

FIG. 3A

| Seq ID No. | LINE | V | D | J | FR1 | CDR1 | FR2 |
|---|---|---|---|---|---|---|---|
| 70 | Germline | | | | EVQLLESGGGLVQPGGSLRLSCAAS | GFTFSSYAMS | WVRQAPGKGLEWVS |
| 71 | 23B5 | VH3-23 | D2-8 | JH4B | ----- | -----N | ---- |
| 72 | 25G4 | VH3-23 | D2-8 | JH4B | ----- | -----N | ---- |
| 73 | 30A4 | Germline | | | QVQLVESGGGVVQPGRSLRLSCAAS | GFTFSSYGMH | WVRQAPGKGLEWVA |
| 74 | 30A4 | VH3-33 | | JH6B | ----- | ----- | ---- |
| 75 | | Germline | | | QVQLVESGGGVVQPGRSLRLSCAAS | GFTFSSYGMH | WVRQAPGKGLEWVA |
| 76 | 27A6 | VH3-33 | D6-6 | JH6B | ---H--- | ---N-F--- | ---- |
| 77 | 28B12 | VH3-33 | D6-6 | JH6B | ----- | ------F--- | ---- |
| 289 | 28B12v1 | VH3-33 | D6-6 | JH6B | ---H--- | ------F--- | ---- |
| 78 | 28D6 | VH3-33 | D6-6 | JH6B | ----- | ------F--- | ---- |
| 79 | 16F12 | VH3-33 | D6-6 | JH6B | ---H--- | ---N-F--- | ---- |
| 80 | 22E2 | VH3-33 | D6-6 | JH6B | ----- | ------F--- | ---- |
| 81 | 31B12 | VH3-33 | D6-6 | JH6B | ----- | ----- | ---- |
| 290 | 31B12v1 | VH3-33 | D6-6 | JH6B | ----- | ----- | ---C |
| 82 | | Germline | | JH6B | QVQLVESGGGVVQPGRSLRLSCAAS | GFTFSSYGMH | WVRQAPGKGLEWVA |
| 83 | 31G11 | VH3-33 | D6-19 | JH6B | ----- | ------R--- | ---- |
| 84 | | Germline | | | QVQLQESGPGLVKPSQTLSLTCTVS | GGSISSGGYYWS | WIRQHPGKGLEWIG |
| 85 | 3C4 | VH4-31 | | JH6B | ----- | -----SD--- | ---- |
| 86 | | Germline | | | QVQLQESGPGLVKPSQTLSLTCTVS | GGSISSGGYYWS | WIRQHPGKGLEWIG |
| 87 | 27B2 | VH4-31 | D5-5 | JH4B | ----- | ----- | ---- |
| 88 | | Germline | | | QVQLQQWGAGLLKPSETLSLTCAVY | GGSFSGYYWS | WIRQPPGKGLEWIG |
| 89 | 31A4 | VH4-34 | D6-6 | JH4B | ----- | ---A---N | ---- |
| 90 | | Germline | | | QVQLQQSGPGLVKPSQTLSLTCAIS | GDSVSSNSAAWN | WIRQSPSRGLEWLG |
| 91 | 13H1 | VH6-1 | | JH4B | ----- | ----- | ---- |

FIG. 3B

| Seq ID NO. | LINE | CDR2 | FR3 | CDR3 | FR4 |
|---|---|---|---|---|---|
| 47 | | WISAYNGNTNYAQKLQG | RVTMTTDTSTSTAYMELRSLRSDDTAVYYCAR | YGMDV | WGQGTTVTVSS |
| 48 | 20D10 | ---------V--- | S-------V-- | G----- | ------- |
| 49 | 26E10 | -V-F-------- | -G-----P--- | G----- | ------- |
| 49 | 21B12 | -V-F-------- | -G-----P--- | G----- | ------- |
| 50 | 23G1 | -V-F-------- | -G-----P--- | G----- | ------- |
| 51 | 26H5 | ---F------- | ------- | G----- | ------- |
| 52 | 27H5 | ---V--- | ------V--- | G----- | ------- |
| 53 | 31D1 | ---F------- | ------S--- | G----- | ------- |
| 54 | 27E7 | ---F------- | ---F------V-V--- | G----- | ------- |
| 55 | 30B9 | ------- | ------V--- | G----- | ------- |
| 56 | 19H9 | ------- | ------V--- | G----- | ------- |
| 57 | 17C2 | -V------- | ---V--- | G-V--- | ------- |
| 58 | 25A7 | ---E--- | ---V---F--- | G-V--- | ------- |
| 59 | 3B6 | WISAYNGNTNYAQKLQG | RVTMTTDTSTSTAYMELRSLRSDDTAVYYCAR | GY DY | WGQGTLVTVSS |
| 60 | 3B6 | ---V--- | ---V--- | --TR-- | ------- |
| 61 | 9H6 | NIKQDGSEKYYVDSVKG | RFTISRDNAKNSLYLQMNSLRAEDTAVYYCAR | NWG AEDV | WGQGTMVTVSS |
| 62 | 9H6 | ---H--- | ------- | ES---F--- | --H--- |
| 63 | 9C9 | NIKQDGSEKYYVDSVKG | RFTISRDNAKNSLYLQMNSLRAEDTAVYYCAR | NWG AEDI | WGQGTMVTVSS |
| 64 | 9C9 | ------- | ------- | ES---F--- | ------- |
| 65 | 1A12 | ------- | ------S-T- | ES---F--- | ------- |
| 66 | 1A12 | SISSSSSYIYYADSVKG | RFTISRDNAKNSLYLQMNSLRAEDTAVYYCAR | DYDFWSGYYTAFDV | WGQGTMVTVSS |
| 67 | 31H4 | ------S- | ------F--- | A---D---- | ------- |
| 68 | 13B5 | AISGSGGSTYYADSVKG | RFTISRDNSKNTLYLQMNSLRAEDTAVYYCAK | FDY | WGQGTLVTVSS |
| 69 | 13B5 | T-----R--- | ------- | EVGSP--- | ------- |

Figure 3D:
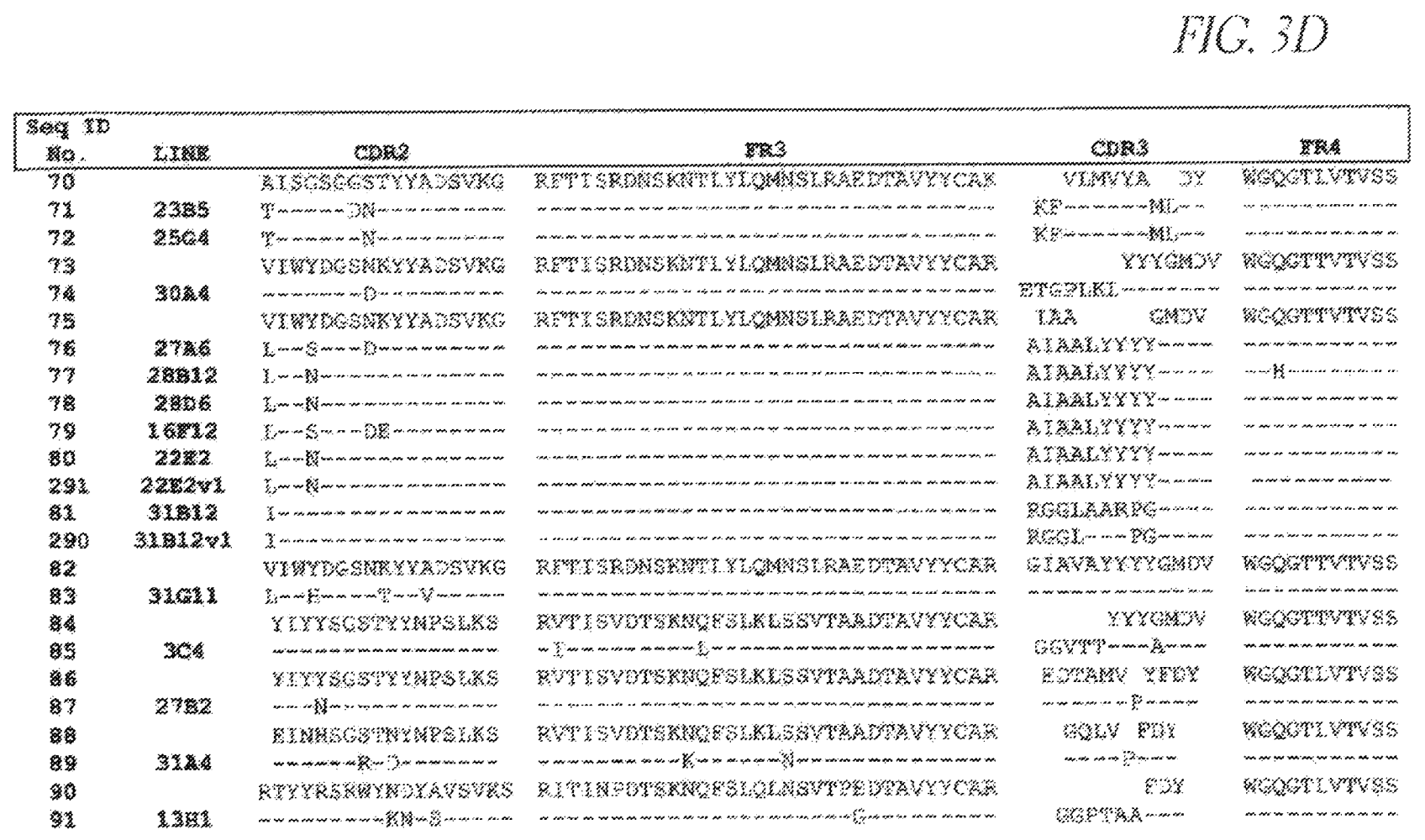

| Seq ID No. | LINE | CDR2 | FR3 | CDR3 | FR4 |
|---|---|---|---|---|---|
| 70 | | RISGSGGSTYYADSVKG | RFTISRDNSKNTLYLQMNSLRAEDTAVYYCAR | VLMVYA SY | WGQGTLVTVSS |
| 71 | 23B5 | T------DN | ------------- | KP------ML-- | ------- |
| 72 | 25C4 | T------N | ------------- | KP------ML-- | ------- |
| 73 | 30A4 | VIWYDGSNKYYADSVKG | RFTISRDNSKNTLYLQMNSLRAEDTAVYYCAR | YYYGMDV | WGQGTTVTVSS |
| 74 | 30A4 | VIWYDGSNKYYADSVKG | RFTISRDNSKNTLYLQMNSLRAEDTAVYYCAR | ETGPIKL | WGQGTTVTVSS |
| 75 | 27A6 | VIWYDGSNKYYADSVKG | RFTISRDNSKNTLYLQMNSLRAEDTAVYYCAR | LKA GMDV | WGQGTTVTVSS |
| 76 | 28B12 | L--S--D------ | ------------- | AIAALYYYY | ------- |
| 77 | 28D6 | L--N------ | ------------- | AIAALYYYY | ---H--- |
| 78 | 16F12 | L--N------ | ------------- | AIAALYYYY | ------- |
| 79 | 22E2 | L--S---DE---- | ------------- | AIAALYYYY | ------- |
| 80 | 22E2v1 | L--N------ | ------------- | AIAALYYYY | ------- |
| 291 | 31B12 | L--N------ | ------------- | AIAALYYYY | ------- |
| 81 | 31B12v1 | I------------ | ------------- | RGGLAARPG | ------- |
| 290 | | I------------ | ------------- | RGGL---PG | ------- |
| 82 | 31G11 | VIWYDGSNKYYADSVKG | RFTISRDNSKNTLYLQMNSLRAEDTAVYYCAR | GIAVAYYYYGMDV | WGQGTTVTVSS |
| 83 | | L--E---P--V | ------------- | YYYGMDV | WGQGTTVTVSS |
| 84 | 3C4 | YLYYSGSTYYNPSLKS | RVTISVDTSKNQFSLKLSSVTAADTAVYYCAR | GSVYY---A--- | WGQGTTVTVSS |
| 85 | | YLYYSGSTYYNPSLKS | ---I----------L--- | EGYAAV YFDY | WGQGTTVTVSS |
| 86 | 27B2 | YLYYSGSTYYNPSLKS | RVTISVDTSKNQFSLKLSSVTAADTAVYYCAR | ----P---- | WGQGTTVTVSS |
| 87 | | EINHSGGTNYNPSLKS | ------------- | GQLV FDY | WGQGTTVTVSS |
| 88 | 31A4 | RTYYRSKWYNDYAPSVKS | RVTISVDTSKNQFSLKLSSVTAADTAVYYCAR | ----P---- | WGQGTTVTVSS |
| 89 | | ---------K--S------ | RITINPDTSKNQFSLQLNSVTPEDTAVYYCAR | GSPTAA---- | WGQGTTVTVSS |
| 90 | 13B1 | ---------KN--S------ | ------------- | FDY | ------- |
| 91 | | | ------------------C--- | | ------- |

31H4

Nucleotide sequence of heavy chain variable region:
5'GAGGTGCAGCTGGTGGAGTCTGGGGGAGGCCTGGTCAAGCCTGGGGGGTCCCTGA
GACTCTCCTGTGCAGCCTCTGGATTCACCTTCAGTAGCTATAGCATGAACTGGGTCC
GCCAGGCTCCAGGGAAGGGGCTGGAGTGGGTCTCATCCATTAGTAGTAGTAGTAGT
TACATTTCCTACGCAGACTCAGTGAAGGGCCGATTCACCATCTCCAGAGACAACGCC
AAGAACTCACTGTATCTGCAAATGAACAGCCTGAGAGCCGAGGACACGGCTGTGTA
TTTCTGTGCGAGAGATTACGATTTTTGGAGTGCTTACTATGATGCTTTTGATGTCTGG
GGCCAAGGGACAATGGTCACCGTCTCTTCA3' (SEQ ID NO: 152)

Amino acid sequence of heavy chain variable region:
EVQLVESGGGLVKPGGSLRLSCAASGFTFSSYSMNWVRQAPGKGLEWVSSISSSSSYISY
ADSVKGRFTISRDNAKNSLYLQMNSLRAEDTAVYFCARDYDFWSAYYDAFDVWGQGT
MVTVSS (SEQ ID NO: 67)

Nucleotide sequence of light chain variable region:
5'CAGTCTGTGCTGACGCAGCCGCCCTCAGTGTCTGGGGCCCCAGGGCAGAGGGTCA
CCATCTCCTGCACTGGGAGCAGCTCCAACATCGGGGCAGGTTATGATGTACACTGGT
ACCAGCAGCTTCCAGGAACAGCCCCCAAACTCCTCATCTCTGGTAACAGCAATCGGC
CCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCCAGTCCTATGACA
GCAGCCTGAGTGGTTCGGTATTCGGCGGAGGGACCAAGCTGACCGTCCTA3' (SEQ
ID NO: 153)

Amino acid sequence of light chain variable region:
QSVLTQPPSVSGAPGQRVTISCTGSSSNIGAGYDVHWYQQLPGTAPKLLISGNSNRPSGV
PDRFSGSKSGTSASLAITGLQAEDEADYYCQSYDSSLSGSVFGGGTKLTVL (SEQ ID
NO: 12)

Nucleotide sequence of heavy chain variable region:
5'CAGATTCAGCTGGTGCAGTCTGGAGCTGAGGTGAAGAAGCCTGGGGCCTCAGTGA
AGGTCTCCTGCAAGGCTTCTGGTTACCCCTTGACCAGCTATGGTATCAGCTGGGTGC
GACAGGCCCCTGGACAAGGGCTTGAGTGGATGGGATGGATCAGCGCTTACAATGGT
AACACAAACTATGCACAGAAGGTCCAGGGCAGCGTCACCATGACCACAGACACATC
CACGAGCACAGTCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCT3' (SEQ ID NO: 92)

Amino acid sequence of heavy chain variable region:
QIQLVQSGAEVKKPGASVKVSCKASGYPLTSYGISWVRQAPGQGLEWMGWISAYNGN
TNYAQKVQGSVTMTTDTSTSTVYMELRSLRSDDTAVYYCARGYGMDVWGQGTTVTV
SS (SEQ ID NO: 48)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGTACCCAGGCAAACCCCCCAAACTCAAGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGACCGTCCTA3' (SEQ ID NO: 93)

Amino acid sequence of light chain variable region:
QSALTQPASVSGSPGQSITISCTGTSSDVGGYNSVSWYQQYPGKPPKLKIYEVSNRPSGV
SNRFSGSKSGNTASLTISGLQAEDEADYFCSSYTSTSMVFGGGTKLTVL (SEQ ID NO:
19)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACACCTTAACCAGCTATGGTATCAGCTGGGTGC
GACAGGCCCCTGGACAAGGGCTTGAGTGGATGGGATGGGTCAGTTTTTATAATGGT
AACACAAACTATGCACAGAAGCTCCAGGGCAGAGGCACCATGACCACAGACCCATC
CACGAGCACAGCCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCT3' (SEQ ID NO: 94)

Amino acid sequence of heavy chain variable region:
QVQLVQSGAEVKKPGASVKVSCKASGYTLTSYGISWVRQAPGQGLEWMGWVSFYNG
NTNYAQKLQGRGTMTTDPSTSTAYMELRSLRSDDTAVYYCARGYGMDVWGQGTTVT
VSS (SEQ ID NO: 49)

Nucleotide sequence of light chain variable region.
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAAGCCCCCAAACTCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTACTGCAATTCATATACAA
GCACCAGCATGGTATTCGGCGGAGGGACCAAGCTGACCGTCCTA3' (SEQ ID NO: 95)

Amino acid sequence of light chain variable region:
QSALTQPASVSGSPGQSITISCTGTSSDVGGYNSVSWYQQHPGKAPKLMIYEVSNRPSGV
SNRFSGSKSGNTASLTISGLQAEDEADYYCNSYTSTSMVFGGGTKLTVL (SEQ ID NO:
23)

Alternative Nucleotide sequence of light chain variable region (26E10v1):
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAAGCCCCCAAACTCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTACTGCAACTCATATACAA
GCACCAGCATGGTATTCGGCGGAGGGACCAAGCTGACCGTCCTA3' (SEQ ID NO:
293)

Nucleotide sequence of heavy chain variable region:
5'CAGGTTCAGCTGGTGCAGTCTGGAGCTGAAGTGAAGAAGCCTGGGGCCTCAGTGA
AGGTCTCCTGCAAGGCTTCTGGTTACACCTTGACCAGCTATGGTATCAGCTGGGTGC
GACAGGCCCCTGGACAAGGGCTTGAGTGGATGGGATGGATCAGCTTTTACAATGGT
AACACAAACTATGCACAGAAGGTCCAGGGCAGAGTCACCATGACCACAGACACATC
CACGAGCACAGTCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCT3' (SEQ ID NO: 96)

Amino acid sequence of heavy chain variable region:
QVQLVQSGAEVKKPGASVKVSCKASGYTLTSYGISWVRQAPGQGLEWMGWISFYNGN
TNYAQKVQGRVTMTTDTSTSTVYMELRSLRSDDTAVYYCARGYGMDVWGQGTTVTV
SS (SEQ ID NO: 51)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGGTTTCTATTCGCTTCTCTGGCTCCAAGTCTGGCAACACGGCCTCCCTGAC
CATCTCTGGGCTCCAGGCTGAGGACGAGGCTGATTATTTCTGCAGCTCATATACAAG
CACCAGCATGGTCTTCGGCGGAGGGACCAAGCTGACCGTCCTA3' (SEQ ID NO: 97)

Amino acid sequence of light chain variable region:
QSALTQPASVSGSPGQSITISCTGTSSDVGGYNSVSWYQQHPGKPPKLMIYEVSNRPSGV
SIRFSGSKSGNTASLTISGLQAEDEADYFCSSYTSTSMVFGGGTKLTVL (SEQ ID NO:
17)

Nucleotide sequence of heavy chain variable region:
5'CAGATTCAGCTGGTGCAGTCTGGAGCTGAGGTGAAGAAGCCTGGGGCCTCAGTGA
AGGTCTCCTGCAAGGCTTCTGGTTACACCTTGACCAGCTATGGTATCAGCTGGGTGC
GACAGGCCCCTGGACAAGGGCTTGAGTGGATGGGATGGATCAGCTTTTACAATGGT
AACACAAACTATGCACAGAAGGTCCAGGGCAGAGTCACCATGACCACAGACACATC
CACGAGCACAGTCTACATGGAGCTGAGGAGCCTGAGATCTGACGACACGGCCGTGT
ATTTCTGTGCGAGAGGTTACGGTATGGACGTCTGGGGCCAAGGGACCACGGTCACC
GTCTCCTCA3' (SEQ ID NO: 98)

Amino acid sequence of heavy chain variable region:
QIQLVQSGAEVKKPGASVKVSCKASGYTLTSYGISWVRQAPGQGLEWMGWISFYNGNT
NYAQKVQGRVTMTTDTSTSTVYMELRSLRSDDTAVYFCARGYGMDVWGQGTTVTVS
S (SEQ ID NO: 53)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCGTGGTA
CCAACAGCACCCAGGCAAACCCCCCAAACTCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGGCCGTCCTA3' (SEQ ID NO: 99)

Amino acid sequence of light chain variable region:
QSALTQPASVSGSPGQSITISCTGTSSDVGGYNSVSWYQQHPGKPPKLMIYEVSNRPSGV
SNRFSGSKSGNTASLTISGLQAEDEADYFCSSYTSTSMVFGGGTKLAVL (SEQ ID NO:
18)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACACCTTAACCAGCTATGGTATCAGCTGGGTGC
GACAGGCCCCTGGACAAGGGCTTGAGTGGATGGGATGGGTCAGTTTTTATAATGGT
AACACAAACTATGCACAGAAGCTCCAGGGCAGAGGCACCATGACCACAGACCCATC
CACGAGCACAGCCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCA3' (SEQ ID NO: 100)

Amino acid sequence of heavy chain variable region:
QVQLVQSGAEVKKPGASVKVSCKASGYTLTSYGISWVRQAPGQGLEWMGWVSFYNG
NTNYAQKLQGRGTMTTDPSTSTAYMELRSLRSDDTAVYYCARGYGMDVWGQGTTVT
VSS (SEQ ID NO: 50)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAAGCCCCCAAACTCATGATTTATGAGGTCACTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTACTGCAACTCATATACAA
GCACCAGCATGGTGTTCGGCGGAGGGACCAAGCTGACCGTCCTA3' (SEQ ID NO:
101)

Amino acid sequence of light chain variable region:
QSALTQPASVSGSPGQSITISCTGTSSDVGGYNSVSWYQQHPGKAPKLMIYEVTNRPSGV
SNRFSGSKSGNTASLTISGLQAEDEADYYCNSYTSTSMVFGGGTKLTVL (SEQ ID NO:
26)

Nucleotide sequence of heavy chain variable region:
5'CAGGTGCAGCTGCAGGAGTCGGGCCCAGGACTGGTGAAGCCTTCACAGACCCTGT
CCCTCACCTGCACTGTCTCTGGTGGCTCCATCAGCAGTGGTGGTTACTACTGGAGCT
GGATCCGCCAGCACCCAGGGAAGGGCCTGGAGTGGATTGGGTACATATATAACAGT
GGGAGCACCTACTACAACCCGTCCCTCAAGAGTCGAGTTACCATATCAGTAGACAC
GTCTAAGAACCAGTTCTCCCTGAAGCTGAGCTCTGTGACTGCCGCGGACACGGCCGT
GTATTACTGTGCGAGAGAGGATACAGCTATGGTTCCTTACTTTGACTACTGGGGCCA
GGGAACCCTGGTCACCGTCTCCTCA3' (SEQ ID NO: 102)

Amino acid sequence of heavy chain variable region:
QVQLQESGPGLVKPSQTLSLTCTVSGGSISSGGYYWSWIRQHPGKGLEWIGYIYNSGSTY
YNPSLKSRVTISVDTSKNQFSLKLSSVTAADTAVYYCAREDTAMVPYFDYWGQGTLVT
VSS (SEQ ID NO: 87)

Nucleotide sequence of light chain variable region:
5'CAGTCTGTACTGACGCAGCCGCCCTCAGTGTCTGGGGCCCCAGGGCAGAGGGTCA
CCATCTCCTGCACTGGGAGCAGCTCCAACATCGGGGCACATTATGATGTGCACTGGT
ACCAGCAGGTTCCAGGAACAGCCCCCAAACTCCTCATCTATGGTAACACCTATCGGC
CCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCCAGTCCTATGACA
ACAGCCTGAGTGGTGTGGTATTCGGCGGAGGGACCAAGCTGACCGTCCTA3' (SEQ
ID NO: 103)

Amino acid sequence of light chain variable region:
QSVLTQPPSVSGAPGQRVTISCTGSSSNIGAHYDVHWYQQVPGTAPKLLIYGNTYRPSG
VPDRFSGSKSGTSASLAITGLQAEDEADYYCQSYDNSLSGVVFGGGTKLTVL (SEQ ID
NO: 13)

Nucleotide sequence of heavy chain variable region:
5'CAGGTGCACCTGGTGGAGTCTGGGGGAGGCGTGGTCCAGCCTGGGAGGTCCCTGA
GACTCTCCTGTGCAGCGTCTGGATTCACCTTCAACAGCTTTGGCATGCACTGGGTCC
GCCAGGCTCCAGGCAAGGGGCTGGAGTGGGTGGCACTTATCTGGTCTGATGGAAGT
GATGAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGCCATAGCAGCCCTCTACTACTACTACGGTATGGACGTCTGGGG
CCAAGGGACCACGGTCACCGTCTCCTCA3' (SEQ ID NO: 104)

Amino acid sequence of heavy chain variable region:
QVHLVESGGGVVQPGRSLRLSCAASGFTFNSFGMHWVRQAPGKGLEWVALIWSDGSD
EYYADSVKGRFTISRDNSKNTLYLQMNSLRAEDTAVYYCARAIAALYYYYGMDVWGQ
GTTVTVSS (SEQ ID NO: 79)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAGCTCCAACATTGGGAATAATTTTGTATCCTGGTACC
AGCAGCTCCCAGGAACAGCCCCCAAACTCCTCATTTATGACTATAATAAGCGACCCT
CAGGGATTCCTGACCGATTCTCTGGCTCCAAGTCTGGCACGTCAGCCACCCTGGGCA
TCACCGGACTCCAGACTGGGGACGAGGCCGATTATTACTGCGGAACATGGGATAGC
AGCCTGAGTGCTTATGTCTTCGGAACTGGGACCAGGGTCACCGTCCTA3' (SEQ ID
NO: 105)

Amino acid sequence of light chain variable region:
QSVLTQPPSVSAAPGQKVTISCSGSSSNIGNNFVSWYQQLPGTAPKLLIYDYNKRPSGIPD
RFSGSKSGTSATLGITGLQTGDEADYYCGTWDSSLSAYVFGTGTRVTVL (SEQ ID NO:
35)

Nucleotide sequence of heavy chain variable region:

5'CAGGTGCAGCTGGTGGAGTCTGGGGGAGGCGTGGTCCAGCCTGGGAGGTCCCTGA
GACTCTCCTGTGCAGCGTCTGGATTCACCTTCAGCAGCTTTGGCATGCACTGGGTCC
GCCAGGCTCCAGGCAAGGGGCTGGAGTGGGTGGCACTTATATGGAATGATGGAAGT
AATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGCCATAGCAGCCCTCTACTACTACTACGGTATGGACGTCTGGGG
CCAAGGGACCACGGTCACCGTCTCCTCA3' (SEQ ID NO: 106)

Amino acid sequence of heavy chain variable region:
QVQLVESGGGVVQPGRSLRLSCAASGFTFSSFGMHWVRQAPGKGLEWVALIWNDGSN
KYYADSVKGRFTISRDNSKNTLYLQMNSLRAEDTAVYYCARAIAALYYYYGMDVWGQ
GTTVTVSS (SEQ ID NO: 80)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAGCTCCAACATTGGGAATAATTTTGTATCCTGGTACC
AGCAGCTCCCAGGAACAGCCCCCAAACTCCTCATTTATGACTATAATAAGCGACCCT
CAGGGATTCCTGACCGATTCTCTGGCTCCAAGTCTGGCACGTCAGCCACCCTGGGCA
TCACCGGACTCCAGACTGGGGACGAGGCCGATTATTACTGCGGAACATGGGATAGC
AGTCTGAGTGGTTATGTCTTCGGAACTGGGACCAGGGTCACCGTCCTA3' (SEQ ID
NO: 107)

Amino acid sequence of light chain variable region:
QSVLTQPPSVSAAPGQKVTISCSGSSSNIGNNFVSWYQQLPGTAPKLLIYDYNKRPSGIPD
RFSGSKSGTSATLGITGLQTGDEADYYCGTWDSSLSGYVFGTGTRVTVL (SEQ ID NO:
36)

Nucleotide sequence of heavy chain variable region:
5'CAGGTGCACCTGGTGGAGTCTGGGGGAGGCGTGGTCCAGCCTGGGAGGTCCCTGA
GACTCTCCTGTGCAGCGTCTGGATTCACCTTCAACAGCTTTGGCATGCACTGGGTCC
GCCAGGCTCCAGGCAAGGGGCTGGAGTGGGTGGCACTTATATGGTCTGATGGAAGT
GATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGCCATAGCAGCCCTCTACTACTACTACGGTATGGACGTCTGGGG
CCAAGGGACCACGGTCACCGTCTCCTCA3' (SEQ ID NO: 108)

Amino acid sequence of heavy chain variable region:
QVHLVESGGGVVQPGRSLRLSCAASGFTFNSFGMHWVRQAPGKGLEWVALIWSDGSD
KYYADSVKGRFTISRDNSKNTLYLQMNSLRAEDTAVYYCARAIAALYYYYGMDVWGQ
GTTVTVSS (SEQ ID NO: 76)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAGTTCCAACATTGGGAATAATTTTGTATCCTGGTACC
AGCAGTTCCCAGGAACAGCCCCCAAACTCCTCATTTATGACTATAATAAGCGACCCT
CAGGGATTCCTGACCGATTCTCTGGCTCCAAGTCTGGCACGTCAGCCACCCTGGGCA
TCACCGGACTCCAGACTGGGGACGAGGCCGATTATTACTGCGGAACATGGGATAGC
AGCCTGAGTTCTTATGTCTTCGGAACTGGGACCAGGGTCACCGTCCTA3' (SEQ ID
NO: 109)

Amino acid sequence of light chain variable region:
QSVLTQPPSVSAAPGQKVTISCSGSSSNIGNNFVSWYQQFPGTAPKLLIYDYNKRPSGIPD
RFSGSKSGTSATLGITGLQTGDEADYYCGTWDSSLSSYVFGTGTRVTVL (SEQ ID NO:
37)

Nucleotide sequence of heavy chain variable region:
5'CAGGTGCAGCTGGTGGAGTCTGGGGGAGGCGTGGTCCAGCCTGGGAGGTCCCTGA
GACTCTCCTGTGCAGCGTCTGGATTCACCTTCAGCAGCTTTGGCATGCACTGGGTCC
GCCAGGCTCCAGGCAAGGGGCTGGAGTGGGTGGCACTTATATGGAATGATGGAAGT
AATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGCCATAGCAGCCCTCTACTACTACTACGGTATGGACGTCTGGGG
CCACGGGACCACGGTCACCGTCTCCTCA3' (SEQ ID NO: 110)

Amino acid sequence of heavy chain variable region:
QVQLVESGGGVVQPGRSLRLSCAASGFTFSSFGMHWVRQAPGKGLEWVALIWNDGSN
KYYADSVKGRFTISRDNSKNTLYLQMNSLRAEDTAVYYCARAIAALYYYYGMDVWGH
GTTVTVSS (SEQ ID NO: 77)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAGCTCCAACATTGGGAATAATTTTGTATCCTGGTACC
AGCAGCTCCCAGGAACAGCCCCCAAACTCCTCATTTATGACTATAATAAGCGACCCT
CAGGGATTCCTGACCGATTCTCTGGCTCCAAGTCTGGCACGTCAGCCACCCTGGGCA
TCACCGGACTCCAGACTGGGGACGAGGCCGATTATTACTGCGGAACATGGGATAGC
AGCCTGAGTGGTTATGTCTTCGGAACTGGGACCAGGGTCACCGTCCTA3' (SEQ ID
NO: 111)

Amino acid sequence of light chain variable region:
QSVLTQPPSVSAAPGQKVTISCSGSSSNIGNNFVSWYQQLPGTAPKLLIYDYNKRPSGIPD
RFSGSKSGTSATLGITGLQTGDEADYYCGTWDSSLSGYVFGTGTRVTVL (SEQ ID NO:
38)

Nucleotide sequence of heavy chain variable region:
5'CAGGTGCAGCTGGTGGAGTCTGGGGGAGGCGTGGTCCAGCCTGGGAGGTCCCTGA
GACTCTCCTGTGCAGCGTCTGGATTCACCTTCAGCAGCTTTGGCATGCACTGGGTCC
GCCAGGCTCCAGGCAAGGGGCTGGAGTGGGTGGCACTTATATGGAATGATGGAAGT
AATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGCCATAGCAGCCCTCTACTACTACTACGGTATGGACGTCTGGGG
CCAAGGGACCACGGTCACCGTCTCCTCA3' (SEQ ID NO: 112)

Amino acid sequence of heavy chain variable region:
QVQLVESGGGVVQPGRSLRLSCAASGFTFSSFGMHWVRQAPGKGLEWVALIWNDGSN
KYYADSVKGRFTISRDNSKNTLYLQMNSLRAEDTAVYYCARAIAALYYYYGMDVWGQ
GTTVTVSS (SEQ ID NO: 78)

Nucleotide sequence of light chain variable region:
5'CAGTCTGTGTTGACGCAGCCGCCCACAGTGTCTGCGGCCCCAGGACAGAAGGTCA
CCATCTCCTGCTCTGGAAGCAGCTCCAACATTGGGAATAATTTTGTATCCTGGTACC
AGCAGCTCCCAGGAACAGCCCCCAAACTCCTCATTTATGACTATAATAAGCGACCCT
CAGGGATTCCTGACCGATTCTCTGGCTCCAAGTCTGGCACGTCAGCCACCCTGGGCA
TCACCGGACTCCAGACTGGGGACGAGGCCGATTACTACTGCGGAACATGGGATAGC
AGCCTGAGTGGTTATGTCTTCGGAACTGGGACCAGGGTCACCGTCCTA3' (SEQ ID
NO: 113)

Amino acid sequence of light chain variable region:
QSVLTQPPTVSAAPGQKVTISCSGSSSNIGNNFVSWYQQLPGTAPKLLIYDYNKRPSGIPD
RFSGSKSGTSATLGITGLQTGDEADYYCGTWDSSLSGYVFGTGTRVTVL (SEQ ID NO:
39)

Nucleotide sequence of heavy chain variable region:
5'CAGGTGCAGCTGGTGGAGTCTGGGGGAGGCGTGGTCCAGCCTGGGAGGTCCCTGA
GACTCTCCTGTGCAGCGTCTGGATTCACCTTCAGGAGCTATGGCATGCACTGGGTCC
GCCAGGCTCCAGGCAAGGGGCTGGAGTGGGTGGCACTTATATGGCATGATGGAAGT
AATACATACTATGTAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGGTATAGCAGTGGCTTACTACTACTACGGTATGGACGTCTGGGG
CCAAGGGACCACGGTCACCGTCTCCTCA3' (SEQ ID NO: 114)

Amino acid sequence of heavy chain variable region:
QVQLVESGGGVVQPGRSLRLSCAASGFTFRSYGMHWVRQAPGKGLEWVALIWHDGSN
TYYVDSVKGRFTISRDNSKNTLYLQMNSLRAEDTAVYYCARGIAVAYYYYGMDVWGQ
GTTVTVSS (SEQ ID NO: 83)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAGCTCCAACATTGGGAATAATTTTGTATCCTGGTACC
AGCAGCTCCCAGGAACAGCCCCCAAACTCCTCATTTATGACAGTAATAAGCGACCCT
CAGGGATTCCTGACCGATTCTCTGGCTCCAAGTCTGGCACGTCAGCCACCCTGGACA
TCACCGGACTCCAGACTGGGGACGAGGCCGATTATTACTGCGGAACATGGGATAGC
AGCCTGAGTGCTTATGTTTTCGGAACTGGGACCAAGGTCACCGTCCTA3' (SEQ ID
NO: 115)

Amino acid sequence of light chain variable region:
QSVLTQPPSVSAAPGQKVTISCSGSSSNIGNNFVSWYQQLPGTAPKLLIYDSNKRPSGIPD
RFSGSKSGTSATLDITGLQTGDEADYYCGTWDSSLSAYVFGTGTKVTVL (SEQ ID NO:
40)

Nucleotide sequence of heavy chain variable region:
5'GAGGTGCAGCTGTTGGAGTCTGGGGGAGGCTTGGTACAGCCTGGGGGGTCCCTGA
GACTCTCCTGTGCAGCCTCTGGATTCACCTTTAGCAGCTATGCCATGAACTGGGTCC
GCCAGGCTCCAGGGAAGGGGCTGGAGTGGGTCTCAACTATTAGTGGTAGTGGTGAT
AACACATACTACGCAGACTCCGTGAAGGGCCGGTTCACCATCTCCAGAGACAATTC
CAAGAACACGCTGTATCTGCAAATGAACAGCCTGAGAGCCGAGGACACGGCCGTAT
ATTACTGTGCGAAAAAGTTTGTACTAATGGTGTATGCTATGCTTGACTACTGGGGCC
AGGGAACCCTGGTCACCGTCTCCTCA3' (SEQ ID NO: 116)

Amino acid sequence of heavy chain variable region:
EVQLLESGGGLVQPGGSLRLSCAASGFTFSSYAMNWVRQAPGKGLEWVSTISGSGDNT
YYADSVKGRFTISRDNSKNTLYLQMNSLRAEDTAVYYCAKKFVLMVYAMLDYWGQG
TLVTVSS (SEQ ID NO: 71)

Nucleotide sequence of light chain variable region:
5'GACATCCTGATGACCCAGTCTCCATCCTCCCTGTCTGCATCTGTTGGAGACAGAGT
CACCATCACTTGCCGGGCAAGTCAGAGCATTAGCAGTTATTTAAATTGGTATCAGCA
GAAACCAGGGAAAGCCCCTAAGGTCCTGATCTATGCTGCCTCCAGTTTGCAAAGTGG
GGTCCCATCAAGGTTCAGTGGCAGTGGATCTGGGACAGATTTCACTCTCACCATCAA
CAGTCTGCAACCTGAAGATTTTGCAACTTACTACTGTCAACAGAGTTACAGTTCCCC
CATCACCTTCGGCCAAGGGACACGACTGGAGATTAAA3' (SEQ ID NO: 117)

Amino acid sequence of light chain variable region:
DILMTQSPSSLSASVGDRVTITCRASQSISSYLNWYQQKPGKAPKVLIYAASSLQSGVPSR
FSGSGSGTDFTLTINSLQPEDFATYYCQQSYSSPITFGQGTRLEIK (SEQ ID NO: 9)

Nucleotide sequence of heavy chain variable region:
5'GAGGTGCAGCTGTTGGAGTCTGGGGGAGGCTTGGTACAGCCGGGGGGGGTCCCTGA
GACTCTCCTGTGCAGCCTCTGGATTCACCTTTAGCAGCTATGCCATGAACTGGGTCC
GCCAGGCTCCAGGGAAGGGGCTGGAGTGGGTCTCAACTATTAGTGGTAGTGGTGGT
AACACATACTACGCAGACTCCGTGAAGGGCCGGTTCACCATCTCCAGAGACAATTC
CAAGAACACGCTGTATCTGCAAATGAACAGCCTGAGAGCCGAGGACACGGCCGTAT
ATTACTGTGCGAAAAAGTTTGTACTAATGGTGTATGCTATGCTTGACTACTGGGGCC
AGGGAACCCTGGTCACCGTCTCCTCA3' (SEQ ID NO: 118)

Amino acid sequence of heavy chain variable region:
EVQLLESGGGLVQPGGSLRLSCAASGFTFSSYAMNWVRQAPGKGLEWVSTISGSGGNT
YYADSVKGRFTISRDNSKNTLYLQMNSLRAEDTAVYYCAKKFVLMVYAMLDYWGQG
TLVTVSS (SEQ ID NO: 72)

Nucleotide sequence of light chain variable region:
5'GACATCCAGATGACCCAGTCTCCATCCTCCCTATCTGCATCTGTAGGAGACAGAGT
CACCATCACTTGCCGGGCAAGTCAGAGCATTAGCATCTATTTAAATTGGTATCAGCA
GAAGCCAGGGAAAGCCCCTTACCTCCTGATCTATGCTGCAGCCAGTTTGCAAAGTGG
GGTCCCATCAAGGTTCAGTGGCAGTGGATCTGGGACAGATTTCACTCTCACCATCAG
CAGTCTGCAACCTGAAGATTTTGCAACTTACTACTGTCAACAGAGTTACAGTGCCCC
CATCACCTTCGGCCAAGGGACACGACTGGAGATTAAA3' (SEQ ID NO: 119)

Amino acid sequence of light chain variable region:
DIQMTQSPSSLSASVGDRVTITCRASQSISIYLNWYQQKPGKAPYLLIYAAASLQSGVPSR
FSGSGSGTDFTLTISSLQPEDFATYYCQQSYSAPITFGQGTRLEIK (SEQ ID NO: 10)

Nucleotide sequence of heavy chain variable region:
5'CAGGTTCAGCTGGTGCAGTCTGGAGCTGAGGTGAAGAAGCCTGGGGCCTCACTGA
AGGTCTCCTGCAAGGCTTCTGGTTACAGTTTGACCAGCTATGGTATCAGCTGGGTGC
GACAGGCCCCTGGACAAGGGCTTGAGTGGATGGGATGGATCAGCGCTTACAATGGT
AACACAAACTATGCACAGAAGGTCCAGGGCAGAGTCACCATGACCACAGACACATC
CACGAGCACAGTCTACATGGAGGTGAGGAGTCTGAGATCTGACGACACGGCCGTGT
ATTACTGTGCGAGAGGCTACGGTATGGACGTCTGGGGCCAAGGGACCACGGTCACC
GTCTCCTCA3' (SEQ ID NO: 120)

Amino acid sequence of heavy chain variable region:
QVQLVQSGAEVKKPGASLKVSCKASGYSLTSYGISWVRQAPGQGLEWMGWISAYNGN
TNYAQKVQGRVTMTTDTSTSTVYMEVRSLRSDDTAVYYCARGYGMDVWGQGTTVTV
SS (SEQ ID NO: 54)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGGTTTCTAATCGCTTCTCTGGCTCCAAGTCTGGCAATACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGACCGTCCTA3' (SEQ ID NO:
121)

Amino acid sequence of light chain variable region:
QSALTQPASVSGSPGQSITISCTGTSSDVGGYNSVSWYQQHPGKPPKLMIYEVSNRPSGV
SNRFSGSKSGNTASLTISGLQAEDEADYFCSSYTSTSMVFGGGTKLTVL (SEQ ID NO:
20)

Nucleotide sequence of heavy chain variable region:
5'CAGGTTCAGCTGGTGCAGTCTGGAGCTGAGGTGAAGAGGCCTGGGGCCTCAGTGA
AGGTCTCCTGCAAGGCTTCTGGTTACACCTTGACCAGCTATGGTATCAGCTGGGTGC
GACAGGCCCCTGGACAAGGGCTTGAGTGGATGGGATGGATCAGCGTTTACAATGGT
AACACAAACTATGCACAGAAGGTCCAGGGCAGAGTCACCATGACCACAGACACATC
CACGAGCACAGTCTACATGGAGCTGAGGAGCCTGAGCTCTGACGACACGGCCGTGT
ATTACTGTGCGAGAGGCTACGGTATGGACGTCTGGGGCCAAGGGACCACGGTCACC
GTCTCCTCA3' (SEQ ID NO: 122)

Amino acid sequence of heavy chain variable region:
QVQLVQSGAEVKRPGASVKVSCKASGYTLTSYGISWVRQAPGQGLEWMGWISVYNGN
TNYAQKVQGRVTMTTDTSTSTVYMELRSLSSDDTAVYYCARGYGMDVWGQGTTVTV
SS (SEQ ID NO: 52)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGGTTTCTATTCGCTTCTCTGGCTCCAAGTCTGGCAACACGGCCTCCCTGAC
CATCTCTGGGCTCCAGGCTGAGGACGAGGCTGATTATTTCTGCAGCTCATATACAAG
CACCAGCATGGTCTTCGGCGGAGGGACCAAGCTGACCGTCCTA3' (SEQ ID NO: 123)

Amino acid sequence of light chain variable region:
QSALTQPASVSGSPGQSITISCTGTSSDVGGYNSVSWYQQHPGKPPKLMIYEVSNRPSGV
SIRFSGSKSGNTASLTISGLQAEDEADYFCSSYTSTSMVFGGGTKLTVL (SEQ ID NO:
16)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACCCCTTGACCAGCTATGGTATCAGCTGGGTGC
GACAGGCCCCTGGACAAGGGCTTGAGTGGATGGGATGGATCAGCGCTTACAATGGT
AACACAAACTATGCACAGAAGGTCCAGGGCAGAGTCACCATGACCACAGACACATC
CACGAGCACAGTCTACATGGAGTTGAGGAGCCTGAGATCTGACGACACGGCCGTGT
ATTACTGTGCGAGAGGCTACGGTATGGACGTCTGGGGCCAAGGGACCACGGTCACC
GTCTCCTCA3' (SEQ ID NO: 124)

Amino acid sequence of heavy chain variable region:
QVQLVQSGAEVKKPGASVKVSCKASGYPLTSYGISWVRQAPGQGLEWMGWISAYNGN
TNYAQKVQGRVTMTTDTSTSTVYMELRSLRSDDTAVYYCARGYGMDVWGQGTTVTV
SS (SEQ ID NO: 55)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGGTTTCTAATCGCTTCTCTGGCTCCAAGTCTGGCAATACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGACCGTCCTA3' (SEQ ID NO:
125)

Alternative Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGACCGTCCTA3' (SEQ ID NO:
294)

Amino acid sequence of light chain variable region:
QSALTQPASVSGSPGQSITISCTGTSSDVGGYNSVSWYQQHPGKPPKLMIYEVSNRPSGV
SNRFSGSKSGNTASLTISGLQAEDEADYFCSSYTSTSMVFGGGTKLTVL (SEQ ID NO:
21)

Nucleotide sequence of heavy chain variable region:
5'CAGGTTCAGTTGGTGCAGTCTGGAGCTGAGGTGAAGAAGCCTGGGGCCTCAGTGA
AGGTCTCCTGCAAGGCTTCTGGTTACGCCTTGACCAGCTATGGTATCAGCTGGGTGC
GACAGGCCCCTGGACAAGGGCTTGAGTGGATGGGATGGATCAGCGCTTACAATGGT
AACACAAACTATGCACAGAAGGTCCAGGGCAGAGTCACCATGACCACAGACACATC
CACGAGCACAGTCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCA3' (SEQ ID NO: 126)

Amino acid sequence of heavy chain variable region:
QVQLVQSGAEVKKPGASVKVSCKASGYALTSYGISWVRQAPGQGLEWMGWISAYNGN
TNYAQKVQGRVTMTTDTSTSTVYMELRSLRSDDTAVYYCARGYGMDVWGQGTTVTV
SS (SEQ ID NO: 56)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAACAGTGACGTTGGTGGTTATAACTCTGTCTCCTGGTA
CCAACAGCACCCAGGCAAACCCCCCAAACTCATGATTTATGAGGTCAGTAATCGGC
CCTCAGGGATTTCTAATCGCTTCTCTGGCTCCAAGTCTGGCAACACGGCCTCCCTGA
CCATCTCTGGGCTCCAGGCTGAGGACGAGGCTGATTATTTCTGCAGCTCATATACAA
GCACCAGCATGGTCTTCGGCGGAGGGACCAAGCTGACCGTCCTA3' (SEQ ID NO:
127)

Amino acid sequence of light chain variable region:
QSALTQPASVSGSPGQSITISCTGTNSDVGGYNSVSWYQQHPGKPPKLMIYEVSNRPSGI
SNRFSGSKSGNTASLTISGLQAEDEADYFCSSYTSTSMVFGGGTKLTVL (SEQ ID NO:
22)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACAGCTTTACCAGCTATGGTATCAGCTGGGTGC
GACAGGCCCCTGGACAAGGGCTTGAGTGGATGGGATGGGTCAGCGCTTACAATGGT
AACACAAACTATGCACAGAAGTTCCAGGGCAGAGTCACCATGACCACAGACACATC
CACGAGCACAGCCTACATGGAACTGAGGAGCCTGAGATCTGACGACACGGCCGTGT
ATTACTGTGCGAGAGGCTACGTTATGGACGTCTGGGGCCAAGGGACCACGGTCACC
GTCTCCTCA3' (SEQ ID NO: 128)

Amino acid sequence of heavy chain variable region:
QVQLVQSGAEVKKPGASVKVSCKASGYSFTSYGISWVRQAPGQGLEWMGWVSAYNG
NTNYAQKFQGRVTMTTDTSTSTAYMELRSLRSDDTAVYYCARGYVMDVWGQGTTVT
VSS (SEQ ID NO: 57)

Nucleotide sequence of light chain variable region:
5'CAGTCTGCCCTGACTCAGCCTGCCTCCGTTTCTGGGTCTCCTGGACAGTCGATCAC
CATCTCCTGCACTGGAACCAGCAGTGACGTTGGTGCTTATAACTCTGTCTCCTGGTA
CCAACAGCACCCAGGCAAAGCCCCCAAACGCATGATTTATGAGGTCAGTAATCGGC
CCTCAGGGGGTTTCTAATCGCTTCTCTGGCTCCAAGTCTGGCAACACGGCCTCCCTGA
CCATCTCTGGGCTCCAGGCTGAGGACGAGGCTGATTATTACTGCAGCTCATATACAA
GCACCAACATGGTATTCGGCGGAGGGACCAAGCTGACCGTCCTA3' (SEQ ID NO:
129)

Amino acid sequence of light chain variable region:
QSALTQPASVSGSPGQSITISCTGTSSDVGAYNSVSWYQQHPGKAPKRMIYEVSNRPSGV
SNRFSGSKSGNTASLTISGLQAEDEADYYCSSYTSTNMVFGGGTKLTVL (SEQ ID NO:
24)

Nucleotide sequence of heavy chain variable region:
5'CAGGTACAGTTGCAGCAGTCAGGTCCAGGACTGGTGAAGCCCTCGCAGACCCTCT
CACTCACCTGTGCCATCTCCGGGGACAGTGTCTCTAGCAACAGTGCTGCTTGGAACT
GGATCAGGCAGTCCCCATCGAGAGGCCTTGAGTGGCTGGGAAGGACATACTACAGG
TCCAAGTGGTATAAAAATTATTCAGTATCTGTGAAAAGTCGAATAACCATCAACCCA
GACACATCCAAGAACCAGTTCTCTCTGCAACTGAACTCTGTGACTCCCGGGGACACG
GCTGTGTATTACTGTGCAAGAGGGGGGCCAACTGCTGCTTTTGACTACTGGGGCCAG
GGAACCCTGGTCACCGTCTCCTCA3' (SEQ ID NO: 130)

Amino acid sequence of heavy chain variable region:
QVQLQQSGPGLVKPSQTLSLTCAISGDSVSSNSAAWNWIRQSPSRGLEWLGRTYYRSK
WYKNYSVSVKSRITINPDTSKNQFSLQLNSVTPGDTAVYYCARGGPTAAFDYWGQGTL
VTVSS (SEQ ID NO: 91)

Nucleotide sequence of light chain variable region:
5'CTTTCTGCCCTGACTCAGCCTGCCTCCGTGTCTGGGTCTCCTGGACAGTCGATCAC
CATCTCCTGCACTGGAACCAGCAGTGATGTTGGGAATTATAACCTTGTCTCCTGGTA
CCAACAGTATTCAGGCAAAGCCCCCAAACTCATGATTTATGAGGTCAGTAAGCGGC
CCTCAGGGGTTTCTAATCGCTTCTCTGGCTCCAAGTCTGGCAACACGGCCTCCCTGA
CAATCTCTGGGCTCCAGGCTGAGGACGAGGCTGATTATTACTGCTGCTCATATGCAG
GTAGTAGCACTTTGGTTTTCGGCGGAGGGACCAAGCTGACCGTCCTA3' (SEQ ID
NO: 131)

Amino acid sequence of light chain variable region:
LSALTQPASVSGSPGQSITISCTGTSSDVGNYNLVSWYQQYSGKAPKLMIYEVSKRPSGV
SNRFSGSKSGNTASLTISGLQAEDEADYYCCSYAGSSTLVFGGGTKLTVL (SEQ ID NO:
28)

Nucleotide sequence of heavy chain variable region:
5'GAGGTGCAGTTGGTGGAGTCTGGGGGAGGCTTGGTCCAGCCTGGGGGGTCCCTGA
GACTCTCCTGTGTAGTCTCTGGATTCACCTTTAGTAGCTATTGGATGAGCTGGGTCCG
CCAGGCTCCAGGGAAGGGGCTGGAGTGGGTGGCCAACATAAAGCAAGATGGAAGT
GAGAAATACTATGTGGACTCTGTGAAGGGCCGATTCACCATCTCCAGAGACAACGC
CAAGAACTCACTGTATCTGCAAATGAACAGCCTGAGAGCCGAGGACACGGCTGTAT
ATTACTGTGCGAGAGAGTCAAACTGGGGATTTGCTTTTGATATCTGGGGCCAAGGGA
CAATGGTCACCGTCTCTTCA3' (SEQ ID NO: 132)

Amino acid sequence of heavy chain variable region:
EVQLVESGGGLVQPGGSLRLSCVVSGFTFSSYWMSWVRQAPGKGLEWVANIKQDGSE
KYYVDSVKGRFTISRDNAKNSLYLQMNSLRAEDTAVYYCARESNWGFAFDIWGQGTM
VTVSS (SEQ ID NO: 64)

Nucleotide sequence of light chain variable region:
5'CAGTCTGTGCTGACTCAGCCACCCTCAGCGTCTGGGACCCCCGGGCAGAGGGTCA
CCATCTCTTGTTCTGGAAGCAGCTCCAACATCGGAAGTAAGACTGTAAACTGGTACC
AACAGGTCCCAGGAACGGCCCCCAAACTCCTCATCTATAGGAATAATCAGCGGCCC
TTAGGGGTCCCTGACCGATTCTCTGGCTCCAAGTCTGGCACCTCAGCCTCCCTGGCC
ATCAGTGGGCTCCAGTCTGAGGATGAGGCTGATTATTATTGTGCAGCATGGGATGAC
AGCCTGAATTGGGTGTTCGGCGGAGGGACCAAGCTGACCGTCCTA3' (SEQ ID NO:
133)

Amino acid sequence of light chain variable region:
QSVLTQPPSASGTPGQRVTISCSGSSSNIGSKTVNWYQQVPGTAPKLLIYRNNQRPLGVP
DRFSGSKSGTSASLAISGLQSEDEADYYCAAWDDSLNWVFGGGTKLTVL (SEQ ID NO:
30)

Nucleotide sequence of heavy chain variable region:
5'GAGGTGCAGCTGGTGGAGTCTGGGGGAGGCTTGGTCCAGCCTGGGGGGTCCCTGA
GACTCTCCTGTGCAGCCTCTGGATTCACCTTTAGTCGCTATTGGATGAGCTGGGTCCG
CCAGGCTCCAGGGAAGGGGCTGGAGTGGGTGGCCAACATAAAGCATGATGGAAGTG
AGAAATACTATGTGGACTCTGTGAAGGGCCGATTCACCATTTCCAGAGACAACGCC
AAGAACTCACTGTATCTGCAAATGAACAGCCTGAGAGCCGAGGACACGGCTGTGTA
TTACTGTGCGAGAGAGTCAAACTGGGGATTTGCTTTTGATGTCTGGGGCCACGGGAC
AATGGTCACCGTCTCTTCA3' (SEQ ID NO: 134)

Amino acid sequence of heavy chain variable region:
EVQLVESGGGLVQPGGSLRLSCAASGFTFSRYWMSWVRQAPGKGLEWVANIKHDGSE
KYYVDSVKGRFTISRDNAKNSLYLQMNSLRAEDTAVYYCARESNWGFAFDVWGHGT
MVTVSS (SEQ ID NO: 62)

Nucleotide sequence of light chain variable region:
5'CAGTCTGTGCTGACTCAGCCACCCTCAGCGTCTGGGCCCCCCGGACAGAGGGTCA
CCATCTCTTGTTCTGGAAGCAGCTCCAACATCGGAAGTAATACTGTAAACTGGTACC
AGCAGCTCCCAGGAACGGCCCCCAAACTCCTCATCTATAGTAATAATCGGCGGCCCT
CAGGGGTCCCTGACCGATTCTCTGGCTCCAAGTCTGGCACCTCAGCCTCCCTGGCCA
TCAGTGGGCTCCAGTCTGAGGATGAGGCTGATTATTACTGTGCAGCATGGGATGACA
GCCTGAATTGGGTGTTCGGCGGAGGGACCAAGCTGACCGTCCTA3' (SEQ ID NO:
135)

Amino acid sequence of light chain variable region:
QSVLTQPPSASGPPGQRVTISCSGSSSNIGSNTVNWYQQLPGTAPKLLIYSNNRRPSGVPD
RFSGSKSGTSASLAISGLQSEDEADYYCAAWDDSLNWVFGGGTKLTVL (SEQ ID NO:
31)

Nucleotide sequence of heavy chain variable region:
5'GAGGTGCAGCTGTTGGAGTCTGGGGGAGGCTTGGTACAGCCTGGGGGGTCCCTGA
GACTCTCCTGTGCAGCCTCTGGATTCACCTTTAGCAGCTATGCCATGAGCTGGGTCC
GCCAGGCTCCAGGGAAGGGGCTGGAGTGGGTCTCAACTATTAGTGGTAGTGGTGGT
AGGACATATTACGCAGACTCCGTGAAGGGCCGGTTCACCATCTCCAGAGACAATTC
CAAGAACACGCTGTATCTGCAAATGAACAGCCTGAGAGCCGAGGACACGGCCGTAT
ATTACTGTGCGAAAGAAGTTGGCAGTCCCTTTGACTACTGGGGCCAGGGAACCCTGG
TCACCGTCTCCTCA3' (SEQ ID NO: 136)

Amino acid sequence of heavy chain variable region:
EVQLLESGGGLVQPGGSLRLSCAASGFTFSSYAMSWVRQAPGKGLEWVSTISGSGGRTY
YADSVKGRFTISRDNSKNTLYLQMNSLRAEDTAVYYCAKEVGSPFDYWGQGTLVTVSS
(SEQ ID NO: 69)

Nucleotide sequence of light chain variable region:
5'CAGTCTGTGTTGACGCAGCCGCCCTCAGTGTCTGCGGCCCCAGGACAGAAGGTCA
CCATCTCCTGCTCTGGAAGCAACTCCAACATTGGGAATAATTATGTATCCTGGTACC
AGCAGCTCCCAGGAACAGCCCCCAAACTCCTCATTTATGACAATAATAAGCGACCCT
CAGGGATTCCTGACCGATTCTCTGGCTCCAACTCTGGCACGTCAGCCACCCTGGGCA
TCACCGGACTCCAGACTGGGGACGAGGCCGATTATTACTGCGGAACATGGGATAGC
AGCCTGAGTGCTGTGGTATTCGGCGGAGGGACCAAGCTGACCGTCCTA3' (SEQ ID
NO: 137)

Amino acid sequence of light chain variable region:
QSVLTQPPSVSAAPGQKVTISCSGSNSNIGNNYVSWYQQLPGTAPKLLIYDNNKRPSGIP
DRFSGSNSGTSATLGITGLQTGDEADYYCGTWDSSLSAVVFGGGTKLTVL (SEQ ID
NO: 42)

Nucleotide sequence of heavy chain variable region:
5'CAGGTGCAGCTGGTGGAGTCTGGGGGAGGCGTGGTCCAGCCTGGGAGGTCCCTGA
GACTCTCCTGTGCAGCGTCTGGATTCACCTTCAGTAGCTATGGCATGCACTGGGTCC
GCCAGGCTCCAGGCAAGGGGCTGGAGTGGGTGGCAATTATATGGTATGATGGAAGT
AATAAATACTATGCAGACTCCGTGAAGGGCCGATTCACCATCTCCAGAGACAATTCC
AAGAACACACTGTATCTTCAAATGAACAGCCTGAGAGCCGAGGACACGGCTGTGTA
TTACTGTGCGAGGAGGGGGGGGTCTGGCAGCTCGTCCGGGCGGTATGGACGTCTGGG
GCCAAGGGACCACGGTCACCGTCTCCTCA3' (SEQ ID NO: 138)

Amino acid sequence of heavy chain variable region:
QVQLVESGGGVVQPGRSLRLSCAASGFTFSSYGMHWVRQAPGKGLEWVAIIWYDGSN
KYYADSVKGRFTISRDNSKNTLYLQMNSLRAEDTAVYYCARRGGLAARFGGMDVWG
QGTTVTVSS (SEQ ID NO: 81)

Nucleotide sequence of light chain variable region:
5'TCCTATGAGCTGACTCAGCCACCCTCAGTGTCTGTGTCCCCAGGACAGACAGCCAG
AATCACCTGCTCTGGAGATAAATTGGGGGATAAATATGCTTGCTGGTATCAGCAGAA
ACCAGGCCAGTCCCCTGTGCTGGTCATCTATCAAAATACCAAGTGGCCCTTAGGGAT
CCCTGAGCGATTCTCTGGCTCCAAGTCTGGGAACACAGTCACTCTGACCATCAGCGG
GACCCAGGCTATGGATGAGGCTGACTATTACTGTCAGGCGTGGGACAGCAGCACTG
TGGTATTCGGCGGAGGGACCAAGCTGACCGTCCTA3' (SEQ ID NO: 139)

Amino acid sequence of light chain variable region:
SYELTQPPSVSVSPGQTARITCSGDKLGDKYACWYQQKPGQSPVLVIYQNTKWPLGIPE
RFSGSKSGNTVTLTISGTQAMDEADYYCQAWDSSTVVFGGGTKLTVL (SEQ ID NO:
44)

Alternative Nucleotide sequence of light chain variable region:
5'TCCTATGAGCTGACTCAGCCACCCTCAGTGTCCGTGTCCCCAGGACAGACAGCCA
GAATCACCTGCTCTGGAGATAAATTGGGGGATAAATATGCTTGCTGGTATCAGCAGA
AGCCAGGCCAGTCCCCTGTGCTGGTCATCTATCAAAATACCAAGTGGCCCTTAGGGA
TCCCTGAGCGATTCTCTGGCTCCAAGTCTGGGAACACAGTCACTCTGACCATCAGCG
GGACCCAGGCTATGGATGAGGCTGACTATTACTGTCAGGCGTGGGACAGCAGCACT
GTGGTATTCGGCGGAGGGACCAAGCTGACCGTCCTA3' (SEQ ID NO: 295)

Nucleotide sequence of heavy chain variable region:
5'CAGGTGCAGCTGCAGGAGTCGGGCCCAGGACTGGTGAAGCCTTCACAGACCCTGT
CCCTCACCTGCACTGTCTCTGGTGGCTCCATCAGCAGTAGTGATTACTACTGGAGCT
GGATCCGCCAGCACCCAGGGAAGGGCCTGGAGTGGATTGGGTACATCTATTACAGT
GGGAGCACCTACTACAACCCGTCCCTCAAGAGTCGAATTACCATATCAGTAGACAC
GTCTAAGAACCTGTTCTCCCTGAAGTTGAGCTCTGTGACTGCCGCGGACACGGCCGT
GTATTACTGTGCGAGAGGGGGGGTGACTACGTACTACTACGCTATGGACGTCTGGG
GCCAAGGGACCACGGTCACCGTCTCCTCA3' (SEQ ID NO: 140)

Amino acid sequence of heavy chain variable region:
QVQLQESGPGLVKPSQTLSLTCTVSGGSISSSDYYWSWIRQHPGKGLEWIGYIYYSGSTY
YNPSLKSRITISVDTSKNLFSLKLSSVTAADTAVYYCARGGVTYYYAMDVWGQGTTV
TVSS (SEQ ID NO: 85)

Nucleotide sequence of light chain variable region:
5'GACATACAGATGACCCAGTCTCCATCCTCCCTGTCTGCATCTGTAGGAGACAGAGT
CACCATCACTTGCCGGGCAAGTCAGCGCATTAGCAACTATTTAAGTTGGTATCTGCA
GAAACCAGGGATTGCCCCTAAGCTCCTGATCTATGCTGCATCCAGTTTGCAGAGTGG
GGTCCCATCAAGGTTCAGTGGCAGTGGATCTGGGACAGATTTCACTCTCACCATCAG
CAGTCTGCAATCTGAAGATTTTGCAACTTACTACTGTCAACAGAGTTACAGTACCCC
GCTCATTTTCGGCGGAGGGACCAAGGTGGAGATCAAA3' (SEQ ID NO: 141)

Amino acid sequence of light chain variable region:
DIQMTQSPSSLSASVGDRVTITCRASQRISNYLSWYLQKPGIAPKLLIYAASSLQSGVPSR
FSGSGSGTDFTLTISSLQSEDFATYYCQQSYSTPLIFGGGTKVEIK (SEQ ID NO: 7)

Nucleotide sequence of heavy chain variable region:
5'CAGGTGCAGCTGGTGGAGTCTGGGGGAGGCGTGGTCCAGCCTGGGAGGTCCCTGA
GACTCTCCTGTGCAGCGTCTGGATTCACCTTCAGTAGCTATGGCATGCACTGGGTCC
GCCAGGCTCCAGGCAAGGGGCTGGAGTGGGTGGCAGTTATATGGTATGATGGAAGT
GATAAATACTATGCAGACTCCGTGAAGGGCCGATTCACCATCTCCAGAGACAATTCC
AAGAACACGCTGTATCTGCAAATGAACAGCCTGAGAGCCGAGGACACGGCTGTGTA
TTACTGTGCGAGAGAGACTGGTCCCTTGAAACTCTACTACTACGGTATGGACGTCTG
GGGCCAAGGGACCACGGTCACCGTCTCCTCA3'  (SEQ ID NO: 142)

Amino acid sequence of heavy chain variable region:
QVQLVESGGGVVQPGRSLRLSCAASGFTFSSYGMHWVRQAPGKGLEWVAVIWYDGSD
KYYADSVKGRFTISRDNSKNTLYLQMNSLRAEDTAVYYCARETGPLKLYYYGMDVWG
QGTTVTVSS  (SEQ ID NO: 74)

Nucleotide sequence of light chain variable region:
5'GATATTGTGATGACTCAGTCTCCACTCTCCCTGTCCGTCACCCCTGGAGAGCCGCC
CTCCATCTCCTGCAGGTCTAGTCAGAGCCTCCTGCATAGTAATGGATACAACTTTTTG
AATTGGTACCTGCAGAAGCCAGGGCAGTCTCCACAACTCCTGATCTATTTGGGTTCT
CATCGGGCCTCCGGGGTCCCTGACAGGTTCAGTGGCAGTGGATCAGGCACAGATTTT
ACACTGGAAATCAGCAGAGTGGAGGCTGAGGATGTTGGGGTTTATTACTGCATGCA
AGTTCTACAAACTCCATTCACTTTCGGCCCTGGGACCAAAGTGGATATCAAA3'
(SEQ ID NO: 143)

Amino acid sequence of light chain variable region:
DIVMTQSPLSLSVTPGEPPSISCRSSQSLLHSNGYNFLNWYLQKPGQSPQLLIYLGSHRAS
GVPDRFSGSGSGTDFTLEISRVEAEDVGVYYCMQVLQTPFTFGPGTKVDIK  (SEQ ID
NO: 5 )

Nucleotide sequence of heavy chain variable region:
5'GAGGTGCAGCTGGTGGAGTCTGGGGGAGGCTTGGTCCAGCCTGGGGGGTCCCTGA
GACTCTCCTGTGCAGCCTCTGGACTCACCTTTAGTAACTTTTGGATGAGCTGGGTCCG
CCAGGCTCCAGGGAAGGGGCTGGAGTGGGTGGCCAACATAAAGCAAGATGGAAGT
GAGAAATACTATGTGGACTCTGTGAAGGGCCGATTCACCATCTCCAGAGACAACGC
CAAGAATTCACTGTATCTGCAAATGAACAGCCTGAGAGCCGAGGACACGGCTGTGT
ATTCCTGTACGAGAGAGTCAAACTGGGGATTTGCTTTTGATATCTGGGGCCAAGGGA
CAATGGTCACCGTCTCTTCA3' (SEQ ID NO: 144)

Amino acid sequence of heavy chain variable region:
EVQLVESGGGLVQPGGSLRLSCAASGLTFSNFWMSWVRQAPGKGLEWVANIKQDGSE
KYYVDSVKGRFTISRDNAKNSLYLQMNSLRAEDTAVYSCTRESNWGFAPDIWGQGTM
VTVSS (SEQ ID NO: 65)

Nucleotide sequence of light chain variable region:
5'CAGTCTGTGCTGACTCAGCCACCCTCAGCGTCTGGGACCCCCGGGCAGAGGGTCA
CCATCTCTTGTTCTGGAAGCAGCTCCAACATCGGAAGTAAAACTGTAAACTGGTACC
AGCAGTTCCCAGGAACGGCCCCCAAACTCCTCATCTATAGTAATAATCGGCGGCCCT
CAGGGGTCCCTGACCGATTCTCTGGCTCCAAGTCTGGCACCTCAGCCTCCCTGGCCA
TCAGTGGGCTCCAGTCTGAGGATGAGGCTGATTATTACTGTGCAGCATGGGATGACA
GCCTGAATTGGGTGTTCGGCGCAGGGACCAAGCTGACCGTCCTA3' (SEQ ID NO:
145)

Amino acid sequence of light chain variable region:
QSVLTQPPSASGTPGQRVTISCSGSSSNIGSKTVNWYQQFPGTAPKLLIYSNNRRPSGVPD
RFSGSKSGTSASLAISGLQSEDEADYYCAAWDDSLNWVFGAGTKLTVL (SEQ ID NO:
33)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACACCTTTACCAGCTATGGTATCAGCTGGGTGC
GACAGGCCCCTGGACAAGGGCTTGAGTGGATGGGATGGATCAGCACTTACAATGGT
AACACAAACTATGCACAGAAGGTCCAGGGCAGAGTCACCATGACCACAGACACATC
CACGAGCACAGCCTACATGGAGCTGAGGAGCCTGAGATCTGACGACACGGCCGTTT
ATTACTGTGCGAGAGGGTATACTCGGGACTACTGGGGCCAGGGAACCCTGGTCACC
GTCTCCTCA3'   (SEQ ID NO: 146)

Amino acid sequence of heavy chain variable region:
QVQLVQSGAEVKKPGASVKVSCKASGYTFTSYGISWVRQAPGQGLEWMGWISTYNGN
TNYAQKVQGRVTMTTDTSTSTAYMELRSLRSDDTAVYYCARGYTRDYWGQGTLVTVS
S (SEQ ID NO: 60)

Nucleotide sequence of light chain variable region:
5'CAGCCTGTGCTGACTCAGCCACTTTTTGCATCAGCCTCCCTGGGAGCCTCGGTCAC
ACTCACCTGCACCCTGAGCAGCGGCTACAGTAGTTATGAAGTGGACTGGTATCAGCA
GAGACCAGGGAAGGGCCCCCGGTTTGTCATGCGAGTGGACACTGGTGGGATTGTGG
GATCCAAGGGGGAAGGCATCCCTGATCGCTTCTCAGTTTTGGGCTCAGGCCTGAATC
GGTATCTGACCATCAAGAACATCCAGGAAGAGGATGAGAGTGACTACCACTGTGGG
GCAGACCATGGCAGTGGGACCAACTTCGTGGTGGTATTCGGCGGAGGGACCAAGCT
GACCGTCCTA3'   (SEQ ID NO: 147)

Amino acid sequence of light chain variable region:
QPVLTQPLFASASLGASVTLTCTLSSGYSSYEVDWYQQRPGKGPRFVMRVDTGGIVGSK
GEGIPDRFSVLGSGLNRYLTIKNIQEEDESDYHCGADHGSGTNFVVVFGGGTKLTVL
(SEQ ID NO: 46)

Nucleotide sequence of heavy chain variable region:
5'CAGGTGCAGCTACAGCAGTGGGGCGCAGGACTGTTGAAGCCTTCGGAGACCCTGT
CCCTCACCTGCGCTGTCTATGGTGGGTCCTTCAGTGCGTACTACTGGAACTGGATCC
GCCAGCCCCCAGGGAAGGGGCTGGAGTGGATTGGGGAAATCAATCATAGTGGAAGA
ACCGACTACAACCCGTCCCTCAAGAGTCGAGTCACCATATCAGTAGACACGTCCAA
GAAGCAGTTCTCCCTGAAGCTGAACTCTGTGACCGCCGCGGACACGGCTGTGTATTA
CTGTGCGAGAGGGCAGCTCGTCCCCTTTGACTACTGGGGCCAGGGAACCCTGGTCAC
·CGTCTCTTCA3'   (SEQ ID NO: 148)

Amino acid sequence of heavy chain variable region:
QVQLQQWGAGLLKPSETLSLTCAVYGGSFSAYYWNWIRQPPGKGLEWIGEINHSGRTD
YNPSLKSRVTISVDTSKKQFSLKLNSVTAADTAVYYCARGQLVPFDYWGQGTLVTVSS
(SEQ ID NO: 89)

Nucleotide sequence of light chain variable region:
5'CAGTCTGTGCTGACTCAGCCACCCTCAGCGTCTGGGACCCCCGGGCAGAGGGTCA
CCATCTCTTGTTCTGGAAGCAGCTCCAACATCGGAAGTAATACTGTAAATTGGTATC
AGCAACTCCCAGGAACGGCCCCCAAACTCCTCATCTATAGTAATAATCAGCGGCCCT
CAGGGGTCCCTGACCGATTCTCTGGCTCCAAGTCTGGCACCTCAGCCTCCCTGGCCA
TCAGTGGGCTCCAGTCTGAGGATGAGGCTGATTATTACTGTGCAGTATGGGATGACA
GCCTGAATGGTTGGGTGTTCGGCGGAGGGACCAAGCTGACCGTCCTA3'   (SEQ ID
NO: 149)

Amino acid sequence of light chain variable region:
QSVLTQPPSASGTPGQRVTISCSGSSSNIGSNTVNWYQQLPGTAPKLLIYSNNQRPSGVPD
RFSGSKSGTSASLAISGLQSEDEADYYCAVWDDSLNGWVFGGGTKLTVL (SEQ ID NO:
32)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACACCTTTCCCAGCTATGGTATCAGCTGGGTGC
GACAGGCCCCTGGACAAGGGCTTGAGTGGATGGGATGGATCAGCGCTTACAATGGT
AACACAAACTATGCAGAGAAGCTCCAGGGCAGAGTCACCATGACCACAGACACATC
CACGAGCACAGCCTACATGGAGGTGAGGAGCCTGAGATCTGACGACACGGCCGTGT
TTTACTGTGCGAGAGGCTACGTTATGGACGTCTGGGGCCAAGGGACCACGGTCACC
GTCTCCTCT3'   (SEQ ID NO: 150)

Amino acid sequence of heavy chain variable region:
QVQLVQSGAEVKKPGASVKVSCKASGYTFPSYGISWVRQAPGQGLEWMGWISAYNGN
TNYAEKLQGRVTMTTDTSTSTAYMEVRSLRSDDTAVFYCARGYVMDVWGQGTTVTVS
S (SEQ ID NO: 58)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTCGTTATAATTCTGTCTCCTGGTAC
CAACACCACCCAGGCAAAGCCCCCAAAGTCATGATTTATGAGGTCAGTAATCGGCC
CTCAGGGGTTTCTACTCGCTTCTCTGGCTCCAAGTCTGGCAACACGGCCTCCCTGAC
CATCTCTGGGCTCCAGGCTGAGGACGAGGCTGATTATTACTGCAGCTCATATACAAG
CAGCAGCGTTGTATTCGGCGGAGGGACCAAACTGACCGTCCTA3'   (SEQ ID NO:
151)

Amino acid sequence of light chain variable region:
QSALTQPASVSGSPGQSITISCTGTSSDVGRYNSVSWYQHHPGKAPKVMIYEVSNRPSGV
STRFSGSKSGNTASLTISGLQAEDEADYYCSSYTSSSVVFGGGTKLTVL (SEQ ID NO:
15)

Nucleotide sequence of heavy chain variable region:
5'CAGGTTCAGCTGGTGCAGTCTGGAGCTGAGGTGAAGAAGCCTGGGGCCTCAGTGA
AGGTCTCCTGCAAGGCTTCTGGTTACACCTTAACCAGCTATGGTATCAGCTGGGTGC
GACAGGCCCCTGGACAAGGGCTTGAGTGGATGGGATGGGTCAGTTTTTATAATGGT
AACACAAACTATGCACAGAAGCTCCAGGGCAGAGGCACCATGACCACAGACCCATC
CACGAGCACAGCCTACATGGAGCTGAGGAGCCTGAGATCTGACGACACGGCCGTGT
ATTACTGTGCGAGAGGCTACGGTATGGACGTCTGGGGCCAAGGGACCACGGTCACC
GTCTCCTCT3' (SEQ ID NO: 94)

Amino acid sequence of heavy chain variable region:
QVQLVQSGAEVKKPGASVKVSCKASGYTLTSYGISWVRQAPGQGLEWMGWVSFYNG
NTNYAQKLQGRGTMTTDPSTSTAYMELRSLRSDDTAVYYCARGYGMDVWGQGTTVT
VSS (SEQ ID NO: 49)

Nucleotide sequence of light chain variable region:
5'CAGTCTGCCCTGACTCAGCCTGCCTCCGTGTCTGGGTCTCCTGGACAGTCGATCAC
CATCTCCTGCACTGGAACCAGCAGTGACGTTGGTGGTTATAACTCTGTCTCCTGGTA
CCAACAGCACCCAGGCAAAGCCCCCAAACTCATGATTTATGAGGTCAGTAATCGGC
CCTCAGGGGTTTCTAATCGCTTCTCTGGCTCCAAGTCTGGCAACACGGCCTCCCTGA
CCATCTCTGGGCTCCAGGCTGAGGACGAGGCTGATTATTACTGCAATTCATATACAA
GCACCAGCATGGTATTCGGCGGAGGGACCAAGCTGACCGTCCTA3' (SEQ ID NO:
296)

Amino acid sequence of light chain variable region:
QSALTQPASVSGSPGQSITISCTGTSSDVGGYNSVSWYQQHPGKAPKLMIYEVSNRPSGV
SNRFSGSKSGNTASLTISGLQAEDEADYYCNSYTSTSMVFGGGTKLTVL (SEQ ID NO:
23)

FIG. 3JJ

Constant Domains

Human IgG2:

ASTKGPSVFPLAPCSRSTSESTAALGCLVKDYFPEPVTVSWNSGALTSGVHTFPAVLQSSGLYSLSSVVT
VPSSNFGTQTYTCNVDHKPSNTKVDKTVERKCCVECPPCPAPPVAGPSVFLFPPKPKDTLMISRTPEVTC
VVVDVSHEDPEVQFNWYVDGVEVHNAKTKPREEQFNSTFRVVSVLTVVHQDWLNGKEYKCKVSNKGLP
APIEKTISKTKGQPREPQVYTLPPSREEMTKNQVSLTCLVKGFYPSDIAVEWESNGQPENNYKTTPPMLD
SDGSFFLYSKLTVDKSRWQQGNVFSCSVMHEALHNHYTQKSLSLSPGK (SEQ ID NO: 154)

Human IgG4:

ASTKGPSVFPLAPCSRSTSESTAALGCLVKDYFPEPVTVSWNSGALTSGVHTFPAVLQSSGLYSLSSVVT
VPSSSLGTKTYTCNVDHKPSNTKVDKRVESKYGPPCPSCPAPEFLGGPSVFLFPPKPKDTLMISRTPEVT
CVVVDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLGK (SEQ ID NO: 155)

Human lambda:

QPKAAPSVTLFPPSSEELQANKATLVCLISDFYPGAVTVAWKADSSPVKAGVETTTPSKQSNNKYAASSY
LSLTPEQWKSHRSYSCQVTHEGSTVEKTVAPTECS (SEQ ID NO: 156)

Human kappa:

TVAAPSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO: 157)

Nucleotide sequence of heavy chain variable region:

5'CAGGTGCAGGTGGTGCAGTCTGGGGCTGAGGTGAAGAAGCCTGGGGCCTC
AGTGAAGGTCTCCTGCAAGGCTTCTGGATACACCTTCACCGGCTACTATATAC
ACTGGGTGCGACAGGCCCCTGGACAAGGGCTTGAGTGGATGGGATGGATCAA
CCCTCACAGTGGTGGCGCAAACTATGCACAGAAGTTTCAGGGCAGGGTCACC
ATGACCAGGGACACGTCCATCAGCACAGCCTACATGGAGCTGAGCAGGCTGA
GATCTGACGACACGGCCGTGTATTACTGTGCGAGAGGCAACTGGAACTACGA
CTACTACGGTATGGACGTCTGGGGCCAAGGGACCACGGTCACCGTCTCCTCA
3` (SEQ ID NO:418)

Amino acid sequence of heavy chain variable region:

QVQVVQSGAEVKKPGASVKVSCKASGYTFTGYYIHWVRQAPGQGLEWMGWIN
PHSGGANYAQKFQGRVTMTRDTSISTAYMELSRLRSDDTAVYYCARGNWNYD
YYGMDVWGQGTTVTVSS (SEQ ID NO:419)

Nucleotide sequence of light chain variable region:

5'GACATCCAGATGACCCAGTCTCCATCCTCCCTGTCTGCATCTGTAGGAGAC
AGAGTCACCATCACTTGCCGGGCGAGTCAGGACATTAGCAATTATTTAGCCT
GGTATCAGCAGAAACCAGGGAAAGTTCCTAAGCTCCTGATCTATGCTGCATC
CACTTTGCAATCAGGGGTCCCATCTCGGTTCAGTGGCAGTGGATCTGGGACA
GATTTCACTCTCACCATCAGCAGCCTACAGCCTGAAGATGTTGCAACTTATTT
CTGTCAAAGGTATCAGATTGCCCCATTCACTTTCGGCCCTGGGACCAAGGTGG
ATATCAAA3' (SEQ ID NO:420)

Amino acid sequence of light chain variable region:

DIQMTQSPSSLSASVGDRVTITCRASQDISNYLAWYQQKPGKVPKLLIYAASTLQ
SGVPSRFSGSGSGTDFTLTISSLQPEDVATYFCQRYQIAPFTFGPGTKVDIK (SEQ
ID NO:421)

Nucleotide sequence of heavy chain variable region:

5'CAGGTGCAGCTGGTGGAGTCTGGGGGAGGCGTGGTCCAGCCTGGGAGGTC
CCTGAGACTCTCCTGTGCAGCGTCTGGATTCACCTTCAGTAGCTATGGCATGC
ACTGGGTCCGCCAGGCTCCAGGCAAGGGGCTGGAGTGGGTGGCAGTTATCTG
GTATGATGGAAGTACTAAATACTATGCAGACTCCGTGAAGGGCCGATCCACC
ATCTCCAGAGACAATTCCAAGAACACGCTGTATCTGCAAATGAACAGCCTGA
GAGCCGAGGACACGGCTGTGTATTACTGTGCGAGGTCAGTGGCTGGTTACCA
CTACTACTACGGTATGGACGTCTGGGGCCAAGGGACCACGGTCACCGTCTCC
TCA3' (SEQ ID NO:422)

Amino acid sequence of heavy chain variable region:

QVQLVESGGGVVQPGRSLRLSCAASGFTFSSYGMHWVRQAPGKGLEWVAVIW
YDGSTKYYADSVKGRSTISRDNSKNTLYLQMNSLRAEDTAVYYCARSVAGYHY
YYGMDVWGQGTTVTVSS (SEQ ID NO: 423)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAGGCTATTATGCAACCTGGT
ACCAGCAGAAGCCAAGACAGGCCCCTGTACTTGTCATCTATGGTAAAAACTA
CCGGCCCTCAGGGATCCCAGACCGATTCTCTGGCTCCACCTCAGGAAACACA
GCTTCCTTGACCATCACTGGGGCTCAGGCGGAAGATGAGGCTGACTATTACT
GTAACTCCCGGGACAGCATTGGTAACCATCTGGTGTTCGGCGGAGGGACCAA
GCTGACCGTCCTA3' (SEQ ID NO:424)

Amino acid sequence of light chain variable region:

SSELTQDPAVSVALGQTVRITCQGDSLRGYYATWYQQKPRQAPVLVIYGKNYRP
SGIPDRFSGSTSGNTASLTITGAQAEDEADYYCNSRDSIGNHLVFGGGTKLTVL
(SEQ ID NO:425)

Nucleotide sequence of heavy chain variable region:

5'CAGGTGCAGCTGGTGGAGTCTGGGGGAGGCGTGGTCCAGCCTGGGAGGTC
CCTGAGACTCTCCTGTGCAGCGTCTGGATTCACCTTCAGTAGCTATGGCTTGC
ACTGGGTCCGCCAGGCTCCAGGCAAGGGGCTGGAGTGGGTGGCAGTTATATG
GTTAGATGGAAGTAATAAATACTATGCAGACTCCGTGAAGGGCCGATCCACC
ATCTCCAGAGACAATTCCAAGAACACGCTGTATCTGCAAATGAACAGCCTGA
GAGCCGAGGACACGGCTGTGTATTACTGTGCGAGGTCAGTGGCTGGTTACCA
CTACTACTACGGTATGGACGTCTGGGGCCAAGGGACCACGGTCACCGTCTCC
TCA3' (SEQ ID NO:426)

Amino acid sequence of heavy chain variable region:

QVQLVESGGGVVQPGRSLRLSCAASGFTFSSYGLHWVRQAPGKGLEWVAVIWL
DGSNKYYADSVKGRSTISRDNSKNTLYLQMNSLRAEDTAVYYCARSVAGYHYY
YGMDVWGQGTTVTVSS (SEQ ID NO:427)

Nucleotide sequence of light chain variable region:
5'TCTTCTGAGCTGACTCAGGACCCTGCTGTGTCTGTGGCCTTGGGACAGACA
GTCAGGATCACATGCCAAGGAGACAGCCTCAGAAGTTATTATGGAAGCTGGT
ACCAGCAGAAGCCAAGACAGGCCCCTGTACTTGTCATCTTTGGTAAAAACAA
CCGGCCCTCAGGGATCCCAGACCGATTCTCTGGCTCCACCTCAGGAAACACA
GCTTCCTTGACCATCACTGGGGCTCAGGCGGAAGATGAGGCTGACTATTACT
GTAACTCACGGGACATCATTGGTGACCATCTGCTGTTCGGCGGAGGGACCAA
GCTGACCGTCCTA3' (SEQ ID NO:428)

Amino acid sequence of light chain variable region:

SSELTQDPAVSVALGQTVRITCQGDSLRSYYGSWYQQKPRQAPVLVIFGKNNRP
SGIPDRFSGSTSGNTASLTITGAQAEDEADYYCNSRDIIGDHLLFGGGTKLTVL
(SEQ ID NO:429)

Nucleotide sequence of heavy chain variable region:

5'CAGGTGCAGCTGGTGGAGTCTGGGGGAGGCGTGGTCCAGTCTGGGAGGTCC
CTGAGACTCTCCTGTGCAGCGTCTGGATTCACCTTCAGGAACTATGGCATGCA
CTGGGTCCGCCAGGCTCCAGGCAAGGGGCTGGAGTGGGTGGCAGTTATATGG
TTTGATGGAAGTAATAAATACTATGCAGACTCCGTGAAGGGCCGATCCACCA
TCTCCAGAGACAATTCCAAGAACACGCTGTATCTGCTAATGAACAGCCTGAG
AGCCGAGGACACGGCTGTGTATTACTGTGCGAGGTCAGTGGCTGGTTACCAC
TACTACTACGGTATGGACGTCTGGGGCCAAGGGACCACGGTCACCGTCTCCT
CA3'(SEQ ID NO:430)

Amino acid sequence of heavy chain variable region:

QVQLVESGGGVVQSGRSLRLSCAASGFTFRNYGMHWVRQAPGKGLEWVAVIW
FDGSNKYYADSVKGRSTISRDNSKNTLYLLMNSLRAEDTAVYYCARSVAGYHY
YYGMDVWGQGTTVTVSS (SEQ ID NO:431)

Nucleotide sequence of light chain variable region:

5'TCTTCTGAGCTGACTCAGGACCCTGCTGTGTCTGTGGCCTTGGGACAGACA
GTCAGGATCACATGCCAGGGAGACAGCCTCAGAAGCTATTATGCAAGCTGGT
ACCAGCAGAAGCCAAGACAGGCCCCTGTACTTGTCATCTATGGTAAAAACAA
CCGGCCCTCAGGGATCCCAGACCGAATCTCTGGCTCCACCTCAGGAAACACA
GCTTCCTTGACCATCACTGGGGCTCAGGCGGAAGATGAGGCTGACTATTACT
GTAAATCCCGGGACATCATTGGTGACCATCTGGTGTTCGGCGGAGGGACCAA
ACTGACCGTCCTA3' (SEQ ID NO:432)

Amino acid sequence of light chain variable region:

SSELTQDPAVSVALGQTVRITCQGDSLRSYYASWYQQKPRQAPVLVIYGKNNRP
SGIPDRISGSTSGNTASLTITGAQAEDEADYYCKSRDIIGDHLVFGGGTKLTVL
(SEQ ID NO:433)

Nucleotide sequence of heavy chain variable region:

5'CAGGTGCAGCTGGTGGAGTCTGGGGGAGGCGTGGTCCAGCCTGGGAGGTC
CCTGAGACTCTCCTGTGCAGCGTCTGGATTCACCTTCAGTAGCTATGGCATGC
ACTGGGTCCGCCAGGCTCCAGGCAAGGGGCTGGAGTGGGTGGCAGTTATATG
GTATGATGGAAGTAATAAATACTATGCAGACTCCGTGAAGGGCCGATTCACC
ATCTCCAGAGACAATTCCAAGAACACGCTGTATCTGCAAATGAACAGCCTGA
GAGCCGAGGACACGGCTGTGTATTACTGTGTGAGAGATCGGGGACTGGACTG
GGGCCAGGGAACCCTGGTCACCGTCTCCTCA3' (SEQ ID NO:434)

Amino acid sequence of heavy chain variable region:

QVQLVESGGGVVQPGRSLRLSCAASGFTFSSYGMHWVRQAPGKGLEWVAVIW
YDGSNKYYADSVKGRFTISRDNSKNTLYLQMNSLRAEDTAVYYCVRDRGLDW
GQGTLVTVSS (SEQ ID NO:435)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAGGCTATTATGCAAGCTGGT
ACCAGCAGAAGCCAAGACAGGCCCCTGTACTTGTCATCTATGGTAAAAACAA
CCGGCCCTCAGGGATCCCAGACCGATTCTCTGGCTCCACCTCAGGAAACACA
GCTTCCTTGACCATCACTGGGGCTCAGGCGGAAGATGAGGCTGACTATTACT
GTAAGTCCCGGGACAGCAGTGGTGACCATCTGGTGTTCGGCGGAGGGACCAA
GCTGACCGTCCTA3' (SEQ ID NO:436)

Amino acid sequence of light chain variable region:

SSELTQDPAVSVALGQTVRITCQGDSLRGYYASWYQQKPRQAPVLVIYGKNNRP
SGIPDRFSGSTSGNTASLTITGAQAEDEADYYCKSRDSSGDHLVFGGGTKLTVL
(SEQ ID NO:437)

Nucleotide sequence of heavy chain variable region:

5'CAGGTGCAGGTGGTGGAGTCTGGGGGAGGCGTGGTCCAGCCTGGGGGGTC
CCTGAGACTCTCCTGTGCAGCGTCTGGATTCACCTTCAGTAACTATGGCATGC
ACTGGGTCCGCCAGGCTCCAGGCAAGGGGCTGGAGTGGGTGGCAGTTATTTG
GTATGATGGAAGTAGTAAATACTATGCAGACTCCGTGAAGGGCCGATCCACC
ATCTCCAGAGACAATTCCAAGAACACGGTGTATCTGCAAATGAACAGCCTGA
GAGCCGAGGACACGGCTGTGTATTACTGTGCGAGGTCAGTGGCTGGTTACCA
CTACTACTACGGTATGGACGTCTGGGGCCAAGGGACCACGGTCACCGTCTCC
TCA3'(SEQ ID NO:438)

Amino acid sequence of heavy chain variable region:

QVQVVESGGGVVQPGGSLRLSCAASGFTFSNYGMHWVRQAPGKGLEWVAVIW
YDGSSKYYADSVKGRSTISRDNSKNTVYLQMNSLRAEDTAVYYCARSVAGYHY
YYGMDVWGQGTTVTVSS (SEQ ID NO:439)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAGGCTATTATGCAAGCTGGT
ACCAGCAGAAGCCAAGACAGGCCCCTGTACTTGTCATCTATGGTAAAAACAA
CCGGCCCTCAGGGATCCCAGACCGATTCTCTGGCTCCACCTCAGGAAACACA
GCTTCCTTGACCATCACTGGGGCTCAGGCGGAAGATGAGGCTGACTATTACT
GTAAGTCCCGGGACAGCAGTGGTGACCATCTGGTGTTCGGCGGAGGGACCAA
GCTGACCGTCCTA3' (SEQ ID NO:440)

Amino acid sequence of light chain variable region:

SSELTQDPAVSVALGQTVRITCQGDSLRGYYASWYQQKPRQAPVLVIYGKNNRP
SGIPDRFSGSTSGNTASLTITGAQAEDEADYYCKSRDSSGDHLVFGGGTKLTVL
(SEQ ID NO:441)

Nucleotide sequence of heavy chain variable region:

5'CAGGTGCAGCTGGTGGAGTCTGGGGGAGGCGTGGTCCAGCCTGGGAGGTC
CCTGAGTCTCTCCTGTGCAGCGTCTGGATTCACCTTCAGTAGCTATGGCATGC
ACTGGGTCCGCCAGGCTCCAGGCAAGGGGCTGGAGTGGGTGGCAGTTATATG
GTATGATGGAAGTTATAAAGACTATGCAGACTCCGTGAAGGGCCGATCCACC
ATCTCCAGAGACAACTCCAAGAACACGCTGTATCTGCAAATGAACAGCCTGA
GAGCCGAGGACACGGCTGTGTATTATTGTGCGAGGTCAGTGGCTGGTTACCA
CTACTACTACGGTATGGACGTCTGGGGCCAAGGGACCACGGTCACCGTCTCC
TCA3' (SEQ ID NO:442)

Amino acid sequence of heavy chain variable region:

QVQLVESGGGVVQPGRSLSLSCAASGFTFSSYGMHWVRQAPGKGLEWVAVIWY
DGSYKDYADSVKGRSTISRDNSKNTLYLQMNSLRAEDTAVYYCARSVAGYHYY
YGMDVWGQGTTVTVSS (SEQ ID NO:443)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAACCTATTATGCAAGCTGGT
ACCAGCAGAAGCCAAGACAGGCCCCTATTCTTGTCATCTATGGTAAAAACAA
CCGGCCCTCAGGGATCCCAGACCGATTCTCTGGCTCCACCTCAGGAATCACA
GCTTCCTTGACCATCACTGGGGCTCAGGCGGAAGATGAGGCTGACTATTACT
GTAAATCCCGGGACATCATTGGTAACCATCTGCTGTTCGGCGGAGGGACTAA
GCTGACCGTCCTA3' (SEQ ID NO:444)

Amino acid sequence of light chain variable region:

SSELTQDPAVSVALGQTVRITCQGDSLRTYYASWYQQKPRQAPILVIYGKNNRPS
GIPDRFSGSTSGITASLTITGAQAEDEADYYCKSRDIIGNHLLFGGGTKLTVL (SEQ
ID NO:445)

<div align="center">

FIG. 3RR

</div>

20A5.2

Nucleotide sequence of heavy chain variable region:

5'CAGGTGCAGCTGGTGGCGTCTGGGGGAGGCGTGGTCCAGCCTGGGAGGTCC
CTGAGACTCTCCTGTGCAGCGTCTGGATTCACCCTCAGTAGCTATGGCATGCA
CTGGGTCCGCCAGGCTCCAGGCCAGGGGCTGGAGTGGGTGGCAGTCATATGG
TATGATGGAAGTAACAAATACTATGCAGCCTCCGTGAAGGGCCGATTCACCA
TCTCCAGAGACAATTCCAAGAACACGCTGTATCTGCAAATGAACAGTCTGAG
AGCCGAGGACACGGCTGTGTATTACTGTGCGAGAGGGGGTGGTTCGGGGAGT
CATCGCTACTACTACTACGGTATGGACGTCTGGGGCCAAGGGACCACGGTCA
CCGTCTCCTCA3' (SEQ ID NO:446)

Amino acid sequence of heavy chain variable region:

QVQLVASGGGVVQPGRSLRLSCAASGFTLSSYGMHWVRQAPGQGLEWVAVIW
YDGSNKYYAASVKGRFTISRDNSKNTLYLQMNSLRAEDTAVYYCARGGGSGSH
RYYYYGMDVWGQGTTVTVSS (SEQ ID NO:447)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAACCTATTATGCAAGCTGGT
ACCAGCAGAAGCCAAGACAGGCCCCTATTCTTGTCATCTATGGTAAAAACAA
CCGGCCCTCAGGGATCCCAGACCGATTCTCTGGCTCCACCTCAGGAATCACA
GCTTCCTTGACCATCACTGGGGCTCAGGCGGAAGATGAGGCTGACTATTACT
GTAAATCCCGGGACATCATTGGTAACCATCTGCTGTTCGGCGGAGGGACTAA
GCTGACCGTCCTA3' (SEQ ID NO:448)

Amino acid sequence of light chain variable region:

SSELTQDPAVSVALGQTVRITCQGDSLRTYYASWYQQKPRQAPILVIYGKNNRPS
GIPDRFSGSTSGITASLTITGAQAEDEADYYCKSRDIIGNHLLFGGGTKLTVL (SEQ
ID NO:449)

FIG. 3SS

28E5.1 – version1 (v1)

Nucleotide sequence of heavy chain variable region:

5'CAGGTGCAAGTGGTGGAGTCTGGGGGAGGCGTGGTCCAGCCTGGGAGGTC
CCTGAGACTCTCCTGTGCAGCGTCTGGATTCACCTTCAGTAACTATGGCATGC
ACTGGGTCCGCCAGGCTCCAGGCAAGGGGCTGGAGTGGGTGGCAGTTATATG
GTATGATGGAGGTAATAAATACTATGCAGACTCCGTGAAGGGCCGATCCATC
ATCTCCAGAGACAATTCCAAGAGCACGCTGTATCTGCAAATGAACAGCCTGA
GAGCCGAGGACACGGCTGTTTATTATTGTGCGAGGTCAGTGGCTGGTTACCA
TTATTACTACGGTATGGACGTCTGGGGCCAAGGGACCACGGTCACCGTCGCC
TCA3'  (SEQ ID NO:450)

Amino acid sequence of heavy chain variable region:

QVQVVESGGGVVQPGRSLRLSCAASGFTFSNYGMHWVRQAPGKGLEWVAVIW
YDGGNKYYADSVKGRSIISRDNSKSTLYLQMNSLRAEDTAVYYCARSVAGYHY
YYGMDVWGQGTTVIVAS (SEQ ID NO:451)

Nucleotide sequence of light chain variable region:

5'CAGTCTGCCCTGACTCAGCCTGCCTCCGTGTCTGGGTCTCCTGGACAGTCGA
TCACCATCTCCTGCACTGGAACCAGCAGTGACGTTGGTGGTTATAACTCTGTC
TCCTGGTACCAACAGCACCCAGGCAAACCCCCCAAACTCATGATTTATGAGG
TCAGTAATCGGCCCTCAGGGATTTCTAATCGCTTCTCTGGCTCCAAGTCTGGC
AACACGGCCTCCCTGACCATCTCTGGGCTCCAGGCTGAGGACGAGGCTGATT
ATTTCTGCAGCTCATATACAAGCACCAGCATGGTCTTCGGCGGAGGGACCAA
GCTGGCCGTCCTA3' (SEQ ID NO:452)

Amino acid sequence of light chain variable region:

QSALTQPASVSGSPGQSITISCTGTSSDVGGYNSVSWYQQHPGKPPKLMIYEVSN
RPSGISNRFSGSKSGNTASLTISGLQAEDEADYFCSSYTSTSMVFGGGTKLAVL
(SEQ ID NO:453)

FIG. 3TT

20E5.1 – version2 (v2)

Nucleotide sequence of heavy chain variable region:

5'CAGGTGCAAGTGGTGGAGTCTGGGGGAGGCGTGGTCCAGCCTGGGAGGTC
CCTGAGACTCTCCTGTGCAGCGTCTGGATTCACCTTCAGTAACTATGGCATGC
ACTGGGTCCGCCAGGCTCCAGGCAAGGGGCTGGAGTGGGTGGCAGTTATATG
GTATGATGGAGGTAATAAATACTATGCAGACTCCGTGAAGGGCCGATCCATC
ATCTCCAGAGACAATTCCAAGAGCACGCTGTATCTGCAAATGAACAGCCTGA
GAGCCGAGGACACGGCTGTTTATTATTGTGCGAGGTCAGTGGCTGGTTACCA
TTATTACTACGGTATGGACGTCTGGGGCCAAGGGACCACGGTCACCGTCGCC
TCA3' (SEQ ID NO:454)

Amino acid sequence of heavy chain variable region:

QVQVVESGGGVVQPGRSLRLSCAASGFTFSNYGMHWVRQAPGKGLEWVAVIW
YDGGNKYYADSVKGRSIISRDNSKSTLYLQMNSLRAEDTAVYYCARSVAGYHY
YYGMDVWGQGTTVTVAS (SEQ ID NO:455)

Nucleotide sequence of light chain variable region:

5'TCTTCTGAGCTGACTCAGGACCCTGCTGTGTCTGTGGCCTTGGGACAGACA
GTCAGGATCACATGCCAAGGAGACAGCCTCAGAGGCTATTATGCAAGCTGGT
ACCAGCAGAAGCCAAGACAGGCCCCTGTACTTGTCATCTATGGTAAAAACAA
CCGGCCCTCAGGGATCCCAGACCGATTCTCTGGCTCCACGTCAGGAAACACA
GCTTCCTTGACCATCACTGGGGCTCAGGCGGAAGATGAGGCTGACTATTACT
GTAACTCCCGGGACAACATTGGTGACCATCTGGTGTTCGGCGGAGGGACCAA
GCTGACCGTCCTA3' (SEQ ID NO:456)

Amino acid sequence of light chain variable region:

SSELTQDPAVSVALGQTVRITCQGDSLRGYYASWYQQKPRQAPVLVIYGKNNRP
SGIPDRFSGSTSGNTASLTITGAQAEDEADYYCNSRDNIGDHLVFGGGTKLTVL
(SEQ ID NO:457)

Nucleotide sequence of heavy chain variable region:

5'GAGGTGCAGCTGGTGGAGTCTGGGGGAGGCTTGGTCCAGCCTGGGGGGGTCC
CTGAGACTCTCCTGTGCAGCCTCCGGATTCACCTTTAGTAGCTATTGGATGAG
CTGGGTCCGCCAGGCTCCAGGGAAGGGGCTGGAGTGGGTGGCCAGCATAAA
ACAAGATGGAAGTGAGAAATACTATGTGGACTCTGTGAAGGGCCGATTCACC
ATCTCCAGAGACAACGCCAGGAACTCACTGTATCTGCAAATGAACAGCCTGA
GAGCCGAGGACACGGCTGTGTATTACTGTGCGAGAGATCTTGTATTAATGGT
GTATGATATAGACTACTACTACTACGGTATGGACGTCTGGGGCCAAGGGACC
ACGGTCACCGTCTCCTCA3' (SEQ ID NO:458)

Amino acid sequence of heavy chain variable region:

EVQLVESGGGLVQPGGSLRLSCAASGFTFSSYWMSWVRQAPGKGLEWVASIKQ
DGSEKYYVDSVKGRFTISRDNARNSLYLQMNSLRAEDTAVYYCARDLVLMVYD
IDYYYYGMDVWGQGTTVTVSS (SEQ ID NO:459)

Nucleotide sequence of light chain variable region:

5'GATATTGTGATGACTCAGTCTCCACTCTCCCTGCCCGTCACCCCTGGAGAGC
CGGCCTCCATCTCCTGCAGGTCTAGTCAGAGCCTCCTGCATAGTAATGGATAC
AACTATTTGGATTGGTACCTGCAGAAGCCAGGGCAGTCTCCACAGCTCCTGA
TCTATTTGGGTTCTAATCGGGCCTCCGGGGTCCCTGACAGGTTCAGTGGCAGT
GGATCAGGCACAGATTTTACACTGAAAATCAGCAGAGTGGAGGCTGAGGATG
TTGGGGTTTATTACTGCATGCAAGCTCTACAAACTCCGCTCACTTTCGGCGGA
GGGACCAAGGTAGAGATCAAA3' (SEQ ID NO:460)

Amino acid sequence of light chain variable region:

DIVMTQSPLSLPVTPGEPASISCRSSQSLLHSNGYNYLDWYLQKPGQSPQLLIYLG
SNRASGVPDRFSGSGSGTDFTLKISRVEAEDVGVYYCMQALQTPLTFGGGTKVEI
K (SEQ ID NO:461)

Nucleotide sequence of heavy chain variable region:

5'GAGGTGCAGCTGGTGGAGTCTGGGGGAGGCTTGGTCCAGCCTGGGGGGTCC
CTGAGACTCTCCTGTGCAGCCTCCGGATTCACCTTTAGTAACTATTGGATGAG
CTGGGTCCGCCAGGCTCCAGGGAAGGGGCTGGAGTGGGTGGCCAGCATAAA
ACAAGATGGAAGTGAGAAATACTATGTGGACTCTGTGAAGGGCCGATTCGCC
ATCTCCAGAGACAACGCCAAGAACTCACTGTTTCTGCAAATGAACAGCCTGA
GAGCCGAGGACACGGCTGTGTATTACTGTGCGAGAGATCTTGTACTAATGGT
GTATGATATAGACTACTACTACTACGGTATGGACGTCTGGGGCCAAGGGACC
ACGGTCACCGTCTCCTCA3' (SEQ ID NO:462)

Amino acid sequence of heavy chain variable region:

EVQLVESGGGLVQPGGSLRLSCAASGFTFSNYWMSWVRQAPGKGLEWVASIKQ
DGSEKYYVDSVKGRFAISRDNAKNSLFLQMNSLRAEDTAVYYCARDLVLMVYD
IDYYYYGMDVWGQGTTVTVSS (SEQ ID NO:463)

Nucleotide sequence of light chain variable region:

5'GATATTGTGATGACTCAGTCTCCACTCTCCCTGCCTGTCACCCCTGGAGAGC
CGGCCTCCATCTCTTGCAGGTCTAGTCAGAGCCTCCTGCATAGTAATGGGTAC
AACTATTTGGATTGGTACCTGCAGAAGCCAGGGCAGTCTCCACAGCTCCTGA
TCTATTTGGGTTCTAATCGGGCCTCCGGGGTCCCTGACAGGTTCAGTGGCAGT
GGATCAGGCACACATCTTACACTGAAAATCAGCAGAGTGGAGGCTGAGGATG
TTGGAGTTTATTACTGCATGCAAACTCTACAAACTCCGCTCACTTTCGGCGGA
GGGACCAAGGTGGAGATCAAA3' (SEQ ID NO:464)

Amino acid sequence of light chain variable region:

DIVMTQSPLSLPVTPGEPASISCRSSQSLLHSNGYNYLDWYLQKPGQSPQLLIYLG
SNRASGVPDRFSGSGSGTHLTLKISRVEAEDVGVYYCMQTLQTPLTFGGGTKVEI
K (SEQ ID NO:465)

Nucleotide sequence of heavy chain variable region:

5'CAGGTGCAGCTGGTGGAGTCTGGGGGAGGCGTGGCCCAGCCTGGGAGGTC
CCTGAGACTCTCCTGTGCAGCGTCTGGATTCACCTTCAGTAGCTATGGCATGC
ACTGGGTCCGCCAGGCTCCAGGCAAGGGGCTGGAGTGGGTGGCAGTTATATA
CTATGATGGAATTAATAAACACTATGCAGACTCCGTGAAGGGCCGATTCACC
ATCTCCAGAGACAATTCCAAGAACACGCTGTATCTGCAAATGAACAGCCTGA
GAGCCGAGGACACGGCTGTGTATTACTGTGCGAGAGATCGGGGACTGGACTG
GGGCCAGGGAACCCTGGTCACCGTCTCCTCA3' (SEQ ID NO:466)

Amino acid sequence of heavy chain variable region:

QVQLVESGGGVAQPGRSLRLSCAASGFTFSSYGMHWVRQAPGKGLEWVAVIYY
DGINKHYADSVKGRFTISRDNSKNTLYLQMNSLRAEDTAVYYCARDRGLDWGQ
GTLVTVSS (SEQ ID NO:467)

Nucleotide sequence of light chain variable region:

5'GACATCGTGATGACCCAGTCTCCAGACTCCCTGGCTGTGTCTCTGGGCGAG
AGGGCCACCATCAACTGCAAGTCCAGCCAGAGTGTTTTATACAGCTCCAACA
GTAAGAACTACTTAGTTTGGTACCAGCAGAAACCAGGACAGCCTCCTAAGCT
GCTCATTTACTGGGCCTCTACCCGGGAATCCGGGGTCCCTGACCGATTCAGTG
GCAGCGGGTCTGGGACAGATTTCACTCTCACCATCAGCAGCCTGCAGGCTGA
AGATGTGGCAGTTTATTACTGTCAACAATATTATAGTACTCCGTGGACGTTCG
GCCAAGGGACCAAGGTGGAAATCAAA3' (SEQ ID NO:468)

Amino acid sequence of light chain variable region:

DIVMTQSPDSLAVSLGERATINCKSSQSVLYSSNSKNYLVWYQQKPGQPPKLLIY
WASTRESGVPDRFSGSGSGTDFTLTISSLQAEDVAVYYCQQYYSTPWTFGQGTK
VEIK (SEQ ID NO:469)

Nucleotide sequence of heavy chain variable region:

5'GAGGTGCAGCTGGTGGAGTCTGGGGGAGGCTTGGTCCAGCCTGGGGGGTCC
CTGAGACTCTCCTGTGCAGCCTCTGGACTCACCTTTAGTAACTTTTGGATGAG
CTGGGTCCGCCAGGCTCCAGGGAAGGGGCTGGAGTGGGTGGCCAACATAAA
GCAAGATGGAAATGATAAATACTATGTGGACTCTGTGAAGGGCCGATTCACC
ATCTCCAGAGACAACGCCAAGAATTCACTGTATCTGCAAATGAACAGCCTGA
GAGCCGAGGACACGGCTGTGTATTACTGTGCGAGAGAGTCAAACTGGGGATT
TGCTTTTGATATCTGGGGCCAAGGGACAATGGTCACCGTCTCTTCA3' (SEQ ID
NO:470)

Amino acid sequence of heavy chain variable region:

EVQLVESGGGLVQPGGSLRLSCAASGLTFSNFWMSWVRQAPGKGLEWVANIKQ
DGNDKYYVDSVKGRFTISRDNAKNSLYLQMNSLRAEDTAVYYCARESNWGFAF
DIWGQGTMVTVSS (SEQ ID NO:471)

Nucleotide sequence of light chain variable region:

5'CAGTCTGTGCTGACTCAGCCACCCTCAGCGTCTGGGACCCCCGGGCAGAGG
GTCACCATCTCTTGTTCTGGAAGCAGCTCCAACATCGGAAGTAAAACTGTAA
ACTGGTACCAGCAGTTCCCAGGAACGGCCCCCAAACTCCTCATCTATAGTAA
TAATCGGCGGCCCTCAGGGGTCCCTGACCGATTCTCTGGCTCCAAGTCTGGCA
CCTCAGCCTCCCTGGCCATCAGTGGGCTCCAGTCTGAGGATGAGGCTGATTAT
TACTGTGCAGCATGGGATGACAGCCTGAATTGGGTGTTCGGCGGAGGGACCA
AGCTGACCGTCCTA3' (SEQ ID NO:472)

Amino acid sequence of light chain variable region:

QSVLTQPPSASGTPGQRVTISCSGSSSNIGSKTVNWYQQFPGTAPKLLIYSNNRRP
SGVPDRFSGSKSGTSASLAISGLQSEDEADYYCAAWDDSLNWVFGAGTKLTVL
(SEQ ID NO:473)

Nucleotide sequence of heavy chain variable region:

5'GAGGTGCAGCTGGTGGAGTCTGGGGGAGGTTTGGTCCAGCCTGGGGGGGTCC
CTGAGACTCTCCTGTGCAGCCTCTGGACTCACCTTTAGTAACTTTTGGATGAG
CTGGGTCCGCCAGGCTCCAGGGAAGGGGCTGGAGTGGGTGGCCAACATAAA
GCAAGATGGAAGTGAGAAATACTATGTGGACTCTGTGAAGGGCCGATTCACC
ATCTCCAGAGACAACGCCAAGAATTCACTGTATCTGCAAATGAACAGCCTGA
GAGCCGAGGACACGGCTGTGTATTACTGTGCGAGAGAGTCAAACTGGGGATT
TGCTTTTGATATCTGGGGCCAAGGGACAATGGTCACCGTCTCTTCA3' (SEQ ID
NO:474)

Amino acid sequence of heavy chain variable region:

EVQLVESGGGLVQPGGSLRLSCAASGLTFSNFWMSWVRQAPGKGLEWVANIKQ
DGSEKYYVDSVKGRFTISRDNAKNSLYLQMNSLRAEDTAVYYCARESNWGFAF
DIWGQGTMVTVSS (SEQ ID NO:475)

Nucleotide sequence of light chain variable region:

5'CAGTCTGTGCTGACTCAGCCACCCTCAGCGTCTGGGACCCCCGGGCAGAGG
GTCACCATCTCTTGTTCTGGAAGCAGCTCCAACATCGGAAGTAAAACTGTAA
ACTGGTACCAGCAGTTCCCAGGAACGGCCCCCAAACTCCTCATCTATAGTAA
TAATCGGCGGCCCTCAGGGGTCCCTGACCGATTCTCTGGCTCCAAGTCTGGCA
CCTCAGCCTCCCTGGCCATCAGTGGGCTCCAGTCTGAGGATGAGGCTGATTAT
TACTGTGCAACATGGGATGACAGACTGAATTGGGTGTTCGGCGCAGGGACCA
AGCTGACCGTCCTA3' (SEQ ID NO:476)

Amino acid sequence of light chain variable region:

QSVLTQPPSASGTPGQRVTISCSGSSSNIGSKTVNWYQQFPGTAPKLLIYSNNRRP
SGVPDRFSGSKSGTSASLAISGLQSEDEADYYCATWDDRLNWVFGAGTKLTVL
(SEQ ID NO:477)

Nucleotide sequence of heavy chain variable region:

5'CAGGTCACCTTGAAGGAGTCTGGTCCTGTGCTGGTGAAACCCACAGAGACC
CTCACGCTGACCTGCACCGTCTCTGGGTTCTCACTCAGCAATGTTAGAATGGG
TGTGAGCTGGATCCGTCAGCCCCCAGGGAAGGCCCTGGAGTGGCTTGCACAC
ATTTTTTCGAATGACGAAAATTCCTACAGAACATCTCTGAAGAGCAGGCTCA
CCATCTCCAAGGACACCTCCAAAAGCCAGGTGGTCCTTACCATGACCAACAT
GGACCCTGTGGACACAGCCACATATTACTGTGCACGGATAGTGGGAGCTACA
ACGGATGATGCTTTTGATATCTGGGGCCAAGGGACAATGGTCACCGTCTCTTC
A3' (SEQ ID NO:478)

Amino acid sequence of heavy chain variable region:

QVTLKESGPVLVKPTETLTLTCTVSGFSLSNVRMGVSWIRQPPGKALEWLAHIFS
NDENSYRTSLKSRLTISKDTSKSQVVLTMTNMDPVDTATYYCARIVGATTDDAF
DIWGQGTMVTVSS (SEQ ID NO:479)

Nucleotide sequence of light chain variable region:

5'TCCTATGTGCTGACTCAGCCACCCTCGGTGTCAGTGGCCCCAGGACAGACG
GCCAGGATTACCTGTGGGGGAAACAACATTGGAAGTAAAAGTGTGCACTGGT
ACCAGCAGAAGCCAGGCCAGGCCCCTGTGCTGGTCGTCTATGATGATAGCGA
CCGGCCCTCAGGGATCCCTGAGCGATTCTCTGGCTCCAACTCTGGGAACACG
GCCACCCTGACCATCAGCAGGGTCGAAGCCGGGGATGAGGCCGACTTTTACT
GTCAGGTGTGGGATAGTAGTAGTGATCCTGTGGTATTCGGCGGAGGGACCAA
GCTGACCGTCCTA3' (SEQ ID NO:480)

Amino acid sequence of light chain variable region:

SYVLTQPPSVSVAPGQTARITCGGNNIGSKSVHWYQQKPGQAPVLVVYDDSDRP
SGIPERFSGSNSGNTATLTISRVEAGDEADFYCQVWDSSSDPVVFGGGTKLTVL
(SEQ ID NO:481)

Nucleotide sequence of heavy chain variable region:

5'GAGGTGCAGCTGGTGGAGTCTGGGGGAGGCTTGGTCCAGCCTGGGGGGTCC
CTGAGACTCTCCTGTGCAGCCTCTGGATTCACCTTTAGTAACTATTGGATGAC
CTGGGTCCGCCAGGCTCCAGGGAAGGGGCTGGAGTGGGTGGCCAGCATAAA
GCAAGATGGAAGTGAGAGATACTATGTGGACTCTGTGAAGGGCCGATTCACC
ATCTCCCGAGACACCGCCAAGAACTCTCTGTATCTCCAAATGAACAGCCTGC
GAGCCGAGGACACGGCTGTGTATTACTGTGCGAGACCTCTTGTACTAATGGT
GTATGCTCTACACTACTACTACTACGGTATGGACGTCTGGGGCCACGGGACC
ACGGTCACCGTCTCCTCA3' (SEQ ID NO:482)

Amino acid sequence of heavy chain variable region:

EVQLVESGGGLVQPGGSLRLSCAASGFTFSNYWMTWVRQAPGKGLEWVASIKQ
DGSERYYVDSVKGRFTISRDTAKNSLYLQMNSLRAEDTAVYYCARPLVLMVYA
LHYYYYGMDVWGHGTTVTVSS (SEQ ID NO:483)

Nucleotide sequence of light chain variable region:

5'GATATTGTGATGACTCAGTCTCCACTCTCCCTGCCCGTCACCCCTGGAGAGC
CGGCCTCCATCTCCTGCAGGTCTAGTCAGAGCCTCCTGCATAGTAATGGATAC
AACTATTTGGATTGGTACCTGCAGAAGCCAGGGCAGTCTCCACAGCTCCTGA
TCTATTTGGGTTCTAATCGGGCCTCCGGGGTCCCTGACAGGTTCAGTGGCAGT
GGATCAGGCACAGATTTTACACTGAAAATCAGCAGAGTGGAGGCTGAGGATG
TTGGGGTTTATTACTGCATGCAAGCTCTACAAACTCCGCTCACTTTCGGCGGA
GGGACCAAGGTGGAGATCAAA3' (SEQ ID NO:484)

Amino acid sequence of light chain variable region:

DIVMTQSPLSLPVTPGEPASISCRSSQSLLHSNGYNYLDWYLQKPGQSPQLLIYLG
SNRASGVPDRFSGSGSGTDFTLKISRVEAEDVGVYYCMQALQTPLTFGGGTKVEI
K (SEQ ID NO:485)

| Heavy variable | SEQ ID NO: | Germline | Germline | FR1 | CDR1 | FR2 |
|---|---|---|---|---|---|---|
|  | 493 |  | Germline | QVQLVQSGAEVKKPGASVKVSCKAS | GYTVTGYYMH | WVRQAPGQGLEWMG |
| 5H5.1G | 419 | VH1-02 | JH6 | -----?--- | -----I- | ------ |
|  | 494 |  | Germline | QVQLVESGGGVVQPGRSLRLSCAAS | GFTFSSYGMH | WVRQAPGKGLEWVA |
| 24B9.1G | 435 | VH3-33 | JH4 | ------------ | ------ | ------ |
|  | 495 |  | Germline | QVQLVESGGGVVQPGRSLRLSCAAS | GFTFSSYGMH | WVRQAPGKGLEWVA |
| 24B7.1G | 423 | VH3-33 | JH6 | ------ | -----I- | ------ |
| 22B11.1G | 427 | VH3-33 | JH6 | ------ | ------ | ------ |
| 20A5.1G | 443 | VH3-33 | JH6 | ----S--- | ------ | ------ |
| 20A5.2G | 447 | VH3-33 | JH6 | ----A----- | ----I- | ----Q- |
| 30F1.1G | 431 | VH3-33 | JH6 | -----S- | --N--- | ------ |
| 20E5.1GV1 | 451 | VH3-33 | JH6 | ---V----- | ----V- | ------ |
| 24B9.2G | 439 | VH3-33 | JH6 | ----V------G- | ----N- | ------ |

Figure 3:
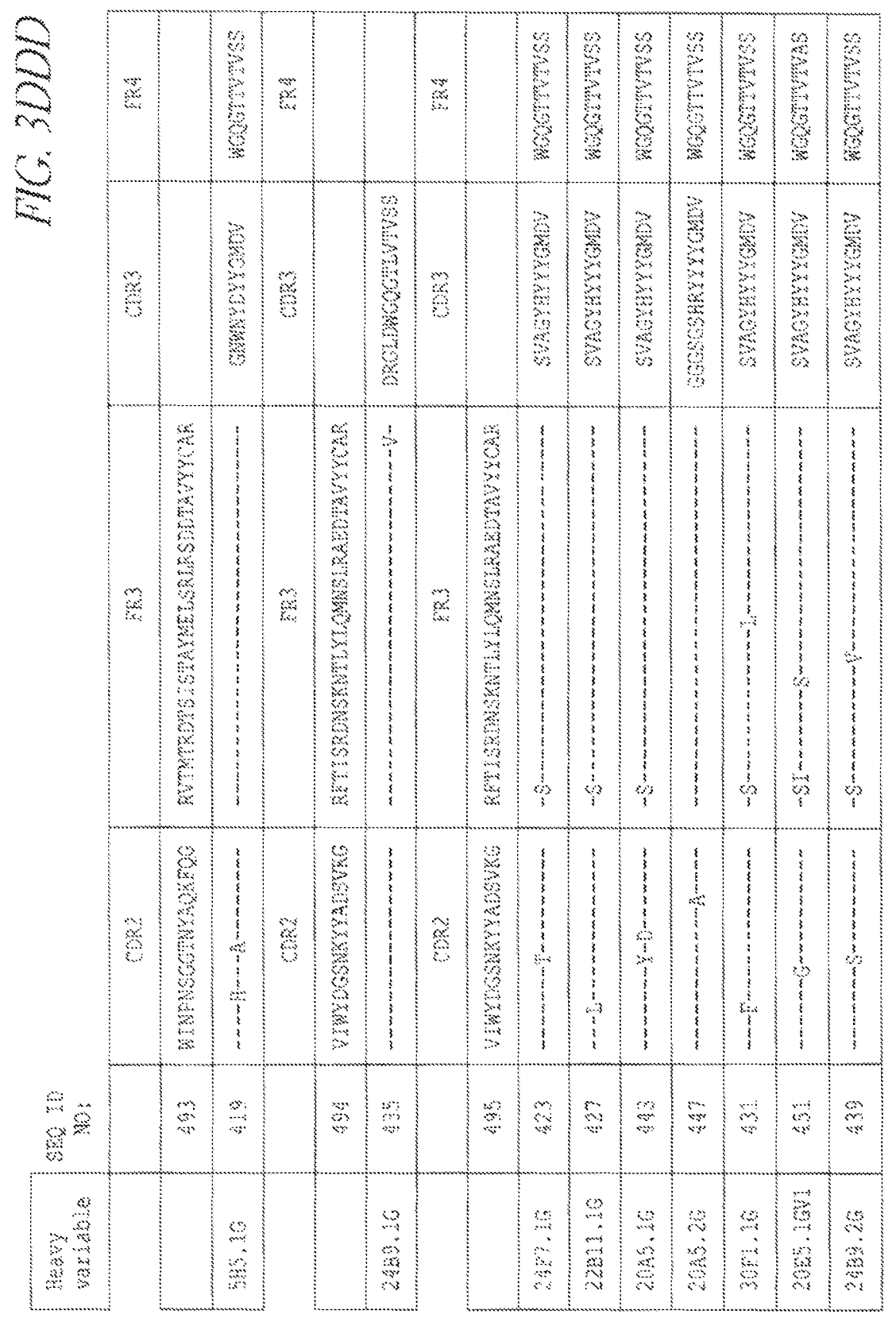

*FIG. 3DDD*

| Heavy variable | SEQ ID NO: | CDR2 | FR3 | CDR3 | FR4 |
|---|---|---|---|---|---|
| | 493 | WIMPNSGGTNYAQKFQG | RVTMTRDTSISTAYMELSRLRSDDTAVYYCAR | | |
| 5B3.1G | 419 | ----R---A------- | ------------- | CRMRYYYGMDV | WGQGTTVTVSS |
| | 494 | VIWYDGSNKYYADSVKG | RFTISRDNSKNTLYLQMNSLRAEDTAVYYCAR | CDR3 | FR4 |
| 24B9.1G | 435 | ---------------- | -------V- | DRGLDWGQGTLVTVSS | |
| | 495 | VIWYKSNKYYADSVKG | RFTISRDNSKNTLYLQMNSLRAEDTAVYYCAR | CDR3 | FR4 |
| 24F7.1G | 423 | -------T-------- | -S----------- | SVAGYHYYYGMDV | WGQGTTVTVSS |
| 22B11.1G | 427 | -------L-------- | -S----------- | SVAGYHYYYGMDV | WGQGTTVTVSS |
| 20A5.1G | 443 | ----Y-D--------- | -S----------- | SVAGYHYYYGMDV | WGQGTTVTVSS |
| 20A5.2G | 447 | -------A-------- | ------------- | GGSGSHKYYYGMDV | WGQGTTVTVSS |
| 30F1.1G | 431 | -------F-------- | -S-----L----- | SVAGYHYYYGMDV | WGQGTTVTVSS |
| 20B5.1GV1 | 451 | -------G-------- | -S1-------S--- | SVAGYHYYYGMDV | WGQGTTVTVAS |
| 24B9.2G | 439 | -------S-------- | -S--------Q--- | SVAGYHYYYGMDV | WGQGTTVTVSS |

| Kappa variable | SEQ ID NO: | Germline | Germline | FR1 | CDR1 | FR2 |
|---|---|---|---|---|---|---|
| | 496 | VK1A20 | | DIQMTQSPSSLSASVGDRVTITC | RASQGISNYLA | WYQQKPGKVPKLLIY |
| 5H5.1K | 421 | VK1A20 | JK3 | ------------------- | ---D------- | --------------- |

| Lambda variable | SEQ ID NO: | Germline | Germline | FR1 | CDR1 | FR2 |
|---|---|---|---|---|---|---|
| | 497 | VL2|2a2 | | QSALTQPASVSGSPGQSITISC | TGTSSDVGGYNYVS | WYQQHPSKAPKLMIY |
| 20E5.1L v1 | 453 | VL2|2a2 | JL2 | ------------------S--- | ----------S--- | ---------P----- |

| | SEQ ID NO: | Germline | Germline | FR1 | CDR1 | FR2 |
|---|---|---|---|---|---|---|
| Germline | 498 | VL3|3l | JL2 | SSELTQDPAVSVALGQTVRITC | QGDSLRSYYAS | WYQQRPGQAPVLVIY |
| 30F1.1L | 433 | VL3|3l | JL2 | ---------------------- | ----------- | ---R----------- |
| 22B11.1L | 429 | VL3|3l | JL2 | ---------------------- | ----G------ | ---R----------F |
| 24B9.1L | 437 | VL3|3l | JL2 | ---------------------- | ----G------ | ---R----------- |
| 24B9.2L | 441 | VL3|3l | JL2 | ---------------------- | ----G------ | ---R----------- |
| 20E5.1L v2 | 457 | VL3|3l | JL2 | ---------------------- | ----G------ | ---R----------- |
| 24F7.1L | 425 | VL3|3l | JL2 | ---------------------- | ----G----T- | ---R----------- |
| 20A5.1L | 445 | VL3|3l | JL2 | ---------------------- | ----T------ | ---R------I---- |
| 20A5.2L | 449 | VL3|3l | JL2 | ---------------------- | ----T------ | ---R------I---- |

*FIG. 3EEE*

Kappa variable

| SEQ ID NO: | CDR2 | FR3 | CDR3 | FR4 |
|---|---|---|---|---|
| 495 | AASTLQS | GVPSRFSGSGSGTDFTLTISSLQPEDVATYYC | QRYQIAPFT | FGPGTKVDIK |
| 421 (5H3.1K) | ------- | ---------T--- | | |

Lambda variable

| SEQ ID NO: | CDR2 | FR3 | CDR3 | FR4 |
|---|---|---|---|---|
| 497 | EVSNRFS | GVSNRFSQSKSGNTASLTISGLQAEDEADYYC | SSYTSTSMV | FGGGTKLAVL |
| 453 (20E5.1L v1) | ------- | ---I- | -I- | |

| | SEQ ID NO: | CDR2 | FR3 | CDR3 | FR4 |
|---|---|---|---|---|---|
| 30F1.1L | 498 | GKNNRPS | GIPDRFSGSSSGNTASLTITGAQAEDEADYYC | KSRDIIGDHLV | FGGGTKLTVL |
| 22B11.1L | 433 | ------- | ------I--T--- | NSRDIIGDHLL | FGGGTKLTVL |
| 24B9.1L | 429 | ------- | ---------T--- | KSRDSSGDHLV | FGGGTKLTVL |
| 24B9.2L | 437 | ------- | ---------T--- | KSRDSSGDHLV | FGGGTKLTVL |
| 20E5.1L v2 | 441 | ------- | ---------T--- | KSRDSSGDHLV | FGGGTKLTVL |
| 24F7.1L | 457 | ------- | ---------T--- | NSRDNIGDHLV | FGGGTKLTVL |
| 20A5.1L | 425 | ---Y--- | ---------T--- | NSRDSIGNHLV | FGGGTKLTVL |
| 20A5.1L | 445 | ------- | ---------T--I--- | KSRDIIGNHLL | FGGGTKLTVL |
| 20A5.2L | 449 | ------- | ---------T--I--- | KSRDIIGNHLL | FGGGTKLTVL |

FIG. 3FF

| SEQ ID NO: | | Germline | Germline | FR1 | SEQ ID NO: | CDR1 | SEQ ID NO: | FR2 | SEQ ID NO: |
|---|---|---|---|---|---|---|---|---|---|
| 486 | | VH2|226 | Germline | QVTLRESGPVLVKPTETLTLTCTVS | 506 | GFSLSRARMGVS | 507 | WIRQPPGKALEWLA | 509 |
| 479 | 11G1.5 | VH2|226 | JH3 | ------ | 506 | ------V---- | 508 | ------ | 509 |
| 487 | | VH3|307 | Germline | EVQLVESGGGLVQPGGSLRLSCAAS | 510 | GFTFSSYWMS | 511 | WVRQAPGKGLEWVA | 514 |
| 475 | 11H8.1 | VH3|307 | JH3 | ------ | 510 | ---L---WT-- | 512 | ------ | 514 |
| 471 | 11H4.1 | VH3|307 | JH3 | ------ | 510 | ---L---WT-- | 512 | ------ | 514 |
| 459 | 8A3.1 | VH3|307 | JH6 | ------ | 510 | ------YMS | 511 | ------ | 514 |
| 463 | 11F1.1 | VH3|307 | JH6 | ------ | 510 | ------N-- | 500 | ------ | 514 |
| 483 | 8A1.2 | VH3|307 | JH6 | ------ | 510 | ---N--T | 513 | ------ | 514 |
| 488 | | VH3|3-33 | Germline | EVQLVESGGGVVQPGRSLRLSCAAS | 515 | GFTFSSYGMH | 517 | WVRQAPGKGLEWVA | 518 |
| 467 | 12H11.1 | VH3|3-33 | JH4 | ---A--- | 516 | ------ | 517 | ------ | 518 |

FIG. 3GGG

Figure 3:
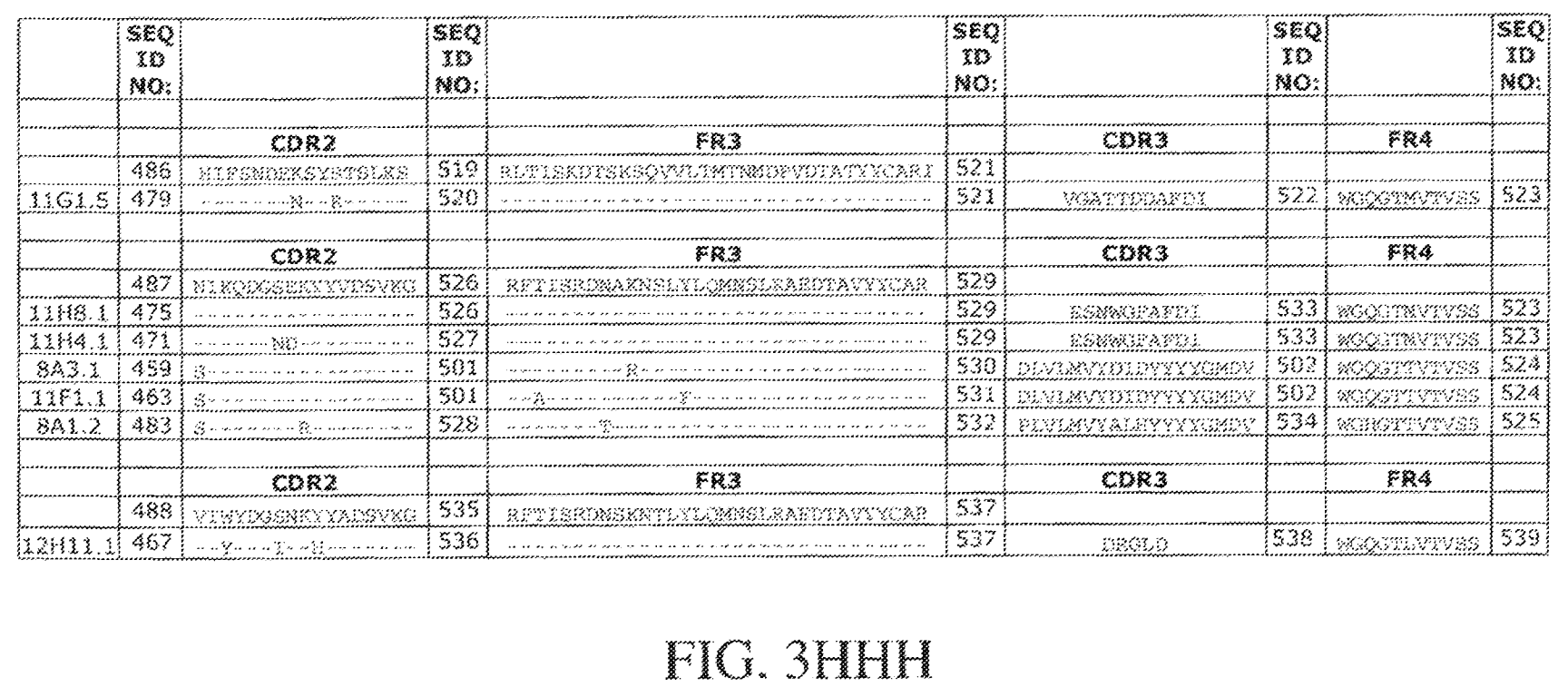

| SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|
| | CDR2 | | FR3 | | CDR3 | | FR4 | |
| 486 | RIPSMDRKSYRTGLKS | 510 | RLTLRDTSKSQVLLKTNRLDPVDTATYYCARI | 521 | | | | |
| 479 | ---N--R--- | 520 | | 531 | WKATTDFAFDY | 522 | WGXGTMVTVSS | 523 |
| | CDR2 | | FR3 | | CDR3 | | FR4 | |
| 487 | HLKKXXSENYYNTSVKG | 526 | RFTISRDNAKNSLYLQMNSLRAEDTAVYYCAR | 529 | | 533 | WGQGTTVTVSS | 523 |
| 475 | --------- | 526 | | 529 | RSWNRPAFDL | 533 | WGQGTTVTVSS | 523 |
| 471 | ---NG---- | 527 | | 529 | RSWNRPAFDL | 502 | WGQGTTVTVSS | 524 |
| 459 | G-------- | 501 | ----R---- | 530 | DLVLMVYDIHYYYGMDV | 502 | WGQGTTVTVSS | 524 |
| 463 | S-------- | 501 | ----A---- | 531 | DLMLMVYDIHYYYGMDY | 502 | WGQGTTVTVSS | 524 |
| 483 | S-------R | 528 | ----T---- | 532 | FLVLMVYALAYYYGMDV | 534 | WGXGTVASS | 525 |
| | CDR2 | | FR3 | | CDR3 | | FR4 | |
| 488 | VERYXXSNYYANSVKG | 535 | RFTISRDNSKNTLYLQMNSLRAEDTAVYYCAR | 537 | | | | |
| 467 | Y----X--N | 536 | | 537 | DRGLD | 539 | WGQGTLVTVSS | 539 |

FIG. 3HHHH

| | SEQ ID NO: | Germline | Germline | FR1 | SEQ ID NO: | CDR1 | SEQ ID NO: | FR2 | SEQ ID NO: |
|---|---|---|---|---|---|---|---|---|---|
| 8A1.2 | 489 | VK2|A19 | | DIVMTQSPLSLPVTPGEPASISC | 540 | RSSQSLLHSNGYNYLD | 503 | WYLQKPGQSPQLLIY | 541 |
| | 485 | VK2|A19 | JK4 | ----------------------- | 540 | ---------------- | 503 | --------------- | 541 |
| 8A3.1 | 461 | VK2|A19 | JK4 | ----------------------- | 540 | ---------------- | 503 | --------------- | 541 |
| 11F1.1 | 465 | VK2|A19 | JK4 | ----------------------- | 540 | ---------------- | 503 | --------------- | 541 |
| | | | | | | | | | |
| | 490 | VK4|B3 | | DIVMTQSPDSLAVSLGERATINC | 542 | KSSQSVLYSSNNKNYLA | 543 | WYQQKPGQPPKVLIY | 545 |
| 12H11.1 | 469 | VK4|B3 | JK1 | ----------------------- | 542 | -------------V--- | 544 | --------------- | 545 |
| | | | | | | | | | |
| | 491 | VL111c | | QSVLTQPPSASGTPGQRVTISC | 546 | SGSSSNIGSNTVN | 547 | WYQQLPGTAPKLLIY | 549 |
| 11H4.1 | 473 | VL111c | JL3b | ---------------------- | 546 | ----K-------- | 548 | -------I------- | 550 |
| 11H8.1 | 477 | VL111c | JL3b | ---------------------- | 546 | ----K-------- | 548 | -------F------- | 550 |
| | | | | | | | | | |
| | 492 | VL3|3h | | SYVLTQPPSVSVAPGKTARITC | 551 | GGNNIGSKSVH | 553 | WYQQKPGQAPVLVIY | 554 |
| 11G1.5 | 481 | VL3|3h | JL2 | ---------------------- | 552 | ----------- | 553 | -------------V- | 555 |

FIG. 3III

| | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|
| 8A1.2 | 489 | LANNRAS | 504 | GVPDRFSGSGSGTDFTLTISRVEAEDVAVYYC | 556 | MQALQTPLT | 558 | FGGGTKVEIK | 559 |
| 8A3.1 | 485 | ------- | 504 | --- | 556 | MQALQTPLK | 558 | FGQGTKVEIK | 559 |
| 11F1.1 | 461 | ------- | 504 | --- | 556 | MQTLQTPLK | 505 | FGGGTKVEIK | 559 |
| | 465 | ------- | 504 | ...W... | 557 | | | | |
| 12H11.1 | 490 | WASTRES | 560 | GVPSRFSGSGSGTDFTLTISSLQAEDVAVYYC | 561 | QQYYSTPYT | 562 | FGQGTKVEIK | 563 |
| | 469 | ------- | 560 | --- | 561 | | | | |
| 11H4.1 | 491 | GASSRES | 564 | GVPDRFSGSGSGTEFTLTISSLQPEDFAVYYC | 566 | AAWDDSLNWV | 567 | FGGGTKLTVL | 569 |
| | 473 | ---R--- | 565 | --- | 566 | AAWDDSLNWV | 568 | FGAGTKLTVL | 569 |
| 11H8.1 | 477 | ---R--- | 565 | --- | 566 | | | | |
| 11G1.5 | 492 | YDSDRPS | 570 | GVPDRFSGSKSGTSASLAISGLRSEDEADYYC | 572 | QVWDSSSDPVV | 574 | FGGGTKLTVL | 575 |
| | 481 | D------- | 571 | ...R... | 573 | | | | |

FIG. 3JIJ 10 or 100pM 16F 12 + (0.1pM ~ 10nM) hPCSK9

$K_D$ = 15 pM
95% CI: 11~22 pM

[hPCSK9] (M)

% Free 16F12

12% Tris-Glycine gel,
QuickBlue stain, 1μg/Lane

1. Marker 12
2. hPCSK9
3. mPCSK9
4. cPCSK9
5. 16F12
6. 21B12
7. 31H4
8. Marker 12
9. hPCSK9
10. mPCSK9
11. cPCSK9
12. 16F12
13. 21B12
14. 31H4
15. SeeBlue Plus2

FIG. 13A 10.00
substitutions per 100 residues

FIG. 13C

Heavy Chain:

| | | | |
|---|---|---|---|
| 20D10_heavy_cdr | ~GYTLTSYGIS (SEQ ID NO:148) | WISAYNG.NTNYAQKVQG (SEQ ID NO:174) | GYCWDY~~~~~~ (SEQ ID NO:180) |
| 30B9_heavy_cdr | ~GYTLTSYGIS (SEQ ID NO:149) | WISAYNG.NTNYAQKVQG (SEQ ID NO:174) | GYCWDY~~~~~~ (SEQ ID NO:180) |
| 27E7_heavy_cdr | ~GYSLTSYGIS (SEQ ID NO:360) | WISAYNG.NTNYAQKVQG (SEQ ID NO:174) | GYCWDY~~~~~~ (SEQ ID NO:180) |
| 19B9_heavy_cdr | ~GIALTSYGIS (SEQ ID NO:367) | WISAYNG.NTNYAQKVQG (SEQ ID NO:174) | GYCWDY~~~~~~ (SEQ ID NO:180) |
| 21B12_heavy_cdr | ~GYTLTSYGIS (SEQ ID NO:368) | WVSFYNG.NTNYAQKLQG (SEQ ID NO:175) | GYCWDY~~~~~~ (SEQ ID NO:180) |
| 23G1_heavy_cdr | ~GYTLTSYGIS (SEQ ID NO:368) | WYSFYNG.NTNYAQKLQG (SEQ ID NO:175) | GYCWDY~~~~~~ (SEQ ID NO:180) |
| 26E6_heavy_cdr | ~GYTLTSYGIS (SEQ ID NO:368) | WISFYNG.NTNYAQKVQG (SEQ ID NO:176) | GYCWDY~~~~~~ (SEQ ID NO:180) |
| 31D1_heavy_cdr | ~GYTLTSYGIS (SEQ ID NO:368) | WISFYNG.NTNYAQKVQG (SEQ ID NO:176) | GYCWDY~~~~~~ (SEQ ID NO:180) |
| 27B5_heavy_cdr | ~GYSFTSYGIS (SEQ ID NO:368) | WISYYNG.NTNYAQKVQG (SEQ ID NO:177) | GYCWDY~~~~~~ (SEQ ID NO:180) |
| 17C2_heavy_cdr | ~GYSFTSYGIS (SEQ ID NO:369) | WVSAYNG.NTNYAEKLQG (SEQ ID NO:177) | GYVWDY~~~~~~ (SEQ ID NO:387) |
| 25A7_heavy_cdr | ~GTTFTSYGIS (SEQ ID NO:370) | WISAYNG.NTNYAQKVQG (SEQ ID NO:178) | GYTWDY~~~~~~ (SEQ ID NO:387) |
| 3B6_heavy_cdr | ~GYTFTSYGMH (SEQ ID NO:244) | WISTDNG.NTNYAQKVQG (SEQ ID NO:179) | GYTRDY~~~~~~ (SEQ ID NO:261) |
| 9C9_heavy_cdr | ~GFTFSAYWMH (SEQ ID NO:371) | NIKQDGS.EKYYVDSVKG (SEQ ID NO:252) | K.......SNNGFAPDI (SEQ ID NO:305) |
| 9B6_heavy_cdr | ~GFTFSAYWMH (SEQ ID NO:372) | NIKQDGS.EKYYVDSVKG (SEQ ID NO:349) | K.......SNNGFAPDI (SEQ ID NO:386) |
| 1A12_heavy_cdr | ~GLTFSNYAMS (SEQ ID NO:373) | NIKQDGS.NYYADSVKG (SEQ ID NO:349) | K.......SNNGFAPDI (SEQ ID NO:386) |
| 23B5_heavy_cdr | ~GFTFSSYAMS (SEQ ID NO:374) | WISGGGD.NFYYADSVKG (SEQ ID NO:210) | KFVLNFYIAMLDI~~~ (SEQ ID NO:210) |
| 23G4_heavy_cdr | ~GFTFSSYAMS (SEQ ID NO:374) | TISGSGG.NFYYADSVKG (SEQ ID NO:240) | KFVLNFYIAMLDY~~~ (SEQ ID NO:210) |
| 13B5_heavy_cdr | ~GFTFSSYAMS (SEQ ID NO:245) | WISGSGG.NTYYADSVKG (SEQ ID NO:253) | K........VGHPDY~~ (SEQ ID NO:262) |
| 22B2_heavy_cdr | ~GFTFSSYGMH (SEQ ID NO:188) | LINWDGS.NKYYADSVKG (SEQ ID NO:193) | AIAAL.YYYCGMDV (SEQ ID NO:195) |
| 26B12_heavy_cdr | ~GFTFSSYGMH (SEQ ID NO:188) | LINWDGS.NKYYADSVKG (SEQ ID NO:193) | AIAAL.YYYCGMDV (SEQ ID NO:195) |
| 28D6_heavy_cdr | ~GFTFSSYGMH (SEQ ID NO:373) | LINWDGS.DKYYADSVKG (SEQ ID NO:193) | AIAAL.YYYCGMDV (SEQ ID NO:195) |
| 16B12_heavy_cdr | ~GFTFNSYGMH (SEQ ID NO:375) | LINWDGS.DKYYADSVRG (SEQ ID NO:193) | AIAAL.YYYCGMDV (SEQ ID NO:195) |
| 27A6_heavy_cdr | ~GFTFNSYGMH (SEQ ID NO:376) | LINWDGS.DKYYADSVRG (SEQ ID NO:193) | AIAAL.YYYCGMDV (SEQ ID NO:193) |
| 31G11_heavy_cdr | ~GFTFSSYGMH (SEQ ID NO:246) | LINWDGS.NFYYADSVKG (SEQ ID NO:193) | SIAVA.YYYCGMDV (SEQ ID NO:196) |
| 30A4_heavy_cdr | ~GFTFSSYGMH (SEQ ID NO:246) | VINTDGS.NKYYADSVKG (SEQ ID NO:254) | STGHLLKLYYYGMDV (SEQ ID NO:264) |
| 31B12_heavy_cdr | ~GFTFSSYGMH (SEQ ID NO:247) | SISSSS.VIG.ADSVKG (SEQ ID NO:255) | R.GGLAARPCGMDV (SEQ ID NO:265) |
| 31B4_heavy_cdr | GGSISSGGYYWS (SEQ ID NO:248) | YIYYSGSTY..NPSLKS (SEQ ID NO:256) | DYDPWSAYYDAPDV (SEQ ID NO:266) |
| 27B2_heavy_cdr | GGSISSGSYYWS (SEQ ID NO:249) | YIYYSGSTY..NPSLKS (SEQ ID NO:257) | ED.TRWFFY.MDY~ (SEQ ID NO:267) |
| 3C4_heavy_cdr | GGSIRSGGSRD..YYWN (SEQ ID NO:250) | ENHSGSRD.YNPSLKS (SEQ ID NO:258) | GG.VYYYKKAMDV~ (SEQ ID NO:268) |
| 31A6_heavy_cdr | GGSFSA..YYWN (SEQ ID NO:250) | NYYTRSNTD.YNPSLKS (SEQ ID NO:259) | GQ.IVPDY~~~~~~ (SEQ ID NO:268) |
| 13H1_heavy_cdr | GDSVSSNRAAWN (SEQ ID NO:251) | RYYTRSWTDH.SVSVKS (SEQ ID NO:260) | GGFIRAFDK~~~ (SEQ ID NO:269) |

Consensus

*

Consensus for Group 1:

Consensus for Group 2:

FIG. 13F

Group 1 (11 members)

| | LV_CDR1 | SEQ ID NO: | LV_CDR2 | SEQ ID NO: | LV_CDR3 | SEQ ID NO: | H_CDR1 | SEQ ID NO: | H_CDR2 | SEQ ID NO: | H_CDR3 | SEQ ID NO: |
|---|---|---|---|---|---|---|---|---|---|---|---|---|
| CONSENSUS | TGTSSDVGGYNSVS | 305 | EVSNRPS | 306 | SSYTSTSMV | 307 | SYGIS | 308 | WISAYNGMTNYAQKVQG | 309 | GYGMDV | 310 |
| 25A7 | ....R.... | 311 | ........ | 312 | ...S.V. | 313 | ........ | 308 | ....E.L.. | 314 | ...V.. | 315 |
| 17C2 | ....A.... | 316 | ........ | 312 | ....N.. | 317 | ........ | 308 | ...V... | 318 | ...V.. | 315 |
| 21B12 | ......... | 305 | ........ | 312 | N..... | 319 | ........ | 308 | ..V.F... | 320 | ...L.. | 310 |
| 23G1 | ......... | 305 | ...T.... | 321 | N..... | 319 | ........ | 308 | ..V.F... | 320 | ...L.. | 310 |
| 19H9 | ...N.... | 322 | ........ | 312 | ...... | 307 | ........ | 308 | ........ | 309 | ...... | 310 |
| 27H5 | ......... | 305 | ........ | 312 | ...... | 307 | ........ | 308 | ..V..... | 323 | ...... | 310 |
| 26H5 | ......... | 305 | ........ | 312 | ...... | 307 | ........ | 308 | ..F..... | 324 | ...... | 310 |
| 31D1 | ......... | 305 | ........ | 312 | ...... | 307 | ........ | 308 | ..F..... | 324 | ...... | 310 |
| 27E7 | ......... | 305 | ........ | 312 | ...... | 307 | ........ | 308 | ........ | 309 | ...... | 310 |
| 20D10 | ......... | 305 | ........ | 312 | ...... | 307 | ........ | 308 | ........ | 309 | ...... | 310 |
| 30B9 | ......... | 305 | ........ | 312 | ...... | 307 | ........ | 308 | ........ | 309 | ...... | 310 |

SEQ ID NO: 58

Group 2 (6 members)
Light chain:

| | LV_CDR1 | SEQ ID NO: | LV_CDR2 | SEQ ID NO: | LV_CDR3 | SEQ ID NO: |
|---|---|---|---|---|---|---|
| CONSENSUS | SGSSSNIGNNFVS | 325 | DNNKRPS | 326 | GTWDSSLSGYV | 327 |
| 31G11 | .......... | 325 | ..S..... | 331 | ........A.. | 332 |
| 28D6 | .......... | 325 | ........ | 326 | ........... | 327 |
| 28B12 | .......... | 325 | ........ | 326 | ........... | 327 |
| 22B2 | .......... | 325 | ........ | 326 | ........... | 327 |
| 16F12 | .......... | 325 | ........ | 326 | ......A.. | 332 |
| 27A6 | .......... | 325 | ........ | 326 | ....S... | 337 |

FIG. 13H

Group 2, continued
Heavy chain:

| | H_CDR1 | SEQ ID NO: | H_CDR2 | SEQ ID NO: | H_CDR3 | SEQ ID NO: |
|---|---|---|---|---|---|---|
| CONSENSUS | SFGMH | 328 | LIWNDGSNKYYADSVKG | 329 | AIAALYYYGMDV | 330 |
| 31G11 | .Y... | 333 | ...H..T..V..... | 334 | G..VA....... | 335 |
| 28D6 | ..... | 328 | ............... | 329 | ............ | 330 |
| 28B12 | ..... | 328 | ............... | 329 | ............ | 330 |
| 22E2 | ..... | 328 | ............... | 329 | ............ | 330 |
| 16F12 | ..... | 328 | ...S...DE...... | 336 | ............ | 330 |
| 27A6 | ..... | 328 | ...S....D...... | 338 | ............ | 330 |

Group 3 (3 members)

| | LV_CDR1 | SEQ ID NO: | LV_CDR2 | SEQ ID NO: | LV_CDR3 | SEQ ID NO: | H_CDR1 | SEQ ID NO: | H_CDR2 | SEQ ID NO: | H_CDR3 | SEQ ID NO: |
|---|---|---|---|---|---|---|---|---|---|---|---|---|
| CONSENSUS | SGSSSNIGSKTVN | 339 | SNNRRPS | 340 | AARDDSLRWV | 341 | YWMS | 342 | NIKQDGSERYYVDSVKG | 343 | ESNRGFAFDI | 344 |
| 9H6 | .......N... | 345 | ....... | 340 | .......... | 341 | R.... | 346 | .....R.......... | 347 | .........Y | 348 |
| 9C9 | ........... | 339 | R.Q.L | 349 | .......... | 341 | S.... | 350 | ................. | 343 | .......... | 344 |
| 1A12 | ........... | 339 | ....... | 340 | .......... | 341 | NF... | 351 | ................. | 343 | .......... | 344 |

Group 4 (2 members)

| | KV_CDR1 | SEQ ID NO. | KV_CDR2 | SEQ ID NO. | KV_CDR3 | SEQ ID NO. |
|---|---|---|---|---|---|---|
| CONSENSUS | RASQSIS YLR | 352 | AA SLQS | 353 | QQSYS PIT | 354 |
| 25G4 | .......I... | 355 | ..A... | 356 | ....A... | 357 |
| 23B5 | .......S... | 358 | ..S... | 359 | ....S... | 360 |

| | H_CDR1 | SEQ ID NO: | H_CDR2 | SEQ ID NO: | H_CDR3 | SEQ ID NO: |
|---|---|---|---|---|---|---|
| CONSENSUS | SYAMM | 361 | TISGSG NTYYADSVKG | 362 | KFVLMVYAMLDY | 363 |
| 25G4 | ..... | 361 | .......G......... | 362 | ............ | 363 |
| 23B5 | ..... | 361 | .......D......... | 362 | ............ | 363 |

FIG. 13J

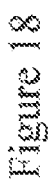
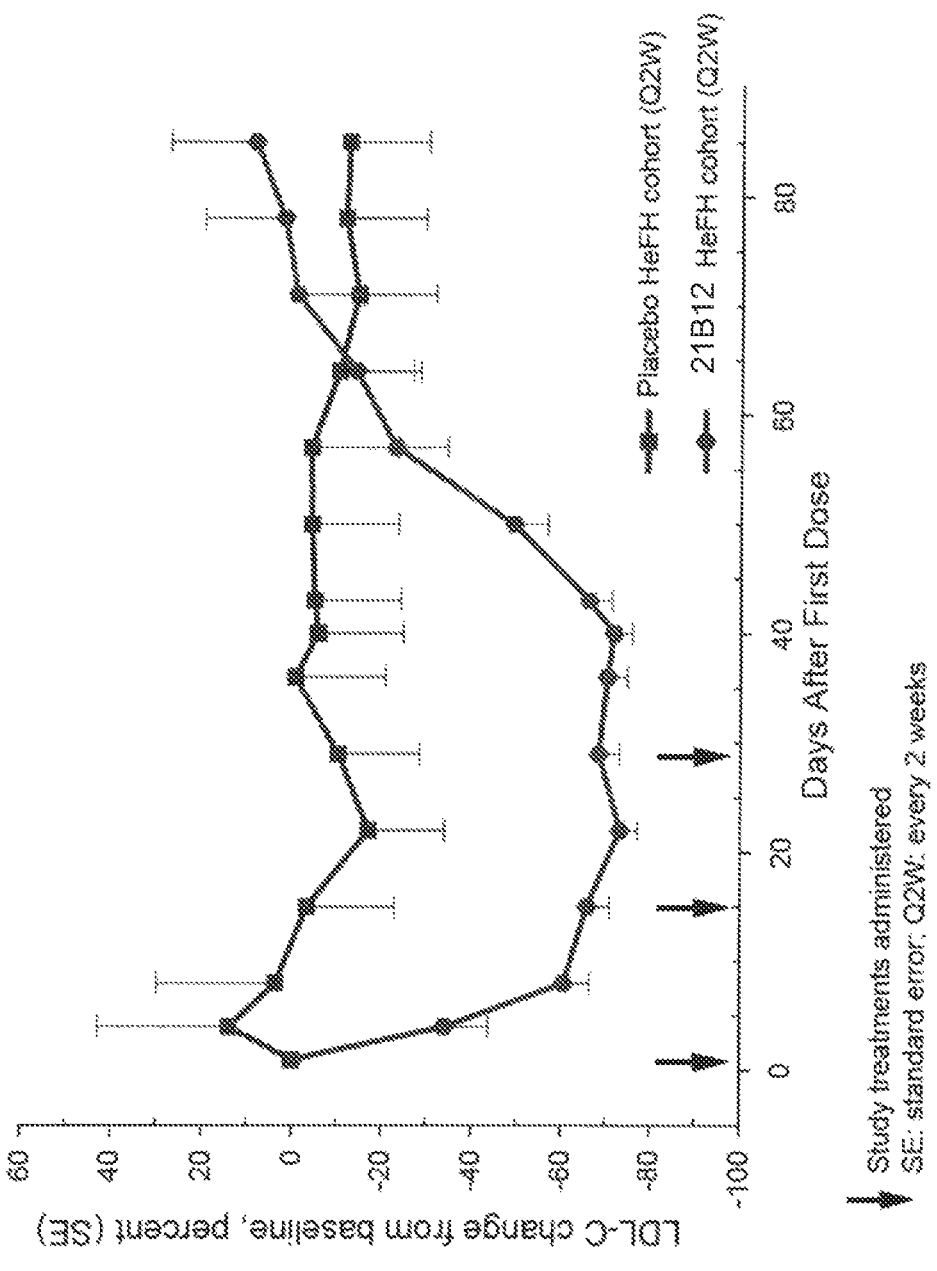
Figure 18

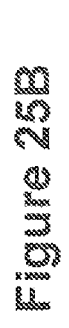
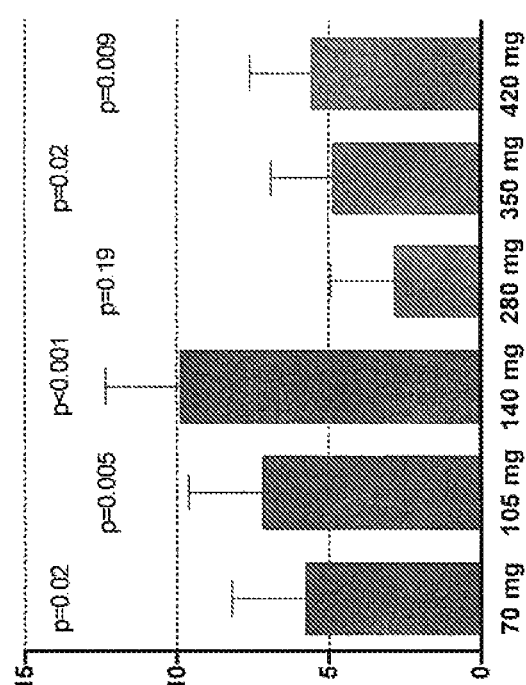
Figure 25B
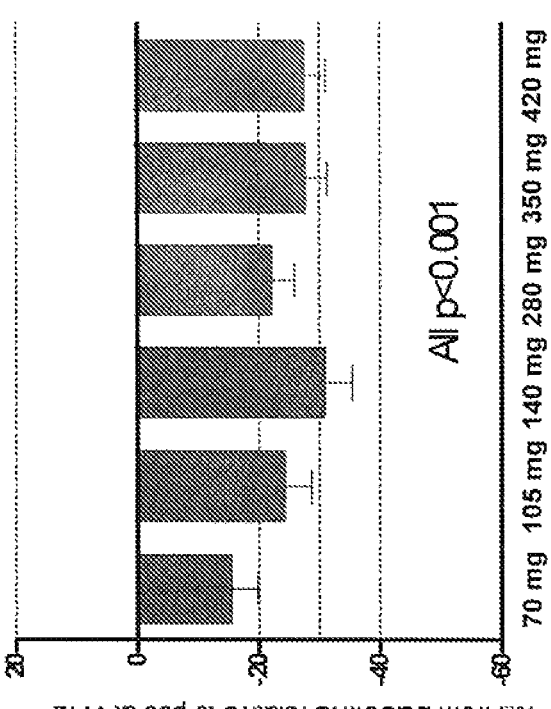
Figure 25A

4 @ 25C

4 @ 40C

1 @ 25C

1 @ 40C

Viscosity (cP)

Protein Concentration (mg/mL)

Figure 30A
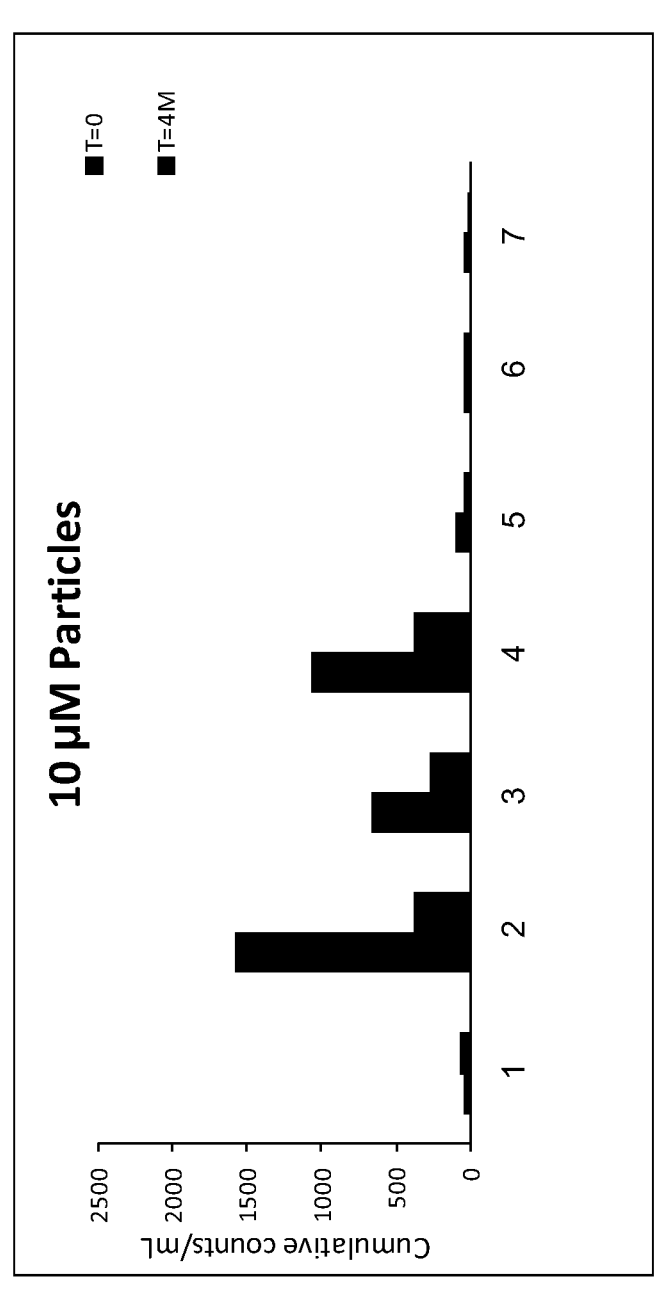

| Antibody | $AUC_{0-t}$ ($\mu g \cdot h/mL$) | $CL_{0-t}$ (mL/h/kg) | Apparent $t_{1/2}$ (h) |
|----------|------------------|-----------------|-------------------|
| IgG2 | 23,500 | 0.511 | >120 |
| 11F1 | 34,700 | 0.865 | 83 |
| 8A3 | 36,700 | 0.817 | 59 |

Figure 40

| Antibody | Mean (± SD) Pharmacokinetic Parameters | | | |
|---|---|---|---|---|
| | $t_{1/2,z}$ (h) | CL/F (mL/h/kg) | Cmax (µg/mL) | $AUC_{0 \to \infty}$ (µg*h/mL) |
| Anti-KLH | 220 ± 130 | 0.234 ± 0.036 | 5.08 ± 0.15 | 2,170 ± 320 |
| 21B12 | 40 ± 6 | 1.57 ± 0.68 | 6.22 ± 2.21 | 355 ± 109 |
| 11F1 | 210 ± 110 | 0.228 ± 0.081 | 6.72 ± 0.62 | 2,440 ± 910 |
| 8A3 | 190 ± 40 | 0.255 ± 0.039 | 6.63 ± 0.66 | 1,990 ± 290 |

Figure 47

SEQUENCE LISTING

```
<160> NUMBER OF SEQ ID NOS: 575

<210> SEQ ID NO 1
<211> LENGTH: 662
<212> TYPE: PRT
<213> ORGANISM: Homo sapiens

<400> SEQUENCE: 1

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
            35                  40                  45

Val Val Val Leu Lys Glu Glu Thr His Leu Ser Gln Ser Glu Arg Thr
        50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270
```

```
Arg Leu Ala Arg Ala Gly Val Val Leu Val Thr Ala Ala Gly Asn Phe
    275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
                340                 345                 350

Ser Gly Thr Ser Gln Ala Ala Ala His Val Ala Gly Ile Ala Ala Met
                355                 360                 365

Met Leu Ser Ala Glu Pro Glu Leu Thr Leu Ala Glu Leu Arg Gln Arg
    370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
                420                 425                 430

Ala His Ser Gly Pro Thr Arg Met Ala Thr Ala Ile Ala Arg Cys Ala
                435                 440                 445

Pro Asp Glu Glu Leu Leu Ser Cys Ser Ser Phe Ser Arg Ser Gly Lys
    450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
                500                 505                 510

Glu Ala Ser Met Gly Thr Arg Val His Cys His Gln Gln Gly His Val
                515                 520                 525

Leu Thr Gly Cys Ser Ser His Trp Glu Val Glu Asp Leu Gly Thr His
    530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Gly Gln Val
                580                 585                 590

Thr Val Ala Cys Glu Glu Gly Trp Thr Leu Thr Gly Cys Ser Ala Leu
                595                 600                 605

Pro Gly Thr Ser His Val Leu Gly Ala Tyr Ala Val Asp Asn Thr Cys
    610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660
```

<210> SEQ ID NO 2
<211> LENGTH: 2076

<212> TYPE: DNA
<213> ORGANISM: Homo sapiens

<400> SEQUENCE: 2
atgggcaccg tcagctccag gcggtcctgg tggccgctgc cactgctgct gctgctgctg      60
ctgctcctgg gtcccgcggg cgcccgtgcg caggaggacg aggacggcga ctacgaggag     120
ctggtgctag ccttgcgctc cgaggaggac ggcctggccg aagcacccga gcacggaacc     180
acagccacct tccaccgctg cgccaaggat ccgtggaggt tgcctggcac ctacgtggtg     240
gtgctgaagg aggagaccca cctctcgcag tcagagcgca ctgcccgccg cctgcaggcc     300
caggctgccc gccgggggata cctcaccaag atcctgcatg tcttccatgg ccttcttcct     360
ggcttcctgg tgaagatgag tggcgacctg ctggagctgg ccttgaagtt gccccatgtc     420
gactacatcg aggaggactc ctctgtcttt gcccagagca tcccgtggaa cctggagcgg     480
attacccctc cgcggtaccg ggcggatgaa taccagcccc ccgacggagg cagcctggtg     540
gaggtgtatc tcctagacac cagcatacag agtgaccacc gggaaatcga gggcagggtc     600
atggtcaccg acttcgagaa tgtgcccgag gaggacggga cccgcttcca cagacaggcc     660
agcaagtgtg acagtcatgg cacccacctg gcagggtggt cagcggccg ggatgccggc     720 gtggccaagg gtgccagcat cgcgcagcctg cgcgtgctca actgccaagg gaagggcacg     780
gttagcggca ccctcatagg cctggagttt attcggaaaa gccagctggt ccagcctgtg     840
gggccactgg tggtgctgct gccctggcg ggtgggtaca gccgcgtcct caacgccgcc     900
tgccagcgcc tggcgagggc tggggtcgtg ctggtcaccg ctgccggcaa cttccgggac     960
gatgcctgcc tctactcccc agcctcagct cccgaggtca tcacagttgg ggccaccaat    1020
gcccaggacc agccggtgac cctggggact ttggggacca actttggccg ctgtgtggac    1080
ctctttgccc aggggagga catcattggt gcctccagcg actgcagcac ctgctttgtg    1140
tcacagagtg ggacatcaca ggctgctgcc cacgtggctg gcattgcagc catgatgctg    1200
tctgccgagc cggagctcac cctggccgag ttgaggcaga gactgatcca cttctctgcc    1260
aaagatgtca tcaatgaggc ctggttccct gaggaccagc gggtactgac ccccaacctg    1320
gtggccgccc tgcccccag cacccatggg gcaggttggc agctgttttg caggactgtg    1380
tggtcagcac actcggggcc tacacggatg gccacagcca tcgcccgctg cgccccagat    1440
gaggagctgc tgagctgctc cagtttctcc aggagtggga agcggcgggg cgagcgcatg    1500
gaggcccaag ggggcaagct ggtctgccgg gcccacaacg cttttggggg tgagggtgtc    1560
tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc cacagggagg ccagcatcca cgcttcctgc    1800
tgccatgccc caggtctgga atgcaaagtc aaggagcatg gaatcccggc ccctcagggg    1860
caggtgaccg tggcctgcga ggagggctgg accctgactg gctgcagcgc cctccctggg    1920
acctcccacg tcctgggggc ctacgccgta gacaacacgt gtgtagtcag gagccgggac    1980
gtcagcacta caggcagcac cagcgaagag gccgtgacac ccgttgccat ctgctgccgg    2040
agccggcacc tggcgcaggc ctcccaggag ctccag                              2076

<210> SEQ ID NO 3
<211> LENGTH: 692
<212> TYPE: PRT

-continued

<213> ORGANISM: Homo sapiens

<400> SEQUENCE: 3

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400
```

-continued

Ser Ala Glu Pro Glu Leu Thr Leu Ala Glu Leu Arg Gln Arg Leu Ile
                405                     410                     415

His Phe Ser Ala Lys Asp Val Ile Asn Glu Ala Trp Phe Pro Glu Asp
                420                     425                     430

Gln Arg Val Leu Thr Pro Asn Leu Val Ala Ala Leu Pro Pro Ser Thr
                435                     440                     445

His Gly Ala Gly Trp Gln Leu Phe Cys Arg Thr Val Trp Ser Ala His
    450                     455                     460

Ser Gly Pro Thr Arg Met Ala Thr Ala Ile Ala Arg Cys Ala Pro Asp
465                     470                     475                     480

Glu Glu Leu Leu Ser Cys Ser Ser Phe Ser Arg Ser Gly Lys Arg Arg
                485                     490                     495

Gly Glu Arg Met Glu Ala Gln Gly Gly Lys Leu Val Cys Arg Ala His
                500                     505                     510

Asn Ala Phe Gly Gly Glu Gly Val Tyr Ala Ile Ala Arg Cys Cys Leu
                515                     520                     525

Leu Pro Gln Ala Asn Cys Ser Val His Thr Ala Pro Pro Ala Glu Ala
                530                     535                     540

Ser Met Gly Thr Arg Val His Cys His Gln Gln Gly His Val Leu Thr
545                     550                     555                     560

Gly Cys Ser Ser His Trp Glu Val Glu Asp Leu Gly Thr His Lys Pro
                565                     570                     575

Pro Val Leu Arg Pro Arg Gly Gln Pro Asn Gln Cys Val Gly His Arg
                580                     585                     590

Glu Ala Ser Ile His Ala Ser Cys Cys His Ala Pro Gly Leu Glu Cys
                595                     600                     605

Lys Val Lys Glu His Gly Ile Pro Ala Pro Gln Gly Gln Val Thr Val
    610                     615                     620

Ala Cys Glu Glu Gly Trp Thr Leu Thr Gly Cys Ser Ala Leu Pro Gly
625                     630                     635                     640

Thr Ser His Val Leu Gly Ala Tyr Ala Val Asp Asn Thr Cys Val Val
                645                     650                     655

Arg Ser Arg Asp Val Ser Thr Thr Gly Ser Thr Ser Glu Glu Ala Val
                660                     665                     670

Thr Ala Val Ala Ile Cys Cys Arg Ser Arg His Leu Ala Gln Ala Ser
                675                     680                     685

Gln Glu Leu Gln
    690

<210> SEQ ID NO 4
<211> LENGTH: 112
<212> TYPE: PRT
<213> ORGANISM: Homo sapiens

<400> SEQUENCE: 4

Asp Ile Val Met Thr Gln Ser Pro Leu Ser Leu Pro Val Thr Pro Gly
1               5                       10                      15

Glu Pro Ala Ser Ile Ser Cys Arg Ser Ser Gln Ser Leu Leu His Ser
                20                      25                      30

Asn Gly Tyr Asn Tyr Leu Asp Trp Tyr Leu Gln Lys Pro Gly Gln Ser
            35                      40                      45

Pro Gln Leu Leu Ile Tyr Leu Gly Ser Asn Arg Ala Ser Gly Val Pro
    50                      55                      60

Asp Arg Phe Ser Gly Ser Gly Ser Gly Thr Asp Phe Thr Leu Lys Ile
65                      70                      75                      80

-continued

```
Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 5
<211> LENGTH: 112
<212> TYPE: PRT
<213> ORGANISM: Homo sapiens

<400> SEQUENCE: 5

Asp Ile Val Met Thr Gln Ser Pro Leu Ser Leu Ser Val Thr Pro Gly
1               5                   10                  15

Glu Pro Pro Ser Ile Ser Cys Arg Ser Ser Gln Ser Leu Leu His Ser
            20                  25                  30

Asn Gly Tyr Asn Phe Leu Asn Trp Tyr Leu Gln Lys Pro Gly Gln Ser
        35                  40                  45

Pro Gln Leu Leu Ile Tyr Leu Gly Ser His Arg Ala Ser Gly Val Pro
    50                  55                  60

Asp Arg Phe Ser Gly Ser Gly Ser Gly Thr Asp Phe Thr Leu Glu Ile
65                  70                  75                  80

Ser Arg Val Glu Ala Glu Asp Val Gly Val Tyr Tyr Cys Met Gln Val
                85                  90                  95

Leu Gln Thr Pro Phe Thr Phe Gly Pro Gly Thr Lys Val Asp Ile Lys
            100                 105                 110

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 7
<211> LENGTH: 107
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Asn Tyr
            20                  25                  30
```

-continued

```
Leu Ser Trp Tyr Leu Gln Lys Pro Gly Ile Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Ser
65              70              75              80

Glu Asp Phe Ala Thr Tyr Tyr Cys Gln Gln Ser Tyr Ser Thr Pro Leu
                85              90              95

Ile Phe Gly Gly Gly Thr Lys Val Glu Ile Lys
            100             105
```

```
<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Ile Ser Ser Tyr
            20              25              30

Leu Asn Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Ile
                85              90              95

Thr Phe Gly Gln Gly Thr Arg Leu Glu Ile Lys
            100             105
```

```
<210> SEQ ID NO 9
<211> LENGTH: 107
<212> TYPE: PRT
<213> ORGANISM: Homo sapiens

<400> SEQUENCE: 9

Asp Ile Leu Met Thr Gln Ser Pro Ser Ser Leu Ser Ala Ser Val Gly
1               5               10              15

Asp Arg Val Thr Ile Thr Cys Arg Ala Ser Gln Ser Ile Ser Ser Tyr
            20              25              30

Leu Asn Trp Tyr Gln Gln Lys Pro Gly Lys Ala Pro Lys Val Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Asn Ser Leu Gln Pro
65              70              75              80

Glu Asp Phe Ala Thr Tyr Tyr Cys Gln Gln Ser Tyr Ser Ser Pro Ile
                85              90              95

Thr Phe Gly Gln Gly Thr Arg Leu Glu Ile Lys
            100             105
```

```
<210> SEQ ID NO 10
<211> LENGTH: 107
<212> TYPE: PRT
<213> ORGANISM: Homo sapiens
```

```
<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ile Tyr
            20                  25                  30

Leu Asn Trp Tyr Gln Gln Lys Pro Gly Lys Ala Pro Tyr Leu Leu Ile
        35                  40                  45

Tyr Ala Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Ile
                85                  90                  95

Thr Phe Gly Gln Gly Thr Arg Leu Glu Ile Lys
            100                 105

<210> SEQ ID NO 11
<211> LENGTH: 111
<212> TYPE: PRT
<213> ORGANISM: Homo sapiens

<400> SEQUENCE: 11

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 12
<211> LENGTH: 111
<212> TYPE: PRT
<213> ORGANISM: Homo sapiens

<400> SEQUENCE: 12

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Ser Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
```

-continued

```
              100              105              110
```

```
<210> SEQ ID NO 13
<211> LENGTH: 111
<212> TYPE: PRT
<213> ORGANISM: Homo sapiens

<400> SEQUENCE: 13

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala His
                20                  25                  30

Tyr Asp Val His Trp Tyr Gln Gln Val Pro Gly Thr Ala Pro Lys Leu
            35                  40                  45

Leu Ile Tyr Gly Asn Thr Tyr Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Gly Val Val Phe Gly Gly Gly Thr Lys Leu Thr Val Leu
            100                 105                 110

<210> SEQ ID NO 14
<211> LENGTH: 108
<212> TYPE: PRT
<213> ORGANISM: Homo sapiens

<400> SEQUENCE: 14

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Val Phe Gly Gly Gly Thr Lys Leu Thr Val Leu
            100                 105

<210> SEQ ID NO 15
<211> LENGTH: 109
<212> TYPE: PRT
<213> ORGANISM: Homo sapiens

<400> SEQUENCE: 15

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr
                20                  25                  30

Asn Ser Val Ser Trp Tyr Gln His His Pro Gly Lys Ala Pro Lys Val
            35                  40                  45

Met Ile Tyr Glu Val Ser Asn Arg Pro Ser Gly Val Ser Thr Arg Phe
        50                  55                  60
```

-continued

```
Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Val Val Phe Gly Gly Gly Thr Lys Leu Thr Val Leu
            100                 105

<210> SEQ ID NO 16
<211> LENGTH: 109
<212> TYPE: PRT
<213> ORGANISM: Homo sapiens

<400> SEQUENCE: 16

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Pro Pro Lys Leu
            35                  40                  45

Met Ile Tyr Glu Val Ser Asn Arg Pro Ser Gly Val Ser Ile Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 17
<211> LENGTH: 109
<212> TYPE: PRT
<213> ORGANISM: Homo sapiens

<400> SEQUENCE: 17

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Pro Pro Lys Leu
            35                  40                  45

Met Ile Tyr Glu Val Ser Asn Arg Pro Ser Gly Val Ser Ile Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 18
<211> LENGTH: 109
<212> TYPE: PRT
<213> ORGANISM: Homo sapiens

<400> SEQUENCE: 18

Gln Ser Ala Leu Thr Gln Pro Ala Ser Val Ser Gly Ser Pro Gly Gln
1               5                   10                  15
```

-continued

```
Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Ala Val Leu
            100                 105
```

```
<210> SEQ ID NO 19
<211> LENGTH: 109
<212> TYPE: PRT
<213> ORGANISM: Homo sapiens

<400> SEQUENCE: 19
```

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln Tyr Pro Gly Lys Pro Pro Lys Leu
        35                  40                  45

Lys Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105
```

```
<210> SEQ ID NO 20
<211> LENGTH: 109
<212> TYPE: PRT
<213> ORGANISM: Homo sapiens

<400> SEQUENCE: 20
```

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105
```

```
<210> SEQ ID NO 21
<211> LENGTH: 109
```

```
<212> TYPE: PRT
<213> ORGANISM: Homo sapiens

<400> SEQUENCE: 21

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 22
<211> LENGTH: 109
<212> TYPE: PRT
<213> ORGANISM: Homo sapiens

<400> SEQUENCE: 22

Gln Ser Ala Leu Thr Gln Pro Ala Ser Val Ser Gly Ser Pro Gly Gln
1               5                   10                  15

Ser Ile Thr Ile Ser Cys Thr Gly Thr Asn Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 23
<211> LENGTH: 109
<212> TYPE: PRT
<213> ORGANISM: Homo sapiens

<400> SEQUENCE: 23

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
```

-continued

```
              85              90              95

Ser Met Val Phe Gly Gly Gly Thr Lys Leu Thr Val Leu
            100             105

<210> SEQ ID NO 24
<211> LENGTH: 109
<212> TYPE: PRT
<213> ORGANISM: Homo sapiens

<400> SEQUENCE: 24

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
                20                  25                  30

Asn Ser Val Ser Trp Tyr Gln Gln His Pro Gly Lys Ala Pro Lys Arg
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Asn Met Val Phe Gly Gly Gly Thr Lys Leu Thr Val Leu
            100             105

<210> SEQ ID NO 25
<211> LENGTH: 108
<212> TYPE: PRT
<213> ORGANISM: Homo sapiens

<400> SEQUENCE: 25

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Val Phe Gly Gly Gly Thr Lys Leu Thr Val Leu
            100             105

<210> SEQ ID NO 26
<211> LENGTH: 109
<212> TYPE: PRT
<213> ORGANISM: Homo sapiens

<400> SEQUENCE: 26

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45
```

-continued

```
Met Ile Tyr Glu Val Thr Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 27
<211> LENGTH: 108
<212> TYPE: PRT
<213> ORGANISM: Homo sapiens

<400> SEQUENCE: 27

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe Gly Gly Gly Thr Lys Leu Thr Val Leu
            100                 105

<210> SEQ ID NO 28
<211> LENGTH: 110
<212> TYPE: PRT
<213> ORGANISM: Homo sapiens

<400> SEQUENCE: 28

Leu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asn Tyr
            20                  25                  30

Asn Leu Val Ser Trp Tyr Gln Gln Tyr Ser Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Leu Val Phe Gly Gly Gly Thr Lys Leu Thr Val Leu
            100                 105                 110

<210> SEQ ID NO 29
<211> LENGTH: 108
<212> TYPE: PRT
<213> ORGANISM: Homo sapiens

<400> SEQUENCE: 29
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Val Phe Gly Gly Gly Thr Lys Leu Thr Val Leu
                100                 105

<210> SEQ ID NO 30
<211> LENGTH: 109
<212> TYPE: PRT
<213> ORGANISM: Homo sapiens

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Lys
            20                  25                  30

Thr Val Asn Trp Tyr Gln Gln Val Pro Gly Thr Ala Pro Lys Leu Leu
        35                  40                  45

Ile Tyr Arg Asn Asn Gln Arg Pro Leu Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Trp Val Phe Gly Gly Gly Thr Lys Leu Thr Val Leu
                100                 105

<210> SEQ ID NO 31
<211> LENGTH: 109
<212> TYPE: PRT
<213> ORGANISM: Homo sapiens

<400> SEQUENCE: 31

Gln Ser Val Leu Thr Gln Pro Pro Ser Ala Ser Gly Pro Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Trp Val Phe Gly Gly Gly Thr Lys Leu Thr Val Leu
                100                 105
```

```
<210> SEQ ID NO 32
<211> LENGTH: 110
<212> TYPE: PRT
<213> ORGANISM: Homo sapiens

<400> SEQUENCE: 32

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Val Trp Asp Asp Ser Leu
                85                  90                  95

Asn Gly Trp Val Phe Gly Gly Gly Thr Lys Leu Thr Val Leu
            100                 105                 110

<210> SEQ ID NO 33
<211> LENGTH: 109
<212> TYPE: PRT
<213> ORGANISM: Homo sapiens

<400> SEQUENCE: 33

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Lys
            20                  25                  30

Thr Val Asn Trp Tyr Gln Gln Phe Pro Gly Thr Ala Pro Lys Leu Leu
        35                  40                  45

Ile Tyr Ser Asn Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Trp Val Phe Gly Ala Gly Thr Lys Leu Thr Val Leu
            100                 105

<210> SEQ ID NO 34
<211> LENGTH: 110
<212> TYPE: PRT
<213> ORGANISM: Homo sapiens

<400> SEQUENCE: 34

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
```

```
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
                100                 105                 110

<210> SEQ ID NO 35
<211> LENGTH: 110
<212> TYPE: PRT
<213> ORGANISM: Homo sapiens

<400> SEQUENCE: 35

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Phe Val Ser Trp Tyr Gln Gln Leu Pro Gly Thr Ala Pro Lys Leu Leu
                35                  40                  45

Ile Tyr Asp Tyr Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Arg Val Thr Val Leu
                100                 105                 110

<210> SEQ ID NO 36
<211> LENGTH: 110
<212> TYPE: PRT
<213> ORGANISM: Homo sapiens

<400> SEQUENCE: 36

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Phe Val Ser Trp Tyr Gln Gln Leu Pro Gly Thr Ala Pro Lys Leu Leu
                35                  40                  45

Ile Tyr Asp Tyr Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Tyr Val Phe Gly Thr Gly Thr Arg Val Thr Val Leu
                100                 105                 110

<210> SEQ ID NO 37
<211> LENGTH: 110
<212> TYPE: PRT
<213> ORGANISM: Homo sapiens

<400> SEQUENCE: 37

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30
```

-continued

```
Phe Val Ser Trp Tyr Gln Gln Phe Pro Gly Thr Ala Pro Lys Leu Leu
        35                  40                  45

Ile Tyr Asp Tyr Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ser Tyr Val Phe Gly Thr Gly Thr Arg Val Thr Val Leu
            100                 105                 110
```

<210> SEQ ID NO 38
<211> LENGTH: 110
<212> TYPE: PRT
<213> ORGANISM: Homo sapiens

<400> SEQUENCE: 38

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Gln Leu Pro Gly Thr Ala Pro Lys Leu Leu
        35                  40                  45

Ile Tyr Asp Tyr Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Tyr Val Phe Gly Thr Gly Thr Arg Val Thr Val Leu
            100                 105                 110
```

<210> SEQ ID NO 39
<211> LENGTH: 110
<212> TYPE: PRT
<213> ORGANISM: Homo sapiens

<400> SEQUENCE: 39

```
Gln Ser Val Leu Thr Gln Pro Pro Thr Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Gln Leu Pro Gly Thr Ala Pro Lys Leu Leu
        35                  40                  45

Ile Tyr Asp Tyr Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Tyr Val Phe Gly Thr Gly Thr Arg Val Thr Val Leu
            100                 105                 110
```

<210> SEQ ID NO 40
<211> LENGTH: 110
<212> TYPE: PRT
<213> ORGANISM: Homo sapiens

<400> SEQUENCE: 40

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Phe Val Ser Trp Tyr Gln Gln Leu Pro Gly Thr Ala Pro Lys Leu Leu
            35                  40                  45

Ile Tyr Asp Ser Asn Lys Arg Pro Ser Gly Ile Pro Asp Arg Phe Ser
        50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
                100                 105                 110

<210> SEQ ID NO 41
<211> LENGTH: 110
<212> TYPE: PRT
<213> ORGANISM: Homo sapiens

<400> SEQUENCE: 41

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
                100                 105                 110

<210> SEQ ID NO 42
<211> LENGTH: 110
<212> TYPE: PRT
<213> ORGANISM: Homo sapiens

<400> SEQUENCE: 42

Gln Ser Val Leu Thr Gln Pro Pro Ser Val Ser Ala Ala Pro Gly Gln
1               5                   10                  15

Lys Val Thr Ile Ser Cys Ser Gly Ser Asn Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Asn Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

```
Ser Ala Val Val Phe Gly Gly Gly Thr Lys Leu Thr Val Leu
            100                 105                 110

<210> SEQ ID NO 43
<211> LENGTH: 107
<212> TYPE: PRT
<213> ORGANISM: Homo sapiens

<400> SEQUENCE: 43

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu
            100                 105

<210> SEQ ID NO 44
<211> LENGTH: 106
<212> TYPE: PRT
<213> ORGANISM: Homo sapiens

<400> SEQUENCE: 44

Ser Tyr Glu Leu Thr Gln Pro Pro Ser Val Ser Val Ser Pro Gly Gln
1               5                   10                  15

Thr Ala Arg Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asn Thr Lys Trp Pro Leu Gly Ile Pro Glu Arg Phe Ser Gly Ser
    50                  55                  60

Lys Ser Gly Asn Thr Val Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 45
<211> LENGTH: 116
<212> TYPE: PRT
<213> ORGANISM: Homo sapiens

<400> SEQUENCE: 45

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
```

```
              50                 55                 60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                    85                  90                  95

His Gly Ser Gly Ser Asn Phe Val Val Val Phe Gly Gly Gly Thr Lys
                    100                 105                 110

Leu Thr Val Leu
          115

<210> SEQ ID NO 46
<211> LENGTH: 116
<212> TYPE: PRT
<213> ORGANISM: Homo sapiens

<400> SEQUENCE: 46

Gln Pro Val Leu Thr Gln Pro Leu Phe Ala Ser Ala Ser Leu Gly Ala
1                   5                   10                  15

Ser Val Thr Leu Thr Cys Thr Leu Ser Ser Gly Tyr Ser Ser Tyr Glu
                    20                  25                  30

Val Asp Trp Tyr Gln Gln Arg Pro Gly Lys Gly Pro Arg Phe Val Met
                    35                  40                  45

Arg Val Asp Thr Gly Gly Ile Val Gly Ser Lys Gly Glu Gly Ile Pro
          50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                    85                  90                  95

His Gly Ser Gly Thr Asn Phe Val Val Val Phe Gly Gly Gly Thr Lys
                    100                 105                 110

Leu Thr Val Leu
          115

<210> SEQ ID NO 47
<211> LENGTH: 114
<212> TYPE: PRT
<213> ORGANISM: Homo sapiens

<400> SEQUENCE: 47

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Ser Tyr
                    20                  25                  30

Gly Ile Ser Trp Val Arg Gln Ala Pro Gly Gln Gly Leu Glu Trp Met
          35                  40                  45

Gly Trp Ile Ser Ala Tyr Asn Gly Asn Thr Asn Tyr Ala Gln Lys Leu
          50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                    85                  90                  95

Ala Arg Tyr Gly Met Asp Val Trp Gly Gln Gly Thr Thr Val Thr Val
                    100                 105                 110

Ser Ser

<210> SEQ ID NO 48
```

```
<211> LENGTH: 115
<212> TYPE: PRT
<213> ORGANISM: Homo sapiens

<400> SEQUENCE: 48

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Pro Leu Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Val
        50                  55                  60

Gln Gly Ser Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 49
<211> LENGTH: 115
<212> TYPE: PRT
<213> ORGANISM: Homo sapiens

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Gly Ile Ser Trp Val Arg Gln Ala Pro Gly Gln Gly Leu Glu Trp Met
            35                  40                  45

Gly Trp Val Ser Phe Tyr Asn Gly Asn Thr Asn Tyr Ala Gln Lys Leu
        50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 50
<211> LENGTH: 115
<212> TYPE: PRT
<213> ORGANISM: Homo sapiens

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Gly Ile Ser Trp Val Arg Gln Ala Pro Gly Gln Gly Leu Glu Trp Met
            35                  40                  45
```

-continued

```
Gly Trp Val Ser Phe Tyr Asn Gly Asn Thr Asn Tyr Ala Gln Lys Leu
    50              55              60

Gln Gly Arg Gly Thr Met Thr Thr Asp Pro Ser Thr Ser Thr Ala Tyr
65              70              75              80

Met Glu Leu Arg Ser Leu Arg Ser Asp Asp Thr Ala Val Tyr Tyr Cys
                85              90              95

Ala Arg Gly Tyr Gly Met Asp Val Trp Gly Gln Gly Thr Thr Val Thr
            100             105             110

Val Ser Ser
        115

<210> SEQ ID NO 51
<211> LENGTH: 115
<212> TYPE: PRT
<213> ORGANISM: Homo sapiens

<400> SEQUENCE: 51

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Leu Thr Ser Tyr
            20              25              30

Gly Ile Ser Trp Val Arg Gln Ala Pro Gly Gln Gly Leu Glu Trp Met
        35              40              45

Gly Trp Ile Ser Phe Tyr Asn Gly Asn Thr Asn Tyr Ala Gln Lys Val
    50              55              60

Gln Gly Arg Val Thr Met Thr Thr Asp Thr Ser Thr Ser Thr Val Tyr
65              70              75              80

Met Glu Leu Arg Ser Leu Arg Ser Asp Asp Thr Ala Val Tyr Tyr Cys
                85              90              95

Ala Arg Gly Tyr Gly Met Asp Val Trp Gly Gln Gly Thr Thr Val Thr
            100             105             110

Val Ser Ser
        115

<210> SEQ ID NO 52
<211> LENGTH: 115
<212> TYPE: PRT
<213> ORGANISM: Homo sapiens

<400> SEQUENCE: 52

Gln Val Gln Leu Val Gln Ser Gly Ala Glu Val Lys Arg Pro Gly Ala
1               5               10              15

Ser Val Lys Val Ser Cys Lys Ala Ser Gly Tyr Thr Leu Thr Ser Tyr
            20              25              30

Gly Ile Ser Trp Val Arg Gln Ala Pro Gly Gln Gly Leu Glu Trp Met
        35              40              45

Gly Trp Ile Ser Val Tyr Asn Gly Asn Thr Asn Tyr Ala Gln Lys Val
    50              55              60

Gln Gly Arg Val Thr Met Thr Thr Asp Thr Ser Thr Ser Thr Val Tyr
65              70              75              80

Met Glu Leu Arg Ser Leu Ser Ser Asp Asp Thr Ala Val Tyr Tyr Cys
                85              90              95

Ala Arg Gly Tyr Gly Met Asp Val Trp Gly Gln Gly Thr Thr Val Thr
            100             105             110

Val Ser Ser
        115
```

-continued

<210> SEQ ID NO 53
<211> LENGTH: 115
<212> TYPE: PRT
<213> ORGANISM: Homo sapiens

<400> SEQUENCE: 53

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Phe Tyr Asn Gly Asn Thr Asn Tyr Ala Gln Lys Val
    50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Phe Cys
                85                  90                  95

Ala Arg Gly Tyr Gly Met Asp Val Trp Gly Gln Gly Thr Thr Val Thr
            100                 105                 110

Val Ser Ser
        115
```

<210> SEQ ID NO 54
<211> LENGTH: 115
<212> TYPE: PRT
<213> ORGANISM: Homo sapiens

<400> SEQUENCE: 54

```
Gln Val Gln Leu Val Gln Ser Gly Ala Glu Val Lys Lys Pro Gly Ala
1               5                   10                  15

Ser Leu Lys Val Ser Cys Lys Ala Ser Gly Tyr Ser Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Val
    50                  55                  60

Gln Gly Arg Val Thr Met Thr Thr Asp Thr Ser Thr Ser Thr Val Tyr
65                  70                  75                  80

Met Glu Val Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115
```

<210> SEQ ID NO 55
<211> LENGTH: 115
<212> TYPE: PRT
<213> ORGANISM: Homo sapiens

<400> SEQUENCE: 55

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Leu Thr Ser Tyr
            20                  25                  30

Gly Ile Ser Trp Val Arg Gln Ala Pro Gly Gln Gly Leu Glu Trp Met
```

-continued

```
                35                    40                    45
Gly Trp Ile Ser Ala Tyr Asn Gly Asn Thr Asn Tyr Ala Gln Lys Val
    50                    55                    60
Gln Gly Arg Val Thr Met Thr Thr Asp Thr Ser Thr Ser Thr Val Tyr
65                    70                    75                    80
Met Glu Leu Arg Ser Leu Arg Ser Asp Asp Thr Ala Val Tyr Tyr Cys
                85                    90                    95
Ala Arg Gly Tyr Gly Met Asp Val Trp Gly Gln Gly Thr Thr Val Thr
                100                   105                   110
Val Ser Ser
        115

<210> SEQ ID NO 56
<211> LENGTH: 115
<212> TYPE: PRT
<213> ORGANISM: Homo sapiens

<400> SEQUENCE: 56

Gln Val Gln Leu Val Gln Ser Gly Ala Glu Val Lys Lys Pro Gly Ala
1                 5                    10                    15
Ser Val Lys Val Ser Cys Lys Ala Ser Gly Tyr Ala Leu Thr Ser Tyr
                20                    25                    30
Gly Ile Ser Trp Val Arg Gln Ala Pro Gly Gln Gly Leu Glu Trp Met
            35                    40                    45
Gly Trp Ile Ser Ala Tyr Asn Gly Asn Thr Asn Tyr Ala Gln Lys Val
    50                    55                    60
Gln Gly Arg Val Thr Met Thr Thr Asp Thr Ser Thr Ser Thr Val Tyr
65                    70                    75                    80
Met Glu Leu Arg Ser Leu Arg Ser Asp Asp Thr Ala Val Tyr Tyr Cys
                85                    90                    95
Ala Arg Gly Tyr Gly Met Asp Val Trp Gly Gln Gly Thr Thr Val Thr
                100                   105                   110
Val Ser Ser
        115

<210> SEQ ID NO 57
<211> LENGTH: 115
<212> TYPE: PRT
<213> ORGANISM: Homo sapiens

<400> SEQUENCE: 57

Gln Val Gln Leu Val Gln Ser Gly Ala Glu Val Lys Lys Pro Gly Ala
1                 5                    10                    15
Ser Val Lys Val Ser Cys Lys Ala Ser Gly Tyr Ser Phe Thr Ser Tyr
                20                    25                    30
Gly Ile Ser Trp Val Arg Gln Ala Pro Gly Gln Gly Leu Glu Trp Met
            35                    40                    45
Gly Trp Val Ser Ala Tyr Asn Gly Asn Thr Asn Tyr Ala Gln Lys Phe
    50                    55                    60
Gln Gly Arg Val Thr Met Thr Thr Asp Thr Ser Thr Ser Thr Ala Tyr
65                    70                    75                    80
Met Glu Leu Arg Ser Leu Arg Ser Asp Asp Thr Ala Val Tyr Tyr Cys
                85                    90                    95
Ala Arg Gly Tyr Val Met Asp Val Trp Gly Gln Gly Thr Thr Val Thr
                100                   105                   110
Val Ser Ser
```

```
          115

<210> SEQ ID NO 58
<211> LENGTH: 115
<212> TYPE: PRT
<213> ORGANISM: Homo sapiens

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Glu Lys Leu
    50                  55                  60

Gln Gly Arg Val Thr Met Thr Thr Asp Thr Ser Thr Ser Thr Ala Tyr
65                  70                  75                  80

Met Glu Val Arg Ser Leu Arg Ser Asp Asp Thr Ala Val Phe Tyr Cys
                85                  90                  95

Ala Arg Gly Tyr Val Met Asp Val Trp Gly Gln Gly Thr Thr Val Thr
            100                 105                 110

Val Ser Ser
        115

<210> SEQ ID NO 59
<211> LENGTH: 113
<212> TYPE: PRT
<213> ORGANISM: Homo sapiens

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Asp Tyr Trp Gly Gln Gly Thr Leu Val Thr Val Ser
            100                 105                 110

Ser

<210> SEQ ID NO 60
<211> LENGTH: 115
<212> TYPE: PRT
<213> ORGANISM: Homo sapiens

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Gly Ile Ser Trp Val Arg Gln Ala Pro Gly Gln Gly Leu Glu Trp Met
    35                  40                  45
Gly Trp Ile Ser Thr Tyr Asn Gly Asn Thr Asn Tyr Ala Gln Lys Val
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Gly Tyr Thr Arg Asp Tyr Trp Gly Gln Gly Thr Leu Val Thr
            100                 105                 110
Val Ser Ser
        115

<210> SEQ ID NO 61
<211> LENGTH: 116
<212> TYPE: PRT
<213> ORGANISM: Homo sapiens

<400> SEQUENCE: 61

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Trp Met Ser Trp Val Arg Gln Ala Pro Gly Lys Gly Leu Glu Trp Val
            35                  40                  45
Ala Asn Ile Lys Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asn Trp Gly Ala Phe Asp Val Trp Gly Gln Gly Thr Met Val
            100                 105                 110
Thr Val Ser Ser
        115

<210> SEQ ID NO 62
<211> LENGTH: 119
<212> TYPE: PRT
<213> ORGANISM: Homo sapiens

<400> SEQUENCE: 62

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Arg Tyr
                20                  25                  30
Trp Met Ser Trp Val Arg Gln Ala Pro Gly Lys Gly Leu Glu Trp Val
            35                  40                  45
Ala Asn Ile Lys His Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Ser Asn Trp Gly Phe Ala Phe Asp Val Trp Gly His Gly
            100                 105                 110
```

```
Thr Met Val Thr Val Ser Ser
        115

<210> SEQ ID NO 63
<211> LENGTH: 116
<212> TYPE: PRT
<213> ORGANISM: Homo sapiens

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Gly Ala Phe Asp Ile Trp Gly Gln Gly Thr Met Val
            100                 105                 110

Thr Val Ser Ser
        115

<210> SEQ ID NO 64
<211> LENGTH: 119
<212> TYPE: PRT
<213> ORGANISM: Homo sapiens

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Asn Trp Gly Phe Ala Phe Asp Ile Trp Gly Gln Gly
            100                 105                 110

Thr Met Val Thr Val Ser Ser
        115

<210> SEQ ID NO 65
<211> LENGTH: 119
<212> TYPE: PRT
<213> ORGANISM: Homo sapiens

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Phe
```

-continued

```
                20              25              30

Trp Met Ser Trp Val Arg Gln Ala Pro Gly Lys Gly Leu Glu Trp Val
        35              40              45

Ala Asn Ile Lys Gln Asp Gly Ser Glu Lys Tyr Tyr Val Asp Ser Val
    50              55              60

Lys Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Val Tyr Ser Cys
                85              90              95

Thr Arg Glu Ser Asn Trp Gly Phe Ala Phe Asp Ile Trp Gly Gln Gly
            100             105             110

Thr Met Val Thr Val Ser Ser
        115

<210> SEQ ID NO 66
<211> LENGTH: 123
<212> TYPE: PRT
<213> ORGANISM: Homo sapiens

<400> SEQUENCE: 66

Glu Val Gln Leu Val Glu Ser Gly Gly Gly Leu Val Lys Pro Gly Gly
1               5               10              15

Ser Leu Arg Leu Ser Cys Ala Ala Ser Gly Phe Thr Phe Ser Ser Tyr
            20              25              30

Ser Met Asn Trp Val Arg Gln Ala Pro Gly Lys Gly Leu Glu Trp Val
        35              40              45

Ser Ser Ile Ser Ser Ser Ser Ser Tyr Ile Tyr Tyr Ala Asp Ser Val
    50              55              60

Lys Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Val Tyr Tyr Cys
                85              90              95

Ala Arg Asp Tyr Asp Phe Trp Ser Gly Tyr Tyr Thr Ala Phe Asp Val
            100             105             110

Trp Gly Gln Gly Thr Met Val Thr Val Ser Ser
        115             120

<210> SEQ ID NO 67
<211> LENGTH: 123
<212> TYPE: PRT
<213> ORGANISM: Homo sapiens

<400> SEQUENCE: 67

Glu Val Gln Leu Val Glu Ser Gly Gly Gly Leu Val Lys Pro Gly Gly
1               5               10              15

Ser Leu Arg Leu Ser Cys Ala Ala Ser Gly Phe Thr Phe Ser Ser Tyr
            20              25              30

Ser Met Asn Trp Val Arg Gln Ala Pro Gly Lys Gly Leu Glu Trp Val
        35              40              45

Ser Ser Ile Ser Ser Ser Ser Ser Tyr Ile Ser Tyr Ala Asp Ser Val
    50              55              60

Lys Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Val Tyr Phe Cys
                85              90              95

Ala Arg Asp Tyr Asp Phe Trp Ser Ala Tyr Tyr Asp Ala Phe Asp Val
```

-continued

```
                 100                105                110
Trp Gly Gln Gly Thr Met Val Thr Val Ser Ser
        115                120
```

<210> SEQ ID NO 68
<211> LENGTH: 112
<212> TYPE: PRT
<213> ORGANISM: Homo sapiens

<400> SEQUENCE: 68

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Asp Tyr Trp Gly Gln Gly Thr Leu Val Thr Val Ser Ser
            100                105                110
```

<210> SEQ ID NO 69
<211> LENGTH: 117
<212> TYPE: PRT
<213> ORGANISM: Homo sapiens

<400> SEQUENCE: 69

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Val Gly Ser Pro Phe Asp Tyr Trp Gly Gln Gly Thr Leu
            100                105                110

Val Thr Val Ser Ser
        115
```

<210> SEQ ID NO 70
<211> LENGTH: 117
<212> TYPE: PRT
<213> ORGANISM: Homo sapiens

<400> SEQUENCE: 70

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

Ala Met Ser Trp Val Arg Gln Ala Pro Gly Lys Gly Leu Glu Trp Val
        35                          40                          45

Ser Ala Ile Ser Gly Ser Gly Gly Ser Thr Tyr Tyr Ala Asp Ser Val
    50                          55                      60

Lys Gly Arg Phe Thr Ile Ser Arg Asp Asn Ser Lys Asn Thr Leu Tyr
65                      70                      75                      80

Leu Gln Met Asn Ser Leu Arg Ala Glu Asp Thr Ala Val Tyr Tyr Cys
                85                      90                      95

Ala Lys Val Leu Met Val Tyr Ala Asp Tyr Trp Gly Gln Gly Thr Leu
            100                     105                     110

Val Thr Val Ser Ser
        115

<210> SEQ ID NO 71
<211> LENGTH: 121
<212> TYPE: PRT
<213> ORGANISM: Homo sapiens

<400> SEQUENCE: 71

Glu Val Gln Leu Leu Glu Ser Gly Gly Gly Leu Val Gln Pro Gly Gly
1               5                       10                      15

Ser Leu Arg Leu Ser Cys Ala Ala Ser Gly Phe Thr Phe Ser Ser Tyr
            20                      25                      30

Ala Met Asn Trp Val Arg Gln Ala Pro Gly Lys Gly Leu Glu Trp Val
        35                          40                          45

Ser Thr Ile Ser Gly Ser Gly Asp Asn Thr Tyr Tyr Ala Asp Ser Val
    50                          55                      60

Lys Gly Arg Phe Thr Ile Ser Arg Asp Asn Ser Lys Asn Thr Leu Tyr
65                      70                      75                      80

Leu Gln Met Asn Ser Leu Arg Ala Glu Asp Thr Ala Val Tyr Tyr Cys
                85                      90                      95

Ala Lys Lys Phe Val Leu Met Val Tyr Ala Met Leu Asp Tyr Trp Gly
            100                     105                     110

Gln Gly Thr Leu Val Thr Val Ser Ser
        115                 120

<210> SEQ ID NO 72
<211> LENGTH: 121
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
1               5                       10                      15

Ser Leu Arg Leu Ser Cys Ala Ala Ser Gly Phe Thr Phe Ser Ser Tyr
            20                      25                      30

Ala Met Asn Trp Val Arg Gln Ala Pro Gly Lys Gly Leu Glu Trp Val
        35                          40                          45

Ser Thr Ile Ser Gly Ser Gly Gly Asn Thr Tyr Tyr Ala Asp Ser Val
    50                          55                      60

Lys Gly Arg Phe Thr Ile Ser Arg Asp Asn Ser Lys Asn Thr Leu Tyr
65                      70                      75                      80

Leu Gln Met Asn Ser Leu Arg Ala Glu Asp Thr Ala Val Tyr Tyr Cys
                85                      90                      95

Ala Lys Lys Phe Val Leu Met Val Tyr Ala Met Leu Asp Tyr Trp Gly
            100                     105                     110

-continued

```
Gln Gly Thr Leu Val Thr Val Ser Ser
        115                 120

<210> SEQ ID NO 73
<211> LENGTH: 116
<212> TYPE: PRT
<213> ORGANISM: Homo sapiens

<400> SEQUENCE: 73

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Gly Met Asp Val Trp Gly Gln Gly Thr Thr Val
            100                 105                 110

Thr Val Ser Ser
        115

<210> SEQ ID NO 74
<211> LENGTH: 123
<212> TYPE: PRT
<213> ORGANISM: Homo sapiens

<400> SEQUENCE: 74

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Gly Pro Leu Lys Leu Tyr Tyr Tyr Gly Met Asp Val
            100                 105                 110

Trp Gly Gln Gly Thr Thr Val Thr Val Ser Ser
        115                 120

<210> SEQ ID NO 75
<211> LENGTH: 116
<212> TYPE: PRT
<213> ORGANISM: Homo sapiens

<400> SEQUENCE: 75

Gln Val Gln Leu Val Glu Ser Gly Gly Gly Val Val Gln Pro Gly Arg
1               5                   10                  15
```

-continued

```
Ser Leu Arg Leu Ser Cys Ala Ala Ser Gly Phe Thr Phe Ser Ser Tyr
        20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Ala Ala Gly Met Asp Val Trp Gly Gln Gly Thr Thr Val
            100                 105                 110

Thr Val Ser Ser
        115
```

<210> SEQ ID NO 76
<211> LENGTH: 122
<212> TYPE: PRT
<213> ORGANISM: Homo sapiens

<400> SEQUENCE: 76

```
Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Ser Phe
        20                  25                  30

Gly Met His Trp Val Arg Gln Ala Pro Gly Lys Gly Leu Glu Trp Val
        35                  40                  45

Ala Leu Ile Trp Ser Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
            100                 105                 110

Gly Gln Gly Thr Thr Val Thr Val Ser Ser
        115                 120
```

<210> SEQ ID NO 77
<211> LENGTH: 122
<212> TYPE: PRT
<213> ORGANISM: Homo sapiens

<400> SEQUENCE: 77

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
        20                  25                  30

Gly Met His Trp Val Arg Gln Ala Pro Gly Lys Gly Leu Glu Trp Val
        35                  40                  45

Ala Leu Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Ala Ile Ala Ala Leu Tyr Tyr Tyr Tyr Gly Met Asp Val Trp
        100                 105                 110

Gly His Gly Thr Thr Val Thr Val Ser Ser
        115                 120

<210> SEQ ID NO 78
<211> LENGTH: 122
<212> TYPE: PRT
<213> ORGANISM: Homo sapiens

<400> SEQUENCE: 78

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Leu Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
        100                 105                 110

Gly Gln Gly Thr Thr Val Thr Val Ser Ser
        115                 120

<210> SEQ ID NO 79
<211> LENGTH: 122
<212> TYPE: PRT
<213> ORGANISM: Homo sapiens

<400> SEQUENCE: 79

Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Ser Phe
            20                  25                  30

Gly Met His Trp Val Arg Gln Ala Pro Gly Lys Gly Leu Glu Trp Val
        35                  40                  45

Ala Leu Ile Trp Ser Asp Gly Ser Asp Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
        100                 105                 110

Gly Gln Gly Thr Thr Val Thr Val Ser Ser
        115                 120

<210> SEQ ID NO 80
<211> LENGTH: 122
<212> TYPE: PRT
<213> ORGANISM: Homo sapiens

<400> SEQUENCE: 80

Gln Val Gln Leu Val Glu Ser Gly Gly Gly Val Val Gln Pro Gly Arg

-continued

```
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
            35                  40                  45

Ala Leu Ile Trp Asn Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
                100                 105                 110

Gly Gln Gly Thr Thr Val Thr Val Ser Ser
            115                 120
```

<210> SEQ ID NO 81
<211> LENGTH: 122
<212> TYPE: PRT
<213> ORGANISM: Homo sapiens

<400> SEQUENCE: 81

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ile Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Leu Ala Ala Arg Pro Gly Gly Met Asp Val Trp
                100                 105                 110

Gly Gln Gly Thr Thr Val Thr Val Ser Ser
            115                 120
```

<210> SEQ ID NO 82
<211> LENGTH: 122
<212> TYPE: PRT
<213> ORGANISM: Homo sapiens

<400> SEQUENCE: 82

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                    85              90              95
Ala Arg Gly Ile Ala Val Ala Tyr Tyr Tyr Tyr Gly Met Asp Val Trp
                100             105             110
Gly Gln Gly Thr Thr Val Thr Val Ser Ser
        115             120

<210> SEQ ID NO 83
<211> LENGTH: 122
<212> TYPE: PRT
<213> ORGANISM: Homo sapiens

<400> SEQUENCE: 83

Gln Val Gln Leu Val Glu Ser Gly Gly Gly Val Val Gln Pro Gly Arg
1               5               10              15

Ser Leu Arg Leu Ser Cys Ala Ala Ser Gly Phe Thr Phe Arg Ser Tyr
            20              25              30

Gly Met His Trp Val Arg Gln Ala Pro Gly Lys Gly Leu Glu Trp Val
        35              40              45

Ala Leu Ile Trp His Asp Gly Ser Asn Thr Tyr Tyr Val Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Gly Ile Ala Val Ala Tyr Tyr Tyr Tyr Gly Met Asp Val Trp
                100             105             110

Gly Gln Gly Thr Thr Val Thr Val Ser Ser
        115             120

<210> SEQ ID NO 84
<211> LENGTH: 117
<212> TYPE: PRT
<213> ORGANISM: Homo sapiens

<400> SEQUENCE: 84

Gln Val Gln Leu Gln Glu Ser Gly Pro Gly Leu Val Lys Pro Ser Gln
1               5               10              15

Thr Leu Ser Leu Thr Cys Thr Val Ser Gly Gly Ser Ile Ser Ser Gly
            20              25              30

Gly Tyr Tyr Trp Ser Trp Ile Arg Gln His Pro Gly Lys Gly Leu Glu
        35              40              45

Trp Ile Gly Tyr Ile Tyr Tyr Ser Gly Ser Thr Tyr Tyr Asn Pro Ser
    50              55              60

Leu Lys Ser Arg Val Thr Ile Ser Val Asp Thr Ser Lys Asn Gln Phe
65              70              75              80

Ser Leu Lys Leu Ser Ser Val Thr Ala Ala Asp Thr Ala Val Tyr Tyr
                85              90              95

Cys Ala Arg Tyr Tyr Tyr Gly Met Asp Val Trp Gly Gln Gly Thr Thr
                100             105             110

Val Thr Val Ser Ser
        115

<210> SEQ ID NO 85
<211> LENGTH: 122
<212> TYPE: PRT
<213> ORGANISM: Homo sapiens

<400> SEQUENCE: 85
```

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Ile Thr Ile Ser Val Asp Thr Ser Lys Asn Leu Phe
65                  70                  75                  80

Ser Leu Lys Leu Ser Ser Val Thr Ala Ala Asp Thr Ala Val Tyr Tyr
                85                  90                  95

Cys Ala Arg Gly Gly Val Thr Thr Tyr Tyr Tyr Ala Met Asp Val Trp
            100                 105                 110

Gly Gln Gly Thr Thr Val Thr Val Ser Ser
            115                 120
```

```
<210> SEQ ID NO 86
<211> LENGTH: 120
<212> TYPE: PRT
<213> ORGANISM: Homo sapiens

<400> SEQUENCE: 86
```

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Ala Met Val Tyr Phe Asp Tyr Trp Gly Gln
            100                 105                 110

Gly Thr Leu Val Thr Val Ser Ser
            115                 120
```

```
<210> SEQ ID NO 87
<211> LENGTH: 121
<212> TYPE: PRT
<213> ORGANISM: Homo sapiens

<400> SEQUENCE: 87
```

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Tyr Ile Tyr Asn Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80
```

```
Ser Leu Lys Leu Ser Ser Val Thr Ala Ala Asp Thr Ala Val Tyr Tyr
                85                  90                  95

Cys Ala Arg Glu Asp Thr Ala Met Val Pro Tyr Phe Asp Tyr Trp Gly
            100                 105                 110

Gln Gly Thr Leu Val Thr Val Ser Ser
        115                 120

<210> SEQ ID NO 88
<211> LENGTH: 115
<212> TYPE: PRT
<213> ORGANISM: Homo sapiens

<400> SEQUENCE: 88

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gln Leu Val Phe Asp Tyr Trp Gly Gln Gly Thr Leu Val Thr
            100                 105                 110

Val Ser Ser
        115

<210> SEQ ID NO 89
<211> LENGTH: 116
<212> TYPE: PRT
<213> ORGANISM: Homo sapiens

<400> SEQUENCE: 89

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ala Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Arg Thr Asp Tyr Asn Pro Ser Leu Lys
    50                  55                  60

Ser Arg Val Thr Ile Ser Val Asp Thr Ser Lys Lys Gln Phe Ser Leu
65                  70                  75                  80

Lys Leu Asn Ser Val Thr Ala Ala Asp Thr Ala Val Tyr Tyr Cys Ala
                85                  90                  95

Arg Gly Gln Leu Val Pro Phe Asp Tyr Trp Gly Gln Gly Thr Leu Val
            100                 105                 110

Thr Val Ser Ser
        115

<210> SEQ ID NO 90
<211> LENGTH: 115
<212> TYPE: PRT
<213> ORGANISM: Homo sapiens
```

<400> SEQUENCE: 90

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Phe Asp Tyr Trp Gly Gln Gly Thr Leu Val Thr
            100                 105                 110

Val Ser Ser
        115
```

<210> SEQ ID NO 91
<211> LENGTH: 121
<212> TYPE: PRT
<213> ORGANISM: Homo sapiens

<400> SEQUENCE: 91

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Lys Asn Tyr Ser
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Gly Asp Thr Ala Val
                85                  90                  95

Tyr Tyr Cys Ala Arg Gly Gly Pro Thr Ala Ala Phe Asp Tyr Trp Gly
            100                 105                 110

Gln Gly Thr Leu Val Thr Val Ser Ser
        115                 120
```

<210> SEQ ID NO 92
<211> LENGTH: 345
<212> TYPE: DNA
<213> ORGANISM: Homo sapiens

<400> SEQUENCE: 92

```
cagattcagc tggtgcagtc tggagctgag gtgaagaagc ctggggcctc agtgaaggtc      60
tcctgcaagg cttctggtta ccccttgacc agctatggta tcagctgggt gcgacaggcc     120
cctggacaag gcttgagtg atgggatgg atcagcgctt acaatggtaa cacaaactat       180
gcacagaagg tccagggcag cgtcaccatg accacagaca catccacgag cacagtctac     240
atggagctga ggagcctgag atctgacgac acggccgtgt attactgtgc gagaggctac     300
ggtatggacg tctggggcca aggaccacg gtcaccgtct cctct                      345
```

```
<210> SEQ ID NO 93
<211> LENGTH: 327
<212> TYPE: DNA
<213> ORGANISM: Homo sapiens

<400> SEQUENCE: 93
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
tacccaggca aacccccaa actcaagatt tatgaggtca gtaatcggcc ctcagggggtt     180 tctaatcgct tctctggctc caagtctggc aacacggcct ccctgaccat ctctgggctc     240
caggctgagg acgaggctga ttatttctgc agctcatata caagcaccag catggtcttc     300
ggcggaggga ccaagctgac cgtccta                                         327

<210> SEQ ID NO 94
<211> LENGTH: 345
<212> TYPE: DNA
<213> ORGANISM: Homo sapiens

<400> SEQUENCE: 94
caggttcagc tggtgcagtc tggagctgag gtgaagaagc ctggggcctc agtgaaggtc      60
tcctgcaagg cttctggtta caccttaacc agctatggta tcagctgggt gcgacaggcc     120
cctggacaag ggcttgagtg gatgggatgg gtcagttttt ataatggtaa cacaaactat     180
gcacagaagc tccagggcag aggcaccatg accacagacc catccacgag cacagcctac     240
atggagctga ggagcctgag atctgacgac acggccgtgt attactgtgc gagaggctac     300
ggtatggacg tctggggcca agggaccacg gtcaccgtct cctct                     345

<210> SEQ ID NO 95
<211> LENGTH: 327
<212> TYPE: DNA
<213> ORGANISM: Homo sapiens

<400> SEQUENCE: 95
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca aagcccccaa actcatgatt tatgaggtca gtaatcggcc ctcagggggtt     180 tctaatcgct tctctggctc caagtctggc aacacggcct ccctgaccat ctctgggctc     240
caggctgagg acgaggctga ttattactgc aattcatata caagcaccag catggtattc     300
ggcggaggga ccaagctgac cgtccta                                         327

<210> SEQ ID NO 96
<211> LENGTH: 345
<212> TYPE: DNA
<213> ORGANISM: Homo sapiens

<400> SEQUENCE: 96
caggttcagc tggtgcagtc tggagctgaa gtgaagaagc ctggggcctc agtgaaggtc      60
tcctgcaagg cttctggtta caccttacc agctatggta tcagctgggt gcgacaggcc     120
cctggacaag ggcttgagtg gatgggatgg atcagctttt acaatggtaa cacaaactat     180
gcacagaagg tccagggcag agtcaccatg accacagaca catccacgag cacagtctac     240
atggagctga ggagcctgag atctgacgac acggccgtgt attactgtgc gagaggctac     300
ggtatggacg tctggggcca agggaccacg gtcaccgtct cctct                     345
```

```
<210> SEQ ID NO 97
<211> LENGTH: 327
<212> TYPE: DNA
<213> ORGANISM: Homo sapiens

<400> SEQUENCE: 97
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca aaccccccaa actcatgatt tatgaggtca gtaatcggcc ctcaggggtt     180
tctattcgct tctctggctc caagtctggc aacacggcct ccctgaccat ctctgggctc     240
caggctgagg acgaggctga ttatttctgc agctcatata caagcaccag catggtcttc     300
ggcggaggga ccaagctgac cgtccta                                         327

<210> SEQ ID NO 98
<211> LENGTH: 345
<212> TYPE: DNA
<213> ORGANISM: Homo sapiens

<400> SEQUENCE: 98
cagattcagc tggtgcagtc tggagctgag gtgaagaagc ctggggcctc agtgaaggtc      60
tcctgcaagg cttctggtta caccttgacc agctatggta tcagctgggt gcgacaggcc     120
cctggacaag ggcttgagtg gatgggatgg atcagctttt acaatggtaa cacaaactat     180
gcacagaagg tccagggcag agtcaccatg accacagaca catccacgag cacagtctac     240
atggagctga ggagcctgag atctgacgac acggccgtgt atttctgtgc gagaggttac     300
ggtatggacg tctggggcca agggaccacg gtcaccgtct cctca                     345

<210> SEQ ID NO 99
<211> LENGTH: 327
<212> TYPE: DNA
<213> ORGANISM: Homo sapiens

<400> SEQUENCE: 99
cagtctgccc tgactcagcc tgcctccgtg tctgggtctc ctggacagtc gatcaccatc      60
tcctgcactg gaaccagcag tgacgttggt ggttataact ctgtctcgtg gtaccaacag     120
cacccaggca aacccccaa actcatgatt tatgaggtca gtaatcggcc ctcaggggtt      180
tctaatcgct tctctggctc caagtctggc aacacggcct ccctgaccat ctctgggctc     240
caggctgagg acgaggctga ttatttctgc agctcatata caagcaccag catggtcttc     300
ggcggaggga ccaagctggc cgtccta                                         327

<210> SEQ ID NO 100
<211> LENGTH: 345
<212> TYPE: DNA
<213> ORGANISM: Homo sapiens

<400> SEQUENCE: 100
caggttcagc tggtgcagtc tggagctgag gtgaagaagc ctggggcctc agtgaaggtc      60
tcctgcaagg cttctggtta caccttaacc agctatggta tcagctgggt gcgacaggcc     120
cctggacaag ggcttgagtg gatgggatgg gtcagttttt ataatggtaa cacaaactat     180
gcacagaagc tccagggcag aggcaccatg accacagacc catccacgag cacagcctac     240
atggagctga ggagcctgag atctgacgac acggccgtgt attactgtgc gagaggctac     300
```

-continued

```
ggtatggacg tctggggcca agggaccacg gtcaccgtct cctca                    345

<210> SEQ ID NO 101
<211> LENGTH: 327
<212> TYPE: DNA
<213> ORGANISM: Homo sapiens

<400> SEQUENCE: 101
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca aagcccccaa actcatgatt tatgaggtca ctaatcggcc ctcagggggtt     180 tctaatcgct tctctggctc caagtctggc aacacggcct ccctgaccat ctctgggctc     240
caggctgagg acgaggctga ttattactgc aactcatata caagcaccag catggtgttc     300
ggcggaggga ccaagctgac cgtccta                                          327

<210> SEQ ID NO 102
<211> LENGTH: 363
<212> TYPE: DNA
<213> ORGANISM: Homo sapiens

<400> SEQUENCE: 102
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatat ataacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagag     300
gatacagcta tggttcctta ctttgactac tggggccagg gaaccctggt caccgtctcc     360
tca                                                                    363

<210> SEQ ID NO 103
<211> LENGTH: 333
<212> TYPE: DNA
<213> ORGANISM: Homo sapiens

<400> SEQUENCE: 103
cagtctgtac tgacgcagcc gccctcagtg tctggggccc cagggcagag ggtcaccatc      60
tcctgcactg ggagcagctc caacatcggg gcacattatg atgtgcactg gtaccagcag     120
gttccaggaa cagcccccaa actcctcatc tatggtaaca cctatcggcc ctcagggggtc     180 cctgaccgat tctctggctc caagtctggc acctcagcct ccctggccat cactgggctc     240
caggctgagg atgaggctga ttattactgc cagtcctatg acaacagcct gagtggtgtg     300
gtattcggcg gagggaccaa gctgaccgtc cta                                   333

<210> SEQ ID NO 104
<211> LENGTH: 366
<212> TYPE: DNA
<213> ORGANISM: Homo sapiens

<400> SEQUENCE: 104
caggtgcacc tggtggagtc tggggggaggc gtggtccagc ctgggaggtc cctgagactc      60
tcctgtgcag cgtctggatt caccttcaac agctttggca tgcactgggt ccgccaggct     120
ccaggcaagg ggctggagtg ggtggcactt atctggtctg atggaagtga tgaatactat     180
gcagactccg tgaagggccg attcaccatc tccagagaca attccaagaa cacgctgtat     240
```

```
ctgcaaatga acagcctgag agccgaggac acggctgtgt attactgtgc gagagccata      300
gcagccctct actactacta cggtatggac gtctggggcc aagggaccac ggtcaccgtc      360
tcctca                                                                 366

<210> SEQ ID NO 105
<211> LENGTH: 330
<212> TYPE: DNA
<213> ORGANISM: Homo sapiens

<400> SEQUENCE: 105
cagtctgtgt tgacgcagcc gccctcagtg tctgcggccc caggacagaa ggtcaccatc       60
tcctgctctg gaagcagctc caacattggg aataattttg tatcctggta ccagcagctc      120
ccaggaacag cccccaaact cctcatttat gactataata agcgaccctc agggattcct      180
gaccgattct ctggctccaa gtctggcacg tcagccaccc tgggcatcac cggactccag      240 actgggacg aggccgatta ttactgcgga acatgggata gcagcctgag tgcttatgtc      300
ttcggaactg ggaccagggt caccgtccta                                       330

<210> SEQ ID NO 106
<211> LENGTH: 366
<212> TYPE: DNA
<213> ORGANISM: Homo sapiens

<400> SEQUENCE: 106
caggtgcagc tggtggagtc tgggggaggc gtggtccagc ctgggaggtc cctgagactc       60
tcctgtgcag cgtctggatt caccttcagc agctttggca tgcactgggt ccgccaggct      120
ccaggcaagg ggctggagtg ggtggcactt atatggaatg atggaagtaa taaatactat      180
gcagactccg tgaagggccg attcaccatc tccagagaca attccaagaa cacgctgtat      240
ctgcaaatga acagcctgag agccgaggac acggctgtgt attactgtgc gagagccata      300
gcagccctct actactacta cggtatggac gtctggggcc aagggaccac ggtcaccgtc      360
tcctca                                                                 366

<210> SEQ ID NO 107
<211> LENGTH: 330
<212> TYPE: DNA
<213> ORGANISM: Homo sapiens

<400> SEQUENCE: 107
cagtctgtgt tgacgcagcc gccctcagtg tctgcggccc caggacagaa ggtcaccatc       60
tcctgctctg gaagcagctc caacattggg aataattttg tatcctggta ccagcagctc      120
ccaggaacag cccccaaact cctcatttat gactataata agcgaccctc agggattcct      180
gaccgattct ctggctccaa gtctggcacg tcagccaccc tgggcatcac cggactccag      240 actgggacg aggccgatta ttactgcgga acatgggata gcagtctgag tggttatgtc      300
ttcggaactg ggaccagggt caccgtccta                                       330

<210> SEQ ID NO 108
<211> LENGTH: 366
<212> TYPE: DNA
<213> ORGANISM: Homo sapiens

<400> SEQUENCE: 108
caggtgcacc tggtggagtc tgggggaggc gtggtccagc ctgggaggtc cctgagactc       60
```

```
tcctgtgcag cgtctggatt caccttcaac agctttggca tgcactgggt ccgccaggct      120
ccaggcaagg ggctggagtg ggtggcactt atatggtctg atggaagtga taaatactat      180
gcagactccg tgaagggccg attcaccatc tccagagaca attccaagaa cacgctgtat      240
ctgcaaatga acagcctgag agccgaggac acggctgtgt attactgtgc gagagccata      300
gcagccctct actactacta cggtatggac gtctggggcc aagggaccac ggtcaccgtc      360
tcctca                                                                  366
```

<210> SEQ ID NO 109
<211> LENGTH: 330
<212> TYPE: DNA
<213> ORGANISM: Homo sapiens

<400> SEQUENCE: 109

```
cagtctgtgt tgacgcagcc gccctcagtg tctgcggccc caggacagaa ggtcaccatc       60
tcctgctctg gaagcagttc caacattggg aataattttg tatcctggta ccagcagttc      120
ccaggaacag cccccaaact cctcatttat gactataata agcgaccctc agggattcct      180
gaccgattct ctggctccaa gtctggcacg tcagccaccc tgggcatcac cggactccag      240
actggggacg aggccgatta ttactgcgga acatgggata gcagcctgag ttcttatgtc      300
ttcggaactg ggaccagggt caccgtccta                                        330
```

<210> SEQ ID NO 110
<211> LENGTH: 366
<212> TYPE: DNA
<213> ORGANISM: Homo sapiens

<400> SEQUENCE: 110

```
caggtgcagc tggtggagtc tgggggaggc gtggtccagc ctgggaggtc cctgagactc       60
tcctgtgcag cgtctggatt caccttcagc agctttggca tgcactgggt ccgccaggct      120
ccaggcaagg ggctggagtg ggtggcactt atatggaatg atggaagtaa taaatactat      180
gcagactccg tgaagggccg attcaccatc tccagagaca attccaagaa cacgctgtat      240
ctgcaaatga acagcctgag agccgaggac acggctgtgt attactgtgc gagagccata      300
gcagccctct actactacta cggtatggac gtctggggcc acgggaccac ggtcaccgtc      360
tcctca                                                                  366
```

<210> SEQ ID NO 111
<211> LENGTH: 330
<212> TYPE: DNA
<213> ORGANISM: Homo sapiens

<400> SEQUENCE: 111

```
cagtctgtgt tgacgcagcc gccctcagtg tctgcggccc caggacagaa ggtcaccatc       60
tcctgctctg gaagcagctc caacattggg aataattttg tatcctggta ccagcagctc      120
ccaggaacag cccccaaact cctcatttat gactataata agcgaccctc agggattcct      180
gaccgattct ctggctccaa gtctggcacg tcagccaccc tgggcatcac cggactccag      240
actggggacg aggccgatta ttactgcgga acatgggata gcagcctgag tggttatgtc      300
ttcggaactg ggaccagggt caccgtccta                                        330
```

<210> SEQ ID NO 112
<211> LENGTH: 366
<212> TYPE: DNA
<213> ORGANISM: Homo sapiens

<400> SEQUENCE: 112
caggtgcagc tggtggagtc tggggggaggc gtggtccagc ctgggaggtc cctgagactc      60
tcctgtgcag cgtctggatt caccttcagc agctttggca tgcactgggt ccgccaggct     120
ccaggcaagg ggctggagtg ggtggcactt atatggaatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagccata     300
gcagccctct actactacta cggtatggac gtctggggcc aagggaccac ggtcaccgtc     360
tcctca                                                                366

<210> SEQ ID NO 113
<211> LENGTH: 330
<212> TYPE: DNA
<213> ORGANISM: Homo sapiens

<400> SEQUENCE: 113
cagtctgtgt tgacgcagcc gcccacagtg tctgcggccc caggacagaa ggtcaccatc      60
tcctgctctg gaagcagctc caacattggg aataattttg tatcctggta ccagcagctc     120
ccaggaacag cccccaaact cctcatttat gactataata gcgaccctc agggattcct      180 gaccgattct ctggctccaa gtctggcacg tcagccaccc tgggcatcac cggactccag     240
actggggacg aggccgatta ctactgcgga acatgggata gcagcctgag tggttatgtc     300
ttcggaactg ggaccagggt caccgtccta                                      330

<210> SEQ ID NO 114
<211> LENGTH: 366
<212> TYPE: DNA
<213> ORGANISM: Homo sapiens

<400> SEQUENCE: 114
caggtgcagc tggtggagtc tggggggaggc gtggtccagc ctgggaggtc cctgagactc      60
tcctgtgcag cgtctggatt caccttcagg agctatggca tgcactgggt ccgccaggct     120
ccaggcaagg ggctggagtg ggtggcactt atatggcatg atggaagtaa tacatactat     180
gtagactccg tgaagggccg attcaccatc tccagagaca attccaagaa cacgctgtat     240
ctgcaaatga acagcctgag agccgaggac acggctgtgt attactgtgc gagaggtata     300
gcagtggctt actactacta cggtatggac gtctggggcc aagggaccac ggtcaccgtc     360
tcctca                                                                366

<210> SEQ ID NO 115
<211> LENGTH: 330
<212> TYPE: DNA
<213> ORGANISM: Homo sapiens

<400> SEQUENCE: 115
cagtctgtgt tgacgcagcc gccctcagtg tctgcggccc caggacagaa ggtcaccatc      60
tcctgctctg gaagcagctc caacattggg aataattttg tatcctggta ccagcagctc     120
ccaggaacag cccccaaact cctcatttat gacagtaata gcgaccctc agggattcct      180 gaccgattct ctggctccaa gtctggcacg tcagccaccc tggacatcac cggactccag     240
actggggacg aggccgatta ttactgcgga acatgggata gcagcctgag tgcttatgtt     300
ttcggaactg ggaccaaggt caccgtccta                                      330

```
<210> SEQ ID NO 116
<211> LENGTH: 363
<212> TYPE: DNA
<213> ORGANISM: Homo sapiens

<400> SEQUENCE: 116
gaggtgcagc tgttggagtc tggggggaggc ttggtacagc ctggggggtc cctgagactc      60
tcctgtgcag cctctggatt caccttttagc agctatgcca tgaactgggt ccgccaggct     120
ccagggaagg ggctggagtg ggtctcaact attagtggta gtggtgataa cacatactac     180
gcagactccg tgaagggccg gttcaccatc tccagagaca attccaagaa cacgctgtat     240
ctgcaaatga acagcctgag agccgaggac acggccgtat attactgtgc gaaaaagttt     300
gtactaatgg tgtatgctat gcttgactac tggggccagg gaaccctggt caccgtctcc     360
tca                                                                    363

<210> SEQ ID NO 117
<211> LENGTH: 321
<212> TYPE: DNA
<213> ORGANISM: Homo sapiens

<400> SEQUENCE: 117
gacatcctga tgacccagtc tccatcctcc ctgtctgcat ctgttggaga cagagtcacc      60
atcacttgcc gggcaagtca gagcattagc agttatttaa attggtatca gcagaaacca     120
gggaaagccc ctaaggtcct gatctatgct gcctccagtt tgcaaagtgg ggtcccatca     180
aggttcagtg gcagtggatc tgggacagat ttcactctca ccatcaacag tctgcaacct     240
gaagattttg caacttacta ctgtcaacag agttacagtt cccccatcac cttcggccaa     300
gggacacgac tggagattaa a                                                321

<210> SEQ ID NO 118
<211> LENGTH: 363
<212> TYPE: DNA
<213> ORGANISM: Homo sapiens

<400> SEQUENCE: 118
gaggtgcagc tgttggagtc tggggggaggc ttggtacagc cggggggggtc cctgagactc      60 tcctgtgcag cctctggatt caccttttagc agctatgcca tgaactgggt ccgccaggct     120
ccagggaagg ggctggagtg ggtctcaact attagtggta gtggtggtaa cacatactac     180
gcagactccg tgaagggccg gttcaccatc tccagagaca attccaagaa cacgctgtat     240
ctgcaaatga acagcctgag agccgaggac acggccgtat attactgtgc gaaaaagttt     300
gtactaatgg tgtatgctat gcttgactac tggggccagg gaaccctggt caccgtctcc     360
tca                                                                    363

<210> SEQ ID NO 119
<211> LENGTH: 321
<212> TYPE: DNA
<213> ORGANISM: Homo sapiens

<400> SEQUENCE: 119
gacatccaga tgacccagtc tccatcctcc ctatctgcat ctgtaggaga cagagtcacc      60
atcacttgcc gggcaagtca gagcattagc atctatttaa attggtatca gcagaagcca     120
gggaaagccc cttacctcct gatctatgct gcagccagtt tgcaaagtgg ggtcccatca     180
aggttcagtg gcagtggatc tgggacagat ttcactctca ccatcagcag tctgcaacct     240
```

-continued

```
gaagattttg caacttacta ctgtcaacag agttacagtg cccccatcac cttcggccaa     300
gggacacgac tggagattaa a                                               321

<210> SEQ ID NO 120
<211> LENGTH: 345
<212> TYPE: DNA
<213> ORGANISM: Homo sapiens

<400> SEQUENCE: 120
caggttcagc tggtgcagtc tggagctgag gtgaagaagc ctggggcctc actgaaggtc      60
tcctgcaagg cttctggtta cagtttgacc agctatggta tcagctgggt gcgacaggcc     120
cctggacaag ggcttgagtg gatgggatgg atcagcgctt acaatggtaa cacaaactat     180
gcacagaagg tccagggcag agtcaccatg accacagaca catccacgag cacagtctac     240
atggaggtga ggagtctgag atctgacgac acggccgtgt attactgtgc gagaggctac     300
ggtatggacg tctggggcca agggaccacg gtcaccgtct cctca                     345

<210> SEQ ID NO 121
<211> LENGTH: 327
<212> TYPE: DNA
<213> ORGANISM: Homo sapiens

<400> SEQUENCE: 121
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca aaccccccaa actcatgatt tatgaggtca gtaatcggcc ctcaggggtt     180
tctaatcgct tctctggctc caagtctggc aatacggcct ccctgaccat ctctgggctc     240
caggctgagg acgaggctga ttatttctgc agctcatata caagcaccag catggtcttc     300
ggcggaggga ccaagctgac cgtccta                                         327

<210> SEQ ID NO 122
<211> LENGTH: 345
<212> TYPE: DNA
<213> ORGANISM: Homo sapiens

<400> SEQUENCE: 122
caggttcagc tggtgcagtc tggagctgag gtgaagaggc ctggggcctc agtgaaggtc      60
tcctgcaagg cttctggtta caccttgacc agctatggta tcagctgggt gcgacaggcc     120
cctggacaag ggcttgagtg gatgggatgg atcagcgttt acaatggtaa cacaaactat     180
gcacagaagg tccagggcag agtcaccatg accacagaca catccacgag cacagtctac     240
atggagctga ggagcctgag ctctgacgac acggccgtgt attactgtgc gagaggctac     300
ggtatggacg tctggggcca agggaccacg gtcaccgtct cctca                     345

<210> SEQ ID NO 123
<211> LENGTH: 327
<212> TYPE: DNA
<213> ORGANISM: Homo sapiens

<400> SEQUENCE: 123
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca aaccccccaa actcatgatt tatgaggtca gtaatcggcc ctcaggggtt     180
```

```
tctattcgct tctctggctc caagtctggc aacacggcct ccctgaccat ctctgggctc      240
caggctgagg acgaggctga ttatttctgc agctcatata caagcaccag catggtcttc      300
ggcggaggga ccaagctgac cgtccta                                         327

<210> SEQ ID NO 124
<211> LENGTH: 345
<212> TYPE: DNA
<213> ORGANISM: Homo sapiens

<400> SEQUENCE: 124
caggttcagc tggtgcagtc tggagctgag gtgaagaagc ctggggcctc agtgaaggtc       60
tcctgcaagg cttctggtta ccccttgacc agctatggta tcagctgggt gcgacaggcc      120
cctggacaag ggcttgagtg gatgggatgg atcagcgctt acaatggtaa cacaaactat      180
gcacagaagg tccagggcag agtcaccatg accacagaca tccacgag cacagtctac       240 atggagttga ggagcctgag atctgacgac acggccgtgt attactgtgc gagaggctac      300
ggtatggacg tctggggcca aggaccacg gtcaccgtct cctca                      345

<210> SEQ ID NO 125
<211> LENGTH: 327
<212> TYPE: DNA
<213> ORGANISM: Homo sapiens

<400> SEQUENCE: 125
cagtctgccc tgactcagcc tgcctccgtg tctgggtctc ctggacagtc gatcaccatc       60
tcctgcactg gaaccagcag tgacgttggt ggttataact ctgtctcctg gtaccaacag      120
cacccaggca aacccccaa actcatgatt tatgaggtca gtaatcggcc ctcaggggtt      180
tctaatcgct tctctggctc caagtctggc aatacggcct ccctgaccat ctctgggctc      240
caggctgagg acgaggctga ttatttctgc agctcatata caagcaccag catggtcttc      300
ggcggaggga ccaagctgac cgtccta                                         327

<210> SEQ ID NO 126
<211> LENGTH: 345
<212> TYPE: DNA
<213> ORGANISM: Homo sapiens

<400> SEQUENCE: 126
caggttcagt tggtgcagtc tggagctgag gtgaagaagc ctggggcctc agtgaaggtc       60
tcctgcaagg cttctggtta cgccttgacc agctatggta tcagctgggt gcgacaggcc      120
cctggacaag ggcttgagtg gatgggatgg atcagcgctt acaatggtaa cacaaactat      180
gcacagaagg tccagggcag agtcaccatg accacagaca tccacgag cacagtctac       240 atggagctga ggagcctgag atctgacgac acggccgtgt attactgtgc gagaggctac      300
ggtatggacg tctggggcca aggaccacg gtcaccgtct cctca                      345

<210> SEQ ID NO 127
<211> LENGTH: 327
<212> TYPE: DNA
<213> ORGANISM: Homo sapiens

<400> SEQUENCE: 127
cagtctgccc tgactcagcc tgcctccgtg tctgggtctc ctggacagtc gatcaccatc       60
tcctgcactg gaaccaacag tgacgttggt ggttataact ctgtctcctg gtaccaacag      120
cacccaggca aacccccaa actcatgatt tatgaggtca gtaatcggcc ctcagggatt      180
```

-continued

```
tctaatcgct tctctggctc caagtctggc aacacggcct ccctgaccat ctctgggctc      240
caggctgagg acgaggctga ttatttctgc agctcatata caagcaccag catggtcttc      300
ggcggaggga ccaagctgac cgtccta                                          327

<210> SEQ ID NO 128
<211> LENGTH: 345
<212> TYPE: DNA
<213> ORGANISM: Homo sapiens

<400> SEQUENCE: 128
caggttcagc tggtgcagtc tggagctgag gtgaagaagc ctgggggctc agtgaaggtc       60
tcctgcaagg cttctggtta cagctttacc agctatggta tcagctgggt gcgacaggcc      120
cctggacaag ggcttgagtg gatgggatgg gtcagcgctt acaatggtaa cacaaactat      180
gcacagaagt tccagggcag agtcaccatg accacagaca catccacgag cacagcctac      240
atggaactga ggagcctgag atctgacgac acggccgtgt attactgtgc gagaggctac      300
gttatggacg tctggggcca aggggaccacg gtcaccgtct cctca                     345

<210> SEQ ID NO 129
<211> LENGTH: 327
<212> TYPE: DNA
<213> ORGANISM: Homo sapiens

<400> SEQUENCE: 129
cagtctgccc tgactcagcc tgcctccgtt tctgggtctc ctggacagtc gatcaccatc       60
tcctgcactg gaaccagcag tgacgttggt gcttataact ctgtctcctg gtaccaacag      120
cacccaggca aagcccccaa acgcatgatt tatgaggtca gtaatcggcc ctcagggggtt     180 tctaatcgct tctctggctc caagtctggc aacacggcct ccctgaccat ctctgggctc      240
caggctgagg acgaggctga ttattactgc agctcatata caagcaccaa catggtattc      300
ggcggaggga ccaagctgac cgtccta                                          327

<210> SEQ ID NO 130
<211> LENGTH: 363
<212> TYPE: DNA
<213> ORGANISM: Homo sapiens

<400> SEQUENCE: 130
caggtacagt tgcagcagtc aggtccagga ctggtgaagc cctcgcagac cctctcactc       60
acctgtgcca tctccgggga cagtgtctct agcaacagtg ctgcttggaa ctggatcagg      120
cagtccccat cgagaggcct tgagtggctg ggaaggacat actacaggtc caagtggtat      180
aaaaattatt cagtatctgt gaaaagtcga ataaccatca acccagacac atccaagaac      240
cagttctctc tgcaactgaa ctctgtgact cccggggaca cggctgtgta ttactgtgca      300
agaggggggc caactgctgc ttttgactac tggggccagg gaaccctggt caccgtctcc      360
tca                                                                    363

<210> SEQ ID NO 131
<211> LENGTH: 330
<212> TYPE: DNA
<213> ORGANISM: Homo sapiens

<400> SEQUENCE: 131
ctttctgccc tgactcagcc tgcctccgtg tctgggtctc ctggacagtc gatcaccatc       60
```
tcctgcactg gaaccagcag tgatgttggg aattataacc ttgtctcctg gtaccaacag          120
tattcaggca aagcccccaa actcatgatt tatgaggtca gtaagcggcc ctcagggtt           180 tctaatcgct tctctggctc caagtctggc aacacggcct ccctgacaat ctctgggctc          240
caggctgagg acgaggctga ttattactgc tgctcatatg caggtagtag cactttggtt          300
ttcggcggag ggaccaagct gaccgtccta                                           330

<210> SEQ ID NO 132
<211> LENGTH: 357
<212> TYPE: DNA
<213> ORGANISM: Homo sapiens

<400> SEQUENCE: 132
gaggtgcagt tggtggagtc tggggggaggc ttggtccagc ctggggggtc cctgagactc         60
tcctgtgtag tctctggatt cacctttagt agctattgga tgagctgggt ccgccaggct          120
ccagggaagg ggctggagtg ggtggccaac ataaagcaag atggaagtga gaaatactat          180
gtggactctg tgaagggccg attcaccatc tccagagaca acgccaagaa ctcactgtat          240
ctgcaaatga acagcctgag agccgaggac acggctgtat attactgtgc gagagagtca          300
aactggggat ttgcttttga tatctggggc caagggacaa tggtcaccgt ctcttca            357

<210> SEQ ID NO 133
<211> LENGTH: 327
<212> TYPE: DNA
<213> ORGANISM: Homo sapiens

<400> SEQUENCE: 133
cagtctgtgc tgactcagcc accctcagcg tctgggaccc ccgggcagag ggtcaccatc          60
tcttgttctg gaagcagctc caacatcgga agtaagactg taaactggta ccaacaggtc         120
ccaggaacgg cccccaaact cctcatctat aggaataatc agcggccctt aggggtccct         180
gaccgattct ctggctccaa gtctggcacc tcagcctccc tggccatcag tgggctccag         240
tctgaggatg aggctgatta ttattgtgca gcatgggatg acagcctgaa ttgggtgttc         300
ggcggaggga ccaagctgac cgtccta                                             327

<210> SEQ ID NO 134
<211> LENGTH: 357
<212> TYPE: DNA
<213> ORGANISM: Homo sapiens

<400> SEQUENCE: 134
gaggtgcagc tggtggagtc tggggggaggc ttggtccagc ctggggggtc cctgagactc         60
tcctgtgcag cctctggatt cacctttagt cgctattgga tgagctgggt ccgccaggct          120
ccagggaagg ggctggagtg ggtggccaac ataaagcatg atggaagtga gaaatactat          180
gtggactctg tgaagggccg attcaccatt tccagagaca acgccaagaa ctcactgtat          240
ctgcaaatga acagcctgag agccgaggac acggctgtgt attactgtgc gagagagtca          300
aactggggat ttgcttttga tgtctggggc cacgggacaa tggtcaccgt ctcttca            357

<210> SEQ ID NO 135
<211> LENGTH: 327
<212> TYPE: DNA
<213> ORGANISM: Homo sapiens

<400> SEQUENCE: 135
cagtctgtgc tgactcagcc accctcagcg tctgggcccc ccggacagag ggtcaccatc          60

-continued

```
tcttgttctg gaagcagctc caacatcgga agtaatactg taaactggta ccagcagctc      120
ccaggaacgg cccccaaact cctcatctat agtaataatc ggcggccctc aggggtccct      180
gaccgattct ctggctccaa gtctggcacc tcagcctccc tggccatcag tgggctccag      240
tctgaggatg aggctgatta ttactgtgca gcatgggatg acagcctgaa ttgggtgttc      300
ggcggaggga ccaagctgac cgtccta                                         327

<210> SEQ ID NO 136
<211> LENGTH: 351
<212> TYPE: DNA
<213> ORGANISM: Homo sapiens

<400> SEQUENCE: 136
gaggtgcagc tgttggagtc tgggggaggc ttggtacagc ctggggggtc cctgagactc       60
tcctgtgcag cctctggatt cacctttagc agctatgcca tgagctgggt ccgccaggct      120
ccagggaagg ggctggagtg ggtctcaact attagtggta gtggtggtag gacatattac      180
gcagactccg tgaagggccg gttcaccatc tccagagaca attccaagaa cacgctgtat      240
ctgcaaatga acagcctgag agccgaggac acggccgtat attactgtgc gaaagaagtt      300
ggcagtccct ttgactactg gggccaggga accctggtca ccgtctcctc a              351

<210> SEQ ID NO 137
<211> LENGTH: 330
<212> TYPE: DNA
<213> ORGANISM: Homo sapiens

<400> SEQUENCE: 137
cagtctgtgt tgacgcagcc gccctcagtg tctgcggccc caggacagaa ggtcaccatc       60
tcctgctctg gaagcaactc caacattggg aataattatg tatcctggta ccagcagctc      120
ccaggaacag cccccaaact cctcatttat gacaataata gcgaccctc agggattcct       180 gaccgattct ctggctccaa ctctggcacg tcagccaccc tgggcatcac cggactccag      240 actgggacg aggccgatta ttactgcgga acatgggata gcagcctgag tgctgtggta       300
ttcggcggag ggaccaagct gaccgtccta                                      330

<210> SEQ ID NO 138
<211> LENGTH: 366
<212> TYPE: DNA
<213> ORGANISM: Homo sapiens

<400> SEQUENCE: 138
caggtgcagc tggtggagtc tgggggaggc gtggtccagc ctgggaggtc cctgagactc       60
tcctgtgcag cgtctggatt caccttcagt agctatggca tgcactgggt ccgccaggct      120
ccaggcaagg ggctggagtg ggtggcaatt atatggtatg atggaagtaa taaatactat      180
gcagactccg tgaagggccg attcaccatc tccagagaca attccaagaa cacactgtat      240
cttcaaatga acagcctgag agccgaggac acggctgtgt attactgtgc gaggaggggg      300
ggtctggcag ctcgtccggg cggtatggac gtctggggc aagggaccac ggtcaccgtc       360
tcctca                                                                366

<210> SEQ ID NO 139
<211> LENGTH: 318
<212> TYPE: DNA
<213> ORGANISM: Homo sapiens
```

<400> SEQUENCE: 139

```
tcctatgagc tgactcagcc accctcagtg tctgtgtccc caggacagac agccagaatc      60
acctgctctg gagataaatt gggggataaa tatgcttgct ggtatcagca gaaaccaggc     120
cagtcccctg tgctggtcat ctatcaaaat accaagtggc ccttaggat ccctgagcga      180 ttctctggct ccaagtctgg gaacacagtc actctgacca tcagcgggac ccaggctatg     240
gatgaggctg actattactg tcaggcgtgg gacagcagca ctgtggtatt cggcggaggg     300
accaagctga ccgtcccta                                                  318
```

<210> SEQ ID NO 140
<211> LENGTH: 366
<212> TYPE: DNA
<213> ORGANISM: Homo sapiens

<400> SEQUENCE: 140

```
caggtgcagc tgcaggagtc gggcccagga ctggtgaagc cttcacagac cctgtccctc      60
acctgcactg tctctggtgg ctccatcagc agtagtgatt actactggag ctggatccgc     120
cagcacccag ggaagggcct ggagtggatt gggtacatct attacagtgg gagcacctac     180
tacaacccgt ccctcaagag tcgaattacc atatcagtag acacgtctaa gaacctgttc     240
tccctgaagt tgagctctgt gactgccgcg gacacggccg tgtattactg tgcgagaggg     300
ggggtgacta cgtactacta cgctatggac gtctggggcc aagggaccac ggtcaccgtc     360
tcctca                                                                366
```

<210> SEQ ID NO 141
<211> LENGTH: 321
<212> TYPE: DNA
<213> ORGANISM: Homo sapiens

<400> SEQUENCE: 141

```
gacatacaga tgacccagtc tccatcctcc ctgtctgcat ctgtaggaga cagagtcacc      60
atcacttgcc gggcaagtca gcgcattagc aactatttaa gttggtatct gcagaaacca     120
gggattgccc ctaagctcct gatctatgct gcatccagtt tgcagagtgg ggtcccatca     180
aggttcagtg gcagtggatc tgggacagat ttcactctca ccatcagcag tctgcaatct     240
gaagattttg caacttacta ctgtcaacag agttacagta ccccgctcat tttcggcgga     300
gggaccaagg tggagatcaa a                                               321
```

<210> SEQ ID NO 142
<211> LENGTH: 369
<212> TYPE: DNA
<213> ORGANISM: Homo sapiens

<400> SEQUENCE: 142

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtga taaatactat     180
gcagactccg tgaagggccg attcaccatc tccagagaca attccaagaa cacgctgtat     240
ctgcaaatga acagcctgag agccgaggac acggctgtgt attactgtgc gagagagact     300
ggtcccttga aactctacta ctacggtatg gacgtctggg gccaagggac cacggtcacc     360
gtctcctca                                                             369
```

```
<210> SEQ ID NO 143
<211> LENGTH: 336
<212> TYPE: DNA
<213> ORGANISM: Homo sapiens

<400> SEQUENCE: 143
gatattgtga tgactcagtc tccactctcc ctgtccgtca cccctggaga gccgccctcc      60
atctcctgca ggtctagtca gagcctcctg catagtaatg gatacaactt tttgaattgg     120
tacctgcaga agccagggca gtctccacaa ctcctgatct atttgggttc tcatcgggcc     180
tccggggtcc ctgacaggtt cagtggcagt ggatcaggca cagattttac actggaaatc     240
agcagagtgg aggctgagga tgttgggggtt tattactgca tgcaagttct acaaactcca     300
ttcactttcg gccctgggac caaagtggat atcaaa                               336

<210> SEQ ID NO 144
<211> LENGTH: 357
<212> TYPE: DNA
<213> ORGANISM: Homo sapiens

<400> SEQUENCE: 144
gaggtgcagc tggtggagtc tgggggaggc ttggtccagc ctgggggggtc cctgagactc      60 tcctgtgcag cctctggact cacctttagt aactttftgga tgagctgggt ccgccaggct     120
ccagggaagg ggctggagtg ggtggccaac ataaagcaag atggaagtga gaaatactat     180
gtggactctg tgaagggccg attcaccatc tccagagaca acgccaagaa ttcactgtat     240
ctgcaaatga acagcctgag agccgaggac acggctgtgt attcctgtac gagagagtca     300
aactggggat ttgcttttga tatctggggc caagggacaa tggtcaccgt ctcttca        357

<210> SEQ ID NO 145
<211> LENGTH: 327
<212> TYPE: DNA
<213> ORGANISM: Homo sapiens

<400> SEQUENCE: 145
cagtctgtgc tgactcagcc accctcagcg tctgggaccc ccgggcagag ggtcaccatc      60
tcttgttctg gaagcagctc caacatcgga agtaaaactg taaactggta ccagcagttc     120
ccaggaacgg cccccaaact cctcatctat agtaataatc ggcggccctc agggcgtccct     180 gaccgattct ctggctccaa gtctggcacc tcagcctccc tggccatcag tgggctccag     240
tctgaggatg aggctgatta ttactgtgca gcatgggatg acagcctgaa ttgggtgttc     300
ggcgcaggga ccaagctgac cgtccta                                         327

<210> SEQ ID NO 146
<211> LENGTH: 345
<212> TYPE: DNA
<213> ORGANISM: Homo sapiens

<400> SEQUENCE: 146
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcactt acaatggtaa cacaaactat     180
gcacagaagg tccagggcag agtcaccatg accacagaca catccacgag cacagcctac     240
atggagctga ggagcctgag atctgacgac acggccgttt attactgtgc gagagggtat     300
actcgggact actggggcca gggaaccctg gtcaccgtct cctca                     345
```

-continued

<210> SEQ ID NO 147
<211> LENGTH: 348
<212> TYPE: DNA
<213> ORGANISM: Homo sapiens

<400> SEQUENCE: 147

```
cagcctgtgc tgactcagcc actttttgca tcagcctccc tgggagcctc ggtcacactc      60
acctgcaccc tgagcagcgg ctacagtagt tatgaagtgg actggtatca gcagagacca     120
gggaagggcc cccggtttgt catgcgagtg dacactggtg ggattgtggg atccaagggg     180
gaaggcatcc ctgatcgctt ctcagtttg ggctcaggcc tgaatcggta tctgaccatc     240
aagaacatcc aggaagagga tgagagtgac taccactgtg gggcagacca tggcagtggg     300
accaacttcg tggtggtatt cggcggaggg accaagctga ccgtccta              348
```

<210> SEQ ID NO 148
<211> LENGTH: 348
<212> TYPE: DNA
<213> ORGANISM: Homo sapiens

<400> SEQUENCE: 148

```
caggtgcagc tacagcagtg gggcgcagga ctgttgaagc cttcggagac cctgtccctc      60
acctgcgctg tctatggtgg gtccttcagt gcgtactact ggaactggat ccgccagccc     120
ccagggaagg ggctggagtg gattggggaa atcaatcata gtggaagaac cgactacaac     180
ccgtccctca agagtcgagt caccatatca gtagacacgt ccaagaagca gttctccctg     240
aagctgaact ctgtgaccgc cgcggacacg gctgtgtatt actgtgcgag agggcagctc     300
gtcccctttg actactgggg ccagggaacc ctggtcaccg tctcttca               348
```

<210> SEQ ID NO 149
<211> LENGTH: 330
<212> TYPE: DNA
<213> ORGANISM: Homo sapiens

<400> SEQUENCE: 149

```
cagtctgtgc tgactcagcc accctcagcg tctgggaccc ccgggcagag ggtcaccatc      60
tcttgttctg gaagcagctc caacatcgga agtaatactg taaattggta tcagcaactc     120
ccaggaacgg cccccaaact cctcatctat agtaataatc agcggccctc aggggtccct     180
gaccgattct ctggctccaa gtctggcacc tcagcctccc tggccatcag tgggctccag     240
tctgaggatg aggctgatta ttactgtgca gtatgggatg acagcctgaa tggttgggtg     300
ttcggcggag ggaccaagct gaccgtccta                                  330
```

<210> SEQ ID NO 150
<211> LENGTH: 345
<212> TYPE: DNA
<213> ORGANISM: Homo sapiens

<400> SEQUENCE: 150

```
caggttcagc tggtgcagtc tggagctgag gtgaagaagc ctggggcctc agtgaaggtc      60
tcctgcaagg cttctggtta cacctttccc agctatggta tcagctgggt gcgacaggcc     120
cctggacaag ggcttgagtg gatgggatgg atcagcgctt acaatggtaa cacaaactat     180
gcagagaagc tccagggcag agtcaccatg accacagaca catccacgag cacagcctac     240
atggaggtga ggagcctgag atctgacgac acggccgtgt tttactgtgc gagaggctac     300
gttatggacg tctggggcca aggaccacg gtcaccgtct cctct                  345
```

<210> SEQ ID NO 151
<211> LENGTH: 327
<212> TYPE: DNA
<213> ORGANISM: Homo sapiens

<400> SEQUENCE: 151
cagtctgccc tgactcagcc tgcctccgtg tctgggtctc ctggacagtc gatcaccatc        60
tcctgcactg gaaccagcag tgacgttggt cgttataatt ctgtctcctg gtaccaacac       120
cacccaggca aagcccccaa agtcatgatt tatgaggtca gtaatcggcc ctcaggggtt       180
tctactcgct tctctggctc caagtctggc aacacggcct ccctgaccat ctctgggctc       240
caggctgagg acgaggctga ttattactgc agctcatata caagcagcag cgttgtattc       300
ggcggaggga ccaaactgac cgtccta                                           327

<210> SEQ ID NO 152
<211> LENGTH: 369
<212> TYPE: DNA
<213> ORGANISM: Homo sapiens

<400> SEQUENCE: 152
gaggtgcagc tggtggagtc tgggggaggc ctggtcaagc ctggggggtc cctgagactc        60
tcctgtgcag cctctggatt caccttcagt agctatagca tgaactgggt ccgccaggct       120
ccagggaagg ggctggagtg ggtctcatcc attagtagta gtagtagtta catttcctac       180
gcagactcag tgaagggccg attcaccatc tccagagaca acgccaagaa ctcactgtat       240
ctgcaaatga acagcctgag agccgaggac acggctgtgt atttctgtgc gagagattac       300
gattttggga gtgcttacta tgatgctttt gatgtctggg gccaagggac aatggtcacc       360
gtctcttca                                                               369

<210> SEQ ID NO 153
<211> LENGTH: 333
<212> TYPE: DNA
<213> ORGANISM: Homo sapiens

<400> SEQUENCE: 153
cagtctgtgc tgacgcagcc gccctcagtg tctggggccc cagggcagag ggtcaccatc        60
tcctgcactg ggagcagctc caacatcggg gcaggttatg atgtacactg gtaccagcag       120
cttccaggaa cagcccccaa actcctcatc tctggtaaca gcaatcggcc ctcaggggtc       180
cctgaccgat tctctggctc caagtctggc acctcagcct ccctggccat cactgggctc       240
caggctgagg atgaggctga ttattactgc cagtcctatg acagcagcct gagtggttcg       300
gtattcggcg gagggaccaa gctgaccgtc cta                                    333

<210> SEQ ID NO 154
<211> LENGTH: 326
<212> TYPE: PRT
<213> ORGANISM: Homo sapiens

<400> SEQUENCE: 154

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

```
<210> SEQ ID NO 155
<211> LENGTH: 327
<212> TYPE: PRT
<213> ORGANISM: Homo sapiens

<400> SEQUENCE: 155
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
```

-continued

```
                    85              90              95

Arg Val Glu Ser Lys Tyr Gly Pro Pro Cys Pro Ser Cys Pro Ala Pro
                100             105             110

Glu Phe Leu Gly Gly Pro Ser Val Phe Leu Phe Pro Pro Lys Pro Lys
            115             120             125

Asp Thr Leu Met Ile Ser Arg Thr Pro Glu Val Thr Cys Val Val Val
            130             135             140

Asp Val Ser Gln Glu Asp Pro Glu Val Gln Phe Asn Trp Tyr Val Asp
        145             150             155             160

Gly Val Glu Val His Asn Ala Lys Thr Lys Pro Arg Glu Glu Gln Phe
                165             170             175

Asn Ser Thr Tyr Arg Val Val Ser Val Leu Thr Val Leu His Gln Asp
                180             185             190

Trp Leu Asn Gly Lys Glu Tyr Lys Cys Lys Val Ser Asn Lys Gly Leu
            195             200             205

Pro Ser Ser Ile Glu Lys Thr Ile Ser Lys Ala Lys Gly Gln Pro Arg
        210             215             220

Glu Pro Gln Val Tyr Thr Leu Pro Pro Ser Gln Glu Glu Met Thr Lys
    225             230             235             240

Asn Gln Val Ser Leu Thr Cys Leu Val Lys Gly Phe Tyr Pro Ser Asp
                245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
            275             280             285

Arg Leu Thr Val Asp Lys Ser Arg Trp Gln Glu Gly Asn Val Phe Ser
        290             295             300

Cys Ser Val Met His Glu Ala Leu His Asn His Tyr Thr Gln Lys Ser
    305             310             315             320

Leu Ser Leu Ser Leu Gly Lys
                325

<210> SEQ ID NO 156
<211> LENGTH: 105
<212> TYPE: PRT
<213> ORGANISM: Homo sapiens

<400> SEQUENCE: 156

Gln Pro Lys Ala Ala Pro Ser Val Thr Leu Phe Pro Pro Ser Ser Glu
1               5               10              15

Glu Leu Gln Ala Asn Lys Ala Thr Leu Val Cys Leu Ile Ser Asp Phe
            20              25              30

Tyr Pro Gly Ala Val Thr Val Ala Trp Lys Ala Asp Ser Ser Pro Val
            35              40              45

Lys Ala Gly Val Glu Thr Thr Thr Pro Ser Lys Gln Ser Asn Asn Lys
        50              55              60

Tyr Ala Ala Ser Ser Tyr Leu Ser Leu Thr Pro Glu Gln Trp Lys Ser
65              70              75              80

His Arg Ser Tyr Ser Cys Gln Val Thr His Glu Gly Ser Thr Val Glu
                85              90              95

Lys Thr Val Ala Pro Thr Glu Cys Ser
                100             105

<210> SEQ ID NO 157
<211> LENGTH: 106
```

```
<212> TYPE: PRT
<213> ORGANISM: Homo sapiens

<400> SEQUENCE: 157

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 158
<211> LENGTH: 14
<212> TYPE: PRT
<213> ORGANISM: Homo sapiens

<400> SEQUENCE: 158

Thr Gly Thr Ser Ser Asp Val Gly Gly Tyr Asn Ser Val Ser
1               5                   10

<210> SEQ ID NO 159
<211> LENGTH: 14
<212> TYPE: PRT
<213> ORGANISM: Homo sapiens

<400> SEQUENCE: 159

Thr Gly Thr Asn Ser Asp Val Gly Gly Tyr Asn Ser Val Ser
1               5                   10

<210> SEQ ID NO 160
<211> LENGTH: 14
<212> TYPE: PRT
<213> ORGANISM: Homo sapiens

<400> SEQUENCE: 160

Thr Gly Thr Ser Ser Asp Val Gly Ala Tyr Asn Ser Val Ser
1               5                   10

<210> SEQ ID NO 161
<211> LENGTH: 14
<212> TYPE: PRT
<213> ORGANISM: Homo sapiens

<400> SEQUENCE: 161

Thr Gly Thr Ser Ser Asp Val Gly Arg Tyr Asn Ser Val Ser
1               5                   10

<210> SEQ ID NO 162
<211> LENGTH: 7
<212> TYPE: PRT
<213> ORGANISM: Homo sapiens

<400> SEQUENCE: 162

Glu Val Ser Asn Arg Pro Ser
```

-continued 1               5

<210> SEQ ID NO 163
<211> LENGTH: 7
<212> TYPE: PRT
<213> ORGANISM: Homo sapiens

<400> SEQUENCE: 163

Glu Val Thr Asn Arg Pro Ser
1               5

<210> SEQ ID NO 164
<211> LENGTH: 9
<212> TYPE: PRT
<213> ORGANISM: Homo sapiens

<400> SEQUENCE: 164

Ser Ser Tyr Thr Ser Thr Ser Met Val
1               5

<210> SEQ ID NO 165
<211> LENGTH: 9
<212> TYPE: PRT
<213> ORGANISM: Homo sapiens

<400> SEQUENCE: 165

Asn Ser Tyr Thr Ser Thr Ser Met Val
1               5

<210> SEQ ID NO 166
<211> LENGTH: 9
<212> TYPE: PRT
<213> ORGANISM: Homo sapiens

<400> SEQUENCE: 166

Ser Ser Tyr Thr Ser Thr Asn Met Val
1               5

<210> SEQ ID NO 167
<211> LENGTH: 9
<212> TYPE: PRT
<213> ORGANISM: Homo sapiens

<400> SEQUENCE: 167

Ser Ser Tyr Thr Ser Ser Ser Val Val
1               5

<210> SEQ ID NO 168
<211> LENGTH: 10
<212> TYPE: PRT
<213> ORGANISM: Homo sapiens

<400> SEQUENCE: 168

Gly Tyr Pro Leu Thr Ser Tyr Gly Ile Ser
1               5                   10

<210> SEQ ID NO 169
<211> LENGTH: 10
<212> TYPE: PRT
<213> ORGANISM: Homo sapiens

<400> SEQUENCE: 169

Gly Tyr Ser Leu Thr Ser Tyr Gly Ile Ser
1               5                   10

-continued

```
<210> SEQ ID NO 170
<211> LENGTH: 10
<212> TYPE: PRT
<213> ORGANISM: Homo sapiens

<400> SEQUENCE: 170

Gly Tyr Ala Leu Thr Ser Tyr Gly Ile Ser
1               5                   10

<210> SEQ ID NO 171
<211> LENGTH: 10
<212> TYPE: PRT
<213> ORGANISM: Homo sapiens

<400> SEQUENCE: 171

Gly Tyr Thr Leu Thr Ser Tyr Gly Ile Ser
1               5                   10

<210> SEQ ID NO 172
<211> LENGTH: 10
<212> TYPE: PRT
<213> ORGANISM: Homo sapiens

<400> SEQUENCE: 172

Gly Tyr Ser Phe Thr Ser Tyr Gly Ile Ser
1               5                   10

<210> SEQ ID NO 173
<211> LENGTH: 10
<212> TYPE: PRT
<213> ORGANISM: Homo sapiens

<400> SEQUENCE: 173

Gly Tyr Thr Phe Pro Ser Tyr Gly Ile Ser
1               5                   10

<210> SEQ ID NO 174
<211> LENGTH: 17
<212> TYPE: PRT
<213> ORGANISM: Homo sapiens

<400> SEQUENCE: 174

Trp Ile Ser Ala Tyr Asn Gly Asn Thr Asn Tyr Ala Gln Lys Val Gln
1               5                   10                  15

Gly

<210> SEQ ID NO 175
<211> LENGTH: 17
<212> TYPE: PRT
<213> ORGANISM: Homo sapiens

<400> SEQUENCE: 175

Trp Val Ser Phe Tyr Asn Gly Asn Thr Asn Tyr Ala Gln Lys Leu Gln
1               5                   10                  15

Gly

<210> SEQ ID NO 176
<211> LENGTH: 17
<212> TYPE: PRT
<213> ORGANISM: Homo sapiens

<400> SEQUENCE: 176

Trp Ile Ser Phe Tyr Asn Gly Asn Thr Asn Tyr Ala Gln Lys Val Gln
```

```
1               5               10              15

Gly

<210> SEQ ID NO 177
<211> LENGTH: 17
<212> TYPE: PRT
<213> ORGANISM: Homo sapiens

<400> SEQUENCE: 177

Trp Ile Ser Val Tyr Asn Gly Asn Thr Asn Tyr Ala Gln Lys Val Gln
1               5               10              15

Gly

<210> SEQ ID NO 178
<211> LENGTH: 17
<212> TYPE: PRT
<213> ORGANISM: Homo sapiens

<400> SEQUENCE: 178

Trp Val Ser Ala Tyr Asn Gly Asn Thr Asn Tyr Ala Gln Lys Phe Gln
1               5               10              15

Gly

<210> SEQ ID NO 179
<211> LENGTH: 17
<212> TYPE: PRT
<213> ORGANISM: Homo sapiens

<400> SEQUENCE: 179

Trp Ile Ser Ala Tyr Asn Gly Asn Thr Asn Tyr Ala Glu Lys Leu Gln
1               5               10              15

Gly

<210> SEQ ID NO 180
<211> LENGTH: 6
<212> TYPE: PRT
<213> ORGANISM: Homo sapiens

<400> SEQUENCE: 180

Gly Tyr Gly Met Asp Val
1               5

<210> SEQ ID NO 181
<211> LENGTH: 6
<212> TYPE: PRT
<213> ORGANISM: Homo sapiens

<400> SEQUENCE: 181

Gly Tyr Val Met Asp Val
1               5

<210> SEQ ID NO 182
<211> LENGTH: 13
<212> TYPE: PRT
<213> ORGANISM: Homo sapiens

<400> SEQUENCE: 182

Ser Gly Ser Ser Ser Asn Ile Gly Asn Asn Phe Val Ser
1               5               10

<210> SEQ ID NO 183
<211> LENGTH: 7
```

```
<212> TYPE: PRT
<213> ORGANISM: Homo sapiens

<400> SEQUENCE: 183

Asp Tyr Asn Lys Arg Pro Ser
1               5

<210> SEQ ID NO 184
<211> LENGTH: 7
<212> TYPE: PRT
<213> ORGANISM: Homo sapiens

<400> SEQUENCE: 184

Asp Ser Asn Lys Arg Pro Ser
1               5

<210> SEQ ID NO 185
<211> LENGTH: 11
<212> TYPE: PRT
<213> ORGANISM: Homo sapiens

<400> SEQUENCE: 185

Gly Thr Trp Asp Ser Ser Leu Ser Gly Tyr Val
1               5                   10

<210> SEQ ID NO 186
<211> LENGTH: 11
<212> TYPE: PRT
<213> ORGANISM: Homo sapiens

<400> SEQUENCE: 186

Gly Thr Trp Asp Ser Ser Leu Ser Ala Tyr Val
1               5                   10

<210> SEQ ID NO 187
<211> LENGTH: 11
<212> TYPE: PRT
<213> ORGANISM: Homo sapiens

<400> SEQUENCE: 187

Gly Thr Trp Asp Ser Ser Leu Ser Ser Tyr Val
1               5                   10

<210> SEQ ID NO 188
<211> LENGTH: 10
<212> TYPE: PRT
<213> ORGANISM: Homo sapiens

<400> SEQUENCE: 188

Gly Phe Thr Phe Ser Ser Phe Gly Met His
1               5                   10

<210> SEQ ID NO 189
<211> LENGTH: 10
<212> TYPE: PRT
<213> ORGANISM: Homo sapiens

<400> SEQUENCE: 189

Gly Phe Thr Phe Asn Ser Phe Gly Met His
1               5                   10

<210> SEQ ID NO 190
<211> LENGTH: 10
<212> TYPE: PRT
<213> ORGANISM: Homo sapiens
```

-continued

```
<400> SEQUENCE: 190

Gly Phe Thr Phe Arg Ser Tyr Gly Met His
1               5                   10

<210> SEQ ID NO 191
<211> LENGTH: 17
<212> TYPE: PRT
<213> ORGANISM: Homo sapiens

<400> SEQUENCE: 191

Leu Ile Trp Asn Asp Gly Ser Asn Lys Tyr Tyr Ala Asp Ser Val Lys
1               5                   10                  15

Gly

<210> SEQ ID NO 192
<211> LENGTH: 17
<212> TYPE: PRT
<213> ORGANISM: Homo sapiens

<400> SEQUENCE: 192

Leu Ile Trp Ser Asp Gly Ser Asp Glu Tyr Tyr Ala Asp Ser Val Lys
1               5                   10                  15

Gly

<210> SEQ ID NO 193
<211> LENGTH: 17
<212> TYPE: PRT
<213> ORGANISM: Homo sapiens

<400> SEQUENCE: 193

Leu Ile Trp Ser Asp Gly Ser Asp Lys Tyr Tyr Ala Asp Ser Val Lys
1               5                   10                  15

Gly

<210> SEQ ID NO 194
<211> LENGTH: 17
<212> TYPE: PRT
<213> ORGANISM: Homo sapiens

<400> SEQUENCE: 194

Leu Ile Trp His Asp Gly Ser Asn Thr Tyr Tyr Val Asp Ser Val Lys
1               5                   10                  15

Gly

<210> SEQ ID NO 195
<211> LENGTH: 13
<212> TYPE: PRT
<213> ORGANISM: Homo sapiens

<400> SEQUENCE: 195

Ala Ile Ala Ala Leu Tyr Tyr Tyr Tyr Gly Met Asp Val
1               5                   10

<210> SEQ ID NO 196
<211> LENGTH: 13
<212> TYPE: PRT
<213> ORGANISM: Homo sapiens

<400> SEQUENCE: 196

Gly Ile Ala Val Ala Tyr Tyr Tyr Tyr Gly Met Asp Val
1               5                   10
```

<210> SEQ ID NO 197
<211> LENGTH: 13
<212> TYPE: PRT
<213> ORGANISM: Homo sapiens

<400> SEQUENCE: 197

Ser Gly Ser Ser Ser Asn Ile Gly Ser Asn Thr Val Asn
1               5                   10

<210> SEQ ID NO 198
<211> LENGTH: 13
<212> TYPE: PRT
<213> ORGANISM: Homo sapiens

<400> SEQUENCE: 198

Ser Gly Ser Ser Ser Asn Ile Gly Ser Lys Thr Val Asn
1               5                   10

<210> SEQ ID NO 199
<211> LENGTH: 7
<212> TYPE: PRT
<213> ORGANISM: Homo sapiens

<400> SEQUENCE: 199

Ser Asn Asn Arg Arg Pro Ser
1               5

<210> SEQ ID NO 200
<211> LENGTH: 7
<212> TYPE: PRT
<213> ORGANISM: Homo sapiens

<400> SEQUENCE: 200

Arg Asn Asn Gln Arg Pro Leu
1               5

<210> SEQ ID NO 201
<211> LENGTH: 10
<212> TYPE: PRT
<213> ORGANISM: Homo sapiens

<400> SEQUENCE: 201

Ala Ala Trp Asp Asp Ser Leu Asn Trp Val
1               5                   10

<210> SEQ ID NO 202
<211> LENGTH: 10
<212> TYPE: PRT
<213> ORGANISM: Homo sapiens

<400> SEQUENCE: 202

Gly Phe Thr Phe Ser Arg Tyr Trp Met Ser
1               5                   10

<210> SEQ ID NO 203
<211> LENGTH: 10
<212> TYPE: PRT
<213> ORGANISM: Homo sapiens

<400> SEQUENCE: 203

Gly Leu Thr Phe Ser Asn Phe Trp Met Ser
1               5                   10

<210> SEQ ID NO 204
<211> LENGTH: 10
<212> TYPE: PRT
<213> ORGANISM: Homo sapiens

<400> SEQUENCE: 204

Gly Phe Thr Phe Ser Ser Tyr Trp Met Ser
1               5                   10

<210> SEQ ID NO 205
<211> LENGTH: 17
<212> TYPE: PRT
<213> ORGANISM: Homo sapiens

<400> SEQUENCE: 205

Asn Ile Lys His Asp Gly Ser Glu Lys Tyr Tyr Val Asp Ser Val Lys
1               5                   10                  15

Gly

<210> SEQ ID NO 206
<211> LENGTH: 17
<212> TYPE: PRT
<213> ORGANISM: Homo sapiens

<400> SEQUENCE: 206

Asn Ile Lys Gln Asp Gly Ser Glu Lys Tyr Tyr Val Asp Ser Val Lys
1               5                   10                  15

Gly

<210> SEQ ID NO 207
<211> LENGTH: 10
<212> TYPE: PRT
<213> ORGANISM: Homo sapiens

<400> SEQUENCE: 207

Glu Ser Asn Trp Gly Phe Ala Phe Asp Val
1               5                   10

<210> SEQ ID NO 208
<211> LENGTH: 10
<212> TYPE: PRT
<213> ORGANISM: Homo sapiens

<400> SEQUENCE: 208

Glu Ser Asn Trp Gly Phe Ala Phe Asp Ile
1               5                   10

<210> SEQ ID NO 209
<211> LENGTH: 11
<212> TYPE: PRT
<213> ORGANISM: Homo sapiens

<400> SEQUENCE: 209

Arg Ala Ser Gln Ser Ile Ser Ser Tyr Leu Asn
1               5                   10

<210> SEQ ID NO 210
<211> LENGTH: 11
<212> TYPE: PRT
<213> ORGANISM: Homo sapiens

<400> SEQUENCE: 210

Arg Ala Ser Gln Ser Ile Ser Ile Tyr Leu Asn
1               5                   10

```
<210> SEQ ID NO 211
<211> LENGTH: 7
<212> TYPE: PRT
<213> ORGANISM: Homo sapiens

<400> SEQUENCE: 211

Ala Ala Ser Ser Leu Gln Ser
1               5

<210> SEQ ID NO 212
<211> LENGTH: 7
<212> TYPE: PRT
<213> ORGANISM: Homo sapiens

<400> SEQUENCE: 212

Ala Ala Ala Ser Leu Gln Ser
1               5

<210> SEQ ID NO 213
<211> LENGTH: 9
<212> TYPE: PRT
<213> ORGANISM: Homo sapiens

<400> SEQUENCE: 213

Gln Gln Ser Tyr Ser Ser Pro Ile Thr
1               5

<210> SEQ ID NO 214
<211> LENGTH: 9
<212> TYPE: PRT
<213> ORGANISM: Homo sapiens

<400> SEQUENCE: 214

Gln Gln Ser Tyr Ser Ala Pro Ile Thr
1               5

<210> SEQ ID NO 215
<211> LENGTH: 10
<212> TYPE: PRT
<213> ORGANISM: Homo sapiens

<400> SEQUENCE: 215

Gly Phe Thr Phe Ser Ser Tyr Ala Met Asn
1               5                   10

<210> SEQ ID NO 216
<211> LENGTH: 17
<212> TYPE: PRT
<213> ORGANISM: Homo sapiens

<400> SEQUENCE: 216

Thr Ile Ser Gly Ser Gly Asp Asn Thr Tyr Tyr Ala Asp Ser Val Lys
1               5                   10                  15

Gly

<210> SEQ ID NO 217
<211> LENGTH: 17
<212> TYPE: PRT
<213> ORGANISM: Homo sapiens

<400> SEQUENCE: 217

Thr Ile Ser Gly Ser Gly Gly Asn Thr Tyr Tyr Ala Asp Ser Val Lys
1               5                   10                  15
```

-continued

```
Gly

<210> SEQ ID NO 218
<211> LENGTH: 12
<212> TYPE: PRT
<213> ORGANISM: Homo sapiens

<400> SEQUENCE: 218

Lys Phe Val Leu Met Val Tyr Ala Met Leu Asp Tyr
1               5                   10

<210> SEQ ID NO 219
<211> LENGTH: 11
<212> TYPE: PRT
<213> ORGANISM: Homo sapiens

<400> SEQUENCE: 219

Arg Ala Ser Gln Arg Ile Ser Asn Tyr Leu Ser
1               5                   10

<210> SEQ ID NO 220
<211> LENGTH: 16
<212> TYPE: PRT
<213> ORGANISM: Homo sapiens

<400> SEQUENCE: 220

Arg Ser Ser Gln Ser Leu Leu His Ser Asn Gly Tyr Asn Phe Leu Asn
1               5                   10                  15

<210> SEQ ID NO 221
<211> LENGTH: 14
<212> TYPE: PRT
<213> ORGANISM: Homo sapiens

<400> SEQUENCE: 221

Thr Gly Thr Ser Ser Asp Val Gly Asn Tyr Asn Leu Val Ser
1               5                   10

<210> SEQ ID NO 222
<211> LENGTH: 14
<212> TYPE: PRT
<213> ORGANISM: Homo sapiens

<400> SEQUENCE: 222

Thr Gly Ser Ser Ser Asn Ile Gly Ala Gly Tyr Asp Val His
1               5                   10

<210> SEQ ID NO 223
<211> LENGTH: 14
<212> TYPE: PRT
<213> ORGANISM: Homo sapiens

<400> SEQUENCE: 223

Thr Gly Ser Ser Ser Asn Ile Gly Ala His Tyr Asp Val His
1               5                   10

<210> SEQ ID NO 224
<211> LENGTH: 13
<212> TYPE: PRT
<213> ORGANISM: Homo sapiens

<400> SEQUENCE: 224

Ser Gly Ser Asn Ser Asn Ile Gly Asn Asn Tyr Val Ser
1               5                   10
```

-continued

```
<210> SEQ ID NO 225
<211> LENGTH: 11
<212> TYPE: PRT
<213> ORGANISM: Homo sapiens

<400> SEQUENCE: 225

Ser Gly Asp Lys Leu Gly Asp Lys Tyr Ala Cys
1               5               10

<210> SEQ ID NO 226
<211> LENGTH: 12
<212> TYPE: PRT
<213> ORGANISM: Homo sapiens

<400> SEQUENCE: 226

Thr Leu Ser Ser Gly Tyr Ser Ser Tyr Glu Val Asp
1               5               10

<210> SEQ ID NO 227
<211> LENGTH: 7
<212> TYPE: PRT
<213> ORGANISM: Homo sapiens

<400> SEQUENCE: 227

Leu Gly Ser His Arg Ala Ser
1               5

<210> SEQ ID NO 228
<211> LENGTH: 7
<212> TYPE: PRT
<213> ORGANISM: Homo sapiens

<400> SEQUENCE: 228

Glu Val Ser Lys Arg Pro Ser
1               5

<210> SEQ ID NO 229
<211> LENGTH: 7
<212> TYPE: PRT
<213> ORGANISM: Homo sapiens

<400> SEQUENCE: 229

Gly Asn Ser Asn Arg Pro Ser
1               5

<210> SEQ ID NO 230
<211> LENGTH: 7
<212> TYPE: PRT
<213> ORGANISM: Homo sapiens

<400> SEQUENCE: 230

Gly Asn Thr Tyr Arg Pro Ser
1               5

<210> SEQ ID NO 231
<211> LENGTH: 7
<212> TYPE: PRT
<213> ORGANISM: Homo sapiens

<400> SEQUENCE: 231

Ser Asn Asn Gln Arg Pro Ser
1               5
```

-continued

```
<210> SEQ ID NO 232
<211> LENGTH: 7
<212> TYPE: PRT
<213> ORGANISM: Homo sapiens

<400> SEQUENCE: 232

Asp Asn Asn Lys Arg Pro Ser
1               5

<210> SEQ ID NO 233
<211> LENGTH: 7
<212> TYPE: PRT
<213> ORGANISM: Homo sapiens

<400> SEQUENCE: 233

Gln Asn Thr Lys Trp Pro Leu
1               5

<210> SEQ ID NO 234
<211> LENGTH: 7
<212> TYPE: PRT
<213> ORGANISM: Homo sapiens

<400> SEQUENCE: 234

Val Asp Thr Gly Gly Ile Val
1               5

<210> SEQ ID NO 235
<211> LENGTH: 9
<212> TYPE: PRT
<213> ORGANISM: Homo sapiens

<400> SEQUENCE: 235

Gln Gln Ser Tyr Ser Thr Pro Leu Ile
1               5

<210> SEQ ID NO 236
<211> LENGTH: 9
<212> TYPE: PRT
<213> ORGANISM: Homo sapiens

<400> SEQUENCE: 236

Met Gln Val Leu Gln Thr Pro Phe Thr
1               5

<210> SEQ ID NO 237
<211> LENGTH: 10
<212> TYPE: PRT
<213> ORGANISM: Homo sapiens

<400> SEQUENCE: 237

Cys Ser Tyr Ala Gly Ser Ser Thr Leu Val
1               5                   10

<210> SEQ ID NO 238
<211> LENGTH: 11
<212> TYPE: PRT
<213> ORGANISM: Homo sapiens

<400> SEQUENCE: 238

Gln Ser Tyr Asp Ser Ser Leu Ser Gly Ser Val
1               5                   10

<210> SEQ ID NO 239
<211> LENGTH: 11
```

```
<212> TYPE: PRT
<213> ORGANISM: Homo sapiens

<400> SEQUENCE: 239

Gln Ser Tyr Asp Asn Ser Leu Ser Gly Val Val
1               5                   10

<210> SEQ ID NO 240
<211> LENGTH: 11
<212> TYPE: PRT
<213> ORGANISM: Homo sapiens

<400> SEQUENCE: 240

Ala Val Trp Asp Asp Ser Leu Asn Gly Trp Val
1               5                   10

<210> SEQ ID NO 241
<211> LENGTH: 11
<212> TYPE: PRT
<213> ORGANISM: Homo sapiens

<400> SEQUENCE: 241

Gly Thr Trp Asp Ser Ser Leu Ser Ala Val Val
1               5                   10

<210> SEQ ID NO 242
<211> LENGTH: 9
<212> TYPE: PRT
<213> ORGANISM: Homo sapiens

<400> SEQUENCE: 242

Gln Ala Trp Asp Ser Ser Thr Val Val
1               5

<210> SEQ ID NO 243
<211> LENGTH: 18
<212> TYPE: PRT
<213> ORGANISM: Homo sapiens

<400> SEQUENCE: 243

Ser Asp Tyr His Cys Gly Ala Asp His Gly Ser Gly Thr Asn Phe Val
1               5                   10                  15

Val Val

<210> SEQ ID NO 244
<211> LENGTH: 10
<212> TYPE: PRT
<213> ORGANISM: Homo sapiens

<400> SEQUENCE: 244

Gly Tyr Thr Phe Thr Ser Tyr Gly Ile Ser
1               5                   10

<210> SEQ ID NO 245
<211> LENGTH: 10
<212> TYPE: PRT
<213> ORGANISM: Homo sapiens

<400> SEQUENCE: 245

Gly Phe Thr Phe Ser Ser Tyr Ala Met Ser
1               5                   10

<210> SEQ ID NO 246
<211> LENGTH: 10
```

-continued

```
<212> TYPE: PRT
<213> ORGANISM: Homo sapiens

<400> SEQUENCE: 246

Gly Phe Thr Phe Ser Ser Tyr Gly Met His
1               5                   10

<210> SEQ ID NO 247
<211> LENGTH: 10
<212> TYPE: PRT
<213> ORGANISM: Homo sapiens

<400> SEQUENCE: 247

Gly Phe Thr Phe Ser Ser Tyr Ser Met Asn
1               5                   10

<210> SEQ ID NO 248
<211> LENGTH: 12
<212> TYPE: PRT
<213> ORGANISM: Homo sapiens

<400> SEQUENCE: 248

Gly Gly Ser Ile Ser Ser Gly Gly Tyr Tyr Trp Ser
1               5                   10

<210> SEQ ID NO 249
<211> LENGTH: 12
<212> TYPE: PRT
<213> ORGANISM: Homo sapiens

<400> SEQUENCE: 249

Gly Gly Ser Ile Ser Ser Ser Asp Tyr Tyr Trp Ser
1               5                   10

<210> SEQ ID NO 250
<211> LENGTH: 10
<212> TYPE: PRT
<213> ORGANISM: Homo sapiens

<400> SEQUENCE: 250

Gly Gly Ser Phe Ser Ala Tyr Tyr Trp Asn
1               5                   10

<210> SEQ ID NO 251
<211> LENGTH: 12
<212> TYPE: PRT
<213> ORGANISM: Homo sapiens

<400> SEQUENCE: 251

Gly Asp Ser Val Ser Ser Asn Ser Ala Ala Trp Asn
1               5                   10

<210> SEQ ID NO 252
<211> LENGTH: 17
<212> TYPE: PRT
<213> ORGANISM: Homo sapiens

<400> SEQUENCE: 252

Trp Ile Ser Thr Tyr Asn Gly Asn Thr Asn Tyr Ala Gln Lys Val Gln
1               5                   10                  15

Gly

<210> SEQ ID NO 253
<211> LENGTH: 17
```

<212> TYPE: PRT
<213> ORGANISM: Homo sapiens

<400> SEQUENCE: 253

Thr Ile Ser Gly Ser Gly Gly Arg Thr Tyr Tyr Ala Asp Ser Val Lys
1               5                   10                  15

Gly

<210> SEQ ID NO 254
<211> LENGTH: 17
<212> TYPE: PRT
<213> ORGANISM: Homo sapiens

<400> SEQUENCE: 254

Val Ile Trp Tyr Asp Gly Ser Asp Lys Tyr Tyr Ala Asp Ser Val Lys
1               5                   10                  15

Gly

<210> SEQ ID NO 255
<211> LENGTH: 17
<212> TYPE: PRT
<213> ORGANISM: Homo sapiens

<400> SEQUENCE: 255

Ile Ile Trp Tyr Asp Gly Ser Asn Lys Tyr Tyr Ala Asp Ser Val Lys
1               5                   10                  15

Gly

<210> SEQ ID NO 256
<211> LENGTH: 17
<212> TYPE: PRT
<213> ORGANISM: Homo sapiens

<400> SEQUENCE: 256

Ser Ile Ser Ser Ser Ser Ser Tyr Ile Ser Tyr Ala Asp Ser Val Lys
1               5                   10                  15

Gly

<210> SEQ ID NO 257
<211> LENGTH: 16
<212> TYPE: PRT
<213> ORGANISM: Homo sapiens

<400> SEQUENCE: 257

Tyr Ile Tyr Asn Ser Gly Ser Thr Tyr Tyr Asn Pro Ser Leu Lys Ser
1               5                   10                  15

<210> SEQ ID NO 258
<211> LENGTH: 16
<212> TYPE: PRT
<213> ORGANISM: Homo sapiens

<400> SEQUENCE: 258

Tyr Ile Tyr Tyr Ser Gly Ser Thr Tyr Tyr Asn Pro Ser Leu Lys Ser
1               5                   10                  15

<210> SEQ ID NO 259
<211> LENGTH: 16
<212> TYPE: PRT
<213> ORGANISM: Homo sapiens

<400> SEQUENCE: 259

```
Glu Ile Asn His Ser Gly Arg Thr Asp Tyr Asn Pro Ser Leu Lys Ser
1               5                   10                  15

<210> SEQ ID NO 260
<211> LENGTH: 18
<212> TYPE: PRT
<213> ORGANISM: Homo sapiens

<400> SEQUENCE: 260

Arg Thr Tyr Tyr Arg Ser Lys Trp Tyr Lys Asn Tyr Ser Val Ser Val
1               5                   10                  15

Lys Ser

<210> SEQ ID NO 261
<211> LENGTH: 6
<212> TYPE: PRT
<213> ORGANISM: Homo sapiens

<400> SEQUENCE: 261

Gly Tyr Thr Arg Asp Tyr
1               5

<210> SEQ ID NO 262
<211> LENGTH: 8
<212> TYPE: PRT
<213> ORGANISM: Homo sapiens

<400> SEQUENCE: 262

Glu Val Gly Ser Pro Phe Asp Tyr
1               5

<210> SEQ ID NO 263
<211> LENGTH: 14
<212> TYPE: PRT
<213> ORGANISM: Homo sapiens

<400> SEQUENCE: 263

Glu Thr Gly Pro Leu Lys Leu Tyr Tyr Tyr Gly Met Asp Val
1               5                   10

<210> SEQ ID NO 264
<211> LENGTH: 13
<212> TYPE: PRT
<213> ORGANISM: Homo sapiens

<400> SEQUENCE: 264

Arg Gly Gly Leu Ala Ala Arg Pro Gly Gly Met Asp Val
1               5                   10

<210> SEQ ID NO 265
<211> LENGTH: 14
<212> TYPE: PRT
<213> ORGANISM: Homo sapiens

<400> SEQUENCE: 265

Asp Tyr Asp Phe Trp Ser Ala Tyr Tyr Asp Ala Phe Asp Val
1               5                   10

<210> SEQ ID NO 266
<211> LENGTH: 11
<212> TYPE: PRT
<213> ORGANISM: Homo sapiens

<400> SEQUENCE: 266
```

-continued

```
Glu Asp Thr Ala Met Val Pro Tyr Phe Asp Tyr
1               5                   10

<210> SEQ ID NO 267
<211> LENGTH: 12
<212> TYPE: PRT
<213> ORGANISM: Homo sapiens

<400> SEQUENCE: 267

Gly Gly Val Thr Thr Tyr Tyr Tyr Ala Met Asp Val
1               5                   10

<210> SEQ ID NO 268
<211> LENGTH: 8
<212> TYPE: PRT
<213> ORGANISM: Homo sapiens

<400> SEQUENCE: 268

Gly Gln Leu Val Pro Phe Asp Tyr
1               5

<210> SEQ ID NO 269
<211> LENGTH: 9
<212> TYPE: PRT
<213> ORGANISM: Homo sapiens

<400> SEQUENCE: 269

Gly Gly Pro Thr Ala Ala Phe Asp Tyr
1               5

<210> SEQ ID NO 270
<211> LENGTH: 109
<212> TYPE: PRT
<213> ORGANISM: Homo sapiens

<400> SEQUENCE: 270

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Phe Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 271
<211> LENGTH: 109
<212> TYPE: PRT
<213> ORGANISM: Homo sapiens

<400> SEQUENCE: 271

Gln Ser Ala Leu Thr Gln Pro Ala Ser Val Phe Gly Ser Pro Gly Gln
1               5                   10                  15

Ser Ile Thr Ile Ser Cys Thr Gly Thr Ser Ser Asp Val Gly Ala Tyr
            20                  25                  30
```

```
Asn Ser Val Ser Trp Tyr Gln Gln His Pro Gly Lys Ala Pro Lys Arg
        35              40              45

Met Ile Tyr Glu Val Ser Asn Arg Pro Ser Gly Val Ser Asn Arg Phe
    50              55              60

Ser Gly Ser Lys Ser Gly Asn Thr Ala Ser Leu Thr Ile Ser Gly Leu
65              70              75              80

Gln Ala Glu Asp Glu Ala Asp Tyr Tyr Cys Ser Ser Tyr Thr Ser Thr
                85              90              95

Asn Met Val Phe Gly Gly Gly Thr Lys Leu Thr Val Leu
            100             105
```

```
<210> SEQ ID NO 272
<211> LENGTH: 109
<212> TYPE: PRT
<213> ORGANISM: Homo sapiens

<400> SEQUENCE: 272

Gln Ser Val Leu Thr Gln Pro Pro Ser Ala Ser Gly Pro Pro Gly Gln
1               5               10              15

Arg Val Thr Ile Ser Cys Ser Gly Ser Ser Ser Asn Ile Gly Ser Asn
                20              25              30

Thr Val Asn Trp Tyr Gln Gln Leu Pro Gly Thr Ala Pro Lys Leu Leu
        35              40              45

Ile Tyr Ser Asn Asn Arg Arg Pro Ser Gly Val Pro Asp Arg Phe Ser
    50              55              60

Gly Ser Lys Ser Gly Thr Ser Ala Ser Leu Ala Ile Ser Gly Leu Gln
65              70              75              80

Ser Glu Asp Glu Ala Asp Tyr Tyr Cys Ala Ala Trp Asp Asp Ser Leu
                85              90              95

Asn Trp Val Phe Gly Gly Gly Thr Lys Leu Thr Val Leu
            100             105
```

```
<210> SEQ ID NO 273
<211> LENGTH: 109
<212> TYPE: PRT
<213> ORGANISM: Homo sapiens

<400> SEQUENCE: 273

Gln Ser Val Leu Thr Gln Pro Pro Ser Ala Ser Gly Pro Pro Gly Gln
1               5               10              15

Arg Val Thr Ile Phe Cys Ser Gly Ser Ser Ser Asn Ile Gly Ser Asn
                20              25              30

Thr Val Asn Trp Tyr Gln Gln Leu Pro Gly Thr Ala Pro Lys Leu Leu
        35              40              45

Ile Tyr Ser Asn Asn Arg Arg Pro Ser Gly Val Pro Asp Arg Phe Ser
    50              55              60

Gly Ser Lys Ser Gly Thr Ser Ala Ser Leu Ala Ile Ser Gly Leu Gln
65              70              75              80

Ser Glu Asp Glu Ala Asp Tyr Tyr Cys Ala Ala Trp Asp Asp Ser Leu
                85              90              95

Asn Trp Val Phe Gly Gly Gly Thr Lys Leu Thr Val Leu
            100             105
```

```
<210> SEQ ID NO 274
<211> LENGTH: 106
<212> TYPE: PRT
<213> ORGANISM: Homo sapiens
```

<400> SEQUENCE: 274

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105
```

<210> SEQ ID NO 275
<211> LENGTH: 106
<212> TYPE: PRT
<213> ORGANISM: Homo sapiens

<400> SEQUENCE: 275

```
Ser Tyr Glu Leu Thr Gln Pro Pro Ser Val Ser Val Ser Pro Gly Gln
1               5                   10                  15

Thr Ala Arg Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
            35                  40                  45

Gln Asn Thr Lys Trp Pro Leu Gly Ile Pro Glu Arg Phe Ser Gly Ser
        50                  55                  60

Lys Ser Gly Asn Thr Val Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105
```

<210> SEQ ID NO 276
<211> LENGTH: 107
<212> TYPE: PRT
<213> ORGANISM: Homo sapiens

<400> SEQUENCE: 276

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu
```

-continued

```
                100                105

<210> SEQ ID NO 277
<211> LENGTH: 107
<212> TYPE: PRT
<213> ORGANISM: Homo sapiens

<400> SEQUENCE: 277

Ser Tyr Glu Leu Ile Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Arg Lys Pro Gly Gln Ser Pro Ile Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu
            100                 105

<210> SEQ ID NO 278
<211> LENGTH: 120
<212> TYPE: PRT
<213> ORGANISM: Homo sapiens

<400> SEQUENCE: 278

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Tyr Ser Ser Gly Trp Phe Glu Phe Asp Tyr Trp Gly Gln
                100                 105                 110

Gly Thr Leu Val Thr Val Ser Ser
        115                 120

<210> SEQ ID NO 279
<211> LENGTH: 12
<212> TYPE: PRT
<213> ORGANISM: Homo sapiens

<400> SEQUENCE: 279

Thr Leu Ser Ser Gly Tyr Ser Ser Tyr Glu Val Asp
1               5                   10

<210> SEQ ID NO 280
<211> LENGTH: 12
<212> TYPE: PRT
<213> ORGANISM: Homo sapiens
```

-continued

<400> SEQUENCE: 280

Val Asp Thr Gly Gly Ile Val Gly Ser Lys Gly Glu
1               5                   10

<210> SEQ ID NO 281
<211> LENGTH: 13
<212> TYPE: PRT
<213> ORGANISM: Homo sapiens

<400> SEQUENCE: 281

Gly Ala Asp His Gly Ser Gly Thr Asn Phe Val Val Val
1               5                   10

<210> SEQ ID NO 282
<211> LENGTH: 22
<212> TYPE: PRT
<213> ORGANISM: Homo sapiens

<400> SEQUENCE: 282

Gln Pro Val Leu Thr Gln Pro Leu Phe Ala Ser Ala Ser Leu Gly Ala
1               5                   10                  15

Ser Val Thr Leu Thr Cys
            20

<210> SEQ ID NO 283
<211> LENGTH: 15
<212> TYPE: PRT
<213> ORGANISM: Homo sapiens

<400> SEQUENCE: 283

Trp Tyr Gln Gln Arg Pro Gly Lys Gly Pro Arg Phe Val Met Arg
1               5                   10                  15

<210> SEQ ID NO 284
<211> LENGTH: 32
<212> TYPE: PRT
<213> ORGANISM: Homo sapiens

<400> SEQUENCE: 284

Gly Ile Pro Asp Arg Phe Ser Val Leu Gly Ser Gly Leu Asn Arg Tyr
1               5                   10                  15

Leu Thr Ile Lys Asn Ile Gln Glu Glu Asp Glu Ser Asp Tyr His Cys
            20                  25                  30

<210> SEQ ID NO 285
<211> LENGTH: 10
<212> TYPE: PRT
<213> ORGANISM: Homo sapiens

<400> SEQUENCE: 285

Phe Gly Gly Gly Thr Lys Leu Thr Val Leu
1               5                   10

<210> SEQ ID NO 286
<211> LENGTH: 108
<212> TYPE: PRT
<213> ORGANISM: Homo sapiens

<400> SEQUENCE: 286

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr

-continued

```
            20              25              30

Asn Ser Val Ser Trp Tyr Gln His His Pro Gly Lys Ala Pro Lys Val
        35              40              45

Met Ile Tyr Glu Val Ser Asn Arg Pro Ser Gly Val Ser Thr Arg Phe
    50              55              60

Ser Gly Ser Lys Ser Gly Asn Thr Ala Ser Leu Thr Ile Ser Gly Leu
65              70              75              80

Gln Ala Glu Asp Glu Ala Asp Tyr Tyr Cys Ser Ser Tyr Thr Ser Ser
            85              90              95

Ser Val Val Phe Gly Gly Gly Thr Lys Leu Thr Val
            100             105

<210> SEQ ID NO 287
<211> LENGTH: 108
<212> TYPE: PRT
<213> ORGANISM: Homo sapiens

<400> SEQUENCE: 287

Gln Ser Ala Leu Thr Gln Pro Ala Ser Val Ser Gly Ser Pro Gly Gln
1               5               10              15

Ser Ile Thr Ile Ser Cys Thr Gly Thr Ser Ser Asp Val Gly Gly Tyr
            20              25              30

Asn Ser Val Ser Trp Tyr Gln Gln His Pro Gly Lys Pro Pro Lys Leu
        35              40              45

Met Ile Tyr Glu Val Ser Asn Arg Pro Ser Gly Val Ser Ile Arg Phe
    50              55              60

Ser Gly Ser Lys Ser Gly Asn Thr Ala Ser Leu Thr Ile Ser Gly Leu
65              70              75              80

Gln Ala Glu Asp Glu Ala Asp Tyr Phe Cys Ser Ser Tyr Thr Ser Thr
            85              90              95

Ser Met Val Phe Gly Gly Gly Thr Lys Leu Thr Val
            100             105

<210> SEQ ID NO 288
<211> LENGTH: 108
<212> TYPE: PRT
<213> ORGANISM: Homo sapiens

<400> SEQUENCE: 288

Gln Ser Ala Leu Thr Gln Pro Ala Ser Val Ser Gly Ser Pro Gly Gln
1               5               10              15

Ser Ile Thr Ile Ser Cys Thr Gly Thr Asn Ser Asp Val Gly Gly Tyr
            20              25              30

Asn Ser Val Ser Trp Tyr Gln Gln His Pro Gly Lys Pro Pro Lys Leu
        35              40              45

Met Ile Tyr Glu Val Ser Asn Arg Pro Ser Gly Ile Ser Asn Arg Phe
    50              55              60

Ser Gly Ser Lys Ser Gly Asn Thr Ala Ser Leu Thr Ile Ser Gly Leu
65              70              75              80

Gln Ala Glu Asp Glu Ala Asp Tyr Phe Cys Ser Ser Tyr Thr Ser Thr
            85              90              95

Ser Met Val Phe Gly Gly Gly Thr Lys Leu Thr Val
            100             105

<210> SEQ ID NO 289
<211> LENGTH: 122
<212> TYPE: PRT
```

-continued

```
<213> ORGANISM: Homo sapiens

<400> SEQUENCE: 289

Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Leu Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
            100                 105                 110

Gly His Gly Thr Thr Val Thr Val Ser Ser
        115                 120

<210> SEQ ID NO 290
<211> LENGTH: 122
<212> TYPE: PRT
<213> ORGANISM: Homo sapiens

<400> SEQUENCE: 290

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Cys Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Leu Ala Ala Arg Pro Gly Gly Met Asp Val Trp
            100                 105                 110

Gly Gln Gly Thr Thr Val Thr Val Ser Ser
        115                 120

<210> SEQ ID NO 291
<211> LENGTH: 121
<212> TYPE: PRT
<213> ORGANISM: Homo sapiens

<400> SEQUENCE: 291

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Leu Ile Trp Asn Asp Gly Ser Asn Lys Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
            100                 105                 110

Gly Gln Gly Thr Thr Val Thr Val Ser
        115                 120

<210> SEQ ID NO 292
<211> LENGTH: 119
<212> TYPE: PRT
<213> ORGANISM: Homo sapiens

<400> SEQUENCE: 292

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Leu Pro Gly Gly Met Asp Val Trp Gly Gln Gly
            100                 105                 110

Thr Thr Val Thr Val Ser Ser
        115

<210> SEQ ID NO 293
<211> LENGTH: 327
<212> TYPE: DNA
<213> ORGANISM: Homo sapiens

<400> SEQUENCE: 293
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca aagcccccaa actcatgatt tatgaggtca gtaatcggcc ctcagggggtt     180 tctaatcgct tctctggctc caagtctggc aacacggcct ccctgaccat ctctgggctc     240
caggctgagg acgaggctga ttattactgc aactcatata caagcaccag catggtattc     300
ggcggaggga ccaagctgac cgtccta                                          327

<210> SEQ ID NO 294
<211> LENGTH: 327
<212> TYPE: DNA
<213> ORGANISM: Homo sapiens

<400> SEQUENCE: 294
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca aaccccccaa actcatgatt tatgaggtca gtaatcggcc ctcagggggtt     180
```

```
tctaatcgct tctctggctc caagtctggc aacacggcct ccctgaccat ctctgggctc      240
caggctgagg acgaggctga ttatttctgc agctcatata caagcaccag catggtcttc      300
ggcggaggga ccaagctgac cgtccta                                          327

<210> SEQ ID NO 295
<211> LENGTH: 318
<212> TYPE: DNA
<213> ORGANISM: Homo sapiens

<400> SEQUENCE: 295
tcctatgagc tgactcagcc accctcagtg tccgtgtccc caggacagac agccagaatc       60
acctgctctg gagataaatt gggggataaa tatgcttgct ggtatcagca gaagccaggc      120
cagtcccctg tgctggtcat ctatcaaaat accaagtggc ccttagggat ccctgagcga      180
ttctctggct ccaagtctgg gaacacagtc actctgacca tcagcgggac ccaggctatg      240
gatgaggctg actattactg tcaggcgtgg gacagcagca ctgtggtatt cggcggaggg      300
accaagctga ccgtccta                                                    318

<210> SEQ ID NO 296
<211> LENGTH: 327
<212> TYPE: DNA
<213> ORGANISM: Homo sapiens

<400> SEQUENCE: 296
cagtctgccc tgactcagcc tgcctccgtg tctgggtctc ctggacagtc gatcaccatc       60
tcctgcactg gaaccagcag tgacgttggt ggttataact ctgtctcctg gtaccaacag      120
cacccaggca aagcccccaa actcatgatt tatgaggtca gtaatcggcc ctcagggggtt      180 tctaatcgct tctctggctc caagtctggc aacacggcct ccctgaccat ctctgggctc      240
caggctgagg acgaggctga ttattactgc aattcatata caagcaccag catggtattc      300
ggcggaggga ccaagctgac cgtccta                                          327

<210> SEQ ID NO 297
<211> LENGTH: 215
<212> TYPE: PRT
<213> ORGANISM: Homo sapiens

<400> SEQUENCE: 297

Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
```

```
     130             135             140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
            195                 200                 205

Val Ala Pro Thr Glu Cys Ser
    210             215

<210> SEQ ID NO 298
<211> LENGTH: 230
<212> TYPE: PRT
<213> ORGANISM: Homo sapiens

<400> SEQUENCE: 298

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Gly Ile Ser Trp Val Arg Gln Ala Pro Gly Gln Gly Leu Glu Trp Met
            35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Ala Ala Asp Glu Val Asp
    210             215                 220

His His His His His His
225                 230

<210> SEQ ID NO 299
<211> LENGTH: 217
<212> TYPE: PRT
<213> ORGANISM: Homo sapiens

<400> SEQUENCE: 299

Glu Ser Val Leu Thr Gln Pro Pro Ser Val Ser Gly Ala Pro Gly Gln
```

-continued

```
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Ser Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 300
<211> LENGTH: 238
<212> TYPE: PRT
<213> ORGANISM: Homo sapiens

<400> SEQUENCE: 300

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Tyr Asp Phe Trp Ser Ala Tyr Tyr Asp Ala Phe Asp Val
            100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160
```

Thr Val Ser Trp Asn Ser Gly Ala Leu Thr Ser Gly Val His Thr Phe
            165             170             175

Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220

Ser Cys Ala Ala Asp Glu Val Asp His His His His His His
225             230             235

<210> SEQ ID NO 301
<211> LENGTH: 218
<212> TYPE: PRT
<213> ORGANISM: Homo sapiens

<400> SEQUENCE: 301

Ala Leu Gln Ser Val Leu Thr Gln Pro Pro Ser Ala Ser Gly Thr Pro
1               5               10              15

Gly Gln Arg Val Thr Ile Ser Cys Ser Gly Ser Ser Ser Asn Ile Gly
            20              25              30

Ser Asn Thr Val Asn Trp Tyr Gln Gln Leu Pro Gly Thr Ala Pro Lys
        35              40              45

Leu Leu Ile Tyr Ser Asn Asn Gln Arg Pro Ser Gly Val Pro Asp Arg
    50              55              60

Phe Ser Gly Ser Lys Ser Gly Thr Ser Ala Ser Leu Ala Ile Ser Gly
65              70              75              80

Leu Gln Ser Glu Asp Glu Ala Asp Tyr Tyr Cys Ala Val Trp Asp Asp
            85              90              95

Ser Leu Asn Gly Trp Val Phe Gly Gly Gly Thr Lys Leu Thr Val Leu
            100             105             110

Gly Gln Pro Lys Ala Ala Pro Ser Val Thr Leu Phe Pro Pro Ser Ser
            115             120             125

Glu Glu Leu Gln Ala Asn Lys Ala Thr Leu Val Cys Leu Ile Ser Asp
    130             135             140

Phe Tyr Pro Gly Ala Val Thr Val Ala Trp Lys Ala Asp Ser Ser Pro
145             150             155             160

Val Lys Ala Gly Val Glu Thr Thr Thr Pro Ser Lys Gln Ser Asn Asn
            165             170             175

Lys Tyr Ala Ala Ser Ser Tyr Leu Ser Leu Thr Pro Glu Gln Trp Lys
            180             185             190

Ser His Arg Ser Tyr Ser Cys Gln Val Thr His Glu Gly Ser Thr Val
            195             200             205

Glu Lys Thr Val Ala Pro Thr Glu Cys Ser
    210             215

<210> SEQ ID NO 302
<211> LENGTH: 231
<212> TYPE: PRT
<213> ORGANISM: Homo sapiens

<400> SEQUENCE: 302

Gln Val Gln Leu Gln Gln Trp Gly Ala Gly Leu Leu Lys Pro Ser Glu
1               5               10              15

Thr Leu Ser Leu Thr Cys Ala Val Tyr Gly Gly Ser Phe Ser Ala Tyr
            20              25              30

-continued

```
Tyr Trp Asn Trp Ile Arg Gln Pro Pro Gly Lys Gly Leu Glu Trp Ile
        35              40              45

Gly Glu Ile Asn His Ser Gly Arg Thr Asp Tyr Asn Pro Ser Leu Lys
    50              55              60

Ser Arg Val Thr Ile Ser Val Asp Thr Ser Lys Lys Gln Phe Ser Leu
65              70              75              80

Lys Leu Asn Ser Val Thr Ala Ala Asp Thr Ala Val Tyr Tyr Cys Ala
            85              90              95

Arg Gly Gln Leu Val Pro Phe Asp Tyr Trp Gly Gln Gly Thr Leu Val
            100             105             110

Thr Val Ser Ser Ala Ser Thr Lys Gly Pro Ser Val Phe Pro Leu Ala
            115             120             125

Pro Ser Ser Lys Ser Thr Ser Gly Gly Thr Ala Ala Leu Gly Cys Leu
    130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
            165             170             175

Gly Leu Tyr Ser His Ser Ser Val Val Thr Val Pro Ser Ser Ser Leu
            180             185             190

Gly Thr Gln Thr Tyr Ile Cys Asn Val Asn His Lys Pro Ser Asn Thr
            195             200             205

Lys Val Asp Lys Lys Val Glu Pro Lys Ser Cys Ala Ala Asp Glu Val
    210             215             220

Asp His His His His His
225             230
```

```
<210> SEQ ID NO 303
<211> LENGTH: 680
<212> TYPE: PRT
<213> ORGANISM: Homo sapiens

<400> SEQUENCE: 303
```

```
Gln Glu Asp Glu Asp Gly Asp Tyr Glu Glu Leu Val Leu Ala Leu Arg
1               5               10              15

Ser Glu Glu Asp Gly Leu Ala Glu Ala Pro Glu His Gly Thr Thr Ala
            20              25              30

Thr Phe His Arg Cys Ala Lys Asp Pro Trp Arg Leu Pro Gly Thr Tyr
        35              40              45

Val Val Val Leu Lys Glu Glu Thr His Leu Ser Gln Ser Glu Arg Thr
    50              55              60

Ala Arg Arg Leu Gln Ala Gln Ala Ala Arg Arg Gly Tyr Leu Thr Lys
65              70              75              80

Ile Leu His Val Phe His Gly Leu Leu Pro Gly Phe Leu Val Lys Met
            85              90              95

Ser Gly Asp Leu Leu Glu Leu Ala Leu Lys Leu Pro His Val Asp Tyr
            100             105             110

Ile Glu Glu Asp Ser Ser Val Phe Ala Gln Ser Ile Pro Trp Asn Leu
            115             120             125

Glu Arg Ile Thr Pro Pro Arg Tyr Arg Ala Asp Glu Tyr Gln Pro Pro
    130             135             140

Asp Gly Gly Ser Leu Val Glu Val Tyr Leu Leu Asp Thr Ser Ile Gln
145             150             155             160

Ser Asp His Arg Glu Ile Glu Gly Arg Val Met Val Thr Asp Phe Glu
            165             170             175
```

```
Asn Val Pro Glu Glu Asp Gly Thr Arg Phe His Arg Gln Ala Ser Lys
            180               185               190

Cys Asp Ser His Gly Thr His Leu Ala Gly Val Val Ser Gly Arg Asp
            195               200               205

Ala Gly Val Ala Lys Gly Ala Ser Met Arg Ser Leu Arg Val Leu Asn
            210               215               220

Cys Gln Gly Lys Gly Thr Val Ser Gly Thr Leu Ile Gly Leu Glu Phe
225               230               235               240

Ile Arg Lys Ser Gln Leu Val Gln Pro Val Gly Pro Leu Val Val Leu
            245               250               255

Leu Pro Leu Ala Gly Gly Tyr Ser Arg Val Leu Asn Ala Ala Cys Gln
            260               265               270

Arg Leu Ala Arg Ala Gly Val Val Leu Val Thr Ala Ala Gly Asn Phe
            275               280               285

Arg Asp Asp Ala Cys Leu Tyr Ser Pro Ala Ser Ala Pro Glu Val Ile
            290               295               300

Thr Val Gly Ala Thr Asn Ala Gln Asp Gln Pro Val Thr Leu Gly Thr
305               310               315               320

Leu Gly Thr Asn Phe Gly Arg Cys Val Asp Leu Phe Ala Pro Gly Glu
            325               330               335

Asp Ile Ile Gly Ala Ser Ser Asp Cys Ser Thr Cys Phe Val Ser Gln
            340               345               350

Ser Gly Thr Ser Gln Ala Ala Ala His Val Ala Gly Ile Ala Ala Met
            355               360               365

Met Leu Ser Ala Glu Pro Glu Leu Thr Leu Ala Glu Leu Arg Gln Arg
            370               375               380

Leu Ile His Phe Ser Ala Lys Asp Val Ile Asn Glu Ala Trp Phe Pro
385               390               395               400

Glu Asp Gln Arg Val Leu Thr Pro Asn Leu Val Ala Ala Leu Pro Pro
            405               410               415

Ser Thr His Gly Ala Gly Trp Gln Leu Phe Cys Arg Thr Val Trp Ser
            420               425               430

Ala His Ser Gly Pro Thr Arg Met Ala Thr Ala Ile Ala Arg Cys Ala
            435               440               445

Pro Asp Glu Glu Leu Leu Ser Cys Ser Ser Phe Ser Arg Ser Gly Lys
            450               455               460

Arg Arg Gly Glu Arg Met Glu Ala Gln Gly Gly Lys Leu Val Cys Arg
465               470               475               480

Ala His Asn Ala Phe Gly Gly Glu Gly Val Tyr Ala Ile Ala Arg Cys
            485               490               495

Cys Leu Leu Pro Gln Ala Asn Cys Ser Val His Thr Ala Pro Pro Ala
            500               505               510

Glu Ala Ser Met Gly Thr Arg Val His Cys His Gln Gln Gly His Val
            515               520               525

Leu Thr Gly Cys Ser Ser His Trp Glu Val Glu Asp Leu Gly Thr His
            530               535               540

Lys Pro Pro Val Leu Arg Pro Arg Gly Gln Pro Asn Gln Cys Val Gly
545               550               555               560

His Arg Glu Ala Ser Ile His Ala Ser Cys Cys His Ala Pro Gly Leu
            565               570               575

Glu Cys Lys Val Lys Glu His Gly Ile Pro Ala Pro Gln Glu Gln Val
            580               585               590
```

-continued

```
Thr Val Ala Cys Glu Glu Gly Trp Thr Leu Thr Gly Cys Ser Ala Leu
        595                 600                 605

Pro Gly Thr Ser His Val Leu Gly Ala Tyr Ala Val Asp Asn Thr Cys
        610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln Gly Ser Ser Asp Tyr Lys Asp Asp Asp Lys
            660                 665                 670

His His His His His His His His
        675                 680

<210> SEQ ID NO 304
<211> LENGTH: 680
<212> TYPE: PRT
<213> ORGANISM: Homo sapiens

<400> SEQUENCE: 304

Arg Arg Arg Arg Arg Arg Arg Arg Arg Arg Arg Arg Leu Arg Arg Arg
1               5                   10                  15

Arg Arg Arg Arg Arg Arg Arg Arg Arg His Arg Arg Arg Arg
            20                  25                  30

Arg Phe Arg Arg Cys Arg Arg Pro Trp Arg Pro Gly Arg Tyr
            35                  40                  45

Val Val Val Leu Arg Arg Arg Arg Arg Ser Arg Ser Arg Glu Thr
        50                  55                  60

Ala Glu Glu Leu Gln Arg Arg Ala Arg Glu Glu Gly Arg Arg Thr Lys
65                  70                  75                  80

Ile Arg Arg Arg Phe Arg Gly Leu Leu Pro Gly Phe Leu Val Arg Met
                85                  90                  95

Arg Arg Arg Leu Arg Arg Leu Ala Arg Arg Leu Pro Arg Val Arg Tyr
            100                 105                 110

Ile Glu Glu Asp Ser Ser Val Phe Arg Gln Arg Ile Pro Arg Asn Arg
            115                 120                 125

Arg Glu Ile Arg Pro Pro Arg Tyr Arg Ala Arg Arg Arg Pro Pro
        130                 135                 140

Arg Gly Gly Arg Arg Val Glu Val Tyr Leu Leu Asp Thr Arg Ile Arg
145                 150                 155                 160

Arg Arg His Glu Glu Ile Arg Gly Arg Val Arg Arg Arg Phe Arg
                165                 170                 175

Arg Arg Pro Arg Arg Arg Arg Glu Arg Glu Arg Arg Arg Arg
        180                 185                 190

Cys Asp Arg Arg Gly Thr His Leu Ala Gly Val Val Ser Gly Glu Arg
            195                 200                 205

Ala Gly Val Ala Arg Arg Ala Arg Met Arg Ser Leu Glu Val Leu Asn
        210                 215                 220

Cys Arg Gly Arg Gly Arg Val Ser Gly Thr Leu Ile Gly Leu Glu Arg
225                 230                 235                 240

Ile Glu Arg Arg Arg Arg Arg Arg Pro Arg Arg Pro Leu Val Val Leu
                245                 250                 255

Leu Pro Leu Ala Gly Arg Tyr Ser Glu Val Leu Asn Arg Ala Cys Arg
            260                 265                 270

Arg Leu Ala Glu Arg Gly Val Val Leu Val Thr Ala Ala Gly Asn Phe
            275                 280                 285
```

-continued

```
Glu Asp Asp Ala Cys Arg Tyr Ser Pro Ala Arg Ala Pro Glu Val Ile
    290                 295                 300

Thr Val Gly Ala Thr Asn Arg Arg Arg Arg Pro Val Arg Arg Gly Arg
305                 310                 315                 320

Arg Gly Thr Asn Phe Gly Arg Cys Val Asp Leu Phe Ala Pro Gly Arg
                325                 330                 335

Arg Ile Ile Gly Ala Ser Ser Arg Cys Ser Arg Cys Arg Arg Arg Arg
            340                 345                 350

Ser Gly Thr Ser Gln Ala Ala Ala His Val Ala Gly Ile Ala Ala Arg
            355                 360                 365

Met Leu Arg Arg Arg Pro Arg Leu Arg Arg Ala Arg Leu Arg Gln Glu
    370                 375                 380

Leu Arg Arg Arg Ser Arg Arg Arg Ile Arg Arg Arg Phe Pro
385                 390                 395                 400

Arg Arg Arg Glu Arg Leu Thr Pro Arg Leu Val Ala Arg Leu Pro Pro
            405                 410                 415

Arg Arg Arg Arg Arg Gly Arg Arg Leu Phe Cys Arg Thr Val Trp Ser
            420                 425                 430

Arg Arg Ser Gly Pro Arg Glu Arg Ala Arg Ala Ile Ala Glu Cys Ala
            435                 440                 445

Pro Arg Glu Glu Leu Leu Ser Cys Ser Ser Phe Ser Arg Ser Gly Lys
    450                 455                 460

Arg Arg Gly Glu Arg Met Glu Arg Gln Gly Gly Lys Leu Val Cys Arg
465                 470                 475                 480

Ala His Asn Ala Arg Arg Gly Arg Gly Val Tyr Ala Ile Ala Arg Cys
            485                 490                 495

Cys Leu Leu Pro Gln Ala Arg Cys Ser Val His Arg Ala Pro Pro Ala
            500                 505                 510

Arg Arg Arg Arg Gly Thr Glu Val Arg Cys Arg Arg Arg Gly His Val
            515                 520                 525

Leu Thr Gly Cys Ser Ser His Trp Arg Arg Arg Asp Arg Gly Thr Arg
    530                 535                 540

Lys Pro Pro Arg Leu Arg Pro Glu Gly Arg Pro Arg Gln Cys Val Gly
545                 550                 555                 560

His Arg Glu Ala Ser Ile His Ala Ser Cys Cys His Ala Pro Gly Leu
            565                 570                 575

Glu Cys Arg Arg Arg Arg Arg Ile Pro Ala Pro Arg Glu Arg Val
            580                 585                 590

Thr Val Arg Cys Arg Arg Gly Trp Thr Leu Thr Gly Cys Ser Ala Leu
            595                 600                 605

Pro Gly Thr Ser His Val Leu Gly Ala Tyr Ala Arg Asp Asn Thr Cys
    610                 615                 620

Val Val Arg Ser Glu Asp Arg Arg Arg Arg Arg Arg Arg Glu
625                 630                 635                 640

Arg Val Thr Ala Val Ala Ile Cys Cys Glu Ser Glu His Leu Ala Gln
            645                 650                 655

Ala Ser Gln Glu Leu Gln Gly Ser Ser Asp Tyr Lys Asp Asp Asp Lys
            660                 665                 670

His His His His His His His His
            675                 680
```

<210> SEQ ID NO 305
<211> LENGTH: 14

```
<212> TYPE: PRT
<213> ORGANISM: Homo sapiens

<400> SEQUENCE: 305

Thr Gly Thr Ser Ser Asp Val Gly Gly Tyr Asn Ser Val Ser
1               5                   10

<210> SEQ ID NO 306
<211> LENGTH: 7
<212> TYPE: PRT
<213> ORGANISM: Homo sapiens

<400> SEQUENCE: 306

Glu Val Ser Asn Arg Pro Ser
1               5

<210> SEQ ID NO 307
<211> LENGTH: 9
<212> TYPE: PRT
<213> ORGANISM: Homo sapiens

<400> SEQUENCE: 307

Ser Ser Tyr Thr Ser Thr Ser Met Val
1               5

<210> SEQ ID NO 308
<211> LENGTH: 5
<212> TYPE: PRT
<213> ORGANISM: Homo sapiens

<400> SEQUENCE: 308

Ser Tyr Gly Ile Ser
1               5

<210> SEQ ID NO 309
<211> LENGTH: 17
<212> TYPE: PRT
<213> ORGANISM: Homo sapiens

<400> SEQUENCE: 309

Trp Ile Ser Ala Tyr Asn Gly Asn Thr Asn Tyr Ala Gln Lys Val Gln
1               5                   10                  15

Gly

<210> SEQ ID NO 310
<211> LENGTH: 6
<212> TYPE: PRT
<213> ORGANISM: Homo sapiens

<400> SEQUENCE: 310

Gly Tyr Gly Met Asp Val
1               5

<210> SEQ ID NO 311
<211> LENGTH: 14
<212> TYPE: PRT
<213> ORGANISM: Homo sapiens

<400> SEQUENCE: 311

Thr Gly Thr Ser Ser Asp Val Gly Arg Tyr Asn Ser Val Ser
1               5                   10

<210> SEQ ID NO 312
<211> LENGTH: 7
```

-continued

```
<212> TYPE: PRT
<213> ORGANISM: Homo sapiens

<400> SEQUENCE: 312

Glu Val Ser Asn Arg Pro Ser
1               5

<210> SEQ ID NO 313
<211> LENGTH: 9
<212> TYPE: PRT
<213> ORGANISM: Homo sapiens

<400> SEQUENCE: 313

Ser Ser Tyr Thr Ser Ser Ser Val Val
1               5

<210> SEQ ID NO 314
<211> LENGTH: 17
<212> TYPE: PRT
<213> ORGANISM: Homo sapiens

<400> SEQUENCE: 314

Trp Ile Ser Ala Tyr Asn Gly Asn Thr Asn Tyr Ala Glu Lys Leu Gln
1               5                   10                  15

Gly

<210> SEQ ID NO 315
<211> LENGTH: 6
<212> TYPE: PRT
<213> ORGANISM: Homo sapiens

<400> SEQUENCE: 315

Gly Tyr Val Met Asp Val
1               5

<210> SEQ ID NO 316
<211> LENGTH: 14
<212> TYPE: PRT
<213> ORGANISM: Homo sapiens

<400> SEQUENCE: 316

Thr Gly Thr Ser Ser Asp Val Gly Ala Tyr Asn Ser Val Ser
1               5                   10

<210> SEQ ID NO 317
<211> LENGTH: 9
<212> TYPE: PRT
<213> ORGANISM: Homo sapiens

<400> SEQUENCE: 317

Ser Ser Tyr Thr Ser Thr Asn Met Val
1               5

<210> SEQ ID NO 318
<211> LENGTH: 17
<212> TYPE: PRT
<213> ORGANISM: Homo sapiens

<400> SEQUENCE: 318

Trp Val Ser Ala Tyr Asn Gly Asn Thr Asn Tyr Ala Gln Lys Phe Gln
1               5                   10                  15

Gly
```

-continued

```
<210> SEQ ID NO 319
<211> LENGTH: 9
<212> TYPE: PRT
<213> ORGANISM: Homo sapiens

<400> SEQUENCE: 319

Asn Ser Tyr Thr Ser Thr Ser Met Val
1               5

<210> SEQ ID NO 320
<211> LENGTH: 17
<212> TYPE: PRT
<213> ORGANISM: Homo sapiens

<400> SEQUENCE: 320

Trp Val Ser Phe Tyr Asn Gly Asn Thr Asn Tyr Ala Gln Lys Leu Gln
1               5                   10                  15

Gly

<210> SEQ ID NO 321
<211> LENGTH: 7
<212> TYPE: PRT
<213> ORGANISM: Homo sapiens

<400> SEQUENCE: 321

Glu Val Thr Asn Arg Pro Ser
1               5

<210> SEQ ID NO 322
<211> LENGTH: 14
<212> TYPE: PRT
<213> ORGANISM: Homo sapiens

<400> SEQUENCE: 322

Thr Gly Thr Asn Ser Asp Val Gly Gly Tyr Asn Ser Val Ser
1               5                   10

<210> SEQ ID NO 323
<211> LENGTH: 17
<212> TYPE: PRT
<213> ORGANISM: Homo sapiens

<400> SEQUENCE: 323

Trp Ile Ser Val Tyr Asn Gly Asn Thr Asn Tyr Ala Gln Lys Val Gln
1               5                   10                  15

Gly

<210> SEQ ID NO 324
<211> LENGTH: 17
<212> TYPE: PRT
<213> ORGANISM: Homo sapiens

<400> SEQUENCE: 324

Trp Ile Ser Phe Tyr Asn Gly Asn Thr Asn Tyr Ala Gln Lys Val Gln
1               5                   10                  15

Gly

<210> SEQ ID NO 325
<211> LENGTH: 13
<212> TYPE: PRT
<213> ORGANISM: Homo sapiens

<400> SEQUENCE: 325
```

-continued

```
Ser Gly Ser Ser Ser Asn Ile Gly Asn Asn Phe Val Ser
1               5                   10

<210> SEQ ID NO 326
<211> LENGTH: 7
<212> TYPE: PRT
<213> ORGANISM: Homo sapiens

<400> SEQUENCE: 326

Asp Tyr Asn Lys Arg Pro Ser
1               5

<210> SEQ ID NO 327
<211> LENGTH: 11
<212> TYPE: PRT
<213> ORGANISM: Homo sapiens

<400> SEQUENCE: 327

Gly Thr Trp Asp Ser Ser Leu Ser Gly Tyr Val
1               5                   10

<210> SEQ ID NO 328
<211> LENGTH: 5
<212> TYPE: PRT
<213> ORGANISM: Homo sapiens

<400> SEQUENCE: 328

Ser Phe Gly Met His
1               5

<210> SEQ ID NO 329
<211> LENGTH: 17
<212> TYPE: PRT
<213> ORGANISM: Homo sapiens

<400> SEQUENCE: 329

Leu Ile Trp Asn Asp Gly Ser Asn Lys Tyr Tyr Ala Asp Ser Val Lys
1               5                   10                  15

Gly

<210> SEQ ID NO 330
<211> LENGTH: 13
<212> TYPE: PRT
<213> ORGANISM: Homo sapiens

<400> SEQUENCE: 330

Ala Ile Ala Ala Leu Tyr Tyr Tyr Tyr Gly Met Asp Val
1               5                   10

<210> SEQ ID NO 331
<211> LENGTH: 7
<212> TYPE: PRT
<213> ORGANISM: Homo sapiens

<400> SEQUENCE: 331

Asp Ser Asn Lys Arg Pro Ser
1               5

<210> SEQ ID NO 332
<211> LENGTH: 11
<212> TYPE: PRT
<213> ORGANISM: Homo sapiens

<400> SEQUENCE: 332
```

```
Gly Thr Trp Asp Ser Ser Leu Ser Ala Tyr Val
1               5                   10

<210> SEQ ID NO 333
<211> LENGTH: 5
<212> TYPE: PRT
<213> ORGANISM: Homo sapiens

<400> SEQUENCE: 333

Ser Tyr Gly Met His
1               5

<210> SEQ ID NO 334
<211> LENGTH: 17
<212> TYPE: PRT
<213> ORGANISM: Homo sapiens

<400> SEQUENCE: 334

Leu Ile Trp His Asp Gly Ser Asn Thr Tyr Tyr Val Asp Ser Val Lys
1               5                   10                  15

Gly

<210> SEQ ID NO 335
<211> LENGTH: 13
<212> TYPE: PRT
<213> ORGANISM: Homo sapiens

<400> SEQUENCE: 335

Gly Ile Ala Val Ala Tyr Tyr Tyr Tyr Gly Met Asp Val
1               5                   10

<210> SEQ ID NO 336
<211> LENGTH: 17
<212> TYPE: PRT
<213> ORGANISM: Homo sapiens

<400> SEQUENCE: 336

Leu Ile Trp Ser Asp Gly Ser Asp Glu Tyr Tyr Ala Asp Ser Val Lys
1               5                   10                  15

Gly

<210> SEQ ID NO 337
<211> LENGTH: 11
<212> TYPE: PRT
<213> ORGANISM: Homo sapiens

<400> SEQUENCE: 337

Gly Thr Trp Asp Ser Ser Leu Ser Ser Tyr Val
1               5                   10

<210> SEQ ID NO 338
<211> LENGTH: 17
<212> TYPE: PRT
<213> ORGANISM: Homo sapiens

<400> SEQUENCE: 338

Leu Ile Trp Ser Asp Gly Ser Asp Lys Tyr Tyr Ala Asp Ser Val Lys
1               5                   10                  15

Gly

<210> SEQ ID NO 339
<211> LENGTH: 13
<212> TYPE: PRT
```

-continued

```
<213> ORGANISM: Homo sapiens

<400> SEQUENCE: 339

Ser Gly Ser Ser Ser Asn Ile Gly Ser Lys Thr Val Asn
1               5                   10

<210> SEQ ID NO 340
<211> LENGTH: 7
<212> TYPE: PRT
<213> ORGANISM: Homo sapiens

<400> SEQUENCE: 340

Ser Asn Asn Arg Arg Pro Ser
1               5

<210> SEQ ID NO 341
<211> LENGTH: 10
<212> TYPE: PRT
<213> ORGANISM: Homo sapiens

<400> SEQUENCE: 341

Ala Ala Trp Asp Asp Ser Leu Asn Trp Val
1               5                   10

<210> SEQ ID NO 342
<211> LENGTH: 4
<212> TYPE: PRT
<213> ORGANISM: Homo sapiens

<400> SEQUENCE: 342

Tyr Trp Met Ser
1

<210> SEQ ID NO 343
<211> LENGTH: 17
<212> TYPE: PRT
<213> ORGANISM: Homo sapiens

<400> SEQUENCE: 343

Asn Ile Lys Gln Asp Gly Ser Glu Lys Tyr Tyr Val Asp Ser Val Lys
1               5                   10                  15

Gly

<210> SEQ ID NO 344
<211> LENGTH: 10
<212> TYPE: PRT
<213> ORGANISM: Homo sapiens

<400> SEQUENCE: 344

Glu Ser Asn Trp Gly Phe Ala Phe Asp Ile
1               5                   10

<210> SEQ ID NO 345
<211> LENGTH: 13
<212> TYPE: PRT
<213> ORGANISM: Homo sapiens

<400> SEQUENCE: 345

Ser Gly Ser Ser Ser Asn Ile Gly Ser Asn Thr Val Asn
1               5                   10

<210> SEQ ID NO 346
<211> LENGTH: 5
<212> TYPE: PRT
```

```
<213> ORGANISM: Homo sapiens

<400> SEQUENCE: 346

Arg Tyr Trp Met Ser
1               5

<210> SEQ ID NO 347
<211> LENGTH: 17
<212> TYPE: PRT
<213> ORGANISM: Homo sapiens

<400> SEQUENCE: 347

Asn Ile Lys His Asp Gly Ser Glu Lys Tyr Tyr Val Asp Ser Val Lys
1               5                   10                  15

Gly

<210> SEQ ID NO 348
<211> LENGTH: 10
<212> TYPE: PRT
<213> ORGANISM: Homo sapiens

<400> SEQUENCE: 348

Glu Ser Asn Trp Gly Phe Ala Phe Asp Val
1               5                   10

<210> SEQ ID NO 349
<211> LENGTH: 7
<212> TYPE: PRT
<213> ORGANISM: Homo sapiens

<400> SEQUENCE: 349

Arg Asn Asn Gln Arg Pro Leu
1               5

<210> SEQ ID NO 350
<211> LENGTH: 5
<212> TYPE: PRT
<213> ORGANISM: Homo sapiens

<400> SEQUENCE: 350

Ser Tyr Trp Met Ser
1               5

<210> SEQ ID NO 351
<211> LENGTH: 5
<212> TYPE: PRT
<213> ORGANISM: Homo sapiens

<400> SEQUENCE: 351

Asn Phe Trp Met Ser
1               5

<210> SEQ ID NO 352
<211> LENGTH: 10
<212> TYPE: PRT
<213> ORGANISM: Homo sapiens

<400> SEQUENCE: 352

Arg Ala Ser Gln Ser Ile Ser Tyr Leu Asn
1               5                   10

<210> SEQ ID NO 353
<211> LENGTH: 6
<212> TYPE: PRT
```

```
<213> ORGANISM: Homo sapiens

<400> SEQUENCE: 353

Ala Ala Ser Leu Gln Ser
1               5

<210> SEQ ID NO 354
<211> LENGTH: 8
<212> TYPE: PRT
<213> ORGANISM: Homo sapiens

<400> SEQUENCE: 354

Gln Gln Ser Tyr Ser Pro Ile Thr
1               5

<210> SEQ ID NO 355
<211> LENGTH: 11
<212> TYPE: PRT
<213> ORGANISM: Homo sapiens

<400> SEQUENCE: 355

Arg Ala Ser Gln Ser Ile Ser Ile Tyr Leu Asn
1               5                   10

<210> SEQ ID NO 356
<211> LENGTH: 7
<212> TYPE: PRT
<213> ORGANISM: Homo sapiens

<400> SEQUENCE: 356

Ala Ala Ala Ser Leu Gln Ser
1               5

<210> SEQ ID NO 357
<211> LENGTH: 9
<212> TYPE: PRT
<213> ORGANISM: Homo sapiens

<400> SEQUENCE: 357

Gln Gln Ser Tyr Ser Ala Pro Ile Thr
1               5

<210> SEQ ID NO 358
<211> LENGTH: 11
<212> TYPE: PRT
<213> ORGANISM: Homo sapiens

<400> SEQUENCE: 358

Arg Ala Ser Gln Ser Ile Ser Ser Tyr Leu Asn
1               5                   10

<210> SEQ ID NO 359
<211> LENGTH: 7
<212> TYPE: PRT
<213> ORGANISM: Homo sapiens

<400> SEQUENCE: 359

Ala Ala Ser Ser Leu Gln Ser
1               5

<210> SEQ ID NO 360
<211> LENGTH: 9
<212> TYPE: PRT
<213> ORGANISM: Homo sapiens
```

```
<400> SEQUENCE: 360

Gln Gln Ser Tyr Ser Ser Pro Ile Thr
1               5

<210> SEQ ID NO 361
<211> LENGTH: 5
<212> TYPE: PRT
<213> ORGANISM: Homo sapiens

<400> SEQUENCE: 361

Ser Tyr Ala Met Asn
1               5

<210> SEQ ID NO 362
<211> LENGTH: 16
<212> TYPE: PRT
<213> ORGANISM: Homo sapiens

<400> SEQUENCE: 362

Thr Ile Ser Gly Ser Gly Asn Thr Tyr Tyr Ala Asp Ser Val Lys Gly
1               5                   10                  15

<210> SEQ ID NO 363
<211> LENGTH: 12
<212> TYPE: PRT
<213> ORGANISM: Homo sapiens

<400> SEQUENCE: 363

Lys Phe Val Leu Met Val Tyr Ala Met Leu Asp Tyr
1               5                   10

<210> SEQ ID NO 364
<211> LENGTH: 17
<212> TYPE: PRT
<213> ORGANISM: Homo sapiens

<400> SEQUENCE: 364

Thr Ile Ser Gly Ser Gly Gly Asn Thr Tyr Tyr Ala Asp Ser Val Lys
1               5                   10                  15

Gly

<210> SEQ ID NO 365
<211> LENGTH: 17
<212> TYPE: PRT
<213> ORGANISM: Homo sapiens

<400> SEQUENCE: 365

Thr Ile Ser Gly Ser Gly Asp Asn Thr Tyr Tyr Ala Asp Ser Val Lys
1               5                   10                  15

Gly

<210> SEQ ID NO 366
<211> LENGTH: 10
<212> TYPE: PRT
<213> ORGANISM: Homo sapiens

<400> SEQUENCE: 366

Gly Tyr Ser Leu Thr Ser Tyr Gly Ile Ser
1               5                   10

<210> SEQ ID NO 367
<211> LENGTH: 10
<212> TYPE: PRT
```

-continued

```
<213> ORGANISM: Homo sapiens

<400> SEQUENCE: 367

Gly Tyr Ala Leu Thr Ser Tyr Gly Ile Ser
1               5                   10

<210> SEQ ID NO 368
<211> LENGTH: 10
<212> TYPE: PRT
<213> ORGANISM: Homo sapiens

<400> SEQUENCE: 368

Gly Tyr Thr Leu Thr Ser Tyr Gly Ile Ser
1               5                   10

<210> SEQ ID NO 369
<211> LENGTH: 10
<212> TYPE: PRT
<213> ORGANISM: Homo sapiens

<400> SEQUENCE: 369

Gly Tyr Ser Phe Thr Ser Tyr Gly Ile Ser
1               5                   10

<210> SEQ ID NO 370
<211> LENGTH: 10
<212> TYPE: PRT
<213> ORGANISM: Homo sapiens

<400> SEQUENCE: 370

Gly Tyr Thr Phe Pro Ser Tyr Gly Ile Ser
1               5                   10

<210> SEQ ID NO 371
<211> LENGTH: 10
<212> TYPE: PRT
<213> ORGANISM: Homo sapiens

<400> SEQUENCE: 371

Gly Phe Thr Phe Ser Ser Tyr Trp Met Ser
1               5                   10

<210> SEQ ID NO 372
<211> LENGTH: 10
<212> TYPE: PRT
<213> ORGANISM: Homo sapiens

<400> SEQUENCE: 372

Gly Phe Thr Phe Ser Arg Tyr Trp Met Ser
1               5                   10

<210> SEQ ID NO 373
<211> LENGTH: 10
<212> TYPE: PRT
<213> ORGANISM: Homo sapiens

<400> SEQUENCE: 373

Gly Leu Thr Phe Ser Asn Phe Trp Met Ser
1               5                   10

<210> SEQ ID NO 374
<211> LENGTH: 10
<212> TYPE: PRT
<213> ORGANISM: Homo sapiens
```

```
<400> SEQUENCE: 374

Gly Phe Thr Phe Ser Ser Tyr Ala Met Asn
1               5                   10

<210> SEQ ID NO 375
<211> LENGTH: 10
<212> TYPE: PRT
<213> ORGANISM: Homo sapiens

<400> SEQUENCE: 375

Gly Phe Thr Phe Asn Ser Phe Gly Met His
1               5                   10

<210> SEQ ID NO 376
<211> LENGTH: 10
<212> TYPE: PRT
<213> ORGANISM: Homo sapiens

<400> SEQUENCE: 376

Gly Phe Thr Phe Arg Ser Tyr Gly Met His
1               5                   10

<210> SEQ ID NO 377
<211> LENGTH: 16
<212> TYPE: PRT
<213> ORGANISM: Homo sapiens

<400> SEQUENCE: 377

Asn Ile Lys Gln Asp Gly Ser Glu Lys Tyr Val Asp Ser Val Lys Gly
1               5                   10                  15

<210> SEQ ID NO 378
<211> LENGTH: 16
<212> TYPE: PRT
<213> ORGANISM: Homo sapiens

<400> SEQUENCE: 378

Asn Ile Lys His Asp Gly Ser Glu Lys Tyr Val Asp Ser Val Lys Gly
1               5                   10                  15

<210> SEQ ID NO 379
<211> LENGTH: 16
<212> TYPE: PRT
<213> ORGANISM: Homo sapiens

<400> SEQUENCE: 379

Thr Ile Ser Gly Ser Gly Asp Asn Thr Tyr Ala Asp Ser Val Lys Gly
1               5                   10                  15

<210> SEQ ID NO 380
<211> LENGTH: 16
<212> TYPE: PRT
<213> ORGANISM: Homo sapiens

<400> SEQUENCE: 380

Thr Ile Ser Gly Ser Gly Gly Asn Thr Tyr Ala Asp Ser Val Lys Gly
1               5                   10                  15

<210> SEQ ID NO 381
<211> LENGTH: 16
<212> TYPE: PRT
<213> ORGANISM: Homo sapiens

<400> SEQUENCE: 381
```

```
Leu Ile Trp Asn Asp Gly Ser Asn Lys Tyr Ala Asp Ser Val Lys Gly
1               5                   10                  15
```

<210> SEQ ID NO 382
<211> LENGTH: 16
<212> TYPE: PRT
<213> ORGANISM: Homo sapiens

<400> SEQUENCE: 382

```
Leu Ile Trp Ser Asp Gly Ser Asp Glu Tyr Ala Asp Ser Val Lys Gly
1               5                   10                  15
```

<210> SEQ ID NO 383
<211> LENGTH: 16
<212> TYPE: PRT
<213> ORGANISM: Homo sapiens

<400> SEQUENCE: 383

```
Leu Ile Trp Ser Asp Gly Ser Asp Lys Tyr Ala Asp Ser Val Lys Gly
1               5                   10                  15
```

<210> SEQ ID NO 384
<211> LENGTH: 16
<212> TYPE: PRT
<213> ORGANISM: Homo sapiens

<400> SEQUENCE: 384

```
Leu Ile Trp His Asp Gly Ser Asn Thr Tyr Val Asp Ser Val Lys Gly
1               5                   10                  15
```

<210> SEQ ID NO 385
<211> LENGTH: 10
<212> TYPE: PRT
<213> ORGANISM: Homo sapiens

<400> SEQUENCE: 385

```
Glu Ser Asn Trp Gly Phe Ala Phe Asp Ile
1               5                   10
```

<210> SEQ ID NO 386
<211> LENGTH: 10
<212> TYPE: PRT
<213> ORGANISM: Homo sapiens

<400> SEQUENCE: 386

```
Glu Ser Asn Trp Gly Phe Ala Phe Asp Val
1               5                   10
```

<210> SEQ ID NO 387
<211> LENGTH: 6
<212> TYPE: PRT
<213> ORGANISM: Homo sapiens

<400> SEQUENCE: 387

```
Gly Tyr Val Met Asp Val
1               5
```

<210> SEQ ID NO 388
<211> LENGTH: 11
<212> TYPE: PRT
<213> ORGANISM: Homo sapiens

<400> SEQUENCE: 388

```
Arg Ala Ser Gln Ser Ile Ser Ile Tyr Leu Asn
1               5                   10
```

-continued

```
<210> SEQ ID NO 389
<211> LENGTH: 14
<212> TYPE: PRT
<213> ORGANISM: Homo sapiens

<400> SEQUENCE: 389

Thr Gly Thr Asn Ser Asp Val Gly Gly Tyr Asn Ser Val Ser
1               5                   10

<210> SEQ ID NO 390
<211> LENGTH: 14
<212> TYPE: PRT
<213> ORGANISM: Homo sapiens

<400> SEQUENCE: 390

Thr Gly Thr Ser Ser Asp Val Gly Ala Tyr Asn Ser Val Ser
1               5                   10

<210> SEQ ID NO 391
<211> LENGTH: 14
<212> TYPE: PRT
<213> ORGANISM: Homo sapiens

<400> SEQUENCE: 391

Thr Gly Thr Ser Ser Asp Val Gly Arg Tyr Asn Ser Val Ser
1               5                   10

<210> SEQ ID NO 392
<211> LENGTH: 7
<212> TYPE: PRT
<213> ORGANISM: Homo sapiens

<400> SEQUENCE: 392

Arg Asn Asn Gln Arg Pro Leu
1               5

<210> SEQ ID NO 393
<211> LENGTH: 7
<212> TYPE: PRT
<213> ORGANISM: Homo sapiens

<400> SEQUENCE: 393

Ala Ala Ala Ser Leu Gln Ser
1               5

<210> SEQ ID NO 394
<211> LENGTH: 9
<212> TYPE: PRT
<213> ORGANISM: Homo sapiens

<400> SEQUENCE: 394

Gln Gln Ser Tyr Ser Ala Pro Ile Thr
1               5

<210> SEQ ID NO 395
<211> LENGTH: 9
<212> TYPE: PRT
<213> ORGANISM: Homo sapiens

<400> SEQUENCE: 395

Asn Ser Tyr Thr Ser Thr Ser Met Val
1               5
```

-continued

```
<210> SEQ ID NO 396
<211> LENGTH: 9
<212> TYPE: PRT
<213> ORGANISM: Homo sapiens

<400> SEQUENCE: 396

Ser Ser Tyr Thr Ser Ser Ser Val Val
1               5

<210> SEQ ID NO 397
<211> LENGTH: 10
<212> TYPE: PRT
<213> ORGANISM: Homo sapiens

<400> SEQUENCE: 397

Ala Ala Trp Asp Asp Ser Leu Asn Trp Val
1               5                   10

<210> SEQ ID NO 398
<211> LENGTH: 11
<212> TYPE: PRT
<213> ORGANISM: Homo sapiens

<400> SEQUENCE: 398

Gly Thr Trp Asp Ser Ser Leu Ser Ser Tyr Val
1               5                   10

<210> SEQ ID NO 399
<211> LENGTH: 11
<212> TYPE: PRT
<213> ORGANISM: Homo sapiens

<400> SEQUENCE: 399

Gly Thr Trp Asp Ser Ser Leu Ser Ala Tyr Val
1               5                   10

<210> SEQ ID NO 400
<211> LENGTH: 116
<212> TYPE: PRT
<213> ORGANISM: Homo sapiens

<400> SEQUENCE: 400

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Ser Ser Gly Trp Phe Asp Tyr Trp Gly Gln Gly Thr Leu Val
            100                 105                 110

Thr Val Ser Ser
        115

<210> SEQ ID NO 401
<211> LENGTH: 118
<212> TYPE: PRT
```

```
<213> ORGANISM: Homo sapiens

<400> SEQUENCE: 401

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Asn Trp Gly Phe Ala Phe Asp Ile Trp Gly Gln Gly
            100                 105                 110

Thr Met Val Thr Val Ser
        115

<210> SEQ ID NO 402
<211> LENGTH: 115
<212> TYPE: PRT
<213> ORGANISM: Homo sapiens

<400> SEQUENCE: 402

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Gly Ala Phe Asp Ile Trp Gly Gln Gly Thr Met Val
            100                 105                 110

Thr Val Ser
        115

<210> SEQ ID NO 403
<211> LENGTH: 6
<212> TYPE: PRT
<213> ORGANISM: Homo sapiens

<400> SEQUENCE: 403

Glu Asn Leu Tyr Phe Gln
1               5

<210> SEQ ID NO 404
<211> LENGTH: 14
<212> TYPE: PRT
<213> ORGANISM: Homo sapiens
<220> FEATURE:
<221> NAME/KEY: VARIANT
<222> LOCATION: 1
```

-continued

```
<223> OTHER INFORMATION: Xaa= D, A, R or no amino acid
<220> FEATURE:
<221> NAME/KEY: VARIANT
<222> LOCATION: 2
<223> OTHER INFORMATION: Xaa=Y, I, G or no amino acid
<220> FEATURE:
<221> NAME/KEY: VARIANT
<222> LOCATION: 3
<223> OTHER INFORMATION: Xaa=D, A, G or no amino acid
<220> FEATURE:
<221> NAME/KEY: VARIANT
<222> LOCATION: 4
<223> OTHER INFORMATION: Xaa=F, A, L or no amino acid
<220> FEATURE:
<221> NAME/KEY: VARIANT
<222> LOCATION: 5
<223> OTHER INFORMATION: Xaa=W, L, A or no amino acid
<220> FEATURE:
<221> NAME/KEY: VARIANT
<222> LOCATION: 6
<223> OTHER INFORMATION: Xaa=S, Y, A or no amino acid
<220> FEATURE:
<221> NAME/KEY: VARIANT
<222> LOCATION: (7)...(7)
<223> OTHER INFORMATION: Xaa=A, Y, R or no amino acid
<220> FEATURE:
<221> NAME/KEY: VARIANT
<222> LOCATION: (8)...(8)
<223> OTHER INFORMATION: Xaa=Y,  P or no amino acid
<220> FEATURE:
<221> NAME/KEY: VARIANT
<222> LOCATION: (9)...(9)
<223> OTHER INFORMATION: Xaa=Y, G or no amino acid
<220> FEATURE:
<221> NAME/KEY: VARIANT
<222> LOCATION: (10)...(10)
<223> OTHER INFORMATION: Xaa=D, G or no amino acid
<220> FEATURE:
<221> NAME/KEY: VARIANT
<222> LOCATION: (11)...(11)
<223> OTHER INFORMATION: Xaa=A, M or no amino acid
<220> FEATURE:
<221> NAME/KEY: VARIANT
<222> LOCATION: (12)...(12)
<223> OTHER INFORMATION: Xaa=F,D  or no amino acid
<220> FEATURE:
<221> NAME/KEY: VARIANT
<222> LOCATION: (13)...(13)
<223> OTHER INFORMATION: Xaa=D, V or no amino acid
<220> FEATURE:
<221> NAME/KEY: VARIANT
<222> LOCATION: (14)...(14)
<223> OTHER INFORMATION: Xaa=V or no amino acid

<400> SEQUENCE: 404

Xaa Xaa Xaa Xaa Xaa Xaa Xaa Xaa Xaa Xaa Xaa Xaa Xaa Xaa
1               5                   10

<210> SEQ ID NO 405
<211> LENGTH: 11
<212> TYPE: PRT
<213> ORGANISM: Homo sapiens
<220> FEATURE:
<221> NAME/KEY: VARIANT
<222> LOCATION: 1
<223> OTHER INFORMATION: Xaa=Q or G
<220> FEATURE:
<221> NAME/KEY: VARIANT
<222> LOCATION: 2
<223> OTHER INFORMATION: Xaa=S, T, A or no amino acid
<220> FEATURE:
<221> NAME/KEY: VARIANT
<222> LOCATION: 3
<223> OTHER INFORMATION: Xaa=Y, W or no amino acid
<220> FEATURE:
<221> NAME/KEY: VARIANT
<222> LOCATION: 4
```

```
<223> OTHER INFORMATION: Xaa=D or no amino acid
<220> FEATURE:
<221> NAME/KEY: VARIANT
<222> LOCATION: 5
<223> OTHER INFORMATION: Xaa=S or no amino acid
<220> FEATURE:
<221> NAME/KEY: VARIANT
<222> LOCATION: 6
<223> OTHER INFORMATION: Xaa=S or no amino acid
<220> FEATURE:
<221> NAME/KEY: VARIANT
<222> LOCATION: (7)...(7)
<223> OTHER INFORMATION: Xaa=L, T or no amino acid
<220> FEATURE:
<221> NAME/KEY: VARIANT
<222> LOCATION: (8)...(8)
<223> OTHER INFORMATION: Xaa=A, S or no amino acid
<220> FEATURE:
<221> NAME/KEY: VARIANT
<222> LOCATION: (9)...(9)
<223> OTHER INFORMATION: Xaa=G, A, V or no amino acid
<220> FEATURE:
<221> NAME/KEY: VARIANT
<222> LOCATION: (10)...(10)
<223> OTHER INFORMATION: Xaa=S, Y, V or no amino acid
<220> FEATURE:
<221> NAME/KEY: VARIANT
<222> LOCATION: (11)...(11)
<223> OTHER INFORMATION: Xaa=V or no amino acid

<400> SEQUENCE: 405

Xaa Xaa Xaa Xaa Xaa Xaa Xaa Xaa Xaa Xaa Xaa
1               5                   10

<210> SEQ ID NO 406
<211> LENGTH: 10
<212> TYPE: PRT
<213> ORGANISM: Homo sapiens
<220> FEATURE:
<221> NAME/KEY: VARIANT
<222> LOCATION: 1
<223> OTHER INFORMATION: Xaa=G
<220> FEATURE:
<221> NAME/KEY: VARIANT
<222> LOCATION: 2
<223> OTHER INFORMATION: Xaa=Y, F or G
<220> FEATURE:
<221> NAME/KEY: VARIANT
<222> LOCATION: 3
<223> OTHER INFORMATION: Xaa=T or S
<220> FEATURE:
<221> NAME/KEY: VARIANT
<222> LOCATION: 4
<223> OTHER INFORMATION: Xaa=L or F
<220> FEATURE:
<221> NAME/KEY: VARIANT
<222> LOCATION: 5
<223> OTHER INFORMATION: Xaa=T, S or N
<220> FEATURE:
<221> NAME/KEY: VARIANT
<222> LOCATION: 6
<223> OTHER INFORMATION: Xaa=S or A
<220> FEATURE:
<221> NAME/KEY: VARIANT
<222> LOCATION: (7)...(7)
<223> OTHER INFORMATION: Xaa=Y or F
<220> FEATURE:
<221> NAME/KEY: VARIANT
<222> LOCATION: (8)...(8)
<223> OTHER INFORMATION: Xaa=G, S or Y
<220> FEATURE:
<221> NAME/KEY: VARIANT
<222> LOCATION: (9)...(9)
<223> OTHER INFORMATION: Xaa=I, M or W
<220> FEATURE:
<221> NAME/KEY: VARIANT
<222> LOCATION: (10)...(10)
```

```
<223> OTHER INFORMATION: Xaa=S, N or H

<400> SEQUENCE: 406

Xaa Xaa Xaa Xaa Xaa Xaa Xaa Xaa Xaa Xaa
1               5                   10

<210> SEQ ID NO 407
<211> LENGTH: 14
<212> TYPE: PRT
<213> ORGANISM: Homo sapiens
<220> FEATURE:
<221> NAME/KEY: VARIANT
<222> LOCATION: 1
<223> OTHER INFORMATION: Xaa=T or no amino acid
<220> FEATURE:
<221> NAME/KEY: VARIANT
<222> LOCATION: 2
<223> OTHER INFORMATION: Xaa=G or S
<220> FEATURE:
<221> NAME/KEY: VARIANT
<222> LOCATION: 3
<223> OTHER INFORMATION: Xaa=S, T or G
<220> FEATURE:
<221> NAME/KEY: VARIANT
<222> LOCATION: 4
<223> OTHER INFORMATION: Xaa=S
<220> FEATURE:
<221> NAME/KEY: VARIANT
<222> LOCATION: 5
<223> OTHER INFORMATION: Xaa=S
<220> FEATURE:
<221> NAME/KEY: VARIANT
<222> LOCATION: 6
<223> OTHER INFORMATION: Xaa=N, D or S
<220> FEATURE:
<221> NAME/KEY: VARIANT
<222> LOCATION: (7)...(7)
<223> OTHER INFORMATION: Xaa=I, V or N
<220> FEATURE:
<221> NAME/KEY: VARIANT
<222> LOCATION: (8)...(8)
<223> OTHER INFORMATION: Xaa=G or I
<220> FEATURE:
<221> NAME/KEY: VARIANT
<222> LOCATION: (9)...(9)
<223> OTHER INFORMATION: Xaa=A or G
<220> FEATURE:
<221> NAME/KEY: VARIANT
<222> LOCATION: (10)...(10)
<223> OTHER INFORMATION: Xaa=G, Y, S or N
<220> FEATURE:
<221> NAME/KEY: VARIANT
<222> LOCATION: (11)...(11)
<223> OTHER INFORMATION: Xaa=Y or N
<220> FEATURE:
<221> NAME/KEY: VARIANT
<222> LOCATION: (12)...(12)
<223> OTHER INFORMATION: Xaa=D, S, T or F
<220> FEATURE:
<221> NAME/KEY: VARIANT
<222> LOCATION: (13)...(13)
<223> OTHER INFORMATION: Xaa=V
<220> FEATURE:
<221> NAME/KEY: VARIANT
<222> LOCATION: (14)...(14)
<223> OTHER INFORMATION: Xaa=S, N or H

<400> SEQUENCE: 407

Xaa Xaa Xaa Xaa Xaa Xaa Xaa Xaa Xaa Xaa Xaa Xaa Xaa Xaa
1               5                   10

<210> SEQ ID NO 408
<211> LENGTH: 17
<212> TYPE: PRT
<213> ORGANISM: Homo sapiens
```

```
<220> FEATURE:
<221> NAME/KEY: VARIANT
<222> LOCATION: 1
<223> OTHER INFORMATION: Xaa=W, S, L or no amino acid
<220> FEATURE:
<221> NAME/KEY: VARIANT
<222> LOCATION: 2
<223> OTHER INFORMATION: Xaa=V, I or E
<220> FEATURE:
<221> NAME/KEY: VARIANT
<222> LOCATION: 3
<223> OTHER INFORMATION: Xaa=S, W or I
<220> FEATURE:
<221> NAME/KEY: VARIANT
<222> LOCATION: 4
<223> OTHER INFORMATION: Xaa=F, S or N
<220> FEATURE:
<221> NAME/KEY: VARIANT
<222> LOCATION: 5
<223> OTHER INFORMATION: Xaa=Y, S, D or H
<220> FEATURE:
<221> NAME/KEY: VARIANT
<222> LOCATION: 6
<223> OTHER INFORMATION: Xaa=N, S or G
<220> FEATURE:
<221> NAME/KEY: VARIANT
<222> LOCATION: (7)...(7)
<223> OTHER INFORMATION: Xaa=S or G
<220> FEATURE:
<221> NAME/KEY: VARIANT
<222> LOCATION: (8)...(8)
<223> OTHER INFORMATION: Xaa=N, Y, D or R
<220> FEATURE:
<221> NAME/KEY: VARIANT
<222> LOCATION: (9)...(9)
<223> OTHER INFORMATION: Xaa=T, I or E
<220> FEATURE:
<221> NAME/KEY: VARIANT
<222> LOCATION: (10)...(10)
<223> OTHER INFORMATION: Xaa=N, S, Y or D
<220> FEATURE:
<221> NAME/KEY: VARIANT
<222> LOCATION: (11)...(11)
<223> OTHER INFORMATION: Xaa=Y
<220> FEATURE:
<221> NAME/KEY: VARIANT
<222> LOCATION: (12)...(12)
<223> OTHER INFORMATION: Xaa=A and N
<220> FEATURE:
<221> NAME/KEY: VARIANT
<222> LOCATION: (13)...(13)
<223> OTHER INFORMATION: Xaa=Q, D or P
<220> FEATURE:
<221> NAME/KEY: VARIANT
<222> LOCATION: (14)...(14)
<223> OTHER INFORMATION: Xaa=K or S
<220> FEATURE:
<221> NAME/KEY: VARIANT
<222> LOCATION: (15)...(15)
<223> OTHER INFORMATION: Xaa=L or V
<220> FEATURE:
<221> NAME/KEY: VARIANT
<222> LOCATION: (16)...(16)
<223> OTHER INFORMATION: Xaa=Q or K
<220> FEATURE:
<221> NAME/KEY: VARIANT
<222> LOCATION: (17)...(17)
<223> OTHER INFORMATION: Xaa=G or S

<400> SEQUENCE: 408

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 409
<211> LENGTH: 7
```

-continued

```
<212> TYPE: PRT
<213> ORGANISM: Homo sapiens
<220> FEATURE:
<221> NAME/KEY: VARIANT
<222> LOCATION: 1
<223> OTHER INFORMATION: Xaa=G, E, S or D
<220> FEATURE:
<221> NAME/KEY: VARIANT
<222> LOCATION: 2
<223> OTHER INFORMATION: Xaa=N, V or Y
<220> FEATURE:
<221> NAME/KEY: VARIANT
<222> LOCATION: 3
<223> OTHER INFORMATION: Xaa=S or N
<220> FEATURE:
<221> NAME/KEY: VARIANT
<222> LOCATION: 4
<223> OTHER INFORMATION: Xaa=N, Q or K
<220> FEATURE:
<221> NAME/KEY: VARIANT
<222> LOCATION: 5
<223> OTHER INFORMATION: Xaa=R
<220> FEATURE:
<221> NAME/KEY: VARIANT
<222> LOCATION: 6
<223> OTHER INFORMATION: Xaa=P
<220> FEATURE:
<221> NAME/KEY: VARIANT
<222> LOCATION: (7)...(7)
<223> OTHER INFORMATION: Xaa=S

<400> SEQUENCE: 409

Xaa Xaa Xaa Xaa Xaa Xaa Xaa
1               5

<210> SEQ ID NO 410
<211> LENGTH: 14
<212> TYPE: PRT
<213> ORGANISM: Homo sapiens
<220> FEATURE:
<221> NAME/KEY: VARIANT
<222> LOCATION: 1
<223> OTHER INFORMATION: Xaa=D or no amino acid
<220> FEATURE:
<221> NAME/KEY: VARIANT
<222> LOCATION: 2
<223> OTHER INFORMATION: Xaa=Y, A or no amino acid
<220> FEATURE:
<221> NAME/KEY: VARIANT
<222> LOCATION: 3
<223> OTHER INFORMATION: Xaa=D, I or no amino acid
<220> FEATURE:
<221> NAME/KEY: VARIANT
<222> LOCATION: 4
<223> OTHER INFORMATION: Xaa=F, A or no amino acid
<220> FEATURE:
<221> NAME/KEY: VARIANT
<222> LOCATION: 5
<223> OTHER INFORMATION: Xaa=W, A or no amino acid
<220> FEATURE:
<221> NAME/KEY: VARIANT
<222> LOCATION: 6
<223> OTHER INFORMATION: Xaa=S, L or no amino acid
<220> FEATURE:
<221> NAME/KEY: VARIANT
<222> LOCATION: (7)...(7)
<223> OTHER INFORMATION: Xaa=A, Y, G or no amino acid
<220> FEATURE:
<221> NAME/KEY: VARIANT
<222> LOCATION: (8)...(8)
<223> OTHER INFORMATION: Xaa=Y, Q or no amino acid
<220> FEATURE:
<221> NAME/KEY: VARIANT
<222> LOCATION: (9)...(9)
<223> OTHER INFORMATION: Xaa=G, Y or L
<220> FEATURE:
<221> NAME/KEY: VARIANT
```

```
<222> LOCATION: (10)...(10)
<223> OTHER INFORMATION: Xaa=Y, D or V
<220> FEATURE:
<221> NAME/KEY: VARIANT
<222> LOCATION: (11)...(11)
<223> OTHER INFORMATION: Xaa=G, A or P
<220> FEATURE:
<221> NAME/KEY: VARIANT
<222> LOCATION: (12)...(12)
<223> OTHER INFORMATION: Xaa=M or F
<220> FEATURE:
<221> NAME/KEY: VARIANT
<222> LOCATION: (13)...(13)
<223> OTHER INFORMATION: Xaa=D
<220> FEATURE:
<221> NAME/KEY: VARIANT
<222> LOCATION: (14)...(14)
<223> OTHER INFORMATION: Xaa=V or Y

<400> SEQUENCE: 410

Xaa Xaa Xaa Xaa Xaa Xaa Xaa Xaa Xaa Xaa Xaa Xaa Xaa Xaa
1               5                   10

<210> SEQ ID NO 411
<211> LENGTH: 11
<212> TYPE: PRT
<213> ORGANISM: Homo sapiens
<220> FEATURE:
<221> NAME/KEY: VARIANT
<222> LOCATION: 1
<223> OTHER INFORMATION: Xaa=Q, A, G or no amino acid
<220> FEATURE:
<221> NAME/KEY: VARIANT
<222> LOCATION: 2
<223> OTHER INFORMATION: Xaa=S, V, T or no amino acid
<220> FEATURE:
<221> NAME/KEY: VARIANT
<222> LOCATION: 3
<223> OTHER INFORMATION: Xaa=Y, N or W
<220> FEATURE:
<221> NAME/KEY: VARIANT
<222> LOCATION: 4
<223> OTHER INFORMATION: Xaa=S or D
<220> FEATURE:
<221> NAME/KEY: VARIANT
<222> LOCATION: 5
<223> OTHER INFORMATION: Xaa=S, Y or D
<220> FEATURE:
<221> NAME/KEY: VARIANT
<222> LOCATION: 6
<223> OTHER INFORMATION: Xaa=S or T
<220> FEATURE:
<221> NAME/KEY: VARIANT
<222> LOCATION: (7)...(7)
<223> OTHER INFORMATION: Xaa=L or S
<220> FEATURE:
<221> NAME/KEY: VARIANT
<222> LOCATION: (8)...(8)
<223> OTHER INFORMATION: Xaa=S, T or N
<220> FEATURE:
<221> NAME/KEY: VARIANT
<222> LOCATION: (9)...(9)
<223> OTHER INFORMATION: Xaa=G, S or A
<220> FEATURE:
<221> NAME/KEY: VARIANT
<222> LOCATION: (10)...(10)
<223> OTHER INFORMATION: Xaa=S, M, W or Y
<220> FEATURE:
<221> NAME/KEY: VARIANT
<222> LOCATION: (11)...(11)
<223> OTHER INFORMATION: Xaa=V

<400> SEQUENCE: 411

Xaa Xaa Xaa Xaa Xaa Xaa Xaa Xaa Xaa Xaa Xaa
1               5                   10
```

```
<210> SEQ ID NO 412
<211> LENGTH: 10
<212> TYPE: PRT
<213> ORGANISM: Homo sapiens
<220> FEATURE:
<221> NAME/KEY: VARIANT
<222> LOCATION: 1
<223> OTHER INFORMATION: Xaa=G, P or A
<220> FEATURE:
<221> NAME/KEY: VARIANT
<222> LOCATION: 2
<223> OTHER INFORMATION: Xaa=Y, W, F, T or S
<220> FEATURE:
<221> NAME/KEY: VARIANT
<222> LOCATION: 3
<223> OTHER INFORMATION: Xaa=T, P, S, A, C, V, L or I
<220> FEATURE:
<221> NAME/KEY: VARIANT
<222> LOCATION: 4
<223> OTHER INFORMATION: Xaa=L, F, I, V, M, A or Y
<220> FEATURE:
<221> NAME/KEY: VARIANT
<222> LOCATION: 5
<223> OTHER INFORMATION: Xaa=T, P, S or A
<220> FEATURE:
<221> NAME/KEY: VARIANT
<222> LOCATION: 6
<223> OTHER INFORMATION: Xaa=S, T, A or C
<220> FEATURE:
<221> NAME/KEY: VARIANT
<222> LOCATION: (7)...(7)
<223> OTHER INFORMATION: Xaa=Y, W, F, T or S
<220> FEATURE:
<221> NAME/KEY: VARIANT
<222> LOCATION: (8)...(8)
<223> OTHER INFORMATION: Xaa=G, P or A
<220> FEATURE:
<221> NAME/KEY: VARIANT
<222> LOCATION: (9)...(9)
<223> OTHER INFORMATION: Xaa=I, L, V, M, A or F
<220> FEATURE:
<221> NAME/KEY: VARIANT
<222> LOCATION: (10)...(10)
<223> OTHER INFORMATION: Xaa=S, T, A or C

<400> SEQUENCE: 412

Xaa Xaa Xaa Xaa Xaa Xaa Xaa Xaa Xaa Xaa
1               5                   10

<210> SEQ ID NO 413
<211> LENGTH: 14
<212> TYPE: PRT
<213> ORGANISM: Homo sapiens
<220> FEATURE:
<221> NAME/KEY: VARIANT
<222> LOCATION: 1
<223> OTHER INFORMATION: Xaa=T or S
<220> FEATURE:
<221> NAME/KEY: VARIANT
<222> LOCATION: 2
<223> OTHER INFORMATION: Xaa=G, P or A
<220> FEATURE:
<221> NAME/KEY: VARIANT
<222> LOCATION: 3
<223> OTHER INFORMATION: Xaa=T or S
<220> FEATURE:
<221> NAME/KEY: VARIANT
<222> LOCATION: 4
<223> OTHER INFORMATION: Xaa=S, N, T, A, C or Q
<220> FEATURE:
<221> NAME/KEY: VARIANT
<222> LOCATION: 5
<223> OTHER INFORMATION: Xaa=S, T, A or C
<220> FEATURE:
<221> NAME/KEY: VARIANT
<222> LOCATION: 6
```

```
<223> OTHER INFORMATION: Xaa=D or E
<220> FEATURE:
<221> NAME/KEY: VARIANT
<222> LOCATION: (7)...(7)
<223> OTHER INFORMATION: Xaa=V, I, M, L, F or A
<220> FEATURE:
<221> NAME/KEY: VARIANT
<222> LOCATION: (8)...(8)
<223> OTHER INFORMATION: Xaa=G, P or A
<220> FEATURE:
<221> NAME/KEY: VARIANT
<222> LOCATION: (9)...(9)
<223> OTHER INFORMATION: Xaa=G, A, R, P, V, L, I, K, Q or N
<220> FEATURE:
<221> NAME/KEY: VARIANT
<222> LOCATION: (10)...(10)
<223> OTHER INFORMATION: Xaa=Y, W, F, T or S
<220> FEATURE:
<221> NAME/KEY: VARIANT
<222> LOCATION: (11)...(11)
<223> OTHER INFORMATION: Xaa=N or Q
<220> FEATURE:
<221> NAME/KEY: VARIANT
<222> LOCATION: (12)...(12)
<223> OTHER INFORMATION: Xaa=Y, S, W, F, T, S, T, A or C
<220> FEATURE:
<221> NAME/KEY: VARIANT
<222> LOCATION: (13)...(13)
<223> OTHER INFORMATION: Xaa=V, I, M, L, F, or A
<220> FEATURE:
<221> NAME/KEY: VARIANT
<222> LOCATION: (14)...(14)
<223> OTHER INFORMATION: Xaa=S, T, A or C

<400> SEQUENCE: 413

Xaa Xaa Xaa Xaa Xaa Xaa Xaa Xaa Xaa Xaa Xaa Xaa Xaa Xaa
1               5                   10

<210> SEQ ID NO 414
<211> LENGTH: 17
<212> TYPE: PRT
<213> ORGANISM: Homo sapiens
<220> FEATURE:
<221> NAME/KEY: VARIANT
<222> LOCATION: 1
<223> OTHER INFORMATION: Xaa=W, Y or F
<220> FEATURE:
<221> NAME/KEY: VARIANT
<222> LOCATION: 2
<223> OTHER INFORMATION: Xaa=V, I, M, L, F or A
<220> FEATURE:
<221> NAME/KEY: VARIANT
<222> LOCATION: 3
<223> OTHER INFORMATION: Xaa=S, T, A or C
<220> FEATURE:
<221> NAME/KEY: VARIANT
<222> LOCATION: 4
<223> OTHER INFORMATION: Xaa=A, F, V, L, I, Y or M
<220> FEATURE:
<221> NAME/KEY: VARIANT
<222> LOCATION: 5
<223> OTHER INFORMATION: Xaa=Y, W, F, T or S
<220> FEATURE:
<221> NAME/KEY: VARIANT
<222> LOCATION: 6
<223> OTHER INFORMATION: Xaa=N or Q
<220> FEATURE:
<221> NAME/KEY: VARIANT
<222> LOCATION: (7)...(7)
<223> OTHER INFORMATION: Xaa=G, P or A
<220> FEATURE:
<221> NAME/KEY: VARIANT
<222> LOCATION: (8)...(8)
<223> OTHER INFORMATION: Xaa=N or Q
<220> FEATURE:
<221> NAME/KEY: VARIANT
<222> LOCATION: (9)...(9)
```

-continued

```
<223> OTHER INFORMATION: Xaa=T or S
<220> FEATURE:
<221> NAME/KEY: VARIANT
<222> LOCATION: (10)...(10)
<223> OTHER INFORMATION: Xaa=N or Q
<220> FEATURE:
<221> NAME/KEY: VARIANT
<222> LOCATION: (11)...(11)
<223> OTHER INFORMATION: Xaa=Y, W, F, T or S
<220> FEATURE:
<221> NAME/KEY: VARIANT
<222> LOCATION: (12)...(12)
<223> OTHER INFORMATION: Xaa=A, V, L or I
<220> FEATURE:
<221> NAME/KEY: VARIANT
<222> LOCATION: (13)...(13)
<223> OTHER INFORMATION: Xaa=Q, E, N or D
<220> FEATURE:
<221> NAME/KEY: VARIANT
<222> LOCATION: (14)...(14)
<223> OTHER INFORMATION: Xaa=K, R, Q or N
<220> FEATURE:
<221> NAME/KEY: VARIANT
<222> LOCATION: (15)...(15)
<223> OTHER INFORMATION: Xaa=L, F, V, I, M, A or Y
<220> FEATURE:
<221> NAME/KEY: VARIANT
<222> LOCATION: (16)...(16)
<223> OTHER INFORMATION: Xaa=Q or N
<220> FEATURE:
<221> NAME/KEY: VARIANT
<222> LOCATION: (17)...(17)
<223> OTHER INFORMATION: Xaa=G, P or A

<400> SEQUENCE: 414

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 415
<211> LENGTH: 7
<212> TYPE: PRT
<213> ORGANISM: Homo sapiens
<220> FEATURE:
<221> NAME/KEY: VARIANT
<222> LOCATION: 1
<223> OTHER INFORMATION: Xaa=E or D
<220> FEATURE:
<221> NAME/KEY: VARIANT
<222> LOCATION: 2
<223> OTHER INFORMATION: Xaa=V, I, M, L, F or A
<220> FEATURE:
<221> NAME/KEY: VARIANT
<222> LOCATION: 3
<223> OTHER INFORMATION: Xaa=S, T, A or C
<220> FEATURE:
<221> NAME/KEY: VARIANT
<222> LOCATION: 4
<223> OTHER INFORMATION: Xaa=N or Q
<220> FEATURE:
<221> NAME/KEY: VARIANT
<222> LOCATION: 5
<223> OTHER INFORMATION: Xaa=R, K, Q or N
<220> FEATURE:
<221> NAME/KEY: VARIANT
<222> LOCATION: 6
<223> OTHER INFORMATION: Xaa=P or A
<220> FEATURE:
<221> NAME/KEY: VARIANT
<222> LOCATION: (7)...(7)
<223> OTHER INFORMATION: Xaa=S, T, A or C

<400> SEQUENCE: 415

Xaa Xaa Xaa Xaa Xaa Xaa Xaa
1               5
```

```
<210> SEQ ID NO 416
<211> LENGTH: 6
<212> TYPE: PRT
<213> ORGANISM: Homo sapiens
<220> FEATURE:
<221> NAME/KEY: VARIANT
<222> LOCATION: 1
<223> OTHER INFORMATION: Xaa=G, P, A or no amino acid
<220> FEATURE:
<221> NAME/KEY: VARIANT
<222> LOCATION: 2
<223> OTHER INFORMATION: Xaa=Y, W, F, T or S
<220> FEATURE:
<221> NAME/KEY: VARIANT
<222> LOCATION: 3
<223> OTHER INFORMATION: Xaa=G, V, P, A, I, M, L or F
<220> FEATURE:
<221> NAME/KEY: VARIANT
<222> LOCATION: 4
<223> OTHER INFORMATION: Xaa=M, L, F or I
<220> FEATURE:
<221> NAME/KEY: VARIANT
<222> LOCATION: 5
<223> OTHER INFORMATION: Xaa=D or E
<220> FEATURE:
<221> NAME/KEY: VARIANT
<222> LOCATION: 6
<223> OTHER INFORMATION: Xaa=V, I, M, L, F or A

<400> SEQUENCE: 416

Xaa Xaa Xaa Xaa Xaa Xaa
1               5

<210> SEQ ID NO 417
<211> LENGTH: 9
<212> TYPE: PRT
<213> ORGANISM: Homo sapiens
<220> FEATURE:
<221> NAME/KEY: VARIANT
<222> LOCATION: 1
<223> OTHER INFORMATION: Xaa=S, N, T, A, C or Q
<220> FEATURE:
<221> NAME/KEY: VARIANT
<222> LOCATION: 2
<223> OTHER INFORMATION: Xaa=S, T, A or C
<220> FEATURE:
<221> NAME/KEY: VARIANT
<222> LOCATION: 3
<223> OTHER INFORMATION: Xaa=Y, W, F, T or S
<220> FEATURE:
<221> NAME/KEY: VARIANT
<222> LOCATION: 4
<223> OTHER INFORMATION: Xaa=T or S
<220> FEATURE:
<221> NAME/KEY: VARIANT
<222> LOCATION: 5
<223> OTHER INFORMATION: Xaa=S, T, A or C
<220> FEATURE:
<221> NAME/KEY: VARIANT
<222> LOCATION: 6
<223> OTHER INFORMATION: Xaa=S, T, A or C
<220> FEATURE:
<221> NAME/KEY: VARIANT
<222> LOCATION: (7)...(7)
<223> OTHER INFORMATION: Xaa=N, S, Q, T, A or C
<220> FEATURE:
<221> NAME/KEY: VARIANT
<222> LOCATION: (8)...(8)
<223> OTHER INFORMATION: Xaa=M, V, L, F, I or A
<220> FEATURE:
<221> NAME/KEY: VARIANT
<222> LOCATION: (9)...(9)
<223> OTHER INFORMATION: Xaa=V, I, M, L, F or A

<400> SEQUENCE: 417
```

```
Xaa Xaa Xaa Xaa Xaa Xaa Xaa Xaa Xaa
1               5

<210> SEQ ID NO 418
<211> LENGTH: 363
<212> TYPE: DNA
<213> ORGANISM: Homo sapiens

<400> SEQUENCE: 418
caggtgcagg tggtgcagtc tgggggctgag gtgaagaagc ctggggcctc agtgaaggtc      60
tcctgcaagg cttctggata caccttcacc ggctactata tacactgggt gcgacaggcc     120
cctggacaag ggcttgagtg gatgggatgg atcaaccctc acagtggtgg cgcaaactat     180
gcacagaagt ttcagggcag ggtcaccatg accagggaca cgtccatcag cacagcctac     240
atggagctga gcaggctgag atctgacgac acggccgtgt attactgtgc gagaggcaac     300
tggaactacg actactacgg tatggacgtc tggggccaag ggaccacggt caccgtctcc     360
tca                                                                     363

<210> SEQ ID NO 419
<211> LENGTH: 121
<212> TYPE: PRT
<213> ORGANISM: Homo sapiens

<400> SEQUENCE: 419

Gln Val Gln Val Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro His Ser Gly Gly Ala Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Trp Asn Tyr Asp Tyr Tyr Gly Met Asp Val Trp Gly
            100                 105                 110

Gln Gly Thr Thr Val Thr Val Ser Ser
        115                 120

<210> SEQ ID NO 420
<211> LENGTH: 321
<212> TYPE: DNA
<213> ORGANISM: Homo sapiens

<400> SEQUENCE: 420
gacatccaga tgacccagtc tccatcctcc ctgtctgcat ctgtaggaga cagagtcacc      60
atcacttgcc gggcgagtca ggacattagc aattatttag cctggtatca gcagaaacca     120
gggaaagttc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttattt ctgtcaaagg tatcagattg ccccattcac tttcggccct     300
gggaccaagg tggatatcaa a                                                 321
```

-continued

```
<210> SEQ ID NO 421
<211> LENGTH: 107
<212> TYPE: PRT
<213> ORGANISM: Homo sapiens

<400> SEQUENCE: 421

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Arg Tyr Gln Ile Ala Pro Phe
                85                  90                  95

Thr Phe Gly Pro Gly Thr Lys Val Asp Ile Lys
            100                 105

<210> SEQ ID NO 422
<211> LENGTH: 366
<212> TYPE: DNA
<213> ORGANISM: Homo sapiens

<400> SEQUENCE: 422
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atctggtatg atggaagtac taaatactat     180
gcagactccg tgaagggccg atccaccatc tccagagaca attccaagaa cacgctgtat     240
ctgcaaatga acagcctgag agccgaggac acggctgtgt attactgtgc gaggtcagtg     300
gctggttacc actactacta cggtatggac gtctggggcc aagggaccac ggtcaccgtc     360
tcctca                                                               366

<210> SEQ ID NO 423
<211> LENGTH: 122
<212> TYPE: PRT
<213> ORGANISM: Homo sapiens

<400> SEQUENCE: 423

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Thr Lys Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Val Ala Gly Tyr His Tyr Tyr Tyr Gly Met Asp Val Trp
            100                 105                 110
```

-continued

```
Gly Gln Gly Thr Thr Val Thr Val Ser Ser
        115                 120

<210> SEQ ID NO 424
<211> LENGTH: 324
<212> TYPE: DNA
<213> ORGANISM: Homo sapiens

<400> SEQUENCE: 424
tcttctgagc tgactcagga ccctgctgtg tctgtggcct tgggacagac agtcaggatc        60
acatgccaag gagacagcct cagaggctat tatgcaacct ggtaccagca gaagccaaga       120
caggcccctg tacttgtcat ctatggtaaa aactaccggc cctcagggat cccagaccga       180
ttctctggct ccacctcagg aaacacagct tccttgacca tcactggggc tcaggcggaa       240
gatgaggctg actattactg taactcccgg gacagcattg gtaaccatct ggtgttcggc       300
ggagggacca agctgaccgt ccta                                             324

<210> SEQ ID NO 425
<211> LENGTH: 108
<212> TYPE: PRT
<213> ORGANISM: Homo sapiens

<400> SEQUENCE: 425

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Gly Tyr Tyr Ala
            20                  25                  30

Thr Trp Tyr Gln Gln Lys Pro Arg Gln Ala Pro Val Leu Val Ile Tyr
        35                  40                  45

Gly Lys Asn Tyr Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ile Gly Asn His
                85                  90                  95

Leu Val Phe Gly Gly Gly Thr Lys Leu Thr Val Leu
            100                 105

<210> SEQ ID NO 426
<211> LENGTH: 366
<212> TYPE: DNA
<213> ORGANISM: Homo sapiens

<400> SEQUENCE: 426
caggtgcagc tggtggagtc tggggggaggc gtggtccagc ctgggaggtc cctgagactc        60
tcctgtgcag cgtctggatt caccttcagt agctatggct tgcactgggt ccgccaggct       120
ccaggcaagg ggctggagtg ggtggcagtt atatggttag atggaagtaa taaatactat       180
gcagactccg tgaagggccg atccaccatc tccagagaca attccaagaa cacgctgtat       240
ctgcaaatga acagcctgag agccgaggac acggctgtgt attactgtgc gaggtcagtg       300
gctggttacc actactacta cggtatggac gtctggggcc aagggaccac ggtcaccgtc       360
tcctca                                                                 366

<210> SEQ ID NO 427
<211> LENGTH: 122
<212> TYPE: PRT
<213> ORGANISM: Homo sapiens
```

```
<400> SEQUENCE: 427

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Leu His Trp Val Arg Gln Ala Pro Gly Lys Gly Leu Glu Trp Val
            35                  40                  45

Ala Val Ile Trp Leu Asp Gly Ser Asn Lys Tyr Tyr Ala Asp Ser Val
            50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Val Ala Gly Tyr His Tyr Tyr Tyr Gly Met Asp Val Trp
                100                 105                 110

Gly Gln Gly Thr Thr Val Thr Val Ser Ser
            115                 120

<210> SEQ ID NO 428
<211> LENGTH: 324
<212> TYPE: DNA
<213> ORGANISM: Homo sapiens

<400> SEQUENCE: 428
tcttctgagc tgactcagga ccctgctgtg tctgtggcct tgggacagac agtcaggatc    60
acatgccaag agacagcct cagaagttat tatggaagct ggtaccagca gaagccaaga   120
caggcccctg tacttgtcat ctttggtaaa aacaaccggc cctcagggat cccagaccga   180
ttctctggct ccacctcagg aaacacagct tccttgacca tcactgggc tcaggcggaa   240 gatgaggctg actattactg taactcacgg gacatcattg gtgaccatct gctgttcggc   300
ggagggacca agctgaccgt ccta                                         324

<210> SEQ ID NO 429
<211> LENGTH: 108
<212> TYPE: PRT
<213> ORGANISM: Homo sapiens

<400> SEQUENCE: 429

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Gly
                20                  25                  30

Ser Trp Tyr Gln Gln Lys Pro Arg Gln Ala Pro Val Leu Val Ile Phe
            35                  40                  45

Gly Lys Asn Asn Arg Pro Ser Gly Ile Pro Asp Arg Phe Ser Gly Ser
            50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Ile Gly Asp His
                85                  90                  95

Leu Leu Phe Gly Gly Gly Thr Lys Leu Thr Val Leu
                100                 105

<210> SEQ ID NO 430
<211> LENGTH: 366
```

```
<212> TYPE: DNA
<213> ORGANISM: Homo sapiens

<400> SEQUENCE: 430
caggtgcagc tggtggagtc tgggggaggc gtggtccagt ctgggaggtc cctgagactc       60
tcctgtgcag cgtctggatt caccttcagg aactatggca tgcactgggt ccgccaggct      120
ccaggcaagg ggctggagtg ggtggcagtt atatggtttg atggaagtaa taaatactat      180
gcagactccg tgaagggccg atccaccatc tccagagaca attccaagaa cacgctgtat      240
ctgctaatga acagcctgag agccgaggac acggctgtgt attactgtgc gaggtcagtg      300
gctggttacc actactacta cggtatggac gtctggggcc aagggaccac ggtcaccgtc      360
tcctca                                                                 366

<210> SEQ ID NO 431
<211> LENGTH: 122
<212> TYPE: PRT
<213> ORGANISM: Homo sapiens

<400> SEQUENCE: 431

Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Arg Asn Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Lys Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Leu Met Asn Ser Leu Arg Ala Glu Asp Thr Ala Val Tyr Tyr Cys
                85                  90                  95

Ala Arg Ser Val Ala Gly Tyr His Tyr Tyr Tyr Gly Met Asp Val Trp
            100                 105                 110

Gly Gln Gly Thr Thr Val Thr Val Ser Ser
        115                 120

<210> SEQ ID NO 432
<211> LENGTH: 324
<212> TYPE: DNA
<213> ORGANISM: Homo sapiens

<400> SEQUENCE: 432
tcttctgagc tgactcagga ccctgctgtg tctgtggcct tgggacagac agtcaggatc       60
acatgccagg gagacagcct cagaagctat tatgcaagct ggtaccagca gaagccaaga      120
caggcccctg tacttgtcat ctatggtaaa aacaaccggc cctcagggat cccagaccga      180
atctctggct ccacctcagg aaacacagct tccttgacca tcactggggc tcaggcggaa      240
gatgaggctg actattactg taaatcccgg gacatcattg gtgaccatct ggtgttcggc      300
ggagggacca aactgaccgt ccta                                             324

<210> SEQ ID NO 433
<211> LENGTH: 108
<212> TYPE: PRT
<213> ORGANISM: Homo sapiens

<400> SEQUENCE: 433
```

-continued

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Arg Gln Ala Pro Val Leu Val Ile Tyr
        35                  40                  45

Gly Lys Asn Asn Arg Pro Ser Gly Ile Pro Asp Arg Ile Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Ile Ile Gly Asp His
                85                  90                  95

Leu Val Phe Gly Gly Gly Thr Lys Leu Thr Val Leu
            100                 105
```

```
<210> SEQ ID NO 434
<211> LENGTH: 342
<212> TYPE: DNA
<213> ORGANISM: Homo sapiens

<400> SEQUENCE: 434
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgt gagagatcgg     300
ggactggact ggggccaggg aaccctggtc accgtctcct ca                        342
```

```
<210> SEQ ID NO 435
<211> LENGTH: 114
<212> TYPE: PRT
<213> ORGANISM: Homo sapiens

<400> SEQUENCE: 435
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Arg Gly Leu Asp Trp Gly Gln Gly Thr Leu Val Thr Val
            100                 105                 110

Ser Ser
```

```
<210> SEQ ID NO 436
<211> LENGTH: 324
<212> TYPE: DNA
<213> ORGANISM: Homo sapiens

<400> SEQUENCE: 436
```

```
tcttctgagc tgactcagga ccctgctgtg tctgtggcct tgggacagac agtcaggatc      60
acatgccaag agacagcct cagaggctat tatgcaagct ggtaccagca gaagccaaga     120
caggcccctg tacttgtcat ctatggtaaa aacaaccggc cctcagggat cccagaccga     180
ttctctggct ccacctcagg aaacacagct tccttgacca tcactggggc tcaggcggaa     240
gatgaggctg actattactg taagtcccgg gacagcagtg gtgaccatct ggtgttcggc     300
ggagggacca agctgaccgt ccta                                           324
```

<210> SEQ ID NO 437
<211> LENGTH: 108
<212> TYPE: PRT
<213> ORGANISM: Homo sapiens

<400> SEQUENCE: 437

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Gly Tyr Tyr Ala
            20                  25                  30

Ser Trp Tyr Gln Gln Lys Pro Arg Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Ser Ser Gly Asp His
                85                  90                  95

Leu Val Phe Gly Gly Gly Thr Lys Leu Thr Val Leu
            100                 105
```

<210> SEQ ID NO 438
<211> LENGTH: 366
<212> TYPE: DNA
<213> ORGANISM: Homo sapiens

<400> SEQUENCE: 438

```
caggtgcagg tggtggagtc tgggggaggc gtggtccagc ctggggggtc cctgagactc      60
tcctgtgcag cgtctggatt caccttcagt aactatggca tgcactgggt ccgccaggct     120
ccaggcaagg ggctggagtg ggtggcagtt atttggtatg atggaagtag taaatactat     180
gcagactccg tgaagggccg atccaccatc tccagagaca attccaagaa cacggtgtat     240
ctgcaaatga acagcctgag agccgaggac acggctgtgt attactgtgc gaggtcagtg     300
gctggttacc actactacta cggtatggac gtctggggcc aagggaccac ggtcaccgtc     360
tcctca                                                               366
```

<210> SEQ ID NO 439
<211> LENGTH: 122
<212> TYPE: PRT
<213> ORGANISM: Homo sapiens

<400> SEQUENCE: 439

```
Gln Val Gln Val Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
```

```
            35                  40                  45

Ala Val Ile Trp Tyr Asp Gly Ser Ser Lys Tyr Tyr Ala Asp Ser Val
        50                  55                  60

Lys Gly Arg Ser Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Ser Val Ala Gly Tyr His Tyr Tyr Tyr Gly Met Asp Val Trp
            100                 105                 110

Gly Gln Gly Thr Thr Val Thr Val Ser Ser
        115                 120
```

```
<210> SEQ ID NO 440
<211> LENGTH: 324
<212> TYPE: DNA
<213> ORGANISM: Homo sapiens

<400> SEQUENCE: 440
tcttctgagc tgactcagga ccctgctgtg tctgtggcct tgggacagac agtcaggatc      60
acatgccaag agacagcct cagaggctat tatgcaagct ggtaccagca gaagccaaga      120
caggcccctg tacttgtcat ctatggtaaa aacaaccggc cctcagggat cccagaccga      180
ttctctggct ccacctcagg aaacacagct tccttgacca tcactggggc tcaggcggaa      240
gatgaggctg actattactg taagtcccgg gacagcagtg gtgaccatct ggtgttcggc      300
ggagggacca agctgaccgt ccta                                              324
```

```
<210> SEQ ID NO 441
<211> LENGTH: 108
<212> TYPE: PRT
<213> ORGANISM: Homo sapiens

<400> SEQUENCE: 441

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Gly Tyr Tyr Ala
            20                  25                  30

Ser Trp Tyr Gln Gln Lys Pro Arg Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Ser Ser Gly Asp His
                85                  90                  95

Leu Val Phe Gly Gly Gly Thr Lys Leu Thr Val Leu
            100                 105
```

```
<210> SEQ ID NO 442
<211> LENGTH: 366
<212> TYPE: DNA
<213> ORGANISM: Homo sapiens

<400> SEQUENCE: 442
caggtgcagc tggtggagtc tggggagggc gtggtccagc ctggaggtc cctgagtctc      60 tcctgtgcag cgtctggatt caccttcagt agctatggca tgcactgggt ccgccaggct      120
ccaggcaagg ggctggagtg ggtggcagtt atatggtatg atggaagtta taaagactat      180
```

```
gcagactccg tgaagggccg atccaccatc tccagagaca actccaagaa cacgctgtat      240
ctgcaaatga acagcctgag agccgaggac acggctgtgt attattgtgc gaggtcagtg      300
gctggttacc actactacta cggtatggac gtctggggcc aagggaccac ggtcaccgtc      360
tcctca                                                                 366
```

<210> SEQ ID NO 443
<211> LENGTH: 122
<212> TYPE: PRT
<213> ORGANISM: Homo sapiens

<400> SEQUENCE: 443

```
Gln Val Gln Leu Val Glu Ser Gly Gly Gly Val Val Gln Pro Gly Arg
1               5                   10                  15

Ser Leu Ser Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Tyr Lys Asp Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Val Ala Gly Tyr His Tyr Tyr Tyr Gly Met Asp Val Trp
            100                 105                 110

Gly Gln Gly Thr Thr Val Thr Val Ser Ser
        115                 120
```

<210> SEQ ID NO 444
<211> LENGTH: 324
<212> TYPE: DNA
<213> ORGANISM: Homo sapiens

<400> SEQUENCE: 444

```
tcttctgagc tgactcagga ccctgctgtg tctgtggcct tgggacagac agtcaggatc       60
acatgccaag agacagcct cagaacctat tatgcaagct ggtaccagca gaagccaaga      120
caggccccta ttcttgtcat ctatggtaaa aacaaccggc cctcaggat cccagaccga      180 ttctctggct ccacctcagg aatcacagct tccttgacca tcactggggc tcaggcggaa      240
gatgaggctg actattactg taaatcccgg gacatcattg gtaaccatct gctgttcggc      300
ggagggacta agctgaccgt ccta                                             324
```

<210> SEQ ID NO 445
<211> LENGTH: 108
<212> TYPE: PRT
<213> ORGANISM: Homo sapiens

<400> SEQUENCE: 445

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Arg Gln Ala Pro Ile Leu Val Ile Tyr
        35                  40                  45

Gly Lys Asn Asn Arg Pro Ser Gly Ile Pro Asp Arg Phe Ser Gly Ser
```

-continued

```
            50                55                60

Thr Ser Gly Ile Thr Ala Ser Leu Thr Ile Thr Gly Ala Gln Ala Glu
65                70                75                80

Asp Glu Ala Asp Tyr Tyr Cys Lys Ser Arg Asp Ile Ile Gly Asn His
                85                90                95

Leu Leu Phe Gly Gly Gly Thr Lys Leu Thr Val Leu
            100                105

<210> SEQ ID NO 446
<211> LENGTH: 375
<212> TYPE: DNA
<213> ORGANISM: Homo sapiens

<400> SEQUENCE: 446
caggtgcagc tggtggcgtc tgggggaggc gtggtccagc ctgggaggtc cctgagactc    60
tcctgtgcag cgtctggatt caccctcagt agctatggca tgcactgggt ccgccaggct    120
ccaggccagg ggctggagtg ggtggcagtc atatggtatg atggaagtaa caaatactat    180
gcagcctccg tgaagggccg attcaccatc tccagagaca attccaagaa cacgctgtat    240
ctgcaaatga acagtctgag agccgaggac acggctgtgt attactgtgc gagagggggt    300
ggttcgggga gtcatcgcta ctactactac ggtatggacg tctggggcca agggaccacg    360
gtcaccgtct cctca                                                    375

<210> SEQ ID NO 447
<211> LENGTH: 125
<212> TYPE: PRT
<213> ORGANISM: Homo sapiens

<400> SEQUENCE: 447

Gln Val Gln Leu Val Ala Ser Gly Gly Gly Val Val Gln Pro Gly Arg
1                5                10                15

Ser Leu Arg Leu Ser Cys Ala Ala Ser Gly Phe Thr Leu Ser Ser Tyr
            20                25                30

Gly Met His Trp Val Arg Gln Ala Pro Gly Gln Gly Leu Glu Trp Val
            35                40                45

Ala Val Ile Trp Tyr Asp Gly Ser Asn Lys Tyr Tyr Ala Ala Ser Val
        50                55                60

Lys Gly Arg Phe Thr Ile Ser Arg Asp Asn Ser Lys Asn Thr Leu Tyr
65                70                75                80

Leu Gln Met Asn Ser Leu Arg Ala Glu Asp Thr Ala Val Tyr Tyr Cys
            85                90                95

Ala Arg Gly Gly Gly Ser Gly Ser His Arg Tyr Tyr Tyr Tyr Gly Met
            100                105                110

Asp Val Trp Gly Gln Gly Thr Thr Val Thr Val Ser Ser
        115                120                125

<210> SEQ ID NO 448
<211> LENGTH: 324
<212> TYPE: DNA
<213> ORGANISM: Homo sapiens

<400> SEQUENCE: 448
tcttctgagc tgactcagga ccctgctgtg tctgtggcct tgggacagac agtcaggatc    60
acatgccaag agacagcct cagaacctat tatgcaagct ggtaccagca gaagccaaga    120 caggcccta ttcttgtcat ctatggtaaa aacaaccggc cctcagggat cccagaccga    180
```
ttctctggct ccacctcagg aatcacagct tccttgacca tcactggggc tcaggcggaa          240
gatgaggctg actattactg taaatcccgg gacatcattg gtaaccatct gctgttcggc          300
ggagggacta agctgaccgt ccta                                                 324

<210> SEQ ID NO 449
<211> LENGTH: 108
<212> TYPE: PRT
<213> ORGANISM: Homo sapiens

<400> SEQUENCE: 449

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
                20                  25                  30

Ser Trp Tyr Gln Gln Lys Pro Arg Gln Ala Pro Ile Leu Val Ile Tyr
            35                  40                  45

Gly Lys Asn Asn Arg Pro Ser Gly Ile Pro Asp Arg Phe Ser Gly Ser
        50                  55                  60

Thr Ser Gly Ile Thr Ala Ser Leu Thr Ile Thr Gly Ala Gln Ala Glu
65                  70                  75                  80

Asp Glu Ala Asp Tyr Tyr Cys Lys Ser Arg Asp Ile Ile Gly Asn His
                85                  90                  95

Leu Leu Phe Gly Gly Gly Thr Lys Leu Thr Val Leu
            100                 105

<210> SEQ ID NO 450
<211> LENGTH: 366
<212> TYPE: DNA
<213> ORGANISM: Homo sapiens

<400> SEQUENCE: 450
caggtgcaag tggtggagtc tgggggaggc gtggtccagc ctgggaggtc cctgagactc           60
tcctgtgcag cgtctggatt caccttcagt aactatggca tgcactgggt ccgccaggct          120
ccaggcaagg ggctggagtg ggtggcagtt atatggtatg atggaggtaa taaatactat          180
gcagactccg tgaagggccg atccatcatc tccagagaca attccaagag cacgctgtat          240
ctgcaaatga acagcctgag agccgaggac acggctgttt attattgtgc gaggtcagtg          300
gctggttacc attattacta cggtatggac gtctggggcc aagggaccac ggtcaccgtc          360
gcctca                                                                     366

<210> SEQ ID NO 451
<211> LENGTH: 122
<212> TYPE: PRT
<213> ORGANISM: Homo sapiens

<400> SEQUENCE: 451

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Val Ile Trp Tyr Asp Gly Gly Asn Lys Tyr Tyr Ala Asp Ser Val
        50                  55                  60

Lys Gly Arg Ser Ile Ile Ser Arg Asp Asn Ser Lys Ser Thr Leu Tyr
65                  70                  75                  80

```
Leu Gln Met Asn Ser Leu Arg Ala Glu Asp Thr Ala Val Tyr Tyr Cys
                85                  90                  95

Ala Arg Ser Val Ala Gly Tyr His Tyr Tyr Gly Met Asp Val Trp
            100                 105                 110

Gly Gln Gly Thr Thr Val Thr Val Ala Ser
        115                 120
```

```
<210> SEQ ID NO 452
<211> LENGTH: 327
<212> TYPE: DNA
<213> ORGANISM: Homo sapiens

<400> SEQUENCE: 452
cagtctgccc tgactcagcc tgcctccgtg tctgggtctc ctggacagtc gatcaccatc      60
tcctgcactg gaaccagcag tgacgttggt ggttataact ctgtctcctg gtaccaacag     120
cacccaggca aacccccaa actcatgatt tatgaggtca gtaatcggcc ctcagggatt      180
tctaatcgct tctctggctc caagtctggc aacacggcct ccctgaccat ctctgggctc     240
caggctgagg acgaggctga ttatttctgc agctcatata caagcaccag catggtcttc     300
ggcggaggga ccaagctggc cgtccta                                         327
```

```
<210> SEQ ID NO 453
<211> LENGTH: 109
<212> TYPE: PRT
<213> ORGANISM: Homo sapiens

<400> SEQUENCE: 453

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Ala Val Leu
            100                 105
```

```
<210> SEQ ID NO 454
<211> LENGTH: 366
<212> TYPE: DNA
<213> ORGANISM: Homo sapiens

<400> SEQUENCE: 454
caggtgcaag tggtggagtc tggggggaggc gtggtccagc ctgggaggtc cctgagactc      60
tcctgtgcag cgtctggatt caccttcagt aactatggca tgcactgggt ccgccaggct     120
ccaggcaagg ggctggagtg ggtggcagtt atatggtatg atggaggtaa taaatactat     180
gcagactccg tgaagggccg atccatcatc tccagagaca attccaagag cacgctgtat     240
ctgcaaatga acagcctgag agccgaggac acggctgttt attattgtgc gaggtcagtg     300
gctggttacc attattacta cggtatggac gtctggggcc aagggaccac ggtcaccgtc     360
```

-continued

```
gcctca                                                                  366
```

```
<210> SEQ ID NO 455
<211> LENGTH: 122
<212> TYPE: PRT
<213> ORGANISM: Homo sapiens

<400> SEQUENCE: 455

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Gly Asn Lys Tyr Tyr Ala Asp Ser Val
    50                  55                  60

Lys Gly Arg Ser Ile Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Val Ala Gly Tyr His Tyr Tyr Tyr Gly Met Asp Val Trp
            100                 105                 110

Gly Gln Gly Thr Thr Val Thr Val Ala Ser
        115                 120
```

```
<210> SEQ ID NO 456
<211> LENGTH: 324
<212> TYPE: DNA
<213> ORGANISM: Homo sapiens

<400> SEQUENCE: 456
tcttctgagc tgactcagga ccctgctgtg tctgtggcct tgggacagac agtcaggatc      60
acatgccaag agacagcct cagaggctat tatgcaagct ggtaccagca gaagccaaga      120
caggcccctg tacttgtcat ctatggtaaa aacaaccggc cctcagggat cccagaccga      180
ttctctggct ccacgtcagg aaacacagct tccttgacca tcactgggc tcaggcggaa       240 gatgaggctg actattactg taactcccgg gacaacattg gtgaccatct ggtgttcggc      300
ggagggacca agctgaccgt ccta                                            324
```

```
<210> SEQ ID NO 457
<211> LENGTH: 108
<212> TYPE: PRT
<213> ORGANISM: Homo sapiens

<400> SEQUENCE: 457

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Gly Tyr Tyr Ala
            20                  25                  30

Ser Trp Tyr Gln Gln Lys Pro Arg Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Asn Ile Gly Asp His
                85                  90                  95
```

-continued

```
Leu Val Phe Gly Gly Gly Thr Lys Leu Thr Val Leu
        100                 105

<210> SEQ ID NO 458
<211> LENGTH: 381
<212> TYPE: DNA
<213> ORGANISM: Homo sapiens

<400> SEQUENCE: 458
gaggtgcagc tggtggagtc tggggggaggc ttggtccagc ctggggggtc cctgagactc      60
tcctgtgcag cctccggatt caccttttagt agctattgga tgagctgggt ccgccaggct     120
ccagggaagg ggctggagtg ggtggccagc ataaaacaag atggaagtga aaatactat       180 gtggactctg tgaagggccg attcaccatc tccagagaca acgccaggaa ctcactgtat      240
ctgcaaatga acagcctgag agccgaggac acggctgtgt attactgtgc gagagatctt      300
gtattaatgg tgtatgatat agactactac tactacggta tggacgtctg gggccaaggg      360
accacggtca ccgtctcctc a                                                381

<210> SEQ ID NO 459
<211> LENGTH: 127
<212> TYPE: PRT
<213> ORGANISM: Homo sapiens

<400> SEQUENCE: 459

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ser Ile Lys Gln Asp Gly Ser Glu Lys Tyr Tyr Val Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Val Leu Met Val Tyr Asp Ile Asp Tyr Tyr Tyr
            100                 105                 110

Gly Met Asp Val Trp Gly Gln Gly Thr Thr Val Thr Val Ser Ser
            115                 120                 125

<210> SEQ ID NO 460
<211> LENGTH: 336
<212> TYPE: DNA
<213> ORGANISM: Homo sapiens

<400> SEQUENCE: 460
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180 tccgggggtcc ctgacaggtt cagtggcagt ggatcaggca cagattttac actgaaaatc     240
agcagagtgg aggctgagga tgttgggggtt tattactgca tgcaagctct acaaactccg     300
ctcactttcg cggagggggac caaggtagag atcaaa                               336
```

-continued

```
<210> SEQ ID NO 461
<211> LENGTH: 112
<212> TYPE: PRT
<213> ORGANISM: Homo sapiens

<400> SEQUENCE: 461

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 462
<211> LENGTH: 381
<212> TYPE: DNA
<213> ORGANISM: Homo sapiens

<400> SEQUENCE: 462
gaggtgcagc tggtggagtc tgggggaggc ttggtccagc ctggggggtc cctgagactc      60
tcctgtgcag cctccggatt cacctttagt aactattgga tgagctgggt ccgccaggct     120
ccagggaagg ggctggagtg ggtggccagc ataaaacaag atggaagtga gaaatactat     180
gtggactctg tgaagggccg attcgccatc tccagagaca cgccaagaa ctcactgttt      240 ctgcaaatga acagcctgag agccgaggac acggctgtgt attactgtgc gagagatctt     300
gtactaatgg tgtatgatat agactactac tactacggta tggacgtctg gggccaaggg     360
accacggtca ccgtctcctc a                                               381

<210> SEQ ID NO 463
<211> LENGTH: 127
<212> TYPE: PRT
<213> ORGANISM: Homo sapiens

<400> SEQUENCE: 463

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Ser Ile Lys Gln Asp Gly Ser Glu Lys Tyr Tyr Val Asp Ser Val
    50                  55                  60

Lys Gly Arg Phe Ala Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Leu Val Leu Met Val Tyr Asp Ile Asp Tyr Tyr Tyr Tyr
            100                 105                 110
```

Gly Met Asp Val Trp Gly Gln Gly Thr Thr Val Thr Val Ser Ser
        115                 120                 125

<210> SEQ ID NO 464
<211> LENGTH: 336
<212> TYPE: DNA
<213> ORGANISM: Homo sapiens

<400> SEQUENCE: 464
gatattgtga tgactcagtc tccactctcc ctgcctgtca cccctggaga gccggcctcc      60
atctcttgca ggtctagtca gagcctcctg catagtaatg ggtacaacta tttggattgg     120
tacctgcaga agccagggca gtctccacag ctcctgatct atttgggttc taatcgggcc     180
tccggggtcc ctgacaggtt cagtggcagt ggatcaggca cacatcttac actgaaaatc     240
agcagagtgg aggctgagga tgttggagtt tattactgca tgcaaactct acaaactccg     300
ctcactttcg gcggagggac caaggtggag atcaaa                               336

<210> SEQ ID NO 465
<211> LENGTH: 112
<212> TYPE: PRT
<213> ORGANISM: Homo sapiens

<400> SEQUENCE: 465

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr His Leu Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110

<210> SEQ ID NO 466
<211> LENGTH: 342
<212> TYPE: DNA
<213> ORGANISM: Homo sapiens

<400> SEQUENCE: 466
caggtgcagc tggtggagtc tggggggaggc gtggcccagc ctgggaggtc cctgagactc      60
tcctgtgcag cgtctggatt caccttcagt agctatggca tgcactgggt ccgccaggct     120
ccaggcaagg ggctggagtg ggtggcagtt atatactatg atggaattaa taaacactat     180
gcagactccg tgaagggccg attcaccatc tccagagaca attccaagaa cacgctgtat     240
ctgcaaatga acagcctgag agccgaggac acggctgtgt attactgtgc gagagatcgg     300
ggactggact ggggccaggg aaccctggtc accgtctcct ca                        342

<210> SEQ ID NO 467
<211> LENGTH: 114
<212> TYPE: PRT
<213> ORGANISM: Homo sapiens

<400> SEQUENCE: 467

-continued

```
Gln Val Gln Leu Val Glu Ser Gly Gly Gly Val Ala Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Tyr Tyr Asp Gly Ile Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Leu Asp Trp Gly Gln Gly Thr Leu Val Thr Val
            100                 105                 110

Ser Ser
```

```
<210> SEQ ID NO 468
<211> LENGTH: 339
<212> TYPE: DNA
<213> ORGANISM: Homo sapiens

<400> SEQUENCE: 468
gacatcgtga tgacccagtc tccagactcc ctggctgtgt ctctgggcga gagggccacc      60
atcaactgca agtccagcca gagtgtttta tacagctcca acagtaagaa ctacttagtt     120
tggtaccagc agaaaccagg acagcctcct aagctgctca tttactgggc ctctacccgg     180
gaatccgggg tccctgaccg attcagtggc agcgggtctg ggacagattt cactctcacc     240
atcagcagcc tgcaggctga agatgtggca gtttattact gtcaacaata ttatagtact     300
ccgtggacgt tcggccaagg gaccaaggtg gaaatcaaa                           339
```

```
<210> SEQ ID NO 469
<211> LENGTH: 113
<212> TYPE: PRT
<213> ORGANISM: Homo sapiens

<400> SEQUENCE: 469

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys
```

```
<210> SEQ ID NO 470
<211> LENGTH: 357
<212> TYPE: DNA
```

```
<213> ORGANISM: Homo sapiens

<400> SEQUENCE: 470
gaggtgcagc tggtggagtc tggggggaggc ttggtccagc ctggggggtc cctgagactc      60
tcctgtgcag cctctggact caccttagt aactttggga tgagctgggt ccgccaggct     120
ccagggaagg ggctggagtg ggtggccaac ataaagcaag atggaaatga taaatactat     180
gtggactctg tgaagggccg attcaccatc tccagagaca cgccaagaa ttcactgtat      240 ctgcaaatga acagcctgag agccgaggac acggctgtgt attactgtgc gagagagtca     300
aactggggat ttgcttttga tatctggggc caagggacaa tggtcaccgt ctcttca       357

<210> SEQ ID NO 471
<211> LENGTH: 119
<212> TYPE: PRT
<213> ORGANISM: Homo sapiens

<400> SEQUENCE: 471

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Phe
            20                  25                  30

Trp Met Ser Trp Val Arg Gln Ala Pro Gly Lys Gly Leu Glu Trp Val
        35                  40                  45

Ala Asn Ile Lys Gln Asp Gly Asn Asp Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Asn Trp Gly Phe Ala Phe Asp Ile Trp Gly Gln Gly
            100                 105                 110

Thr Met Val Thr Val Ser Ser
        115

<210> SEQ ID NO 472
<211> LENGTH: 327
<212> TYPE: DNA
<213> ORGANISM: Homo sapiens

<400> SEQUENCE: 472
cagtctgtgc tgactcagcc accctcagcg tctgggaccc ccgggcagag ggtcaccatc      60
tcttgttctg gaagcagctc caacatcgga agtaaaactg taaactggta ccagcagttc     120
ccaggaacgg cccccaaact cctcatctat agtaataatc ggcggccctc aggggtccct     180
gaccgattct ctggctccaa gtctggcacc tcagcctccc tggccatcag tgggctccag     240
tctgaggatg aggctgatta ttactgtgca gcatgggatg acagcctgaa ttgggtgttc     300
ggcgcaggga ccaagctgac cgtccta                                         327

<210> SEQ ID NO 473
<211> LENGTH: 109
<212> TYPE: PRT
<213> ORGANISM: Homo sapiens

<400> SEQUENCE: 473

Gln Ser Val Leu Thr Gln Pro Pro Ser Ala Ser Gly Thr Pro Gly Gln
1               5                   10                  15
```

-continued

```
Arg Val Thr Ile Ser Cys Ser Gly Ser Ser Asn Ile Gly Ser Lys
            20              25              30

Thr Val Asn Trp Tyr Gln Gln Phe Pro Gly Thr Ala Pro Lys Leu Leu
            35              40              45

Ile Tyr Ser Asn Asn Arg Arg Pro Ser Gly Val Pro Asp Arg Phe Ser
            50              55              60

Gly Ser Lys Ser Gly Thr Ser Ala Ser Leu Ala Ile Ser Gly Leu Gln
65                  70              75                  80

Ser Glu Asp Glu Ala Asp Tyr Tyr Cys Ala Ala Trp Asp Asp Ser Leu
                85              90                  95

Asn Trp Val Phe Gly Ala Gly Thr Lys Leu Thr Val Leu
                100             105
```

```
<210> SEQ ID NO 474
<211> LENGTH: 357
<212> TYPE: DNA
<213> ORGANISM: Homo sapiens

<400> SEQUENCE: 474
gaggtgcagc tggtggagtc tggggggaggt ttggtccagc ctggggggtc cctgagactc      60
tcctgtgcag cctctggact caccttttagt aactttttgga tgagctgggt ccgccaggct     120
ccagggaagg ggctggagtg ggtggccaac ataaagcaag atggaagtga gaaatactat      180
gtggactctg tgaagggccg attcaccatc tccagagaca cgccaagaa ttcactgtat        240 ctgcaaatga acagcctgag agccgaggac acggctgtgt attactgtgc gagagagtca       300
aactggggat ttgcttttga tatctggggc caagggacaa tggtcaccgt ctcttca         357
```

```
<210> SEQ ID NO 475
<211> LENGTH: 119
<212> TYPE: PRT
<213> ORGANISM: Homo sapiens

<400> SEQUENCE: 475
```

```
Glu Val Gln Leu Val Glu Ser Gly Gly Gly Leu Val Gln Pro Gly Gly
1               5               10              15

Ser Leu Arg Leu Ser Cys Ala Ala Ser Gly Leu Thr Phe Ser Asn Phe
            20              25              30

Trp Met Ser Trp Val Arg Gln Ala Pro Gly Lys Gly Leu Glu Trp Val
            35              40              45

Ala Asn Ile Lys Gln Asp Gly Ser Glu Lys Tyr Tyr Val Asp Ser Val
            50              55              60

Lys Gly Arg Phe Thr Ile Ser Arg Asp Asn Ala Lys Asn Ser Leu Tyr
65                  70              75                  80

Leu Gln Met Asn Ser Leu Arg Ala Glu Asp Thr Ala Val Tyr Tyr Cys
                85              90                  95

Ala Arg Glu Ser Asn Trp Gly Phe Ala Phe Asp Ile Trp Gly Gln Gly
                100             105             110

Thr Met Val Thr Val Ser Ser
        115
```

```
<210> SEQ ID NO 476
<211> LENGTH: 327
<212> TYPE: DNA
<213> ORGANISM: Homo sapiens

<400> SEQUENCE: 476
cagtctgtgc tgactcagcc accctcagcg tctgggaccc ccgggcagag ggtcaccatc      60
```

-continued

```
tcttgttctg gaagcagctc caacatcgga agtaaaactg taaactggta ccagcagttc    120
ccaggaacgg cccccaaact cctcatctat agtaataatc ggcggccctc aggggtccct    180
gaccgattct ctggctccaa gtctggcacc tcagcctccc tggccatcag tgggctccag    240
tctgaggatg aggctgatta ttactgtgca acatgggatg acagactgaa ttgggtgttc    300
ggcgcaggga ccaagctgac cgtccta                                       327
```

<210> SEQ ID NO 477
<211> LENGTH: 109
<212> TYPE: PRT
<213> ORGANISM: Homo sapiens

<400> SEQUENCE: 477

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Lys
                20                  25                  30

Thr Val Asn Trp Tyr Gln Gln Phe Pro Gly Thr Ala Pro Lys Leu Leu
            35                  40                  45

Ile Tyr Ser Asn Asn Arg Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Arg Leu
                85                  90                  95

Asn Trp Val Phe Gly Ala Gly Thr Lys Leu Thr Val Leu
            100                 105
```

<210> SEQ ID NO 478
<211> LENGTH: 366
<212> TYPE: DNA
<213> ORGANISM: Homo sapiens

<400> SEQUENCE: 478

```
caggtcacct tgaaggagtc tggtcctgtg ctggtgaaac ccacagagac cctcacgctg     60
acctgcaccg tctctgggtt ctcactcagc aatgttagaa tgggtgtgag ctggatccgt    120
cagcccccag ggaaggccct ggagtggctt gcacacattt tttcgaatga cgaaaattcc    180
tacagaacat ctctgaagag caggctcacc atctccaagg acacctccaa aagccaggtg    240
gtccttacca tgaccaacat ggaccctgtg gacacagcca catattactg tgcacgdata    300
gtgggagcta caacggatga tgcttttgat atctggggcc aagggacaat ggtcaccgtc    360
tcttca                                                              366
```

<210> SEQ ID NO 479
<211> LENGTH: 122
<212> TYPE: PRT
<213> ORGANISM: Homo sapiens

<400> SEQUENCE: 479

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Val
                20                  25                  30

Arg Met Gly Val Ser Trp Ile Arg Gln Pro Pro Gly Lys Ala Leu Glu
            35                  40                  45
```

-continued

```
Trp Leu Ala His Ile Phe Ser Asn Asp Glu Asn Ser Tyr Arg Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Val Gly Ala Thr Thr Asp Asp Ala Phe Asp Ile Trp
            100                 105                 110

Gly Gln Gly Thr Met Val Thr Val Ser Ser
        115                 120
```

<210> SEQ ID NO 480
<211> LENGTH: 324
<212> TYPE: DNA
<213> ORGANISM: Homo sapiens

<400> SEQUENCE: 480

```
tcctatgtgc tgactcagcc accctcggtg tcagtggccc caggacagac ggccaggatt      60
acctgtgggg gaaacaacat tggaagtaaa agtgtgcact ggtaccagca gaagccaggc     120
caggcccctg tgctggtcgt ctatgatgat agcgaccggc cctcaggat ccctgagcga      180 ttctctggct ccaactctgg gaacacggcc accctgacca tcagcagggt cgaagccggg     240
gatgaggccg actttactg tcaggtgtgg gatagtagta gtgatcctgt ggtattcggc      300
ggagggacca agctgaccgt ccta                                            324
```

<210> SEQ ID NO 481
<211> LENGTH: 108
<212> TYPE: PRT
<213> ORGANISM: Homo sapiens

<400> SEQUENCE: 481

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Ser Ser Ser Asp Pro
                85                  90                  95

Val Val Phe Gly Gly Gly Thr Lys Leu Thr Val Leu
            100                 105
```

<210> SEQ ID NO 482
<211> LENGTH: 381
<212> TYPE: DNA
<213> ORGANISM: Homo sapiens

<400> SEQUENCE: 482

```
gaggtgcagc tggtggagtc tgggggaggc ttggtccagc ctggggggtc cctgagactc      60
tcctgtgcag cctctggatt caccttagt aactattgga tgacctgggt ccgccaggct     120
ccagggaagg ggctggagtg ggtggccagc ataaagcaag atggaagtga gagatactat     180
gtggactctg tgaagggccg attcaccatc tcccgagaca ccgccaagaa ctctctgtat     240
```

```
ctccaaatga acagcctgcg agccgaggac acggctgtgt attactgtgc gagacctctt      300
gtactaatgg tgtatgctct acactactac tactacggta tggacgtctg gggccacggg      360
accacggtca ccgtctcctc a                                                381

<210> SEQ ID NO 483
<211> LENGTH: 127
<212> TYPE: PRT
<213> ORGANISM: Homo sapiens

<400> SEQUENCE: 483

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Ser Ile Lys Gln Asp Gly Ser Glu Arg Tyr Tyr Val Asp Ser Val
    50                  55                  60

Lys Gly Arg Phe Thr Ile Ser Arg Asp Thr Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Val Leu Met Val Tyr Ala Leu His Tyr Tyr Tyr Tyr
            100                 105                 110

Gly Met Asp Val Trp Gly His Gly Thr Thr Val Thr Val Ser Ser
        115                 120                 125

<210> SEQ ID NO 484
<211> LENGTH: 336
<212> TYPE: DNA
<213> ORGANISM: Homo sapiens

<400> SEQUENCE: 484
gatattgtga tgactcagtc tccactctcc ctgcccgtca cccctggaga gccggcctcc       60
atctcctgca ggtctagtca gagcctcctg catagtaatg gatacaacta tttggattgg      120
tacctgcaga agccagggca gtctccacag ctcctgatct atttgggttc taatcgggcc      180
tccggggtcc ctgacaggtt cagtggcagt ggatcaggca cagattttac actgaaaatc      240
agcagagtgg aggctgagga tgttggggtt tattactgca tgcaagctct acaaactccg      300
ctcactttcg gcggagggac caaggtggag atcaaa                                336

<210> SEQ ID NO 485
<211> LENGTH: 112
<212> TYPE: PRT
<213> ORGANISM: Homo sapiens

<400> SEQUENCE: 485

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
                100                 105                 110

<210> SEQ ID NO 486
<211> LENGTH: 100
<212> TYPE: PRT
<213> ORGANISM: Homo sapiens

<400> SEQUENCE: 486

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 487
<211> LENGTH: 98
<212> TYPE: PRT
<213> ORGANISM: Homo sapiens

<400> SEQUENCE: 487

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 488
<211> LENGTH: 98
<212> TYPE: PRT
<213> ORGANISM: Homo sapiens

<400> SEQUENCE: 488

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30
```

-continued

Gly Met His Trp Val Arg Gln Ala Pro Gly Lys Gly Leu Glu Trp Val
       35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 489
<211> LENGTH: 93
<212> TYPE: PRT
<213> ORGANISM: Homo sapiens

<400> SEQUENCE: 489

Asp Ile Val Met Thr Gln Ser Pro Leu Ser Leu Pro Val Thr Pro Gly
1                   5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys
                85                  90

<210> SEQ ID NO 490
<211> LENGTH: 94
<212> TYPE: PRT
<213> ORGANISM: Homo sapiens

<400> SEQUENCE: 490

Asp Ile Val Met Thr Gln Ser Pro Asp Ser Leu Ala Val Ser Leu Gly
1                   5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys
                85                  90

<210> SEQ ID NO 491
<211> LENGTH: 89
<212> TYPE: PRT
<213> ORGANISM: Homo sapiens

<400> SEQUENCE: 491

Gln Ser Val Leu Thr Gln Pro Pro Ser Ala Ser Gly Thr Pro Gly Gln
1                   5                   10                  15

Arg Val Thr Ile Ser Cys Ser Gly Ser Ser Ser Asn Ile Gly Ser Asn

-continued

```
              20                25                30
Thr Val Asn Trp Tyr Gln Gln Leu Pro Gly Thr Ala Pro Lys Leu Leu
          35                40                45
Ile Tyr Ser Asn Asn Gln Arg Pro Ser Gly Val Pro Asp Arg Phe Ser
      50                55                60
Gly Ser Lys Ser Gly Thr Ser Ala Ser Leu Ala Ile Ser Gly Leu Gln
65                70                75                80
Ser Glu Asp Glu Ala Asp Tyr Tyr Cys
              85

<210> SEQ ID NO 492
<211> LENGTH: 87
<212> TYPE: PRT
<213> ORGANISM: Homo sapiens

<400> SEQUENCE: 492

Ser Tyr Val Leu Thr Gln Pro Pro Ser Val Ser Val Ala Pro Gly Lys
1               5                10                15
Thr Ala Arg Ile Thr Cys Gly Gly Asn Asn Ile Gly Ser Lys Ser Val
              20                25                30
His Trp Tyr Gln Gln Lys Pro Gly Gln Ala Pro Val Leu Val Ile Tyr
          35                40                45
Tyr Asp Ser Asp Arg Pro Ser Gly Ile Pro Glu Arg Phe Ser Gly Ser
      50                55                60
Asn Ser Gly Asn Thr Ala Thr Leu Thr Ile Ser Arg Val Glu Ala Gly
65                70                75                80
Asp Glu Ala Asp Tyr Tyr Cys
              85

<210> SEQ ID NO 493
<211> LENGTH: 49
<212> TYPE: PRT
<213> ORGANISM: Homo sapiens

<400> SEQUENCE: 493

Gln Val Gln Leu Val Gln Ser Gly Ala Glu Val Lys Lys Pro Gly Ala
1               5                10                15
Ser Val Lys Val Ser Cys Lys Ala Ser Gly Tyr Thr Phe Thr Gly Tyr
              20                25                30
Tyr Met His Trp Val Arg Gln Ala Pro Gly Gln Gly Leu Glu Trp Met
          35                40                45
Gly

<210> SEQ ID NO 494
<211> LENGTH: 98
<212> TYPE: PRT
<213> ORGANISM: Homo sapiens

<400> SEQUENCE: 494

Gln Val Gln Leu Val Glu Ser Gly Gly Gly Val Val Gln Pro Gly Arg
1               5                10                15
Ser Leu Arg Leu Ser Cys Ala Ala Ser Gly Phe Thr Phe Ser Ser Tyr
              20                25                30
Gly Met His Trp Val Arg Gln Ala Pro Gly Lys Gly Leu Glu Trp Val
          35                40                45
Ala Val Ile Trp Tyr Asp Gly Ser Asn Lys Tyr Tyr Ala Asp Ser Val
      50                55                60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 495
<211> LENGTH: 98
<212> TYPE: PRT
<213> ORGANISM: Homo sapiens

<400> SEQUENCE: 495

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 496
<211> LENGTH: 88
<212> TYPE: PRT
<213> ORGANISM: Homo sapiens

<400> SEQUENCE: 496

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys
                85

<210> SEQ ID NO 497
<211> LENGTH: 90
<212> TYPE: PRT
<213> ORGANISM: Homo sapiens

<400> SEQUENCE: 497

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45
```

407

408

-continued

```
Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys
                85                  90

<210> SEQ ID NO 498
<211> LENGTH: 87
<212> TYPE: PRT
<213> ORGANISM: Homo sapiens

<400> SEQUENCE: 498

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys
                85

<210> SEQ ID NO 499
<211> LENGTH: 13
<212> TYPE: PRT
<213> ORGANISM: Homo sapiens

<400> SEQUENCE: 499

Ser Gly Ser Ser Ser Asn Ile Gly Ser Lys Thr Val Asn
1               5                   10

<210> SEQ ID NO 500
<211> LENGTH: 10
<212> TYPE: PRT
<213> ORGANISM: Homo sapiens

<400> SEQUENCE: 500

Gly Phe Thr Phe Ser Asn Tyr Trp Met Ser
1               5                   10

<210> SEQ ID NO 501
<211> LENGTH: 17
<212> TYPE: PRT
<213> ORGANISM: Homo sapiens

<400> SEQUENCE: 501

Ser Ile Lys Gln Asp Gly Ser Glu Lys Tyr Tyr Val Asp Ser Val Lys
1               5                   10                  15

Gly

<210> SEQ ID NO 502
<211> LENGTH: 18
<212> TYPE: PRT
<213> ORGANISM: Homo sapiens

<400> SEQUENCE: 502

Asp Leu Val Leu Met Val Tyr Asp Ile Asp Tyr Tyr Tyr Tyr Gly Met
```

-continued

```
1               5               10              15

Asp Val

<210> SEQ ID NO 503
<211> LENGTH: 15
<212> TYPE: PRT
<213> ORGANISM: Homo sapiens

<400> SEQUENCE: 503

Arg Ser Ser Gln Ser Leu Leu His Ser Asn Gly Tyr Asn Leu Asp
1               5               10              15

<210> SEQ ID NO 504
<211> LENGTH: 7
<212> TYPE: PRT
<213> ORGANISM: Homo sapiens

<400> SEQUENCE: 504

Leu Gly Ser Asn Arg Ala Ser
1               5

<210> SEQ ID NO 505
<211> LENGTH: 9
<212> TYPE: PRT
<213> ORGANISM: Homo sapiens

<400> SEQUENCE: 505

Met Gln Thr Leu Gln Thr Pro Leu Thr
1               5

<210> SEQ ID NO 506
<211> LENGTH: 25
<212> TYPE: PRT
<213> ORGANISM: Homo sapiens

<400> SEQUENCE: 506

Gln Val Thr Leu Lys Glu Ser Gly Pro Val Leu Val Lys Pro Thr Glu
1               5               10              15

Thr Leu Thr Leu Thr Cys Thr Val Ser
            20              25

<210> SEQ ID NO 507
<211> LENGTH: 12
<212> TYPE: PRT
<213> ORGANISM: Homo sapiens

<400> SEQUENCE: 507

Gly Phe Ser Leu Ser Asn Ala Arg Met Gly Val Ser
1               5               10

<210> SEQ ID NO 508
<211> LENGTH: 12
<212> TYPE: PRT
<213> ORGANISM: Homo sapiens

<400> SEQUENCE: 508

Gly Phe Ser Leu Ser Asn Val Arg Met Gly Val Ser
1               5               10

<210> SEQ ID NO 509
<211> LENGTH: 14
<212> TYPE: PRT
<213> ORGANISM: Homo sapiens
```

-continued

```
<400> SEQUENCE: 509

Trp Ile Arg Gln Pro Pro Gly Lys Ala Leu Glu Trp Leu Ala
1               5                   10

<210> SEQ ID NO 510
<211> LENGTH: 25
<212> TYPE: PRT
<213> ORGANISM: Homo sapiens

<400> SEQUENCE: 510

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 511
<211> LENGTH: 10
<212> TYPE: PRT
<213> ORGANISM: Homo sapiens

<400> SEQUENCE: 511

Gly Phe Thr Phe Ser Ser Tyr Trp Met Ser
1               5                   10

<210> SEQ ID NO 512
<211> LENGTH: 10
<212> TYPE: PRT
<213> ORGANISM: Homo sapiens

<400> SEQUENCE: 512

Gly Leu Thr Phe Ser Asn Phe Trp Met Ser
1               5                   10

<210> SEQ ID NO 513
<211> LENGTH: 10
<212> TYPE: PRT
<213> ORGANISM: Homo sapiens

<400> SEQUENCE: 513

Gly Phe Thr Phe Ser Asn Tyr Trp Met Thr
1               5                   10

<210> SEQ ID NO 514
<211> LENGTH: 14
<212> TYPE: PRT
<213> ORGANISM: Homo sapiens

<400> SEQUENCE: 514

Trp Val Arg Gln Ala Pro Gly Lys Gly Leu Glu Trp Val Ala
1               5                   10

<210> SEQ ID NO 515
<211> LENGTH: 25
<212> TYPE: PRT
<213> ORGANISM: Homo sapiens

<400> SEQUENCE: 515

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 516
```

```
<211> LENGTH: 25
<212> TYPE: PRT
<213> ORGANISM: Homo sapiens

<400> SEQUENCE: 516

Gln Val Gln Leu Val Glu Ser Gly Gly Val Ala Gln Pro Gly Arg
1               5                   10                  15

Ser Leu Arg Leu Ser Cys Ala Ala Ser
            20                  25

<210> SEQ ID NO 517
<211> LENGTH: 10
<212> TYPE: PRT
<213> ORGANISM: Homo sapiens

<400> SEQUENCE: 517

Gly Phe Thr Phe Ser Ser Tyr Gly Met His
1               5                   10

<210> SEQ ID NO 518
<211> LENGTH: 14
<212> TYPE: PRT
<213> ORGANISM: Homo sapiens

<400> SEQUENCE: 518

Trp Val Arg Gln Ala Pro Gly Lys Gly Leu Glu Trp Val Ala
1               5                   10

<210> SEQ ID NO 519
<211> LENGTH: 16
<212> TYPE: PRT
<213> ORGANISM: Homo sapiens

<400> SEQUENCE: 519

His Ile Phe Ser Asn Asp Glu Lys Ser Tyr Ser Thr Ser Leu Lys Ser
1               5                   10                  15

<210> SEQ ID NO 520
<211> LENGTH: 16
<212> TYPE: PRT
<213> ORGANISM: Homo sapiens

<400> SEQUENCE: 520

His Ile Phe Ser Asn Asp Glu Asn Ser Tyr Arg Thr Ser Leu Lys Ser
1               5                   10                  15

<210> SEQ ID NO 521
<211> LENGTH: 33
<212> TYPE: PRT
<213> ORGANISM: Homo sapiens

<400> SEQUENCE: 521

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

Ile

<210> SEQ ID NO 522
<211> LENGTH: 11
<212> TYPE: PRT
<213> ORGANISM: Homo sapiens

<400> SEQUENCE: 522
```

-continued

```
Val Gly Ala Thr Thr Asp Asp Ala Phe Asp Ile
1               5               10

<210> SEQ ID NO 523
<211> LENGTH: 11
<212> TYPE: PRT
<213> ORGANISM: Homo sapiens

<400> SEQUENCE: 523

Trp Gly Gln Gly Thr Met Val Thr Val Ser Ser
1               5               10

<210> SEQ ID NO 524
<211> LENGTH: 11
<212> TYPE: PRT
<213> ORGANISM: Homo sapiens

<400> SEQUENCE: 524

Trp Gly Gln Gly Thr Thr Val Thr Val Ser Ser
1               5               10

<210> SEQ ID NO 525
<211> LENGTH: 11
<212> TYPE: PRT
<213> ORGANISM: Homo sapiens

<400> SEQUENCE: 525

Trp Gly His Gly Thr Thr Val Thr Val Ser Ser
1               5               10

<210> SEQ ID NO 526
<211> LENGTH: 17
<212> TYPE: PRT
<213> ORGANISM: Homo sapiens

<400> SEQUENCE: 526

Asn Ile Lys Gln Asp Gly Ser Glu Lys Tyr Tyr Val Asp Ser Val Lys
1               5               10              15

Gly

<210> SEQ ID NO 527
<211> LENGTH: 17
<212> TYPE: PRT
<213> ORGANISM: Homo sapiens

<400> SEQUENCE: 527

Asn Ile Lys Gln Asp Gly Asn Asp Lys Tyr Tyr Val Asp Ser Val Lys
1               5               10              15

Gly

<210> SEQ ID NO 528
<211> LENGTH: 17
<212> TYPE: PRT
<213> ORGANISM: Homo sapiens

<400> SEQUENCE: 528

Ser Ile Lys Gln Asp Gly Ser Glu Arg Tyr Tyr Val Asp Ser Val Lys
1               5               10              15

Gly

<210> SEQ ID NO 529
<211> LENGTH: 32
```

<212> TYPE: PRT
<213> ORGANISM: Homo sapiens

<400> SEQUENCE: 529

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 530
<211> LENGTH: 32
<212> TYPE: PRT
<213> ORGANISM: Homo sapiens

<400> SEQUENCE: 530

Arg Phe Thr Ile Ser Arg Asp Asn Ala Arg Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 531
<211> LENGTH: 32
<212> TYPE: PRT
<213> ORGANISM: Homo sapiens

<400> SEQUENCE: 531

Arg Phe Ala Ile Ser Arg Asp Asn Ala Lys Asn Ser Leu Phe Leu Gln
1               5                   10                  15

Met Asn Ser Leu Arg Ala Glu Asp Thr Ala Val Tyr Tyr Cys Ala Arg
            20                  25                  30

<210> SEQ ID NO 532
<211> LENGTH: 32
<212> TYPE: PRT
<213> ORGANISM: Homo sapiens

<400> SEQUENCE: 532

Arg Phe Thr Ile Ser Arg Asp Thr Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 533
<211> LENGTH: 10
<212> TYPE: PRT
<213> ORGANISM: Homo sapiens

<400> SEQUENCE: 533

Glu Ser Asn Trp Gly Phe Ala Phe Asp Ile
1               5                   10

<210> SEQ ID NO 534
<211> LENGTH: 18
<212> TYPE: PRT
<213> ORGANISM: Homo sapiens

<400> SEQUENCE: 534

Pro Leu Val Leu Met Val Tyr Ala Leu His Tyr Tyr Tyr Tyr Gly Met
1               5                   10                  15

Asp Val

<210> SEQ ID NO 535

-continued

<211> LENGTH: 17
<212> TYPE: PRT
<213> ORGANISM: Homo sapiens

<400> SEQUENCE: 535

Val Ile Trp Tyr Asp Gly Ser Asn Lys Tyr Tyr Ala Asp Ser Val Lys
1               5                   10                  15

Gly

<210> SEQ ID NO 536
<211> LENGTH: 17
<212> TYPE: PRT
<213> ORGANISM: Homo sapiens

<400> SEQUENCE: 536

Val Ile Tyr Tyr Asp Gly Ile Asn Lys His Tyr Ala Asp Ser Val Lys
1               5                   10                  15

Gly

<210> SEQ ID NO 537
<211> LENGTH: 32
<212> TYPE: PRT
<213> ORGANISM: Homo sapiens

<400> SEQUENCE: 537

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 538
<211> LENGTH: 5
<212> TYPE: PRT
<213> ORGANISM: Homo sapiens

<400> SEQUENCE: 538

Asp Arg Gly Leu Asp
1               5

<210> SEQ ID NO 539
<211> LENGTH: 11
<212> TYPE: PRT
<213> ORGANISM: Homo sapiens

<400> SEQUENCE: 539

Trp Gly Gln Gly Thr Leu Val Thr Val Ser Ser
1               5                   10

<210> SEQ ID NO 540
<211> LENGTH: 23
<212> TYPE: PRT
<213> ORGANISM: Homo sapiens

<400> SEQUENCE: 540

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 541
<211> LENGTH: 15
<212> TYPE: PRT
<213> ORGANISM: Homo sapiens

```
<400> SEQUENCE: 541

Trp Tyr Leu Gln Lys Pro Gly Gln Ser Pro Gln Leu Leu Ile Tyr
1               5                   10                  15

<210> SEQ ID NO 542
<211> LENGTH: 23
<212> TYPE: PRT
<213> ORGANISM: Homo sapiens

<400> SEQUENCE: 542

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 543
<211> LENGTH: 17
<212> TYPE: PRT
<213> ORGANISM: Homo sapiens

<400> SEQUENCE: 543

Lys Ser Ser Gln Ser Val Leu Tyr Ser Ser Asn Asn Lys Asn Tyr Leu
1               5                   10                  15

Ala

<210> SEQ ID NO 544
<211> LENGTH: 17
<212> TYPE: PRT
<213> ORGANISM: Homo sapiens

<400> SEQUENCE: 544

Lys Ser Ser Gln Ser Val Leu Tyr Ser Ser Asn Ser Lys Asn Tyr Leu
1               5                   10                  15

Val

<210> SEQ ID NO 545
<211> LENGTH: 15
<212> TYPE: PRT
<213> ORGANISM: Homo sapiens

<400> SEQUENCE: 545

Trp Tyr Gln Gln Lys Pro Gly Gln Pro Pro Lys Leu Leu Ile Tyr
1               5                   10                  15

<210> SEQ ID NO 546
<211> LENGTH: 22
<212> TYPE: PRT
<213> ORGANISM: Homo sapiens

<400> SEQUENCE: 546

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 547
<211> LENGTH: 13
<212> TYPE: PRT
<213> ORGANISM: Homo sapiens

<400> SEQUENCE: 547
```

```
Ser Gly Ser Ser Ser Asn Ile Gly Ser Asn Thr Val Asn
1               5                   10
```

<210> SEQ ID NO 548
<211> LENGTH: 13
<212> TYPE: PRT
<213> ORGANISM: Homo sapiens

<400> SEQUENCE: 548

```
Ser Gly Ser Ser Ser Asn Ile Gly Ser Lys Thr Val Asn
1               5                   10
```

<210> SEQ ID NO 549
<211> LENGTH: 15
<212> TYPE: PRT
<213> ORGANISM: Homo sapiens

<400> SEQUENCE: 549

```
Trp Tyr Gln Gln Leu Pro Gly Thr Ala Pro Lys Leu Leu Ile Tyr
1               5                   10                  15
```

<210> SEQ ID NO 550
<211> LENGTH: 15
<212> TYPE: PRT
<213> ORGANISM: Homo sapiens

<400> SEQUENCE: 550

```
Trp Tyr Gln Gln Phe Pro Gly Thr Ala Pro Lys Leu Leu Ile Tyr
1               5                   10                  15
```

<210> SEQ ID NO 551
<211> LENGTH: 22
<212> TYPE: PRT
<213> ORGANISM: Homo sapiens

<400> SEQUENCE: 551

```
Ser Tyr Val Leu Thr Gln Pro Pro Ser Val Ser Val Ala Pro Gly Lys
1               5                   10                  15

Thr Ala Arg Ile Thr Cys
            20
```

<210> SEQ ID NO 552
<211> LENGTH: 22
<212> TYPE: PRT
<213> ORGANISM: Homo sapiens

<400> SEQUENCE: 552

```
Ser Tyr Val Leu Thr Gln Pro Pro Ser Val Ser Val Ala Pro Gly Gln
1               5                   10                  15

Thr Ala Arg Ile Thr Cys
            20
```

<210> SEQ ID NO 553
<211> LENGTH: 11
<212> TYPE: PRT
<213> ORGANISM: Homo sapiens

<400> SEQUENCE: 553

```
Gly Gly Asn Asn Ile Gly Ser Lys Ser Val His
1               5                   10
```

<210> SEQ ID NO 554
<211> LENGTH: 15
<212> TYPE: PRT

<213> ORGANISM: Homo sapiens

<400> SEQUENCE: 554

Trp Tyr Gln Gln Lys Pro Gly Gln Ala Pro Val Leu Val Ile Tyr
1               5                   10                  15

<210> SEQ ID NO 555
<211> LENGTH: 15
<212> TYPE: PRT
<213> ORGANISM: Homo sapiens

<400> SEQUENCE: 555

Trp Tyr Gln Gln Lys Pro Gly Gln Ala Pro Val Leu Val Val Tyr
1               5                   10                  15

<210> SEQ ID NO 556
<211> LENGTH: 32
<212> TYPE: PRT
<213> ORGANISM: Homo sapiens

<400> SEQUENCE: 556

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 557
<211> LENGTH: 32
<212> TYPE: PRT
<213> ORGANISM: Homo sapiens

<400> SEQUENCE: 557

Gly Val Pro Asp Arg Phe Ser Gly Ser Gly Ser Gly Thr His Leu Thr
1               5                   10                  15

Leu Lys Ile Ser Arg Val Glu Ala Glu Asp Val Gly Val Tyr Tyr Cys
            20                  25                  30

<210> SEQ ID NO 558
<211> LENGTH: 9
<212> TYPE: PRT
<213> ORGANISM: Homo sapiens

<400> SEQUENCE: 558

Met Gln Ala Leu Gln Thr Pro Leu Thr
1               5

<210> SEQ ID NO 559
<211> LENGTH: 10
<212> TYPE: PRT
<213> ORGANISM: Homo sapiens

<400> SEQUENCE: 559

Phe Gly Gly Gly Thr Lys Val Glu Ile Lys
1               5                   10

<210> SEQ ID NO 560
<211> LENGTH: 7
<212> TYPE: PRT
<213> ORGANISM: Homo sapiens

<400> SEQUENCE: 560

Trp Ala Ser Thr Arg Glu Ser
1               5

-continued

```
<210> SEQ ID NO 561
<211> LENGTH: 32
<212> TYPE: PRT
<213> ORGANISM: Homo sapiens

<400> SEQUENCE: 561

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 562
<211> LENGTH: 9
<212> TYPE: PRT
<213> ORGANISM: Homo sapiens

<400> SEQUENCE: 562

Gln Gln Tyr Tyr Ser Thr Pro Trp Thr
1               5

<210> SEQ ID NO 563
<211> LENGTH: 10
<212> TYPE: PRT
<213> ORGANISM: Homo sapiens

<400> SEQUENCE: 563

Phe Gly Gln Gly Thr Lys Val Glu Ile Lys
1               5                   10

<210> SEQ ID NO 564
<211> LENGTH: 7
<212> TYPE: PRT
<213> ORGANISM: Homo sapiens

<400> SEQUENCE: 564

Ser Asn Asn Gln Arg Pro Ser
1               5

<210> SEQ ID NO 565
<211> LENGTH: 7
<212> TYPE: PRT
<213> ORGANISM: Homo sapiens

<400> SEQUENCE: 565

Ser Asn Asn Arg Arg Pro Ser
1               5

<210> SEQ ID NO 566
<211> LENGTH: 32
<212> TYPE: PRT
<213> ORGANISM: Homo sapiens

<400> SEQUENCE: 566

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 567
<211> LENGTH: 10
<212> TYPE: PRT
<213> ORGANISM: Homo sapiens

<400> SEQUENCE: 567
```

-continued

```
Ala Ala Trp Asp Asp Ser Leu Asn Trp Val
1               5                   10

<210> SEQ ID NO 568
<211> LENGTH: 10
<212> TYPE: PRT
<213> ORGANISM: Homo sapiens

<400> SEQUENCE: 568

Ala Thr Trp Asp Asp Arg Leu Asn Trp Val
1               5                   10

<210> SEQ ID NO 569
<211> LENGTH: 10
<212> TYPE: PRT
<213> ORGANISM: Homo sapiens

<400> SEQUENCE: 569

Phe Gly Ala Gly Thr Lys Leu Thr Val Leu
1               5                   10

<210> SEQ ID NO 570
<211> LENGTH: 7
<212> TYPE: PRT
<213> ORGANISM: Homo sapiens

<400> SEQUENCE: 570

Tyr Asp Ser Asp Arg Pro Ser
1               5

<210> SEQ ID NO 571
<211> LENGTH: 7
<212> TYPE: PRT
<213> ORGANISM: Homo sapiens

<400> SEQUENCE: 571

Asp Asp Ser Asp Arg Pro Ser
1               5

<210> SEQ ID NO 572
<211> LENGTH: 32
<212> TYPE: PRT
<213> ORGANISM: Homo sapiens

<400> SEQUENCE: 572

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 573
<211> LENGTH: 32
<212> TYPE: PRT
<213> ORGANISM: Homo sapiens

<400> SEQUENCE: 573

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Phe Cys
            20                  25                  30

<210> SEQ ID NO 574
<211> LENGTH: 11
```

-continued

```
<212> TYPE: PRT
<213> ORGANISM: Homo sapiens

<400> SEQUENCE: 574

Gln Val Trp Asp Ser Ser Ser Asp Pro Val Val
1               5                   10

<210> SEQ ID NO 575
<211> LENGTH: 10
<212> TYPE: PRT
<213> ORGANISM: Homo sapiens

<400> SEQUENCE: 575

Phe Gly Gly Gly Thr Lys Leu Thr Val Leu
1               5                   10
```

FORMULATIONS COMPRISING PCSK9 SPECIFIC MONOCLONAL ANTIBODIES

RELATED APPLICATIONS

This application claims the benefit of U.S. Provisional Application No. 61/642,363 filed on May 3, 2012, the contents of which are hereby incorporated by reference in their entirety.

REFERENCE TO SEQUENCE LISTING

The present application incorporates by reference in its entirety all subject matter contained in the attached sequence listing which is in txt format is identified by the name of the file, A-1635-US-NP2_Seq_List.txt, created on May 1, 2013, the size of which file is 306 KB.

FIELD OF THE INVENTION

The present invention relates to methods of treating or preventing cholesterol related disorders, such as hypercholesterolemia, hyperlipidemia or dyslipidemia, using antigen binding proteins, including antibodies, against proprotein convertase subtilisin/kexin type 9 (PCSK9). Pharmaceutical formulations and methods of producing said formulations are also described.

BACKGROUND

"Cholesterol related disorders" (which include "serum cholesterol related disorders") include any one or more of the following: hypercholesterolemia, hperlipidemia, heart disease, metabolic syndrome, diabetes, coronary heart disease, stroke, cardiovascular diseases, Alzheimer's disease and generally dyslipidemias, which can be manifested, for example, by an elevated total serum cholesterol, elevated LDL, elevated triglycerides, elevated VLDL, and/or low HDL. Hypercholesterolemia is, in fact, an established risk factor for coronary heart disease (CHD) in humans. Lowering of low-density lipoprotein cholesterol (LDL-C) results in a reduction of cardiovascular risk and is a primary goal in pharmacotherapy for CHD. Statins (hydroxymethylglutaryl coenzyme A [HMG CoA] reductase inhibitors) are currently the treatment of choice for hypercholesterolemia. However, emerging data indicate that more aggressive treatment of hypercholesterolemia is associated with lower risk for CHD events. In addition, a subset of patients are intolerant to, or do not respond adequately to, statin therapy. Thus, novel therapies that can be used alone or in combination with existing agents to more effectively reduce LDL-C may be useful.

It is well established that recycling of the hepatic cell surface low-density lipoprotein receptor (LDLR) plays a critical role in the maintenance of cellular and whole body cholesterol balance by regulating plasma LDL-C levels. More recently it has been shown that proprotein convertase subtilisin/kexin type 9 (PCSK9) plays an important role in the recycling and regulation of LDLR. PCSK9 is a member of the subtilisin family of serine proteases and is expressed predominantly in the liver. Following secretion, it causes post-translational down regulation of hepatic cell surface LDLR by a mechanism that involves direct binding to the LDLR. Down regulation of hepatic LDLR in turn leads to increased levels of circulating LDL-C. Thus PCSK9 may represent a target for inhibition by novel therapeutics in the setting of hypercholesterolemia. Strong rationale for such an approach is available from studies in preclinical models and from findings that humans with PCSK9 loss-of-function mutations have cholesterol levels lower than normal and reduced incidence of CHD.

SUMMARY OF VARIOUS EMBODIMENTS

In some aspects, the invention comprises a method of lowering the serum LDL cholesterol level in a patient. The method comprises administering to a patient in need thereof a dose of about 10 mg to about 1400 mg of at least one anti-PCSK9 antibody described herein. In some embodiments, the dose is about 10 mg to about 70 mg of at least one anti-PCSK9 antibody administered once weekly (QW). In some embodiments, the dose is about 14 mg to about 45 mg of at least one anti-PCSK9 antibody administered once weekly. In some embodiments, the dose is about 14 mg to about 35 mg of at least one anti-PCSK9 antibody administered once weekly. In some embodiments, the dose is about 70 mg to about 420 mg of at least one anti-PCSK9 antibody administered once every 2 weeks (Q2W). In some embodiments, the dose is about 70 mg to about 350 mg of at least one anti-PCSK9 antibody administered once every 2 weeks (Q2W). In some embodiments, the dose is about 105 mg to about 350 mg of at least one anti-PCSK9 antibody administered once every 2 weeks (Q2W). In some embodiments, the dose is about 140 mg to about 280 mg of at least one anti-PCSK9 antibody administered once every 2 weeks (Q2W). In some embodiments, the dose is about 250 mg to about 480 mg of at least one anti-PCSK9 antibody administered once every 4 weeks (Q4W). In some embodiments, the dose is about 280 mg to about 420 mg of at least one anti-PCSK9 antibody administered once every 2 weeks (Q2W). In some embodiments, the dose is about 350 mg to about 420 mg of at least one anti-PCSK9 antibody administered once every 2 weeks (Q4W). In some embodiments, the serum LDL cholesterol level is reduced by at least about 30%. In some embodiments, the serum LDL cholesterol level is reduced by at least about 35%. In some embodiments, the serum LDL cholesterol level is reduced by at least about 40%. In some embodiments, the serum LDL cholesterol level is reduced by at least about 45%. In some embodiments, the serum LDL cholesterol level is reduced by at least about 50%. In some embodiments, the serum LDL cholesterol level is reduced by at least about 55%. In some embodiments, the serum LDL cholesterol level is reduced by at least about 60%. In some embodiments, the serum LDL cholesterol level is reduced by at least about 75%. In some embodiments, the serum LDL cholesterol level is reduced by at least about 70%. In some embodiments, the serum LDL cholesterol level is reduced by at least about 75%. In some embodiments, the serum LDL cholesterol level is reduced by at least about 80%. In some embodiments, the serum LDL cholesterol level is reduced by at least about 85%. %. In some embodiments, the serum LDL cholesterol level is reduced by at least about 90%.

In some aspects, the invention comprises a method of lowering the serum LDL cholesterol level in a patient, the method comprising administering to a patient in need thereof, a dose of at least one anti-PCSK9 antibody, and wherein the dose of anti-PCSK9 antibody is administered on a schedule selected from the group consisting of: (1) at least about 14 mg every week (QW); (2) at least an amount of about 35 mg every week (QW); (3) at least an amount of about 70 mg every other week (Q2W); (4) at least an amount of about 105 mg every two weeks (Q2W); (5) at least an amount of about 140 mg every other week (Q2W); (6) at least an amount of about 280 mg every two weeks (Q2W); and (7) at least an amount of about 280 mg every four weeks (Q4W); (8) at least an amount of about 350 every four weeks (Q4W); (9) at least an amount of about 420 mg every four weeks (Q4W). In some embodiments, the serum LDL cholesterol level is reduced by at least about 30%. In some embodiments, the serum LDL cholesterol level is reduced by at least about 35%. In some embodiments, the serum LDL cholesterol level is reduced by at least about 40%. In some embodiments, the serum LDL cholesterol level is reduced by at least about 45%. In some embodiments, the serum LDL cholesterol level is reduced by at least about 50%. In some embodiments, the serum LDL cholesterol level is reduced by at least about 55%. In some embodiments, the serum LDL cholesterol level is reduced by at least about 60%. In some embodiments, the serum LDL cholesterol level is reduced by at least about 65%. In some embodiments, the serum LDL cholesterol level is reduced by at least about 70%. In some embodiments, the serum LDL cholesterol level is reduced by at least about 75%. In some embodiments, the serum LDL cholesterol level is reduced by at least about 80%. In some embodiments, the serum LDL cholesterol level is reduced by at least about 85%. In some embodiments, the serum LDL cholesterol level is reduced by at least about 90%.

In some aspects, the invention comprises a method of lowering PCSK9 values in a patient, the method comprising administering to a patient in need thereof, a dose of at least one anti-PCSK9 antibody, and wherein the dose of anti-PCSK9 antibody is administered on a schedule selected from the group consisting of: (1) at least about 14 mg every week (QW); (2) at least an amount of about 35 mg every week (QW); (3) at least an amount of about 70 mg every other week (Q2W); (4) at least an amount of about 105 mg every two weeks (Q2W); (5) at least an amount of about 140 mg every other week (Q2W); (6) at least an amount of about 280 mg every other week (Q2W); and (7) at least an amount of about 280 mg every four weeks (Q4W); (8) at least an amount of about 350 every four weeks (Q4W); (9) at least an amount of about 420 mg every four weeks (Q4W). In some embodiments, the serum PCSK9 value is reduced by at least about 60%. In some embodiments, the serum PCSK9 value is reduced by at least about 65%. In some embodiments, the serum PCSK9 value is reduced by at least about 70%. In some embodiments, the serum PCSK9 value is reduced by at least about 75%. In some embodiments, the serum PCSK9 value is reduced by at least about 80%. In some embodiments, the serum PCSK9 value is reduced by at least about 85%. In some embodiments, the serum PCSK9 value is reduced by at least about 90%.

In some aspects, the invention comprises a method of lowering the total cholesterol level in a patient, the method comprising administering to a patient in need thereof, a dose of at least one anti-PCSK9 antibody, and wherein the dose of anti-PCSK9 antibody is administered on a schedule selected from the group consisting of: (1) at least about 14 mg every week (QW); (2) at least an amount of about 35 mg every week (QW); (3) at least an amount of about 70 mg every other week (QW); (4) at least an amount of about 105 mg every other week (QW); (5) at least an amount of about 140 mg every other week (Q2W); (6) at least an amount of about 280 mg every other week (Q2W); and (7) at least an amount of about 280 mg every four weeks (Q4W); (8) at least an amount of about 350 every four weeks (Q4W); (9) at least an amount of about 420 mg every four weeks (Q4W). In some embodiments, the total cholesterol level is reduced by at least about 20%. In some embodiments, the total cholesterol level is reduced by at least about 25%. In some embodiments, the total cholesterol level is reduced by at least about 30%. In some embodiments, the total cholesterol level is reduced by at least about 35%. In some embodiments, the total cholesterol level is reduced by at least about 40%. In some embodiments, the total cholesterol level is reduced by at least about 45%. In some embodiments, the total cholesterol level is reduced by at least about 50%. In some embodiments, the total cholesterol level is reduced by at least about 55%. In some embodiments, the total cholesterol level is reduced by at least about 60%.

In some aspects, the invention comprises a method of lowering the non-HDL cholesterol level in a patient, the method comprising administering to a patient in need thereof, a dose of at least one anti-PCSK9 antibody, and wherein the dose of anti-PCSK9 antibody is administered on a schedule selected from the group consisting of: (1) at least about 14 mg every week (QW); (2) at least an amount of about 35 mg every week (QW); (3) at least an amount of about 70 mg every other week (QW); (4) at least an amount of about 105 mg every other week (QW); (5) at least an amount of about 140 mg every other week (Q2W); (6) at least an amount of about 280 mg every other week (Q2W); and (7) at least an amount of about 280 mg every four weeks (Q4W); (8) at least an amount of about 350 every four weeks (Q4W); (9) at least an amount of about 420 mg every four weeks (Q4W). In some embodiments, the non-HDL cholesterol level is reduced by at least about 30%. In some embodiments, the non-HDL cholesterol level is reduced by at least about 35%. In some embodiments, the non-HDL cholesterol level is reduced by at least about 40%. In some embodiments, the non-HDL cholesterol level is reduced by at least about 45%. In some embodiments, the non-HDL cholesterol level is reduced by at least about 50%. In some embodiments, the non-HDL cholesterol level is reduced by at least about 55%. In some embodiments, the non-HDL cholesterol level is reduced by at least about 60%. In some embodiments, the non-HDL cholesterol level is reduced by at least about 65%. In some embodiments, the non-HDL cholesterol level is reduced by at least about 70%. In some embodiments, the non-HDL cholesterol level is reduced by at least about 75%. In some embodiments, the non-HDL cholesterol level is reduced by at least about 80%. In some embodiments, the non-HDL cholesterol level is reduced by at least about 85%.

In some aspects, the invention comprises a method of lowering ApoB levels in a patient, the method comprising administering to a patient in need thereof, a dose of at least one anti-PCSK9 antibody, and wherein the dose of anti-PCSK9 antibody is administered on a schedule selected from the group consisting of: (1) at least about 14 mg every week (QW); (2) at least an amount of about 35 mg every week (QW); (3) at least an amount of about 70 mg every other week (QW); (4) at least an amount of about 105 mg every other week (QW); (5) at least an amount of about 140 mg every other week (Q2W); (6) at least an amount of about 280 mg every other week (Q2W); and (7) at least an amount of about 280 mg every four weeks (Q4W); (8) at least an amount of about 350 every four weeks (Q4W); (9) at least an amount of about 420 mg every four weeks (Q4W). In some embodiments, the ApoB level is reduced by at least about 20%. In some embodiments, the ApoB level is reduced by at least about 25%. In some embodiments, the ApoB level is reduced by at least about 30%. In some embodiments, the ApoB level is reduced by at least about 35%. In some embodiments, the ApoB level is reduced by at least about 40%. In some embodiments, the ApoB level is reduced by at least about 45%. In some embodiments, the ApoB level is reduced by at least about 50%. In some embodiments, the ApoB level is reduced by at least about 55%. In some embodiments, the ApoB level is reduced by at least about 60%. In some embodiments, the ApoB level is reduced by at least about 65%. In some embodiments, the ApoB level is reduced by at least about 70%. In some embodiments, the ApoB level is reduced by at least about 75%.

In some aspects, the invention comprises a method of lowering Lipoprotein A ("Lp(a)") levels in a patient, the method comprising administering to a patient in need thereof, a dose of at least one anti-PCSK9 antibody, and wherein the dose of anti-PCSK9 antibody is administered on a schedule selected from the group consisting of: (1) at least about 14 mg every week (QW); (2) at least an amount of about 35 mg every week (QW); (3) at least an amount of about 70 mg every other week (QW); (4) at least an amount of about 105 mg every other week (QW); (5) at least an amount of about 140 mg every other week (Q2W); (6) at least an amount of about 280 mg every other week (Q2W); and (7) at least an amount of about 280 mg every four weeks (Q4W); (8) at least an amount of about 350 every four weeks (Q4W); (9) at least an amount of about 420 mg every four weeks (Q4W). In some embodiments, the Lp(a) level is reduced by at least about 10%. In some embodiments, the Lp(a) level is reduced by at least about 15%. In some embodiments, the Lp(a) level is reduced by at least about 20%. In some embodiments, the Lp(a) level is reduced by at least about 25%. In some embodiments, the Lp(a) level is reduced by at least about 30%. In some embodiments, the Lp(a) level is reduced by at least about 35%. In some embodiments, the Lp(a) level is reduced by at least about 40%. In some embodiments, the Lp(a) level is reduced by at least about 45%. In some embodiments, the Lp(a) level is reduced by at least about 50%. In some embodiments, the Lp(a) level is reduced by at least about 55%. In some embodiments, the Lp(a) level is reduced by at least about 60%. In some embodiments, the Lp(a) level is reduced by at least about 65%.

In some aspects, the invention comprises a method for treating or preventing a cholesterol related disorder in a patient, the method comprising administering to a patient in need thereof a dose of about 10 mg to about 480 mg of at least one anti-PCSK9 antibody described herein. In some embodiments, the dose is about 10 mg to about 70 mg of at least one anti-PCSK9 antibody administered once weekly (QW). In some embodiments, the dose is about 14 mg to about 35 mg of at least one anti-PCSK9 antibody administered once weekly. In some embodiments, the dose is about 70 mg to about 420 mg of at least one anti-PCSK9 antibody administered once every 2 weeks (Q2W). In some embodiments, the dose is about 70 mg to about 350 mg of at least one anti-PCSK9 antibody administered once every 2 weeks (Q2W). In some embodiments, the dose is about 105 mg to about 350 mg of at least one anti-PCSK9 antibody administered once every 2 weeks (Q2W). In some embodiments, the dose is about 140 mg to about 280 mg of at least one anti-PCSK9 antibody administered once every 2 weeks (Q2W). In some embodiments, the dose is about 250 mg to about 480 mg of at least one anti-PCSK9 antibody administered once every 4 weeks (Q4W). In some embodiments, the dose is about 280 mg to about 420 mg of at least one anti-PCSK9 antibody administered once every 2 weeks (Q2W). In some embodiments, the dose is about 350 mg to about 420 mg of at least one anti-PCSK9 antibody administered once every 2 weeks (Q4W). In some embodiments, the serum LDL cholesterol level is reduced by at least about 30%. In some embodiments, the serum LDL cholesterol level is reduced by at least about 35%. In some embodiments, the serum LDL cholesterol level is reduced by at least about 40%. In some embodiments, the serum LDL cholesterol level is reduced by at least about 45%. In some embodiments, the serum LDL cholesterol level is reduced by at least about 50%. In some embodiments, the serum LDL cholesterol level is reduced by at least about 55%. In some embodiments, the serum LDL cholesterol level is reduced by at least about 60%. In some embodiments, the serum LDL cholesterol level is reduced by at least about 65%. In some embodiments, the serum LDL cholesterol level is reduced by at least about 70%. In some embodiments, the serum LDL cholesterol level is reduced by at least about 75%. In some embodiments, the serum LDL cholesterol level is reduced by at least about 80%. In some embodiments, the serum LDL cholesterol level is reduced by at least about 85%. In some embodiments, the serum LDL cholesterol level is reduced by at least about 90%. In some embodiments, the cholesterol related disorder is hypercholesterolemia, hyperlipidemia or dyslipidemia.

In some aspects, the invention comprises a method of treating or preventing a cholesterol related disorder in a patient, the method comprising administering to a patient in need thereof, a dose of at least one anti-PCSK9 antibody, and wherein the dose of anti-PCSK9 antibody is administered on a schedule selected from the group consisting of: (1) at least about 14 mg every week (QW); (2) at least an amount of about 35 mg every week (QW); (3) at least an amount of about 70 mg every other week (QW); (4) at least an amount of about 105 mg every other week (QW); (5) at least an amount of about 140 mg every other week (Q2W); (6) at least an amount of about 280 mg every other week (Q2W); and (7) at least an amount of about 280 mg every four weeks (Q4W); (8) at least an amount of about 350 every four weeks (Q4W); (9) at least an amount of about 420 mg every four weeks (Q4W). In some embodiments, the serum LDL cholesterol level is reduced by at least about 30%. In some embodiments, the serum LDL cholesterol level is reduced by at least about 35%. In some embodiments, the serum LDL cholesterol level is reduced by at least about 40%. In some embodiments, the serum LDL cholesterol level is reduced by at least about 45%. In some embodiments, the serum LDL cholesterol level is reduced by at least about 50%. In some embodiments, the serum LDL cholesterol level is reduced by at least about 55%. In some embodiments, the serum LDL cholesterol level is reduced by at least about 60%. In some embodiments, the serum LDL cholesterol level is reduced by at least about 65%. In some embodiments, the serum LDL cholesterol level is reduced by at least about 70%. In some embodiments, the serum LDL cholesterol level is reduced by at least about 75%. In some embodiments, the serum LDL cholesterol level is reduced by at least about 80%. In some embodiments, the serum LDL cholesterol level is reduced by at least about 85%. In some embodiments, the serum LDL cholesterol level is reduced by at least about 90%.

In some embodiments, the anti-PCSK9 antibody is 21B12, 26H5, 31H4, 8A3, 11F1 and/or 8A1.

In some embodiments, the cholesterol related disorder is hypercholesterolemia, hyperlipidemia or dyslipidemia.

In some aspects, the invention comprises pharmaceutical formulations comprising at least one anti-PCSK9 antibody selected from the group consisting of 21B12, 26H5, 31H4, 8A3, 11F1 and 8A1.

Other embodiments of this invention will be readily apparent from the disclosure provided herewith.

BRIEF DESCRIPTION OF THE FIGURES

FIG. 1A depicts an amino acid sequence of the mature form of the PCSK9 with the pro-domain underlined.

FIGS. 1B$_1$-1B$_4$ depict amino acid and nucleic acid sequences of PCSK9 with the pro-domain underlined and the signal sequence in bold.

FIGS. 2A-2D are sequence comparison tables of various light chains of various antigen binding proteins. FIG. 2C continues the sequence started in FIG. 2A. FIG. 2D continues the sequence started on FIG. 2B.

FIGS. 3A-3D are sequence comparison tables of various heavy chains of various antigen binding proteins. FIG. 3C continues the sequence started in FIG. 3A. FIG. 3D continues the sequence started on FIG. 3B.

FIGS. 3E-3JJ depict the amino acid and nucleic acid sequences for the variable domains of some embodiments of the antigen binding proteins.

FIG. 3KK depicts the amino acid sequences for various constant domains.

FIGS. 3LL-3BBB depict the amino acid and nucleic acid sequences for the variable domains of some embodiments of the antigen binding proteins.

FIGS. 3CCC-3JJJ are sequence comparison tables of various heavy and light chains of some embodiments of the antigen binding proteins.

9

Figure 13A:
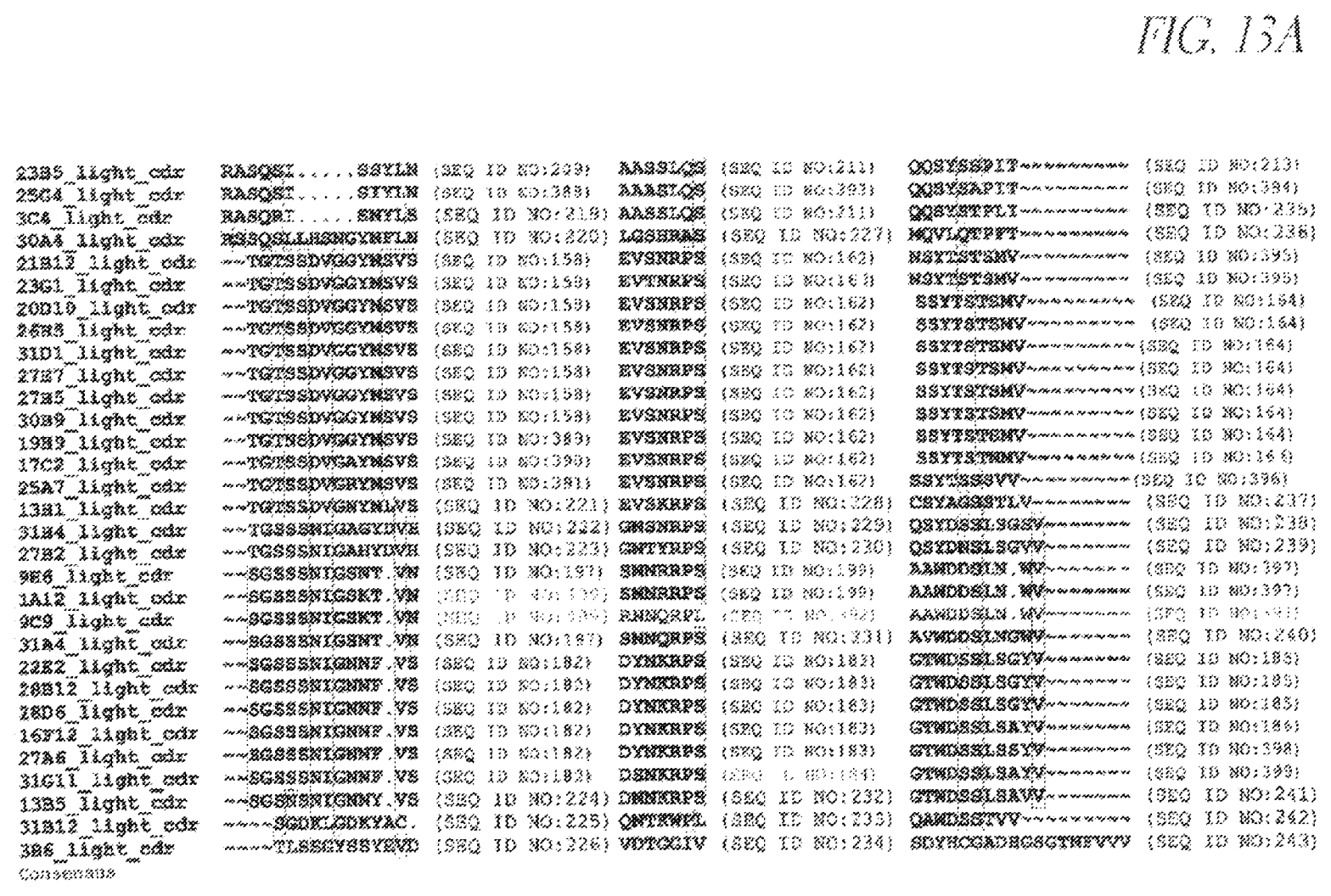
Figure 13B:
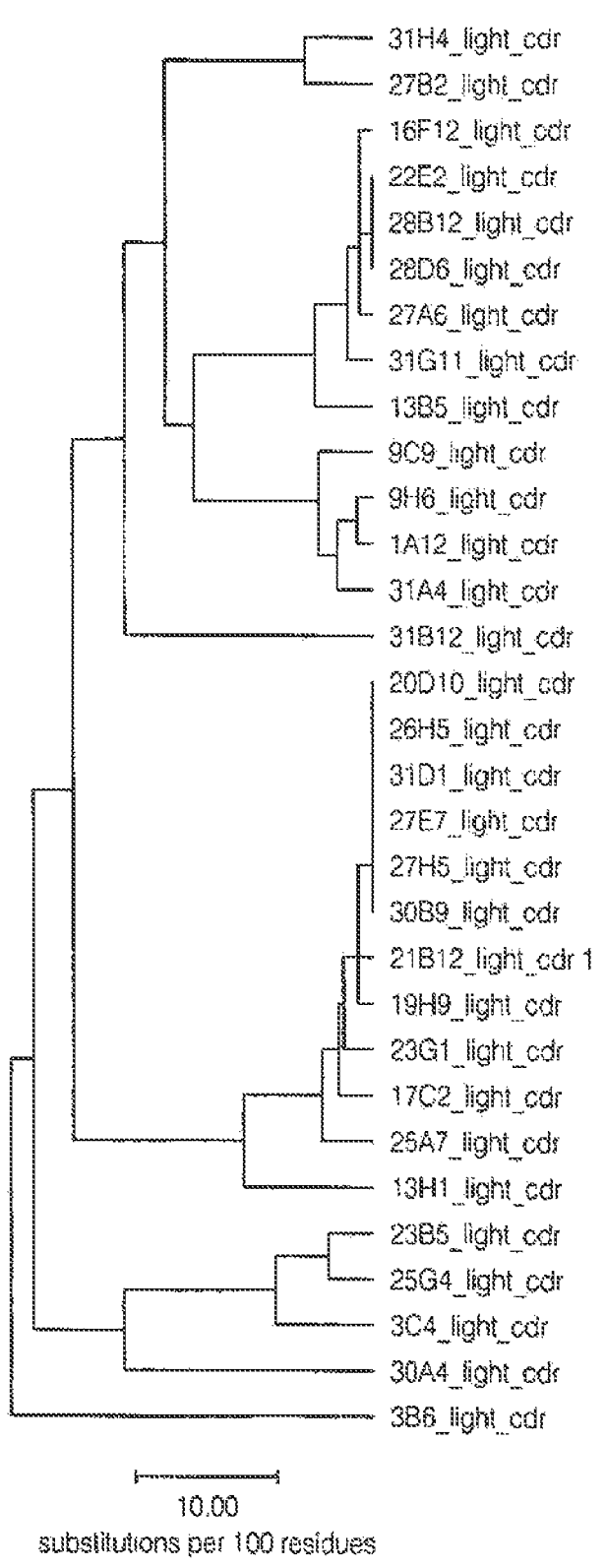
FIG. 13B depicts a light chain cladogram for various ABPs to PCSK9.
Figure 13D:
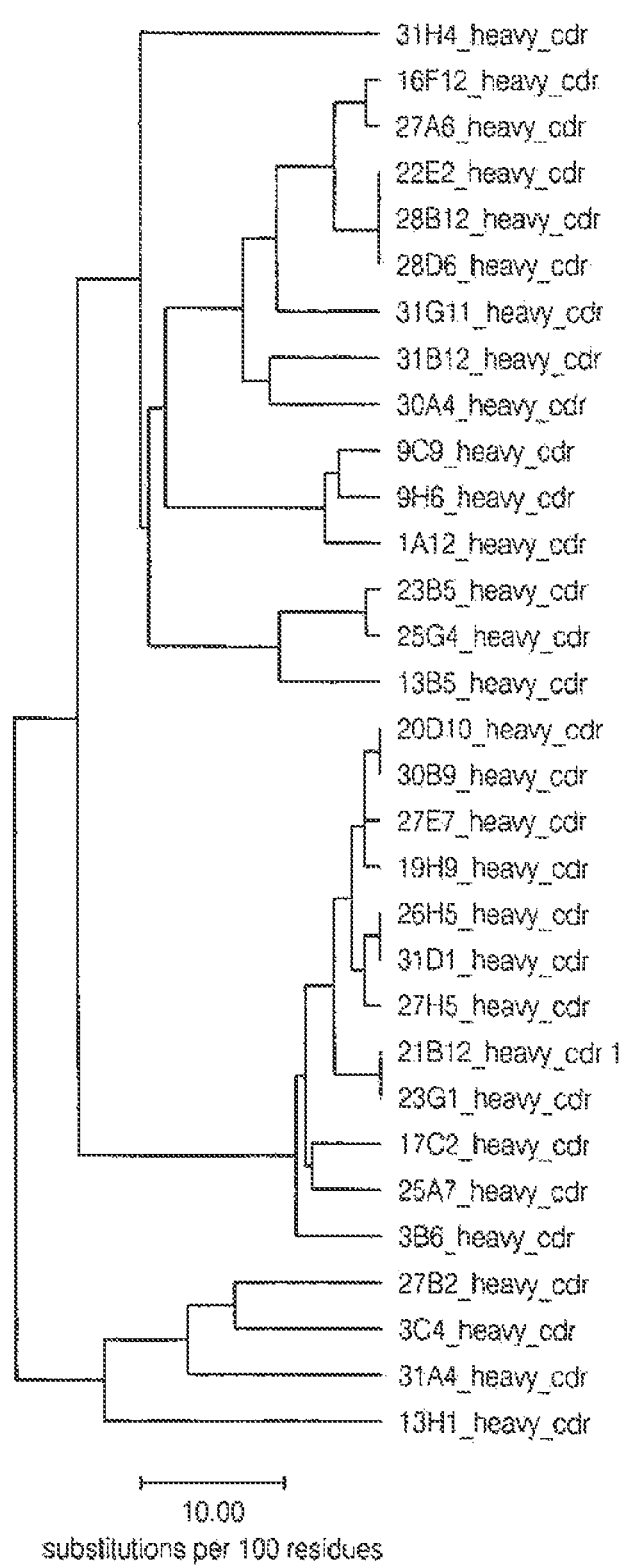
FIG. 13D depicts a heavy chain dendrogram for various ABPs to PCSK9.
Figure 13E:
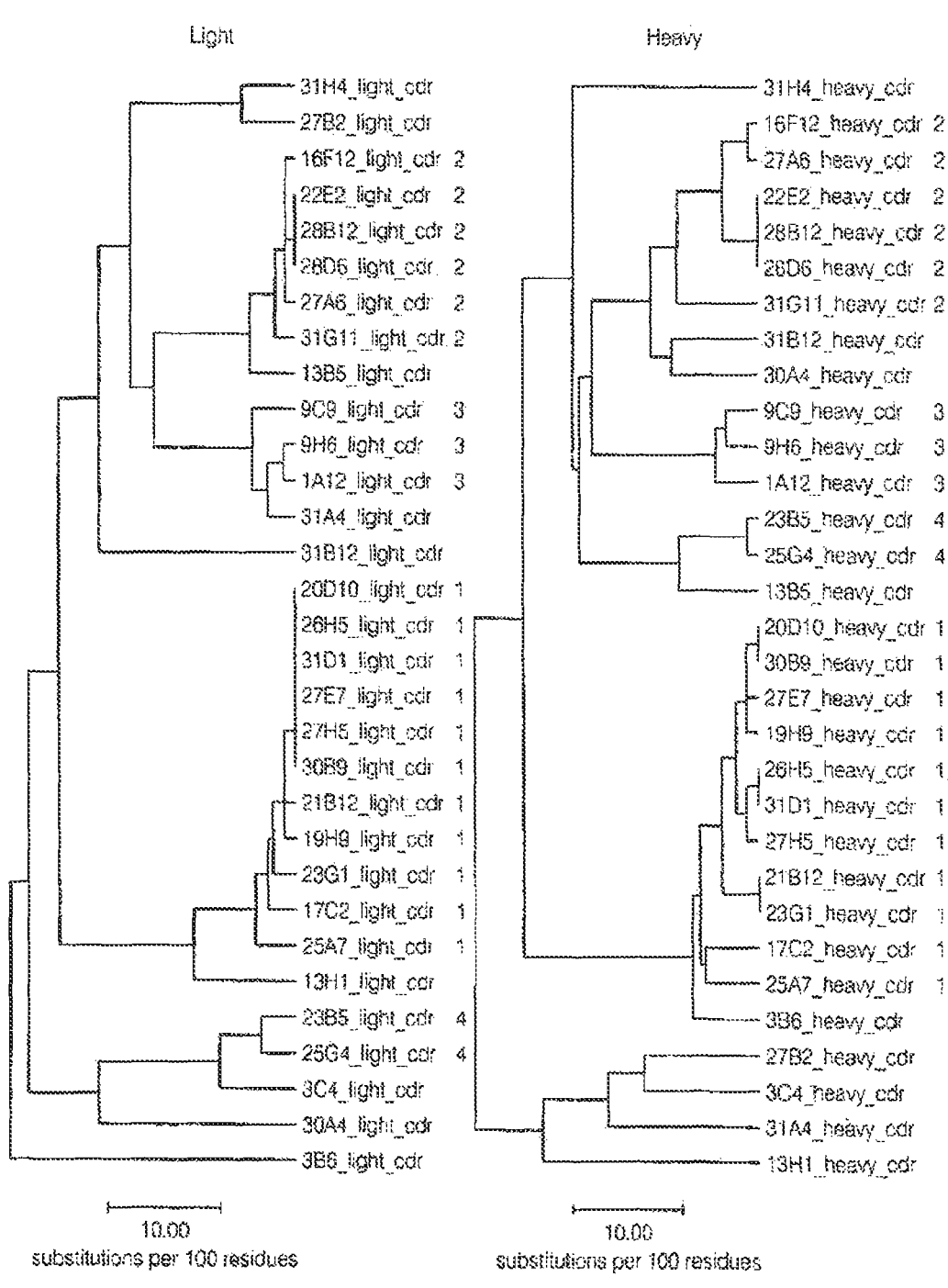
FIG. 13A depicts the various light chain amino acid sequences of various ABPs to PCSK9. The dots (.) indicate no amino acid.
FIG. 13C depicts the various heavy chain amino acid sequences of various ABPs to PCSK9. The dots (.) indicate no amino acid.

FIG. 13E depicts a comparison of light and heavy CDRs and designation of groups from which to derive consensus.

Figure 13F:
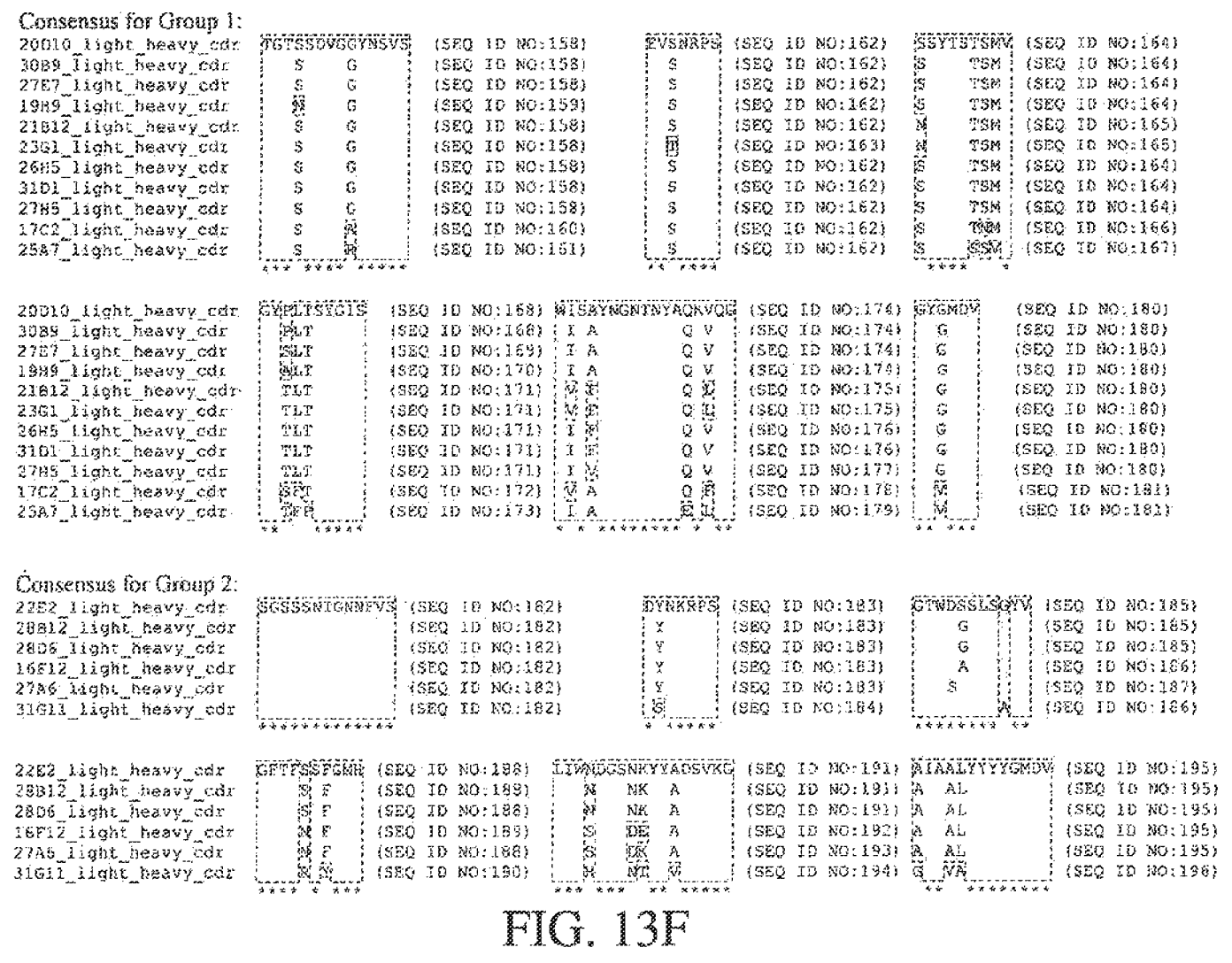

FIG. 13F depicts the consensus sequences for Groups 1 and 2.

Figure 13G:
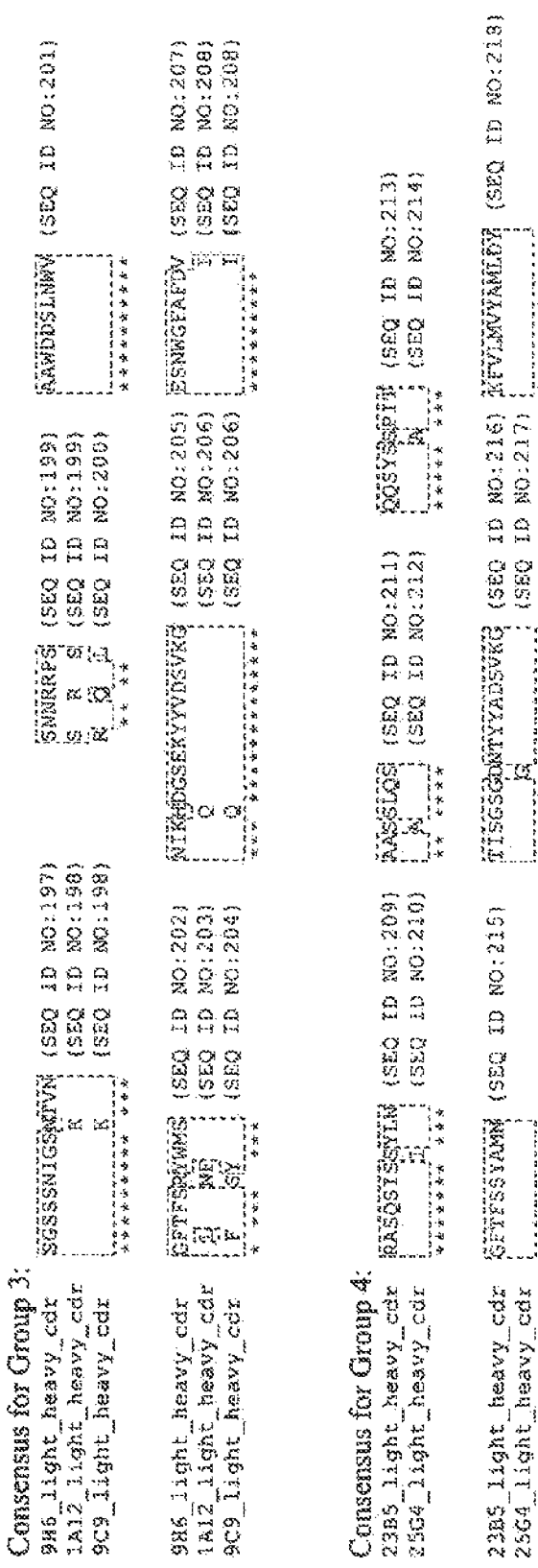

FIG. 13G depicts the consensus sequences for Groups 3 and 4.

FIG. 13H depicts the consensus sequences for Groups 1 and 2. The dots (.) indicated identical residues.

FIG. 13I depicts the consensus sequences for Group 2. The dots (.) indicated identical residues.

FIG. 13J depicts the consensus sequences for Groups 3 and 4. The dots (.) indicated identical residues.

Figure 14:

FIG. 14 is a graph showing the reduction of LDL-c levels in patients receiving multiple-doses of an anti-PCSK9 antibody (21B12).

Figure 15:
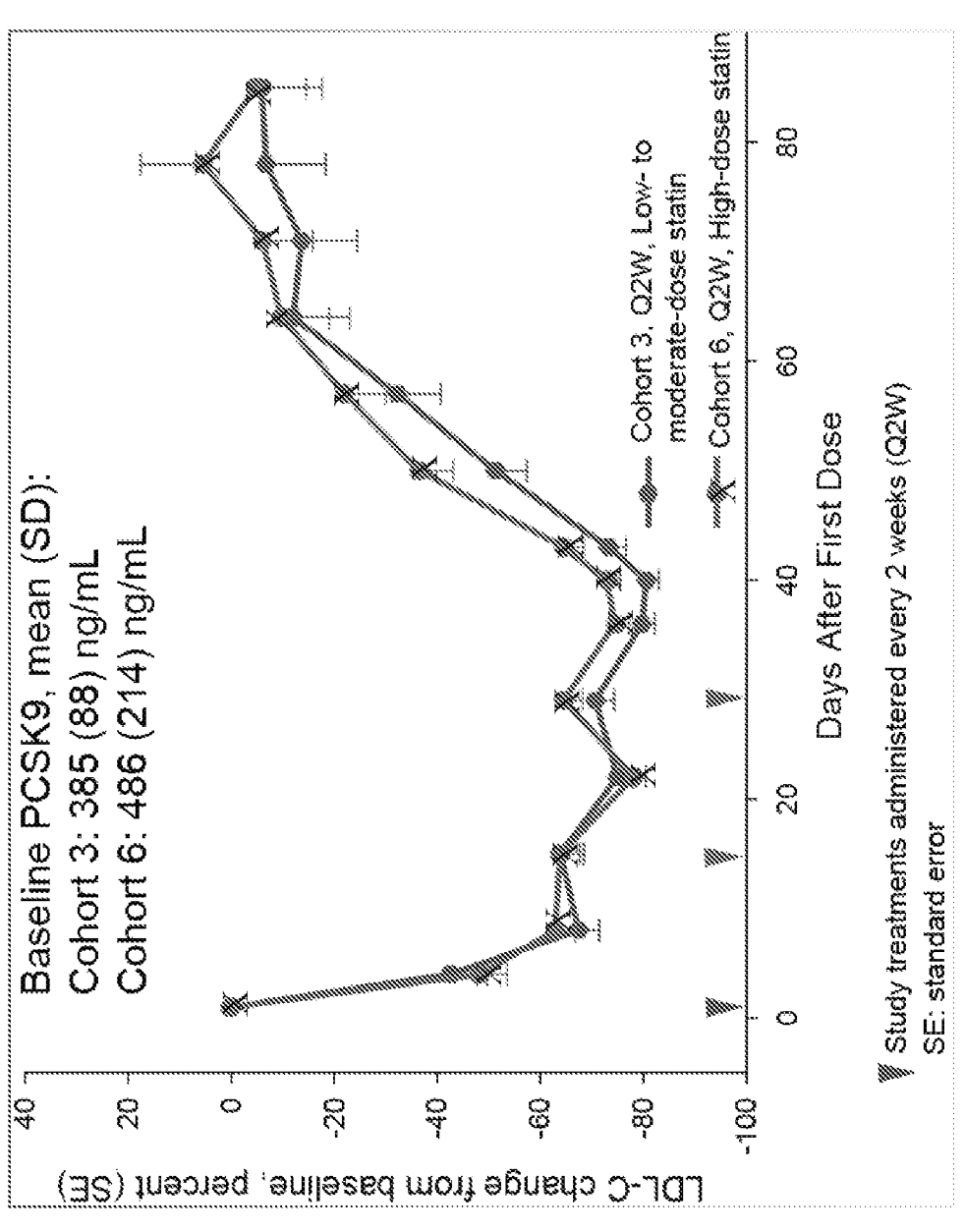

FIG. 15 is a graph showing the reduction of LDL-c levels in patients on low to moderate and high-dose statins receiving multiple-doses of an anti-PCSK9 antibody (21B12).

Figure 16:
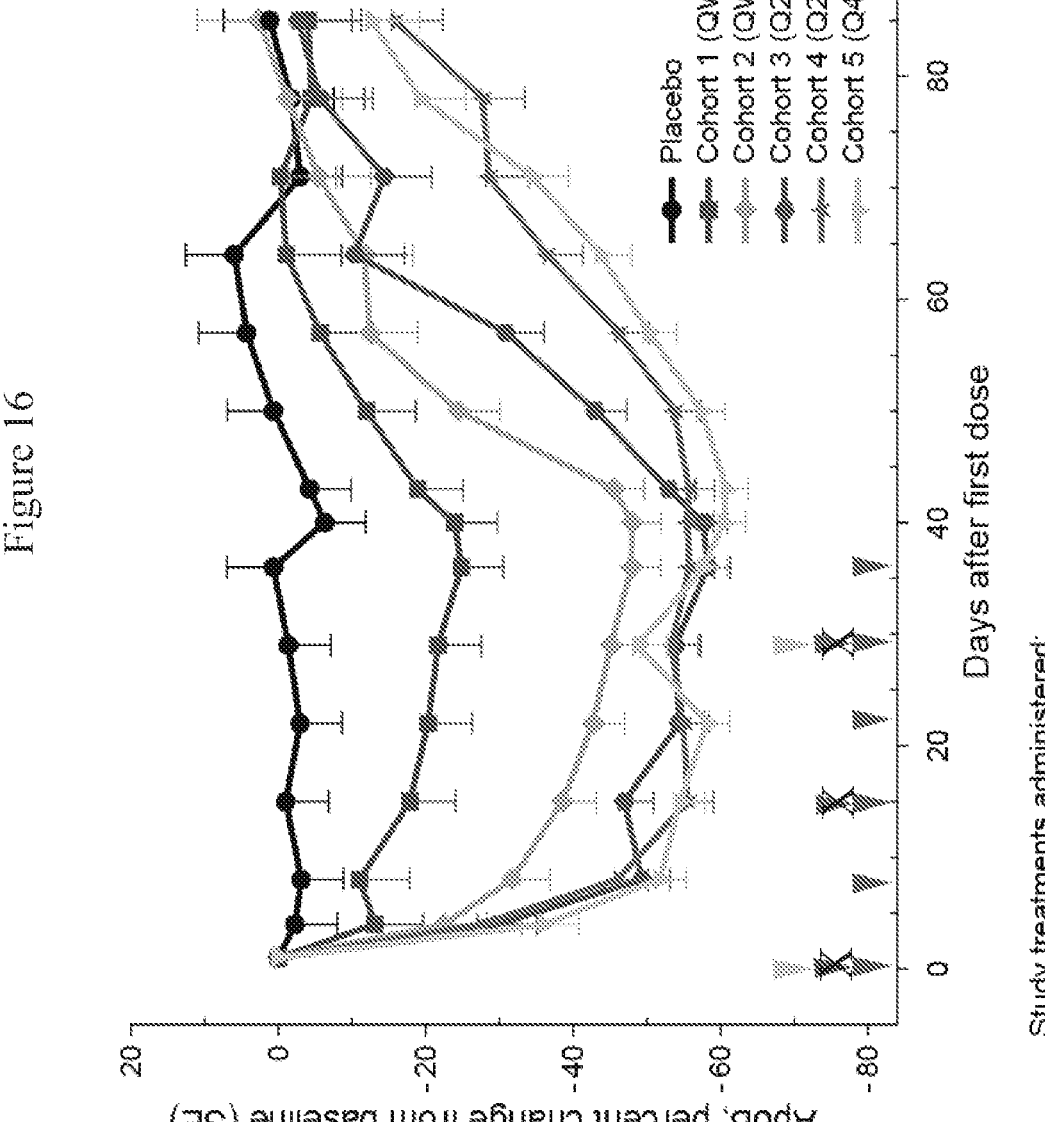

FIG. 16 is a graph showing the reduction of ApoB levels in patients receiving multiple-doses of an anti-PCSK9 antibody (21B12).

Figure 17:
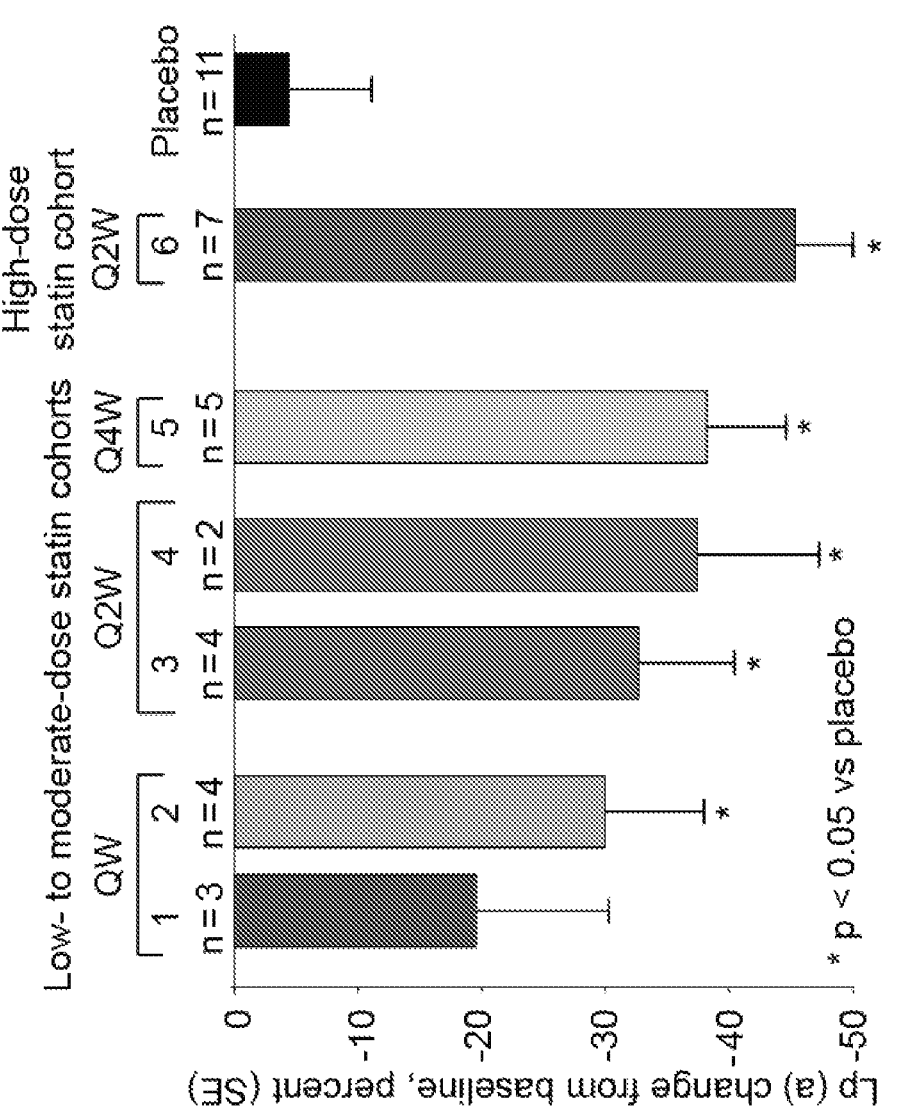

FIG. 17 is a bar graph showing the reduction of lipoprotein a ("Lp(a)") levels in patients on low to moderate and high-dose statins receiving multiple-doses of an anti-PCSK9 antibody (21B12).

FIG. 18 is a graph showing the reduction of LDL-c levels in patients having heterozygous familial hypercholesterolemia ("HeFH") receiving multiple-doses of an anti-PCSK9 antibody (21B12).

Figure 19:

FIG. 19 is a graph showing the reduction of PCSK9 levels in patients having heterozygous familial hypercholesterolemia ("HeFH") receiving multiple-doses of an anti-PCSK9 antibody (21B12).

Figure 20:

FIG. 20 is a graph showing the reduction of total cholesterol levels in patients having heterozygous familial hypercholesterolemia ("HeFH") receiving multiple-doses of an anti-PCSK9 antibody (21B12).

Figure 21:
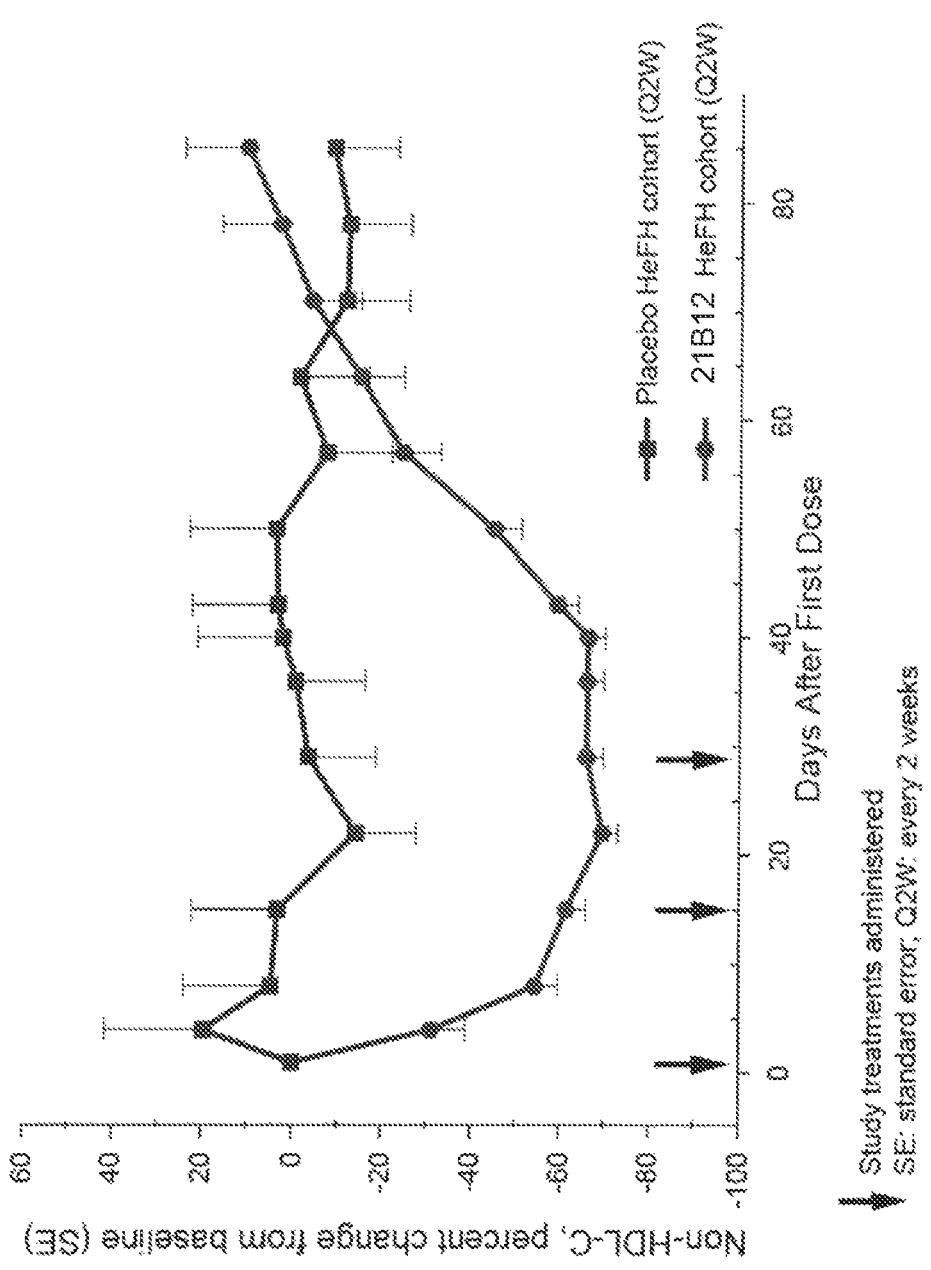

FIG. 21 is a graph showing the reduction of non-HDL cholesterol levels in patients having heterozygous familial hypercholesterolemia ("HeFH") receiving multiple-doses of an anti-PCSK9 antibody (21B12).

Figure 22:
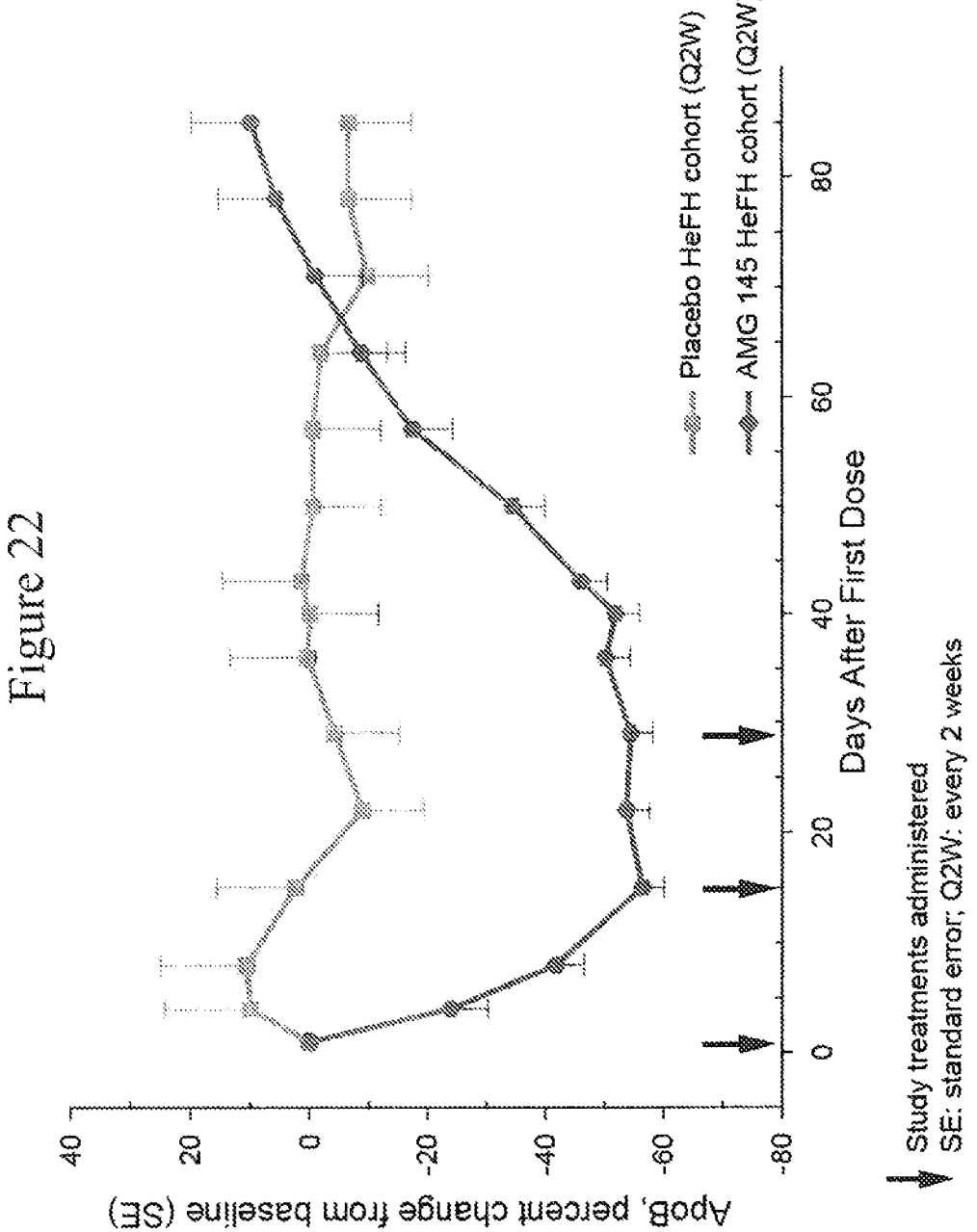

FIG. 22 is a graph showing the reduction of ApoB levels in patients having heterozygous familial hypercholesterolemia ("HeFH") receiving multiple-doses of an anti-PCSK9 antibody (21B12).

Figure 23:
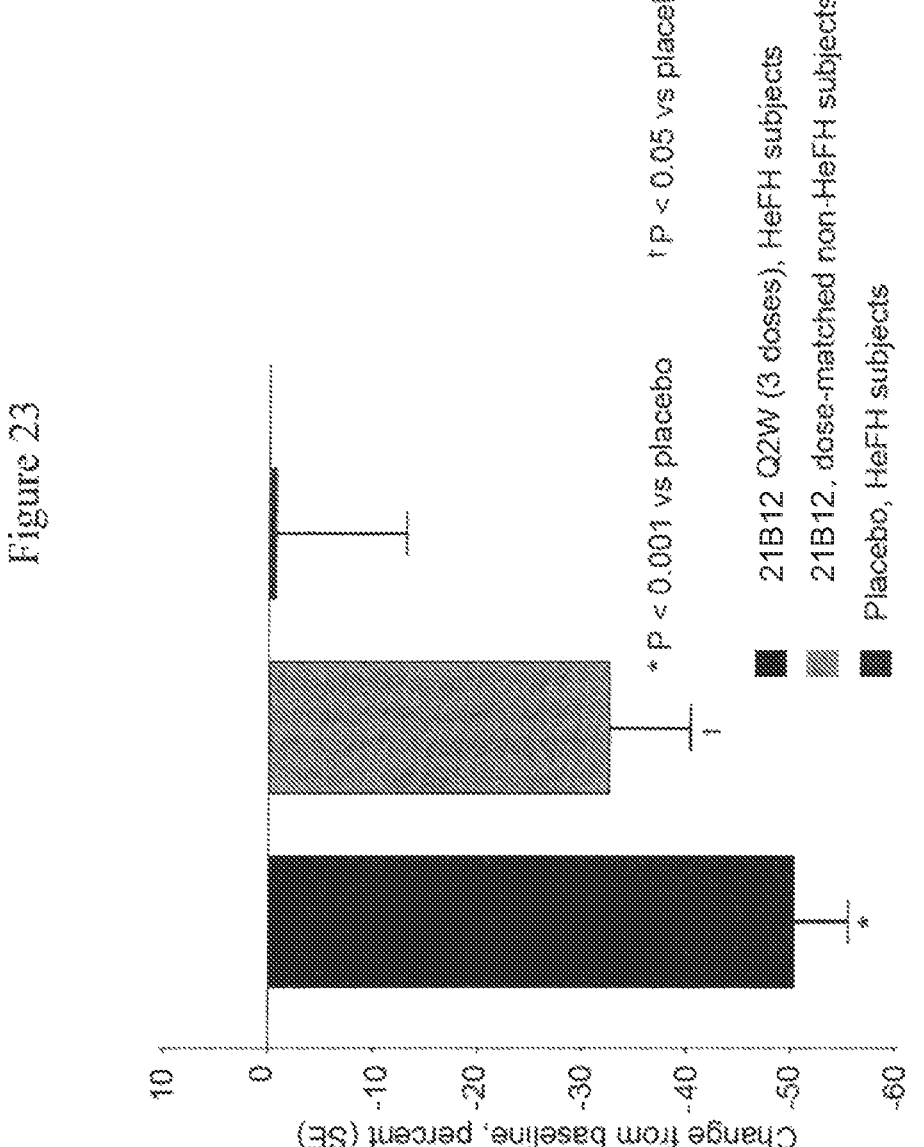

FIG. 23 is a bar graph showing the reduction of lipoprotein a ("Lp(a)") in patients having heterozygous familial hypercholesterolemia ("HeFH") receiving multiple-doses of an anti-PCSK9 antibody (21B12).

Figures 24A, 24B:
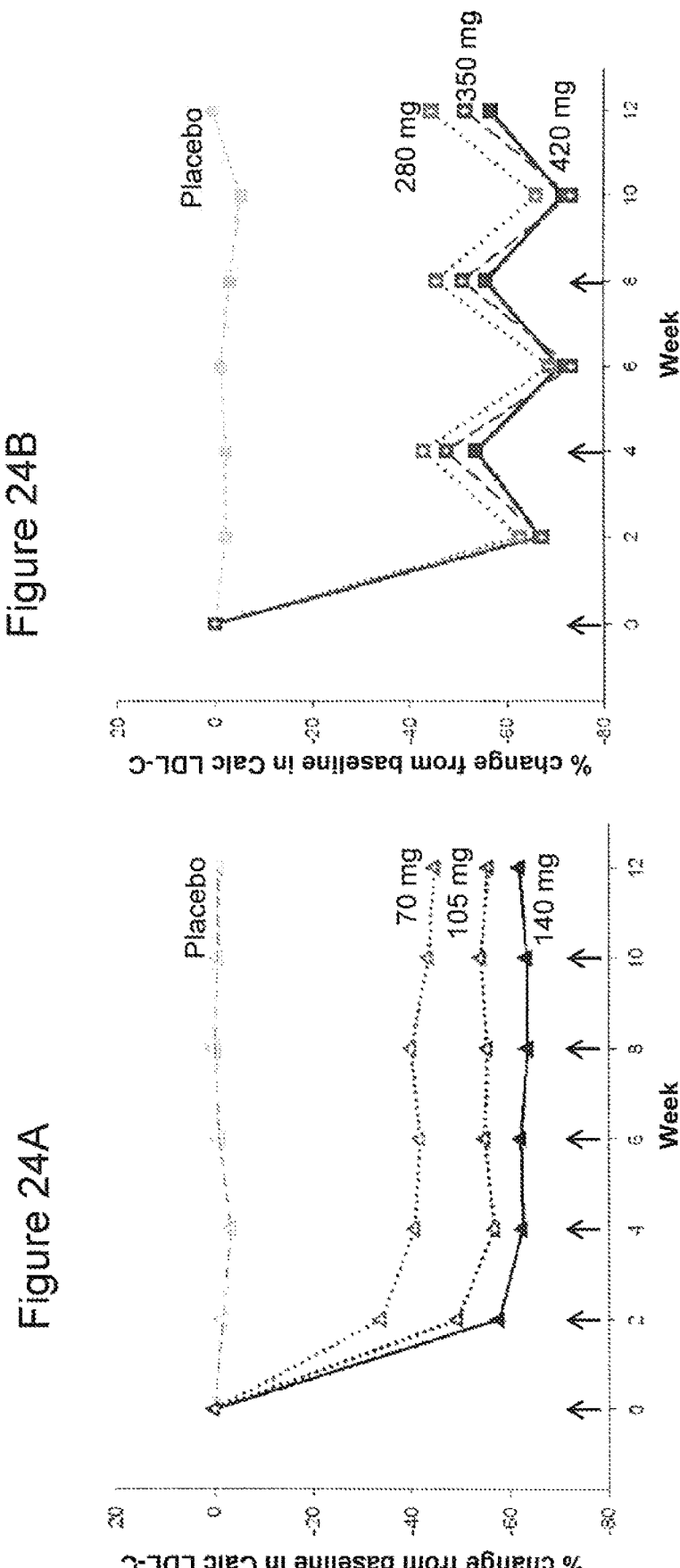

FIG. 24A is a graph showing the aggregate data relating to LDL-C reduction in patients from four studies described in Examples 22-25 who received various doses of an anti-PCSK9 antibody (21B12) every other week (Q2W) over a 12 week period.

FIG. 24B is a graph showing the aggregate data relating to LDL-C reduction in patients from four studies described in Examples 22-25 who received various doses of an anti-PCSK9 antibody (21B12) every four weeks (Q4W) over a 12 week period.

FIG. 25A is a bar graph showing the aggregate data relating to Lp(a) reduction in patients from four studies described in Examples 22-25 who received various doses of an anti-PCSK9 antibody (21B12) either every other week (Q2W) or every 4 weeks (Q4W) over a 12 week period.

FIG. 25B is a bar graph showing the aggregate data relating to HDL-C reduction in patients from four studies described in Examples 22-25 who received various doses of an anti-PCSK9 antibody (21B12) either every other week (Q2W) or every 4 weeks (Q4W) over a 12 week period.

Figure 25D:
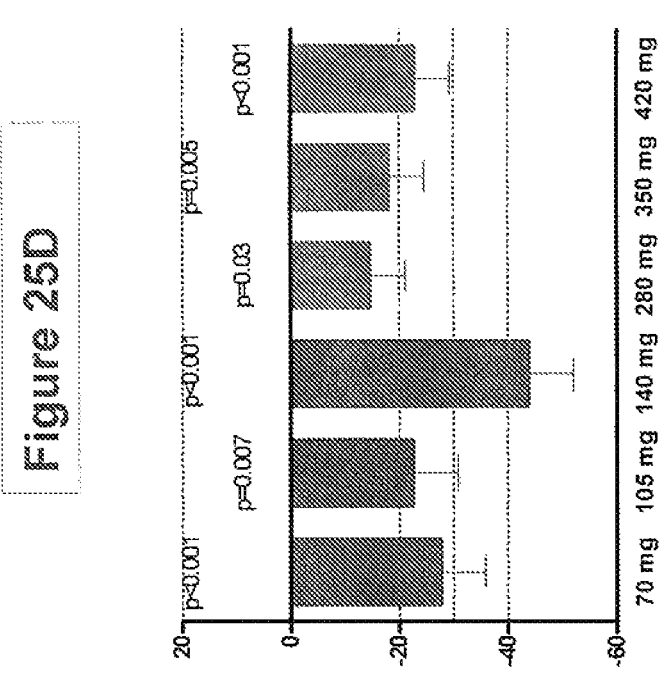
Figure 25C:
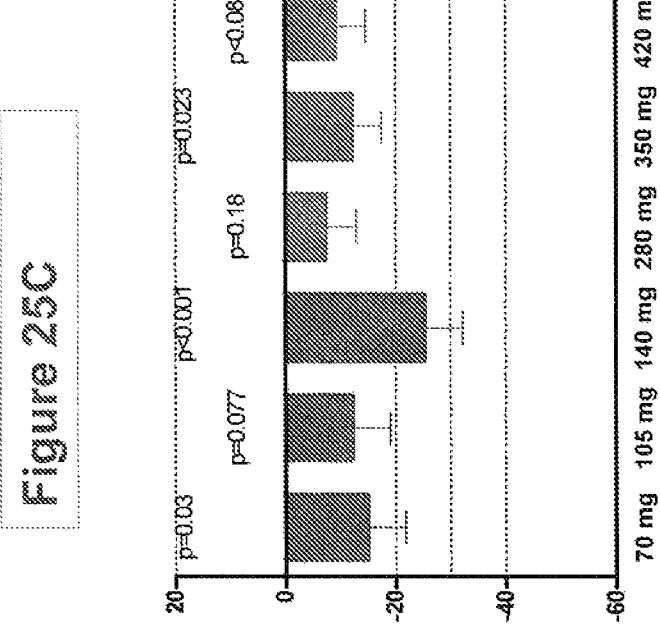

FIG. 25C is a bar graph showing the aggregate data relating to triglyceride reduction in patients from four studies described in Examples 22-25 who received various doses of an anti-PCSK9 antibody (21B12) either every other week (Q2W) or every 4 weeks (Q4W) over a 12 week period.

FIG. 25D is a bar graph showing the aggregate data relating to VLDL-C reduction in patients from four studies described in Examples 22-25 who received various doses of an anti-PCSK9 antibody (21B12) either every other week (Q2W) or every 4 weeks (Q4W) over a 12 week period.

Figure 26:

FIG. 26 is a bar graph showing the viscosity of anti-PCSK9 antibody (21B12) formulations containing various stabilizers/excipients.

Figure 27:
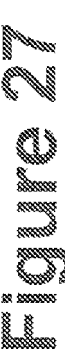

FIG. 27 is a graph showing the stabilizer/excipient, proline, has the ability to lower viscosity of anti-PCSK9 antibody (21B12) formulations having high protein concentrations.

Figure 28A:

FIG. 28A is a graph showing the viscosity of various concentrations of anti-PCSK9 antibody, 21B12, in a formulation comprising 10 mM sodium acetate, and 9% Sucrose pH 5.2 at 25° C. and 40° C.

Figure 28B:

FIG. 28B is a graph showing the viscosity of various concentrations of anti-PCSK9 antibody, 21B12, in a formulation comprising 10 mM sodium acetate, and 9% Sucrose pH 5.2 at 25° C. and 40° C., as compared to a formulation comprising 10 mM sodium acetate, 125 mM arginine, and 3% Sucrose pH 5.0 at 25° C. and 40° C.

Figure 28C:
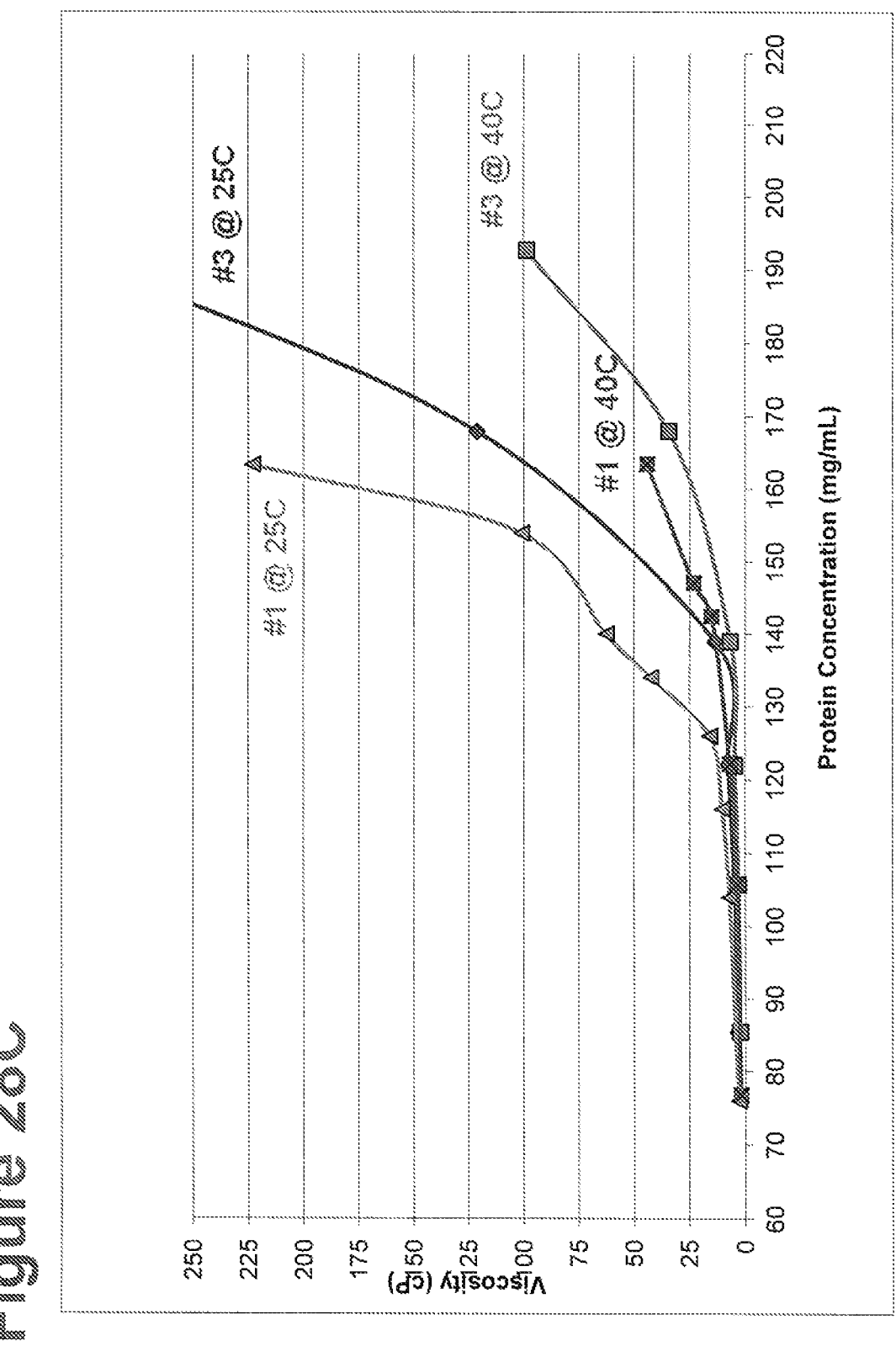

FIG. 28C is a graph showing the viscosity of various concentrations of anti-PCSK9 antibody, 21B12, in a formulation comprising 10 mM sodium acetate, and 9% Sucrose pH 5.2 at 25° C. and 40° C., as compared to a formulation comprising 10 mM sodium acetate, 100 mM methionine, and 4% Sucrose pH 5.0 at 25° C. and 40° C.

Figure 28D:

FIG. 28D is a graph showing the viscosity of various concentrations of anti-PCSK9 antibody, 21B12, in a formulation comprising 10 mM sodium acetate, and 9% Sucrose pH 5.2 at 25° C. and 40° C., as compared to a formulation comprising 10 mM sodium acetate and 250 mM proline, pH 5.0 at 25° C. and 40° C.

Figure 29A:
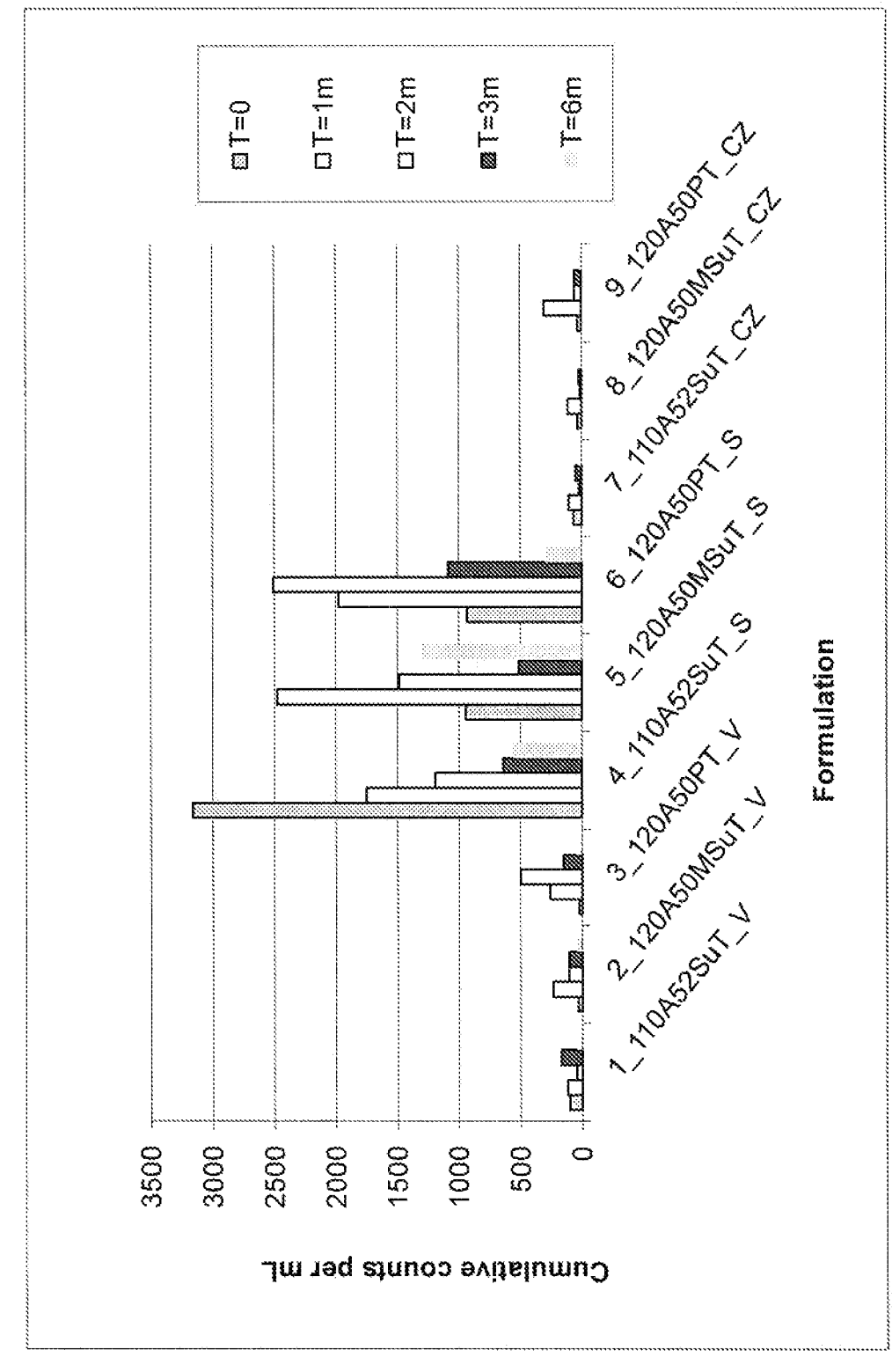

FIG. 29A is a bar graph showing the number of 10 μm particles in various formulations of anti-PCSK9 antibody (i.e., 21B12) formulations over a period of 6 months.

Figure 29B:
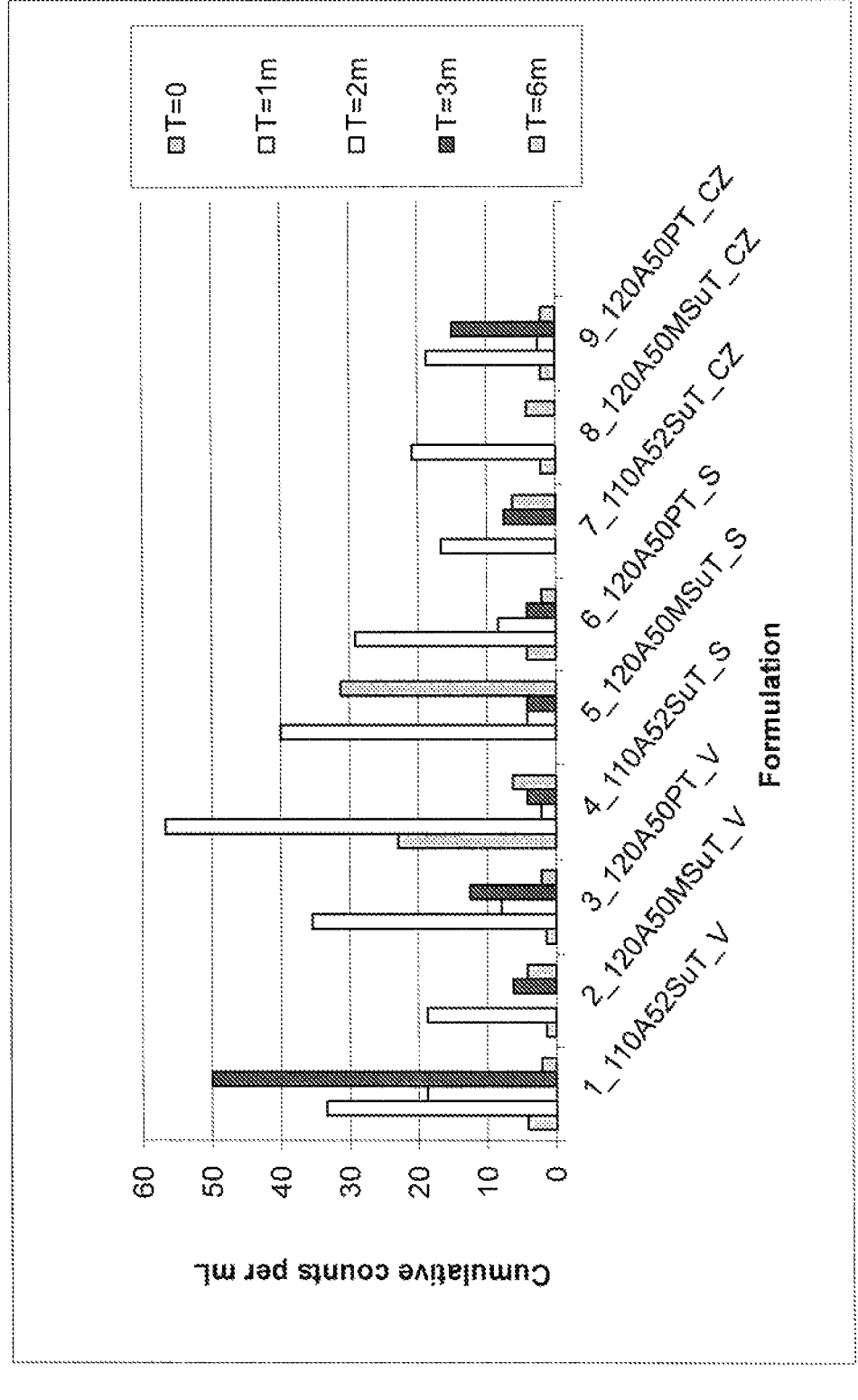

FIG. 29B is a bar graph showing the number of 25 μm particles in various formulations of anti-PCSK9 antibody (i.e., 21B12) formulations over a period of 6 months.

FIG. 30A is a bar graph showing the number of 10 μm particles in various formulations of anti-PCSK9 antibody (i.e., 11F1) formulations over a period of 4 months.

Figure 30B:
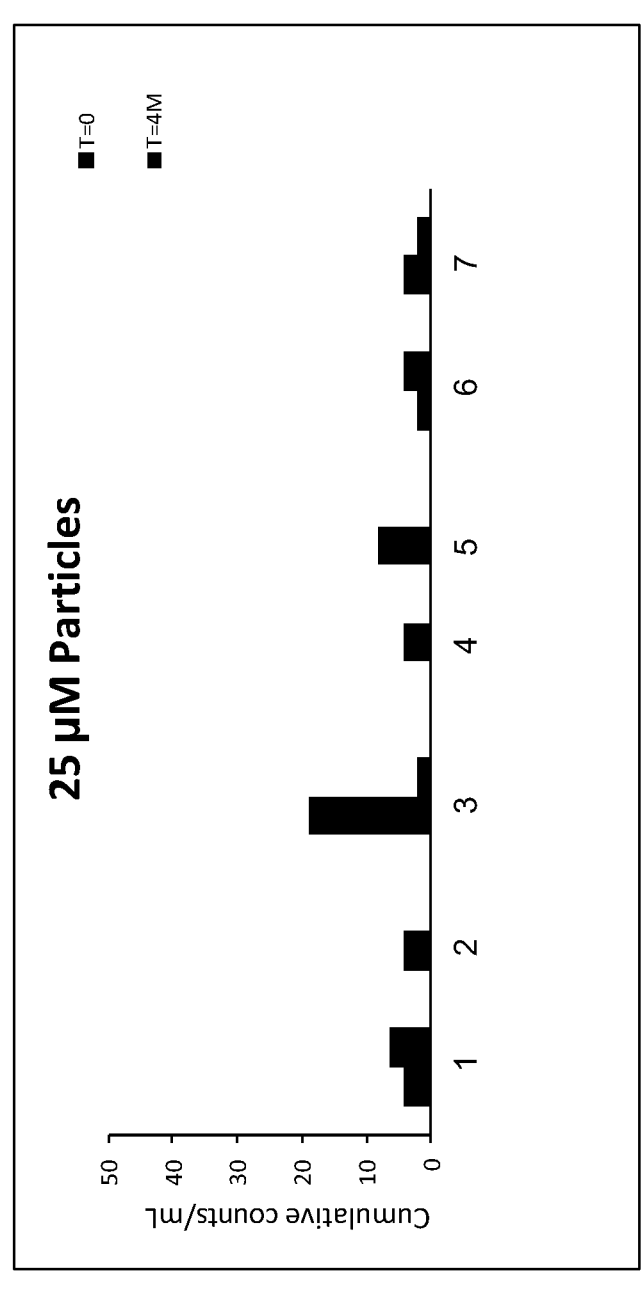

FIG. 30B is a bar graph showing the number of 25 μm particles in various formulations of anti-PCSK9 antibody (i.e., 11F1) formulations over a period of 4 months.

Figure 31:
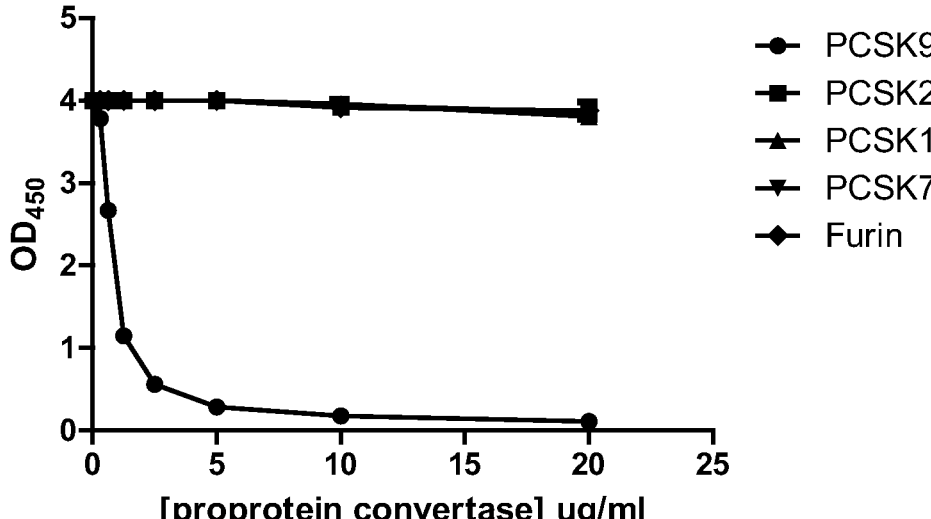

FIG. 31 is a graph illustrating the binding specificity of 11F1 in a competition assay with PCSKP, PCSK2, PCSK1 PCSK7 and Furin with $OD_{450}$ plotted on the vertical axis and concentration of PCSK9 (ug/ml) plotted on the horizontal axis.

Figure 32:
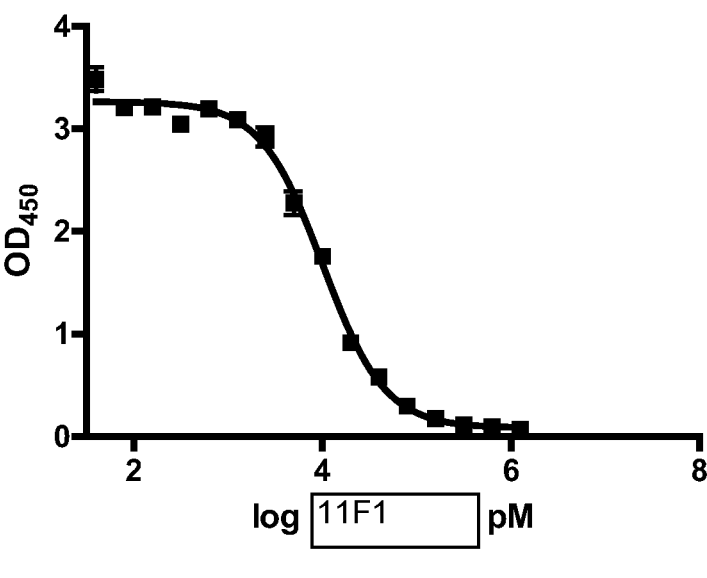

FIG. 32 is a graph showing the dose response curve for inhibition of LDLR:D374Y PCSK9 binding by 11F1 in a competition assay with $OD_{450}$ plotted on the vertical axis and Log [11F1] (pM) plotted on the horizontal axis.

Figure 33:
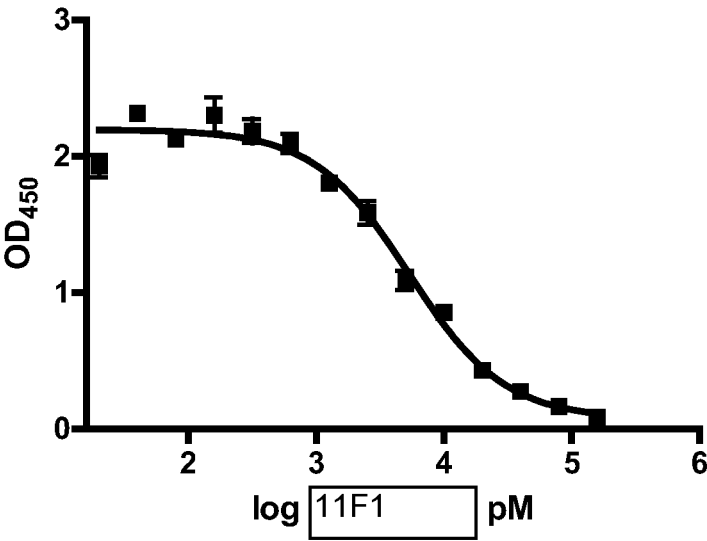

FIG. 33 is a graph depicting the dose response curve for the inhibition of LDLR: WT PCSK9 binding by 11F1 in a competition assay with $OD_{450}$ plotted on the vertical axis and Log [11f1] (pM) plotted on the horizontal axis.

Figure 34:
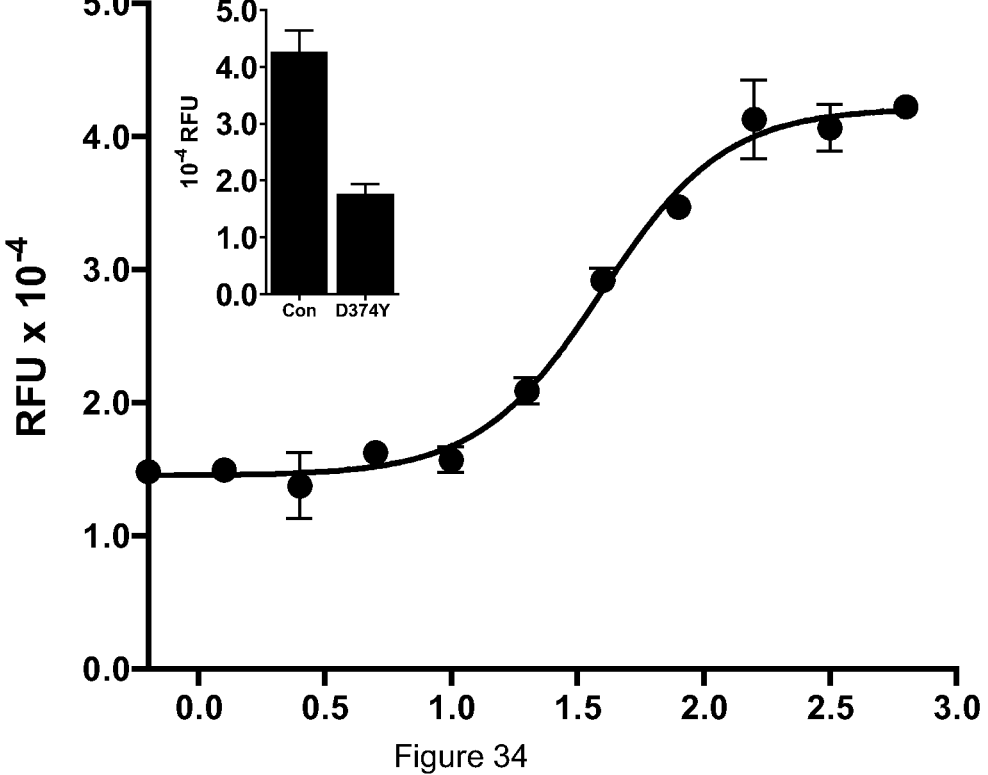

FIG. 34 is a graph depicting the dose response curve for the ability of 11F1 to block human D374Y PCSK9-mediated reduction of LDL uptake in HepG2 cells with relative fluorescence units ($\times 10^4$) plotted on the vertical axis and Log [11F1] (nM) plotted on the horizontal axis.

Figure 35:
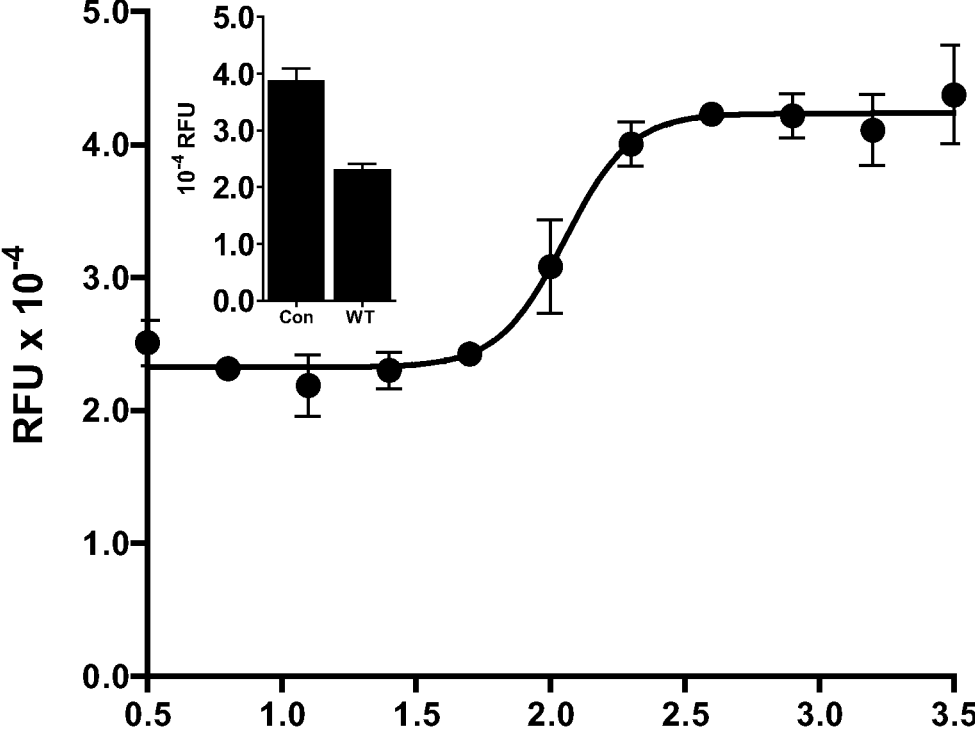

FIG. 35 is a graph depicting the dose response curve for the ability of 11F1 to block human WT PCSK9-mediated reduction of LDL uptake in HepG2 cells with relative fluorescence units plotted ($\times 10^4$) on the vertical axis and Log [11F1] (nM) plotted on the horizontal axis.

Figure 36:
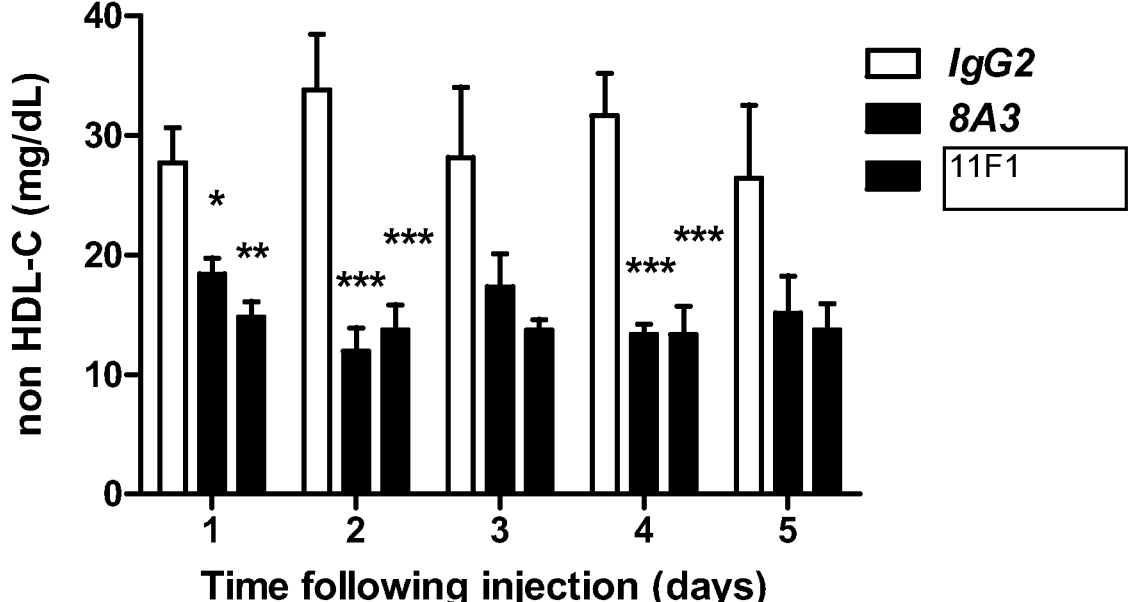

FIG. 36 is a bar graph depicting the effect of 11F1 and 8A3 on serum non-HDL cholesterol in mice expressing human PCSK9 by AAV with non-HDL-C serum concentration (mg/ml) on the vertical axis and time following injection (days) plotted on the horizontal axis.

Figure 37:
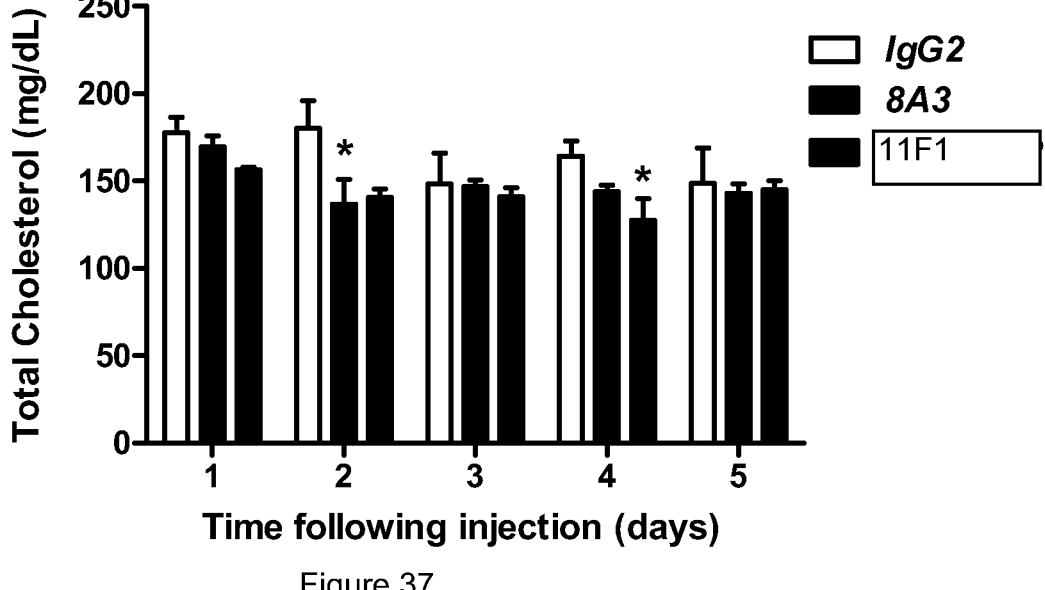

FIG. 37 is a bar graph depicting the effect of 11F1 and 8A3 on Serum Total Cholesterol in mice expressing human PCSK9 by AAV with Serum Total Cholesterol (mg/ml) on the vertical axis and time following injection (days) plotted on the horizontal axis.

Figure 38:
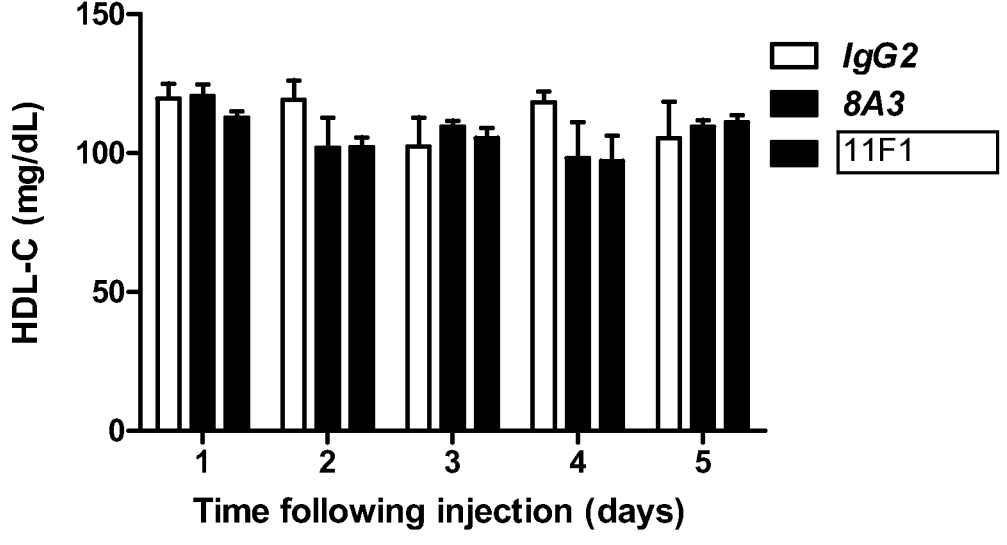

FIG. 38 is a bar graph depicting the effect of 11F1 and 8A3 on Serum HDL Cholesterol (HDL-C) in mice expressing human PCSK9 by AAV with HDL-C (mg/ml) on the vertical axis and time following injection (days) plotted on the horizontal axis.

Figure 39:
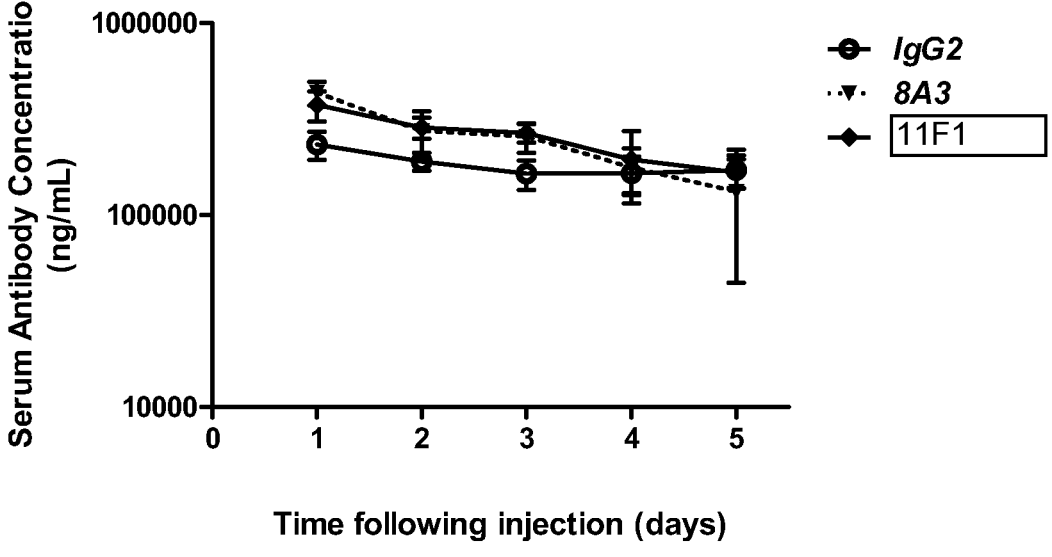

FIG. 39 is a graph depicting IgG2, 8A3 and 11F1 antibody concentration profiles in mice expressing human PCSK9 by AAV with serum antibody concentration (ng/mL) plotted on the vertical axis and time following injection in days plotted on the horizontal axis.

FIG. 40 is a table summarizing PK parameters for IgG2, 11F1 and 8A3 in mice expressing human PCSK9 by AAV.

Figure 41:
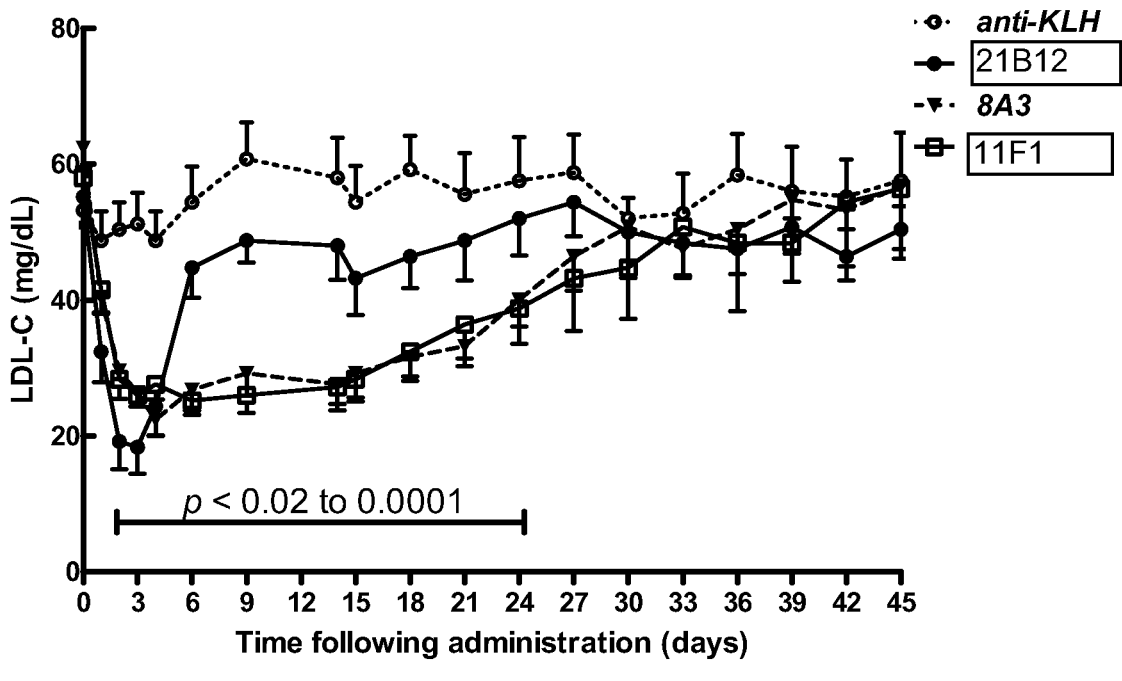

FIG. 41 is a graph depicting the effect of a single subcutaneous administration of an ant-KLH antibody (control), 21B12, 8A3 and 11F1 on serum LDL concentration (LDL-C) in cynomolgus monkeys with LDL-C (mg/dl) plotted on the vertical axis and time following administration in days on the horizontal axis.

Figure 42:
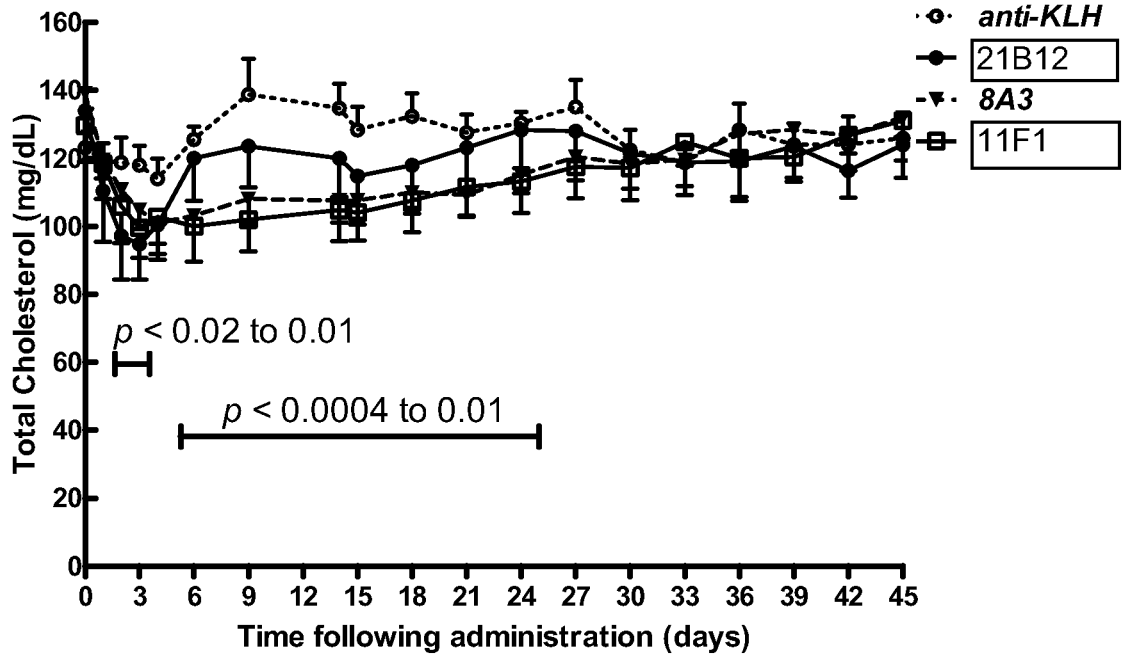

FIG. 42 is a graph depicting the effect of a single subcutaneous administration of an ant-KLH antibody (control), 21B12, 8A3 and 11F1 on Serum Total Cholesterol in cynomolgus monkeys with Total Cholesterol concentration (mg/dl) plotted on the vertical axis and time following administration in days on the horizontal axis.

Figure 43:
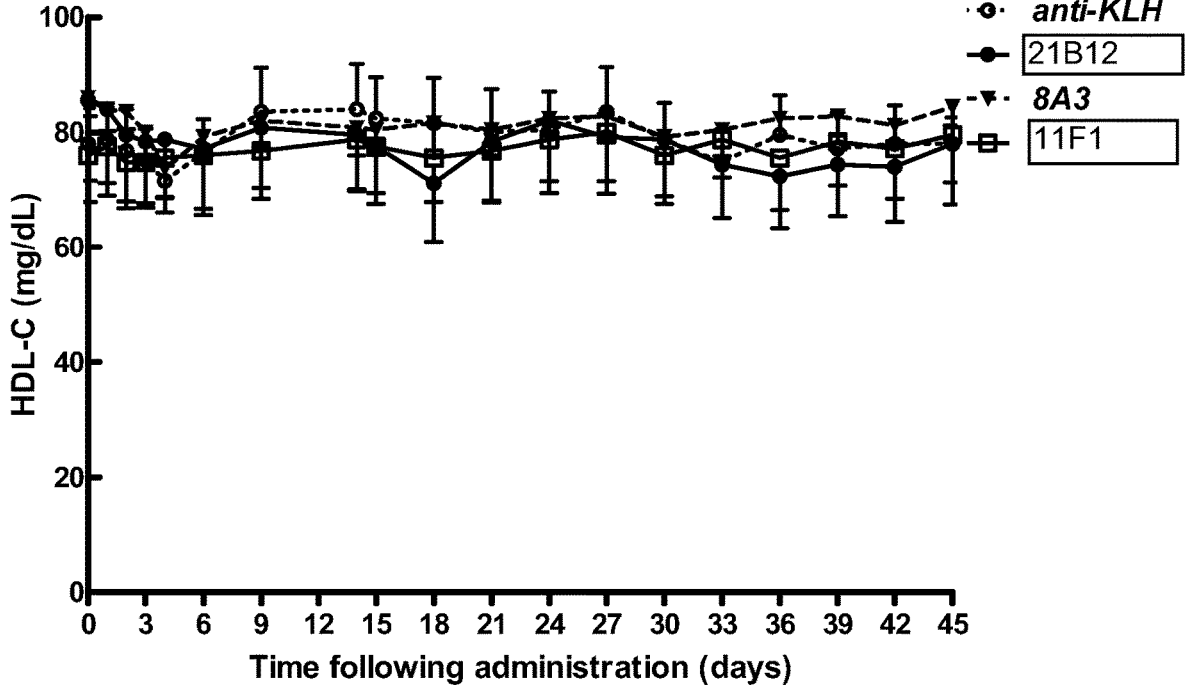

FIG. 43 is a graph depicting the effect of a single subcutaneous administration of an ant-KLH antibody (control), 21B12, 8A3 and 11F1 on Serum HDL Cholesterol in cynomolgus monkeys with HDL-C (mg/dl) plotted on the vertical axis and time following administration in days on the horizontal axis.

Figure 44:
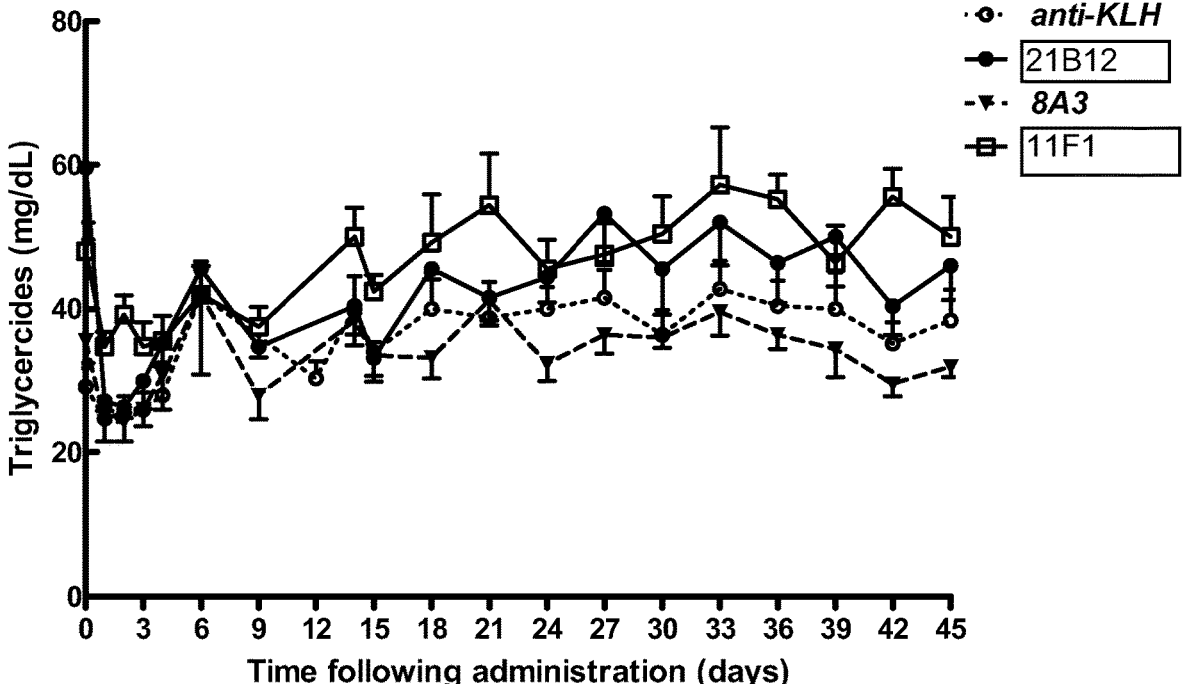

FIG. 44 is a graph depicting the effect of a single subcutaneous administration of an ant-KLH antibody (control), 21B12, 8A3 and 11F1 on Serum Triglycerides in cynomolgus monkeys with Serum Triglyceride concentration (mg/dl) plotted on the vertical axis and time following administration in days on the horizontal axis.

Figure 45:
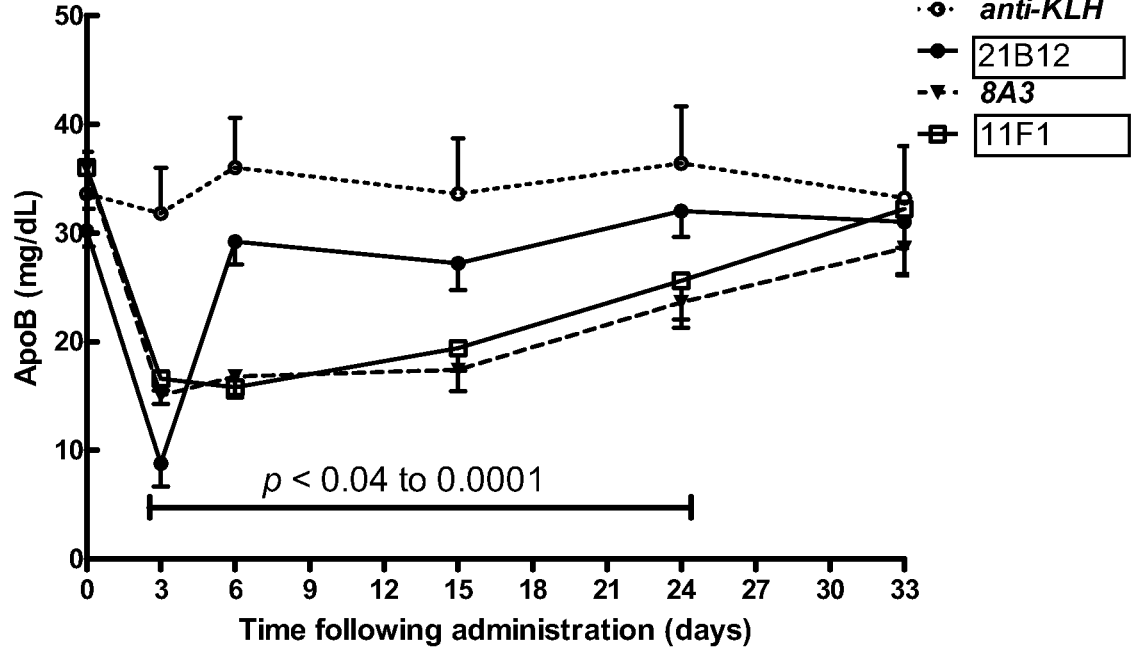

FIG. 45 is a graph depicting the effect of a single subcutaneous administration of an ant-KLH antibody (control), 21B12, 8A3 and 11F1 on Apolipoprotein B (ApoB) in cynomolgus monkeys with APOB concentration (mg/dl) plotted on the vertical axis and time following administration in days on the horizontal axis.

Figure 46:
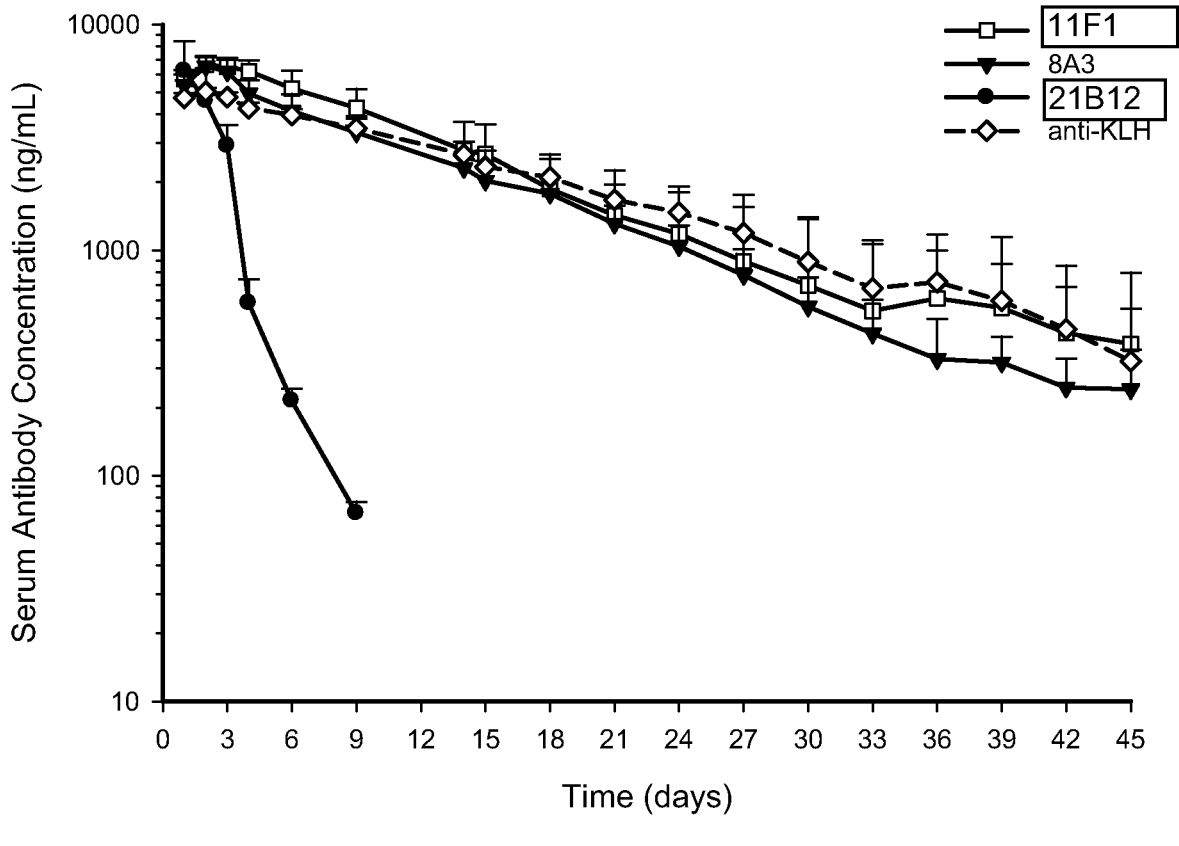

FIG. 46 is a graph depicting the mean pharmacokinetic profiles for the anti-KLH antibody (control), 21B12, 8A3 and 11F1 in cynomolgus monkeys with antibody concentrations (ng/ml) plotted on the vertical axis and time following administration in days on the horizontal axis.

FIG. 47 is a table summarizing PK parameters for the anti-KLH antibody (control), 21B12, 8A3 and 11F1 in cynomolgus monkeys.

DETAILED DESCRIPTION OF CERTAIN EXEMPLARY EMBODIMENTS

Antigen binding proteins (such as antibodies and functional binding fragments thereof) that bind to PCSK9 are disclosed herein. In some embodiments, the antigen binding proteins bind to PCSK9 and prevent PCSK9 from functioning in various ways. In some embodiments, the antigen binding proteins block or reduce the ability of PCSK9 to interact with other substances. For example, in some embodiments, the antigen binding protein binds to PCSK9 in a manner that prevents or reduces the likelihood that PCSK9 will bind to LDLR. In other embodiments, antigen binding proteins bind to PCSK9 but do not block PCSK9's ability to interact with LDLR. In some embodiments, the antigen binding proteins are human monoclonal antibodies.

As will be appreciated by one of skill in the art, in light of the present disclosure, altering the interactions between PCSK9 and LDLR can increase the amount of LDLR available for binding to LDL, which in turn decreases the amount of serum LDL in a subject, resulting in a reduction in the subject's serum cholesterol level. As such, antigen binding proteins to PCSK9 can be used in various methods and formulations for treating subjects with elevated serum cholesterol levels, at risk of elevated serum cholesterol levels, or which could benefit from a reduction in their serum cholesterol levels. Thus, various methods and techniques for lowering, maintaining, or preventing an increase in serum cholesterol are also described herein. In some embodiments, the antigen binding protein allows for binding between PCSK9 and LDLR, but the antigen binding protein prevents or reduces the adverse activity of PCSK9 on LDLR. In some embodiments, the antigen binding protein prevents or reduces the binding of PCSK9 to LDLR.

For convenience, the following sections generally outline the various meanings of the terms used herein. Following this discussion, general aspects regarding antigen binding proteins are discussed, followed by specific examples demonstrating the properties of various embodiments of the antigen binding proteins and how they can be employed.

DEFINITIONS AND EMBODIMENTS

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the present disclosure, the following terms, unless otherwise indicated, shall be understood to have the following meanings:

The term "proprotein convertase subtilisin kexin type 9" or "PCSK9" refers to a polypeptide as set forth in SEQ ID NO: 1 and/or 3 or fragments thereof, as well as related polypeptides, which include, but are not limited to, allelic variants, splice variants, derivative variants, substitution variants, deletion variants, and/or insertion variants including the addition of an N-terminal methionine, fusion polypeptides, and interspecies homologs. In certain embodiments, a PCSK9 polypeptide includes terminal residues, such as, but not limited to, leader sequence residues, targeting residues, amino terminal methionine residues, lysine residues, tag residues and/or fusion protein residues. "PCSK9" has also been referred to as FH3, NARC1, HCHOLA3, proprotein convertase subtilisin/kexin type 9, and neural apoptosis regulated convertase 1. The PCSK9 gene encodes a proprotein convertase protein that belongs to the proteinase K subfamily of the secretory subtilase family. The term "PCSK9" denotes both the proprotein and the product generated following autocatalysis of the proprotein. When only the autocatalyzed product is being referred to (such as for an antigen binding protein that selectively binds to the cleaved PCSK9), the protein can be referred to as the "mature," "cleaved", "processed" or "active" PCSK9. When only the inactive form is being referred to, the protein can be referred to as the "inactive", "pro-form", or "unprocessed" form of PCSK9. The term PCSK9 as used herein also includes naturally occurring alleles, such as the mutations D374Y, S127R and F216L. The term PCSK9 also encompasses PCSK9 molecules incorporating post-translational modifications of the PCSK9 amino acid sequence, such as PCSK9 sequences that have been glycosylated, PEGylated, PCSK9 sequences from which its signal sequence has been cleaved, PCSK9 sequence from which its pro domain has been cleaved from the catalytic domain but not separated from the catalytic domain (e.g., FIGS. 1A and 1B).

The term "PCSK9 activity" includes any biological effect of PCSK9. In certain embodiments, PCSK9 activity includes the ability of PCSK9 to interact or bind to a substrate or receptor. In some embodiments, PCSK9 activity is represented by the ability of PCSK9 to bind to a LDL receptor (LDLR). In some embodiments, PCSK9 binds to and catalyzes a reaction involving LDLR. In some embodiments, PCSK9 activity includes the ability of PCSK9 to alter (e.g., reduce) the availability of LDLR. In some embodiments, PCSK9 activity includes the ability of PCSK9 to increase the amount of LDL in a subject. In some embodiments, PCSK9 activity includes the ability of PCSK9 to decrease the amount of LDLR that is available to bind to LDL. In some embodiments, "PCSK9 activity" includes any biological activity resulting from PCSK9 signaling. Exemplary activities include, but are not limited to, PCSK9 binding to LDLR, PCSK9 enzyme activity that cleaves LDLR or other proteins, PCSK9 binding to proteins other than LDLR that facilitate PCSK9 action, PCSK9 altering APOB secretion (Sun X-M et al, "Evidence for effect of mutant PCSK9 on apoliprotein B secretion as the cause of unusually severe dominant hypercholesterolemia, Human Molecular Genetics 14: 1161-1169, 2005 and Ouguerram K et al, "Apolipoprotein B100 metabolism in autosomal-dominant hypercholesterolemia related to mutations in PCSK9, Arterioscler thromb Vasc Biol. 24: 1448-1453, 2004), PCSK9's role in liver regeneration and neuronal cell differentiation (Seidah N G et al, "The secretory proprotein convertase neural apoptosis-regulated convertase 1 (NARC-1): Liver regeneration and neuronal differentiation" PNAS 100: 928-933, 2003), and PCSK9s role in hepatic glucose metabolism (Costet et al., "Hepatic PCSK9 expression is regulated by nutritional status via insulin and sterol regulatory element-binding protein 1c" *J. Biol. Chem.* 281(10): 6211-18, 2006).

The term "hypercholesterolemia," as used herein, refers to a condition in which cholesterol levels are elevated above a desired level. In some embodiments, this denotes that serum cholesterol levels are elevated. In some embodiments, the desired level takes into account various "risk factors" that are known to one of skill in the art (and are described or referenced herein).

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences can include, in addition to the specified sequences, coding sequences for up to ten or even up to twenty other proteins or portions thereof, or can include operably linked regulatory sequences that control expression of the coding region of the recited nucleic acid sequences, and/or can include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, Molecular Cloning: A Laboratory Manual, supra; Davis et al., 1986, *Basic Methods in Molecular Biology, Elsevier; Chu et al.,* 1981, *Gene* 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass PCSK9 antigen binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a PCSK9-binding antibody, useful fragments include but are not limited to a CDR region, a variable domain of a heavy and/or light chain, a portion of an antibody chain or just its variable region including two CDRs, and the like.

The term "isolated protein" referred means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof can encode such an isolated protein. Preferably, the isolated protein is substantially free from proteins or polypeptides or other contaminants that are found in its natural environment that would interfere with its therapeutic, diagnostic, prophylactic, research or other use.

The term "amino acid" includes its normal meaning in the art.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are typically aligned in a way that gives the largest match between the sequences. One example of a computer program that can be used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSum 62 are used in conjunction with the algorithm. In certain embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. U.S.A.* 89:10915-10919 for the BLOSum 62 comparison matrix) is also used by the algorithm.

Examples of parameters that can be employed in determining percent identity for polypeptides or nucleotide sequences using the GAP program are the following:

Algorithm: Needleman et al., 1970, J. Mol. Biol. 48:443-453

Comparison matrix: BLOSum 62 from Henikoff et al., 1992, supra

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

As used herein, the twenty conventional (e.g., naturally occurring) amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference for any purpose. Stereoisomers (e.g., D-amino acids) of the twenty conventional amino acids, unnatural amino acids such as α-, α-disubstituted amino acids, N-alkyl amino acids, lactic acid, and other unconventional amino acids can also be suitable components for polypeptides of the present invention. Examples of unconventional amino acids include: 4-hydroxyproline, α-carboxyglutamate, ε-N, N,N-trimethyllysine, e-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences."

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues can be divided into classes based on common side chain properties:

1) hydrophobic: norleucine, Met, Ala, Val, Leu, Ile;

2) neutral hydrophilic: Cys, Ser, Thr, Asn, Gln;

3) acidic: Asp, Glu;

4) basic: His, Lys, Arg;

5) residues that influence chain orientation: Gly, Pro; and 6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the antigen binding protein or the PCSK9 protein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and anti-genicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a deriva-tive antigen binding protein is covalently modified to include one or more water soluble polymer attachments, including, but not limited to, polyethylene glycol, polyoxy-ethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dex-tran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and poly-vinyl alcohol, as well as mixtures of such polymers.

In certain embodiments, a derivative is covalently modi-fied with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomi-metics." Fauchere, J., Adv. Drug Res., 15:29 (1986); Veber & Freidinger, TINS, p. 392 (1985); and Evans et al., J. Med. Chem., 30:1229 (1987), which are incorporated herein by reference for any purpose. Such compounds are often devel-oped with the aid of computerized molecular modeling. Peptide mimetics that are structurally similar to therapeuti-cally useful peptides can be used to produce a similar therapeutic or prophylactic effect. Generally, peptidomimet-ics are structurally similar to a paradigm polypeptide (i.e., a polypeptide that has a biochemical property or pharmaco-logical activity), such as human antibody, but have one or more peptide linkages optionally replaced by a linkage selected from: $-CH_2NH-$, $-CH_2S-$, $-CH_2-CH_2-$, $-CH=CH-$(cis and trans), $-COCH_2-$, $-CH(OH)CH_2-$, and $-CH_2SO-$, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch, Ann. Rev. Biochem., 61:387 (1992), incorporated herein by reference for any purpose); for example, by adding internal cysteine residues capable of forming intramolecular disul-fide bridges which cyclize the peptide.

The term "naturally occurring" as used throughout the specification in connection with biological materials such as polypeptides, nucleic acids, host cells, and the like, refers to materials which are found in nature or a form of the materials that is found in nature.

An "antigen binding protein" ("ABP") as used herein means any protein that binds a specified target antigen. In the instant application, the specified target antigen is the PCSK9 protein or fragment thereof "Antigen binding protein" includes but is not limited to antibodies and binding parts thereof, such as immunologically functional fragments. Pep-tibodies are another example of antigen binding proteins. The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. In some embodiments, the fragments can block or reduce the likelihood of the interaction between LDLR and PCSK9. In one aspect, such a fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab')$_2$, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. As will be appreciated by one of skill in the art, an antigen binding protein can include nonprotein components. In some sections of the present disclosure, examples of ABPs are described herein in terms of "number/letter/number" (e.g., 25A7). In these cases, the exact name denotes a specific antibody. That is, an ABP named 25A7 is not necessarily the same as an antibody named 25A7.1, (unless they are explicitly taught as the same in the specification, e.g., 25A7 and 25A7.3). As will be appreciated by one of skill in the art, in some embodiments LDLR is not an antigen binding protein. In some embodiments, binding subsections of LDLR are not antigen binding proteins, e.g., EGFa. In some embodiments, other molecules through which PCSK9 signals in vivo are not antigen binding proteins. Such embodiments will be explicitly identified as such.

Certain antigen binding proteins described herein are antibodies or are derived from antibodies. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the ABP comprises or consists of avimers (tightly binding peptide). These various antigen binding proteins are further described herein.

An "Fc" region comprises two heavy chain fragments comprising the $C_H1$ and $C_H2$ domains of an antibody. The two heavy chain fragments are held together by two or more disulfide bonds and by hydrophobic interactions of the $C_H3$ domains.

A "Fab fragment" comprises one light chain and the $C_H1$ and variable regions of one heavy chain. The heavy chain of a Fab molecule cannot form a disulfide bond with another heavy chain molecule.

A "Fab' fragment" comprises one light chain and a portion of one heavy chain that contains the VH domain and the $C_H1$ domain and also the region between the $C_H1$ and $C_H2$ domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553. The two binding sites of a bispecific antigen binding protein or antibody will bind to two different epitopes, which can reside on the same or different protein targets.

An antigen binding protein is said to "specifically bind" its target antigen when the dissociation constant ($K_d$) is ≤$10^{-7}$ M. The ABP specifically binds antigen with "high affinity" when the $K_d$ is ≤$5×10^{-9}$ M, and with "very high affinity" when the $K_d$ is ≤$5×10^{-10}$ M. In one embodiment, the ABP has a $K_d$ of ≤$10^{-9}$ M. In one embodiment, the off-rate is <$1×10^{-5}$. In other embodiments, the ABPs will bind to human PCSK9 with a $K_d$ of between about $10^{-9}$ M and $10^{-13}$ M, and in yet another embodiment the ABPs will bind with a $K_d$≤$5×10^{-10}$. As will be appreciated by one of skill in the art, in some embodiments, any or all of the antigen binding fragments can specifically bind to PCSK9.

An antigen binding protein is "selective" when it binds to one target more tightly than it binds to a second target.

"Antigen binding region" means a protein, or a portion of a protein, that specifically binds a specified antigen (e.g., a paratope). For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs"). Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen. Structurally, framework regions can be located in antibodies between CDRs. Examples of framework and CDR regions are shown in FIGS. 2A-3D, 3CCC-3JJJ. In some embodiments, the sequences for CDRs for the light chain of antibody 3B6 are as follows: CDR1 TLSSGYSSYEVD (SEQ ID NO: 279); CDR2 VDTG-GIVGSKGE (SEQ ID NO: 280); CDR3 GAD-HGSGTNFVVV (SEQ ID NO: 281), and the FRs are as follows: FR1 QPVLTQPLFASASLGASVTLTC (SEQ ID NO: 282); FR2 WYQQRPGKGPRFVMR (SEQ ID NO: 283); FR3 GIPDRFSVLGSGLNRYLTIK-NIQEEDESDYHC (SEQ ID NO: 284); and FR4 FGGGTKLTVL (SEQ ID NO: 285).

In certain aspects, recombinant antigen binding proteins that bind PCSK9, for example human PCSK9, are provided. In this context, a "recombinant antigen binding protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, J. Mol. Biol., 196:901-917 (1987); Chothia et al., Nature, 342:878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, $V_H$, and three constant region domains, $C_H1$ $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

Some species of mammals also produce antibodies having only a single heavy chain.

Each individual immunoglobulin chain is typically composed of several "immunoglobulin domains," each consisting of roughly 90 to 110 amino acids and having a characteristic folding pattern. These domains are the basic units of which antibody polypeptides are composed. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. IgG heavy chains, for example, contain three C region domains known as $C_H1$ $C_H2$ and $C_H3$. The antibodies that are provided can have any of these isotypes and subtypes. In certain embodiments of the present invention, an anti-PCSK9 antibody is of the IgG2 or IgG4 subtype.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target The term "neutralizing antigen binding protein" or "neutralizing antibody" refers to an antigen binding protein or antibody, respectively, that binds to a ligand and prevents or reduces the biological effect of that ligand. This can be done, for example, by directly blocking a binding site on the ligand or by binding to the ligand and altering the ligand's ability to bind through indirect means (such as structural or energetic alterations in the ligand). In some embodiments, the term can also denote an antigen binding protein that prevents the protein to which it is bound from performing a biological function. In assessing the binding and/or specificity of an antigen binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20, 20-30%, 30-40%, 40-50%, 50-60%, 60-70%, 70-80%, 80-85%, 85-90%, 90-95%, 95-97%, 97-98%, 98-99% or more (as measured in an in vitro competitive binding assay). In some embodiments, in the case of PCSK9 antigen binding proteins, such a neutralizing molecule can diminish the ability of PCSK9 to bind the LDLR. In some embodiments, the neutralizing ability is characterized and/or described via a competition assay. In some embodiments, the neutralizing ability is described in terms of an $IC_{50}$ or $EC_{50}$ value. In some embodiments, ABPs 27B2, 13H1, 13B5 and 3C4 are non-neutralizing ABPs, 3B6, 9C9 and 31A4 are weak neutralizers, and the remaining ABPs in Table 2 are strong neutralizers. In some embodiments, the antibodies or antigen binding proteins neutralize by binding to PCSK9 and preventing PCSK9 from binding to LDLR (or reducing the ability of PCSK9 to bind to LDLR). In some embodiments, the antibodies or ABPs neutralize by binding to PCSK9, and while still allowing PCSK9 to bind to LDLR, preventing or reducing the PCSK9 mediated degradation of LDLR. Thus, in some embodiments, a neutralizing ABP or antibody can still permit PCSK9/LDLR binding, but will prevent (or reduce) subsequent PCSK9 involved degradation of LDLR.

The term "target" refers to a molecule or a portion of a molecule capable of being bound by an antigen binding protein. In certain embodiments, a target can have one or more epitopes. In certain embodiments, a target is an antigen. The use of "antigen" in the phrase "antigen binding protein" simply denotes that the protein sequence that comprises the antigen can be bound by an antibody. In this context, it does not require that the protein be foreign or that it be capable of inducing an immune response.

The term "compete" when used in the context of antigen binding proteins (e.g., neutralizing antigen binding proteins or neutralizing antibodies) that compete for the same epitope means competition between antigen binding proteins as determined by an assay in which the antigen binding protein (e.g., antibody or immunologically functional fragment thereof) being tested prevents or inhibits (e.g., reduces) specific binding of a reference antigen binding protein (e.g., a ligand, or a reference antibody) to a common antigen (e.g., PCSK9 or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619) solid phase direct labeled assay, solid phase direct labeled sandwich assay (see, e.g., Harlow and Lane, 1988, *Antibodies, A Laboratory Manual*, Cold Spring Harbor Press); solid phase direct label RIA using I-125 label (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. J. Immunol.* 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "antigen" refers to a molecule or a portion of a molecule capable of being bound by a selective binding agent, such as an antigen binding protein (including, e.g., an antibody or immunological functional fragment thereof). In some embodiments, the antigen is capable of being used in an animal to produce antibodies capable of binding to that antigen. An antigen can possess one or more epitopes that are capable of interacting with different antigen binding proteins, e.g., antibodies.

The term "epitope" includes any determinant capable being bound by an antigen binding protein, such as an antibody or to a T-cell receptor. An epitope is a region of an antigen that is bound by an antigen binding protein that targets that antigen, and when the antigen is a protein, includes specific amino acids that directly contact the antigen binding protein. Most often, epitopes reside on proteins, but in some instances can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins are known in the art and can be used. Examples of labels for polypeptides include, but are not limited to, the following: radioisotopes or radionuclides (e. $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The term "therapeutically effective amount" refers to the amount of a PCSK9 antigen binding protein determined to produce a therapeutic response in a mammal. Such therapeutically effective amounts are readily ascertained by one of ordinary skill in the art.

The term "modulator," as used herein, is a compound that changes or alters the activity or function of a molecule. For example, a modulator can cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules. Peptibodies are described in, e.g., U.S. Pat. No. 6,660,843 (corresponding to PCT Application No. WO 01/83525).

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., *Molecular Cloning: A Laboratory Manual* (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Antigen Binding Proteins to PCSK9

Proprotein convertase subtilisin kexin type 9 (PCSK9) is a serine protease involved in regulating the levels of the low density lipoprotein receptor (LDLR) protein (Horton et al., 2007; Seidah and Prat, 2007). PCSK9 is a prohormone-proprotein convertase in the subtilisin (S8) family of serine proteases (Seidah et al., 2003). An exemplary human PCSK9 amino acid sequence is presented as SEQ ID NOs: 1 and 3. in FIG. 1A (depicting the "pro" domain of the protein as underlined) and FIG. 1B (depicting the signal sequence in bold and the pro domain underlined). An exemplary human PCSK9 coding sequence is presented as SEQ ID NO: 2 (FIG. 1B). As described herein, PCSK9 proteins can also include fragments of the full length PCSK9 protein. The structure of the PCSK9 protein was solved by two groups (Cunningham et al., Nature Structural & Molecular Biology, 2007, and Piper et al., Structure, 15:1-8, 2007), the entireties of both of which are herein incorporated by reference. PCSK9 includes a signal sequence, a N-terminal prodomain, a subtilisin-like catalytic domain and a C-terminal domain.

Antigen binding proteins (ABPs) that bind PCSK9, including human PCSK9, are provided herein. In some embodiments, the antigen binding proteins provided are polypeptides which comprise one or more complementary determining regions (CDRs), as described herein. In some antigen binding proteins, the CDRs are embedded into a "framework" region, which orients the CDR(s) such that the proper antigen binding properties of the CDR(s) is achieved. In some embodiments, antigen binding proteins provided herein can interfere with, block, reduce or modulate the interaction between PCSK9 and LDLR. Such antigen binding proteins are denoted as "neutralizing." In some embodiments, binding between PCSK9 and LDLR can still occur, even though the antigen binding protein is neutralizing and bound to PCSK9. For example, in some embodiments, the ABP prevents or reduces the adverse influence of PCSK9 on LDLR without blocking the LDLR binding site on PCSK9. Thus, in some embodiments, the ABP modulates or alters PCSK9's ability to result in the degradation of LDLR, without having to prevent the binding interaction between PCSK9 and LDLR. Such ABPs can be specifically described as "non-competitively neutralizing" ABPs. In some embodiments, the neutralizing ABP binds to PCSK9 in a location and/or manner that prevents PCSK9 from binding to LDLR. Such ABPs can be specifically described as "competitively neutralizing" ABPs. Both of the above neutralizers can result in a greater amount of free LDLR being present in a subject, which results in more LDLR binding to LDL (thereby reducing the amount of LDL in the subject). In turn, this results in a reduction in the amount of serum cholesterol present in a subject.

In some embodiments, the antigen binding proteins provided herein are capable of inhibiting PCSK9-mediated activity (including binding). In some embodiments, antigen binding proteins binding to these epitopes inhibit, inter alia, interactions between PCSK9 and LDLR and other physiological effects mediated by PCSK9. In some embodiments, the antigen binding proteins are human, such as fully human antibodies to PCSK9.

In some embodiments, the ABP binds to the catalytic domain of PCSK9. In some embodiments, the ABP binds to the mature form of PCSK9. In some embodiments the ABP binds in the prodomain of PCSK9. In some embodiments, the ABP selectively binds to the mature form of PCSK9. In some embodiments, the ABP binds to the catalytic domain in a manner such that PCSK9 cannot bind or bind as efficiently to LDLR. In some embodiments, the antigen binding protein does not bind to the c-terminus of the catalytic domain. In some embodiments, the antigen binding protein does not bind to the n-terminus of the catalytic domain. In some embodiments, the ABP does not bind to the n- or c-terminus of the PCSK9 protein. In some embodiments, the ABP binds to any one of the epitopes bound by the antibodies discussed herein. In some embodiments, this can be determined by competition assays between the antibodies disclosed herein and other antibodies. In some embodiments, the ABP binds to an epitope bound by one of the antibodies described in Table 2. In some embodiments, the antigen binding proteins bind to a specific conformational state of PCSK9 so as to prevent PCSK9 from interacting with LDLR. In some embodiments, the ABP binds to the V domain of PCSK9. In some embodiments, the ABP binds to the V domain of PCSK9 and prevents (or reduces) PCSK9 from binding to LDLR. In some embodiments, the ABP binds to the V domain of PCSK9, and while it does not prevent (or reduce) the binding of PCSK9 to LDLR, the ABP prevents or reduces the adverse activities mediated through PCSK9 on LDLR.

The antigen binding proteins that are disclosed herein have a variety of utilities.

Some of the antigen binding proteins, for instance, are useful in specific binding assays, affinity purification of PCSK9, in particular human PCSK9 or its ligands and in screening assays to identify other antagonists of PCSK9 activity. Some of the antigen binding proteins are useful for inhibiting binding of PCSK9 to LDLR, or inhibiting PCSK9-mediated activities.

The antigen binding proteins can be used in a variety of therapeutic applications, as explained herein. For example, in some embodiments the PCSK9 antigen binding proteins are useful for treating conditions associated with PCSK9, such as cholesterol related disorders (or "serum cholesterol related disorders") such as hypercholesterolemia, as further described herein. Other uses for the antigen binding proteins include, for example, diagnosis of PCSK9-associated diseases or conditions and screening assays to determine the presence or absence of PCSK9. Some of the antigen binding proteins described herein are useful in treating consequences, symptoms, and/or the pathology associated with PCSK9 activity.

In some embodiments, the antigen binding proteins that are provided comprise one or more CDRs (e.g., 1, 2, 3, 4, 5 or 6 CDRs). In some embodiments, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or can be completely synthetic in nature. Examples of various polypeptide structures are further described below.

In certain embodiments, the polypeptide structure of the antigen binding proteins is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen binding protein is an immunological fragment of an antibody (e.g., a Fab, a Fab', a F(ab')$_2$, or a scFv). The various structures are further described and defined herein.

Certain of the antigen binding proteins as provided herein specifically and/or selectively bind to human PCSK9. In some embodiments, the antigen binding protein specifically and/or selectively binds to human PCSK9 protein having and/or consisting of residues 153-692 of SEQ ID NO: 3. In some embodiments the ABP specifically and/or selectively binds to human PCSK9 having and/or consisting of residues 31-152 of SEQ ID NO: 3. In some embodiments, the ABP selectively binds to a human PCSK9 protein as depicted in FIG. 1A (SEQ ID NO: 1). In some embodiments, the antigen binding protein specifically binds to at least a fragment of the PCSK9 protein and/or a full length PCSK9 protein, with or without a signal sequence.

In embodiments where the antigen binding protein is used for therapeutic applications, an antigen binding protein can inhibit, interfere with or modulate one or more biological activities of PCSK9. In one embodiment, an antigen binding protein binds specifically to human PCSK9 and/or substantially inhibits binding of human PCSK9 to LDLR by at least about 20%-40%, 40-60%, 60-80%, 80-85%, or more (for example, by measuring binding in an in vitro competitive binding assay). Some of the antigen binding proteins that are provided herein are antibodies. In some embodiments, the ABP has a K$_d$ of less (binding more tightly) than $10^{-7}$, $10^{-8}$, $10^{-9}$, $10^{-10}$, $10^{-11}$, $10^{-12}$, $10^{-13}$ M. In some embodiments, the ABP has an IC$_{50}$ for blocking the binding of LDLR to PCSK9 (D374Y, high affinity variant) of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

One example of an IgG2 heavy chain constant domain of an anti-PCSK9 antibody of the present invention has the amino acid sequence as shown in SEQ ID NO: 154, FIG. 3KK.

One example of an IgG4 heavy chain constant domain of an anti-PCSK9 antibody of the present invention has the amino acid sequence as shown in SEQ ID NO: 155, FIG. 3KK.

One example of a kappa light chain constant domain of an anti-PCSK9 antibody has the amino acid sequence as shown in SEQ ID NO: 157, FIG. 3KK.

One example of a lambda light chain constant domain of an anti-PCSK9 antibody has the amino acid sequence as shown in SEQ ID NO: 156, FIG. 3KK.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., PCSK9). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, *J. Mol. Biol.* 196:901-917; Chothia et al., 1989, *Nature* 342: 878-883.

Various heavy chain and light chain variable regions are provided herein and are depicted in FIGS. 2A-3JJ and 3LL-3BBB. In some embodiments, each of these variable regions can be attached to the above heavy and light chain constant regions to form a complete antibody heavy and light chain, respectively. Further, each of the so generated heavy and light chain sequences can be combined to form a complete antibody structure.

Specific examples of some of the variable regions of the light and heavy chains of the antibodies that are provided and their corresponding amino acid sequences are summarized in TABLE 2.

TABLE 2

| EXEMPLARY HEAVY AND LIGHT CHAIN VARIABLE REGIONS | |
| --- | --- |
| Antibody | Light/Heavy SEQ ID NO |
| 30A4 | 5/74 |
| 3C4 | 7/85 |
| 23B5 | 9/71 |
| 25G4 | 10/72 |
| 31H4 | 12/67 |
| 27B2 | 13/87 |

US 12,612,465 B2

33

TABLE 2-continued

EXEMPLARY HEAVY AND LIGHT CHAIN VARIABLE REGIONS

| Antibody | Light/Heavy SEQ ID NO |
|---|---|
| 25A7 | 15/58 |
| 27H5 | 16/52 |
| 26H5 | 17/51 |
| 31D1 | 18/53 |
| 20D10 | 19/48 |
| 27E7 | 20/54 |
| 30B9 | 21/55 |
| 19H9 | 22/56 |
| 26E10 | 23/49 |
| 21B12 | 23/49 |
| 17C2 | 24/57 |
| 23G1 | 26/50 |
| 13H1 | 28/91 |
| 9C9 | 30/64 |
| 9H6 | 31/62 |
| 31A4 | 32/89 |
| 1A12 | 33/65 |
| 16F12 | 35/79 |
| 22E2 | 36/80 |
| 27A6 | 37/76 |
| 28B12 | 38/77 |
| 28D6 | 39/78 |
| 31G11 | 40/83 |
| 13B5 | 42/69 |
| 31B12 | 44/81 |
| 3B6 | 46/60 |
| 5H5 | 421/419 |
| 24F7 | 425/423 |
| 22B11 | 429/427 |
| 30F1 | 433/431 |
| 24B9.1 | 437/435 |
| 24B9.2 | 441/439 |
| 20A5.1 | 445/443 |
| 20A5.2 | 449/447 |
| 20E5.1 | 453/451 |
| 20E5.2 | 457/455 |
| 8A3 | 461/459 |
| 11F1 | 465/463 |
| 12H11 | 469/467 |
| 11H4 | 473/471 |
| 11H8 | 477/475 |
| 11G1 | 481/479 |
| 8A1 | 485/483 |

Again, each of the exemplary variable heavy chains listed in Table 2 can be combined with any of the exemplary variable light chains shown in Table 2 to form an antibody. Table 2 shows exemplary light and heavy chain pairings found in several of the antibodies disclosed herein. In some instances, the antibodies include at least one variable heavy chain and one variable light chain from those listed in Table 2. In other instances, the antibodies contain two identical light chains and two identical heavy chains. As an example, an antibody or antigen binding protein can include a heavy chain and a light chain, two heavy chains, or two light chains. In some embodiments the antigen binding protein comprises (and/or consists) of 1, 2, and/or 3 heavy and/or light CDRs from at least one of the sequences listed in Table 2 (CDRs for the sequences are outlined in FIGS. 2A-3D, and other embodiments in FIGS. 3CCC-3JJJ and 15A-15D). In some embodiments, all 6 CDRs (CDR1-3 from the light (CDRL1, CDRL2, CDRL3) and CDR1-3 from the heavy (CDRH1, CDRH2, and CDRH3)) are part of the ABP. In some embodiments, 1, 2, 3, 4, 5, or more CDRs are included in the ABP. In some embodiments, one heavy and one light CDR from the CDRs in the sequences in Table 2 is included in the ABP (CDRs for the sequences in table 2 are outlined in FIGS. 2A-3D). In some embodiments, additional sections (e.g., as depicted in FIG. 2A-2D, 3A-3D, and other embodiments in 3CCC-3JJJ and 15A-15D) are also included in the ABP. Examples of CDRs and FRs for the heavy and light chains noted in Table 2 are outlined in FIGS. 2A-3D (and other embodiments in FIGS. 3CCC-3JJJ and 15A-15D). Optional light chain variable sequences (including CDR1, CDR2, CDR3, FR1, FR2, FR3, and FR4) can be selected from the following: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 421, 425, 429, 433, 437, 441, 445, 449, 453, 457, 461, 465, 469, 473, 477, 481, and 485. Optional heavy chain variable sequences (including CDR1, CDR2, CDR3, FR1, FR2, FR3, and FR4) can be selected from the following: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, 60, 419, 423, 427, 431, 435, 439, 443, 447, 451, 455, 459, 463, 467, 471, 475, 479, and 483. In some of the entries in FIG. 2A-3D, variations of the sequences or alternative boundaries of the CDRs and FRs are identified. These alternatives are identified with a "v1" following the ABP name. As most of these alternatives are minor in nature, only sections with differences are displayed in the table. It is understood that the remaining section of the light or heavy chain is the same as shown for the base ABP in the other panels. Thus, for example, 19H9v1 in FIG. 2C has the same FR1, CDR1, and FR2 as 19H9 in FIG. 2A as the only difference is noted in FIG. 2C. For three of the nucleic acid sequences (ABPs 26E10, 30B9, and 31B12), additional alternative nucleic acid sequences are provided in the figures. As will be appreciated by one of skill in the art, no more than one such sequence need actually be used in the creation of an antibody or ABP. Indeed, in some embodiments, only one or neither of the specific heavy or light chain nucleic acids need be present.

In some embodiments, the ABP is encoded by a nucleic acid sequence that can encode any of the protein sequences in Table 2.

In some embodiments, the ABP binds selectively to the form of PCSK9 that binds to LDLR (e.g., the autocatalyzed form of the molecule). In some embodiments, the antigen binding protein does not bind to the c-terminus of the catalytic domain (e.g., the 5. 5-10, 10-15, 15-20, 20-25, 25-30, 30-40 most amino acids in the c-terminus). In some embodiments, the antigen binding protein does not bind to the n-terminus of the catalytic domain (e.g., the 5. 5-10, 10-15, 15-20, 20-25, 25-30, 30-40 most amino acids in the n-terminus). In some embodiments, the ABP binds to amino acids within amino acids 1-100 of the mature form of PCSK9. In some embodiments, the ABP binds to amino acids within (and/or amino acid sequences consisting of) amino acids 31-100, 100-200, 31-152, 153-692, 200-300, 300-400, 452-683, 400-500, 500-600, 31-692, 31-449, and/ or 600-692. In some embodiments, the ABP binds to the catalytic domain. In some embodiments, the neutralizing and/or non-neutralizing ABP binds to the prodomain. In some embodiments, the ABP binds to both the catalytic and pro domains. In some embodiments, the ABP binds to the catalytic domain so as to obstruct an area on the catalytic domain that interacts with the pro domain. In some embodiments, the ABP binds to the catalytic domain at a location or surface that the pro-domain interacts with as outlined in Piper et al. (Structure 15:1-8 (2007), the entirety of which is hereby incorporated by reference, including the structural representations therein). In some embodiments, the ABP binds to the catalytic domain and restricts the mobility of the prodomain. In some embodiments, the ABP binds to the catalytic domain without binding to the pro-domain. In some embodiments, the ABP binds to the catalytic domain, without binding to the pro-domain, while preventing the pro-domain from reorienting to allow PCSK9 to bind to LDLR. In some embodiments, the ABP binds in the same epitope as those surrounding residues 149-152 of the pro-domain in Piper et al. In some embodiments, the ABPs bind to the groove (as outlined in Piper et al.) on the V domain. In some embodiments, the ABPs bind to the histidine-rich patch proximal to the groove on the V domain. In some embodiments, such antibodies (that bind to the V domain) are not neutralizing. In some embodiments, antibodies that bind to the V domain are neutralizing. In some embodiments, the neutralizing ABPs prevent the binding of PCSK9 to LDLR. In some embodiments, the neutralizing ABPs, while preventing the PCSK9 degradation of LDLR, do not prevent the binding of PCSK9 to LDLR (for example ABP 31A4). In some embodiments, the ABP binds to or blocks at least one of the histidines depicted in FIG. 4 of the Piper et al. paper. In some embodiments, the ABP blocks the catalytic triad in PCSK9.

In some embodiments, the antibody binds selectively to variant PCSK9 proteins, e.g., D374Y over wild type PCSK9. In some embodiments, these antibodies bind to the variant at least twice as strongly as the wild type, and preferably 2-5, 5-10, 10-100, 100-1000, 1000-10,000 fold or more to the mutant than the wild type (as measured via a $K_d$). In some embodiments, the antibody selectively inhibits variant D374Y PCSK9 from interacting with LDLR over wild type PCSK9's ability to interact with LDLR. In some embodiments, these antibodies block the variant's ability to bind to LDLR more strongly than the wild type's ability, e.g., at least twice as strongly as the wild type, and preferably 2-5, 5-10, 10-100, 100-1000 fold or more to the mutant than the wild type (as measured via an $IC_{50}$). In some embodiments, the antibody binds to and neutralizes both wild type PCSK9 and variant forms of PCSK9, such as D374Y at similar levels. In some embodiments, the antibody binds to PCSK9 to prevent variants of LDLR from binding to PCSK9. In some embodiments, the variants of LDLR are at least 50% identical to human LDLR. It is noted that variants of LDLR are known to those of skill in the art (e.g., Brown M S et al, "Calcium cages, acid baths and recycling receptors" Nature 388: 629-630, 1997). In some embodiments, the ABP can raise the level of effective LDLR in heterozygote familial hypercholesterolemia (where a loss-of function variant of LDLR is present).

In some embodiments, the ABP binds to (but does not block) variants of PCSK9 that are at least 50%, 50-60, 60-70, 70-80, 80-90, 90-95, 95-99, or greater percent identity to the form of PCSK9 depicted in FIG. 1A and/or FIG. 1B. In some embodiments, the ABP binds to (but does not block) variants of PCSK9 that are at least 50%, 50-60, 60-70, 70-80, 80-90, 90-95, 95-99, or greater percent identity to the mature form of PCSK9 depicted in FIG. 1A and/or FIG. 1B. In some embodiments, the ABP binds to and prevents variants of PCSK9 that are at least 50%, 50-60, 60-70, 70-80, 80-90, 90-95, 95-99, or greater percent identity to the form of PCSK9 depicted in FIG. 1A and/or FIG. 1B from interacting with LDLR. In some embodiments, the ABP binds to and prevents variants of PCSK9 that are at least 50, 50-60, 60-70, 70-80, 80-90, 90-95, 95-99, or greater percent identity to the mature form of PCSK9 depicted in FIG. 1B from interacting with LDLR. In some embodiments, the variant of PCSK9 is a human variant, such as variants at position 474, E620G, and/or E670G. In some embodiments, the amino acid at position 474 is valine (as in other humans) or threonine (as in cyno and mouse). Given the cross-reactivity data presented herein, it is believed that the present antibodies will readily bind to the above variants.

In some embodiments, the ABP binds to an epitope bound by one of the antibodies described in Table 2. In some embodiments, the antigen binding proteins bind to a specific conformational state of PCSK9 so as to prevent PCSK9 from interacting with LDLR.

Humanized Antigen Binding Proteins (e.g., Antibodies)

As described herein, an antigen binding protein to PCSK9 can comprise a humanized antibody and/or part thereof. An important practical application of such a strategy is the "humanization" of the mouse humoral immune system.

In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101; 5,693,761; 5,693,762; 5,585,089.

In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619.

In certain embodiments, modification of an antibody by methods known in the art is typically designed to achieve increased binding affinity for a target and/or to reduce immunogenicity of the antibody in the recipient. In certain embodiments, humanized antibodies are modified to eliminate glycosylation sites in order to increase affinity of the antibody for its cognate antigen. See, e.g., Co et al., Mol. Immunol., 30:1361-1367 (1993). In certain embodiments, techniques such as "reshaping," "hyperchimerization," or "veneering/resurfacing" are used to produce humanized antibodies. See, e.g., Vaswami et al., Annals of Allergy, Asthma, & Immunol. 81:105 (1998); Roguska et al., Prot. Engineer., 9:895-904 (1996); and U.S. Pat. No. 6,072,035. In certain such embodiments, such techniques typically reduce antibody immunogenicity by reducing the number of foreign residues, but do not prevent anti-idiotypic and anti-allotypic responses following repeated administration of the antibodies. Certain other methods for reducing immunogenicity are described, e.g., in Gilliland et al., J. Immunol., 62(6): 3663-71 (1999).

In certain instances, humanizing antibodies results in a loss of antigen binding capacity. In certain embodiments, humanized antibodies are "back mutated." In certain such embodiments, the humanized antibody is mutated to include one or more of the amino acid residues found in the donor antibody. See, e.g., Saldanha et al., *Mol Immunol* 36:709-19 (1999).

In certain embodiments the complementarity determining regions (CDRs) of the light and heavy chain variable regions of an antibody to PCSK9 can be grafted to framework regions (FRs) from the same, or another, species. In certain embodiments, the CDRs of the light and heavy chain variable regions of an antibody to PCSK9 can be grafted to consensus human FRs. To create consensus human FRs, in certain embodiments, FRs from several human heavy chain or light chain amino acid sequences are aligned to identify a consensus amino acid sequence. In certain embodiments, the FRs of an antibody to PCSK9 heavy chain or light chain are replaced with the FRs from a different heavy chain or light chain. In certain embodiments, rare amino acids in the FRs of the heavy and light chains of an antibody to PCSK9 are not replaced, while the rest of the FR amino acids are replaced. Rare amino acids are specific amino acids that are in positions in which they are not usually found in FRs. In certain embodiments, the grafted variable regions from an antibody to PCSK9 can be used with a constant region that is different from the constant region of an antibody to PCSK9. In certain embodiments, the grafted variable regions are part of a single chain Fv antibody. CDR grafting is described, e.g., in U.S. Pat. Nos. 6,180,370, 6,054,297, 5,693,762, 5,859,205, 5,693,761, 5,565,332, 5,585,089, and 5,530,101, and in Jones et al., Nature, 321: 522-525 (1986); Riechmann et al., Nature, 332: 323-327 (1988); Verhoeyen et al., Science, 239:1534-1536 (1988), Winter, FEBS Letts., 430:92-94 (1998), which are hereby incorporated by reference for any purpose.

Human Antigen Binding Proteins (e.g., Antibodies)

As described herein, an antigen binding protein that binds to PCSK9 can comprise a human (i.e., fully human) antibody and/or part thereof. In certain embodiments, nucleotide sequences encoding, and amino acid sequences comprising, heavy and light chain immunoglobulin molecules, particularly sequences corresponding to the variable regions are provided. In certain embodiments, sequences corresponding to complementarity determining regions (CDR's), specifically from CDR1 through CDR3, are provided. According to certain embodiments, a hybridoma cell line expressing such an immunoglobulin molecule is provided. According to certain embodiments, a hybridoma cell line expressing such a monoclonal antibody is provided. In certain embodiments a hybridoma cell line is selected from at least one of the cell lines described in Table 2, e.g., 21B12, 16F12 and 31H4. In certain embodiments, a purified human monoclonal antibody to human PCSK9 is provided.

One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in WO 98/24893, U.S. Pat. No. 5,545,807, EP 546073, and EP 546073.

In certain embodiments, one can use constant regions from species other than human along with the human variable region(s).

The ability to clone and reconstruct megabase sized human loci in yeast artificial chromosomes (YACs) and to introduce them into the mouse germline provides an approach to elucidating the functional components of very large or crudely mapped loci as well as generating useful models of human disease. Furthermore, the utilization of such technology for substitution of mouse loci with their human equivalents could provide insights into the expression and regulation of human gene products during development, their communication with other systems, and their involvement in disease induction and progression.

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

Humanized antibodies are those antibodies that, while initially starting off containing antibody amino acid sequences that are not human, have had at least some of these nonhuman antibody amino acid sequences replaced with human antibody sequences. This is in contrast with human antibodies, in which the antibody is encoded (or capable of being encoded) by genes possessed a human.

Antigen Binding Protein Variants

Other antibodies that are provided are variants of the ABPs listed above formed by combination or subparts of the variable heavy and variable light chains shown in Table 2 and comprise variable light and/or variable heavy chains that each have at least 50%, 50-60, 60-70, 70-80%, 80-85%, 85-90%, 90-95%, 95-97%, 97-99%, or above 99% identity to the amino acid sequences of the sequences in Table 2 (either the entire sequence or a subpart of the sequence, e.g., one or more CDR). In some instances, such antibodies include at least one heavy chain and one light chain, whereas in other instances the variant forms contain two identical light chains and two identical heavy chains (or subparts thereof). In some embodiments, the sequence comparison in FIGS. 2A-3D (and 13A-13J and other embodiments in 15A-15D) can be used in order to identify sections of the antibodies that can be modified by observing those variations that impact binding and those variations that do not appear to impact binding. For example, by comparing similar sequences, one can identify those sections (e.g., particular amino acids) that can be modified and how they can be modified while still retaining (or improving) the functionality of the ABP. In some embodiments, variants of ABPs include those consensus groups and sequences depicted in FIGS. 13A, 13C, 13F, 13G, 13H, 13I and/or 13J and variations are allowed in the positions identified as variable in the figures. The CDRs shown in FIGS. 13A, 13C, 13F, and 13G were defined based upon a hybrid combination of the Chothia method (based on the location of the structural loop regions, see, e.g., "Standard conformations for the canonical structures of immunoglobulins," Bissan Al-Lazikani, Arthur M. Lesk and Cyrus Chothia, Journal of Molecular Biology, 273(4): 927-948, 7 Nov. (1997)) and the Kabat method (based on sequence variability, see, e.g., Sequences of Proteins of Immunological Interest, Fifth Edition. NIH Publication No. 91-3242, Kabat et al., (1991)). Each residue determined by either method, was included in the final list of CDR residues (and is presented in FIGS. 13A, 13C, 13F, and 13G). The CDRs in FIGS. 13H, 13I, and 13J were obtained by the Kabat method alone. Unless specified otherwise, the defined consensus sequences, CDRs, and FRs in FIGS. 13H-13J will define and control the noted CDRs and FRs for the referenced ABPs in FIG. 13.

In certain embodiments, an antigen binding protein comprises a heavy chain comprising a variable region comprising an amino acid sequence at least 90% identical to an amino acid sequence selected from at least one of the sequences of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60. In certain embodiments, an antigen binding protein comprises a heavy chain comprising a variable region comprising an amino acid sequence at least 95% identical to an amino acid sequence selected from at least one of the sequences of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60. In certain embodiments, an antigen binding protein comprises a heavy chain comprising a variable region comprising an amino acid sequence at least 99% identical to an amino acid sequence selected from at least one of the sequences of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60.

In some embodiments, the antigen binding protein comprises a sequence that is at least 90%, 90-95%, and/or 95-99% identical to one or more CDRs from the CDRs in at least one of sequences of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60. In some embodiments, 1, 2, 3, 4, 5, or 6 CDR (each being at least 90%, 90-95%, and/or 95-99% identical to the above sequences) is present.

In some embodiments, the antigen binding protein comprises a sequence that is at least 90%, 90-95%, and/or 95-99% identical to one or more FRs from the FRs in at least one of sequences of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60. In some embodiments, 1, 2, 3, or 4 FR (each being at least 90%, 90-95%, and/or 95-99% identical to the above sequences) is present.

In certain embodiments, an antigen binding protein comprises a light chain comprising a variable region comprising an amino acid sequence at least 90% identical to an amino acid sequence selected from at least one of the sequences of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In certain embodiments, an antigen binding protein comprises a light chain comprising a variable region comprising an amino acid sequence at least 95% identical to an amino acid sequence selected from at least one of the sequences of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In certain embodiments, an antigen binding protein comprises a light chain comprising a variable region comprising an amino acid sequence at least 99% identical to an amino acid sequence selected from at least one of the sequences of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46.

In some embodiments, the antigen binding protein comprises a sequence that is at least 90%, 90-95%, and/or 95-99% identical to one or more CDRs from the CDRs in at least one of sequences of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In some embodiments, 1, 2, 3, 4, 5, or 6 CDR (each being at least 90%, 90-95%, and/or 95-99% identical to the above sequences) is present.

In some embodiments, the antigen binding protein comprises a sequence that is at least 90%, 90-95%, and/or 95-99% identical to one or more FRs from the FRs in at least one of sequences of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In some embodiments, 1, 2, 3, or 4 FR (each being at least 90%, 90-95%, and/or 95-99% identical to the above sequences) is present.

In light of the present disclosure, a skilled artisan will be able to determine suitable variants of the ABPs as set forth herein using well-known techniques. In certain embodiments, one skilled in the art can identify suitable areas of the molecule that may be changed without destroying activity by targeting regions not believed to be important for activity. In certain embodiments, one can identify residues and portions of the molecules that are conserved among similar polypeptides. In certain embodiments, even areas that can be important for biological activity or for structure can be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art can opt for chemically similar amino acid substitutions for such predicted important amino acid residues.

One skilled in the art can also analyze the three-dimensional structure and amino acid sequence in relation to that structure in similar ABPs. In view of such information, one skilled in the art can predict the alignment of amino acid residues of an antibody with respect to its three dimensional structure. In certain embodiments, one skilled in the art can choose not to make radical changes to amino acid residues predicted to be on the surface of the protein, since such residues can be involved in important interactions with other molecules. Moreover, one skilled in the art can generate test variants containing a single amino acid substitution at each desired amino acid residue. The variants can then be screened using activity assays known to those skilled in the art. Such variants can be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci. USA, 84(13): 4355-4358 (1987)), and "evolutionary linkage" (See Holm, supra (1999), and Brenner, supra (1997)).

In certain embodiments, antigen binding protein variants include glycosylation variants wherein the number and/or type of glycosylation site has been altered compared to the amino acid sequences of a parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physicochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden & J. Tooze, eds., Garland Publishing, New York, N.Y. (1991)); and Thornton et al., Nature, 354:105 (1991), which are each incorporated herein by reference.

In some embodiments, the variants are variants of the nucleic acid sequences of the ABPs disclosed herein. One of skill in the art will appreciate that the above discussion can be used for identifying, evaluating, and/or creating ABP protein variants and also for nucleic acid sequences that can encode for those protein variants. Thus, nucleic acid sequences encoding for those protein variants (as well as nucleic acid sequences that encode for the ABPs in Table 2, but are different from those explicitly disclosed herein) are contemplated. For example, an ABP variant can have at least 80, 80-85, 85-90, 90-95, 95-97, 97-99 or greater identity to at least one nucleic acid sequence described in SEQ ID NOs: 152, 153, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151 or at least one to six (and various combinations thereof) of the CDR(s) encoded by the nucleic acid sequences in SEQ ID NOs: 152, 153, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, and 151.

In some embodiments, the antibody (or nucleic acid sequence encoding it) is a variant if the nucleic acid sequence that encodes the particular ABP (or the nucleic acid sequence itself) can selectively hybridize to any of the nucleic acid sequences that encode the proteins in Table 2 (such as, but not limited to SEQ ID NO: 152, 153, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, and 151) under stringent conditions. In one embodiment, suitable moderately stringent conditions include prewashing in a solution of 5×SSC; 0.5% SDS, 1.0 mM EDTA (pH 8:0); hybridizing at 50° C., −65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an antibody polypeptide that is encoded by a hybridizing DNA sequence and the amino acid sequences that are encoded by these nucleic acid sequences. In some embodiments, variants of CDRs include nucleic acid sequences and the amino acid sequences encoded by those sequences, that hybridize to one or more of the CDRs within the sequences noted above (individual CDRs can readily be determined in light of FIGS. 2A-3D, and other embodiments in FIGS. 3CCC-3JJJ and 15A-15D). The phrase "selectively hybridize" referred to in this context means to detectably and selectively bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

Preparation of Antigen Binding Proteins (e.g., Antibodies)

In certain embodiments, antigen binding proteins (such as antibodies) are produced by immunization with an antigen (e.g., PCSK9). In certain embodiments, antibodies can be produced by immunization with full-length PCSK9, a soluble form of PCSK9, the catalytic domain alone, the mature form of PCSK9 shown in FIG. 1A, a splice variant form of PCSK9, or a fragment thereof. In certain embodiments, the antibodies of the invention can be polyclonal or monoclonal, and/or can be recombinant antibodies. In certain embodiments, antibodies of the invention are human antibodies prepared, for example, by immunization of transgenic animals capable of producing human antibodies (see, for example, PCT Published Application No. WO 93/12227).

In certain embodiments, certain strategies can be employed to manipulate inherent properties of an antibody, such as the affinity of an antibody for its target. Such strategies include, but are not limited to, the use of site-specific or random mutagenesis of the polynucleotide molecule encoding an antibody to generate an antibody variant. In certain embodiments, such generation is followed by screening for antibody variants that exhibit the desired change, e.g. increased or decreased affinity.

In certain embodiments, the amino acid residues targeted in mutagenic strategies are those in the CDRs. In certain embodiments, amino acids in the framework regions of the variable domains are targeted. In certain embodiments, such framework regions have been shown to contribute to the target binding properties of certain antibodies. See, e.g., Hudson, Curr. Opin. Biotech., 9:395-402 (1999) and references therein.

In certain embodiments, smaller and more effectively screened libraries of antibody variants are produced by restricting random or site-directed mutagenesis to hyper-mutation sites in the CDRs, which are sites that correspond to areas prone to mutation during the somatic affinity maturation process. See, e.g., Chowdhury & Pastan, Nature Biotech., 17: 568-572 (1999) and references therein. In certain embodiments, certain types of DNA elements can be used to identify hyper-mutation sites including, but not limited to, certain direct and inverted repeats, certain consensus sequences, certain secondary structures, and certain palindromes. For example, such DNA elements that can be used to identify hyper-mutation sites include, but are not limited to, a tetrabase sequence comprising a purine (A or G), followed by guanine (G), followed by a pyrimidine (C or T), followed by either adenosine or thymidine (A or T) (i.e., A/G-G-C/T-A/T). Another example of a DNA element that can be used to identify hyper-mutation sites is the serine codon, A-G-C/T.

Preparation of Fully Human ABPs (e.g., Antibodies)

In certain embodiments, a phage display technique is used to generate monoclonal antibodies. In certain embodiments, such techniques produce fully human monoclonal antibodies. In certain embodiments, a polynucleotide encoding a single Fab or Fv antibody fragment is expressed on the surface of a phage particle. See, e.g., Hoogenboom et al., J. Mol. Biol., 227: 381 (1991); Marks et al., *J Mol Biol* 222: 581 (1991); U.S. Pat. No. 5,885,793. In certain embodiments, phage are "screened" to identify those antibody fragments having affinity for target. Thus, certain such processes mimic immune selection through the display of antibody fragment repertoires on the surface of filamentous bacteriophage, and subsequent selection of phage by their binding to target. In certain such procedures, high affinity functional neutralizing antibody fragments are isolated. In certain such embodiments (discussed in more detail below), a complete repertoire of human antibody genes is created by cloning naturally rearranged human V genes from peripheral blood lymphocytes. See, e.g., Mullinax et al., Proc Natl Acad Sci (USA), 87: 8095-8099 (1990).

According to certain embodiments, antibodies of the invention are prepared through the utilization of a transgenic mouse that has a substantial portion of the human antibody producing genome inserted but that is rendered deficient in the production of endogenous, murine antibodies. Such mice, then, are capable of producing human immunoglobulin molecules and antibodies and are deficient in the production of murine immunoglobulin molecules and antibodies. Technologies utilized for achieving this result are disclosed in the patents, applications and references disclosed in the specification, herein. In certain embodiments, one can employ methods such as those disclosed in PCT Published Application No. WO 98/24893 or in Mendez et al., Nature Genetics, 15:146-156 (1997), which are hereby incorporated by reference for any purpose.

Generally, fully human monoclonal ABPs (e.g., antibodies) specific for PCSK9 can be produced as follows. Transgenic mice containing human immunoglobulin genes are immunized with the antigen of interest, e.g. PCSK9, lymphatic cells (such as B-cells) from the mice that express antibodies are obtained. Such recovered cells are fused with a myeloid-type cell line to prepare immortal hybridoma cell lines, and such hybridoma cell lines are screened and selected to identify hybridoma cell lines that produce antibodies specific to the antigen of interest. In certain embodiments, the production of a hybridoma cell line that produces antibodies specific to PCSK9 is provided.

In certain embodiments, fully human antibodies are produced by exposing human splenocytes (B or T cells) to an antigen in vitro, and then reconstituting the exposed cells in an immunocompromised mouse, e.g. SCID or nod/SCID. See, e.g., Brams et al., J. Immunol. 160: 2051-2058 (1998); Carballido et al., Nat. Med., 6: 103-106 (2000). In certain such approaches, engraftment of human fetal tissue into SCID mice (SCID-hu) results in long-term hematopoiesis and human T-cell development. See, e.g., McCune et al., Science, 241:1532-1639 (1988); Ifversen et al., Sem. Immunol., 8:243-248 (1996). In certain instances, humoral immune response in such chimeric mice is dependent on co-development of human T-cells in the animals. See, e.g., Martensson et al., Immunol., 83:1271-179 (1994). In certain approaches, human peripheral blood lymphocytes are transplanted into SCID mice. See, e.g., Mosier et al., Nature, 335:256-259 (1988). In certain such embodiments, when such transplanted cells are treated either with a priming agent, such as Staphylococcal Enterotoxin A (SEA), or with anti-human CD40 monoclonal antibodies, higher levels of B cell production is detected. See, e.g., Martensson et al., Immunol., 84: 224-230 (1995); Murphy et al., Blood, 86:1946-1953 (1995).

Thus, in certain embodiments, fully human antibodies can be produced by the expression of recombinant DNA in host cells or by expression in hybridoma cells. In other embodiments, antibodies can be produced using the phage display techniques described herein.

The antibodies described herein were prepared through the utilization of the XenoMouse® technology, as described herein. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al., Nature Genetics, 15:146-156 (1997), the disclosure of which is hereby incorporated by reference.

Through the use of such technology, fully human monoclonal antibodies to a variety of antigens have been produced. Essentially, XenoMouse® lines of mice are immunized with an antigen of interest (e.g. PCSK9), lymphatic cells (such as B-cells) are recovered from the hyper-immunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to PCSK9 Further, provided herein are characterization of the antibodies produced by such cell lines, including nucleotide and amino acid sequence analyses of the heavy and light chains of such antibodies.

The production of the XenoMouse® strains of mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg & Kay, U.S. Pat. Nos. 5,591,669 and 6,023.010 to Krimpenfort & Berns, U.S. Pat. Nos. 5,612,205, 5,721,367, and 5,789,215 to Berns et al., and U.S. Pat. No. 5,643,763 to Choi & Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™ mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

In some embodiments, the antibodies described herein possess human IgG4 heavy chains as well as IgG2 heavy chains. Antibodies can also be of other human isotypes, including IgG1. The antibodies possessed high affinities, typically possessing a Kd of from about $10^{-6}$ through about $10^{-13}$ M or below, when measured by various techniques.

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912, 040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive PCSK9 binding properties.

In certain embodiments, antibodies and/or ABP are produced by at least one of the following hybridomas: 21B12, 31H4, 16F12, any the other hybridomas listed in Table 2 or disclosed in the examples. In certain embodiments, antigen binding proteins bind to PCSK9 with a dissociation constant ($K_D$) of less than approximately 1 nM, e.g., 1000 pM to 100 pM, 100 pM to 10 pM, 10 pM to 1 pM, and/or 1 pM to 0.1 pM or less.

In certain embodiments, antigen binding proteins comprise an immunoglobulin molecule of at least one of the IgG1, IgG2, IgG3, IgG4, Ig E, IgA, IgD, and IgM isotype. In certain embodiments, antigen binding proteins comprise a human kappa light chain and/or a human heavy chain. In certain embodiments, the heavy chain is of the IgG1, IgG2, IgG3, IgG4, IgE, IgA, IgD, or IgM isotype. In certain embodiments, antigen binding proteins have been cloned for expression in mammalian cells. In certain embodiments, antigen binding proteins comprise a constant region other than any of the constant regions of the IgG1, IgG2, IgG3, IgG4, IgE, IgA, IgD, and IgM isotype.

In certain embodiments, antigen binding proteins comprise a human lambda light chain and a human IgG2 heavy chain. In certain embodiments, antigen binding proteins comprise a human lambda light chain and a human IgG4 heavy chain. In certain embodiments, antigen binding proteins comprise a human lambda light chain and a human IgG1, IgG3, IgE, IgA, IgD or IgM heavy chain. In other embodiments, antigen binding proteins comprise a human kappa light chain and a human IgG2 heavy chain. In certain embodiments, antigen binding proteins comprise a human kappa light chain and a human IgG4 heavy chain. In certain embodiments, antigen binding proteins comprise a human kappa light chain and a human IgG1, IgG3, IgE, IgA, IgD or IgM heavy chain. In certain embodiments, antigen binding proteins comprise variable regions of antibodies ligated to a constant region that is neither the constant region for the IgG2 isotype, nor the constant region for the IgG4 isotype. In certain embodiments, antigen binding proteins have been cloned for expression in mammalian cells.

In certain embodiments, conservative modifications to the heavy and light chains of antibodies from at least one of the hybridoma lines: 21B12, 31H4 and 16F12 (and corresponding modifications to the encoding nucleotides) will produce antibodies to PCSK9 having functional and chemical characteristics similar to those of the antibodies from the hybridoma lines: 21B12, 31H4 and 16F12. In contrast, in certain embodiments, substantial modifications in the functional and/or chemical characteristics of antibodies to PCSK9 can be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" can involve a substitution of a native amino acid residue with a normative residue such that there is little or no effect on the polarity or charge of the amino acid residue at that position. Furthermore, any native residue in the polypeptide can also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of antibodies to PCSK9, or to increase or decrease the affinity of the antibodies to PCSK9 as described herein.

In certain embodiments, antibodies of the present invention can be expressed in cell lines other than hybridoma cell lines. In certain embodiments, sequences encoding particular antibodies can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference for any purpose). In certain embodiments, the transformation procedure used can depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines can be selected through determining which cell lines have high expression levels and produce antibodies with constitutive HGF binding properties. Appropriate expression vectors for mammalian host cells are well known.

In certain embodiments, antigen binding proteins comprise one or more polypeptides. In certain embodiments, any of a variety of expression vector/host systems can be utilized to express polynucleotide molecules encoding polypeptides comprising one or more ABP components or the ABP itself. Such systems include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems.

In certain embodiments, a polypeptide comprising one or more ABP components or the ABP itself is recombinantly expressed in yeast. Certain such embodiments use commercially available expression systems, e.g., the *Pichia* Expression System (Invitrogen, San Diego, Calif.), following the manufacturer's instructions. In certain embodiments, such a system relies on the pre-pro-alpha sequence to direct secretion. In certain embodiments, transcription of the insert is driven by the alcohol oxidase (AOX1) promoter upon induction by methanol.

In certain embodiments, a secreted polypeptide comprising one or more ABP components or the ABP itself is purified from yeast growth medium. In certain embodiments, the methods used to purify a polypeptide from yeast growth medium is the same as those used to purify the polypeptide from bacterial and mammalian cell supernatants.

In certain embodiments, a nucleic acid encoding a polypeptide comprising one or more ABP components or the ABP itself is cloned into a baculovirus expression vector, such as pVL1393 (PharMingen, San Diego, Calif.). In certain embodiments, such a vector can be used according to the manufacturer's directions (PharMingen) to infect *Spodoptera frugiperda* cells in sF9 protein-free media and to produce recombinant polypeptide. In certain embodiments, a polypeptide is purified and concentrated from such media using a heparin-Sepharose column (Pharmacia).

In certain embodiments, a polypeptide comprising one or more ABP components or the ABP itself is expressed in an insect system. Certain insect systems for polypeptide expression are well known to those of skill in the art. In one such system, *Autographa californica* nuclear polyhedrosis virus (AcNPV) is used as a vector to express foreign genes in *Spodoptera frugiperda* cells or in *Trichoplusia larvae*. In certain embodiments, a nucleic acid molecule encoding a polypeptide can be inserted into a nonessential gene of the virus, for example, within the polyhedrin gene, and placed under control of the promoter for that gene. In certain embodiments, successful insertion of a nucleic acid molecule will render the nonessential gene inactive. In certain embodiments, that inactivation results in a detectable characteristic. For example, inactivation of the polyhedrin gene results in the production of virus lacking coat protein.

In certain embodiments, recombinant viruses can be used to infect *S. frugiperda* cells or *Trichoplusia larvae*. See, e.g., Smith et al., J. Virol., 46: 584 (1983); Engelhard et al., Proc. Nat. Acad. Sci. (USA), 91: 3224-7 (1994).

In certain embodiments, polypeptides comprising one or more ABP components or the ABP itself made in bacterial cells are produced as insoluble inclusion bodies in the bacteria. In certain embodiments, host cells comprising such inclusion bodies are collected by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. In certain embodiments, the lysate is cleared by sonication, and cell debris is pelleted by centrifugation for 10 minutes at 12,000×g. In certain embodiments, the polypeptide-containing pellet is resuspended in 50 mM Tris, pH 8, and 10 mM EDTA; layered over 50% glycerol; and centrifuged for 30 minutes at 6000×g. In certain embodiments, that pellet can be resuspended in standard phosphate buffered saline solution (PBS) free of $Mg^{++}$ and $Ca^{++}$. In certain embodiments, the polypeptide is further purified by fractionating the resuspended pellet in a denaturing SDS polyacrylamide gel (See, e.g., Sambrook et al., supra). In certain embodiments, such a gel can be soaked in 0.4 M KCl to visualize the protein, which can be excised and electroeluted in gel-running buffer lacking SDS. According to certain embodiments, a Glutathione-S-Transferase (GST) fusion protein is produced in bacteria as a soluble protein. In certain embodiments, such GST fusion protein is purified using a GST Purification Module (Pharmacia).

In certain embodiments, it is desirable to "refold" certain polypeptides, e.g., polypeptides comprising one or more ABP components or the ABP itself. In certain embodiments, such polypeptides are produced using certain recombinant systems discussed herein. In certain embodiments, polypeptides are "refolded" and/or oxidized to form desired tertiary structure and/or to generate disulfide linkages. In certain embodiments, such structure and/or linkages are related to certain biological activity of a polypeptide. In certain embodiments, refolding is accomplished using any of a number of procedures known in the art. Exemplary methods include, but are not limited to, exposing the solubilized polypeptide agent to a pH typically above 7 in the presence of a chaotropic agent. An exemplary chaotropic agent is guanidine. In certain embodiments, the refolding/oxidation solution also contains a reducing agent and the oxidized form of that reducing agent. In certain embodiments, the reducing agent and its oxidized form are present in a ratio that will generate a particular redox potential that allows disulfide shuffling to occur. In certain embodiments, such shuffling allows the formation of cysteine bridges. Exemplary redox couples include, but are not limited to, cysteine/cystamine, glutathione/dithiobisGSH, cupric chloride, dithiothreitol DTT/dithiane DTT, and 2-mercaptoethanol (bME)/dithio-bME. In certain embodiments, a co-solvent is used to increase the efficiency of refolding. Exemplary cosolvents include, but are not limited to, glycerol, polyethylene glycol of various molecular weights, and arginine.

In certain embodiments, one substantially purifies a polypeptide comprising one or more ABP components or the ABP itself. Certain protein purification techniques are known to those of skill in the art. In certain embodiments, protein purification involves crude fractionation of polypeptide fractionations from non-polypeptide fractions. In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxyapatite chromatography; isoelectric focusing; polyacrylamide gel electrophoresis; and combinations of such and other techniques. In certain embodiments, a polypeptide is purified by fast protein liquid chromatography or by high pressure liquid chromotography (HPLC). In certain embodiments, purification steps can be changed or certain steps can be omitted, and still result in a suitable method for the preparation of a substantially purified polypeptide.

In certain embodiments, one quantitates the degree of purification of a polypeptide preparation. Certain methods for quantifying the degree of purification are known to those of skill in the art. Certain exemplary methods include, but are not limited to, determining the specific binding activity of the preparation and assessing the amount of a polypeptide within a preparation by SDS/PAGE analysis. Certain exemplary methods for assessing the amount of purification of a polypeptide preparation comprise calculating the binding activity of a preparation and comparing it to the binding activity of an initial extract. In certain embodiments, the results of such a calculation are expressed as "fold purification." The units used to represent the amount of binding activity depend upon the particular assay performed.

In certain embodiments, a polypeptide comprising one or more ABP components or the ABP itself is partially purified. In certain embodiments, partial purification can be accomplished by using fewer purification steps or by utilizing different forms of the same general purification scheme. For example, in certain embodiments, cation-exchange column chromatography performed utilizing an HPLC apparatus will generally result in a greater "fold purification" than the same technique utilizing a low-pressure chromatography system. In certain embodiments, methods resulting in a lower degree of purification can have advantages in total recovery of polypeptide, or in maintaining binding activity of a polypeptide.

In certain instances, the electrophoretic migration of a polypeptide can vary, sometimes significantly, with different conditions of SDS/PAGE. See, e.g., Capaldi et al., Biochem. Biophys. Res. Comm, 76: 425 (1977). It will be appreciated that under different electrophoresis conditions, the apparent molecular weights of purified or partially purified polypeptide can be different.

Exemplary Epitopes

Epitopes to which anti-PCSK9 antibodies bind are provided. In some embodiments, epitopes that are bound by the presently disclosed antibodies are particularly useful. In some embodiments, antigen binding proteins that bind to any of the epitopes that are bound by the antibodies described herein are useful. In some embodiments, the epitopes bound by any of the antibodies listed in Table 2 and FIGS. 2 and 3 are especially useful. In some embodiments, the epitope is on the catalytic domain PCSK9.

In certain embodiments, a PCSK9 epitope can be utilized to prevent (e.g., reduce) binding of an anti-PCSK9 antibody or antigen binding protein to PCSK9. In certain embodiments, a PCSK9 epitope can be utilized to decrease binding of an anti-PCSK9 antibody or antigen binding protein to PCSK9. In certain embodiments, a PCSK9 epitope can be utilized to substantially inhibit binding of an anti-PCSK9 antibody or antigen binding protein to PCSK9.

In certain embodiments, a PCSK9 epitope can be utilized to isolate antibodies or antigen binding proteins that bind to PCSK9. In certain embodiments, a PCSK9 epitope can be utilized to generate antibodies or antigen binding proteins which bind to PCSK9. In certain embodiments, a PCSK9 epitope or a sequence comprising a PCSK9 epitope can be utilized as an immunogen to generate antibodies or antigen binding proteins that bind to PCSK9. In certain embodiments, a PCSK9 epitope can be administered to an animal, and antibodies that bind to PCSK9 can subsequently be obtained from the animal. In certain embodiments, a PCSK9 epitope or a sequence comprising a PCSK9 epitope can be utilized to interfere with normal PCSK9-mediated activity, such as association of PCSK9 with the LDLR.

In some embodiments, antigen binding proteins disclosed herein bind specifically to N-terminal prodomain, a subtilisin-like catalytic domain and/or a C-terminal domain. In some embodiments, the antigen binding protein binds to the substrate-binding groove of PCSK-9 (described in Cunningham et al., incorporated herein in its entirety by reference).

In some embodiments, the domain(s)/region(s) containing residues that are in contact with or are buried by an antibody can be identified by mutating specific residues in PCSK9 (e.g., a wild-type antigen) and determining whether the antigen binding protein can bind the mutated or variant PCSK9 protein. By making a number of individual mutations, residues that play a direct role in binding or that are in sufficiently close proximity to the antibody such that a mutation can affect binding between the antigen binding protein and antigen can be identified. From knowledge of these amino acids, the domain(s) or region(s) of the antigen that contain residues in contact with the antigen binding protein or covered by the antibody can be elucidated. Such a domain can include the binding epitope of an antigen binding protein. One specific example of this general approach utilizes an arginine/glutamic acid scanning protocol (see, e.g., Nanevicz, T., et al., 1995, *J. Biol. Chem.,* 270:37, 21619-21625 and Zupnick, A., et al., 2006, *J. Biol. Chem.,* 281:29, 20464-20473). In general, arginine and glutamic acids are substituted (typically individually) for an amino acid in the wild-type polypeptide because these amino acids are charged and bulky and thus have the potential to disrupt binding between an antigen binding protein and an antigen in the region of the antigen where the mutation is introduced. Arginines that exist in the wild-type antigen are replaced with glutamic acid. A variety of such individual mutants are obtained and the collected binding results analyzed to determine what residues affect binding.

An alteration (for example a reduction or increase) in binding between an antigen binding protein and a variant PCSK9 as used herein means that there is a change in binding affinity (e.g., as measured by known methods such as Biacore testing or the bead based assay described below in the examples), $EC_{50}$, and/or a change (for example a reduction) in the total binding capacity of the antigen binding protein (for example, as evidenced by a decrease in Bmax in a plot of antigen binding protein concentration versus antigen concentration). A significant alteration in binding indicates that the mutated residue is directly involved in binding to the antigen binding protein or is in close proximity to the binding protein when the binding protein is bound to antigen.

In some embodiments, a significant reduction in binding means that the binding affinity, EC50, and/or capacity between an antigen binding protein and a mutant PCSK9 antigen is reduced by greater than 10%, greater than 20%, greater than 40%, greater than 50%, greater than 55%, greater than 60%, greater than 65%, greater than 70%, greater than 75%, greater than 80%, greater than 85%, greater than 90% or greater than 95% relative to binding between the antigen binding protein and a wild type PCSK9 (e.g., shown in SEQ ID NO: 1 and/or SEQ ID NO: (303). In certain embodiments, binding is reduced below detectable limits. In some embodiments, a significant reduction in binding is evidenced when binding of an antigen binding protein to a variant PCSK9 protein is less than 50% (for example, less than 40%, 35%, 30%, 25%, 20%, 15% or 10%) of the binding observed between the antigen binding protein and a wild-type PCSK9 protein (for example, the protein of SEQ ID NO: 1 and/or SEQ ID NO: (303). Such binding measurements can be made using a variety of binding assays known in the art.

In some embodiments, antigen binding proteins are provided that exhibit significantly lower binding for a variant PCSK9 protein in which a residue in a wild-type PCSK9 protein (e.g., SEQ ID NO: 1 or SEQ ID NO: 303 is substituted with arginine or glutamic acid. In some embodiments, binding of an antigen binding protein is significantly reduced or increased for a variant PCSK9 protein having any one or more (e.g., 1, 2, 3, 4, 5, 6, 7, 8, 9, 10, or 244) of the following mutations: R207E, D208R, R185E, R439E, E513R, V538R, E539R, T132R, S351R, A390R, A413R, E582R, D162R, R164E, E167R, S123R, E129R, A311R, D313R, D337R, R519E, H521R, and Q554R as compared to a wild-type PCSK9 protein (e.g., SEQ ID NO: 1 or SEQ ID NO: 303. In the shorthand notation used here, the format is: Wild type residue: Position in polypeptide: Mutant residue, with the numbering of the residues as indicated in SEQ ID NO: for SEQ ID NO: 303.

In some embodiments, binding of an antigen binding protein is significantly reduced or increased for a mutant PCSK9 protein having one or more (e.g., 1, 2, 3, 4, 5, or more) mutations at the following positions: 207, 208, 185, 181, 439, 513, 538, 539, 132, 351, 390, 413, 582, 162, 164, 167, 123, 129, 311, 313, 337, 519, 521, and 554, as shown in SEQ ID NO: 1 as compared to a wild-type PCSK9 protein (e.g., SEQ ID NO: 1 or SEQ ID NO: 303. In some embodiments, binding of an antigen binding protein is reduced or increased for a mutant PCSK9 protein having one or more (e.g., 1, 2, 3, 4, 5, or more) mutations at the following positions: 207, 208, 185, 181, 439, 513, 538, 539, 132, 351, 390, 413, 582, 162, 164, 167, 123, 129, 311, 313, 337, 519, 521, and 554, as shown in SEQ ID NO: 1 as compared to a wild-type PCSK9 protein (e.g., SEQ ID NO: 1 or SEQ ID NO: 303. In some embodiments, binding of an antigen binding protein is substantially reduced or increased for a mutant PCSK9 protein having one or more (e.g., 1, 2, 3, 4, 5, or more) mutations at the following positions: 207, 208, 185, 181, 439, 513, 538, 539, 132, 351, 390, 413, 582, 162, 164, 167, 123, 129, 311, 313, 337, 519, 521, and 554, within SEQ ID NO: 1 as compared to a wild-type PCSK9 protein (e.g., SEQ ID NO: 1 or SEQ ID NO: 303.

In some embodiments, binding of an ABP is significantly reduced or increased for a mutant PCSK9 protein having one or more (e.g., 1, 2, 3, 4, 5, etc.) of the following mutations: R207E, D208R, R185E, R439E, E513R, V538R, E539R, T132R, S351R, A390R, A413R, E582R, D162R, R164E, E167R, S123R, E129R, A311R, D313R, D337R, R519E, H521R, and Q554R within SEQ ID NO: 1 or SEQ ID NO: 303, as compared to a wild-type PCSK9 protein (e.g., SEQ ID NO: 1 or SEQ ID NO: 303).

In some embodiments, binding of an ABP is significantly reduced or increased for a mutant PCSK9 protein having one or more (e.g., 1, 2, 3, 4, 5, etc.) of the following mutations: R207E, D208R, R185E, R439E, E513R, V538R, E539R, T132R, S351R, A390R, A413R, and E582R within SEQ ID NO: 1 or SEQ ID NO: 303, as compared to a wild-type PCSK9 protein (e.g., SEQ ID NO: 1 or SEQ ID NO: 303). In some embodiments, the binding is reduced. In some embodiments, the reduction in binding is observed as a change in EC50. In some embodiments, the change in EC50 is an increase in the numerical value of the EC50 (and thus is a decrease in binding).

In some embodiments, binding of an ABP is significantly reduced or increased for a mutant PCSK9 protein having one or more (e.g., 1, 2, 3, 4, 5, etc.) of the following mutations: D162R, R164E, E167R, S123R, E129R, A311R, D313R, D337R, R519E, H521R, and Q554R within SEQ ID NO: 1, as compared to a wild-type PCSK9 protein (e.g., SEQ ID NO: 1 or SEQ ID NO: 303). In some embodiments, the binding is reduced. In some embodiments, the reduction in binding is observed as a change in Bmax. In some embodiments, the shift in Bmax is a reduction of the maximum signal generated by the ABP. In some embodiments, for an amino acid to be part of an epitope, the Bmax is reduced by at least 10%, for example, reductions of at least any of the following amounts: 20, 30, 40, 50, 60, 70, 80, 90, 95, 98, 99, or 100 percent can, in some embodiments, indicate that the residue is part of the epitope.

Although the variant forms just listed are referenced with respect to the wild-type sequence shown in SEQ ID NO: 1 or SEQ ID NO: 303, it will be appreciated that in an allelic variant of PCSK9 the amino acid at the indicated position could differ. Antigen binding proteins showing significantly lower binding for such allelic forms of PCSK9 are also contemplated. Accordingly, in some embodiments, any of the above embodiments can be compared to an allelic sequence, rather than purely the wild-type sequence shown in FIG. 1A In some embodiments, binding of an antigen binding protein is significantly reduced for a variant PCSK9 protein in which the residue at a selected position in the wild-type PCSK9 protein is mutated to any other residue. In some embodiments, the herein described arginine/glutamic acid replacements are used for the identified positions. In some embodiments, alanine is used for the identified positions.

As noted above, residues directly involved in binding or covered by an antigen binding protein can be identified from scanning results. These residues can thus provide an indication of the domains or regions of SEQ ID NO: 1 (or SEQ ID NO: 303 or SEQ ID NO: 3) that contain the binding region(s) to which antigen binding proteins bind. As can be seen from the results summarized in Example 39, in some embodiments an antigen binding protein binds to a domain containing at least one of amino acids: 207, 208, 185, 181, 439, 513, 538, 539, 132, 351, 390, 413, 582, 162, 164, 167, 123, 129, 311, 313, 337, 519, 521, and 554 of SEQ ID NO: 1 or SEQ ID NO: 303. In some embodiments, the antigen binding protein binds to a region containing at least one of amino acids 207, 208, 185, 181, 439, 513, 538, 539, 132, 351, 390, 413, 582, 162, 164, 167, 123, 129, 311, 313, 337, 519, 521, and 554 of SEQ ID NO: 1 or SEQ ID NO: 303.

In some embodiments, the antigen binding protein binds to a region containing at least one of amino acids 162, 164, 167, 207 and/or 208 of SEQ ID NO: 1 or SEQ ID NO: 303. In some embodiments, more than one (e.g., 2, 3, 4, or 5) of the identified residues are part of the region that is bound by the ABP. In some embodiments, the ABP competes with ABP 21B12.

In some embodiments, the antigen binding protein binds to a region containing at least one of amino acid 185 of SEQ ID NO: 1 or SEQ ID NO: 303. In some embodiments, the ABP competes with ABP 31H4.

In some embodiments, the antigen binding protein binds to a region containing at least one of amino acids 439, 513, 538, and/or 539 of SEQ ID NO: 1 or SEQ ID NO: 303. In some embodiments, more than one (e.g., 2, 3, or 4) of the identified residues are part of the region that is bound by the ABP. In some embodiments, the ABP competes with ABP 31A4.

In some embodiments, the antigen binding protein binds to a region containing at least one of amino acids 123, 129, 311, 313, 337, 132, 351, 390, and/or 413 of SEQ ID NO: 1 or SEQ ID NO: 303. In some embodiments, more than one (e.g., 2, 3, 4, 5, 6, 7, 8, or 9) of the identified residues are part of the region that is bound by the ABP. In some embodiments, the ABP competes with ABP 12H11.

In some embodiments, the antigen binding protein binds to a region containing at least one of amino acid 582, 519, 521, and/or 554 of SEQ ID NO: 1 or SEQ ID NO: 303. In some embodiments, more than one (e.g., 2, 3, or 4) of the identified residues are part of the region that is bound by the ABP. In some embodiments, the ABP competes with ABP 3C4.

In some embodiments, the antigen binding proteins binds to the foregoing regions within a fragment or the full length sequence of SEQ ID NO: 1 or SEQ ID NO: 303. In other embodiments, antigen binding proteins bind to polypeptides consisting of these regions. The reference to "SEQ ID NO: 1 or SEQ ID NO: 303" denotes that one or both of these sequences can be employed or relevant. The phrase does not denote that only one should be employed.

As noted above, the above description references specific amino acid positions with reference to SEQ ID NO: 1. However, throughout the specification generally, reference is made to a Pro/Cat domain that commences at position 31, which is provided in SEQ ID NO: 3. As noted below, SEQ ID NO: 1 and SEQ ID NO: 303 lack the signal sequence of PCSK9. As such, any comparison between these various disclosures should take this difference in numbering into account. In particular, any amino acid position in SEQ ID NO: 1, will correspond to an amino acid position 30 amino acids further into the protein in SEQ ID NO: 3. For example, position 207 of SEQ ID NO: 1, corresponds to position 237 of SEQ ID NO: 3 (the full length sequence, and the numbering system used in the present specification generally). Table 39.6 outlines how the above noted positions, which reference SEQ ID NO: 1 (and/or SEQ ID NO: 303) correspond to SEQ ID NO: 3 (which includes the signal sequence). Thus, any of the above noted embodiments that are described in regard to SEQ ID NO: 1 (and/or SEQ ID NO: 303), are described in reference to SEQ ID NO: 3, by the noted corresponding positions.

In some embodiments, ABP 21B12 binds to an epitope including residues 162-167 (e.g., residues D162-E167 of SEQ ID NO: 1). In some embodiments, ABP 12H11 binds to an epitope that includes residues 123-132 (e.g., 5123-T132 of SEQ ID NO: 1). In some embodiments, ABP 12H11 binds to an epitope that includes residues 311-313 (e.g., A311-D313 of SEQ ID NO: 1). In some embodiments, ABPs can bind to an epitope that includes any one of these strands of sequences.

Competing Antigen Binding Proteins

In another aspect, antigen binding proteins are provided that compete with one of the exemplified antibodies or functional fragments binding to the epitope described herein for specific binding to PCSK9. Such antigen binding proteins can also bind to the same epitope as one of the herein exemplified antigen binding proteins, or an overlapping epitope. Antigen binding proteins and fragments that compete with or bind to the same epitope as the exemplified antigen binding proteins are expected to show similar functional properties. The exemplified antigen binding proteins and fragments include those described above, including those with the heavy and light chains, variable region domains and CDRs included in TABLE 2 and/or FIGS. 2-3. Thus, as a specific example, the antigen binding proteins that are provided include those that compete with an antibody or antigen binding protein having:

(a) all 6 of the CDRs listed for an antibody listed in FIGS. 2-3;

(b) a VH and a VL listed for an antibody listed in Table 2; or (c) two light chains and two heavy chains as specified for an antibody listed in Table 2.

Therapeutic Pharmaceutical Formulations and Administration

The present invention provides pharmaceutical formulations containing antigen binding proteins to PCSK9. As used herein, "pharmaceutical formulation" is a sterile composition of a pharmaceutically active drug, namely, at least one antigen binding protein to PCSK9, that is suitable for parenteral administration (including but not limited to intravenous, intramuscular, subcutaneous, aerosolized, intrapulmonary, intranasal, or intrathecal) to a patient in need thereof and includes only pharmaceutically acceptable excipients, diluents, and other additives deemed safe by the Federal Drug Administration or other foreign national authorities. Pharmaceutical formulations include liquid, e.g., aqueous, solutions that may be directly administered, and lyophilized powders which may be reconstituted into solutions by adding a diluent before administration. Specifically excluded from the scope of the term "pharmaceutical formulation" are compositions for topical administration to patients, compositions for oral ingestion, and compositions for parenteral feeding.

In certain embodiments, the pharmaceutical formulation is a stable pharmaceutical formulation. As used herein, the phrases, "stable pharmaceutical formulation, "stable formulation" or "a pharmaceutical formulation is stable" refers to a pharmaceutical formulation of biologically active proteins that exhibit increased aggregation and/or reduced loss of biological activity of not more than 5% when stored at 2-8° C. for at least 1 month, or 2 months, or 3 months, or 6 months, or 1 year or 2 years compared with a control formula sample. Formulation stability can be easily determined by a person of skill in the art using any number of standard assays, including but not limited to size exclusion HPLC ("SEC-HPLC"), cation-exchange HPLC (CEX-HPLC), Subvisible Particle Detection by Light Obscuration ("HIAC") and/or visual inspection.

In certain embodiments, the pharmaceutical formulation comprises any of the antigen binding proteins to PCSK9 depicted in Table 2 and FIGS. 2 and/or 3. In some embodiments the pharmaceutical formulation comprises any one of 21B12, 26H5, 31H4, 8A3, 11F1 or 8A1.

In some embodiments, the pharmaceutical formulation comprises more than one different antigen binding protein to PCSK9. In certain embodiments, pharmaceutical formulations comprise more than one antigen binding protein to PCSK9 wherein the antigen binding proteins to PCSK9 bind more than one epitope. In some embodiments, the various antigen binding proteins will not compete with one another for binding to PCSK9. In some embodiments, any of the antigen binding proteins depicted in Table 2 and FIGS. 2 and/or 3 can be combined together in a pharmaceutical formulation.

In certain embodiments, an antigen binding protein to PCSK9 and/or a therapeutic molecule is linked to a half-life extending vehicle known in the art. Such vehicles include, but are not limited to, polyethylene glycol, glycogen (e.g., glycosylation of the ABP), and dextran. Such vehicles are described, e.g., in U.S. application Ser. No. 09/428,082, now U.S. Pat. No. 6,660,843 and published PCT Application No. WO 99/25044, which are hereby incorporated by reference for any purpose.

In certain embodiments, acceptable formulation materials preferably are nontoxic to recipients at the dosages and concentrations employed. In some embodiments, the formulation material(s) are for s.c. and/or I.V. administration. In certain embodiments, the pharmaceutical formulation comprises formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, suitable formulation materials include, but are not limited to, amino acids (such as proline, arginine, lysine, methionine, taurine, glycine, glutamine, or asparagine); antimicrobials; antioxidants (such as ascorbic acid, sodium sulfite or sodium hydrogen-sulfite); buffers (such as borate, bicarbonate, sodium phosphate ("NaOAC"), Tris-HCl, Tris buffer, citrates, phosphate buffer, phosphate-buffered saline (i.e., PBS buffer) or other organic acids); bulking agents (such as mannitol or glycine); chelating agents (such as ethylenediamine tetra acetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, sucrose, fructose, lactose, mannose, trehelose, or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences*, 18$^{th}$ Edition, A. R. Gennaro, ed., Mack Publishing Company (1995).

In certain embodiments, the optimal pharmaceutical formulation will be determined by one skilled in the art depending upon, for example, the intended route of administration, delivery format and desired dosage. See, for example, *Remington's Pharmaceutical Sciences, supra*. In certain embodiments, such formulations may influence the physical state, stability, rate of in vivo release and rate of in vivo clearance of the antibodies of the invention.

In one aspect, the pharmaceutical formulation comprises high concentrations of antigen binding protein to PCSK9. In certain embodiments, ABP concentration ranges from about 70 mg/ml to about 250 mg/ml, e.g., about 70 mg/ml, about 80 mg/ml, about 90 mg/ml, about 100 mg/ml, about 100 mg/ml, about 120 mg/ml, about 130 mg/ml, about 140 mg/ml, about 150 mg/ml, about 160 mg/ml, about 170 mg/ml, about 180 mg/ml, about 190 mg/ml, about 200 mg/ml, about 210 mg/ml, about 220 mg/ml, about 230 mg/ml, about 240 mg/ml, or about 250 mg/ml, and including all values in between. In some embodiments, the concentration of 21B12, 26H5, or 31H4 ranges from about 100 mg/ml to about 150 mg/ml, e.g., 100 mg/ml, about 100 mg/ml, about 120 mg/ml, about 130 mg/ml, about 140 mg/ml, or about 150 mg/ml. In some embodiments, the concentration of 8A3, 11F1 or 8A1 ranges from about 140 mg/ml to about 220 mg/ml, e.g., 140 mg/ml, about 150 mg/ml, about 160 mg/ml, about 170 mg/ml, about 180 mg/ml, about 190 mg/ml, about 200 mg/ml, about 210 mg/ml, about 220 mg/ml, or about 250 mg/ml.

In another aspect, the pharmaceutical formulation comprises at least one buffering agent such as, for example, sodium acetate, sodium chloride, phosphates, phosphate buffered saline ("PBS"), and/or Tris buffer of about pH 7.0-8.5. The buffer serves to maintain a physiologically suitable pH. In addition, the buffer can serve to enhance isotonicity and chemical stability of the pharmaceutical formulation. In certain embodiments, the buffering agent ranges from about 0.05 mM to about 40 mM, e.g., about 0.05 mM, about 0.1 mM, about 0.5 mM, about 1.0 mM, about 5.0 mM, about 10 mM, about 15 mM, about 20 mM, about 30 mM, about 40 mM, about 50 mM, about 60 mM, about 70 mM, about 80 mM, about 90 mM, or about 100 nM buffering agent, inclusive of all values in between. In certain embodiments, the buffering agent is NaOAC. Exemplary pHs of the pharmaceutical formulation include from about 4 to about 6, or from about 4.8 to about 5.8, or from about 5.0 to about 5.2, or about 5, or about 5.2.

In certain embodiments, the pharmaceutical formulation is isotonic with an osmolality ranging from between about 250 to about 350 miliosmol/kg, e.g., about 250 mOsm/kg, about 260 mOsm/kg, about 270 mOsm/kg, about 280 mOsm/kg, about 290 mOsm/kg, about 300 mOsm/kg, about 310 mOsm/kg, about 320 mOsm/kg, about 330 mOsm/kg, about 340 mOsm/kg, or about 350 mOsm/kg, and including all values in between. As used herein, "osmolality" is the measure of the ratio of solutes to volume fluid. In other words, it is the number of molecules and ions (or molecules) per kilogram of a solution. Osmolality may be measured on an analytical instrument called an osmometer, such as Advanced Instruments 2020 Multi-sample Osmometer, Norwood, Mass. The Advanced Instruments 2020 Multi-sample Osmometer measures osmolality by using the Freezing Point Depression method. The higher the osmolytes in a solution, the temperature in which it will freeze drops. Osmolality may also be measured using any other methods and in any other units known in the art such as linear extrapolation.

In still another aspect, the pharmaceutical formulation comprises at least one surfactant including but not limited to Polysorbate-80, Polysorbate-60, Polysorbate-40, and Polysorbate-20. In certain embodiments, the pharmaceutical formulation comprises a surfactant at a concentration that ranges from about 0.004% to about 10% weight per volume ("w/v") of the formulation, e.g., about 0.004%, about 0.005%, about 0.006%, about 0.007%, about 0.008%, about 0.009%, about 0.01%, about 0.05%, about 0.1%, about 0.5%, about 1%, about 5%, or about 10% surfactant w/v of the formulation. In certain embodiments, the pharmaceutical formulation comprises polysorbate 80 at a concentration that ranges from about 0.004% to about 0.1% w/v of the formulation. In certain embodiments, the pharmaceutical formulation comprises polysorbate 20 at a concentration that ranges from about 0.004% to about 0.1% w/v of the formulation.

In certain embodiments, the pharmaceutical formulation comprises at least one stabilizing agent, such as a polyhydroxy hydrocarbon (including but not limited to sorbitol, mannitol, glycerol and dulcitol) and/or a disaccharide (including but not limited to sucrose, lactose, maltose and threhalose) and/or an amino acid (including but not limited to proline, arginine, lysine, methionine, and taurine) and or benzyl alcohol; the total of said polyhydroxy hydrocarbon and/or disaccharide and/or amino acid and/or benzyl alcohol being about 0.5% to about 10% w/v of the formulation. In certain embodiments, the pharmaceutical formulation comprises a stabilizing agent at a concentration of about 1%, about 2%, about 3%, about 4%, about 5%, about 6%, about 7%, about 8%, about 9% or about 10% sucrose. In certain embodiments, the pharmaceutical formulation comprises a stabilizing agent at a concentration of about 5% sucrose. In certain embodiments, the pharmaceutical formulation comprises a stabilizing agent at a concentration of about 1%, about 2%, about 3%, about 4%, about 5%, about 6%, about 7%, about 8%, about 9% or about 10% sorbital. In certain embodiments, the pharmaceutical formulation comprises a stabilizing agent at a concentration of about 9% sorbital. In certain embodiments, the pharmaceutical formulation comprises a stabilizing agent at a concentration of about 1%, about 2%, about 3%, about 4%, about 5% proline, arginine, lysine, methionine, and/or taurine. In certain embodiments, the pharmaceutical formulation comprises a stabilizing agent at a concentration of between about 2-3% proline. In certain embodiments, the pharmaceutical formulation comprises a stabilizing agent at a concentration of about 1%, about 2%, about 3%, about 4%, about 5% benzyl alcohol. In certain embodiments, the pharmaceutical formulation comprises a stabilizing agent at a concentration of between about 1-2% benzyl alcohol.

In one aspect, the pharmaceutical formulation has a viscosity level of less than about 30 centipoise (cP) as measured at room temperature (i.e., 25 C). As used herein, "viscosity" is a fluid's resistance to flow, and may be measured in units of centipoise (cP) or milliPascal-second (mPa·s), where 1 cP=1 mPa·s, at a given shear rate. Viscosity may be measured by using a viscometer, e.g., Brookfield Engineering Dial Reading Viscometer, model LVT. Viscosity may also be measured using any other methods and in any other units known in the art (e.g., absolute, kinematic or dynamic viscosity or absolute viscosity). In certain embodiments, the pharmaceutical formulation has a viscosity level of less than about 25 cP, about 20 cP, about 18 cP, about 15 cP, about 12 cP, about 10 cP; about 8 cP, about 6 cP, about 4 cP; about 2 cP; or about 1 cP.

In one aspect, the pharmaceutical formulation is stable as measured by at least one stability assay known to one of skill in the art, such as assays that examine the biophysical or biochemical characteristics of biologically active proteins over time. As mentioned above, a stable pharmaceutical formulation of the present invention is a pharmaceutical formulation of biologically active proteins that exhibits increased aggregation and/or reduced loss of biological activity of not more than 5% when stored at 2-8° C. for at least 1 month, or 2 months, or 3 months, or 6 months, or 1 year or 2 years compared with a control formula sample. In certain embodiments, the pharmaceutical formulation stability is measured using size exclusion HPLC ("SEC-HPLC"). SEC-HPLC separates proteins based on differences in their hydrodynamic volumes. Molecules with larger hydrodynamic proteins volumes elute earlier than molecules with smaller volumes. In the case of SEC-HPLC, a stable pharmaceutical formulation should exhibit no more than about a 5% increase in high molecular weight species as compared to a control sample. In certain other embodiments, the pharmaceutical formulation should exhibit no more than about a 4%, no more than about a 3%, no more than about a 2%, no more than about a 1%, no more than about a 0.5% increase in high molecular weight species as compared to a control sample.

In certain embodiments, the pharmaceutical formulation stability is measured using cation-exchange HPLC (CEX-HPLC). CEX-HPLC separates proteins based on differences in their surface charge. At a set pH, charged isoforms of an anti-PCSK9 ABP are separated on a cation-exchange column and eluted using a salt gradient. The eluent is monitored by UV absorbance. The charged isoform distribution is evaluated by determining the peak area of each isoform as a percent of the total peak area. In the case of CEX-HPLC, a stable pharmaceutical formulation should exhibit no more than about a 5% decrease in the main isoform peak as compared to a control sample. In certain other embodiments, a stable pharmaceutical formulation should exhibit no more than about a 3% to about a 5% decrease in the main isoform peak as compared to a control sample. In certain embodiments, the pharmaceutical formulation should exhibit no more than about a 4% decrease, no more than about a 3% decrease, no more than about a 2% decrease, no more than about a 1% decrease, no more than about a 0.5% decrease in the main isoform peak as compared to a control sample.

In certain embodiments, the pharmaceutical formulation stability is measured using Subvisible Particle Detection by Light Obscuration ("HIAC"). An electronic, liquid-borne particle-counting system (HIAC/Royco 9703 or equivalent) containing a light-obscuration sensor (HIAC/Royco HRLD-150 or equivalent) with a liquid sampler quantifies the number of particles and their size range in a given test sample. When particles in a liquid pass between the light source and the detector they diminish or "obscure" the beam of light that falls on the detector. When the concentration of particles lies within the normal range of the sensor, these particles are detected one-by-one. The passage of each particle through the detection zone reduces the incident light on the photo-detector and the voltage output of the photo-detector is momentarily reduced. The changes in the voltage register as electrical pulses that are converted by the instrument into the number of particles present. The method is non-specific and measures particles regardless of their origin. Particle sizes monitored are generally 10 um, and 25 um. In the case of HIAC, a stable pharmaceutical formulation should exhibit no more than 6000 10 μm particles per container (or unit), as compared to a control sample. In certain embodiments, a stable pharmaceutical formulation should exhibit no more than 5000, no more than 4000, no more than 3000, no more than 2000, no more than 1000, 10 μm particles per container (or unit) as compared to a control sample. In still other embodiments, a stable pharmaceutical formulation should exhibit no more than 600 25 μm particles per container (or unit) as compared to a control sample. In certain embodiments, a stable pharmaceutical formulation should exhibit no more than 500, no more than 400, no more than 300, no more than 200, no more than 100, no more than 50 25 μm particles per container (or unit) as compared to a control sample.

In certain embodiments, the pharmaceutical formulation stability is measured using visual assessment. Visual assessment is a qualitative method used to describe the visible physical characteristics of a sample. The sample is viewed against a black and/or white background of an inspection booth, depending on the characteristic being evaluated (e.g., color, clarity, presence of particles or foreign matter). Samples are also viewed against an opalescent reference standard and color reference standards. In the case of visual assessment, a stable pharmaceutical formulation should exhibit no significant change in color, clarity, presence of particles or foreign matter as compared to a control sample.

One aspect of the present invention is a pharmaceutical formulation which comprises: (i) about 70 mg/ml to about 250 mg/ml of antigen binding protein to PCSK9; (ii) about 0.05 mM to about 40 mM of a buffer such as sodium acetate ("NaOAC") serves as a buffering agent; (iii) about 1% to about 5% proline, arginine, lysine, methionine, or taurine (also know as 2-aminoethanesulfonic acid) and/or 0.5% to about 5% benzyl alcohol which serves as a stabilizing agent; and (iv) about 0.004% to about 10% w/v of the formulation of a non-ionic surfactant (including but not limited to Polysorbate-80, Polysorbate-60, Polysorbate-40, and Polysorbate-20); wherein said formulation has a pH in the range of about 4.0 to 6.0. In certain other embodiments, pharmaceutical formulations of this invention comprise (i) at least about 70 mg/ml, about 100 mg/ml, about 120 mg/ml, about 140 mg/ml, about 150 mg/ml, about 160 mg/ml, about 170 mg/ml, about 180 mg/ml, about 190 mg/ml, about 200 mg/ml of an anti-PCSK9 antibody; (ii) about 10 mM NAOAC; (iii) about 0.01% polysorbate 80; and (iv) between about 2%-3% proline (or about 250 mM to about 270 mM proline), wherein the formulation has a pH of about 5. In certain other embodiments, pharmaceutical formulations of this invention comprise (i) at least about 70 mg/ml, about 100 mg/ml, about 120 mg/ml, about 140 mg/ml of the anti-PCSK9 antibody, 21B12, 26H5 and/or 31H4; (ii) about 10 mM NAOAC; (iii) about 0.01% polysorbate 80; and (iv) between about 2%-3% proline (or about 250 mM to about 270 mM proline), wherein the formulation has a pH of about 5. In certain other embodiments, pharmaceutical formulations of this invention comprise (i) at least about 150 mg/ml, about 160 mg/ml, about 170 mg/ml, about 180 mg/ml, about 190 mg/ml, about 200 mg/ml of the anti-PCSK9 antibody, 8A3, 11F1 and/or 8A1; (ii) about 10 mM NAOAC; (iii) about 0.01% polysorbate 80; and (iv) between about 2%-3% proline (or about 250 mM to about 270 mM proline), wherein the formulation has a pH of about 5.

One aspect of the present invention is a pharmaceutical formulation which comprises (i) at least about 70 mg/ml to about 250 mg/ml of an anti-PCSK9 antibody; (ii) about 5 mM to about 20 mM of a buffer, such as NAOAC; (iii) about 1% to about 10% w/v of the formulation comprises a polyhydroxy hydrocarbon such as sorbitol, or a disaccharide such as sucrose; and (iv) about 0.004% to about 10% w/v of the formulation of a surfactant, such as polysorbate 20 or polysorbate 80; wherein said formulation has a pH in the range of about 4.8 to 5.8; and wherein the pharmaceutical formulation optionally comprises about 80 mM to about 300 mM proline, arginine, lysine, methionine, or taurine and/or 0.5% to about 5% benzyl alcohol which serves to reduce viscosity. In certain other embodiments, pharmaceutical formulations of this invention comprise (i) at least about 70 mg/ml to about 250 mg/ml of the anti-PCSK9 antibody; (ii) about 10 mM NAOAC; (iii) about 9% sucrose; and (iv) about 0.004% polysorbate 20, wherein the formulation has a pH of about 5.2. In certain other embodiments, pharmaceutical formulations of this invention comprise (i) at least about 70 mg/ml, about 100 mg/ml, about 120 mg/ml, about 140 mg/ml, about 160 mg/ml, about 180 mg/ml, about 200 mg/ml of an anti-PCSK9 antibody; (ii) about 15 mM NAOAC; (iii) about 9% sucrose; and (iv) about 0.01% polysorbate 20, wherein the formulation has a pH of about 5.2. In certain other embodiments, pharmaceutical formulations of this invention comprise (i) at least about 70 mg/ml, about 100 mg/ml, about 120 mg/ml, about 140 mg/ml, about 160 mg/ml, about 180 mg/ml, about 200 mg/ml of an anti-PCSK9 antibody; (ii) about 20 mM NAOAC; (iii) about 9% sucrose; and (iv) about 0.01% polysorbate 20, wherein the formulation has a pH of about 5.2. In certain other embodiments, pharmaceutical formulations of this invention comprise (i) at least about 70 mg/ml, about 100 mg/ml, about 120 mg/ml, about 140 mg/ml, about 160 mg/ml, about 180 mg/ml, about 200 mg/ml of an anti-PCSK9 antibody; (ii) about 10 mM NAOAC; (iii) about 9% sucrose; (iv) about 0.01% polysorbate 80; and (v) about 250 mM proline, wherein the formulation has a pH of about 5.

Pharmaceutical formulations of the invention can be administered in combination therapy, i.e., combined with other agents. In certain embodiments, the combination therapy comprises an antigen binding protein capable of binding PCSK9, in combination with at least one anti-cholesterol agent. Agents include, but are not limited to, in vitro synthetically prepared chemical formulations, antibodies, antigen binding regions, and combinations and conjugates thereof. In certain embodiments, an agent can act as an agonist, antagonist, allosteric modulator, or toxin. In certain embodiments, an agent can act to inhibit or stimulate its target (e.g., receptor or enzyme activation or inhibition), and thereby promote increased expression of LDLR or decrease serum cholesterol levels.

In certain embodiments, an antigen binding protein to PCSK9 can be administered prior to, concurrent with, and subsequent to treatment with a cholesterol-lowering (serum and/or total cholesterol) agent. In certain embodiments, an antigen binding protein to PCSK9 can be administered prophylacticly to prevent or mitigate the onset of hypercholesterolemia, heart disease, diabetes, and/or any of the cholesterol related disorder. In certain embodiments, an antigen binding protein to PCSK9 can be administered for the treatment of an existing hypercholesterolemia condition. In some embodiments, the ABP delays the onset of the disorder and/or symptoms associated with the disorder. In some embodiments, the ABP is provided to a subject lacking any symptoms of any one of the cholesterol related disorders or a subset thereof.

In certain embodiments, an antigen binding protein to PCSK9 is used with particular therapeutic agents to treat various cholesterol related disorders, such as hypercholesterolemia.

In certain embodiments, in view of the condition and the desired level of treatment, two, three, or more agents can be administered. In certain embodiments, such agents can be provided together by inclusion in the same formulation. In certain embodiments, such agent(s) and an antigen binding protein to PCSK9 can be provided together by inclusion in the same formulation. In certain embodiments, such agents can be formulated separately and provided together by inclusion in a treatment kit. In certain embodiments, such agents and an antigen binding protein to PCSK9 can be formulated separately and provided together by inclusion in a treatment kit. In certain embodiments, such agents can be provided separately.

In certain embodiments, a formulation comprising an antigen binding protein to PCSK9, with or without at least one additional therapeutic agents, can be prepared for storage by mixing the selected formulation having the desired degree of purity with optional formulation agents (*Remington's Pharmaceutical Sciences, supra*) in the form of a lyophilized cake or an aqueous solution. Further, in certain embodiments, a formulation comprising an antigen binding protein to PCSK9, with or without at least one additional therapeutic agent, can be formulated as a lyophilizate using appropriate excipients.

In certain embodiments, when parenteral administration is contemplated, a therapeutic formulation can be in the form of a pyrogen-free, parenterally acceptable aqueous solution comprising a desired antigen binding protein to PCSK9, with or without additional therapeutic agents, in a pharmaceutically acceptable vehicle. In certain embodiments, a vehicle for parenteral injection is sterile distilled water in which an antigen binding protein to PCSK9, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical formulation can be formulated for inhalation. In certain embodiments, an antigen binding protein to PCSK9, with or without at least one additional therapeutic agent, can be formulated as a dry powder for inhalation. In certain embodiments, an inhalation solution comprising an antigen binding protein to PCSK9, with or without at least one additional therapeutic agent, can be formulated with a propellant for aerosol delivery. In certain embodiments, solutions can be nebulized. Pulmonary administration is further described in PCT application no. PCT/US94/001875, which describes pulmonary delivery of chemically modified proteins.

In certain embodiments, a pharmaceutical formulation can involve an effective quantity of an antigen binding protein to PCSK9, with or without at least one additional therapeutic agent, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical formulations will be evident to those skilled in the art, including formulations involving antigen binding proteins to PCSK9, with or without at least one additional therapeutic agent(s), in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical formulations. In certain embodiments, sustained-release preparations can include semi permeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly(2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D(−)-3-hydroxybutyric acid (EP 133, 988). In certain embodiments, sustained release formulations can also include liposomes, which can be prepared by any of several methods known in the art. See, e.g., Eppstein et al., Proc. Natl. Acad. Sci. USA, 82:3688-3692 (1985); EP 036,676; EP 088,046 and EP 143,949.

The pharmaceutical formulation to be used for in vivo administration typically is sterile. In certain embodiments, this can be accomplished by filtration through sterile filtration membranes. In certain embodiments, where the formulation is lyophilized, sterilization using this method can be conducted either prior to or following lyophilization and reconstitution. In certain embodiments, the formulation for parenteral administration can be stored in lyophilized form or in a solution. In certain embodiments, parenteral formulations generally are placed into a container having a sterile access port, for example, an intravenous solution bag or vial having a stopper pierceable by a hypodermic injection needle.

In certain embodiments, once the pharmaceutical formulation has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, once the pharmaceutical formulation has been formulated, it can be stored in pre-filled syringes as a solution or suspension in a ready-to-use form In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical formulation comprising an antigen binding protein to PCSK9, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an antigen binding protein to PCSK9, with or without at least one additional therapeutic agent, is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the formulation can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

Dosage and Dosing Regimens

Any of the antigen binding proteins to PCSK9 depicted in Table 2 and FIGS. 2 and/or 3 can be administered to a patient according to the methods of the present invention. In some embodiments, the antigen binding proteins to PCSK9 include 21B12, 26H5, 31H4, 8A3, 11F1 or 8A1.

The amount of an antigen binding protein to PCSK9 (e.g., an anti-PCSK9 antibody) administered to a patient according to the methods of the present invention is, generally, a therapeutically effective amount. The amount of ABP may be expressed in terms of milligrams of antibody (i.e., mg) or milligrams of antibody per kilogram of patient body weight (i.e., mg/kg). In certain embodiments, a typical dosage of a PCSK9 antigen binding protein can range from about 0.1 µg/kg to up to about 100 mg/kg or more of antigen binding protein to PCSK9. In certain embodiments, the dosage can range from 0.1 µg/kg up to about 100 mg/kg; or 1 µg/kg up to about 100 mg/kg; or 5 µg/kg up to about 100 mg/kg of antigen binding protein to PCSK9; or 1 mg/kg to about 50 mg/kg of antigen binding protein to PCSK9; or 2 mg/kg to about 20 mg/kg of antigen binding protein to PCSK9; or 2 mg/kg to about 10 mg/kg of antigen binding protein to PCSK9.

In certain embodiments, the amount (or dose) of antigen binding protein to PCSK9 can range from at least about 10 mg to at about 1400 mg; or about 14 mg to about 1200 mg; or about 14 mg to about 1000 mg; or about 14 mg to about 800 mg; or about 14 mg to about 700 mg; or about 14 mg to about 480 mg; or about 20 mg up to about 480 mg; or about 70 mg up to about 480 mg; or about 80 mg to about 480 mg; or about 90 mg to about 480 mg; or about 100 mg to about 480 mg, or about 105 mg to about 480 mg; or about 110 mg to about 480 mg; or about 115 mg to about 480 mg; or about 120 mg to about 480 mg; or about 125 mg to about 480 mg; or about 130 mg to about 480 mg; or about 135 mg to about 480 mg; or about 140 mg to about 480 mg; or about 145 mg to about 480 mg; or about 150 mg to about 480 mg; or about 160 mg to about 480 mg; or about 170 mg to about 480 mg; or about 180 mg to about 480 mg or about 190 mg to about 480 mg or about 200 mg to about 480 mg; or about 210 mg to about 480 mg; or about 220 mg to about 480 mg; or about 230 mg to about 480 mg; or about 240 mg to about 480 mg; or about 250 mg to about 480 mg; or about 260 mg to about 480 mg; or about 270 mg to about 480 mg; or about 280 mg to about 480 mg; or about 290 mg to about 480 mg; or about 300 mg to about 480 mg; or about 310 mg to about 480 mg; or about 320 mg to about 480 mg; or about 330 mg to about 480 mg; or about 340 mg to about 480 mg; or about 350 mg to about 480 mg; or about 360 mg to about 480 mg; or about 370 mg to about 480 mg; or about 380 mg to about 480 mg; or about 390 mg to about 480 mg; or about 400 mg to about 480 mg; or about 410 mg to about 480 mg; or about 420 mg to about 480 mg; or about 430 mg to about 480 mg; or about 440 mg to about 480 mg; or about 450 mg to about 480 mg; or about 460 mg to about 480 mg; or about 470 mg to about 480 mg of antigen binding protein to PCSK9.

In certain embodiments, the frequency of dosing will take into account the pharmacokinetic parameters of an antigen binding protein to PCSK9 and/or any additional therapeutic agents in the formulation used. In certain embodiments, a clinician will administer the formulation until a dosage is reached that achieves the desired effect. In certain embodiments, the formulation can therefore be administered as a single dose, or as two, three, four or more doses (which may or may not contain the same amount of the desired molecule) over time, or as a continuous infusion via an implantation device or catheter. The formulation can also be delivered subcutaneously or intravenously with a standard needle and syringe. In addition, with respect to subcutaneous delivery, pen delivery devices, as well as autoinjector delivery devices, have applications in delivering a pharmaceutical formulation of the present invention. Further refinement of the appropriate dosage is routinely made by those of ordinary skill in the art and is within the ambit of tasks routinely performed by them. In certain embodiments, appropriate dosages can be ascertained through use of appropriate dose-response data. In some embodiments, the amount and frequency of administration can take into account the desired cholesterol level (serum and/or total) to be obtained and the subject's present cholesterol level, LDL level, and/or LDLR levels, all of which can be obtained by methods that are well known to those of skill in the art.

In certain embodiments, a dose of at least about 10 mg; or up to about 14 mg; or up to about 20 mg; or up to about 35 mg; or up to about 40 mg, or up to about 45 mg, or up to about 50 mg; or up to about 70 mg of an antigen binding protein to PCSK9 is administered once a week (QW) to a patient in need thereof.

In some other embodiments, a dose of at least about 70 mg, or up to about 100 mg; or up to about 105 mg, or up to about 110 mg; or up to about 115 mg, or up to about 120 mg; or up to about 140 mg; or up to about 160 mg; or up to about 200 mg; or up to about 250 mg; or up to 280 mg; or up to 300 mg; or up to 350 mg; or up to 400 mg; or up to 420 mg of an antigen binding protein to PCSK9 is administered once every other week, (or every two weeks)(Q2W), to a patient in need thereof.

In certain other embodiments, a dose of at least about 250 mg; or up to about 280 mg; or up to about 300 mg; or up to about 350 mg; or up to about 400 mg; or up to about 420 mg; or up to about 450 mg; or up to 480 mg of a an antigen binding protein to PCSK9 is administered once every four weeks, (or once a month), to a patient in need thereof.

In some embodiments, the serum LDL cholesterol level is reduced by at least about 30%. In some embodiments, the serum LDL cholesterol level is reduced by at least about 40%. In some embodiments, the serum LDL cholesterol level is reduced by at least about 50%. In some embodiments, the serum LDL cholesterol level is reduced by at least about 55%. In some embodiments, the serum LDL cholesterol level is reduced by at least about 60%. In some embodiments, the serum LDL cholesterol level is reduced by at least about 65%. In some embodiments, the serum LDL cholesterol level is reduced by at least about 70%. In some embodiments, the serum LDL cholesterol level is reduced by at least about 75%. In some embodiments, the serum LDL cholesterol level is reduced by at least about 80%. In some embodiments, the serum LDL cholesterol level is reduced by at least about 85%. In some embodiments, the serum LDL cholesterol level is reduced by at least about 90%.

In some embodiments, the serum LDL cholesterol level is reduced by at least about 30% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 35% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 40% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 45% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 50% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 55% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 60% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 65% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 70% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 75% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 80% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 85% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

In some embodiments, the serum LDL cholesterol level is reduced by at least about 90% and the reduction is sustained for a period of at least about 3 days, at least about 5 days, at least about 7 days, at least about 10 days, at least about 14 days, at least about 21 days, at least about 25 days, at least about 28 days, or at least about 31 days relative to a predose level.

Certain Therapeutic Applications

As will be appreciated by one of skill in the art, disorders that relate to, involve, or can be influenced by varied cholesterol, LDL, LDLR, PCSK9, VLDL-C, apoprotein B ("ApoB"), lipoprotein A ("Lp(a)"), triglycerides, HDL-C, non-HDL-C, and total cholesterol levels can be addressed by the antigen binding proteins to PCSK9 described in the present invention. In one aspect, antigen binding proteins to PCSK9 can be used in methods to treat and/or prevent and/or reduce the risk of disorders that relate to elevated serum cholesterol levels or in which elevated serum cholesterol levels are relevant. In one aspect, antigen binding proteins to PCSK9 can be used in methods to treat and/or prevent and/or reduce the risk of disorders that relate to elevated PCSK9 values or in which elevated PCSK9 values are relevant. In one aspect, antigen binding proteins to PCSK9 can be used in methods to treat and/or prevent and/or reduce the risk of disorders that relate to elevated total cholesterol levels or in which elevated total cholesterol levels are relevant. In one aspect, antigen binding proteins to PCSK9 can be used in methods to treat and/or prevent and/or reduce the risk of disorders that relate to elevated non-HDL cholesterol levels or in which elevated non-HDL cholesterol levels are relevant. In one aspect, antigen binding proteins to PCSK9 can be used in methods to treat and/or prevent and/or reduce the risk of disorders that relate to elevated ApoB levels or in which elevated ApoB levels are relevant. In one aspect, antigen binding proteins to PCSK9 can be used in methods to treat and/or prevent and/or reduce the risk of disorders that relate to elevated Lp(a) levels or in which elevated Lp(a) levels are relevant. In one aspect, antigen binding proteins to PCSK9 can be used in methods to treat and/or prevent and/or reduce the risk of disorders that relate to elevated triglyceride levels or in which elevated triglyceride levels are relevant. In one aspect, antigen binding proteins to PCSK9 can be used in methods to treat and/or prevent and/or reduce the risk of disorders that relate to elevated VLDL-C levels or in which elevated VLDL-C levels are relevant.

In one aspect, an antigen binding protein to PCSK9 is used to modulate serum LDL cholesterol levels in a patient. In some embodiments, the antigen binding protein to PCSK9 is used to decrease the amount of serum LDL cholesterol from an abnormally high level or even a normal level. In certain embodiments, the serum LDL cholesterol level is reduced by at least about 30%. In certain embodiments, the serum LDL cholesterol level is reduced by at least about 35%. In certain embodiments, the serum LDL cholesterol level is reduced by at least about 40%. In certain embodiments, the serum LDL cholesterol level is reduced by at least about 45%. In certain embodiments, the serum LDL cholesterol level is reduced by at least about 50%. In certain embodiments, the serum LDL cholesterol level is reduced by at least about 55%. In some embodiments, the serum LDL cholesterol level is reduced by at least about 60%. In some embodiments, the serum LDL cholesterol level is reduced by at least about 65%. In some embodiments, the serum LDL cholesterol level is reduced by at least about 70%. In some embodiments, the serum LDL cholesterol level is reduced by at least about 75%. In some embodiments, the serum LDL cholesterol level is reduced by at least about 80%. In some embodiments, the serum LDL cholesterol level is reduced by at least about 85%. In some embodiments, the serum LDL cholesterol level is reduced by at least about 90%.

In one aspect, an antigen binding protein to PCSK9 is used to modulate serum PCSK9 values in a patient. In certain embodiments, the antigen binding protein to PCSK9 is neutralizing. In some embodiments, the antigen binding protein to PCSK9 is used to decrease PCSK9 values from an abnormally high level or even a normal level. In some embodiments, the serum PCSK9 value is reduced by at least about 60%. In some embodiments, the serum PCSK9 value is reduced by at least about 65%. In some embodiments, the serum PCSK9 value is reduced by at least about 70%. In some embodiments, the serum PCSK9 value is reduced by at least about 75%. In some embodiments, the serum PCSK9 value is reduced by at least about 80%. In some embodiments, the serum PCSK9 value is reduced by at least about 85%. In some embodiments, the serum PCSK9 value is reduced by at least about 90%.

In one aspect, an antigen binding protein to PCSK9 is used to modulate total cholesterol level in a patient. In certain embodiments, the antigen binding protein to PCSK9 is neutralizing. In some embodiments, the antigen binding protein to PCSK9 is used to decrease the amount of total cholesterol from an abnormally high level or even a normal level. In some embodiments, the total cholesterol level is reduced by at least about 20%. In some embodiments, the total cholesterol level is reduced by at least about 25%. In some embodiments, the total cholesterol level is reduced by at least about 30%. In some embodiments, the total cholesterol level is reduced by at least about 35%. In some embodiments, the total cholesterol level is reduced by at least about 40%. In some embodiments, the total cholesterol level is reduced by at least about 45%. In some embodiments, the total cholesterol level is reduced by at least about 50%. In some embodiments, the total cholesterol level is reduced by at least about 55%. In some embodiments, the total cholesterol level is reduced by at least about 60%.

In one aspect, an antigen binding protein to PCSK9 is used to modulate the non-HDL cholesterol level in a patient. In certain embodiments, the antigen binding protein to PCSK9 is neutralizing. In some embodiments, the antigen binding protein to PCSK9 is used to decrease the non-HDL cholesterol from an abnormally high level or even a normal level. In some embodiments, the non-HDL cholesterol level is reduced by at least about 30%. In some embodiments, the non-HDL cholesterol level is reduced by at least about 35%. In some embodiments, the non-HDL cholesterol level is reduced by at least about 40%. In some embodiments, the non-HDL cholesterol level is reduced by at least about 50%. In some embodiments, the non-HDL cholesterol level is reduced by at least about 55%. In some embodiments, the non-HDL cholesterol level is reduced by at least about 60%. In some embodiments, the non-HDL cholesterol level is reduced by at least about 65%. In some embodiments, the non-HDL cholesterol level is reduced by at least about 70%. In some embodiments, the non-HDL cholesterol level is reduced by at least about 75%. In some embodiments, the non-HDL cholesterol level is reduced by at least about 80%. In some embodiments, the non-HDL cholesterol level is reduced by at least about 85%.

In one aspect, an antigen binding protein to PCSK9 is used to modulate the ApoB levels in a patient. In certain embodiments, the antigen binding protein to PCSK9 is neutralizing. In some embodiments, the antigen binding protein to PCSK9 is used to decrease the amount of ApoB from an abnormally high level or even a normal level. In some embodiments, the ApoB level is reduced by at least about 25%. In some embodiments, the ApoB level is reduced by at least about 30%. In some embodiments, the ApoB level is reduced by at least about 35%. In some embodiments, the ApoB level is reduced by at least about 40%. In some embodiments, the ApoB level is reduced by at least about 45%. In some embodiments, the ApoB level is reduced by at least about 50%. In some embodiments, the ApoB level is reduced by at least about 55%. In some embodiments, the ApoB level is reduced by at least about 60%. In some embodiments, the ApoB level is reduced by at least about 65%. In some embodiments, the ApoB level is reduced by at least about 70%. In some embodiments, the ApoB level is reduced by at least about 75%.

In one aspect, an antigen binding protein to PCSK9 is used to modulate the Lp(a) levels in a patient. In certain embodiments, the antigen binding protein to PCSK9 is neutralizing. In some embodiments, the antigen binding protein to PCSK9 is used to decrease the amount of Lp(a) from an abnormally high level or even a normal level. In some embodiments, the Lp(a) level is reduced by at least about 5%. In some embodiments, the Lp(a) level is reduced by at least about 10%. In some embodiments, the Lp(a) level is reduced by at least about 15%. In some embodiments, the Lp(a) level is reduced by at least about 20%. In some embodiments, the Lp(a) level is reduced by at least about 25%. In some embodiments, the Lp(a) level is reduced by at least about 30%. In some embodiments, the Lp(a) level is reduced by at least about 35%. In some embodiments, the Lp(a) level is reduced by at least about 40%. In some embodiments, the Lp(a) level is reduced by at least about 45%. In some embodiments, the Lp(a) level is reduced by at least about 50%. In some embodiments, the Lp(a) level is reduced by at least about 55%. In some embodiments, the Lp(a) level is reduced by at least about 60%. In some embodiments, the Lp(a) level is reduced by at least about 65%.

As will be appreciated by one of skill in the art, the antigen binding proteins to PCSK9 of the present invention can be therapeutically useful in treating and/or preventing cholesterol related disorders. In some embodiments, a "cholesterol related disorder" (which includes "serum cholesterol related disorders") includes any one or more of the following: familial hypercholesterolemia, non-familial hypercholesterolemia, hyperlipidemia, heart disease, metabolic syndrome, diabetes, coronary heart disease, stroke, cardiovascular diseases, Alzheimer's disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias that can be treated using an ABP, either alone, or in combination with one or more other agents include the metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apolipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. ABP can also be useful in preventing or treating atherosclerotic diseases, such as, for example, cardiovascular death, non-cardiovascular or all-cause death, coronary heart disease, coronary artery disease, peripheral arterial disease, stroke (ischaemic and hemorrhagic), angina pectoris, or cerebrovascular disease and acute coronary syndrome, myocardial infarction and unstable angina. In some embodiments, the ABP is useful in reducing the risk of: fatal and nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries and/or transplant-related vascular disease. In some embodiments, the ABP is useful in preventing or reducing the cardiovascular risk due to elevated CRP or hsCRP. In some embodiments, the ABP and methods can be used to reduce the risk of recurrent cardiovascular events.

As will be appreciated by one of skill in the art, diseases or disorders that are generally addressable (either treatable or preventable) through the use of statins can also benefit from the application of the instant antigen binding proteins. In addition, in some embodiments, disorders or disease that can benefit from the prevention of cholesterol synthesis or increased LDLR expression can also be treated by various embodiments of the antigen binding proteins. In addition, as will be appreciated by one of skill in the art, the use of the anti-PCSK9 antibodies can be especially useful in the treatment of diabetes. Not only is diabetes a risk factor for coronary heart disease, but insulin increases the expression of PCSK9. That is, people with Diabetes have elevated plasma lipid levels (which can be related to high PCSK9 levels) and can benefit from lowering those levels. This is generally discussed in more detail in Costet et al. ("Hepatic PCSK9 Expression is Regulated by Nutritional Status via Insulin and Sterol Regulatory Element-binding Protein 1C", J. Biol. Chem., 281: 6211-6218, 2006), the entirety of which is incorporated herein by reference.

In some embodiments, the antigen binding protein is administered to those who have diabetes mellitus, abdominal aortic aneurysm, atherosclerosis and/or peripheral vascular disease in order to decrease their serum cholesterol levels to a safer range. In some embodiments, the antigen binding protein is administered to patients at risk of developing any of the herein described disorders. In some embodiments, the ABPs are administered to subjects that smoke, or used to smoke (i.e., former smokers), have hypertension or a familial history of early heart attacks.

In some embodiments, a subject is administered an ABP if they are at a moderate risk or higher on the 2004 NCEP treatment goals. In some embodiments, the ABP is administered to a subject if the subject's LDL cholesterol level is greater than 160 mg/dl. In some embodiments, the ABP is administered if the subjects LDL cholesterol level is greater than 130 (and they have a moderate or moderately high risk according to the 2004 NCEP treatment goals). In some embodiments, the ABP is administered if the subjects LDL cholesterol level is greater than 100 (and they have a high or very high risk according to the 2004 NCEP treatment goals). In some embodiments, the ABP is administered if the subjects LDL cholesterol level is greater than 80 mg/dL. In some embodiments, the ABP is administered if the subjects LDL cholesterol level is greater than 70 mg/dL.

A physician will be able to select appropriate treatment indications and target lipid levels depending on the individual profile of a particular patient. One well-accepted standard for guiding treatment of hyperlipidemia is the Third Report of the National Cholesterol Education Program (NCEP) Expert Panel on Detection, Evaluation, and Treatment of the High Blood Cholesterol in Adults (Adult Treatment Panel III) Final Report, National Institutes of Health, NIH Publication No. 02-5215 (2002), the printed publication of which is hereby incorporated by reference in its entirety.

In some embodiments, antigen binding proteins to PCSK9 are used to treat or prevent hypercholesterolemia, hyperlipidemia or dyslipidemia and/or in the preparation of medicaments therefore and/or for other cholesterol related disorders (such as those noted herein). In certain embodiments, an antigen binding protein to PCSK9 is used to treat or prevent conditions such as hypercholesterolemia in which PCSK9 activity is normal. In such conditions, for example, reduction of PCSK9 activity to below normal can provide a therapeutic effect.

Combination Therapies

In certain embodiments, methods are provided of treating a cholesterol related disorder, such as hypercholesterolemia, hyperlipidemia or dyslipidemia, comprising administering a therapeutically effective amount of one or more antigen binding proteins to PCSK9 and another therapeutic agent. In certain embodiments, an antigen binding protein to PCSK9 is administered prior to the administration of at least one other therapeutic agent. In certain embodiments, an antigen binding protein to PCSK9 is administered concurrent with the administration of at least one other therapeutic agent. In certain embodiments, an antigen binding protein to PCSK9 is administered subsequent to the administration of at least one other therapeutic agent.

Therapeutic agents (apart from the antigen binding protein), include, but are not limited to, at least one other cholesterol-lowering (serum and/or total body cholesterol) agent. In some embodiments, the agent increases the expression of LDLR, have been observed to increase serum HDL levels, lower LDL levels or lower triglyceride levels. Exemplary agents include, but are not limited to, statins (atorvastatin, cerivastatin, fluvastatin, lovastatin, mevastatin, pitavastatin, pravastatin, rosuvastatin, simvastatin), Nicotinic acid (Niacin) (NIACOR, NIASPAN (slow release niacin), SLO-NIACIN (slow release niacin), CORDAPTIVE (laropiprant)), Fibric acid (LOPID (Gemfibrozil), TRICOR (fenofibrate), Bile acid sequestrants (QUESTRAN (cholestyramine), colesevelam (WELCHOL), COLESTID (colestipol)), Cholesterol absorption inhibitors (ZETIA (ezetimibe)), Combining nicotinic acid with statin (ADVICOR (LOVASTATIN and NIASPAN), Combining a statin with an absorption inhibitor (VYTORIN (ZOCOR and ZETIA) and/or lipid modifying agents. In some embodiments, the ABP is combined with PPAR gamma agonsits, PPAR alpha/gamma agonists, squalene synthase inhibitors, CETP inhibitors, anti-hypertensives, anti-diabetic agents (such as sulphonyl ureas, insulin, GLP-1 analogs, DDPIV inhibitors, e.g., metformin), ApoB modulators, such as mipomersan, MTP inhibitoris and/or arteriosclerosis obliterans treatments. In some embodiments, the ABP is combined with an agent that increases the level of LDLR protein in a subject, such as statins, certain cytokines like oncostatin M, estrogen, and/or certain herbal ingredients such as berberine. In some embodiments, the ABP is combined with an agent that increases serum cholesterol levels in a subject (such as certain anti-psycotic agents, certain HIV protease inhibitors, dietary factors such as high fructose, sucrose, cholesterol or certain fatty acids and certain nuclear receptor agonists and antagonists for RXR, RAR, LXR, FXR). In some embodiments, the ABP is combined with an agent that increases the level of PCSK9 in a subject, such as statins and/or insulin. The combination of the two can allow for the undesirable side-effects of other agents to be mitigated by the ABP.

In certain embodiments, an antigen binding protein to PCSK9 can be used with at least one therapeutic agent for inflammation. In certain embodiments, an antigen binding protein to PCSK9 can be used with at least one therapeutic agent for an immune disorder. Exemplary therapeutic agents for inflammation and immune disorders include, but are not limited to cyclooxygenase type 1 (COX-1) and cyclooxygenase type 2 (COX-2) inhibitors small molecule modulators of 38 kDa mitogen-activated protein kinase (p38-MAPK); small molecule modulators of intracellular molecules involved in inflammation pathways, wherein such intracellular molecules include, but are not limited to, jnk, IKK, NF-κB, ZAP70, and lck. Certain exemplary therapeutic agents for inflammation are described, e.g., in C. A. Dinarello & L. L. Moldawer *Proinflammatory and Anti-Inflammatory Cytokines in Rheumatoid Arthritis: A Primer for Clinicians* Third Edition (2001) Amgen Inc. Thousand Oaks, Calif.

Diagnostic Applications

In some embodiments, the ABP is used as a diagnostic tool. The ABP can be used to assay the amount of PCSK9 present in a sample and/or subject. As will be appreciated by one of skill in the art, such ABPs need not be neutralizing ABPs. In some embodiments, the diagnostic ABP is not a neutralizing ABP. In some embodiments, the diagnostic ABP binds to a different epitope than the neutralizing ABP binds to. In some embodiments, the two ABPs do not compete with one another.

In some embodiments, the ABPs disclosed herein are used or provided in an assay kit and/or method for the detection of PCSK9 in mammalian tissues or cells in order to screen/diagnose for a disease or disorder associated with changes in levels of PCSK9. The kit comprises an ABP that binds PCSK9 and means for indicating the binding of the ABP with PCSK9, if present, and optionally PCSK9 protein levels. Various means for indicating the presence of an ABP can be used. For example, fluorophores, other molecular probes, or enzymes can be linked to the ABP and the presence of the ABP can be observed in a variety of ways. The method for screening for such disorders can involve the use of the kit, or simply the use of one of the disclosed ABPs and the determination of whether the ABP binds to PCSK9 in a sample. As will be appreciated by one of skill in the art, high or elevated levels of PCSK9 will result in larger amounts of the ABP binding to PCSK9 in the sample. Thus, degree of ABP binding can be used to determine how much PCSK9 is in a sample. Subjects or samples with an amount of PCSK9 that is greater than a predetermined amount (e.g., an amount or range that a person without a PCSK9 related disorder would have) can be characterized as having a PCSK9 mediated disorder. In some embodiments, the ABP is administered to a subject taking a statin, in order to determine if the statin has increased the amount of PCSK9 in the subject.

In some embodiments, the ABP is a non-neutralizing ABP and is used to determine the amount of PCSK9 in a subject receiving an ABP and/or statin treatment.

EXAMPLES

The following examples, including the experiments conducted and results achieved, are provided for illustrative purposes only and are not to be construed as limiting the present invention.

Example 1

Immunization and Titering

Generation of Anti-PCSK9 Antibodies and Hybridomas

Antibodies to the mature form of PCSK9 (depicted as the sequence in FIG. 1A, with the pro-domain underlined), were raised in XenoMouse® mice (Abgenix, Fremont, Calif.), which are mice containing human immunoglobulin genes. Two groups of XenoMouse® mice, group 1 and 2, were used to produce antibodies to PCSK9. Group 1 included mice of the XenoMouse® strain XMG2-KL, which produces fully human IgG2$_κ$ and IgG2λ antibodies. Group 1 mice were immunized with human PCSK9. PCSK9 was prepared using standard recombinant techniques using the GenBank sequence as reference (NM 174936). Group 2 involved mice of the XenoMouse® strain XMG4-KL, which produce fully human IgG4$_κ$ and IgG4λ antibodies. Group 2 mice were also immunized with human PCSK9.

The mice of both groups were injected with antigen eleven times, according to the schedule in Table 3. In the initial immunizations, each mouse was injected with a total of 10 μg of antigen delivered intraperitoneally into the abdomen. Subsequent boosts are 5 ug doses and injection method is staggered between intraperitoneal injections into the abdomen and sub-cutaneous injections at the base of the tail. For intraperitoneal injections antigen is prepared as an emulsion with TiterMax® Gold (Sigma, Cat # T2684) and for subcutaneous injections antigen is mixed with Alum (aluminum phosphate) and CpG oligos. In injections 2 through 8 and 10, each mouse was injected with a total of 5 μg of antigen in the adjuvant alum gel. A final injection of 5 μg of antigen per mouse is delivered in Phospho buffered saline and delivered into 2 sites 50% IP into the abdomen and 50% SQ at the base of tail. The immunization programs are summarized in Table 3, shown below.

TABLE 3

| | mouse strain | |
| --- | --- | --- |
| | XMG2/kl | XMG4/kl |
| | # of animals | |
| | 10 | 10 |
| | immunogen | |
| | PCSK9-V5/His | PCSK9-V5/His |
| 1st boost | IP injection 10 ug each Titermax Gold | IP injection 10 ug each Titermax Gold |
| 2nd boost | tail injection 5 ug each Alum/CpG ODN | tail injection 5 ug each Alum/CpG ODN |
| 3rd boost | IP injection 5 ug each Titermax Gold | IP injection 5 ug each Titermax Gold |
| 4th boost | tail injection 5 ug each Alum/CpG ODN | tail injection 5 ug each Alum/CpG ODN |
| 5th boost | IP injection 5 ug each Titermax Gold | IP injection 5 ug each Titermax Gold |
| 6th boost | tail injection 5 ug each Alum/CpG ODN | tail injection 5 ug each Alum/CpG ODN |
| 7th boost | IP injection 5 ug each Titermax Gold | IP injection 5 ug each Titermax Gold |
| 8th boost | tail injection 5 ug each Alum/CpG ODN | tail injection 5 ug each Alum/CpG ODN |
| bleed | | |
| 9th boost | IP injection 5 ug each Titermax Gold | IP injection 5 ug each Titermax Gold |
| 10th boost | tail injection 5 ug each Alum/CpG ODN | tail injection 5 ug each Alum/CpG ODN |

TABLE 3-continued

| | mouse strain | |
| --- | --- | --- |
| | XMG2/kl | XMG4/kl |
| | # of animals | |
| | 10 | 10 |
| | immunogen | |
| | PCSK9-V5/His | PCSK9-V5/His |
| 11th boost | BIP<br>5 ug each<br>PBS | BIP<br>5 ug each<br>PBS |
| harvest | | |

The protocol used to titer the XenoMouse animals was as follows: Costar 3368 medium binding plates were coated with neutravadin @ 8 ug/ml (50 ul/well) and incubated at 4° C. in 1×PBS/0.05% azide overnight. They were washed using TiterTek 3-cycle wash with RO water. Plates were blocked using 250 ul of 1×PBS/1% milk and incubated for at least 30 minutes at RT. Block was washed off using TiterTek 3-cycle wash with RO water. One then captured b-human PCSK9 @ 2 ug/ml in 1×PBS/1% milk/10 mM Ca2+ (assay diluent) 50 ul/well and incubated for 1 hr at RT. One then washed using TiterTek 3-cycle wash with RO water. For the primary antibody, sera were titrated 1:3 in duplicate from 1:100. This was done in assay diluent 50 ul/well and incubated for 1 hr at RT. One then washed using TiterTek 3-cycle wash with RO water. The secondary antibody was goat anti Human IgG Fc HRP @ 400 ng/ml in assay diluent at 50 ul/well. This was incubated for 1 hr at RT. This was then washed using TiterTek 3-cycle wash with RO water and patted dry on paper towels. For the substrate, one-step TMB solution (Neogen, Lexington, Ky.) was used (50 ul/well) and it was allowed to develop for 30 min at RT.

The protocols followed in the ELISA assays were as follows: For samples comprising b-PCSK9 with no VSHis tag the following protocol was employed: Costar 3368 medium binding plates (Corning Life Sciences) were employed. The plates were coated with neutravadin at 8 μg/ml in 1×PBS/0.05% Azide, (50 μl/well). The plates were incubated at 4° C. overnight. The plates were then washed using a Titertek M384 plate washer (Titertek, Huntsville, Ala.). A 3-cycle wash was performed. The plates were blocked with 250 μl of 1×PBS/1% milk and incubated approximately 30 minutes at room temperature. The plates were then washed using the M384 plate washer. A 3-cycle wash was performed. The capture was b-hu PCSK9, without a V5 tag, and was added at 2 μg/ml in 1×PBS/1% milk/10 mM Ca²⁺ (40 μl/well). The plates were then incubated for 1 hour at room temperature. A 3-cycle wash was performed. Sera were titrated 1:3 in duplicate from 1:100, and row H was blank for sera. The titration was done in assay diluent, at a volume of 50 μl/well. The plates were incubated for 1 hour at room temperature. Next, a 3-cycle wash was performed. Goat anti Human IgG Fc HRP at 100 ng/ml (1:4000) in 1×PBS/1% milk/10 mM Ca²⁺ (50 μl/well) was added to the plate and was incubated 1 hour at room temperature. The plates were washed once again, using a 3-cycle wash. The plates were then patted dry with paper towel. Finally, 1 step TMB (Neogen, Lexington, Ky.) (50 μl/well) was added to the plate and was quenched with 1N hydrochloric acid (50 μl/well) after 30 minutes at room temperature. OD's were read immediately at 450 nm using a Titertek plate reader.

Positive controls to detect plate bound PCSK9 were soluble LDL receptor (R&D Systems, Cat #2148LD/CF)

and a polyclonal rabbit anti-PCSK9 antibody (Caymen Chemical #10007185) titrated 1:3 in duplicate from 3 μg/ml in assay diluent. LDLR was detected with goat anti LDLR (R&D Systems, Cat # AF2148) and rabbit anti goat IgGFc HRP at a concentration of 400 ng/ml; the rabbit polyclonal was detected with goat anti-rabbit IgG Fc at a concentration of 400 ng/ml in assay diluent. Negative control was naive XMG2-KL and XMG4-KL sera titrated 1:3 in duplicate from 1:100 in assay diluent.

For samples comprising b-PCSK9 with a VSHis tag the following protocol was employed: Costar 3368 medium binding plates (Corning Life Sciences) were employed. The plates were coated with neutravadin at 8 μg/ml in 1×PBS/0.05% Azide, (50 μl/well). The plates were incubated at 4° C. overnight. The plates were then washed using a Titertek M384 plate washer (Titertek, Huntsville, Ala.). A 3-cycle wash was performed. The plates were blocked with 250 μl of 1×PBS/1% milk and incubated approximately 30 minutes at room temperature. The plates were then washed using the M384 plate washer. A 3-cycle wash was performed. The capture was b-hu PCSK9, with a V5 tag, and was added at 2 μg/ml in 1×PBS/1% milk/10 mM Ca²⁺ (40 μl/well). The plates were then incubated for 1 hour at room temperature. A 3-cycle wash was performed. Sera were titrated 1:3 in duplicate from 1:100, and row H was blank for sera. The titration was done in assay diluent, at a volume of 50 μl/well. The plates were incubated for 1 hour at room temperature. Next, the plates were washed using the M384 plate washer operated using a 3-cycle wash. Goat anti Human IgG Fc HRP at 400 ng/ml in 1×PBS/1% milk/10 mM Ca²⁺ was added at 50 μl/well to the plate and the plate was incubated 1 hour at room temperature. The plates were washed once again, using a 3-cycle wash. The plates were then patted dry with paper towel. Finally, 1 step TMB (Neogen, Lexington, Ky.) (50 μl/well) was added to the plate and the plate was quenched with 1N hydrochloric acid (50 μl/well) after 30 minutes at room temperature. OD's were read immediately at 450 nm using a Titertek plate reader.

Positive control was LDLR, rabbit anti-PCSK9 titrated 1:3 in duplicate from 3 μg/ml in assay diluent. LDLR detect with goat anti-LDLR (R&D Systems, Cat # AF2148) and rabbit anti-goat IgG Fc HRP at a concentration of 400 ng/ml; rabbit poly detected with goat anti-rabbit IgG Fc at a concentration of 400 ng/ml in assay diluent. Human anti-His 1.2,3 and anti-V5 1.7.1 titrated 1:3 in duplicate from 1 μg/ml in assay diluent; both detected with goat anti-human IgG Fc HRP at a concentration of 400 ng/ml in assay diluent. Negative control was naive XMG2-KL and XMG4-KL sera titrated 1:3 in duplicate from 1:100 in assay diluent.

Titers of the antibody against human PCSK9 were tested by ELISA assay for mice immunized with soluble antigen as described. Table 4 summarizes the ELISA data and indicates that there were some mice which appeared to be specific for PCSK9. See, e.g., Table 4. Therefore, at the end of the immunization program, 10 mice (in bold in Table 4) were selected for harvest, and splenocytes and lymphocytes were isolated from the spleens and lymph nodes respectively, as described herein.

TABLE 4

| | | Titer | Titer |
|---|---|---|---|
| | Animal ID | b-hu PCSK9 (V5His) @ 2 ug/ml | b-hu PCSK9 @ 2 ug/ml |
| Group 1 - | P175807 | >72900 @ OD 2.2 | 68359 |
| IgG2k/l | P175808 | >72900 @ OD 2.3 | >72900 @ OD 2.5 |
| | P175818 | >72900 @ OD 3.2 | >72900 @ OD 3.0 |
| | P175819 | >72900 @ OD 3.4 | >72900 @ OD 3.2 |
| | P175820 | >72900 @ OD 2.4 | >72900 @ OD 2.5 |
| | P175821 | >72900 @ OD 3.4 | >72900 @ OD 3.0 |
| | P175830 | >72900 @ OD 2.6 | >72900 @ OD 2.5 |
| | P175831 | >72900 @ OD 3.1 | >72900 @ OD 3.1 |
| | P175832 | >72900 @ OD 3.8 | >72900 @ OD 3.6 |
| | P175833 | >72900 @ OD 2.6 | >72900 @ OD 2.3 |
| Group 2 - | P174501 | 19369 | 17109 |
| IgG4k/l | P174503 | 31616 | 23548 |
| | P174508 | 48472 | 30996 |
| | P174509 | 23380 | 21628 |
| | P174510 | 15120 | 9673 |
| | P175773 | 19407 | 15973 |
| | P175774 | 54580 | 44424 |
| | P175775 | 60713 | 55667 |
| | P175776 | 30871 | 22899 |
| | P175777 | 16068 | 12532 |
| | Naïve G2 | <100 @ OD 0.54 | <100 @ OD 0.48 |
| | Naïve G4 | <100 @ OD 1.57 | <100 @ OD 1.32 |

Example 2

Recovery of Lymphocytes, B-Cell Isolations,
Fusions and Generation of Hybridomas This example outlines how the immune cells were recovered and the hybridomas were generated. Selected immunized mice were sacrificed by cervical dislocation and the draining lymph nodes were harvested and pooled from each cohort. The B cells were dissociated from lymphoid tissue by grinding in DMEM to release the cells from the tissues, and the cells were suspended in DMEM. The cells were counted, and 0.9 ml DMEM per 100 million lymphocytes was added to the cell pellet to resuspend the cells gently but completely.

Lymphocytes were mixed with nonsecretory myeloma P3X63Ag8.653 cells purchased from ATCC, cat. # CRL 1580 (Kearney et al., (1979) J. Immunol. 123, 1548-1550) at a ratio of 1:4. The cell mixture was gently pelleted by centrifugation at 400×g 4 min. After decanting of the supernatant, the cells were gently mixed using a 1 ml pipette. Preheated PEG/DMSO solution from Sigma (cat # P7306) (1 ml per million of B-cells) was slowly added with gentle agitation over 1 min followed by 1 min of mixing. Preheated IDMEM (2 ml per million of B cells) (DMEM without glutamine, L-glutamine, pen/strep, MEM non-essential amino acids (all from Invitrogen), was then added over 2 minutes with gentle agitation. Finally preheated IDMEM (8 ml per $10^6$ B-cells) was added over 3 minutes.

The fused cells were spun down 400×g 6 min and resuspended in 20 ml selection media (DMEM (Invitrogen), 15% FBS (Hyclone), supplemented with L-glutamine, pen/strep, MEM Non-essential amino acids, Sodium Pyruvate, 2-Mercaptoethanol (all from Invitrogen), HA-Azaserine Hypoxanthine and OPI (oxaloacetate, pyruvate, bovine insulin) (both from Sigma) and IL-6 (Boehringer Mannheim)) per million B-cells. Cells were incubated for 20-30 min at 37 C and then resuspended in 200 ml selection media and cultured for 3-4 days in T175 flask prior to 96 well plating. Thus, hybridomas that produced antigen binding proteins to PCSK9 were produced.

Example 3

Selection of PCSK9 Antibodies

The present example outlines how the various PCSK9 antigen binding proteins were characterized and selected. The binding of secreted antibodies (produced from the hybridomas produced in Examples 1 and 2) to PCSK9 was assessed. Selection of antibodies was based on binding data and inhibition of PCSK9 binding to LDLR and affinity. Binding to soluble PCSK9 was analyzed by ELISA, as described below. BIAcore® (surface plasmon resonance) was used to quantify binding affinity.

Primary Screen

A primary screen for antibodies which bind to wild-type PCSK9 was performed. The primary screen was performed on two harvests. The primary screen comprised an ELISA assay and was performed using the following protocol:

Costar 3702 medium binding 384 well plates (Corning Life Sciences) were employed. The plates were coated with neutravadin at a concentration of 4 μg/ml in 1×PBS/0.05% Azide, at a volume of 40 μl/well. The plates were incubated at 4° C. overnight. The plates were then washed using a Titertek plate washer (Titertek, Huntsville, Ala.). A 3-cycle wash was performed. The plates were blocked with 90 μl of 1×PBS/1% milk and incubated approximately 30 minutes at room temperature. The plates were then washed. Again, a 3-cycle wash was performed. The capture sample was biotinylated-PCSK9, without a V5 tag, and was added at 0.9 μg/ml in 1×PBS/1% milk/10 mM $Ca^{2+}$ at a volume of 40 μl/well. The plates were then incubated for 1 hour at room temperature. Next, the plates were washed using the Titertek plate washer operated using a 3-cycle wash. 10 μl of supernatant was transferred into 40 μl of 1×PBS/1% milk/10 mM $Ca^{2+}$ and incubated 1.5 hours at room temperature. Again the plates were washed using the Titertek plate washer operated using a 3-cycle wash. 40 μl/well of Goat anti-Human IgG Fc POD at a concentration of 100 ng/ml (1:4000) in 1×PBS/1% milk/10 mM $Ca^{2+}$ was added to the plate and was incubated 1 hour at room temperature. The plates were washed once again, using a 3-cycle wash. Finally, 40 μl/well of One-step TMB (Neogen, Lexington, Ky.) was added to the plate and quenching with 40 μl/well of 1N hydrochloric acid was performed after 30 minutes at room temperature. OD's were read immediately at 450 nm using a Titertek plate reader.

The primary screen resulted in a total of 3104 antigen specific hybridomas being identified from the two harvests. Based on highest ELISA OD, 1500 hybridomas per harvest were advanced for a total of 3000 positives.

Confirmatory Screen

The 3000 positives were then rescreened for binding to wild-type PCSK9 to confirm stable hybridomas were established. The screen was performed as follows: Costar 3702 medium binding 384 well plates (Corning Life Sciences) were employed. The plates were coated with neutravadin at 3 μg/ml in 1×PBS/0.05% Azide at a volume of 40 μl/well. The plates were incubated at 4° C. overnight. The plates were then washed using a Titertek plate washer (Titertek, Huntsville, Ala.). A 3-cycle wash was performed. The plates were blocked with 90 μl of 1×PBS/1% milk and incubated approximately 30 minutes at room temperature. The plates were then washed using the M384 plate washer. A 3-cycle wash was performed. The capture sample was b-PCSK9, without a V5 tag, and was added at 0.9 µg/ml in 1×PBS/1% milk/10 mM $Ca^{2+}$ at a volume of 40 µl/well. The plates were then incubated for 1 hour at room temperature. Next, the plates were washed using a 3-cycle wash. 10 µl of supernatant was transferred into 40 µl of 1×PBS/1% milk/10 mM $Ca^{2+}$ and incubated 1.5 hours at room temperature. Again the plates were washed using the Titertek plate washer operated using a 3-cycle wash. 40 µl/well of Goat anti-Human IgG Fc POD at a concentration of 100 ng/ml (1:4000) in 1×PBS/1% milk/10 mM $Ca^{2+}$ was added to the plate, and the plate was incubated 1 hour at room temperature. The plates were washed once again, using the Titertek plate washer operated using a 3-cycle wash. Finally, 40 µl/well of One-step TMB (Neogen, Lexington, Ky.) was added to the plate and was quenched with 40 µl/well of 1N hydrochloric acid after 30 minutes at room temperature. OD's were read immediately at 450 nm using a Titertek plate reader. A total of 2441 positives repeated in the second screen. These antibodies were then used in the subsequent screenings.

Mouse Cross-Reactivity Screen

The panel of hybridomas was then screened for cross-reactivity to mouse PCSK9 to make certain that the antibodies could bind to both human and mouse PCSK9. The following protocol was employed in the cross-reactivity screen: Costar 3702 medium binding 384 well plates (Corning Life Sciences) were employed. The plates were coated with neutravadin at 3 µg/ml in 1×PBS/0.05% Azide at a volume of 40 µl/well. The plates were incubated at 4° C. overnight. The plates were then washed using a Titertek plate washer (Titertek, Huntsville, Ala.). A 3-cycle wash was performed. The plates were blocked with 90 µl of 1×PBS/1% milk and incubated approximately 30 minutes at room temperature. The plates were then washed using the Titertek plate washer. A 3-cycle wash was performed. The capture sample was biotinylated-mouse PCSK9, and was added at 1 µg/ml in 1×PBS/1% milk/10 mM $Ca^{2+}$ at a volume of 40 µl/well. The plates were then incubated for 1 hour at room temperature. Next, the plates were washed using the Titertek plate washer operated using a 3-cycle wash. 50 µl of supernatant was transferred to the plates and incubated 1 hour at room temperature. Again the plates were washed using a 3-cycle wash. 40 µl/well of Goat anti-Human IgG Fc POD at a concentration of 100 ng/ml (1:4000) in 1×PBS/1% milk/10 mM $Ca^{2+}$ was added to the plate and the plate was incubated 1 hour at room temperature. The plates were washed once again, using a 3-cycle wash. Finally, 40 µl/well One-step TMB (Neogen, Lexington, Ky.) was added to the plate and was quenched with 40 µl/well of 1N hydrochloric acid after 30 minutes at room temperature. OD's were read immediately at 450 nm using a Titertek plate reader. 579 antibodies were observed to cross-react with mouse PCSK9. These antibodies were then used in the subsequent screenings.

D374Y Mutant Binding Screen

The D374Y mutation in PCSK9 has been documented in the human population (e.g., Timms K M et al, "A mutation in PCSK9 causing autosomal-dominant hypercholesterolemia in a Utah pedigree", Hum. Genet. 114: 349-353, 2004). In order to determine if the antibodies were specific for the wild type or also bound to the D374Y form of PCSK9, the samples were then screened for binding to the mutant PCSK9 sequence comprising the mutation D374Y. The protocol for the screen was as follows: Costar 3702 medium binding 384 well plates (Corning Life Sciences) were employed in the screen. The plates were coated with neutravadin at 4 µg/ml in 1×PBS/0.05% Azide at a volume of 40

µl/well. The plates were incubated at 4° C. overnight. The plates were then washed using a Titertek plate washer (Titertek, Huntsville, Ala.). A 3-cycle wash was performed. The plates were blocked with 90 µl of 1×PBS/1% milk and incubated approximately 30 minutes at room temperature. The plates were then washed using the Titertek plate washer. A 3-cycle wash was performed. The plates were coated with biotinylated human PCSK9 D374Y at a concentration of 1 µg/ml in 1×PBS/1% milk/10 mM$Ca^{2+}$ and incubated for 1 hour at room temperature. The plates were then washed using a Titertek plate washer. A 3-cycle wash was performed. Late exhaust hybridoma culture supernatant was diluted 1:5 in PBS/milk/$Ca^{2+}$ (10 ml plus 40 ml) and incubated for 1 hour at room temperature. Next, 40 µl/well of rabbit anti-human PCSK9 (Cayman Chemical) and human anti-His 1.2.3 1:2 at 1 ug/ml in 1×PBS/1% milk/10 mM$Ca^{2+}$ was titrated onto the plates, which were then incubated for 1 hour at room temperature. The plates were then washed using a Titertek plate washer. A 3-cycle wash was performed. 40 µl/well of Goat anti-Human IgG Fc HRP at a concentration of 100 ng/ml (1:4000) in 1×PBS/1% milk/10 mM $Ca^{2+}$ was added to the plate and the plate was incubated 1 hour at room temperature. 40 µl/well of Goat anti-rabbit IgG Fc HRP at a concentration of 100 ng/ml (1:4000) in 1×PBS/1% milk/10 mM $Ca^{2+}$ was added to the plate and the plate was incubated 1 hour at room temperature. The plates were then washed using a Titertek plate washer. A 3-cycle wash was performed. Finally, 40 µl/well of One-step TMB (Neogen, Lexington, Ky.) was added to the plate and was quenched with 40 µL/well of 1N hydrochloric acid after 30 minutes at room temperature. OD's were read immediately at 450 nm using a Titertek plate reader. Over 96% of the positive hits on the wild-type PCSK9 also bound mutant PCSK9.

Large Scale Receptor Ligand Blocking Screen

To screen for the antibodies that block PCSK9 binding to LDLR an assay was developed using the D374Y PCSK9 mutant. The mutant was used for this assay because it has a higher binding affinity to LDLR allowing a more sensitive receptor ligand blocking assay to be developed. The following protocol was employed in the receptor ligand blocking screen: Costar 3702 medium binding 384 well plates (Corning Life Sciences) were employed in the screen. The plates were coated with goat anti-LDLR (R&D Cat # AF2148) at 2 µg/ml in 1×PBS/0.05% Azide at a volume of 40 µl/well. The plates were incubated at 4° C. overnight. The plates were then washed using a Titertek plate washer (Titertek, Huntsville, Ala.). A 3-cycle wash was performed. The plates were blocked with 90 µl of 1×PBS/1% milk and incubated approximately 30 minutes at room temperature. The plates were then washed using the Titertek plate washer. A 3-cycle wash was performed. The capture sample was LDLR (R&D, Cat #2148LD/CF), and was added at 0.4 µg/ml in 1×PBS/1% milk/10 mM $Ca^{2+}$ at a volume of 40 µl/well. The plates were then incubated for 1 hour and 10 minutes at room temperature. Contemporaneously, 20 ng/ml of biotinylated human D374Y PCSK9 was incubated with 15 micro liters of hybridoma exhaust supernatant in Nunc polypropylene plates and the exhaust supernatant concentration was diluted 1:5. The plates were then pre-incubated for about 1 hour and 30 minutes at room temperature. Next, the plates were washed using the Titertek plate washer operated using a 3-cycle wash. 50 µl/well of the pre-incubated mixture was transferred onto the LDLR coated ELISA plates and incubated for 1 hour at room temperature. To detect LDLR-bound b-PCSK9, 40 µl/well streptavidin HRP at 500 ng/ml in assay diluent was added to the plates. The plates were incubated for 1 hour at room temperature. The plates were again washed using a Titertek plate washer. A 3-cycle wash was performed. Finally, 40 μl/well of One-step TMB (Neogen, Lexington, Ky.) was added to the plate and was quenched with 40 μl/well of 1N hydrochloric acid after 30 minutes at room temperature. OD's were read immediately at 450 nm using a Titertek plate reader. The screen identified 384 antibodies that blocked the interaction between PCSK9 and the LDLR well, 100 antibodies blocked the interaction strongly (OD<0.3). These antibodies inhibited the binding interaction of PCSK9 and LDLR greater than 90% (greater than 90% inhibition).

Receptor Ligand Binding Assay on Blocker Subset

The receptor ligand assay was then repeated using the mutant enzyme on the 384 member subset of neutralizers identified in the first large scale receptor ligand inhibition assay. The same protocol was employed in the screen of the 384 member blocker subset assay as was done in the large scale receptor ligand blocking screen. This repeat screen confirmed the initial screening data.

This screen of the 384 member subset identified 85 antibodies that blocked interaction between the PCSK9 mutant enzyme and the LDLR greater than 90%.

Receptor Ligand Binding Assay of Blockers that Bind the Wild Type PCSK9 but not the D374Y Mutant In the initial panel of 3000 sups there were 86 antibodies shown to specifically bind to the wild-type PCSK9 and not to the huPCSK9(D374Y) mutant. These 86 sups were tested for the ability to block wild-type PCSK9 binding to the LDLR receptor. The following protocol was employed: Costar 3702 medium binding 384 well plates (Corning Life Sciences) were employed in the screen. The plates were coated with anti-His 1.2.3 at 10 μg/ml in 1×PBS/0.05% Azide at a volume of 40 μl/well. The plates were incubated at 4° C. overnight. The plates were then washed using a Titertek plate washer (Titertek, Huntsville, Ala.). A 3-cycle wash was performed. The plates were blocked with 90 μl of 1×PBS/1% milk and incubated approximately 30 minutes at room temperature. The plates were then washed using the Titertek plate washer. A 3-cycle wash was performed. LDLR (R&D Systems, #2148LD/CF or R&D Systems, #2148LD) was added at 5 μg/ml in 1×PBS/1% milk/10 mM $Ca^{2+}$ at a volume of 40 μl/well. The plates were then incubated for 1 hour at room temperature. Next, the plates were washed using the Titertek plate washer operated using a 3-cycle wash. Contemporaneously, biotinylated human wild-type PCSK9 was pre-incubated with hybridoma exhaust supernatant in Nunc polypropylene plates. 22 μl of hybridoma sup was transferred into 33 ul of b-PCSK9 at a concentration of 583 ng/ml in 1×PBS/1% milk/10 mMCa2+, giving a final b-PCSK9 concentration=350 ng/ml and the exhaust supernatant at a final dilution of 1:2.5. The plates were preincubated for approximately 1 hour and 30 minutes at room temperature. 50 μl/well of the preincubated mixture was transferred onto LDLR captured ELISA plates and incubated for 1 hour at room temperature. The plates were then washed using the Titertek plate washer. A 3-cycle wash was performed. 40 μl/well streptavidin HRP at 500 ng/ml in assay diluent was added to the plates. The plates were incubated for 1 hour at room temperature. The plates were then washed using a Titertek plate washer. A 3-cycle wash was performed. Finally, 40 μl/well of One-step TMB (Neogen, Lexington, Ky.) was added to the plate and was quenched with 40 μl/well of 1N hydrochloric acid after 30 minutes at room temperature. OD's were read immediately at 450 nm using a Titertek plate reader.

Screening Results

Based on the results of the assays described, several hybridoma lines were identified as producing antibodies with desired interactions with PCSK9. Limiting dilution was used to isolate a manageable number of clones from each line. The clones were designated by hybridoma line number (e.g. 21B12) and clone number (e.g. 21B12.1). In general, no difference among the different clones of a particular line was detected by the functional assays described herein. In a few cases, clones were identified from a particular line that behaved differently in the functional assays, for example, 25A7.1 was found not to block PCSK9/LDLR but 25A7.3 (referred to herein as 25A7) was neutralizing. The isolated clones were each expanded in 50-100 ml of hybridoma media and allowed to grow to exhaustion, (i.e., less than about 10% cell viability). The concentration and potency of the antibodies to PCSK9 in the supernatants of those cultures were determined by ELISA and by in vitro functional testing, as described herein. As a result of the screening described herein, the hybridomas with the highest titer of antibodies to PCSK9 were identified. The selected hybridomas are shown in FIGS. 2A-3D and Table 2.

Example 4.1

Production of Human 31H4 IgG4 Antibodies from Hybridomas

This example generally describes how one of the antigen binding proteins was produced from a hybridoma line. The production work used 50 ml exhaust supernatant generation followed by protein A purification. Integra production was for scale up and was performed later. Hybridoma line 31H4 was grown in T75 flasks in 20 ml of media (Integra Media, Table 5). When the hybridoma was nearly confluent in the T75 flasks, it was transferred to an Integra flask (Integra Biosciences, Integra CL1000, cat #90 005).

The Integra flask is a cell culture flask that is divided by a membrane into two chambers, a small chamber and a large chamber. A volume of 20-30 ml hybridoma cells at a minimum cell density of $1\times10^6$ cells per ml from the 31H4 hybridoma line was placed into the small chamber of an Integra flask in Integra media (see Table 5 for components of Integra media). Integra media alone (1 L) was placed in the large chambers of the Integra flasks. The membrane separating the two chambers is permeable to small molecular weight nutrients but is impermeable to hybridoma cells and to antibodies produced by those cells. Thus, the hybridoma cells and the antibodies produced by those hybridoma cells were retained in the small chamber.

After one week, media was removed from both chambers of the Integra flask and was replaced with fresh Integra media. The collected media from the small chambers was separately retained. After a second week of growth, the media from the small chamber was again collected. The collected media from week 1 from the hybridoma line was combined with the collected media from week 2 from the hybridoma line. The resulting collected media sample from the hybridoma line was spun to remove cells and debris (15 minutes at 3000 rpm) and the resulting supernatant was filtered (0.22 μm). Clarified conditioned media was loaded onto a Protein A-Sepharose column. Optionally, the media can be first concentrated and then loaded onto a Protein A Sepharose column. Non-specific bindings were removed by an extensive PBS wash. Bound antibody proteins on the Protein A column were recovered by standard acidic antibody elution from Protein A columns (such as 50 mM Citrate, pH 3.0). Aggregated antibody proteins in the Protein A Sepharose pool were removed by size exclusion chromatography or binding ion exchange chromatography on anion exchanger resin such as Q Sepharose resin. The specific IEX conditions for the 31H4 proteins are Q-Sepharose HP at pH 7.8-8.0. Antibody was eluted with a NaCl gradient of 10 mM-500 mM in 25 column volumes.

TABLE 5

Composition of Media
INTEGRA MEDIA

HSFM
10% Ultra Low IgG serum
2 mmol/L L-glutamine
1% NEAA
4 g/L glucose

Example 4.2

Production of Recombinant 31H4 Human IgG2 Antibodies from Transfected Cells

The present example outlines how 31H4 IgG2 antibodies were produced from transfected cells. 293 cells for transient expression and CHO cells for stable expression were transfected with plasmids that encode 31H4 heavy and light chains. Conditioned media from transfected cells was recovered by removing cells and cell debris. Clarified conditioned media was loaded onto a Protein A-Sepharose column. Optionally, the media can first be concentrated and then loaded onto a Protein A Sepharose column. Non-specific bindings were removed by extensive PBS wash. Bound antibody proteins on the Protein A column were recovered by standard acidic antibody elution from Protein A columns (such as 50 mM citrate, pH 3.0). Aggregated antibody proteins in the Protein A Sepharose pool were removed by size exclusion chromatography or binding ion exchange chromatography on anion exchanger resin such as Q Sepharose resin. The specific IEX conditions for the 31H4 proteins are Q-Sepharose HP at pH 7.8-8.0. The antibody was eluted with a NaCl gradient of 10 mM-500 mM in 25 column volumes.

Example 5

Production of Human 21B12 IgG4 Antibodies from Hybridomas

The present example outlines how antibody 21B12 IgG4 was produced from hybridomas. Hybridoma line 21B12 was grown in T75 flasks in media (Integra Media, Table 5). When the hybridomas were nearly confluent in the T75 flasks, they were transferred to Integra flasks (Integra Biosciences, Integra CL1000, cat #90 005).

The Integra flask is a cell culture flask that is divided by a membrane into two chambers, a small chamber and a large chamber. A volume of 20-30 ml hybridoma cells at a minimum cell density of $1\times10^6$ cells per ml from the 31H4 hybridoma line was placed into the small chamber of an Integra flask in Integra media (see Table 5 for components of Integra media). Integra media alone (1 L) was placed in the large chambers of the Integra flasks. The membrane separating the two chambers is permeable to small molecular weight nutrients but is impermeable to hybridoma cells and to antibodies produced by those cells. Thus, the hybridoma cells and the antibodies produced by those hybridoma cells were retained in the small chamber.

After one week, media was removed from both chambers of the Integra flask and was replaced with fresh Integra media. The collected media from the small chambers was separately retained. After a second week of growth, the media from the small chamber was again collected. The collected media from week 1 from the hybridoma line was combined with the collected media from week 2 from the hybridoma line. The resulting collected media sample from the hybridoma line was spun to remove cells and debris (15 minutes at 3000 rpm) and the resulting supernatant was filtered (0.22 μm). Clarified conditioned media were loaded onto a Protein A Sepharose column. Optionally, the media are first concentrated and then loaded onto a Protein A Sepharose column. Non-specific bindings were removed by an extensive PBS wash. Bound antibody proteins on the Protein A column were recovered by standard acidic antibody elution from Protein A columns (such as 50 mM Citrate, pH 3.0). Aggregated antibody proteins in the Protein A Sepharose pool were removed by size exclusion chromatography or binding ion exchange chromatography on anion exchanger resin such as Q Sepharose resin. The specific IEX conditions for the 21B12 proteins are Q-Sepharose HP at pH 7.8-8.0. The antibody was eluted with a NaCl gradient of 10 mM-500 mM in 25 column volumes.

Example 6

Production of Human 21B12 IgG2 Antibodies from Transfected Cells

The present example outlines how 21B12 IgG2 antibodies were produced from transfected cells. Cells (293 cells for transient expression and CHO cells for stable expression) were transfected with plasmids that encode 21B12 heavy and light chains. Conditioned media from hybridoma cells were recovered by removing cells and cell debris. Clarified conditioned media were loaded onto a Protein A-Sepharose column. Optionally, the media can first be concentrated and then loaded onto a Protein A Sepharose column. Non-specific bindings were removed by extensive PBS wash. Bound antibody proteins on the Protein A column were recovered by standard acidic antibody elution from Protein A columns (50 mM Citrate, pH 3.0). Aggregated antibody proteins in the Protein A Sepharose pool were removed by size exclusion chromatography or binding ion exchange chromatography on cation exchanger resin such as SP-Sepharose resin. The specific IEX conditions for the 21B12 proteins were SP-Sepharose HP at pH 5.2. Antibodies were eluted with 25 column volumes of buffer that contains a NaCl gradient of 10 mM-500 mM in 20 mM sodium acetate buffer.

Example 7

Sequence Analysis of Antibody Heavy and Light Chains

The nucleic acid and amino acid sequences for the light and heavy chains of the above antibodies were then determined by Sanger (dideoxy) nucleotide sequencing. Amino acid sequences were then deduced for the nucleic acid sequences. The nucleic acid sequences for the variable domains are depicted in FIGS. 3E-3JJ.

The cDNA sequences for the lambda light chain variable regions of 31H4, 21B12, and 16F12 were determined and are disclosed as SEQ ID NOs: 153, 95, and 105 respectively.

The cDNA sequences for the heavy chain variable regions of 31H4, 21B12, and 16F12 were determined and are disclosed as SEQ ID NOs: 152, 94, and 104 respectively.

The lambda light chain constant region (SEQ ID NO: 156), and the IgG2 and IgG4 heavy chain constant regions (SEQ ID NOs: 154 and 155) are shown in FIG. 3KK.

The polypeptide sequences predicted from each of those cDNA sequences were determined. The predicted polypeptide sequences for the lambda light chain variable regions of 31H4, 21B12, and 16F12 were predicted and are disclosed as SEQ ID NOs: 12, 23, and 35 respectively, the lambda light chain constant region (SEQ ID NO: 156), the heavy chain variable regions of 31H4, 21B12, and 16F12 were predicted and are disclosed as (SEQ. ID NOs. 67, 49, and 79 respectively. The IgG2 and IgG4 heavy chain constant regions (SEQ ID NOs: 154 and 155).

The FR1, CDR1, FR2, CDR2, FR3, CDR3, FR4 divisions are shown in FIG. 2A-3D.

Based on the sequence data, the germline genes from which each heavy chain or light chain variable region was derived was determined. The identity of the germline genes are indicated next to the corresponding hybridoma line in FIGS. 2A-3D and each is represented by a unique SEQ ID NO. FIGS. 2A-3D also depict the determined amino acid sequences for additional antibodies that were characterized.

Example 8

Characterization of Binding of Antibodies to PCSK9

Having identified a number of antibodies that bind to PCSK9, several approaches were employed to quantify and further characterize the nature of the binding. In one aspect of the study, a Biacore affinity analysis was performed. In another aspect of the study a KinExA® affinity analysis was performed. The samples and buffers employed in these studies are presented in Table 6 below.

TABLE 6

| sample | [sample] mg/ml | Buffer | [sample] μm |
|---|---|---|---|
| hPCSK9 | 1.26 | PBS | 16.6 |
| mPCSK9-8xHIS | 1.44 | PBS | 18.9 |
| cPCSK9-V5-6xHIS | 0.22 | PBS | 2.9 |
| 16F12, anti-PCSK9 huIgG4 | 4.6 | 20 mM NaOAC, pH 5.2, 50 mM NaCl | 31.9 |
| 21B12, anti-PCSK9 huIgG4 | 3.84 | 10 mM NAOAC, pH 5.2, 9% Sucrose | 27.0 |
| 31H4, anti-PCSK9 huIgG4 | 3.3 | 10 mM NAOAC, pH 5.2, 9% Sucrose | 22.9 |

BIAcore® Affinity Measurements

A BIAcore® (surface plasmon resonance device, Biacore, Inc., Piscataway, N.J.) affinity analysis of the 21B12 antibodies to PCSK9 described in this Example was performed according to the manufacturer's instructions.

Briefly, the surface plasmon resonance experiments were performed using Biacore 2000 optical biosensors (Biacore, GE Healthcare, Piscataway, N.J.). Each individual anti-PCSK9 antibody was immobilized to a research-grade CM5 biosensor chip by amine-coupling at levels that gave a maximum analyte binding response (Rmax) of no more than 200 resonance units (RU). The concentration of PCSK9 protein was varied at 2 fold intervals (the analyte) and was injected over the immobilized antibody surface (at a flow rate of 100 μl/min for 1.5 minutes). Fresh HBS-P buffer (pH 7.4, 0.01 M Hepes, 0.15 M NaCl, 0.005% surfactant P-20, Biacore) supplemented with 0.01% BSA was used as binding buffer. Binding affinities of each anti-PCSK9 antibody were measured in separate experiments against each of the human, mouse, and cynomolgus monkey PCSK9 proteins at pH 7.4 (the concentrations used were 100, 50, 25, 12.5, 6.25, 3.125, and 0 nM).

In addition, the binding affinities of antibody to human PCSK9 were also measured at pH 6.0 with the pH 6.0 HBS-P buffer (pH 6.0, 0.01 M Hepes, 0.15 M NaCl, 0.005% surfactant P-20, Biacore) supplemented with 0.01% BSA. The binding signal obtained was proportional to the free PCSK9 in solution. The dissociation equilibrium constant ($K_D$) was obtained from nonlinear regression analysis of the competition curves using a dual-curve one-site homogeneous binding model (KinExA® software, Sapidyne Instruments Inc., Boise, Id.) (n=1 for the 6.0 pH runs). Interestingly, the antibodies appeared to display a tighter binding affinity at the lower pH (where the Kd was 12.5, 7.3, and 29 pM for 31H4, 21B12, and 16F12 respectively).

Antibody binding kinetic parameters including $k_a$ (association rate constant), $I_Q$ (dissociation rate constant), and $K_D$ (dissociation equilibrium constant) were determined using the BIA evaluation 3.1 computer program (BIAcore, Inc. Piscataway, N.J.). Lower dissociation equilibrium constants indicate greater affinity of the antibody for PCSK9. The $K_D$ values determined by the BIAcore® affinity analysis are presented in Table 7.1, shown below.

TABLE 7.1

| Antibody | hPCSK9 | CynoPCSK9 | mPCSK9 |
|---|---|---|---|
| 31H4 | 210 pM | 190 pM | 6 nM |
| 21B12 | 190 pM | 360 pM | 460 nM |
| 16F12 | 470 pM | 870 pM | 6.4 nM |

Table 7.2 depicts the $k_{on}$ and $k_{off}$ rates.

TABLE 7.2

| — | $K_{on}$ (M−1 s−1) | $K_{off}$ (s−1) | $K_D$ |
|---|---|---|---|
| 31H4.1, pH 7.4 | 2.45e+5 | 5.348e−5 | 210 pM |
| 31H4.1, pH 6 | 5.536e+6 | 6.936e−5 | 12.5 pM |
| 21B12.1, pH 7.4 | 3.4918e+4 | 6.634e−6 | 190 pM |
| 21B12.1, pH 6 | 2.291e+6 | 1.676e−5 | 7.3 pM |
| 16F12.1, pH 7.4 | 1.064e+5 | 4.983e−5 | 470 pM |
| 16F12.1, pH 6 | 2.392e+6 | 7.007e−5 | 29 pM |

KinExA® Affinity Measurements

A KinExA® (Sapidyne Instruments, Inc., Boise, Id.) affinity analysis of 16F12 and 31H4 was performed according to the manufacturer's instructions. Briefly, Reacti-Gel™ (6×) (Pierce) was pre-coated with one of human, V5-tagged cyno or His-tagged mouse PCSK9 proteins and blocked with BSA. 10 or 100 pM of antibody 31H4 and one of the PCSK9 proteins was then incubated with various concentrations (0.1 pM-25 nM) of PCSK9 proteins at room temperature for 8 hours before being passed through the PCSK9-coated beads. The amount of the bead-bound 31H4 was quantified by fluorescently (Cy5) labeled goat anti-human IgG (H+L) antibody (Jackson Immuno Research). The binding signal is proportional to the concentration of free 31H4 at binding equilibrium. Equilibrium dissociation constant ($K_D$) were obtained from nonlinear regression of the two sets of competition curves using a one-site homogeneous binding model. The KinExA® Pro software was employed in the analysis. Binding curves generated in this analysis are presented as FIGS. 4A-4F.

Both the 16F12 and 31H4 antibodies showed similar affinity to human and cyno PCSK9, but approximately 10-250 fold lower affinity to mouse PCSK9. Of the two antibodies tested using the KinExA® system, antibody 31H4 showed higher affinity to both human and cyno PCSK9 with 3 and 2 pM $K_D$, respectively. 16F12 showed slightly weaker affinity at 15 pM $K_D$ to human PCSK9 and 16 pM $K_D$ to cyno PCSK9.

The results of the KinExA® affinity analysis are summarized in Table 8.1, shown below.

TABLE 8.1

| | hPCSK9 | | cPCSK | | mPCSK KD | |
|---|---|---|---|---|---|---|
| Sample | KD (pM) | 95% CI | KD (pM) | 95% CI | (pM) | 95% CI |
| 31H4.1 | 3 | 1~5 | 2 | 1~3 | 500 | 400~620 |

Figure 4A:
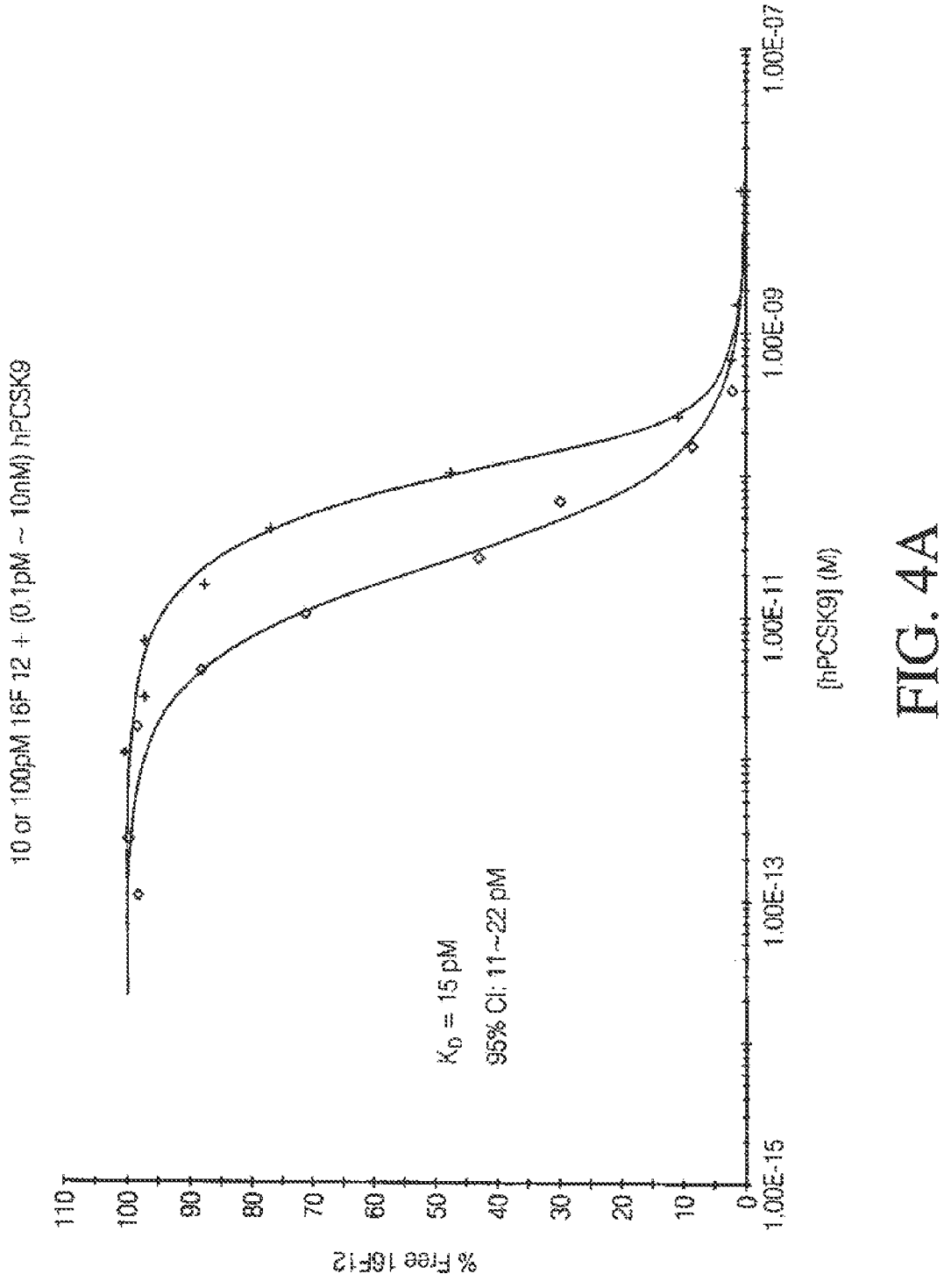
FIG. 4A is a binding curve of an antigen binding protein to human PCSK9.
Figure 4B:
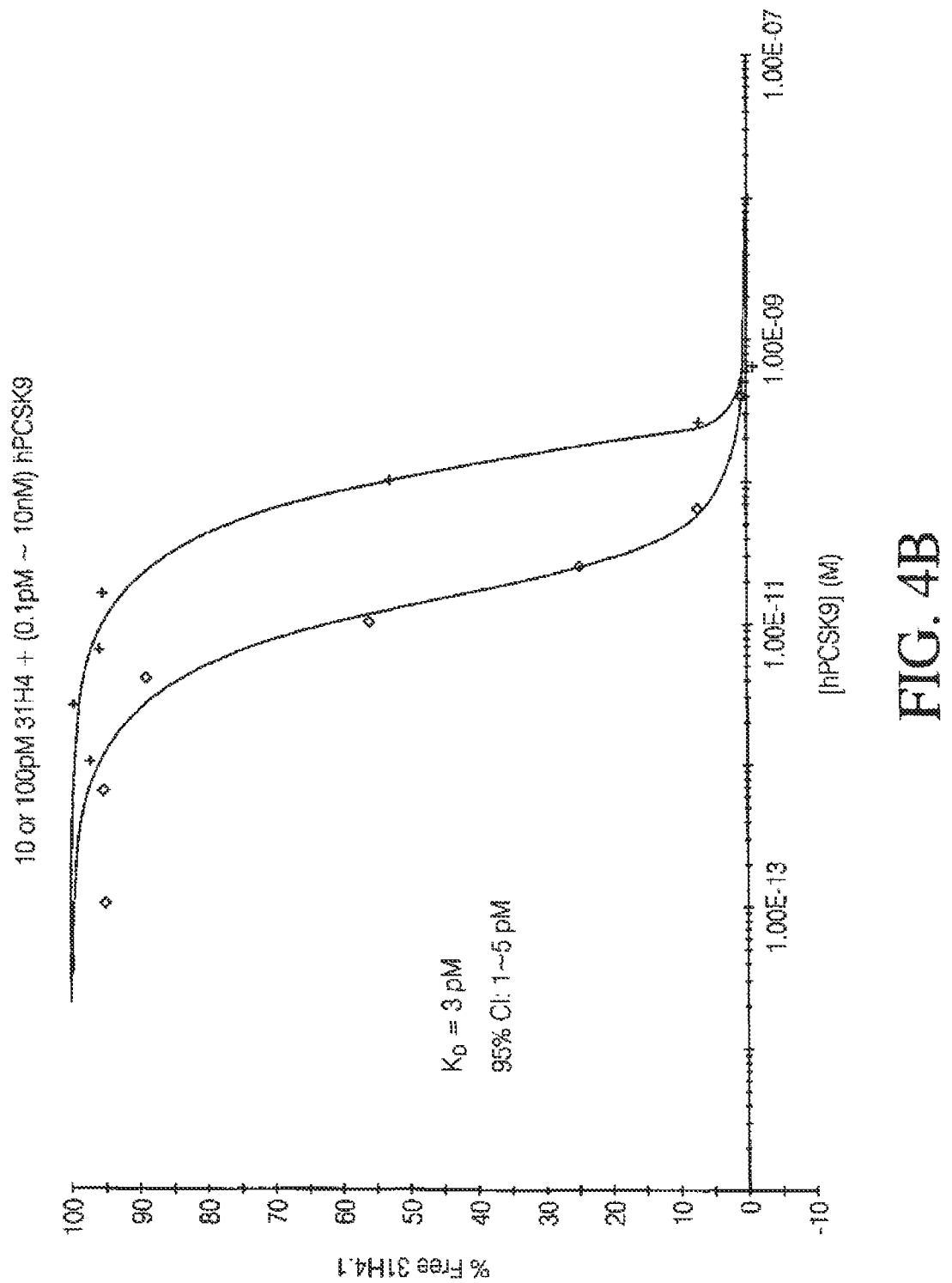
FIG. 4B is a binding curve of an antigen binding protein to human PCSK9.
Figure 4C:
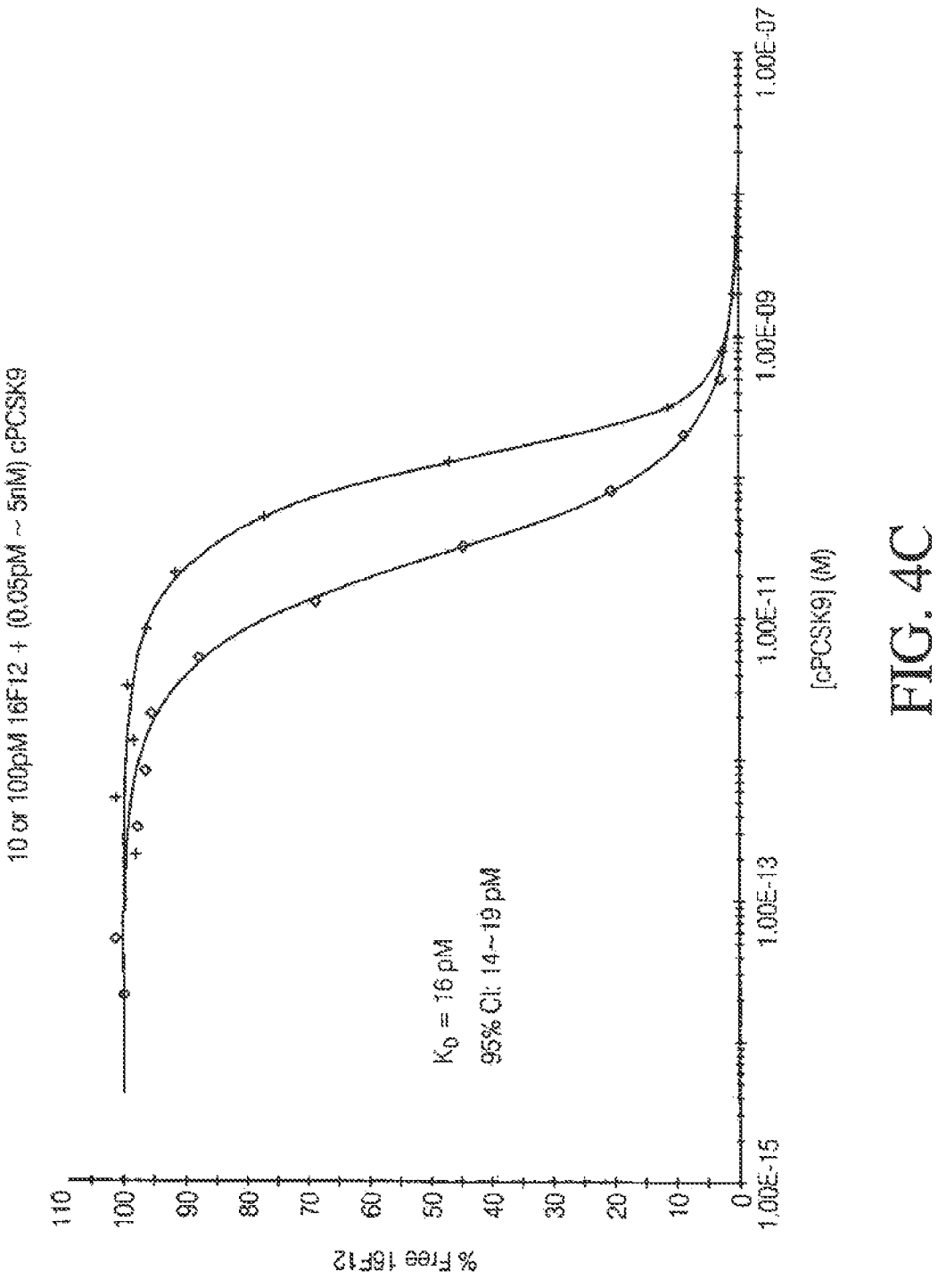
FIG. 4C is a binding curve of an antigen binding protein to cynomolgus PCSK9.
Figure 4D:
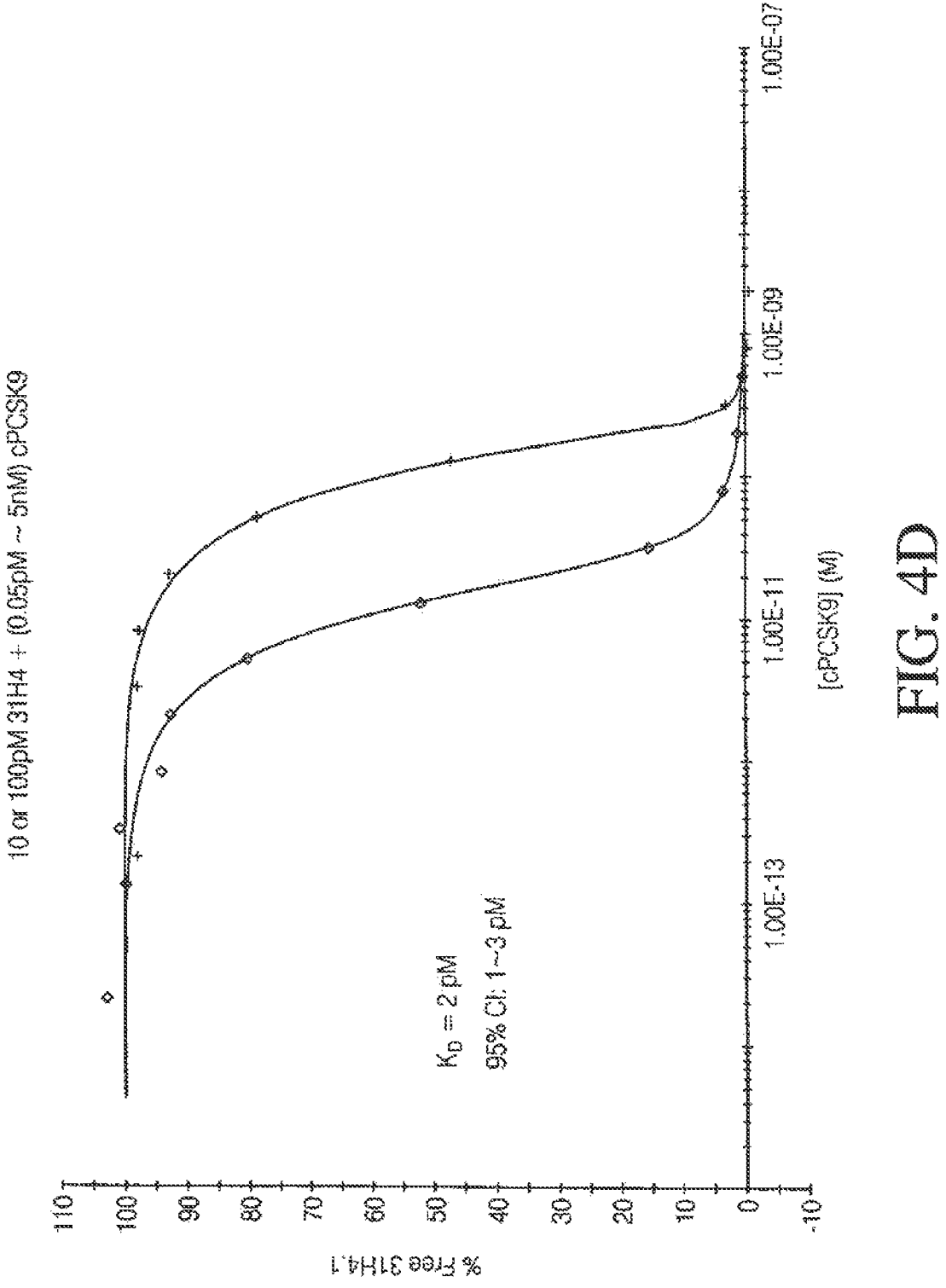
FIG. 4D is a binding curve of an antigen binding protein to cynomolgus PCSK9.
Figure 4E:
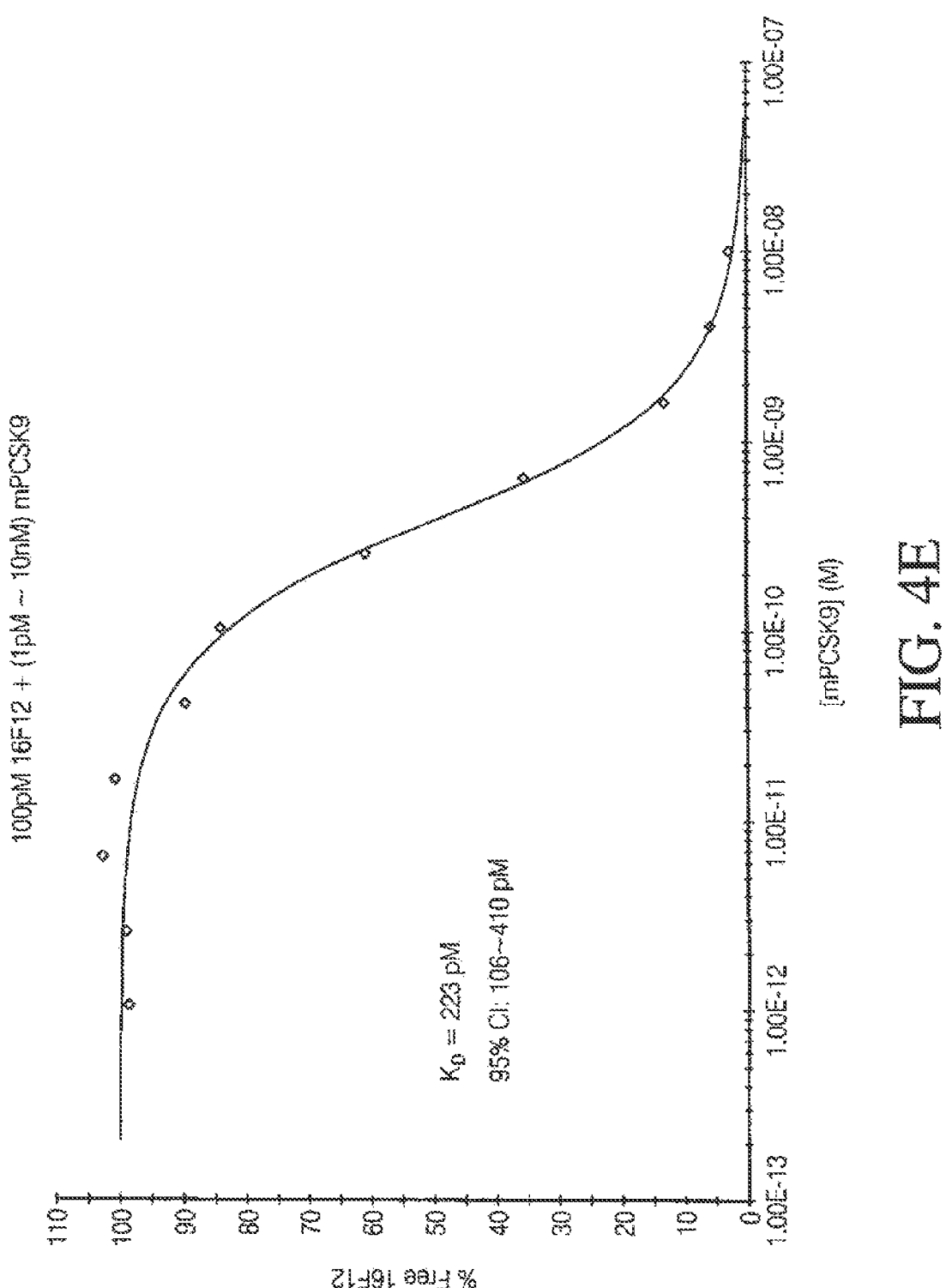
FIG. 4E is a binding curve of an antigen binding protein to mouse PCSK9.
Figure 4F:
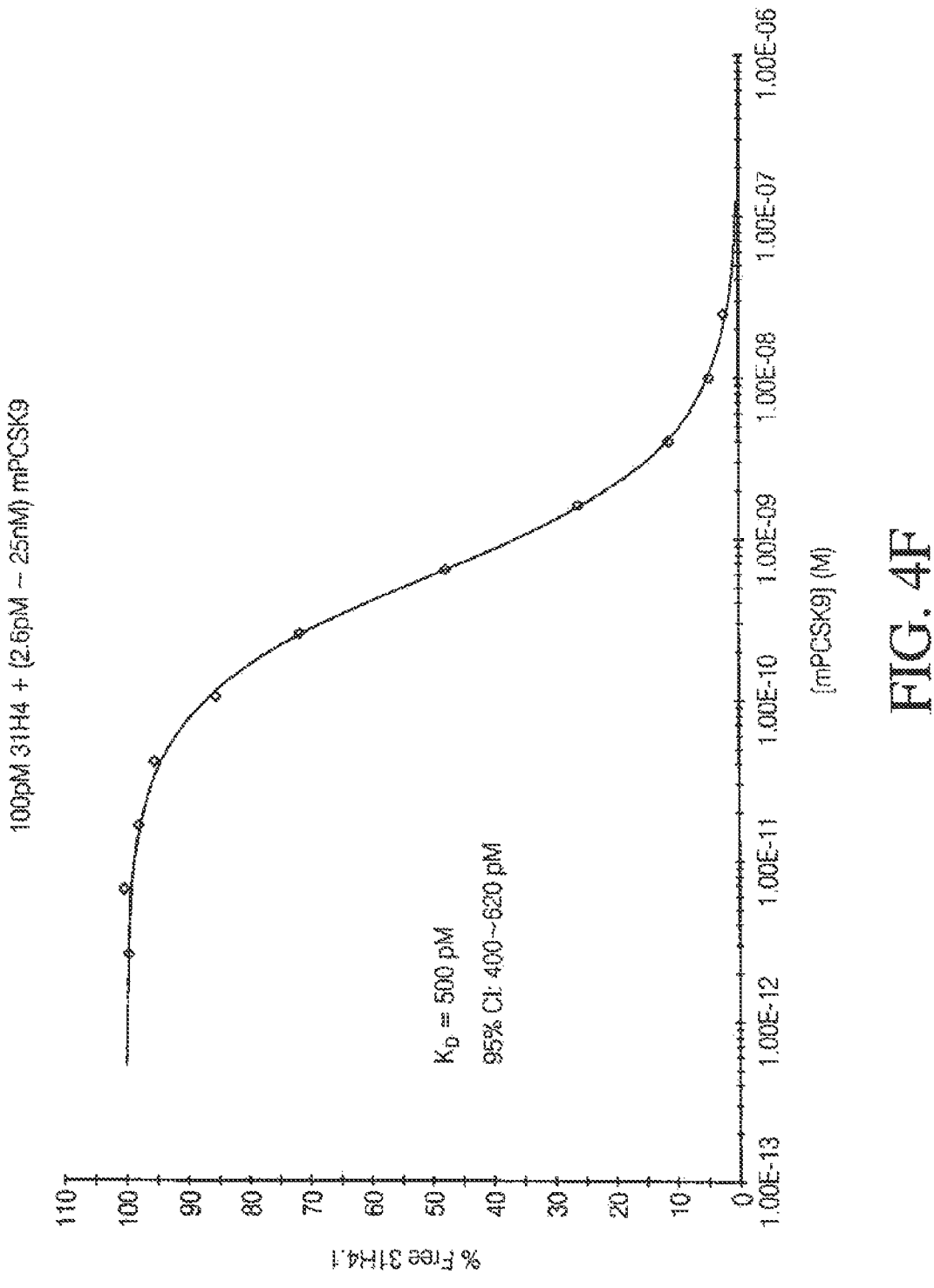
FIG. 4F is a binding curve of an antigen binding protein to mouse PCSK9.
Figure 5A:
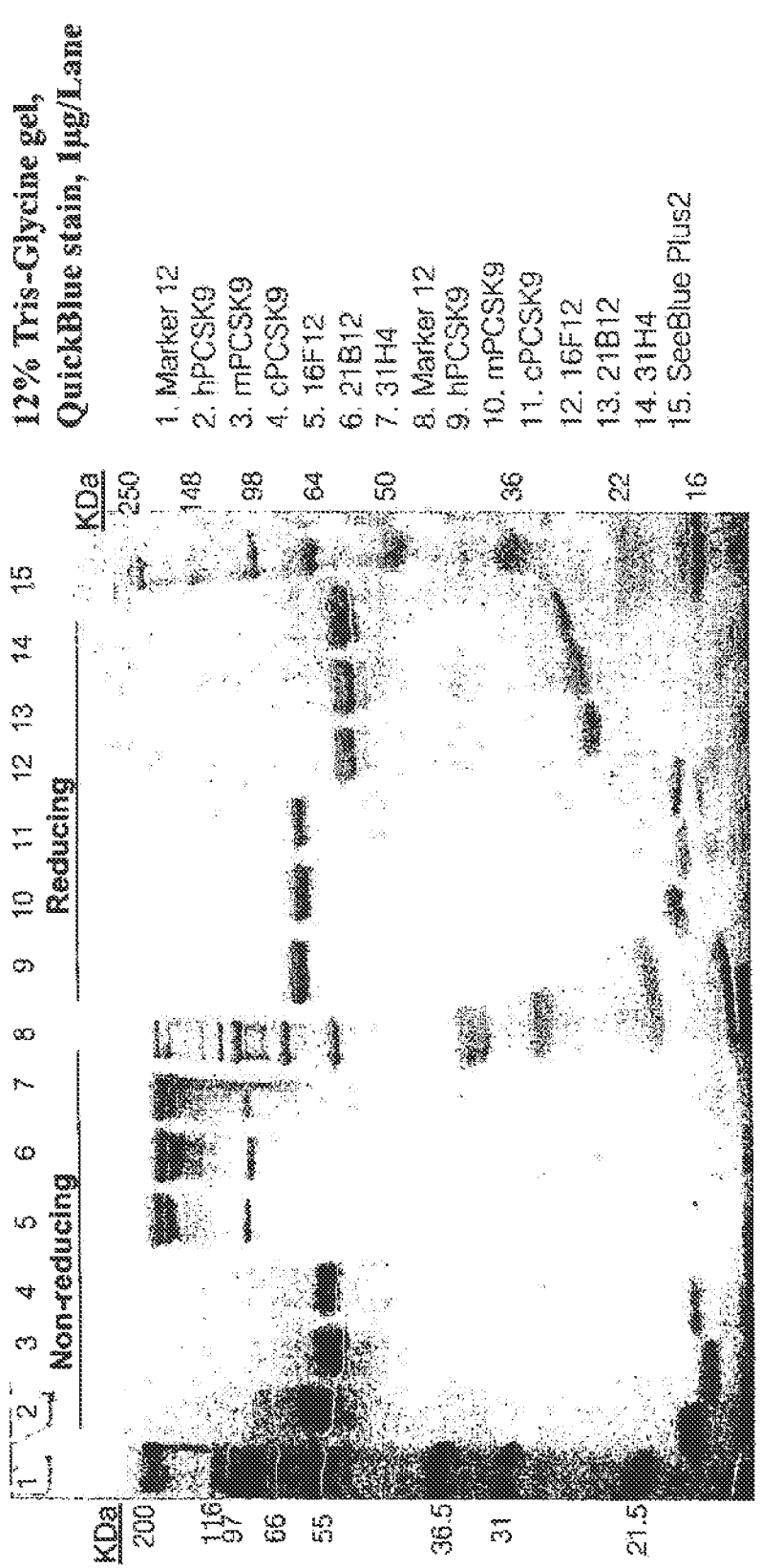
FIG. 5A depicts the results of an SDS PAGE experiment involving PCSK9 and various antigen binding proteins demonstrating the relative purity and concentration of the proteins.

In addition, a SDS PAGE was run to check the quality and quantity of the samples and is shown in FIG. 5A. cPCSK9 showed around 50% less on the gel and also from the active binding concentration calculated from KinExA® assay. Therefore, the $K_D$ of the mAbs to cPCSK9 was adjusted as 50% of the active cPCSK9 in the present.

Figure 5B:
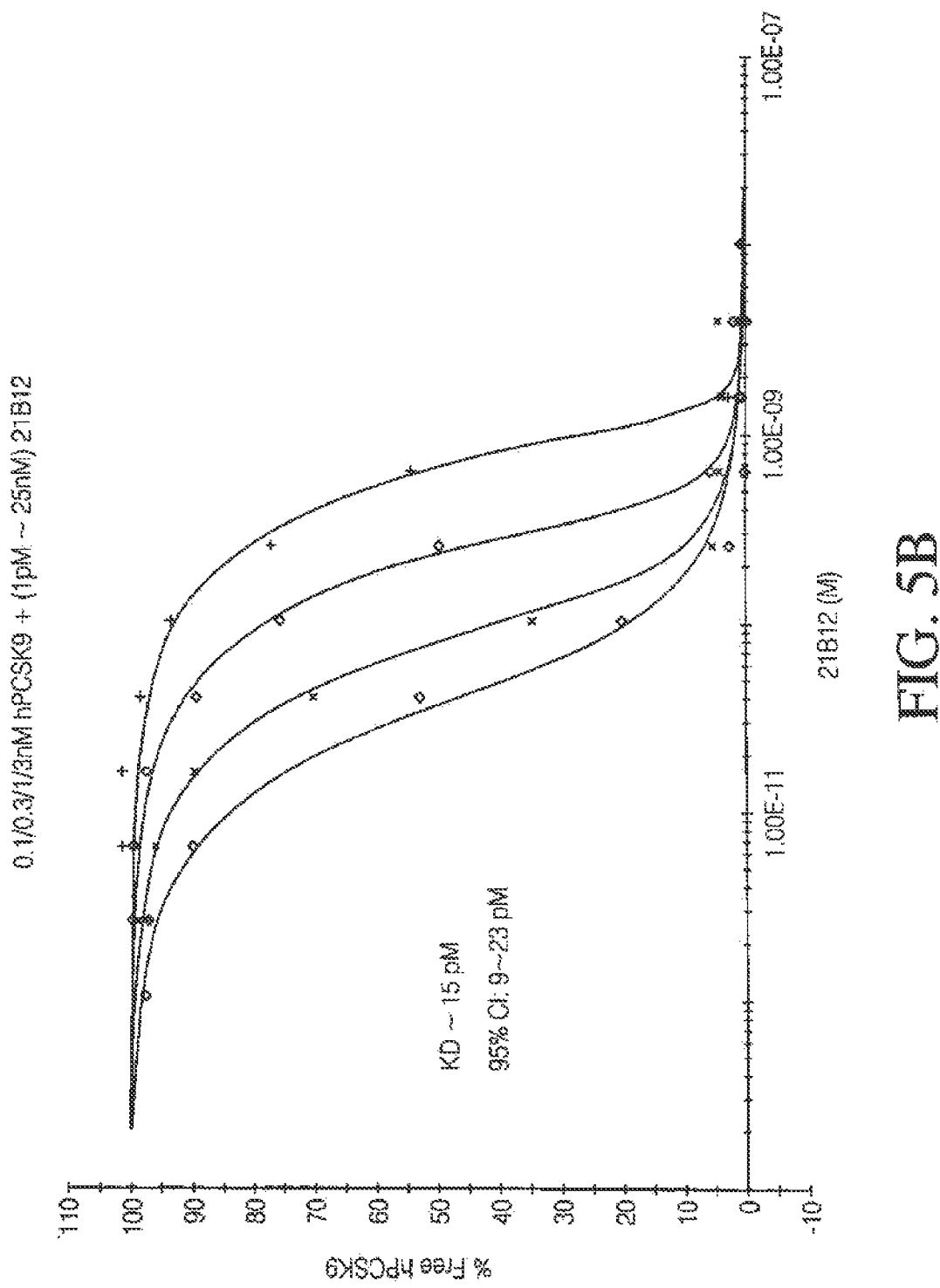
FIGS. 5B and 5C depict graphs from Biacore solution equilibrium assays for 21B12.
Figure 5C:
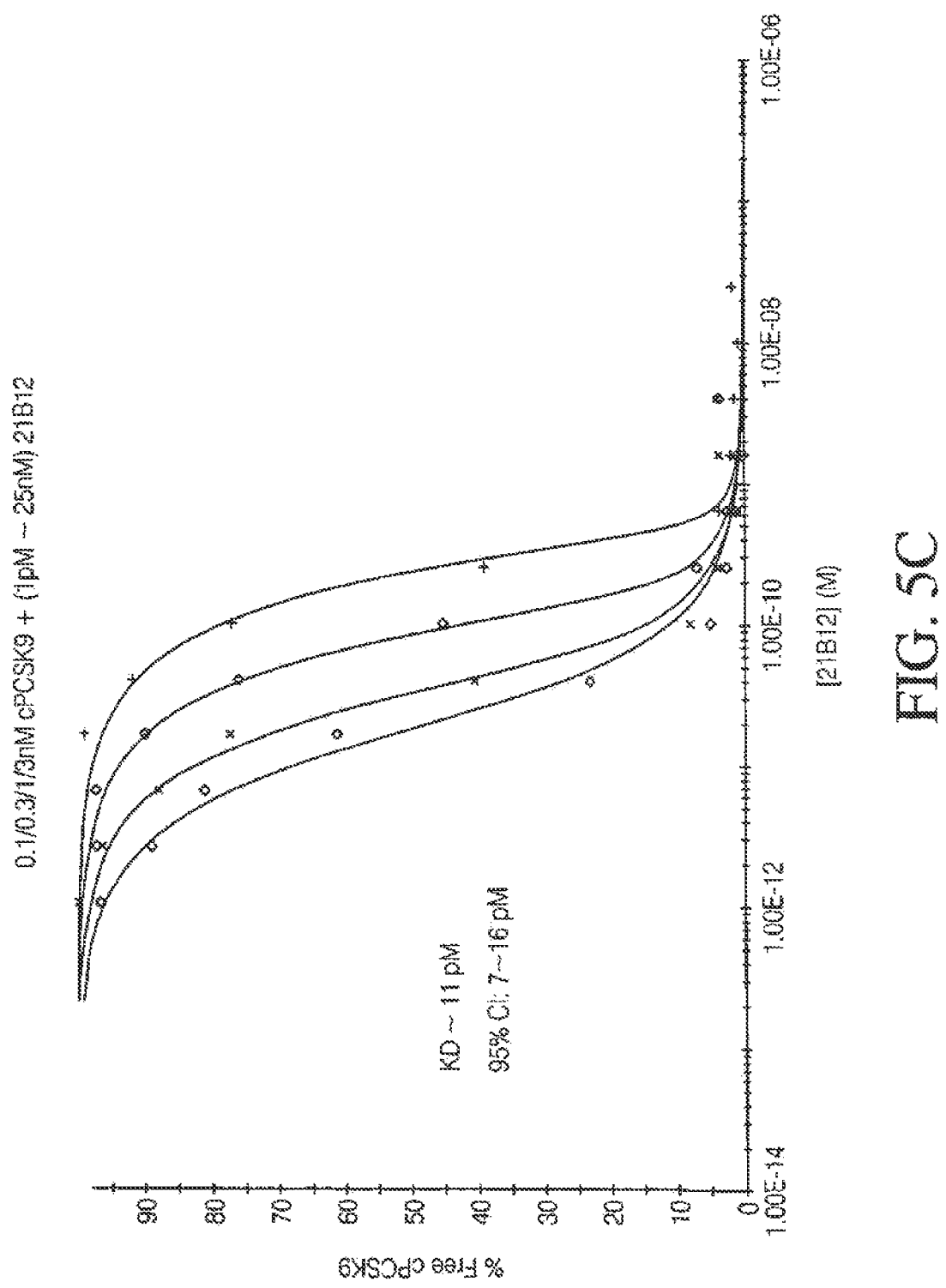
Figure 5D:
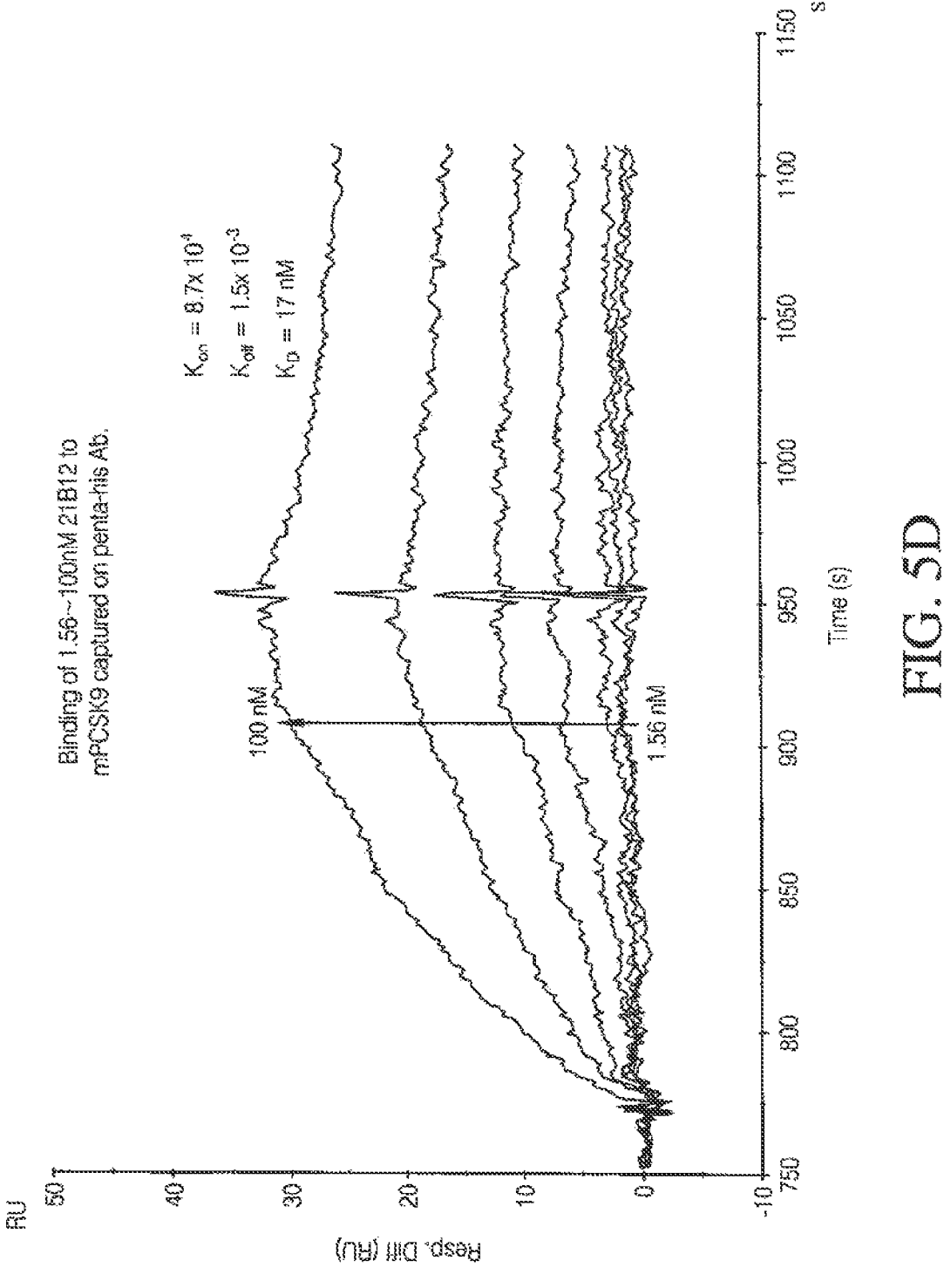
FIG. 5D depicts the graph of the kinetics from a Biacore capture assay.
Figure 5E:
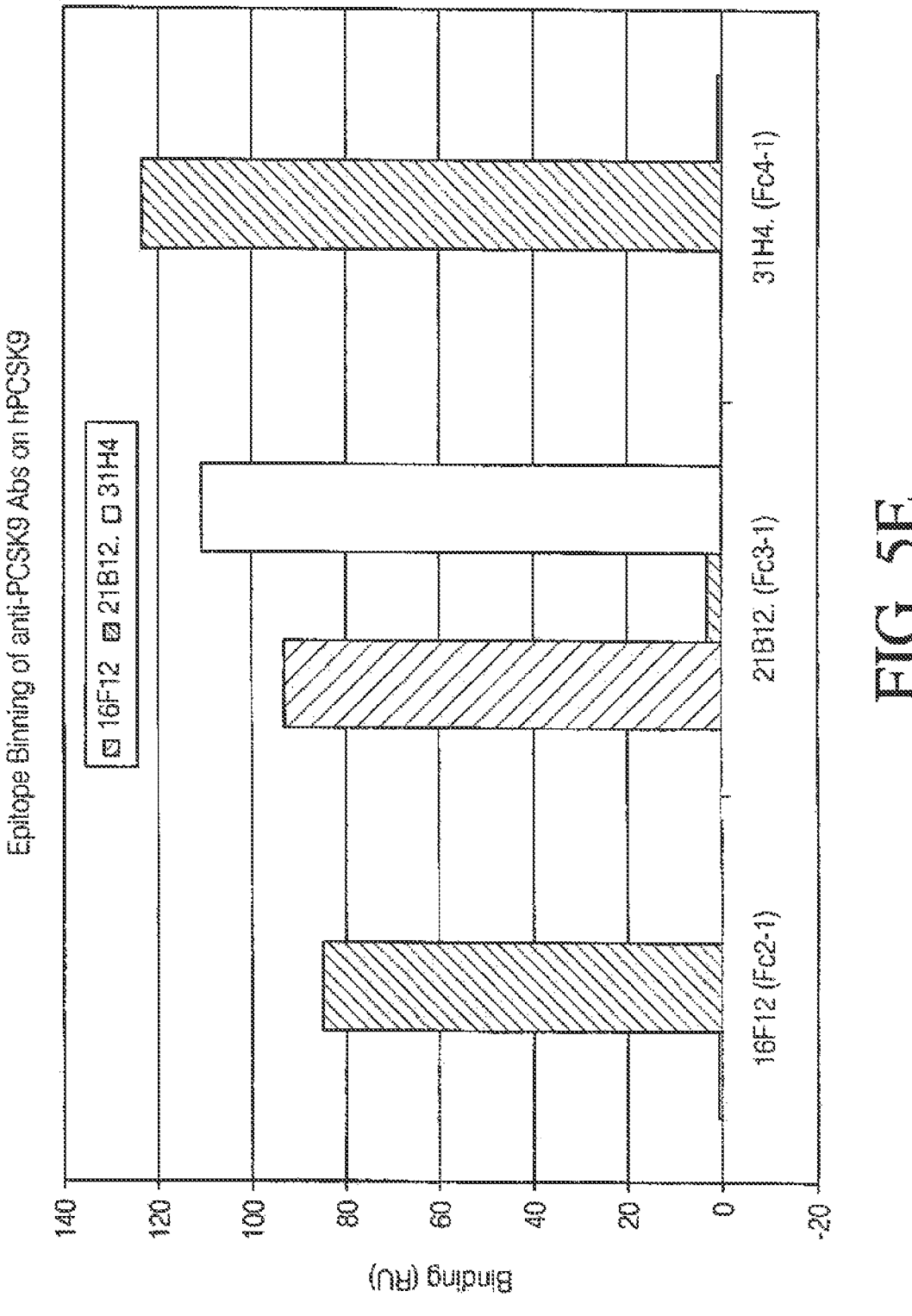
FIG. 5E depicts a bar graph depicting binning results for three ABPs.

A BIAcore solution equilibrium binding assay was used to measure the Kd values for ABP 21B12. 21B12.1 showed little signal using KinExA assay, therefore, biacore solution equilibrium assay was applied. Since no significant binding was observed on binding of antibodies to immobilized PCSK9 surface, 21B12 antibody was immobilized on the flow cell 4 of a CMS chip using amine coupling with density around 7000 RU. Flow cell 3 was used as a background control. 0.3, 1, and 3 nM of human PCSK9 or cyno PCSK9 were mixed with a serial dilutions of 21B12.1 antibody samples (ranged from 0.001~25 nM) in PBS plus 0.1 mg/ml BSA, 0.005% P20. Binding of the free PCSK9 in the mixed solutions were measured by injecting over the 21B12.1 antibody surface. 100% PCSK9 binding signal on 21B12.1 surface was determined in the absence of mAb in the solution. A decreased PCSK9 binding response with increasing concentrations of mAb indicated that PCSK9 binding to mAb in solution, which blocked PCSK9 from binding to the immobilized peptibody surface. Plotting the PCSK9 binding signal versus mAb concentrations, $K_D$ was calculated from three sets of curves (0.3, 1 and 3 nM fixed PCSK9 concentration) using a one-site homogeneous binding model in KinExA Pro™ software. Although cPCSK9 has lower protein concentration observed from KinExA assay and SDS-gel, its concentration was not adjusted here since the concentration of cPCSK9 was not used for calculation of $K_D$. The results are displayed in Table 8.2 below and in FIGS. 5B-5D. FIG. 5B depicts the results from the solution equilibrium assay at three different hPCSK9 concentrations for hPCSK9. FIG. 5C depicts a similar set of results for mPCSK9. FIG. 5D depicts the results from the above biacore capture assay.

TABLE 8.2

| | hPCSK9 | | cPCSK | | mPCSK KD | |
|---|---|---|---|---|---|---|
| Sample | KD (pM) | 95% CI | KD (pM) | 95% CI | (pM) | 95% CI |
| 21B12.1 | 15 | 9~23 | 11 | 7~16 | 17000 | — |

Example 9

Efficacy of 31H4 and 21B12 for Blocking D374Y PCSK9/LDLR Binding

This example provides the IC50 values for two of the antibodies in blocking PCSK9 D374Y's ability to bind to LDLR. Clear 384 well plates (Costar) were coated with 2 micrograms/ml of goat anti-LDL receptor antibody (R&D Systems) diluted in buffer A (100 mM sodium cacodylate, pH 7.4). Plates were washed thoroughly with buffer A and then blocked for 2 hours with buffer B (1% milk in buffer A). After washing, plates were incubated for 1.5 hours with 0.4 micrograms/ml of LDL receptor (R&D Systems) diluted in buffer C (buffer B supplemented with 10 mM $CaCl_2$). Concurrent with this incubation, 20 ng/ml of biotinylated D374Y PCSK9 was incubated with various concentrations of the 31H4 IgG2, 31H4 IgG4, 21B12 IgG2 or 21B12 IgG4 antibody, which was diluted in buffer A, or buffer A alone (control). The LDL receptor containing plates were washed and the biotinylated D374Y PCSK9/antibody mixture was transferred to them and incubated for 1 hour at room temperature. Binding of the biotinylated D374Y to the LDL receptor was detected by incubation with streptavidin-HRP (Biosource) at 500 ng/ml in buffer C followed by TMB substrate (KPL). The signal was quenched with 1N HCl and the absorbance read at 450 nm.

Figure 6A:
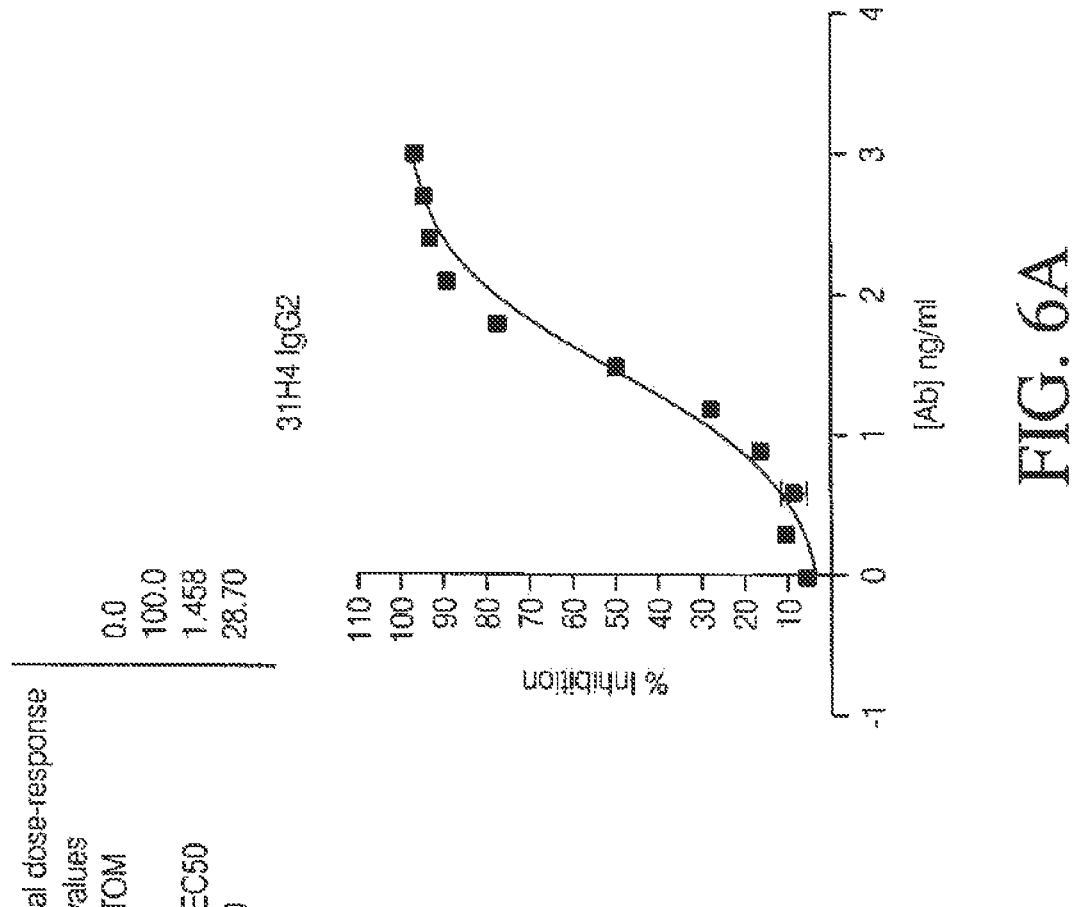
FIG. 6A is an inhibition curve of antigen binding protein 31H4 IgG2 to PCSK9 in an in vitro PCSK9:LDLR binding assay
Figure 6B:
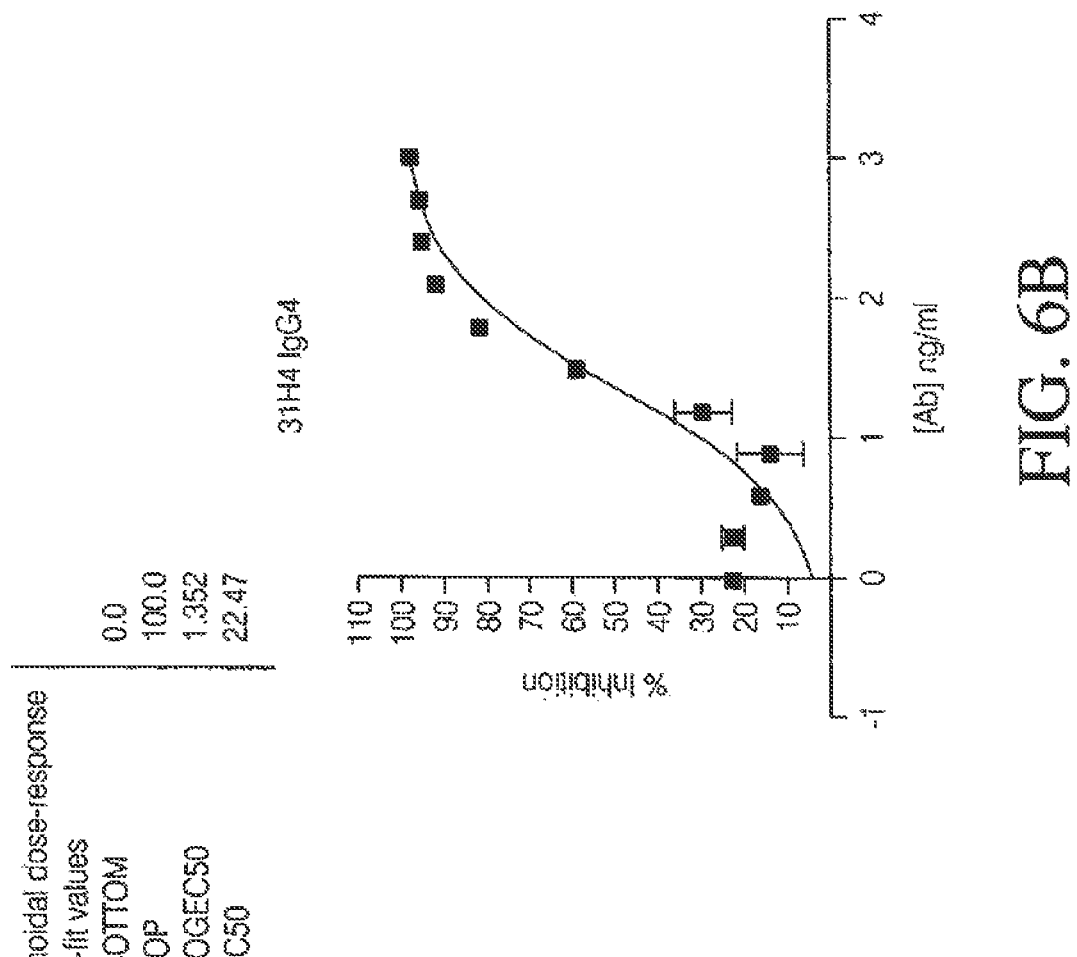
FIG. 6B is an inhibition curve of antigen binding protein 31H4 IgG4 to PCSK9 in an in vitro PCSK9:LDLR binding assay.
Figure 6C:
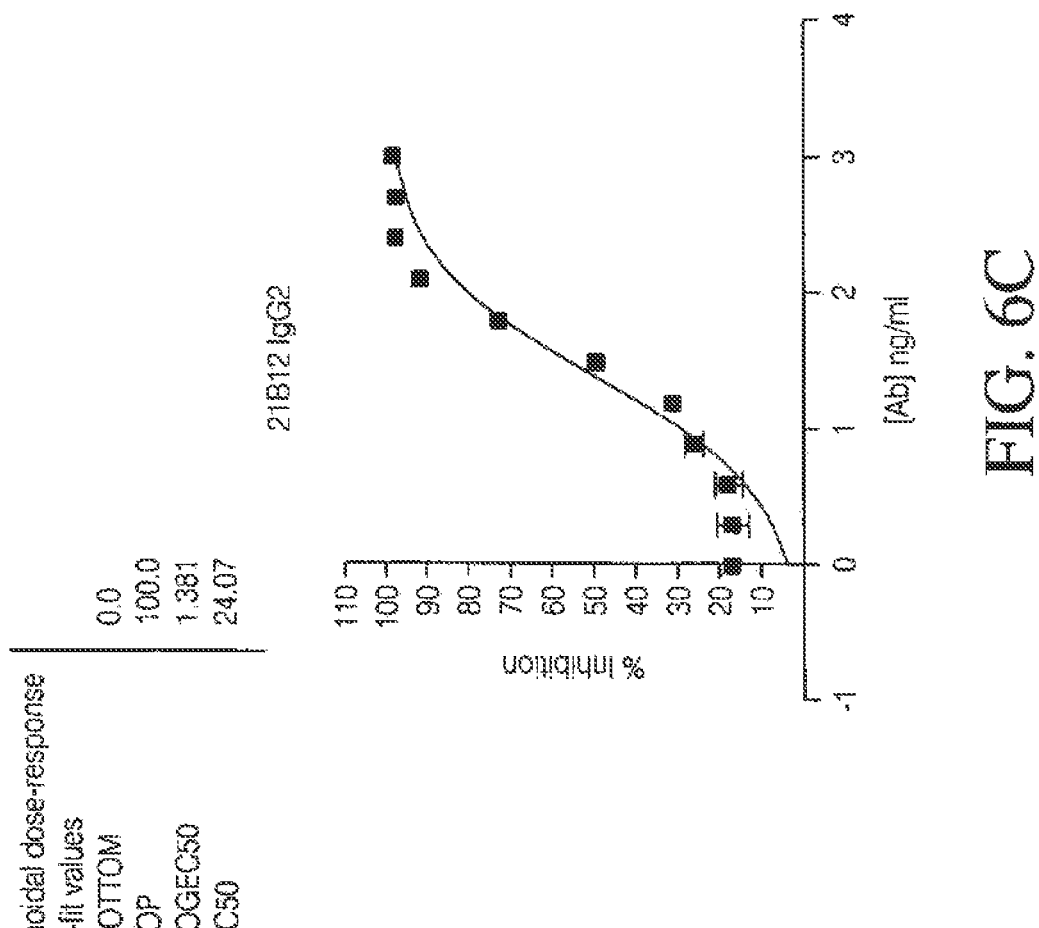
FIG. 6C is an inhibition curve of antigen binding protein 21B12 IgG2 to PCSK9 in an in vitro PCSK9:LDLR binding assay.
Figure 6D:
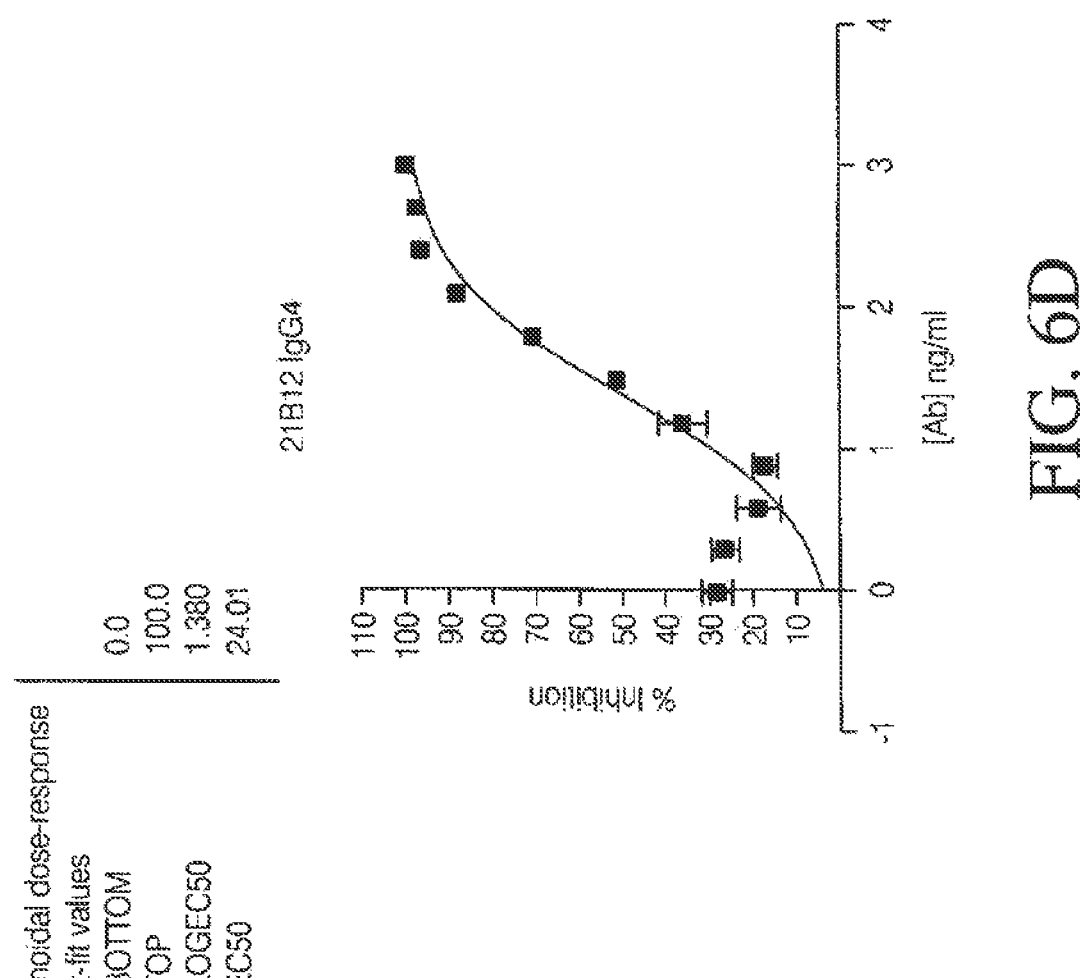
FIG. 6D is an inhibition curve of antigen binding protein 21B12 IgG4 to PCSK9 in an in vitro PCSK9:LDLR binding assay.

The results of this binding study are shown in FIGS. 6A-6D. Summarily, $IC_{50}$ values were determined for each antibody and found to be 199 pM for 31H4 IgG2 (FIG. 6A), 156 pM for 31H4 IgG4 (FIG. 6B), 170 pM for 21B12 IgG2 (FIG. 6C), and 169 pM for 21B12 IgG4 (FIG. 6D).

The antibodies also blocked the binding of wild-type PCSK9 to the LDLR in this assay.

Example 10

Cell LDL Uptake Assay

This example demonstrates the ability of various antigen binding proteins to reduce LDL uptake by cells. Human HepG2 cells were seeded in black, clear bottom 96-well plates (Costar) at a concentration of $5\times10^5$ cells per well in DMEM medium (Mediatech, Inc) supplemented with 10% FBS and incubated at 37° C. (5% CO2) overnight. To form the PCSK9 and antibody complex, 2 µg/ml of D374Y human PCSK9 was incubated with various concentrations of antibody diluted in uptake buffer (DMEM with 1% FBS) or uptake buffer alone (control) for 1 hour at room temperature. After washing the cells with PBS, the D374Y PCSK9/antibody mixture was transferred to the cells, followed by LDL-BODIPY (Invitrogen) diluted in uptake buffer at a final concentration of 6 µg/ml. After incubation for 3 hours at 37° C. (5% CO2), cells were washed thoroughly with PBS and the cell fluorescence signal was detected by Safire™ (TECAN) at 480-520 nm (excitation) and 520-600 nm (emission).

Figure 7A:
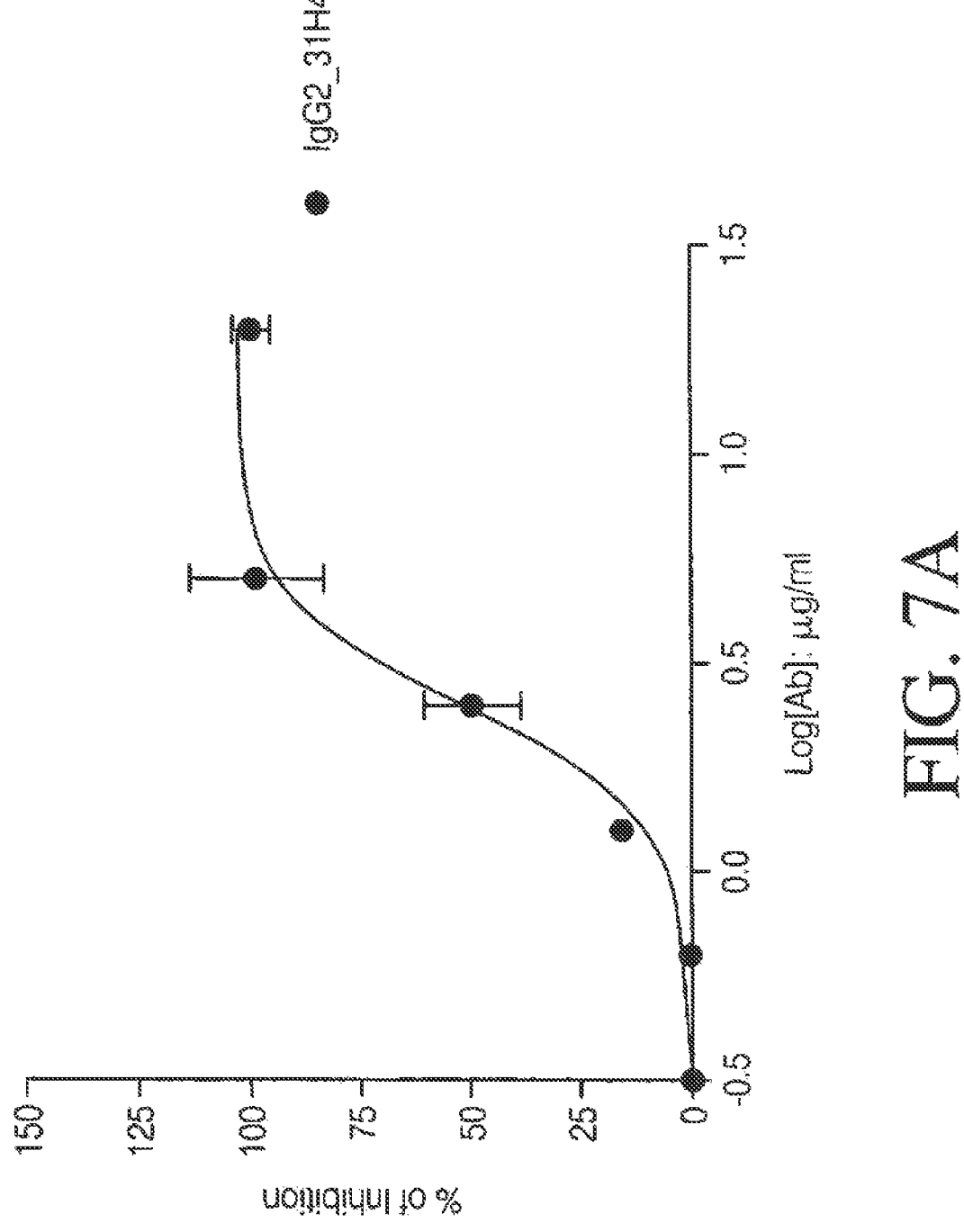
FIG. 7A is an inhibition curve of antigen binding protein 31H4 IgG2 in the cell LDL uptake assay showing the effect of the ABP to reduce the LDL uptake blocking effects of PCSK9
Figure 7B:
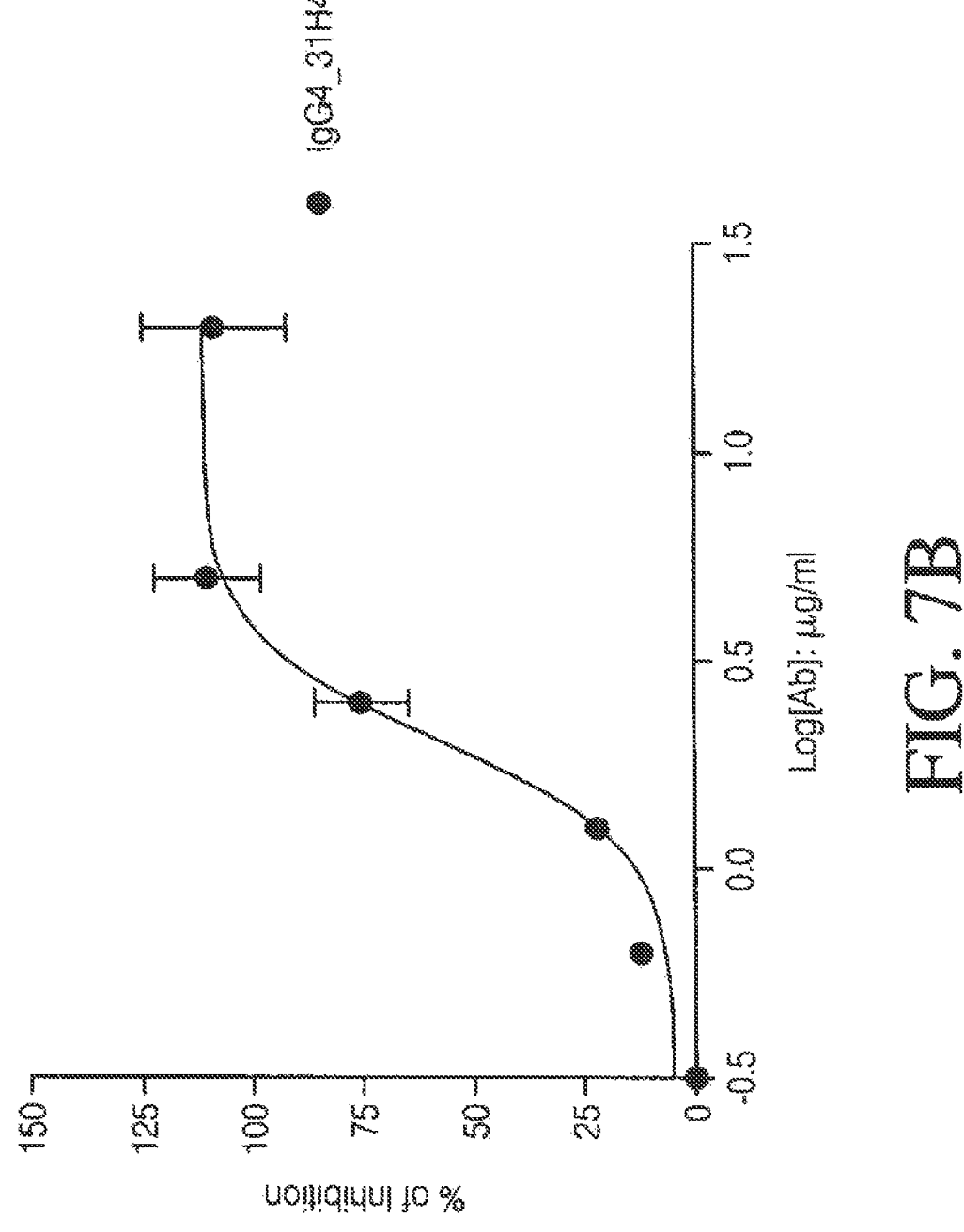
FIG. 7B is an inhibition curve of antigen binding protein 31H4 IgG4 in the cell LDL uptake assay showing the effect of the ABP to reduce the LDL uptake blocking effects of PCSK9
Figure 7C:
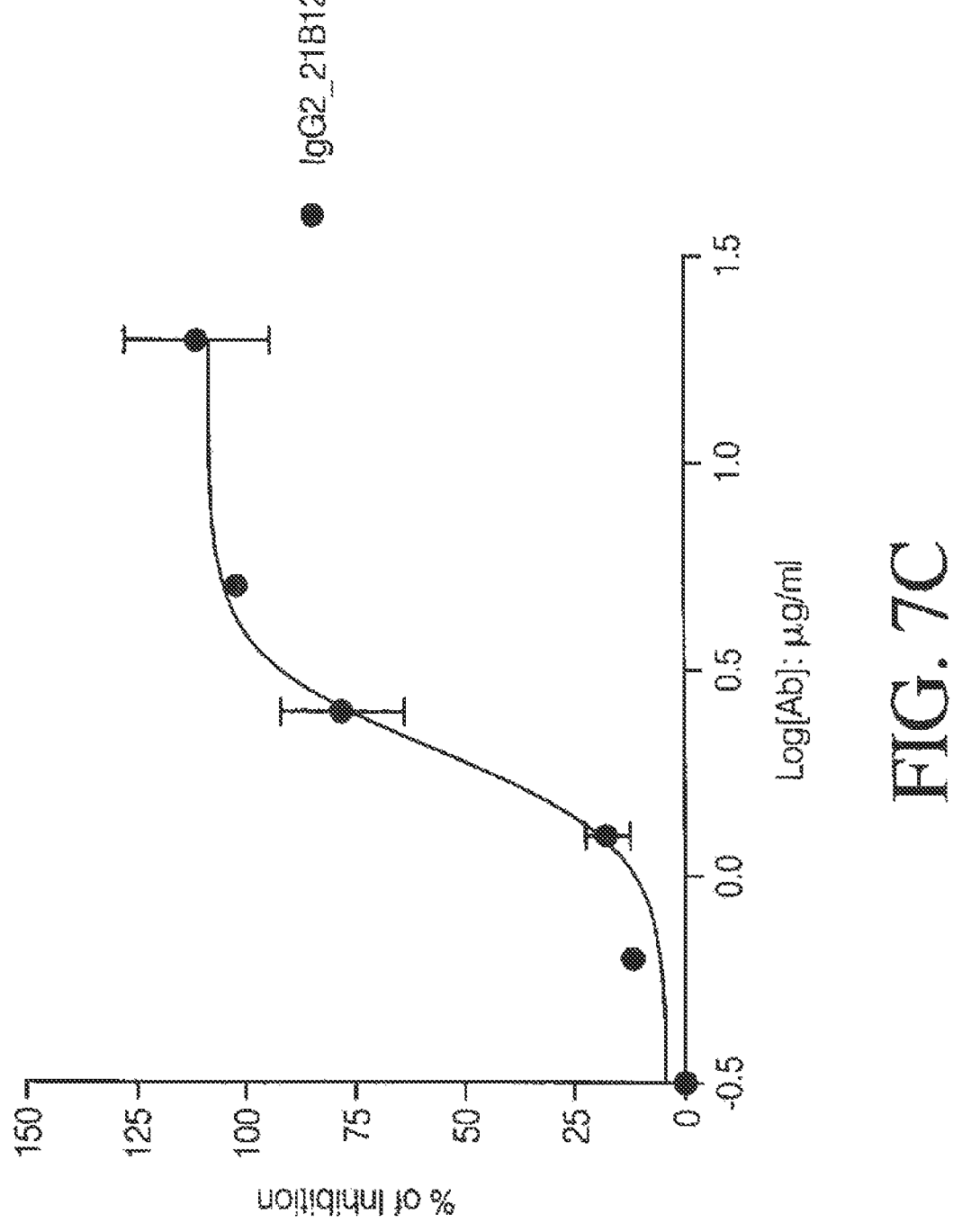
FIG. 7C is an inhibition curve of antigen binding protein 21B12 IgG2 in the cell LDL uptake assay showing the effect of the ABP to reduce the LDL uptake blocking effects of PCSK9
Figure 7D:
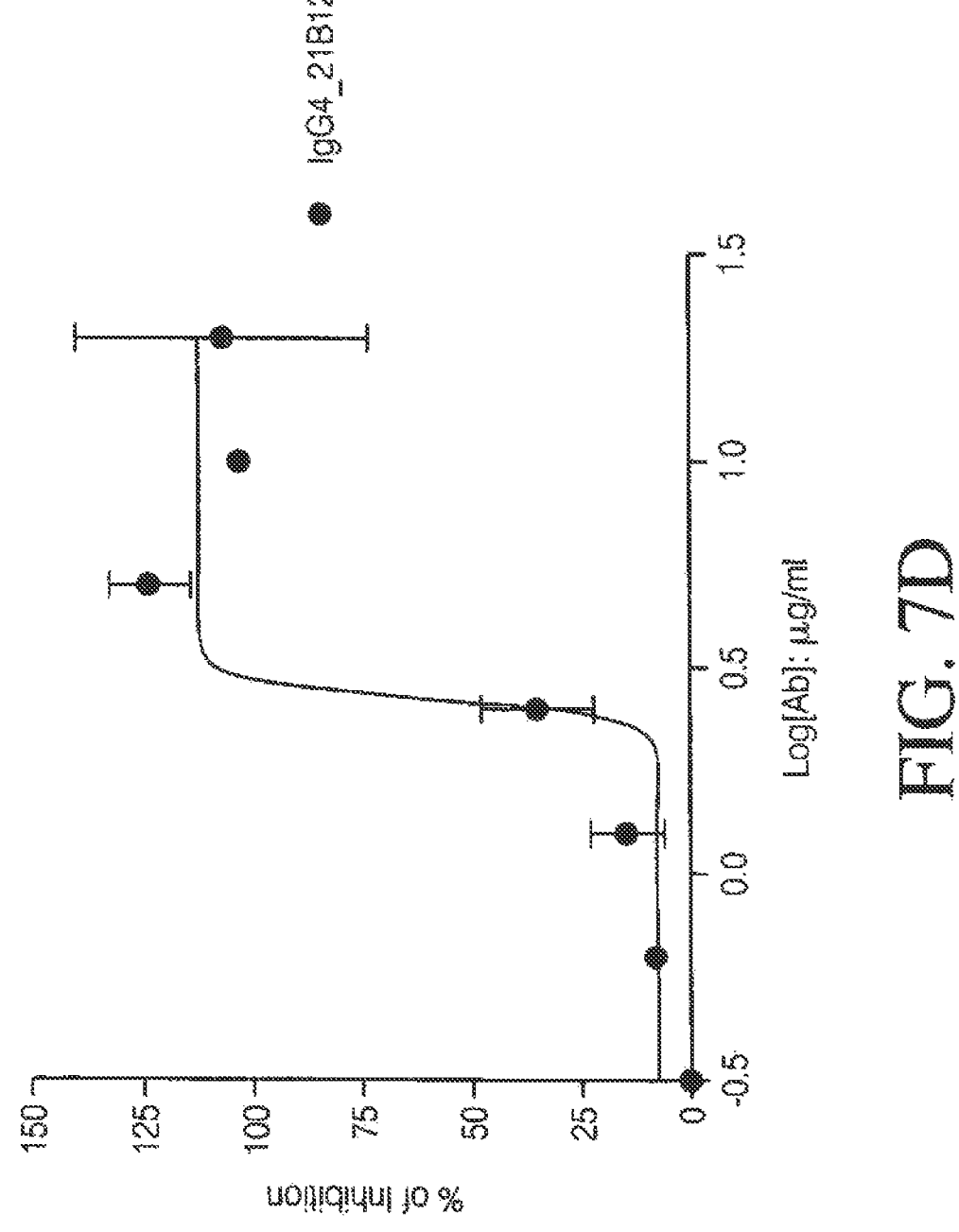
FIG. 7D is an inhibition curve of antigen binding protein 21B12 IgG4 in the cell LDL uptake assay showing the effect of the ABP to reduce the LDL uptake blocking effects of PCSK9

The results of the cellular uptake assay are shown in FIGS. 7A-7D. Summarily, $IC_{50}$ values were determined for each antibody and found to be 16.7 nM for 31H4 IgG2 (FIG. 7A), 13.3 nM for 31H4 IgG4 (FIG. 7B), 13.3 nM for 21B12 IgG2 (FIG. 7C), and 18 nM for 21B12 IgG4 (FIG. 7D). These results demonstrate that the applied antigen binding proteins can reduce the effect of PCSK9 (D374Y) to block LDL uptake by cells The antibodies also blocked the effect of wild-type PCSK9 in this assay.

Example 11

Serum Cholesterol Lowering Effect of the 31H4 Antibody in 6 Day Study

In order to assess total serum cholesterol (TC) lowering in wild type (WT) mice via antibody therapy against PCSK9 protein, the following procedure was performed.

Male WT mice (C57BL/6 strain, aged 9-10 weeks, 17-27 g) obtained from Jackson Laboratory (Bar Harbor, Me.) were fed a normal chow (Harland-Teklad, Diet 2918) through out the duration of the experiment. Mice were administered either anti-PCSK9 antibody 31H4 (2 mg/ml in PBS) or control IgG (2 mg/ml in PBS) at a level of 10 mg/kg through the mouse's tail vein at T=0. Naïve mice were also set aside as a naïve control group. Dosing groups and time of sacrifice are shown in Table 9.

TABLE 9

| Group | Treatment | Time point after dosing | Number |
|---|---|---|---|
| 1 | IgG | 8 hr | 7 |
| 2 | 31H4 | 8 hr | 7 |
| 3 | IgG | 24 hr | 7 |
| 4 | 31H4 | 24 hr | 7 |
| 5 | IgG | 72 hr | 7 |
| 6 | 31H4 | 72 hr | 7 |
| 7 | IgG | 144 hr | 7 |
| 8 | 31H4 | 144 hr | 7 |
| 9 | Naïve | n/a | 7 |

Mice were sacrificed with CO2 asphyxiation at the pre-determined time points shown in Table 9. Blood was collected via vena cava into eppendorf tubes and was allowed to clot at room temperature for 30 minutes. The samples were then spun down in a table top centrifuge at 12,000×g for 10 minutes to separate the serum. Serum total cholesterol and HDL-C were measured using Hitachi 912 clinical analyzer and Roche/Hitachi TC and HDL-C kits.

Figure 8B:
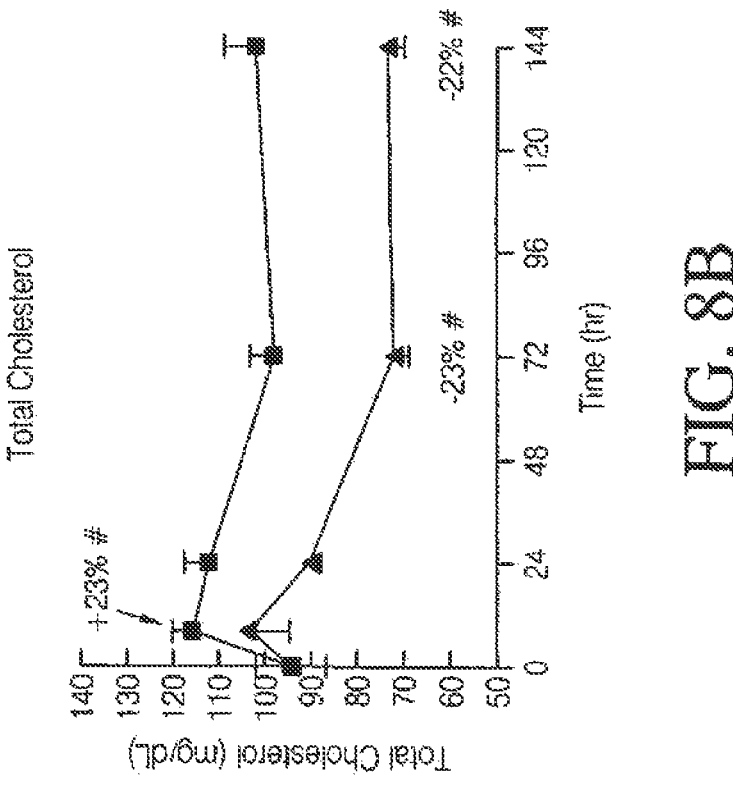
FIG. 8B is a graph depicting the serum cholesterol lowering ability in mice of ABP 31H4, changes relative to time=zero hours (# p, 0.05).
Figure 8A:
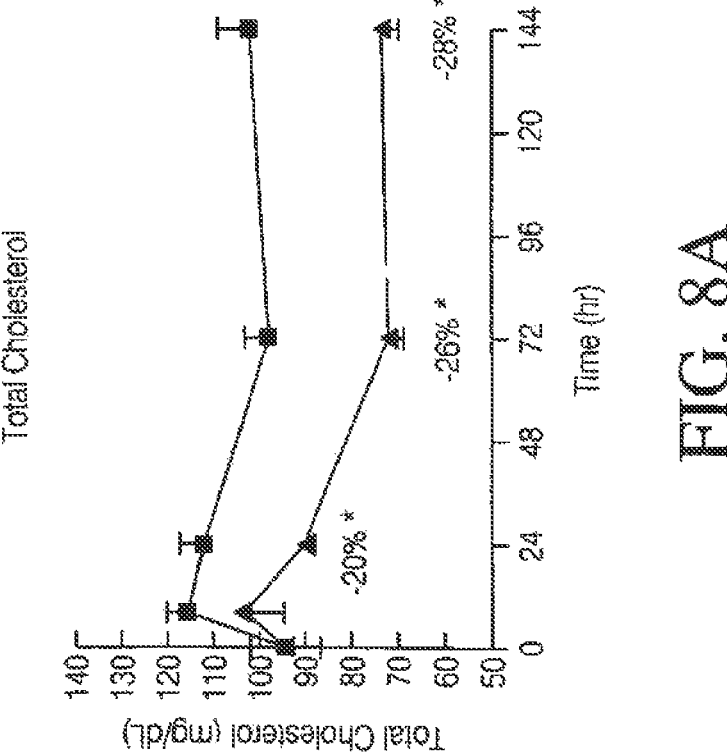
FIG. 8A is a graph depicting the serum cholesterol lowering ability in mice of ABP 31H4, changes relative to the IgG control treated mice (* $p<0.01$).
Figures 8C, 8D:
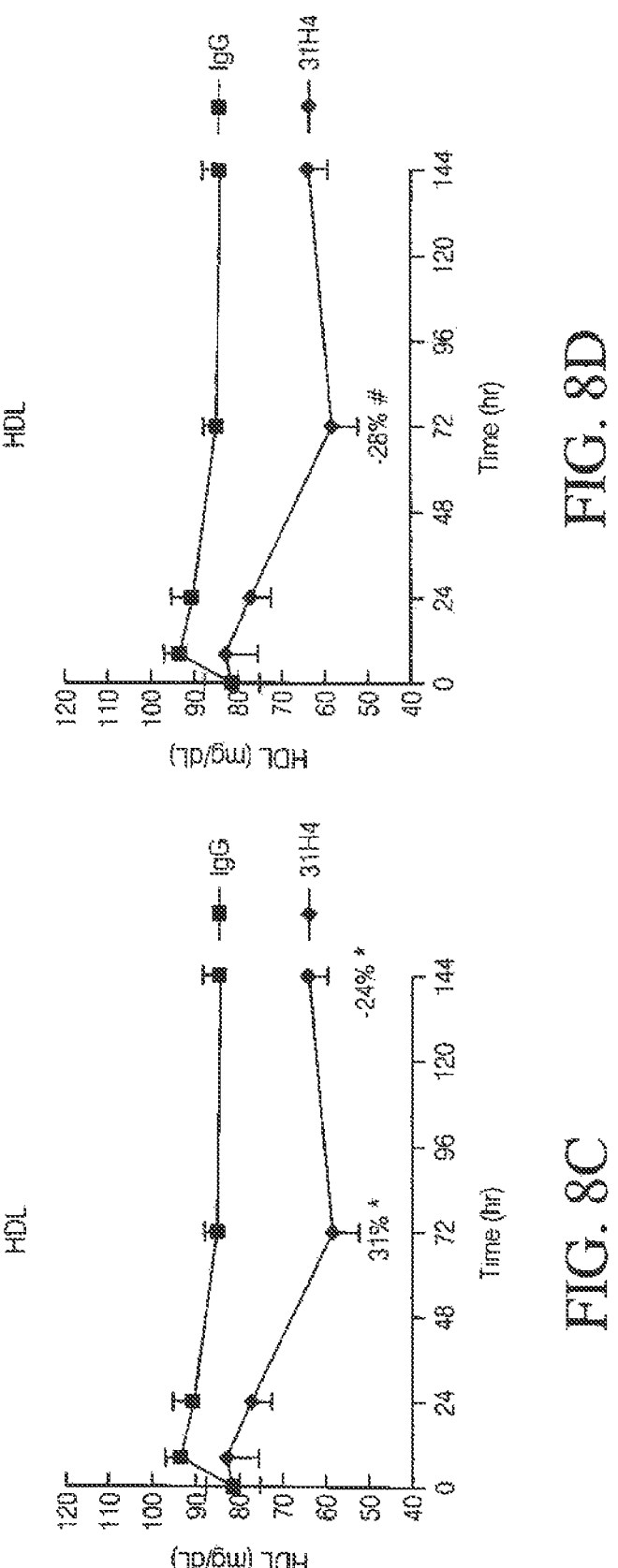
FIG. 8C is a graph depicting the effect of ABP 31H4 on HDL cholesterol levels in C57B1/6 mice (* $p<0.01$).
FIG. 8D is a graph depicting the effect of ABP 31H4 on HDL cholesterol levels in C57B1/6 mice (# $p<0.05$).

The results of the experiment are shown in FIGS. 8A-8D. Summarily, mice to which antibody 31H4 was administered showed decreased serum cholesterol levels over the course of the experiment (FIG. 8A and FIG. 8B). In addition, it is noted that the mice also showed decreased HDL levels (FIG. 8C and FIG. 8D). For FIG. 8A and FIG. 8C, the percentage change is in relation to the control IgG at the same time point (*$P<0.01$, # $P<0.05$). For FIG. 8B and FIG. 8D, the percentage change is in relation to total serum cholesterol and HDL levels measured in naïve animals at t=0 hrs (*$P<0.01$, # $P<0.05$).

In respect to the lowered HDL levels, it is noted that one of skill in the art will appreciate that the decrease in HDL in mice is not indicative that an HDL decrease will occur in humans and merely further reflects that the serum cholesterol level in the organism has decreased. It is noted that mice transport the majority of serum cholesterol in high density lipoprotein (HDL) particles which is different to humans who carry most serum cholesterol on LDL particles.

In mice the measurement of total serum cholesterol most closely resembles the level of serum HDL-C. Mouse HDL contains apolipoprotein E (apoE) which is a ligand for the LDL receptor (LDLR) and allows it to be cleared by the LDLR. Thus, examining HDL is an appropriate indicator for the present example, in mice (with the understanding that a decrease in HDL is not expected for humans). For example, human HDL, in contrast, does not contain apoE and is not a ligand for the LDLR. As PCSK9 antibodies increase LDLR expression in mouse, the liver can clear more HDL and therefore lowers serum HDL-C levels.

Example 12

Effect of Antibody 31H4 on LDLR Levels in a 6 Day Study

Figure 9:
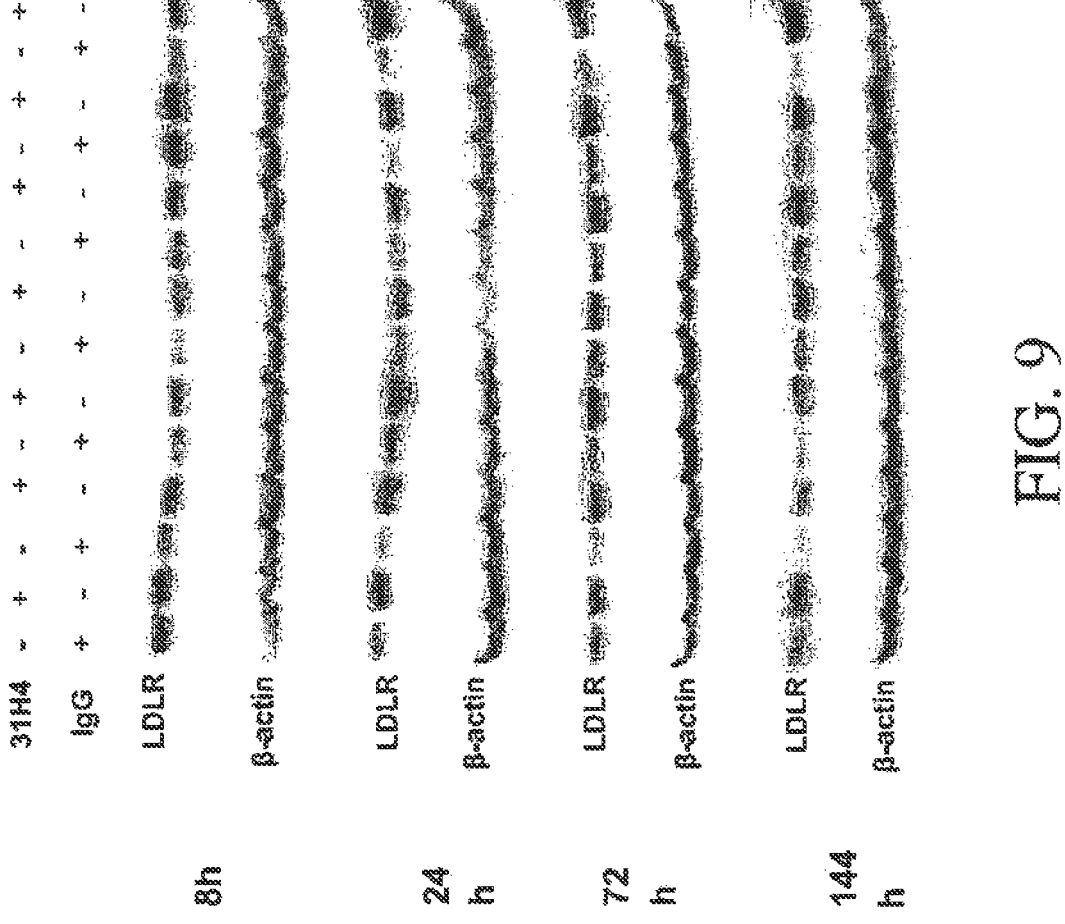
FIG. 9 depicts a western blot analysis of the ability of ABP 31H4 to enhance the amount of liver LDLR protein present after various time points.

The present example demonstrates that an antigen binding protein alters the level of LDLR in a subject, as predicted, over time. A Western blot analysis was performed in order to ascertain the effect of antibody 31H4 on LDLR levels. 50-100 mg of liver tissue obtained from the sacrificed mice described in Example 13 was homogenized in 0.3 ml of RIPA buffer (Santa Cruz Biotechnology Inc.) containing complete protease inhibitor (Roche). The homogenate was incubated on ice for 30 minutes and centrifuged to pellet cellular debris. Protein concentration in the supernatant was measured using BioRad protein assay reagents (BioRad laboratories). 100 μg of protein was denatured at 70° C. for 10 minutes and separated on 4-12% Bis-Tris SDS gradient gel (Invitrogen). Proteins were transferred to a 0.45 μm PVDF membrane (Invitrogen) and blocked in washing buffer (50 mM Tris PH7.5, 150 mM NaCL, 2 mM $CaCl_2$ and 0.05% Tween 20) containing 5% non-fat milk for 1 hour at room temperature. The blot was then probed with goat anti-mouse LDLR antibody (R&D system) 1:2000 or anti-β actin (sigma) 1:2000 for 1 hour at room temperature. The blot was washed briefly and incubated with bovine anti-goat IgG-HRP (Santa Cruz Biotechnology Inc.) 1:2000 or goat anti-mouse IgG-HRP (Upstate) 1:2000. After a 1 hour incubation at room temperature, the blot was washed thoroughly and immunoreactive bands were detected using ECL plus kit (Amersham biosciences). The Western blot showed an increase in LDLR protein levels in the presence of antibody 31H4, as depicted in FIG. 9.

Example 13

Serum Cholesterol Lowering Effect of Antibody 31H4 in a 13 Day Study

In order to assess total serum cholesterol (TC) lowering in wild type (WT) mice via antibody therapy against PCSK9 protein in a 13 day study, the following procedure was performed.

Male WT mice (C57BL/6 strain, aged 9-10 weeks, 17-27 g) obtained from Jackson Laboratory (Bar Harbor, Me.) were fed a normal chow (Harland-Teklad, Diet 2918) through out the duration of the experiment. Mice were administered either anti-PCSK9 antibody 31H4 (2 mg/ml in PBS) or control IgG (2 mg/ml in PBS) at a level of 10 mg/kg through the mouse's tail vein at T=0. Naïve mice were also set aside as naïve control group.

Dosing groups and time of sacrifice are shown in Table 10. Animals were sacrificed and livers were extracted and prepared as in Example 13.

TABLE 10

| Group | Treatment | Time point after dosing | Number | Dose |
|---|---|---|---|---|
| 1 | IgG | 72 hr | 6 | 10 mg/kg |
| 2 | 31H4 | 72 hr | 6 | 10 mg/kg |
| 3 | 31H4 | 72 hr | 6 | 1 mg/kg |
| 4 | IgG | 144 hr | 6 | 10 mg/kg |
| 5 | 31H4 | 144 hr | 6 | 10 mg/kg |
| 6 | 31H4 | 144 hr | 6 | 1 mg/kg |
| 7 | IgG | 192 hr | 6 | 10 mg/kg |
| 8 | 31H4 | 192 hr | 6 | 10 mg/kg |
| 9 | 31H4 | 192 hr | 6 | 1 mg/kg |
| 10 | IgG | 240 hr | 6 | 10 mg/kg |
| 11 | 31H4 | 240 hr | 6 | 10 mg/kg |
| 12 | 31H4 | 240 hr | 6 | 1 mg/kg |
| 13 | IgG | 312 hr | 6 | 10 mg/kg |
| 14 | 31H4 | 312 hr | 6 | 10 mg/kg |
| 15 | 31H4 | 312 hr | 6 | 1 mg/kg |
| 16 | Naive | n/a | 6 | n/a |

Figures 10A, 10B:
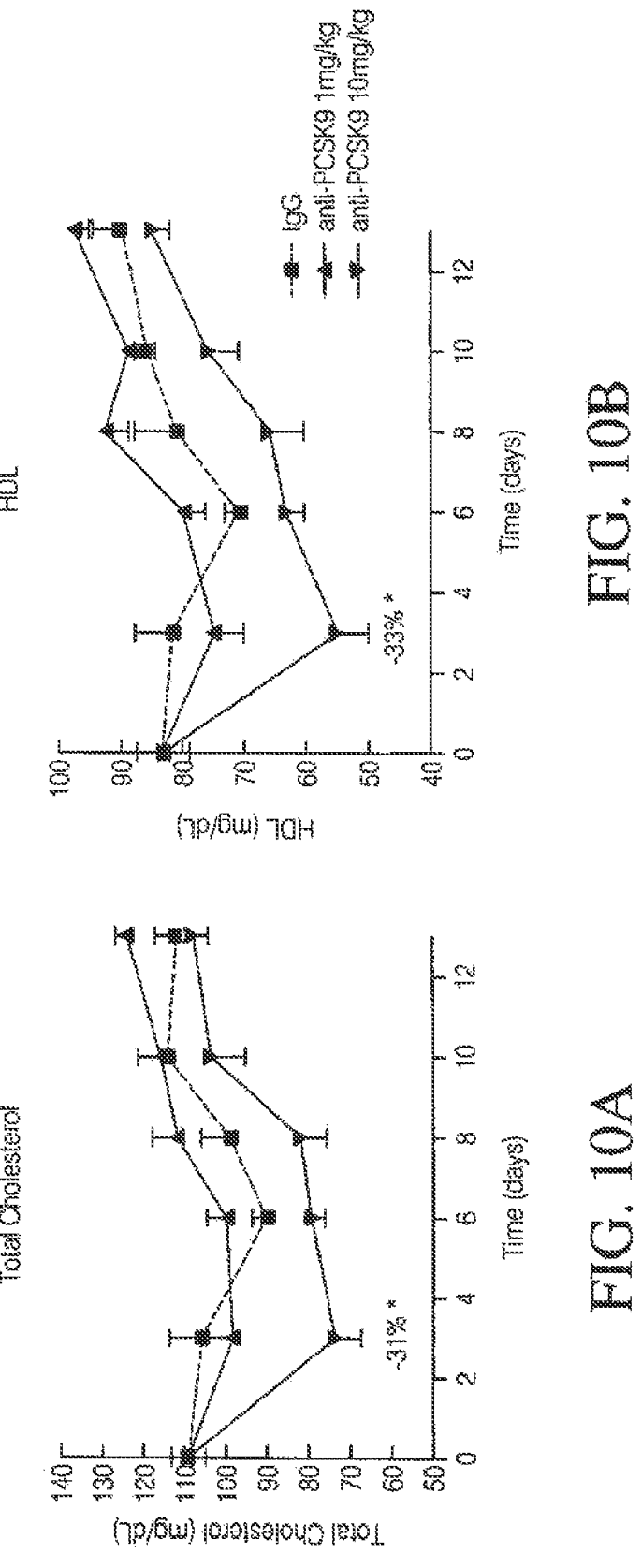
FIG. 10A is a graph depicting the ability of an antigen binding protein 31H4 to lower total serum cholesterol in wild type mice, relative.
FIG. 10B is a graph depicting the ability of an antigen binding protein 31H4 to lower HDL in wild type mice.
Figure 10C:
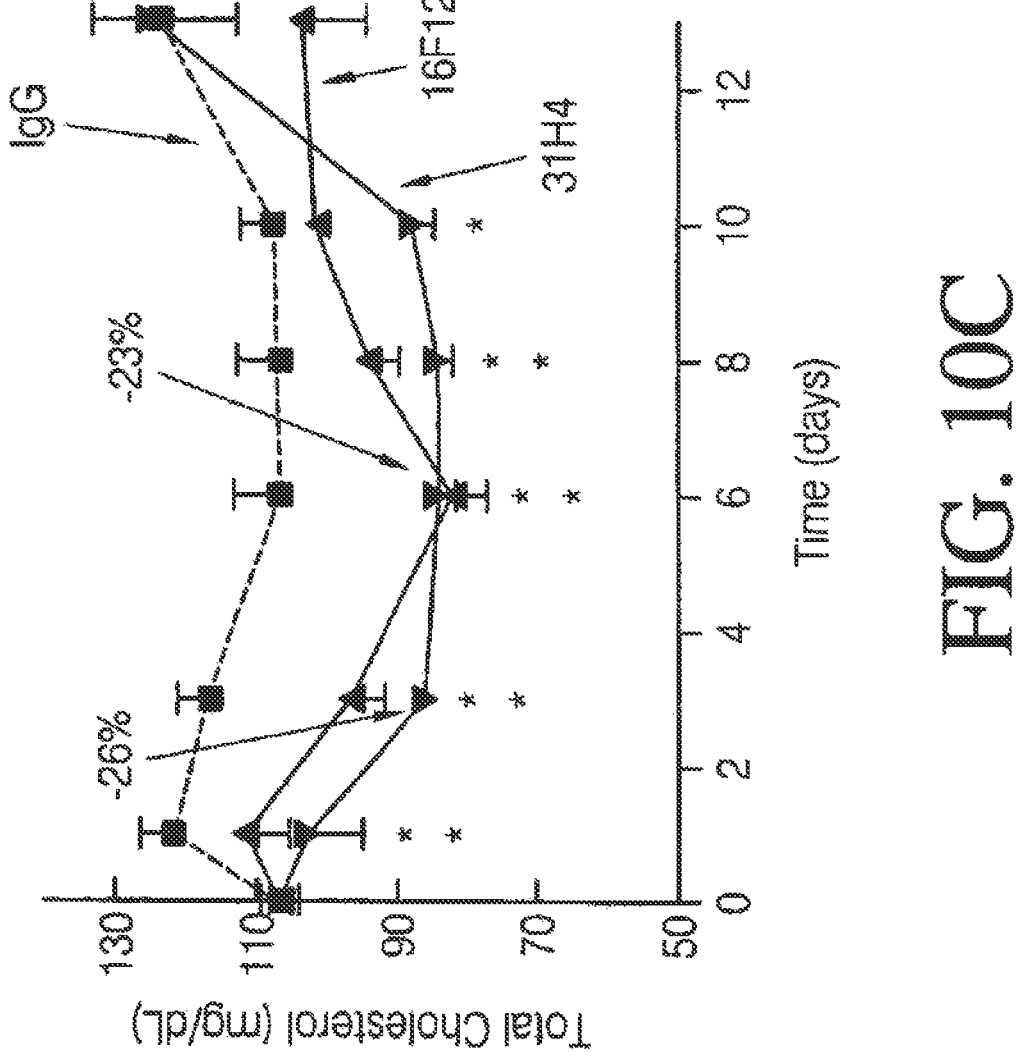
FIG. 10C is a graph depicting the serum cholesterol lowering ability of various antigen binding proteins 31H4 and 16F12.

When the 6 day experiment was extended to a 13 day study, the same serum cholesterol lowering effect observed in the 6 day study was also observed in the 13 day study. More specifically, animals dosed at 10 mg/kg demonstrated a 31% decrease in serum cholesterol on day 3, which gradually returned to pre-dosing levels by day 13. FIG. 10A depicts the results of this experiment. FIG. 10C depicts the results of repeating the above procedure with the 10 mg/kg dose of 31H4, and with another antibody, 16F12, also at 10 mg/kg. Dosing groups and time of sacrifice are shown in Table 11.

TABLE 11

| Group | Treatment | Time point after dosing | Number | Dose |
|---|---|---|---|---|
| 1 | IgG | 24 hr | 6 | 10 mg/kg |
| 2 | 16F12 | 24 hr | 6 | 10 mg/kg |
| 3 | 31H4 | 24 hr | 6 | 10 mg/kg |
| 4 | IgG | 72 hr | 6 | 10 mg/kg |
| 5 | 16F12 | 72 hr | 6 | 10 mg/kg |
| 6 | 31H4 | 72 hr | 6 | 10 mg/kg |
| 7 | IgG | 144 hr | 6 | 10 mg/kg |
| 8 | 16F12 | 144 hr | 6 | 10 mg/kg |
| 9 | 31H4 | 144 hr | 6 | 10 mg/kg |
| 10 | IgG | 192 hr | 6 | 10 mg/kg |
| 11 | 16F12 | 192 hr | 6 | 10 mg/kg |
| 12 | 31H4 | 192 hr | 6 | 10 mg/kg |
| 13 | IgG2 | 240 hr | 6 | 10 mg/kg |
| 14 | 16F12 | 240 hr | 6 | 10 mg/kg |
| 15 | 31H4 | 240 hr | 6 | 10 mg/kg |
| 16 | IgG2 | 312 hr | 6 | 10 mg/kg |
| 17 | 16F12 | 312 hr | 6 | 10 mg/kg |
| 18 | 31H4 | 312 hr | 6 | 10 mg/kg |
| 19 | Naive | n/a | 6 | 10 mg/kg |

As shown in FIG. 10C both 16F12 and 31H4 resulted in significant and substantial decreases in total serum cholesterol after just a single dose and provided benefits for over a week (10 days or more). The results of the repeated 13 day study were consistent with the results of the first 13 day study, with a decrease in serum cholesterol levels of 26% on day 3 being observed. For FIG. 10A and FIG. 10B, the percentage change is in relation to the control IgG at the same time point (*P<0.01). For FIG. 10C, the percentage change is in relation to the control IgG at the same time point (*P<0.05).

Example 14

Effect of Antibody 31H4 on HDL Levels in a 13 Day Study

The HDL levels for the animals in Example 15 were also examined. HDL levels decreased in the mice. More specifically, animals dosed at 10 mg/kg demonstrated a 33% decrease in HDL levels on day 3, which gradually returned to pre-dosing levels by day 13. FIG. 10B depicts the results of the experiment. There was a decrease in HDL levels of 34% on day 3. FIG. 10B depicts the results of the repeated 13 day experiment.

As will be appreciated by one of skill in the art, while the antibodies will lower mouse HDL, this is not expected to occur in humans because of the differences in HDL in humans and other organisms (such as mice). Thus, the decrease in mouse HDL is not indicative of a decrease in human HDL.

Example 15

Figure 11A:
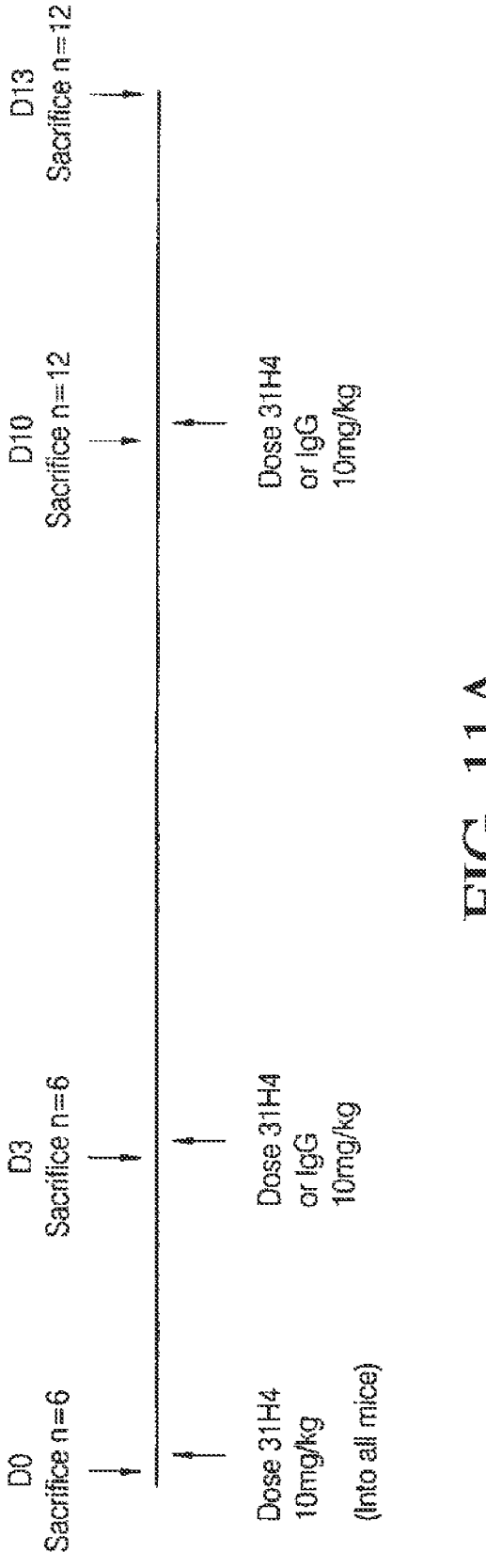
FIG. 11A depicts an injection protocol for testing the duration and ability of antigen binding proteins to lower serum cholesterol.
Figure 11B:
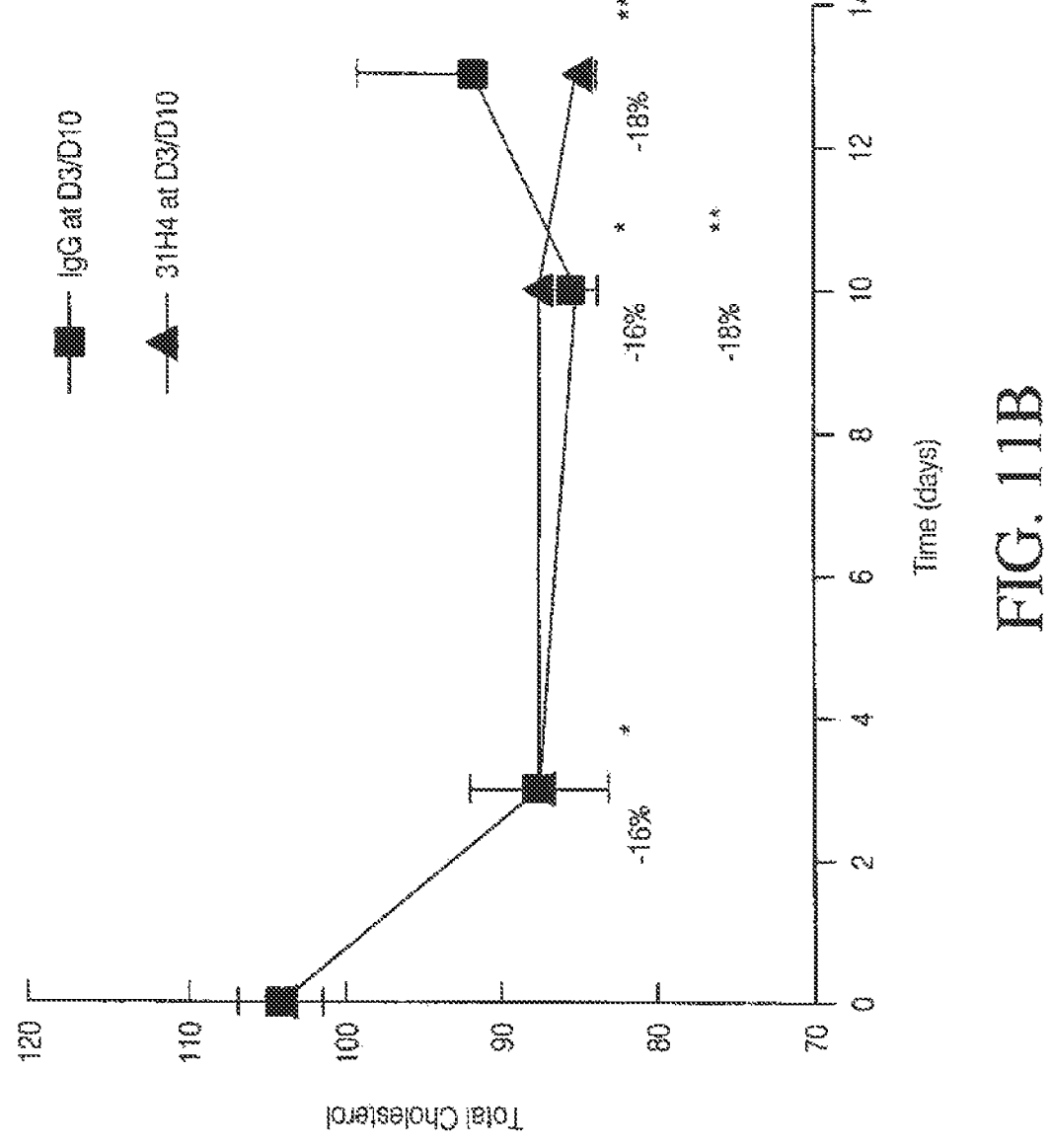
FIG. 11B is a graph depicting the results of the protocol in FIG. 11A.

Repeated Administration of Antibodies Produce Continued Benefits of Antigen Binding Peptides In order to verify that the results obtained in the Examples above can be prolonged for further benefits with additional doses, the Experiments in Examples 15 and 16 were repeated with the dosing schedule depicted in FIG. 11A. The results are displayed in FIG. 11B. As can be seen in the graph in FIG. 11B, while both sets of mice displayed a significant decrease in total serum cholesterol because all of the mice received an initial injection of the 31H4 antigen binding protein, the mice that received additional injections of the 31H4 ABP displayed a continued reduction in total serum cholesterol, while those that only received the control injection eventually displayed an increase in their total serum cholesterol. For FIG. 11, the percentage change is in relation to the naïve animals at t=0 hours (*P<0.01, **P<0.001).

The results from this example demonstrate that, unlike other cholesterol treatment methods, in which repeated applications lead to a reduction in efficacy because of biological adjustments in the subject, the present approach does not seem to suffer from this issue over the time period examined. Moreover, this suggests that the return of total serum cholesterol or HDL cholesterol levels to baseline, observed in the previous examples is not due to some resistance to the treatment being developed by the subject, but rather the depletion of the antibody availability in the subject.

Example 16

Uses of PCSK9 Antibodies for the Treatment of Cholesterol Related Disorders

A human patient exhibiting a Cholesterol Related Disorder (in which a reduction in cholesterol (such as serum cholesterol) can be beneficial) is administered a therapeutically effective amount of PCSK9 antibody, 31H4 (or, for example, 21B12). At periodic times during the treatment, the patient is monitored to determine whether the symptoms of the disorder have subsided. Following treatment, it is found that patients undergoing treatment with the PCSK9 antibody have reduced serum cholesterol levels, in comparison to patients that are not treated.

Example 17

Uses of PCSK9 Antibodies for the Treatment of Hypercholesterolemia

A human patient exhibiting symptoms of hypercholesterolemia is administered a therapeutcially effective amount of PCSK9 antibody, such as 31H4 (or, for example, 21B12). At periodic times during the treatment, the human patient is monitored to determine whether the serum cholesterol level has declined. Following treatment, it is found that the patient receiving the treatment with the PCSK9 antibodies has reduced serum cholesterol levels in comparison to arthritis patients not receiving the treatment.

Example 18

Uses of PCSK9 Antibodies for the Prevention of Coronary Heart Disease and/or Recurrent Cardiovascular Events A human patient at risk of developing coronary heart disease is identified. The patient is administered a therapeutically effective amount of PCSK9 antibody, such as 31H4 (or, for example, 21B12), either alone, concurrently or sequentially with a statin, e.g., simvastatin. At periodic times during the treatment, the human patient is monitored to determine whether the patient's total serum cholesterol level changes. Throughout the preventative treatment, it is found that the patient receiving the treatment with the PCSK9 antibodies has reduced serum cholesterol thereby reducing their risk to coronary heart diseases or recurrent cardiovascular events in comparison to patients not receiving the treatment.

Example 19

Use of PCSK9 Antigen Binding Protein for the Prevention of Hypercholesterolemia A human patient exhibiting a risk of developing hypercholesterolemia is identified via family history analysis and/or lifestyle, and/or current cholesterol levels. The subject is regularly administered (e.g., one time weekly) a therapeutically effective amount of PCSK9 antibody, 31H4 (or, for example, 21B12). At periodic times during the treatment, the patient is monitored to determine whether serum cholesterol levels have decreased. Following treatment, it is found that subjects undergoing preventative treatment with the PCSK9 antibody have lowered serum cholesterol levels, in comparison to subjects that are not treated.

Example 20

A Phase 1, Randomized, Double-Blind, Placebo-Controlled, Ascending Single Dose Study to Evaluate the Safety, Tolerability, Pharmacokinetics and Pharmacodynamics of a Human Anti-PCSK9 Antibody in Healthy Subjects This Study was a randomized, double-blind, placebo-controlled, ascending-single-dose study to evaluate the safety, tolerability, PK, pharmacodynamics (PD) (LDL-C), and immunogenicity of a human anti-PCSK9 antibody (monoclonal antibody 21B12) in healthy subjects. Subjects were randomized in a 3:1 ratio (21B12:placebo; 8 subjects per dose cohort for a total of 56 subjects in 7 cohorts) to receive 21B12 at doses of 7, 21, 70, 210, or 420 mg SC, or corresponding placebo; or 21B12 at doses of 21 or 420 mg IV, or corresponding placebo.

Fifty-six subjects were randomized and received investigational product (42 21B12, 14 placebo); 40 subjects (30 21B12, 10 placebo) received investigational product by the SC route of administration, and 16 subjects (12 21B12, 4 placebo) received investigational product by the IV route. Fifty-three of the 56 subjects (95%) who received investigational product completed the study. Three subjects who received 21B12 withdrew full consent and did not complete the study.

The study population was primarily composed of men (54 [96%]) and had a mean age of 31.2 (range: 20 to 45) years. Eighty-six percent of subjects were white, followed by 9% Hispanic/Latino, 4% black and 1% other. Mean baseline LDL-C values were similar between treatment groups and ranged from 113 to 143 mg/dL.

In this study, 21B12 reduced LDL-C by an average of 55% to 60% at single doses $\geq$70 mg SC with the duration of effect being dose dependent. The LDL-C nadir was observed within 2 weeks of dosing. Complete suppression of PCSK9 was observed at single doses $\geq$70 mg SC, which correlated well with the effects seen on circulating LDL-C.

PK analyses demonstrated that 21B12 exhibited nonlinear (concentration-dependent) elimination. The mean $t_{max}$ ranged from 4 to 6 days. As expected, the highest median maximum observed concentration ($C_{max}$) and area under the concentration-time curve from time 0 to infinity ($AUC_{0-inf}$) occurred in the 420 mg IV group and were 139 µg/mL and 1550 day·µg/mL, respectively.

Treatment-emergent adverse events were reported for 29 of the 42 subjects (69%) who received 21B12 at any dose, and for 10 of the 14 subjects (71%) who received placebo. No relationship was apparent between the subject incidence of adverse events and the dose of 21B12, or between the subject incidence of adverse events and the route of administration of 21B12 (SC versus IV).

No adverse events were reported as serious, and no subjects discontinued study due to an adverse event. There were no deaths on study.

Treatment-related adverse events were reported for 18 of the 42 subjects (43%) who received 21B12 and for 10 of the 14 subjects (71%) who received placebo. No relationship was apparent between the subject incidence of treatment related adverse events and the dose of 21B12, or between the subject incidence of treatment-related adverse events and the route of administration of 21B12 (SC versus IV).

There were no trends indicative of clinically important effects of 21B12 on selected laboratory variables, electro-cardiograms (ECGs), or vital signs.

In this study, 21B12 appeared to be well tolerated at single SC and IV doses up to 420 mg.

Serum samples from subjects enrolled in this study were tested for the presence (baseline) or development (post-treatment) of anti-21B12 antibodies. Samples from all 42 of the subjects who received 21B12 were negative for anti-21B12 antibodies.

Example 21

A Phase 1, Randomized, Double-Blind, Placebo-Controlled, Ascending Multiple Dose Study to Evaluate the Safety, Tolerability, Pharmacokinetics and Pharmacodynamics of a Human Anti-PCSK9 Antibody in Subjects with Hyperlipidemia on Stable Doses of a Statin This Study is a phase 1b, randomized, double-blind, placebo controlled, ascending, multiple-dose study using a human anti-PCSK9 antibody (monoclonal antibody 21B12) in hyperlipidemic (e.g., hypercholesterolemic) subjects currently on stable doses of a statin. The study had seven cohorts. Objectives for all cohorts included characterization of the safety, tolerability, and immunogenicity of 21B12, and characterization of the PK and PD (LDL-C and PCSK9). Cohorts 1 to 5 of the study represented the 21B12 dose-escalation portion, in hypercholesterolemic subjects on stable low to moderate doses of a statin. Subjects in cohorts 1 to 5 (n=8 per cohort) with LDL-C (70-200 mg/dL) on stable daily rosuvastatin <40 mg, atorvastatin <80 mg or simvastatin 20-80 mg for ≥1 month were randomized in a 3:1 ratio to receive 1 of 5 SC dosages of 21B12 (14 or 35 mg QW 6 times; or 140 mg or 280 mg Q2W 3 times; or 420 mg Q4W 2 times) or corresponding placebo, respectively. Cohort 6 was conducted in hypercholesterolemic subjects on high doses of a statin (atorvastatin 80 mg or rosuvastatin 40 mg). Subjects in this cohort (n=12) were on either rosuvastatin 40 mg or atorvastatin 80 mg and were randomized in a 3:1 ratio to receive 21B12 (140 mg SC Q2W 3 times) or corresponding placebo, respectively. Cohort 7 was conducted in subjects with heterozygous familial hypercholesterolemia (identified using WHO criteria); subjects in this cohort (n=6) were randomized in a 2:1 ratio to receive 21B12 (140 mg SC Q2W 3 times) or corresponding placebo, respectively.

Preliminary results were obtained from 40 subjects who had been enrolled and randomized to 21B12 or placebo. Of these 40 subjects, 28 subjects had received ≥1 dose of investigational product (21B12 or placebo) and therefore represented the preliminary safety analysis set (blinded to treatment). Preliminary blinded safety data were available for these 28 subjects, all of whom were from cohorts 1 to 4. No deaths, serious adverse events, or early withdrawals due to adverse events had been reported. Overall, at least 1 adverse event had been reported for 15 of the 28 subjects (54%) who had received ≥1 dose of investigational product. Most adverse events (blinded to treatment) were reported for single subjects, with the exception of fatigue, arthralgia, constipation, and viral upper respiratory tract infection, each of which was reported for 2 of the 28 subjects (7%).

Preliminary pharmacodynamics results (blinded to treatment) were available for cohorts 1, 2, and 3. 21B12-dose-dependent reduction in circulating LDL-C was observed, in subjects on stable moderate doses of statins. The LDL-C nadir was observed within 2 weeks of initial dosing and was in the range of 60% to 80% reduction in cohort 3 (140 mg Q2W SC 3 times). Near-complete suppression of PCSK9 was observed in cohort 3, which correlated well with the effects seen on circulating LDL-C.

In the final results, subjects (N=51) in cohorts 1-6 were randomized to receive 21B12 (N=39) or placebo (N=12); 26 subjects (51%) were male; mean (SD) age was 58 (7) years. No deaths or serious adverse events (AEs) were reported and no subjects discontinued the study due to an AE. No neutralizing antibodies to 21B12 were detected.

Subjects in cohorts 1-5 on low to moderate doses of statins had mean LDL-C reductions of up to 81% vs placebo at maximal reduction and 75% vs placebo at the end of the dosing interval (i.e., at week 6) after 3 biweekly SC doses of 21B12, and 66% at the end of the dosing interval (i.e., at week 8) after 2, every 4 week SC doses. Subjects in cohorts 1-5 on low to moderate doses of statins had maximum LDL-C reductions of up to 81% vs placebo at maximal reduction and 75% vs placebo at the end of the dosing interval (FIG. 14). The magnitude and duration of effect were dose-dependent. Plasma PCSK9 was undetectable at higher doses. Similarly, at the end of the dosing interval after 3 biweekly doses, subjects on high-dose statins (cohort 6)

had a mean reduction in LDL-C of 63% vs placebo, and a maximum reduction in LDL-C of 73% versus placebo (FIG. 15).

These data show that repeated SC doses of 21B12 over 6 weeks decreased circulating LDL-C up to 81% vs placebo, depending on dosing regimen, in subjects on either low-to-moderate or high-dose statins, with no serious AEs. The LDL-C-lowering effect of 21B12 was comparable between the high dose statin and low-to-moderate statin dose groups.

Subjects in cohorts 1-5 on low to moderate doses of statins had mean reduction of PCSK9 levels of up to 94% vs placebo at the end of the dosing interval, data not shown. Subjects in cohorts 1-5 on low-to-moderate doses of statins had mean ApoB reductions of up to 54% vs placebo at the end of the dosing interval, and maximum reductions of up to 59% vs placebo (FIG. 16). In addition, Subjects in cohorts 1-6 on low-to-moderate and high-doses of statins had mean Lp(a) reductions of up to 43% vs placebo at the end of the dosing interval (FIG. 17).

Subjects in cohort 7 with heFH had a mean reduction in LDL-C of 65% vs placebo at the end of the dosing interval (i.e., week 6, 2 weeks after the third biweekly SC dose of 21B12), and a maximum LDL-C reduction of 70% versus placebo (FIG. 18). LDL-C reductions during the dosing interval were comparable to those observed in subjects without heFH. After 21B12 treatment, circulating PCSK9 was undetectable in heFH subjects.

Subjects in cohort 7 with heFH had a mean reduction in serum PCSK9 values of 78% vs placebo at the end of the dosing interval (i.e., week 6, 2 weeks after the third biweekly SC dose of 21B12)(FIG. 19). Subjects in cohort 7 with heFH had a mean reduction in total cholesterol of up to 42% vs placebo at the end of the dosing interval (i.e., week 6, 2 weeks after the third biweekly SC dose of 21B12), and a maximum total cholesterol reduction of 47% versus placebo (FIG. 20). Subjects in cohort 7 with heFH had a mean reduction in non-HDL cholesterol of 61% vs placebo at the end of the dosing interval (i.e., week 6, 2 weeks after the third biweekly SC dose of 21B12), and a maximum reduction of non-HDL cholesterol of 67% versus placebo (FIG. 21). Subjects in cohort 7 with heFH had a mean reduction in ApoB levels of up to 47% vs placebo at the end of the dosing interval (i.e., week 6, 2 weeks after the third biweekly SC dose of 21B12), and a maximum reduction of ApoB of 57% versus placebo (FIG. 22). Subjects in cohort 7 with heFH had a mean reduction in lipoprotein a (Lp(a)) of 50% vs placebo at the end of the dosing interval (i.e., week 6, 2 weeks after the third biweekly SC dose of 21B12) (FIG. 23).

In cohort 7, 21B12 decreased unbound PCSK9 levels and substantially lowered circulating LDL-C levels in subjects with heFH and hyperlipidemia who were receiving standard-of-care therapy. The bi-weekly dose tested provided LDL-C reductions in heFH subjects that were comparable to those in non-heFH subjects. No serious AEs were reported.

Example 22

A Double-Blind, Randomized, Placebo-Controlled Study to Evaluate Tolerability and Efficacy of a Human Anti-PCSK9 Antibody in Patients with Heterozygous Familial Hypercholesterolemia The objective of this study is to evaluate the effect of 12 weeks of subcutaneous (SC) human, anti-PCSK9 antibody (monoclonal antibody 21B12) compared with placebo, on percent change from baseline in low-density lipoprotein cholesterol (LDL-C) in subjects with heterozygous familial hypercholesterolemia (HeFH).

This study is a double-blind, randomized, stratified, placebo-controlled clinical trial evaluating the safety, tolerability, and efficacy of monocloncal antibody 21B12 in subjects having a diagnosis of HeFH. A total enrollment of 150 subjects is planned. Subjects who meet all inclusion/exclusion criteria will be randomized with equal allocation into 3 treatment groups: monoclonal antibody, 21B12 at 350 mg or 420 mg Q4W SC (once every 4 weeks, subcutaneous) or placebo Q4W SC. Randomization will be stratified by screening LDL-C level (<130 mg/dL [3.4 mmol/L] vs ≥130 mg/dL) and ezetimibe use at baseline (yes vs no). Randomization should occur within 5-10 days of the screening LDL-C evaluation used to determine eligibility. Monoclonal antibody, 21B12, and placebo will be blinded. Study visits are at weeks 2, 4, 8, and 12. Final administration of monoclonal antibody, 21B12, or placebo is at week 8. The end-of-study (EOS) visit and the last evaluation of lipids is at week 12.

Males and females, ≥18 to ≤75 years of age, and with a diagnosis of heterozygous familial hypercholesterolemia by the diagnostic criteria of the Simon Broome Register Group (SBRG), are eligible for this study. For enrollment, subjects must be on an approved statin, with stable dose(s) for all allowed (eg, ezetimibe, bile-acid sequestering resin, stanols, or regulatory-approved and marketed niacin (eg, Niaspan or Niacor)) lipid-regulating drugs for at least 4 weeks before LDL-C screening and, in the opinion of the investigator, not requiring uptitration. Fasting LDL-C must be ≥100 mg/dL (2.6 mmol/L) and fasting triglycerides ≤400 mg/dL (4.5 mmol/L) by central laboratory at screening.

Preliminary data (data not shown) demonstrated that subjects treated with 350 mg 21B12 had a least squares (LS) mean percent reduction from baseline in LDL-C of 38.46% at the end of the dosing interval, and subjects treated with 420 mg 21B12 had a LS mean percent reduction from baseline in LDL-C of 45.68%. Subjects treated with 350 mg 21B12 had a LS mean percent reduction from baseline in Lp(a) of 21.69% at the end of the dosing interval, and subjects treated with 420 mg 21B12 had a LS mean percent reduction from baseline in Lp(a) of 28.23%. Subjects treated with 350 mg 21B12 had a LS mean percent increase from baseline in HDL-C of 15.39% at the end of the dosing interval, and subjects treated with 420 mg 21B12 had a LS mean percent increase from baseline in HDL-C of 6.77%. Subjects treated with 350 mg 21B12 had a LS mean percent reduction from baseline in VLDL-C of 17.16% at the end of the dosing interval, and subjects treated with 420 mg 21B12 had a LSmean percent reduction from baseline in VLDL-C of 18.49%. Subjects treated with 350 mg 21B12 had a LS mean percent reduction from baseline in triglycerides of 17.24% at the end of the dosing interval, and subjects treated with 420 mg 21B12 had a LS mean percent reduction from baseline in triglycerides 4.56%. Subjects treated with 350 mg 21B12 had a LS mean percent reduction from baseline in non-HDL cholesterol of 36.16% at the end of the dosing interval, and subjects treated with 420 mg 21B12 had a LS mean percent reduction from baseline in non-HDL cholesterol of 41.81%. Finally, subjects treated with 350 mg 21B12 had a LS mean percent reduction from baseline in total cholesterol of 24.82% at the end of the dosing interval, and subjects treated with 420 mg 21B12 had a LS mean percent reduction from baseline in total cholesterol of 29.45%. (data not shown)

FIG. 24 is a graph representing the LDL-C reduction data for following doses of 21B12: 70 mg, 105 mg and 140 mg (Q2W or once every two weeks dosing) and 280 mg, 350 mg and 420 (Q4W or once a month dosing). This data is the aggregate data from the studies described in Examples 22-25). In brief, the aggregate data shows that 140 mg Q2W results in an approximate 60% reduction from baseline in LDL-C at week 12 and smooth maintenance of LDL-C reduction. In addition, this data shows that the 420 mg Q4W results in an approximate 56% reduction from baseline in LDL-C at week 12 and less LDL-C rebound at end of dosing interval.

FIGS. 25A-25D are bar graphs showing the beneficial effects of doses of 21B12 on Lp(a), HDL-C, triglycerides and VLDL-C, respectively, derived from the aggregate data from the studies described in Examples 22-25. In addition, dose dependent reductions from baseline were observed for total cholesterol (25-37%, p values<0.001), non-HDL-C (36-53%, p values<0.001), and ApoB (36-53%, p values<0.001) (data not shown).

Example 23

A Randomized Study to Evaluate Tolerability and Efficacy of a Human Anti-PCSK9 Antibody on LDL-C Compared with Ezetimibe in Hypercholesterolemic Patients Unable to Tolerate an Effective Dose of a HMG-Co-A Reductase Inhibitor The objective of this study is to evaluate the effect of 12 weeks of subcutaneous (SC) human, anti-PCSK9 antibody (monoclonal antibody 21B12) compared with ezetimibe, on percent change from baseline in low-density lipoprotein cholesterol (LDL-C) in hypercholesterolemic subjects unable to tolerate an effective dose of an HMG-CoA reductase inhibitor.

This study is a randomized, stratified, parallel group clinical trial for the human anti-PCSK9 antibody, monoclonal antibody, 21B12. It is planned to enroll 150 subjects. Subjects who meet all inclusion/exclusion criteria will be randomized with equal allocation into 5 treatment groups: monoclonal antibody, 21B12 at 280 mg, 350 mg or 420 mg Q4W SC (once every 4 weeks, subcutaneous); ezetimibe at 10 mg daily (QD) oral (PO) with monoclonal antibody, 21B12 at 420 mg Q4W SC; or ezetimibe 10 mg QD PO with placebo Q4W SC. Randomization will be stratified by screening LDL-C level (<130 mg/dL [3.4 mmol/L] vs ≥130 mg/dL) and statin use at baseline (yes vs no). Randomization should occur within 5-10 days of the screening LDL-C evaluation used to determine eligibility. Monoclonal antibody, 21B12, and placebo will be blinded. Ezetimibe is not blinded. Study visits are at weeks 2, 4, 8, and 12. Final administration of monoclonal antibody, 21B12, or placebo is at week 8. The end-of-study visit and the last evaluation of lipids is at week 12.

Males and females, ≥18 to ≤75 years of age, are eligible for this study. Subject must have tried at least 1 statin and have been unable to tolerate any dose or an increase in statin dose above the following total weekly maximum doses due to myalgia or myopathy: atorvastatin ≤70 mg, simvastatin ≤140 mg, pravastatin ≤140 mg, rosuvastatin ≤35 mg, lovastatin ≤140 mg, fluvastatin ≤280 mg. For unlisted statins, the maximal total weekly dose should not exceed 7 times the smallest available tablet size. Symptoms must have resolved when statin was discontinued or the dose reduced. If receiving statin (not exceeding the maximal dose defined above), bile-acid sequestering resin, and/or stanol therapy, the dose(s) must be stable for at least 4 weeks prior to LDL-C screening. If the subject is on ezetimibe at start of screening, ezetimibe must be discontinued for ≥4 weeks before LDL-C screening. Depending on their risk category (based on NCEP ATP III treatment goals) subjects must meet the following fasting LDL-C (by central laboratory) criteria at screening: ≥100 mg/dL (2.6 mmol/L) for subjects with diagnosed coronary heart disease (CHD) or CHD risk equivalent; ≥130 mg/dL (3.4 mmol/L) for subjects without diagnosed CHD or risk equivalent and 2 or more risk factors; ≥160 mg/dL (4.1 mmol/L) for subjects without diagnosed CHD or risk equivalent and with 1 or no risk factors. Fasting triglycerides must be ≤400 mg/dL (4.5 mmol/L) as determined by the central laboratory analysis at screening.

Preliminary data (data not shown) demonstrated that subjects treated with 280 mg 21B12 had a LS mean percent reduction from baseline in LDL-C of 38.79% at the end of the dosing interval; subjects treated with 350 mg 21B12 had a LS mean percent reduction from baseline in LDL-C of 40.01% at the end of the dosing interval; and subjects treated with 420 mg 21B12 had a LS mean percent reduction from baseline in LDL-C of 50.63% Preliminary data demonstrated that subjects treated with 280 mg 21B12 had a LS mean percent reduction from baseline in Lp(a) of 27.38% at the end of the dosing interval; subjects treated with 350 mg 21B12 had a LS mean percent reduction from baseline in Lp(a) of 16.04% at the end of the dosing interval; and subjects treated with 420 mg 21B12 had a LS mean percent reduction from baseline in Lp(a) of 23.84%. Preliminary data demonstrated that subjects treated with 280 mg 21B12 had a LS mean percent increase from baseline in HDL-C of 8.62% at the end of the dosing interval; subjects treated with 350 mg 21B12 had a LS mean percent increase from baseline in HDL-C of 4.62% at the end of the dosing interval; and subjects treated with 420 mg 21B12 had a LS mean percent increase from baseline in HDL-C of 7.55%. Preliminary data demonstrated that subjects treated with 280 mg 21B12 had a LS mean percent reduction from baseline in VLDL-C of 31.02% at the end of the dosing interval; subjects treated with 350 mg 21B12 had a LS mean percent reduction from baseline in VLDL-C of 38.14% at the end of the dosing interval; and subjects treated with 420 mg 21B12 had a LS mean percent reduction from baseline in VLDL-C of 37.27%. Preliminary data demonstrated that subjects treated with 280 mg 21B12 had a LS mean percent reduction from baseline in triglycerides of 15.35% at the end of the dosing interval; subjects treated with 350 mg 21B12 had a LS mean percent reduction from baseline in triglycerides of 19.22% at the end of the dosing interval; and subjects treated with 420 mg 21B12 had a LS mean percent reduction from baseline in triglycerides of 19.55%. Preliminary data demonstrated that subjects treated with 280 mg 21B12 had a LS mean percent reduction from baseline in total cholesterol of 31.03% at the end of the dosing interval; subjects treated with 350 mg 21B12 had a LS mean percent reduction from baseline in total cholesterol of 34.46% at the end of the dosing interval; and subjects treated with 420 mg 21B12 had a LS mean percent reduction from baseline in total cholesterol of 42.23%. Preliminary data demonstrated that subjects treated with 280 mg 21B12 had a LS mean percent reduction from baseline in non-HDL-C of 39.92% at the end of the dosing interval; subjects treated with 350 mg 21B12 had a LS mean percent reduction from baseline in non-HDL-C of 42.86% at the end of the dosing interval; and subjects treated with 420 mg 21B12 had a LS mean percent reduction from baseline in non-HDL-C of 53.49%.

Example 24

A Randomized, Placebo and Ezetimibe-Controlled, Dose-Ranging Study to Evaluate Tolerability and Efficacy of a Human Anti-PCSK9 Antibody on LDL-C in Hypercholesterolemic Patients with a 10 Year Framingham Risk Score of 10% or Less The objective of this study was to evaluate the effect of 12 weeks of subcutaneous (SC) human, anti-PCSK9 antibody (monoclonal antibody 21B12) every 2 weeks (Q2W) or every 4 weeks (Q4W), compared with placebo, on percent change from baseline in low-density lipoprotein cholesterol (LDL-C) when used as monotherapy in hypercholesterolemic subjects with a 10 year Framingham risk score of 10% or less.

This study was a randomized, stratified, placebo and ezetimibe controlled, parallel group dose ranging clinical trial for the human anti-PCSK9 antibody, monoclonal antibody, 21B12, enrolling 411 subjects. Subjects who meet all inclusion/exclusion criteria were randomized with equal allocation into 9 treatment groups: 1 of 6 dose regimens of monoclonal antibody, 21B12 (70 mg, 105 mg, or 140 mg Q2W SC, or 280 mg, 350 mg or 420 mg Q4W SC (once every 4 weeks, subcutaneous), placebo with either Q2W or Q4W SC administration, or ezetimibe with daily (QD) oral (PO) administration. Randomization was stratified by screening LDL-C level (<130 mg/dL [3.4 mmol/L] vs >130 mg/dL). Randomization occurred within 5-10 days of the screening LDL-C evaluation used to determine eligibility. Study visits were every 2 weeks, irrespective whether the subject receives Q2W SC or Q4W treatment or ezetimibe. The 3 Q2W dose groups of monoclonal antibody, 21B12, and 1 Q2W placebo group was blinded against each other, and the 3 Q4W dose groups and 1 Q4W placebo group was blinded against each other. Ezetimibe was not blinded. The end-of-study visit and the last estimation of lipids was at week 12 for subjects on Q4W IP schedule or on ezetimibe and week 14 for subjects on Q2W IP schedule.

Males and females, ≥18 to ≤75 years of age, were eligible for this study. Fasting LDL-C was ≥100 mg/dL (2.6 mmol/L) and ≤190 mg/dL (4.9 mmol/L) and fasting triglycerides ≤400 mg/dL (4.5 mmol/L) by central laboratory at screening. Subjects had a National Cholesterol Education Panel Adult Treatment Panel III (NCEP ATP III) Framingham risk score of 10% or less.

The primary endpoint was the percent change from baseline in LDL-C at week 12. Secondary endpoints included percent changes in apolipoprotein B (ApoB), lipoprotein (a) (Lp(a)), and in the ratio of total cholesterol to high-density lipoprotein (HDL)-C. Tolerability and safety were also evaluated.

Preliminary data demonstrated that subjects treated with 70 mg 21B12 (Q2W) had a mean percent reduction from baseline in LDL-C of 41.21% at the end of the dosing interval; subjects treated with 105 mg 21B12 (Q2W) had a mean percent reduction from baseline in LDL-C of 45.44% at the end of the dosing interval; and subjects treated with 140 mg 21B12 (Q2W) had a mean percent reduction from baseline in LDL-C of 51.56% (data not shown).

Preliminary data demonstrated that subjects treated with 280 mg 21B12 (Q4W) had a mean percent reduction from baseline in LDL-C of 37.53% at the end of the dosing interval; subjects treated with 350 mg 21B12 had a mean percent reduction from baseline in LDL-C of 42.16% at the end of the dosing interval; and subjects treated with 420 mg 21B12 had a mean percent reduction from baseline in LDL-C of 47.52% (data not shown).

Final data demonstrated that at week 12, subjects receiving 21B12 had a least-squares (LS) mean percent reducton from baseline in LDL-C of up to 51% (Table 12); the percent change from baseline for ezetimibe was 14%. The change from baseline to week 12 was up to 72 mg/dL greater with 21B12 than with placebo. Subjects receiving 21B12 had LDL-C reductions from baseline 37%-53% greater than placebo and 37% greater than ezetimibe. Mean reductions from baseline for ApoB (up to 44%), Lp(a) (up to 29%) and total cholesterol/HDL ratio (up to 38%) were greater with 21B12 than with placebo.

irrespective whether the subject receives Q2W SC or Q4W treatment. The 3 Q2W dose groups of monoclonal antibody, 21B12, and 1 Q2W placebo group will be blinded against each other, and the 3 Q4W dose groups and 1 Q4W placebo group will be blinded against each other. The end-of-study visit and the last estimation of lipids is at week 12 for subjects on Q4W IP schedule and week 14 for subjects on Q2W IP schedule.

Males and females, ≥18 to ≤80 years of age, are eligible for this study. For enrollment, subjects must be on a statin, with or without ezetimibe, with stable dose(s) for at least 4 weeks before LDL-C screening and not requiring uptitration. Fasting LDL-C at screening

TABLE 12

| Week 12 Percent Change from Baseline in LDL-C: SC 21B12 vs Ezetimibe or Placebo | | | | | | | | |
|---|---|---|---|---|---|---|---|---|
| | Q2W | | | Q4W | | | | Ezetimibe |
| | Placebo (N = 45) | 70 mg (N = 45) | 105 mg (N = 46) | 140 mg (N = 45) | Placebo (N = 45) | 280 mg (N = 45) | 350 mg (N = 45) | 420 mg (N = 45) | QD (N = 45) |
| Least squares mean percent change from baseline (%) | −3.71 | −40.98 | −43.87 | −50.93 | 4.54 | −39.02 | −43.20 | −47.98 | −14.26 |
| Treatment difference vs placebo (%) | — | −37.27* | −40.17* | −47.23* | — | −43.57* | −47.74* | −52.53* | — |
| Treatment difference vs ezetimibe (%) | — | −26.73* | −29.62* | −36.68* | — | −25.17* | −29.34* | −34.14* | — |

SC: subcutaneous
Q2W: every 2 weeks;
Q4W: every 4 weeks or once a month;
QD: daily
*P < 0.001

Example 25

A Double-Blind, Randomized, Placebo-Controlled, Dose-Ranging Study to Evaluate Tolerability and Efficacy of a Human Anti-PCSK9 Antibody on LDL-C in Combination with HMG-Co-A Reductase Inhibitors in Hypercholesterolemic Patients The objective of this study is to evaluate the effect of 12 weeks of subcutaneous (SC) human, anti-PCSK9 antibody (monoclonal antibody 21B12) every 2 weeks (Q2W) or every 4 weeks (Q4W), compared with placebo, on percent change from baseline in low-density lipoprotein cholesterol (LDL-C) when used in addition to HMG-Co-A reductase inhibitor (e.g., a statin) in subjects with hypercholesterolemia.

This study is a double-blind, randomized, stratified, placebo controlled, parallel group dose ranging clinical trial for the human anti-PCSK9 antibody, monoclonal antibody, 21B12, enrolling 631 subjects. Subjects who are on stable dose(s) for at least 4 weeks of statin therapy with or without ezetimibe and who meet all inclusion/exclusion criteria will be randomized with equal allocation into 8 treatment groups: monoclonal antibody, 21B12 subcutaneous (SC) (70 mg Q2W, 105 mg Q2W, 140 mg Q2W, 280 mg Q4W, 350 mg Q4W, and 420 mg Q4W, placebo Q2W SC, or placebo Q4W SC). Randomization will be stratified by screening LDL-C level (<130 mg/dL [3.4 mmol/L] vs ≥130 mg/dL) and ezetimibe use at baseline (yes vs no). Randomization should occur within 5-10 days of the screening LDL-C evaluation used to determine eligibility. Study visits are every 2 weeks, must be ≥85 mg/dL (2.2 mmol/L). Enrollment of subjects with screening fasting LDL-C between ≥85 mg/dL (2.2 mmol/L) and <100 mg/dL (2.6 mmol/L) will be limited to no more than approximately 20% of total planned enrollment. Fasting triglycerides must be ≤400 mg/dL (4.5 mmol/L) as determined by the central laboratory analysis at screening.

Preliminary data demonstrated that subjects treated with 70 mg 21B12 (Q2W) had a LS mean percent reduction from baseline in LDL-C of 39.22% at the end of the dosing interval; subjects treated with 105 mg 21B12 (Q2W) had a LS mean percent reduction from baseline in LDL-C of 56.38% at the end of the dosing interval; and subjects treated with 140 mg 21B12 (Q2W) had a LS mean percent reduction from baseline in LDL-C of 68.76% (data not shown). Preliminary data demonstrated that subjects treated with 70 mg 21B12 (Q2W) had a LS mean percent reduction from baseline in Lp(a) of 21.17% at the end of the dosing interval; subjects treated with 105 mg 21B12 (Q2W) had a LS mean percent reduction from baseline in Lp(a) of 33.41% at the end of the dosing interval; and subjects treated with 140 mg 21B12 (Q2W) had a LS mean percent reduction from baseline in Lp(a) of 33.87% (data not shown). Preliminary data demonstrated that subjects treated with 70 mg 21B12 (Q2W) had a LS mean percent increase from baseline in HDL-C of 21.17% at the end of the dosing interval; subjects treated with 105 mg 21B12 (Q2W) had a LS mean percent increase from baseline in HDL-C of 6.80% at the end of the dosing interval; and subjects treated with 140 mg 21B12 (Q2W) had a LS mean percent increase from baseline in HDL-C of 8.43% (data not shown). Preliminary data demonstrated that subjects treated with 70 mg 21B12 (Q2W) had a LS mean percent reduction from baseline in VLDL-C of 14.84% at the end of the dosing interval; subjects treated with 105 mg 21B12 (Q2W) had a LS mean percent reduction from baseline in VLDL-C of 12.75% at the end of the dosing interval; and subjects treated with 140 mg 21B12 (Q2W) had a LS mean percent reduction from baseline in VLDL-C of 45.14% (data not shown). Preliminary data demonstrated that subjects treated with 70 mg 21B12 (Q2W) had a LS mean percent reduction from baseline in triglycerides of 7.20% at the end of the dosing interval; subjects treated with 105 mg 21B12 (Q2W) had a LS mean percent reduction from baseline in triglycerides of 5.65% at the end of the dosing interval; and subjects treated with 140 mg 21B12 (Q2W) had a LS mean percent reduction from baseline in triglycerides of 17.60% (data not shown). Preliminary data demonstrated that subjects treated with 70 mg 21B12 (Q2W) had a LS mean percent reduction from baseline in non-HDL-C of 36.20% at the end of the dosing interval; subjects treated with 105 mg 21B12 (Q2W) had a LS mean percent reduction from baseline in non-HDL-C of 51.20% at the end of the dosing interval; and subjects treated with 140 mg 21B12 (Q2W) had a LS mean percent reduction from baseline in non-HDL-C of 64.61% (data not shown). Preliminary data demonstrated that subjects treated with 70 mg 21B12 (Q2W) had a LS mean percent reduction from baseline in total cholesterol of 26.33% at the end of the dosing interval; subjects treated with 105 mg 21B12 (Q2W) had a LS mean percent reduction from baseline in total cholesterol of 36.91% at the end of the dosing interval; and subjects treated with 140 mg 21B12 (Q2W) had a LS mean percent reduction from baseline in total cholesterol of 46.17% (data not shown).

Preliminary data demonstrated that subjects treated with 280 mg 21B12 (Q4W) had a LS mean percent reduction from baseline in LDL-C of 42.62% at the end of the dosing interval; subjects treated with 350 mg 21B12 had a LS mean percent reduction from baseline in LDL-C of 56.84% at the end of the dosing interval; and subjects treated with 420 mg 21B12 had a LS mean percent reduction from baseline in LDL-C of 52.19% (data not shown). Preliminary data demonstrated that subjects treated with 280 mg 21B12 (Q2W) had a LS mean percent reduction from baseline in Lp(a) of 22.54% at the end of the dosing interval; subjects treated with 350 mg 21B12 (Q2W) had a LS mean percent reduction from baseline in Lp(a) of 29.43% at the end of the dosing interval; and subjects treated with 420 mg 21B12 (Q2W) had a LS mean percent reduction from baseline in Lp(a) of 23.29% (data not shown). Preliminary data demonstrated that subjects treated with 280 mg 21B12 (Q2W) had a LS mean percent increase from baseline in HDL-C of 2.17% at the end of the dosing interval; subjects treated with 350 mg 21B12 (Q2W) had a LS mean percent increase from baseline in HDL-C of 6.92% at the end of the dosing interval; and subjects treated with 420 mg 21B12 (Q2W) had a LS mean percent increase from baseline in HDL-C of 7.42% (data not shown). Preliminary data demonstrated that subjects treated with 280 mg 21B12 (Q2W) had a LS mean percent reduction from baseline in VLDL-C of 18.12% at the end of the dosing interval; subjects treated with 350 mg 21B12 (Q2W) had a LS mean percent reduction from baseline in VLDL-C of 20.89% at the end of the dosing interval; and subjects treated with 420 mg 21B12 (Q2W) had a LS mean percent reduction from baseline in VLDL-C of 28.66% (data not shown). Preliminary data demonstrated that subjects treated with 280 mg 21B12 (Q2W) had a LS mean percent reduction from baseline in triglycerides of 6.75% at the end of the dosing interval; subjects treated with 350 mg 21B12 (Q2W) had a LS mean percent reduction from baseline in triglycerides of 9.17% at the end of the dosing interval; and subjects treated with 420 mg 21B12 (Q2W) had a LS mean percent reduction from baseline in triglycerides of 11.13% (data not shown). Preliminary data demonstrated that subjects treated with 280 mg 21B12 (Q2W) had a LS mean percent reduction from baseline in non-HDL-C of 38.89% at the end of the dosing interval; subjects treated with 350 mg 21B12 (Q2W) had a LS mean percent reduction from baseline in non-HDL-C of 50.83% at the end of the dosing interval; and subjects treated with 420 mg 21B12 (Q2W) had a LS mean percent reduction from baseline in non-HDL-C of 48.54% (data not shown). Preliminary data demonstrated that subjects treated with 280 mg 21B12 (Q2W) had a LS mean percent reduction from baseline in total cholesterol of 28.08% at the end of the dosing interval; subjects treated with 350 mg 21B12 (Q2W) had a LS mean percent reduction from baseline in total cholesterol of 36.04% at the end of the dosing interval; and subjects treated with 420 mg 21B12 (Q2W) had a LS mean percent reduction from baseline in total cholesterol of 42.76% (data not shown).

Example 26

PCSK9 ABPs Further Upregulated LDLR in the Presence of Statins

This example demonstrates that ABPs to PCSK9 produced further increases in LDLR availability when used in the presence of statins, demonstrating that further benefits can be achieved by the combined use of the two.

Figure 12A:
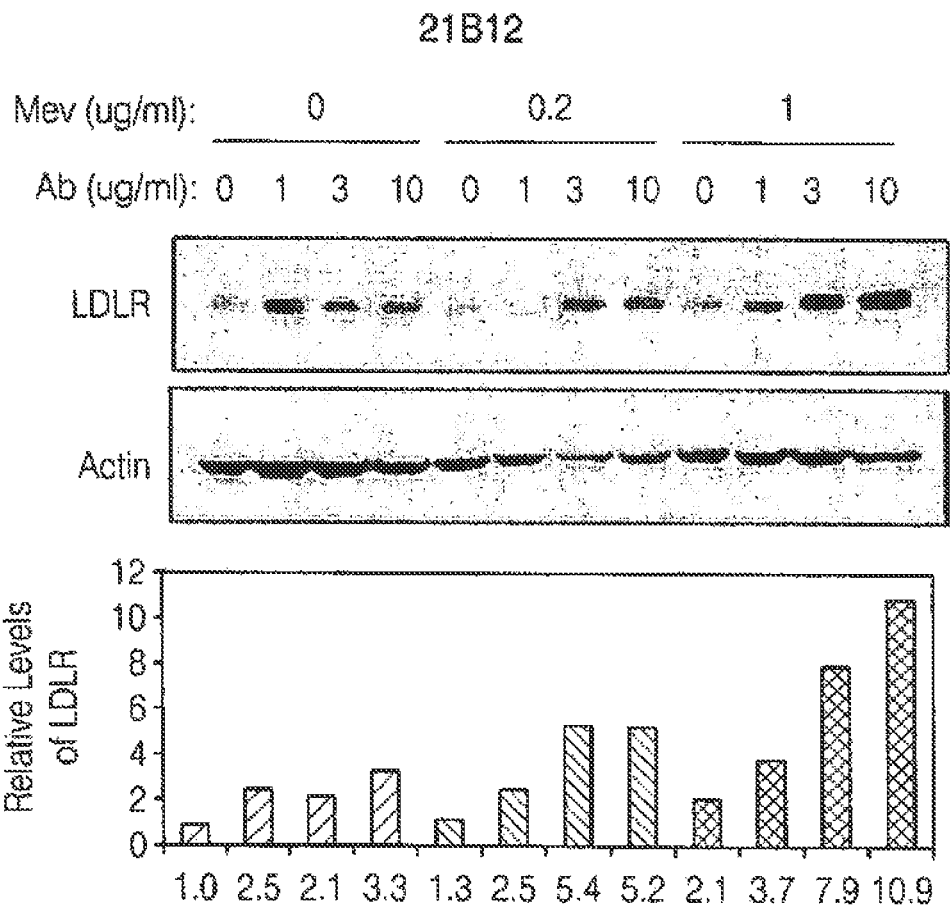
FIG. 12A depicts LDLR levels in response to the combination of a statin and ABP 21B12 in HepG2 cells.
Figure 12B:
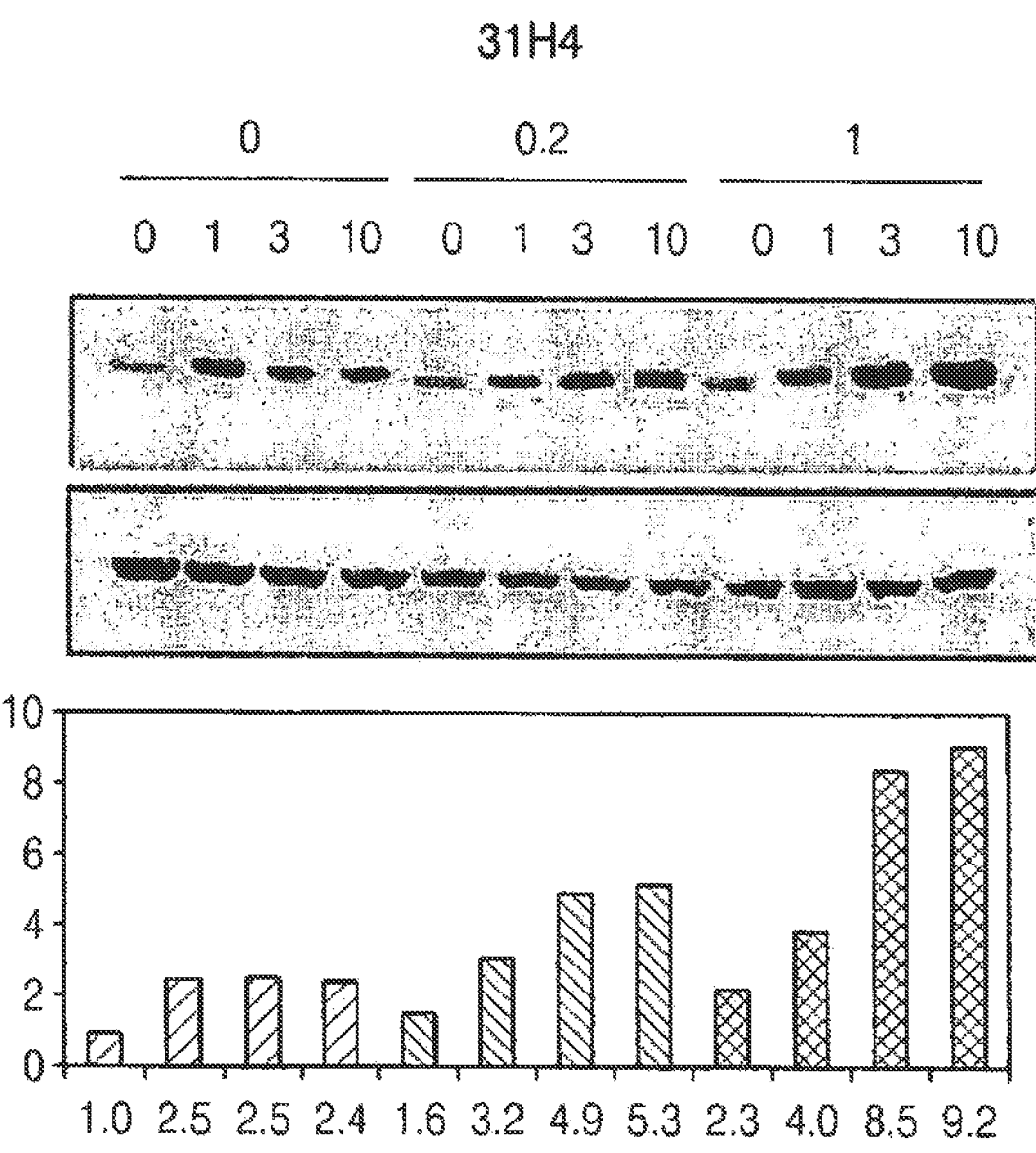
FIG. 12B depicts LDLR levels in response to the combination of a statin and ABP 31H4 in HepG2 cells.
Figure 12C:
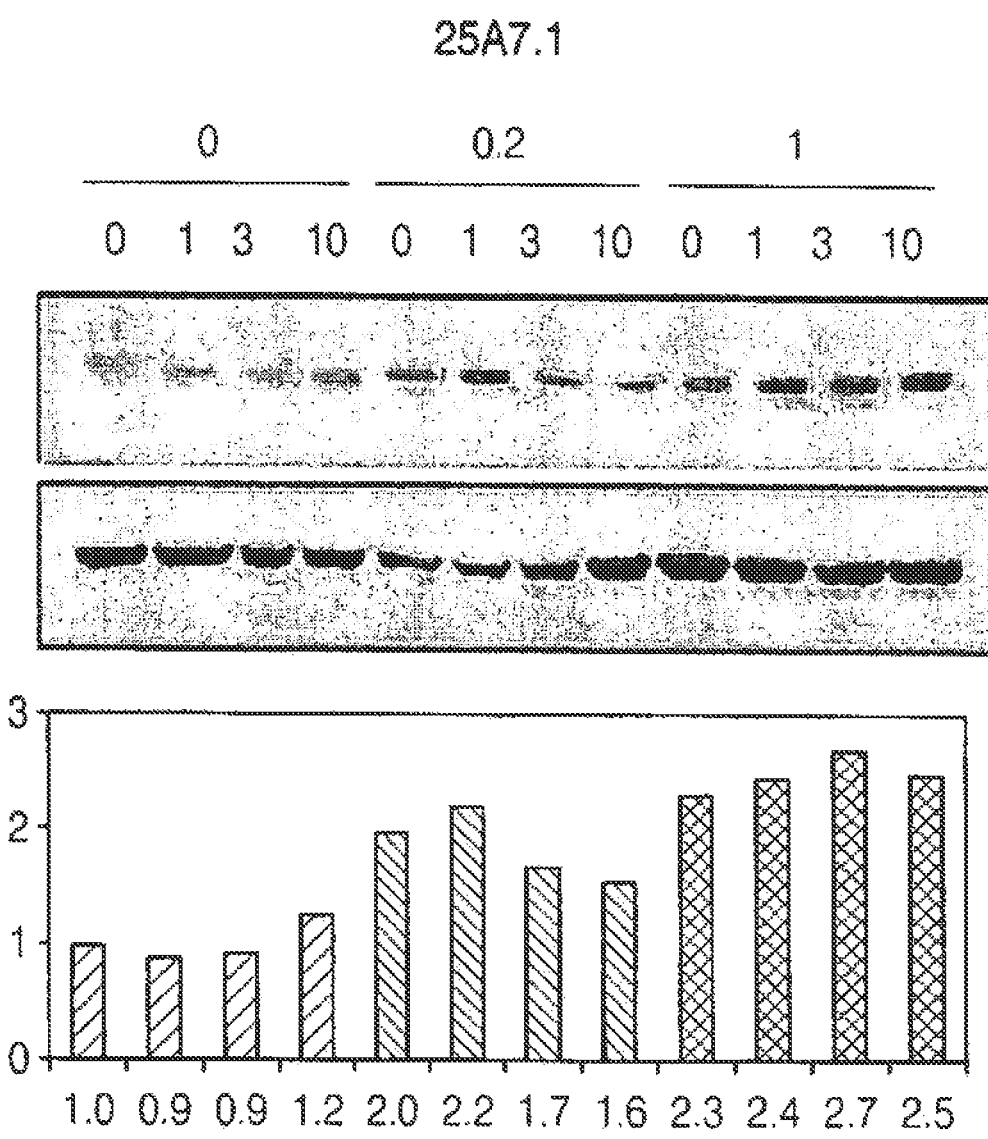
FIG. 12C depicts LDLR levels in response to the combination of a statin and ABP 25A7.1, a non-neutralizing antibody, (in contrast the "25A7" a neutralizing antibody) in HepG2 cells.

HepG2 cells were seeded in DMEM with 10% fetal bovine serum (FBS) and grown to ~90% confluence. The cells were treated with indicated amounts of mevinolin (a statin, Sigma) and PCSK9 ABPs (FIGS. 12A-12C) in DMEM with 3% FBS for 48 hours. Total cell lysates were prepared. 50 mg of total proteins were separated by gel electrophoresis and transferred to PVDF membrane. Immunoblots were performed using rabbit anti-human LDL receptor antibody (Fitzgerald) or rabbit anti-human b-actin antibody. The enhanced chemiluminescent results are shown in the top panels of FIGS. 12A-12C. The intensity of the bands were quantified by ImageJ software and normalized by b-actin. The relative levels of LDLR are shown in the lower panels of FIGS. 12A-12C. ABPs 21B12 and 31H4 are PCSK9 neutralizing antibodies, while 25A7.1 is a non-neutralizing antibody.

Figure 12D:
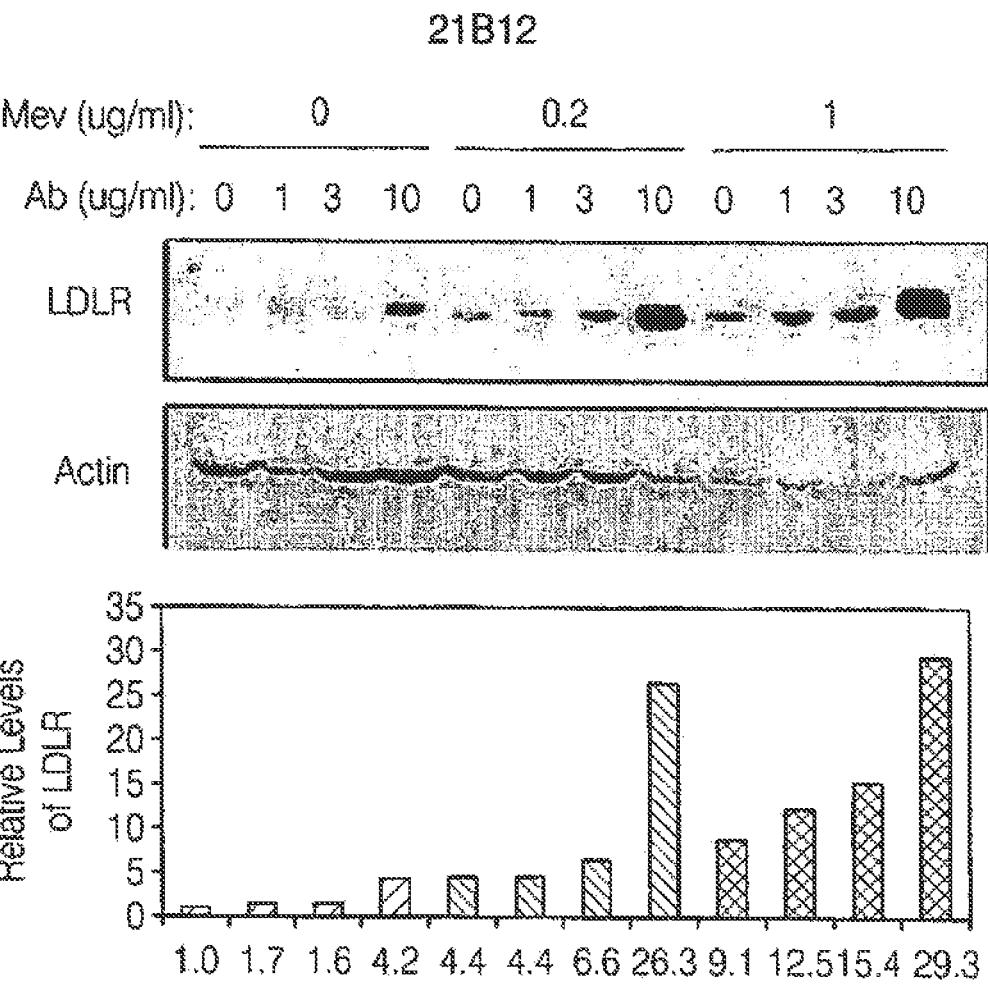
FIG. 12D depicts LDLR levels in response to the combination of a statin and ABP 21B12 in HepG2 cells over expressing PCSK9.
Figure 12E:
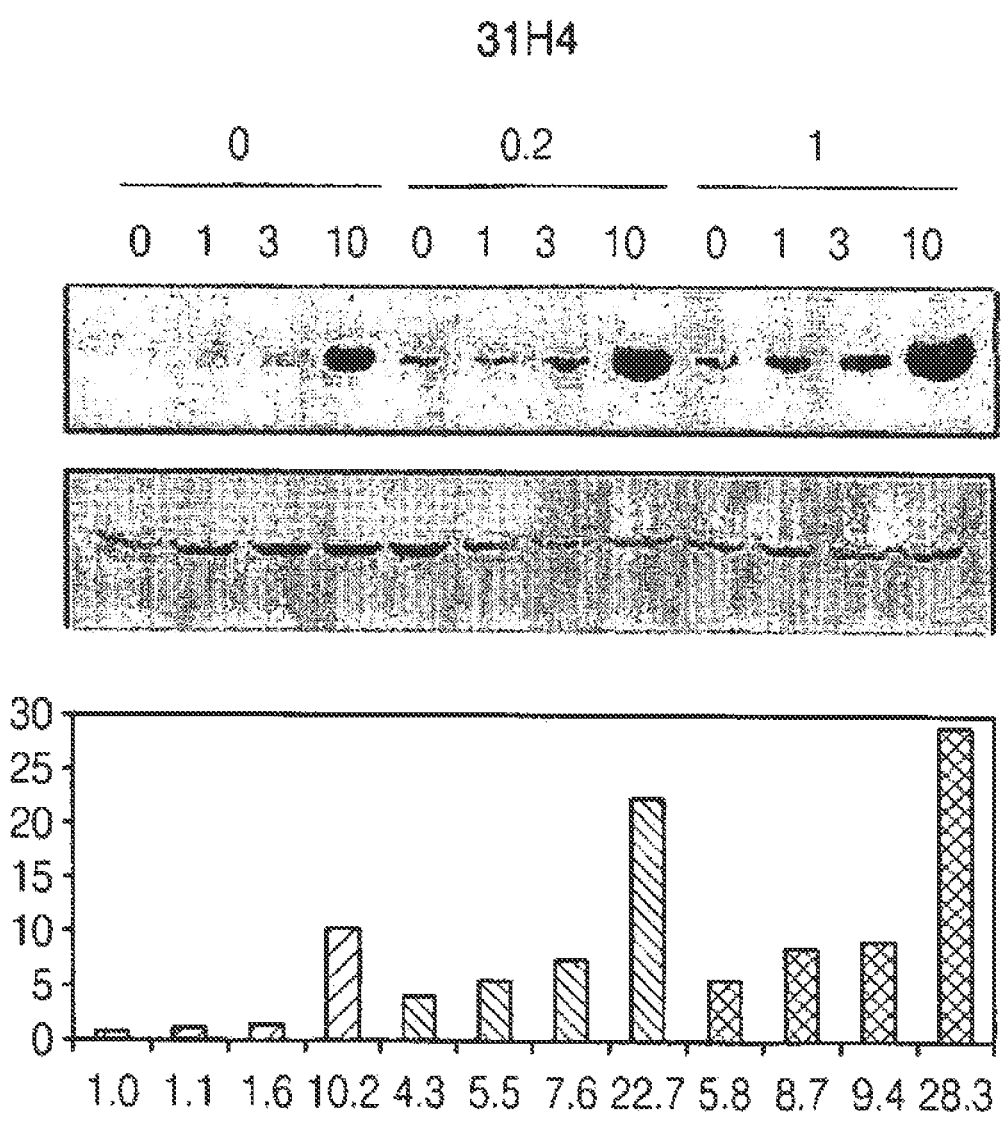
FIG. 12E depicts LDLR levels in response to the combination of a statin and ABP 31H4 in HepG2 cells over expressing PCSK9.
Figure 12F:
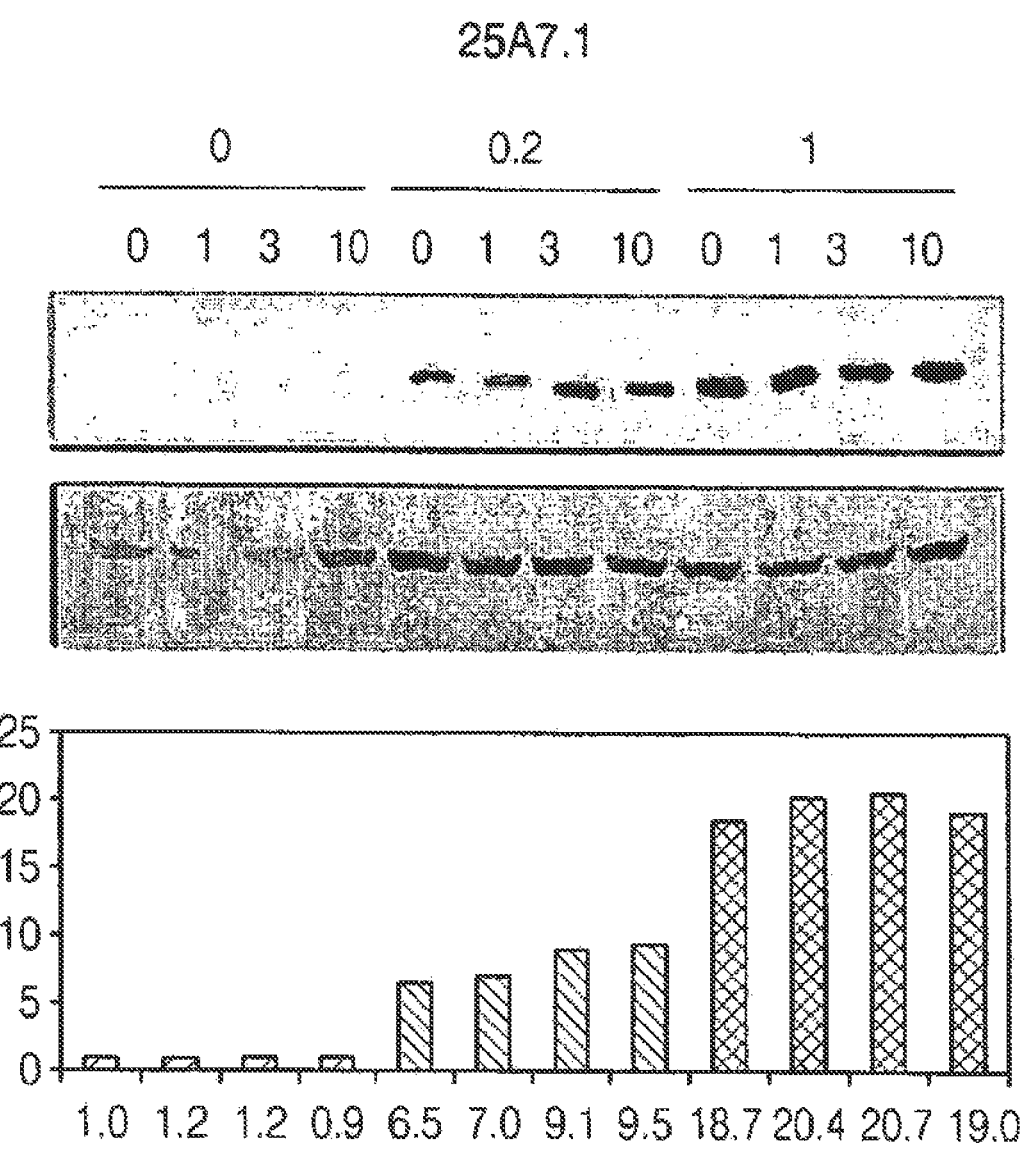
FIG. 12F depicts LDLR levels in response to the combination of a statin and ABP 25A7.1, a non-neutralizing antibody, (in contrast the "25A7" a neutralizing antibody) in HepG2 cells over expressing PCSK9.

HepG2-PCSK9 cells were also created. These were stable HepG2 cell line transfected with human PCSK9. The cells were seeded in DMEM with 10% fetal bovine serum (FBS) and grew to ~90% confluence. The cells were treated with indicated amounts of mevinolin (Sigma) and PCSK9 ABPs (FIGS. 12D-12F) in DMEM with 3% FBS for 48 hours. Total cell lysates were prepared. 50 mg of total proteins were separated by gel electrophoresis and transferred to PVDF membrane Immunoblots were performed using rabbit anti-human LDL receptor antibody (Fitzgerald) or rabbit anti-human b-actin antibody. The enhanced chemiluminescent results are shown in the top panels. The intensity of the bands were quantified by ImageJ software and normalized by b-actin.

As can be seen in the results depicted in FIGS. 12A-12F, increasing amounts of the neutralizing antibody and increasing amounts of the statin generally resulted in increases in the level of LDLR. This increase in effectiveness for increasing levels of the ABP is especially evident in FIGS. 12D-

12F, in which the cells were also transfected with PCSK9, allowing the ABPs to demonstrate their effectiveness to a greater extent.

Interestingly, as demonstrated by the results in the comparison of FIGS. 12D-12F to 12A-12C, the influence of the ABP concentrations on LDLR levels increased dramatically when PCSK9 was being produced by the cells. In addition, it is clear that the neutralizing ABPs (21B12 and 31H4) resulted in a greater increase in LDLR levels, even in the presence of statins, than the 25A7.1 ABP (a non-neutralizer), demonstrating that additional benefits can be achieved by the use of both statins and ABPs to PCSK9.

Example 27

Consensus Sequences

Consensus sequences were determined using standard phylogenic analyses of the CDRs corresponding to the $V_H$ and $V_L$ of anti-PCSK9 ABPs. The consensus sequences were determined by keeping the CDRs contiguous within the same sequence corresponding to a $V_H$ or $V_L$. Briefly, amino acid sequences corresponding to the entire variable domains of either $V_H$ or $V_L$ were converted to FASTA formatting for ease in processing comparative alignments and inferring phylogenies. Next, framework regions of these sequences were replaced with an artificial linker sequence ("bbbbbbbbbb" placeholders, non-specific nucleic acid construct) so that examination of the CDRs alone could be performed without introducing any amino acid position weighting bias due to coincident events (e.g., such as unrelated antibodies that serendipitously share a common germline framework heritage) while still keeping CDRs contiguous within the same sequence corresponding to a $V_H$ or $V_L$. $V_H$ or $V_L$ sequences of this format were then subjected to sequence similarity alignment interrogation using a program that employs a standard ClutalW-like algorithm (see, Thompson et al., 1994, *Nucleic Acids Res.* 22:4673-4680). A gap creation penalty of 8.0 was employed along with a gap extension penalty of 2.0. This program likewise generated phylograms (phylogenic tree illustrations) based on sequence similarity alignments using either UPGMA (unweighted pair group method using arithmetic averages) or Neighbor-Joining methods (see, Saitou and Nei, 1987, *Molecular Biology and Evolution* 4:406-425) to construct and illustrate similarity and distinction of sequence groups via branch length comparison and grouping. Both methods produced similar results but UPGMA-derived trees were ultimately used as the method employs a simpler and more conservative set of assumptions. UPGMA-derived trees were generated where similar groups of sequences were defined as having fewer than 15 substitutions per 100 residues (see, legend in tree illustrations for scale) amongst individual sequences within the group and were used to define consensus sequence collections. The results of the comparisons are depicted in FIGS. 13A-13J. In FIG. 13E, the groups were chosen so that sequences in the light chain that Glade are also a Glade in the heavy chain and have fewer than 15 substitutions.

Example 28

Preparation of PCSK9 ABP Formulations

UF/DF—Ultrafiltration/Diafiltration Methodology

Drug substance, e.g., antibody 21B12 and antibody 11F1, was buffer exchanged into formulation buffer, including stabilizer, with a bench scale Millipore TFF UF/DF system using a Millipore Pellicon XL Filter, 50 cm² size (regenerated cellulose, 30,000 Molecular Weight Cut-Off) membrane. The diafiltration step was performed until at least ten volumes of diafiltration buffer were exchanged. Once the diafiltration step was completed, the UF/DF system was switched to ultrafiltration mode and each formulation was concentrated to the target concentration levels.

After the UF/DF step was completed, the appropriate amount of polysorbate 20 or 80 was added to each formulation from a 1.0% (w/w) freshly prepared polysorbate ("PS") stock solution to reach the desired polysorbate concentration.

Prior to filling primary containers, each formulation was filtered aseptically under a laminar flow hood and using a 0.2 micron filter. Filling was also performed aseptically and was performed manually or automatically using the appropriate filling instrumentation.

Example 29

High Concentration PCSK9 ABP Formulations with Lowed Viscosity

To evaluate the effects of different excipients on viscosity of high protein concentrations, a viscosity, stability and solubility screening assay was used to explore excipient viscosity modulators for high concentration protein formulations. Specifically, all sample preparation, e.g., antibody 21B12 sample, was done aseptically under a laminar-flow hood. Lyophilization of the samples to be tested allowed a simple method for achieving high protein concentrations. 1.5 mL of 70 mg/mL protein (e.g., 21B12) was pipetted into 3 cc glass vials for lyophilization. Lyophilization was performed using a generic Lyophilization cycle on a VirTis Lab Scale Lyophilizer. The lyophilization buffer was 10 mM L-glutamate with 1.0% sucrose, pH 4.8. Lyophilized samples (e.g., lyophilized 21B12 sample) were reconstituted individually with approximately 0.65 mL of the excipient buffers, shown in Table 13 below, to a final protein concentration of 150-200 mg/mL. Reconstituted samples sat overnight to allow complete dissolution. Viscosity was then measured as described below.

TABLE 13

| Excipient Type | Excipient Level | Adjusted pH |
|---|---|---|
| Amino Acids | 150 mM L-Alanine | pH 4.5 |
| | 150 mM L-Glycine | pH 4.2 |
| | 75 mM L-Lysine | pH 4.2 |
| | 150 mM L-Methionine | pH 4.5 |
| | 150 mM L-Proline | pH 4.2 |
| | 150 mM L-Serine | pH 4.2 |
| | 70 mM L-Arginine | pH 4.5 |
| | 150 mM L-Serine | pH 4.4 |
| Salts | 30 mM Magnesium chloride | pH 4.2 |
| | 70 mM Sodium chloride | pH 4.2 |
| | 30 mM Calcium chloride | pH 4.4 |
| | 50 mM Sodium sulfate | pH 4.1 |
| | 30 mM Zinc chloride | pH 4.7 |
| Polyols | 150 mM Glycerol | pH 4.5 |
| | 150 mM Sucrose | pH 4.2 |
| Other | 150 mM Carnitine | pH 4.8 |
| | 150 mM Creatinine | pH 5.0 |
| | 150 mM Taurine | pH 4.4 |

Results from the viscosity, stability, solubility screen showed changes in 21B12 viscosity after addition of various excipients (FIG. 26). Not all excipients used in for screening purposes resulted in a lowering of solution viscosity; L-alanine, glycerol, sodium sulfate, sucrose, and zinc chloride addition resulted in a much higher viscosity as compared to the control sample. Several excipients used in the screen appeared to be good viscosity modulating candidates, for example, L-arginine, carnitine, creatinine, L-methionine, and taurine.

To evaluate the effects of different formulations on viscosity of a specific PCSK9 ABP, compositions of 21B12 were formulated in six different formulations shown in Table 29.2 below. The concentration of 21B12 in all formulations was 134 mg/ml. Compositions were filled to a final volume of 1.0 ml in vials. Compositions were incubated at room temperature (i.e., 25° C.).

Dialysis and Concentration of 21B12

Sucrose removal from 21B12 originally in 10 mM Sodium acetate, 9.0% (w/v) sucrose was achieved via dialysis by adding approximately 10 mL 21B12 to Pierce Slide-A-Lyzer (Rockford, Ill.) dialysis cassettes and dialyzing against 2 L buffer at 4° C. for 3 cycles (2 hours×2 and 16 hours×1) for complete buffer exchange. Buffer for dialysis contained 10 mM sodium acetate (made from acetic acid) at pH 5.0. All samples were subsequently concentrated using Millipore Amicon UltraPrep Devices (Billerica, Mass.) in a Beckman Coulter Allegra 6R Centrifuge (Fullerton, Calif.) spun at 3000 rpm until the sample volume was slightly below the volume required for the desired concentration.

Concentration determination was then carried out by measuring absorbance at A280 using an Agilent 8453 Spectrophotometer (Santa Clara, Calif.). Protein concentration was calculated using the appropriate extinction coefficient. The appropriate amount of buffer was then added to the sample to dilute it back down to the desired concentration and another A280 was performed to obtain the final concentration for the experiment.

Addition of Stabilizers that May Also Act to Lower Viscosity:

Excipients, such as proline, benzyl alcohol, creatinine, methionine, taurine, etc., were tested in an attempt to lower viscosity. These excipients were added individually to the 21B12 formulation samples from high concentration stock solutions.

Viscosity Measurements

Viscosity was measured using Brookfield LV-DVII cone and plate viscometer (Middleboro, Mass.) with a CPE-40 spindle with matching sample cup temperature regulated by a circulating water bath at constant 25 C. 500 ul of sample was added to sample cup with positive displacement pipettor. After sample cup was secured the rotational speed of the spindle was gradually increased until about 80% torque was achieved. At this point the rotational speed was stopped and a viscosity reading was generated by Rheocalc software.

TABLE 14

| Buffer | Stabilizer | Stabilizer/ Excipients Added to Lower Viscosity | Viscosity (cP) |
|---|---|---|---|
| 10 mM Na acetate | | | 42.4 |
| 10 mM Na acetate | 9.0% sucrose | 2% L-Proline (174 mM) | 20.3 |
| 10 mM Na acetate | 9.0% sucrose | 3% L-Proline (261 mM) | 17.9 |
| 10 mM Na acetate | 9.0% sucrose | 3% Benzyl alcohol | 17.8 |
| 10 mM Na acetate | 9.0% sucrose | 150 mM Creatinine | 11.97 |
| 10 mM Na acetate | 9.0% sucrose | 150 mM L-Methionine | 16.0 |
| 10 mM Na acetate | 9.0% sucrose | 150 mM L-Taurine | 16.8 |

The results show that L-proline, benzyl alcohol, creatinine, methionine and taurine all had a significant viscosity lowering effect in high concentrations of PCSK9 ABP, 21B12 (see Table 14).

To further evaluate the effects of different formulations on a specific PCSK9 ABP, compositions of 21B12 were formulated in different formulations shown in Table 15 below. The formulations fall into three groups: (1) a set of various concentrations of 21B12 in 10 mM sodium acetate buffer, pH 5.2, (2) a set of various concentrations of 21B12 in 10 mM sodium acetate buffer, pH 5.2 with 3% (approximately 261 mM) L-Proline spiked into each sample, and (3) a set of 21B12 samples concentrated at about 117-134 mg/mL in 10 mM sodium acetate buffer at different pH levels (4.0 to 5.5) plus two samples in 10 mM sodium acetate buffer, pH 5.2 with either NaCl or a L-Methionine/Benzyl alcohol combination added.

TABLE 15

| 21B12 conc. (mg/mL) | Formulation | Additional Excipients | Viscosity (Cp) @ 25° C. | Viscosity (Cp) @ 40° C. | Osmolality (mOsmol/kg) |
|---|---|---|---|---|---|
| 76 | 10 mM Na acetate, pH 5.2 | N/A | 2.84 | | 53 |
| 104 | 10 mM Na acetate, pH 5.2 | N/A | 7.1 | | 57 |
| 126 | 10 mM Na acetate, pH 5.2 | N/A | 16 | 8.9 | 58 |
| 154 | 10 mM Na acetate, pH 5.2 | N/A | 101 | 49 | Did not freeze |
| 73 | 10 mM Na acetate, pH 5.2 | +3% proline | 2.6 | | 253 |
| 104 | 10 mM Na acetate, pH 5.2 | +3% proline | 5 | | 252 |
| 122 | 10 mM Na acetate, pH 5.2 | +3% proline | 8.8 | | 274 |
| 148 | 10 mM Na acetate, pH 5.2 | +3% proline | 24.4 | 9.5 | 301 |
| 125 | 10 mM Na acetate, pH 5.2 | +150 mM NaCl | 11 | 6.6 | 346 |
| 134 | 10 mM Na acetate, pH 4 | N/A | 13.3 | 8.87 | 59 |
| 117 | 10 mM Na acetate, pH 4.5 | N/A | 10.8 | 6 | 59 |
| 130 | 10 mM Na acetate, pH 5 | N/A | 16.2 | 7.1 | 59 |
| 133 | 10 mM Na acetate, pH 5.5 | N/A | 23 | 12.6 | 64 |
| 134 | 10 mM Na acetate, pH 5.5 | +150 Mm methionine and 3% benzyl alcohol | 6.5 | | 520 |

The results showed that L-Proline had a significant viscosity lowering effect in high concentrations of PCSK9 ABP, 21B12 (See FIG. 27).

To still further evaluate the effects of different formulations on a specific PCSK9 ABP, compositions of 21B12 were formulated in different formulations shown in Table 16 below.

pH 5.2 at 25° C. and 40° C., as compared to a formulation comprising 10 mM sodium acetate, 125 mM arginine, and 3% Sucrose pH 5.0 at 25° C. and 40° C.

FIG. 28C is a graph showing the viscosity of various concentrations of anti-PCSK9 antibody, 21B12, in a formulation comprising 10 mM sodium acetate, and 9% Sucrose pH 5.2 at 25° C. and 40° C., as compared to a formulation

TABLE 16

| 21B12 conc. (mg/mL) | Formulation | Excipients | Viscosity (cP) @ 25° C. | Osmolality (mOsmol/kg) |
|---|---|---|---|---|
| 116 | 10 mM sodium acetate, pH 4.8 | N/A | 10.4 | 72 |
| 116 | 10 mM sodium acetate, pH 4.8 | 50 mM methionine + 2% benzyl alcohol | 7 | 329 |
| 116 | 10 mM sodium acetate, pH 4.8 | 150 mM arginine | 3.7 | 241 |
| 116 | 10 mM sodium acetate, pH 4.8 | 2% proline + 1% benzyl alcohol | 7 | 313 |
| 116 | 10 mM sodium acetate, pH 4.8 | 1.5% proline + 1% benzyl alcohol | 7.3 | 277 |

The results show that 21B12 formulations formulated with 1.5% or 2.0% proline (approximately 131 nM-174 mM proline) and 1% benzyl alcohol had a significant viscosity lowering effect in high concentrations of PCSK9 ABP, 21B12.

To still further evaluate the effects of different formulations on a specific PCSK9 ABP, compositions of 21B12 were formulated in different formulations shown in Table 17 below.

comprising 10 mM sodium acetate, 100 mM methionine, and 4% Sucrose pH 5.0 at 25° C. and 40° C.

FIG. 28D is a graph showing the viscosity of various concentrations of anti-PCSK9 antibody, 21B12, in a formulation comprising 10 mM sodium acetate, and 9% Sucrose pH 5.2 at 25° C. and 40° C., as compared to a formulation comprising 10 mM sodium acetate and 250 mM proline, pH 5.0 at 25° C. and 40° C.

TABLE 17

| Final Excipient Buffers | Final Ave A280 21B12 Conc (mg/mL) | Viscosity (cP) @ 25 C. | Shear Stress (Pa) @ 25 C. | Shear Rate (1/sec) @ 25 C. |
|---|---|---|---|---|
| #1 | 79 | 3.43 | 18.50 | 540 |
| 10 mM sodium | 96 | 4.97 | 18.60 | 375 |
| acetate, 9% Sucrose | 110 | 7.68 | 18.44 | 240 |
| pH 5.2 | 166 | 223.19 | 18.40 | 8.25 |
| #2 | 89 | 4.80 | 18.00 | 375 |
| 10 mM sodium | 105 | 5.97 | 18.30 | 307.5 |
| acetate, 125 mM | 122 | 9.10 | 18.40 | 202.5 |
| Arginine, 3% Sucrose | 150 | 19.31 | 18.80 | 97.5 |
| pH 5.0 | 167 | 40.10 | 18.10 | 45 |
|  | 195 | 193.80 | 18.90 | 9.75 |
| #3 | 85 | 3.20 | 18.00 | 562.5 |
| 10 mM sodium | 106 | 4.89 | 18.30 | 375 |
| acetate, 100 mM | 122 | 7.85 | 18.90 | 240 |
| Methionine, 4% | 139 | 13.55 | 18.30 | 135 |
| Sucrose pH 5.0 | 168 | 121.22 | 18.20 | 15 |
|  | 193 | 309.56 | 18.60 | 6 |
| #4 | 85 | 3.20 | 18.00 | 562.5 |
| 10 mM sodium | 108 | 4.57 | 18.85 | 412.5 |
| acetate, 250 mM | 125 | 7.61 | 18.27 | 240 |
| Proline pH 5.0 | 139 | 13.54 | 18.30 | 135 |
|  | 180 | 133.73 | 19.00 | 14.3 |
|  | 203 | 323.35 | 19.40 | 6 |

The results show the ability to attain high concentrations of 21B12 protein having reduced viscosity with formulations having specific stabilizers/excipients (See FIGS. 28A-28D). Specifically, FIG. 28A is a graph showing the viscosity of various concentrations of anti-PCSK9 antibody, 21B12, in a formulation comprising 10 mM sodium acetate, and 9% Sucrose pH 5.2 at 25° C. and 40° C.

FIG. 28B is a graph showing the viscosity of various concentrations of anti-PCSK9 antibody, 21B12, in a formulation comprising 10 mM sodium acetate, and 9% Sucrose Example 30

High Concentration 11F1 Viscosity Studies

Table 30 shows the viscosity of the 11F1 antibody at 25 degrees Celsius at various antibody concentrations and in various formulations.

High concentration stock solution of 11F1 was prepared similarly as described for 21B12 in Example 29 above. Concentration determination was then carried out by measuring absorbance at A280 using an Agilent 8453 Spectro-photometer (Santa Clara, Calif.). Protein concentration was calculated using the appropriate extinction coefficient. The appropriate amount of buffer was then added to the sample to dilute it back down to the desired concentration and another A280 was performed to obtain the final concentration for the experiment. Excipients were added individually to the 11F1 formulations samples derived from the high concentration stock solutions.

Viscosity was measured using Brookfield LV-DVII cone and plate viscometer (Middleboro, Mass.) with a CPE-40 spindle with matching sample cup temperature regulated by a circulating water bath at constant 25° C. 500 µL of sample was added to sample cup with positive displacement pipettor. After sample cup was secured the rotational speed of the spindle was gradually increased until about 80% torque was achieved. At this point the rotational speed was stopped and a viscosity reading was generated by Rheocalc software.

High concentration protein formulations were sometimes measured using a different type of viscometer, an Anton Paar Physica Model MCR300 with a CP50-1 spindle. A 600 uL sample is used in this instrument and Rheoplus software version 3.4 was use to calculate solution viscosity. There was not a large difference in measurements using either viscometer.

TABLE 30

| Final Excipient Buffers | Final Ave A280 11F1 Conc (mg/mL) | Viscosity (cP) @ 25 C. |
|---|---|---|
| 10 mM sodium acetate, 9% Sucrose 0.01% Poly Sorbate ("PS") 20, pH 5.2 | 133 | 8 |
| | 145 | 14 |
| | 172 | 23 |
| | 186 | 45 |
| | 191 | 53 |
| | 224 | 133 |
| 10 mM sodium acetate, 150 mM Methionine, 3% Sucrose, 0.01% PS 20, pH 5.2 | 147 | 13 |
| | 162 | 18 |
| | 192 | 31 |
| | 212 | 54 |
| 10 mM sodium acetate, 250 mM Praline, 0.01% PS 20, pH 5.0 | 139 | 10 |
| | 170 | 18 |
| | 196 | 36 |
| | 212 | 47 |

TABLE 30-continued

| Final Excipient Buffers | Final Ave A280 11F1 Conc (mg/mL) | Viscosity (cP) @ 25 C. |
|---|---|---|
| 10 mM sodium acetate, 9% Sucrose, 100 mM Arginine, pH 5.2 | 211 | 26 |
| 10 mM sodium acetate, 9% Sucrose, 150 mM sodium chloride, pH 5.2 | 211 | 62 |
| 10 mM sodium acetate, 9% Sucrose, 150 mM Glycine, pH 5.2 | 211 | 45 |
| 10 mM sodium acetate, 9% Sucrose, 150 mM Serine, pH 5.2 | 211 | 48 |
| 10 mM sodium acetate, 9% Sucrose, 150 mM Alanine, pH 5.2 | 211 | 43 |
| 10 mM sodium acetate, 9% Sucrose, pH 5.2 | 211 | 73 |
| 10 mM sodium acetate, pH 5.2 | 211 | 58 |

The results shown in Table 30 demonstrate the ability to attain high concentrations of the 11F1 antibody with relatively low viscosity in formulations having specific stabilizers/excipients. Formulations comprising the stabilizers methionine, proline, arginine, glycine, serine and alanine exhibited particularly lower viscosity.

Example 31

Stability Study of High Concentration PCSK9 ABP Formulations

To evaluate the effects of stability on high protein PCSK9 ABP formulations, compositions of 21B12 were formulated in different formulations shown in Table 31.1 below. Formulations were incubated in the indicated containers at −30° C. or 4° C. for 0 weeks, 1 month, 2 months, 3 months, and 6 months, and 1 year. For each formulation at each time point, a sample was removed from each package for monitoring of antibody monomer by native Size Exclusion HPLC (SEC-HPLC) and Subvisible Particle Detection by Light Obscuration (HIAC).

TABLE 31.1

| Formulations | 21B12 Conc (mg/mL) | Fill Vol. (mL) | Package | Buffer | Excipients | Polysorbate 80 | Target pH |
|---|---|---|---|---|---|---|---|
| 1 | 110 | 3.0 | 5 cc Vial | 10 mM Na acetate | 9.0% Sucrose | 0.010% | 5.2 |
| 2 | 120 | 3.0 | 5 cc Vial | 10 mM Na acetate | 100 mM Methionine, 4% Sucrose | 0.010% | 5.0 |
| 3 | 120 | 3.0 | 5 cc Vial | 10 mM Na acetate | 250 mM Proline | 0.010% | 5.0 |
| 4 | 110 | 1.0 | BD Glass Syringe | 10 mM Na acetate | 9.0% Sucrose | 0.010% | 5.2 |
| 5 | 120 | 1.0 | BD Glass Syringe | 10 mM Na acetate | 100 mM Methionine, 4% Sucrose | 0.010% | 5.0 |
| 6 | 120 | 1.0 | BD Glass Syringe | 10 mM Na acetate | 250 mM Proline | 0.010% | 5.0 |
| 7 | 110 | 1.2 | CZ Plastic Syringe | 10 mM Na acetate | 9.0% Sucrose | 0.010% | 5.2 |

TABLE 31.1-continued

| Formulations | 21B12 Conc (mg/mL) | Fill Vol. (mL) | Package | Buffer | Excipients | Polysorbate 80 | Target pH |
|---|---|---|---|---|---|---|---|
| 8 | 120 | 1.2 | CZ Plastic Syringe | 10 mM Na acetate | 100 mM Methionine, 4% Sucrose | 0.010% | 5.0 |
| 9 | 120 | 1.2 | CZ Plastic Syringe | 10 mM Na acetate | 250 mM Proline | 0.010% | 5.0 |

SEC-HPLC:

SEC-HPLC separates proteins based on differences in their hydrodynamic volumes. Molecules with larger hydrodynamic proteins volumes elute earlier than molecules with smaller volumes. Native SEC-HPLC was performed using a TSK-GEL G3000SWXL 7.8 mm×300 mm column (Tosoh Bioscience), with 5 um particle size, on an Agilent HPLC with a Variable Wavelength Detector. The mobile phase was 100 mM Sodium Phosphate, 250 mM Sodium Chloride, pH 6.8±0.1. The flow rate was 0.5 mL/minute. The column eluate was monitored at 280 nm. Integrated peak areas in the chromatograms were used to quantify the amounts of monomer and high molecular weight species.

are converted by the instrument into the number of particles present. The method is non-specific and measures particles regardless of their origin. The particle sizes that were monitored were 10 µm, and 25 µm.

In this example, HIAC analysis was performed using samples that had been stored at 4° C. Specifically, samples of 21B12 formulations in Table 31.1 were subject to vacuum (also called "degassing") in order to remove air bubbles that could be detected as particles in the particle-counting system. For the 21B12 samples, the method was to subject the samples to vacuum at 75 torr for 1 to 2 hours. Particle counting was performed within 2 hours of completing the degassing process.

TABLE 31.2

| | % HMW at –30 C. | | | | % HMW at 4 C. | | | | | |
|---|---|---|---|---|---|---|---|---|---|---|
| Formulations | T = 0 | T = 1 M | T = 6 M | T = 1 Y | T = 0 | T = 1 M | T = 2 M | T = 3 M | T = 6 M | T = 1 Y |
| 1 | 0.03 | 0.03 | 0.04 | 0.04 | 0.03 | 0.04 | 0.01 | 0.03 | 0.06 | 0.07 |
| 2 | 0.06 | 0.15 | 0.12 | 0.15 | 0.06 | 0.06 | 0.03 | 0.05 | 0.06 | 0.06 |
| 3 | 0.03 | 0.03 | 0.04 | 0.04 | 0.03 | 0.03 | 0.01 | 0.02 | 0.02 | 0.07 |
| 4 | 0.04 | 0.05 | 0.09 | 0.05 | 0.04 | 0.05 | 0.01 | 0.04 | 0.06 | 0.09 |
| 5 | 0.06 | 0.20 | 0.24 | 0.21 | 0.06 | 0.06 | 0.03 | 0.05 | 0.01 | 0.07 |
| 6 | 0.04 | 0.04 | 0.1 | 0.05 | 0.04 | 0.03 | 0.01 | 0.03 | 0.1 | 0.07 |
| 7 | 0.04 | 0.04 | 0.09 | 0.06 | 0.04 | 0.05 | 0.01 | 0.03 | 0.07 | 0.09 |
| 8 | 0.06 | 0.18 | 0.19 | 0.17 | 0.06 | 0.06 | 0.03 | 0.05 | 0.1 | 0.06 |
| 9 | 0.04 | 0.04 | 0.02 | 0.05 | 0.04 | 0.04 | 0.01 | 0.03 | 0.06 | 0.08 |

Table 31.2 shows the results of native SEC-HPLC analysis of 21B12 formulations listed in Table 31.1 incubated at X° C. for 0 weeks, 1 month, 2 months, 3 months, and 6 months. "% HMW" reflects the quantity of high molecular weight 21B12 monomer in a sample. These results indicate that no formulation issues were observed after 6 months; however some high molecular weight species did increase in the methionine formulation (i.e., formulations 2, 5 and 8). Subvisible Particle Detection by Light Obscuration (HIAC):

An electronic, liquid-borne particle-counting system (HIAC/Royco 9703 or equivalent) containing a light-obscuration sensor (HIAC/Royco HRLD-150 or equivalent) with a liquid sampler quantifies the number of particles and their size range in a given test sample. When particles in a liquid pass between the light source and the detector they diminish or "obscure" the beam of light that falls on the detector. When the concentration of particles lies within the normal range of the sensor, these particles are detected one-by-one. The passage of each particle through the detection zone reduces the incident light on the photo-detector and the voltage output of the photo-detector is momentarily reduced. The changes in the voltage register as electrical pulses that FIGS. 29A and 29B shows the results of the HIAC assays for the above-identified formulations incubated in containers for 0 weeks, 1 month, 2 months, 3 months, and 6 months. 10 nm, and 25 µm particles were counted. FIGS. 29A and 29B demonstrate that all of the formulations of 21B12 were stable as measured with HIAC. Although the formulations in glass syringes, i.e., formulations 4-6, showed higher levels of particles across protein concentration and formulation, those particle counts are below USP limits for each particle size (10 µm and 25 nm). USP limits for 10 µm particles is 6000 per container and for 25 µm particles, 600 per container.

Example 32

11F1 Stability Studies

To study high concentration formulations (150 mg/mL) of 11F1, several formulations were made using candidate excipients as indicated in Table 32A below. The formulations were stored in the indicated containers at –30° C. or 4° C. for at least six months.

TABLE 32A

| | | | | | Polysorbate | Final |
| Formulation Name | Target Conc (mg/mL) | Container | Buffer[a] | Target Excipients | 20 | pH[c] |
| --- | --- | --- | --- | --- | --- | --- |
| 1 | 150 | 5 cc Glass Vial | 10 mM Na acetate | 9.0% Sucrose | 0.010% | 5.2 |
| 2 | 150 | BD Glass Syringe | 10 mM Na acetate | 9.0% Sucrose | 0.010% | 5.2 |
| 3 | 150 | BD Glass Syringe | 10 mM Na acetate | 150 mM Methionine, 3% Sucrose | 0.010% | 5.2 |
| 4 | 150 | BD Glass Syringe | 10 mM Na acetate | 250 mM Proline | 0.010% | 5.2 |
| 5 | 150 | CZ Plastic Syringe | 10 mM Na acetate | 9.0% Sucrose | 0.010% | 5.2 |
| 6 | 150 | CZ Plastic Syringe | 10 mM Na acetate | 150 mM Methionine, 3% Sucrose | 0.010% | 5.2 |
| 7 | 150 | CZ Plastic Syringe | 10 mM Na acetate | 250 mM Proline | 0.010% | 5.2 |

% HMW species was assessed by size exclusion HPLC after storage at −30° C. and 4° C. at the time points indicated in Table 32B below. Briefly, size exclusion HPLC separates proteins based on differences in their hydrodynamic volumes. Molecules with larger hydrodynamic proteins volumes elute earlier than molecules with smaller volumes. Native SEC-HPLC was performed using a TSK-GEL G3000SWXL 7.8 mm×300 mm column (Tosoh Bioscience), with 5 μm particle size, on an Agilent HPLC with a Variable Wavelength Detector. The mobile phase was 100 mM Sodium Phosphate, 250 mM Sodium Chloride, pH 6.8+/−0.1. The flow rate was 0.5 mL/minute. The column eluate was monitored at 280 nm. Integrated peak areas in the chromatograms were used to quantify the amounts of monomer and high molecular weight species.

TABLE 32B

| | % HMW at | | % HMW at 4° C. | | | |
| | −30° C. | | | | | T = |
| Formulations | T = 0 | T = 4 M | T = 0 | T = 2 M | T = 4 M | 6 M |
| --- | --- | --- | --- | --- | --- | --- |
| 1_ | 0.05 | 0.05 | 0.05 | 0.06 | 0.05 | 0.05 |
| 2_ | 0.05 | 0.05 | 0.05 | 0.06 | 0.04 | 0.02 |

TABLE 32B-continued

| | % HMW at | | % HMW at 4° C. | | | |
| | −30° C. | | | | | T = |
| Formulations | T = 0 | T = 4 M | T = 0 | T = 2 M | T = 4 M | 6 M |
| --- | --- | --- | --- | --- | --- | --- |
| 3_ | 0.07 | 0.26 | 0.07 | 0.07 | 0.07 | 0.06 |
| 4_ | 0.06 | 0.07 | 0.06 | 0.07 | 0.06 | 0.08 |
| 5_ | 0.05 | 0.04 | 0.05 | 0.05 | 0.04 | 0.06 |
| 6_ | 0.06 | 0.32 | 0.06 | 0.06 | 0.06 | 0.06 |
| 7_ | 0.08 | 0.07 | 0.08 | 0.06 | 0.07 | 0.08 |

Table 32B shows the results of native SEC-HPLC analysis of 11F1 formulations listed in Table 32A incubated at 4° C. or −30° C. for 0 weeks, 2 months, 4 months, or 6 months. "% HMW" reflects the quantity of high molecular weight 11F1 in a sample. These results indicate that no formulation issues were observed up to 6 months, however some high molecular weight species did increase in the methionine formulations stored at −30° C. (i.e. formulations 3, and 6).

The stability of additional high concentration 11F1 formulations was assessed by preparing the formulations in the primary containers as indicated in Table 32C below:

TABLE 32C

| Formulation | 11F1 Conc (mg/mL) | Primary Container | Excipients | 0.010% Polysorbate | Buffer | Final pH |
| --- | --- | --- | --- | --- | --- | --- |
| 10 | 150 | Glass Vials | 9.0% Sucrose | PS 20 | 10 mM Na acetate | 5.2 |
| 20 | 150 | Glass Vials | 9.0% Sucrose | PS 80 | 10 mM Na acetate | 5.2 |
| 30 | 180 | BD Glass Syringe | 150 mM Methionine, 3% Sucrose | PS 20 | 10 mM Na acetate | 5.2 |
| 40 | 180 | BD Glass Syringe | 150 mM MET, 3% Sucrose | PS 80 | 10 mM Na acetate | 5.2 |
| 50 | 180 | BD Glass Syringe | 250 mM Proline | PS 20 | 10 mM Na acetate | 5.2 |
| 60 | 180 | BD Glass Syringe | 250 mM Proline | PS 80 | 10 mM Na acetate | 5.2 |
| 70 | 180 | CZ Plastic Syringe | 150 mM Methionine, 3% Sucrose | PS 20 | 10 mM Na acetate | 5.2 |

TABLE 32C-continued

| Formulation | 11F1 Conc (mg/mL) | Primary Container | Excipients | 0.010% Polysorbate | Buffer | Final pH |
|---|---|---|---|---|---|---|
| 80 | 180 | CZ Plastic Syringe | 150 mM Methionine, 3% Sucrose | PS 80 | 10 mM Na acetate | 5.2 |
| 90 | 180 | CZ Plastic Syringe | 250 mM Proline | PS 20 | 10 mM Na acetate | 5.2 |
| 100 | 180 | CZ Plastic Syringe | 250 mM Proline | PS 80 | 10 mM Na acetate | 5.2 |

The formulations were incubated at 4° Celsius for one year. At the time points indicated in the Table 32D below, a sample was removed from each container and analyzed by SEC-HPLC as described for Table 32B above.

TABLE 32D

Size exclusion % HMW forms after 1 year storage at 4° C.
4° C. % HMW

| Formulations | T = 0 | T = 2 wk | T = 4 wk | T = 6 wk | T = 6 M | T = 6.5 M | T = 1 Yr | % Change |
|---|---|---|---|---|---|---|---|---|
| 10 | 0.04 | 0.07 | 0.08 | 0.06 | 0.07 | N/A | 0.07 | 0.03 |
| 20 | 0.05 | 0.07 | 0.07 | 0.07 | 0.06 | N/A | 0.06 | 0.01 |
| 30 | 0.08 | 0.14 | N/A | N/A | N/A | N/A | 0.05 | −0.03 |
| 40 | 0.09 | 0.15 | 0 | N/A | N/A | N/A | 0.06 | −0.03 |
| 50 | 0.08 | 0.15 | 0 | 0 | N/A | N/A | 0.07 | −0.01 |
| 60 | 0.07 | 0.16 | 0 | 0 | N/A | N/A | 0.08 | 0.01 |
| 70 | 0.08 | 0.14 | 0 | 0 | N/A | 0.09 | 0.06 | −0.02 |
| 80 | 0.07 | 0.14 | 0 | 0 | N/A | N/A | 0.07 | 0.00 |
| 90 | 0.09 | 0.15 | 0 | 0 | N/A | 0.09 | 0.05 | −0.04 |
| 100 | 0.08 | 0.15 | 0 | 0 | N/A | N/A | 0.08 | 0.00 |

At the time points indicated in the Table 32E below, a sample was removed from each container analyzed by cation-exchange HPLC (CEX-HPLC). Cation-exchange HPLC separates proteins based on differences in their surface charge. At a set pH, charged isoforms of 11F1 are separated on a cation-exchange column and eluted using a salt gradient. The eluent is monitored by UV absorbance. The charged isoform distribution is evaluated by determining the peak area of each isoform as a percent of the total peak area.

Native CEX-HPLC was performed using a Dionex G3000SWXL 4.0 mm ID×250 mm column (Tosoh Bioscience), with 10 μm particle size, on an Agilent HPLC with a Variable Wavelength Detector. The mobile phase was a linear gradient of 20 mM MES, pH 6.0+/−0.1 and the same buffer with 500 mM Sodium Chloride. The flow rate was 0.6 mL/minute. The column eluate was monitored at 280 nm. Integrated peak areas in the chromatograms were used to quantify the amounts of differently charged isoforms.

TABLE 32E

Cation exchange HPLC % Main Isoform Peak after
1 year storage at 4° C.
4° C. % Main Isoform Peak

| Formulation | T = 0 | 2 W | 4 W | 6 W | 1 Y | % Change |
|---|---|---|---|---|---|---|
| 10 | 76.0 | 75.9 | 75.7 | 75.6 | 76.2 | 0.3 |
| 20 | 76.0 | 76.4 | 75.7 | 75.6 | 76.4 | 0.5 |
| 30 | 76.0 | N/A | N/A | N/A | 76.3 | 0.4 |
| 40 | 75.8 | N/A | N/A | N/A | 76.0 | 0.2 |
| 50 | 76.0 | N/A | N/A | N/A | 76.3 | 0.4 |
| 60 | 75.8 | N/A | N/A | N/A | 75.8 | 0.1 |
| 70 | 75.9 | N/A | N/A | N/A | 76.2 | 0.5 |
| 80 | 76.1 | N/A | N/A | N/A | 76.3 | 0.3 |

TABLE 32E-continued

Cation exchange HPLC % Main Isoform Peak after
1 year storage at 4° C.
4° C. % Main Isoform Peak

| Formulation | T = 0 | 2 W | 4 W | 6 W | 1 Y | % Change |
|---|---|---|---|---|---|---|
| 90 | 76.0 | N/A | N/A | N/A | 76.0 | 0.0 |
| 100 | 75.8 | N/A | N/A | N/A | 75.9 | 0.0 |

Both tables 32D and 32E demonstrate that the described 11F1 formulations exhibited less than 5% increase in % HMW (SEC-HPLC) or less than a 3-5% variation in the Main Isoform Peak (CATION HPLC) up to 1 year storage at 4° C. In fact changes in both parameters were very low which is indicative of highly stable formulations, Subvisible Particle Detection by Light Obscuration (HIAC):

An electronic, liquid-borne particle-counting system (HIAC/Royco 9703 or equivalent) containing a light-obscuration sensor (HIAC/Royco HRLD-150 or equivalent) with a liquid sampler quantifies the number of particles and their size range in a given test sample. When particles in a liquid pass between the light source and the detector they diminish or "obscure" the beam of light that falls on the detector. When the concentration of particles lies within the normal range of the sensor, these particles are detected one-by-one. The passage of each particle through the detection zone reduces the incident light on the photo-detector and the voltage output of the photo-detector is momentarily reduced. The changes in the voltage register as electrical pulses that are converted by the instrument into the number of particles present. The method is non-specific and measures particles regardless of their origin. The particle sizes that were monitored were 10 μm, and 25 μm.

In this example, HIAC analysis was performed using samples that had been stored at 4° C. Specifically, samples of 11F1 formulations in Table 32a were subject to vacuum (also called "degassing") in order to remove air bubbles that could be detected as particles in the particle-counting system. For the 11F1 samples, the method was to subject the samples to vacuum at 75 torr for 1 to 2 hours. Particle counting was performed within 2 hours of completing the degassing process.

FIGS. 30A and 30B show the results of the HIAC assays for the above-identified formulations incubated in containers for 0 weeks, and four months. 10 μm, and 25 μm particles were counted. FIGS. 30A and 30B demonstrate that all of the formulations of 11F1 were stable as measured with HIAC. Particle counts for all formulations are below USP limits for each particle size (10 μm and 25 μm). USP limits for 10 μm particles is 6000 per container and for 25 μm particles, 600 per container.

Example 33

11F1 Binding Specificity

Results from this assay demonstrate that 11F1 binds to PCSK9 and not to PCSK1, PCSK2, PCSK7, or furin, demonstrating the specificity of 11F1 for PCSK9.

Biotinylated PCSK9, diluted in buffer A (25 mM Tris, 150 mM NaCl, 0.1% BSA, 0.05% tween, pH 7.5) was bound to neutravidin coated 96 well plates at a concentration of 0.2 μg/mL, for one hour incubation at room temperature. Separately, 0.4 μg/mL of 11F1 was incubated for one hour at room temperature with various concentrations (ranging from 0 to 20 μg/mL) of either PCSK1, PCSK2, PCSK7, PCSK9 or furin (R&D Systems, Minneapolis, Minn.) (diluted in buffer A w/o tween). Furin inhibitor, at 4.5 μg/mL, was included with all furin containing reactions. The PCSK9 coated streptavidin plate was washed with buffer A and the antibody/proprotein convertase mixture was added to the plate and incubated at room temperature for one hour. After washing, bound antibody was detected by incubation with goat-α-human Fc-HRP (160 ng/mL, diluted in buffer A) (Jackson Laboratories, Bar Harbor, Me.) followed by TMB substrate. The reaction was stopped with 1 N HCl and the absorbance was read at a wavelength of 450 nm on a Spectramax Plus 384 spectrophotometer (Molecular Devices Inc., Sunnyvale, Calif.).

This assay relied on the ability of proprotein convertase in solution to compete for the binding of 11F1 to plate-captured PCSK9. Pre-incubation of 11F1 and PCSK9 in solution dose dependently and robustly reduced the amount of 11F1 binding to plate-captured PCSK9 detected as reduced OD450 (FIG. 31). All results were expressed as the mean OD450 value±standard deviation versus concentration of the proprotein convertase. Pre-incubation of 11F1 with PCSK1, PCSK2, PCSK7, or furin, in solution, did not significantly impact the binding of 11F1 to plate-captured PCSK9. Therefore, at the protein concentrations studied, 11F1 binds only to PCSK9 and not to the other proprotein convertase family members tested.

Example 33

Efficacy of 11F1 Inhibition of LDLR:PCSK9 Binding

The example demonstrates that nanomolar concentrations of 11F1 can inhibit binding of both D374Y and wild-type PCSK9 to the LDLR under the conditions of this assay.

Briefly, clear, 384 well plates were coated with 2 mg/mL of goat anti-LDL receptor antibody (R&D Systems, Minneapolis, Minn.), diluted in PBS, by overnight incubation at 4° C. Plates were washed thoroughly with buffer A (100 mM sodium cacodylate pH 7.5) and then blocked with buffer B (1% non-fat dry milk [Bio-Rad Laboratories, Hercules, Calif.] in buffer A) for 2 hours at room temperature. After washing, plates were incubated with 0.4 mg/mL of LDL receptor (R&D Systems, Minneapolis, Minn.) diluted in buffer C (buffer B supplemented with 10 mM CaCl$_2$) for 1.5 hours at room temperature. Concurrent with this incubation, 20 ng/mL of biotinylated D374Y PCSK9 or 100 ng/mL of biotinylated WT PCSK9 was incubated with various concentrations of anti-PCSK9 antibody 11F1 diluted in buffer A (final concentrations ranging from 6.0 ng/mL to 200 ug/mL for the D374Y PCSK9 assay or 3.1 ng/mL to 25 ug/mL for the WT PCSK9 assay). The LDLR-coated plates were washed and the biotinylated PCSK9/antibody mixture was added. The LDLR plate was incubated at room temperature for 1 hour. Binding of the biotinylated PCSK9 to the LDLR was detected by incubation with streptavidin-HRP (500 ng/mL in buffer C) followed by TMB substrate. The reaction was stopped with 1N HCl and the absorbance was read at a wavelength of 450 nm on a SpectraMax Plus 384 Spectrophotometer (Molecular Devices Inc., Sunnyvale, Calif.). GraphPad Prism (v 4.01) software was used to plot log of antibody concentration versus OD450 to determine IC50 values by nonlinear regression.

11F1 inhibited LDLR:PCSK9 binding. The IC50 values for 11F1 in the D374Y PCSK9 assay ranged from 7.3 nM to 10.1 nM with an average (±SD) of 9.1 nM±1.5 nM (n=3). The IC50 values for 11F1 in the wild-type PCSK9 assay ranged from 4.4 nM to 8.1 nM with an average (±SD) of 5.9 nM±1.9 nM (n=3). It should be noted that these IC50 values are dependent on the amount of recombinant D374Y PCSK9 or WT PCSK9 used in the binding assay. A representative dose response curve for both the D374Y and wild-type assays are presented in FIG. 32 and FIG. 33, respectively.

Example 34

Efficacy of 11F1 in Blocking Cell LDL Uptake

11F1 blocks the interaction between PCSK9 and LDLR in vitro and can prevent the PCSK9-mediated reduction of LDL uptake in HepG2 cells.

Briefly, human' HepG2 cells were seeded in black, clear bottom 96-well plates (Fisher Scientific CO LLC, Santa Clara, Calif.) at a density of 5×104 cells per well in DMEM (Mediatech Inc., Herndon, Va.) supplemented with 10% FBS and 1% of antibiotic-antimycotic solution (Mediatech Inc., Herndon, Va.). Cells were incubated at 37° C. (5% CO2) overnight. To form the complex between D374Y PCSK9 and antibody or WT PCSK9 and antibody, serial dilutions (1:2) of 11F1, from 666.7 nM to 0.7 nM (for blocking D374Y PCSK9) or from 3.3 μm to 3.3 nM (for blocking WT PCSK9), were prepared in formulation buffer (25 mM HEPES, pH 7.5, 0.15 M NaCL). Either D374Y PCSK9 (2 ng/mL) or WT PCSK9 (25 ng/mL) were diluted in uptake buffer (DMEM containing 1% FBS) and incubated with the various concentrations of 11F1 or uptake buffer alone (negative control) for 1 hour at room temperature with shaking. BODIPY-LDL (Invitrogen, Carlsbad, Calif.) was diluted in uptake buffer to a concentration of 12 ng/mL. Following overnight incubation, HepG2 cells were rinsed twice with DPBS (Mediatech Inc., Herndon, Va.). Twenty-five microliters of the D374Y PCSK9 or WT PCSK9 complex with 11F1 and 25 µL of diluted BODIPY-LDL (Invitrogen, Carlsbad, Calif.) were added to the cells and incubated at 37° C. (5% CO2) for 3 hours. Cells were washed with DPBS 5 times and resuspended in 100 µL DPBS. Fluorescent signals were detected using a Safire plate reader (Tecan Systems Inc., San Jose, Calif.) at 480-520 nm (excitation) and 520-600 nm (emission) and expressed as relative fluorescence unit (RFU).

GraphPad Prism (Version 4.02, GraphPad Software Inc., San Diego, Calif.) software was used to plot log of antibody concentration versus RFU and to determine EC50 values by nonlinear regression using the sigmoidal dose-response (variable slope) curve fitting program.

This example shows that 11F1 blocked D374Y PCSK9 or WT PCSK9-mediated decrease of LDL uptake in HepG2 cells in a dose-dependent manner. Adding recombinant purified D374Y PCSK9 (2 µg/mL) or WT PCSK9 (25 µg/mL) to HepG2 cells reduced the uptake of BODIPY-LDL to ~50 to 60% and ~40% of the level measured in untreated cells, respectively. The antibodies dose-dependently restored LDL uptake to the level observed in untreated cells. The mean (±SD) EC50 value for the ability of 11F1 to block D374Y PCSK9-mediated decrease of LDL uptake was 35.3±9.1 nM (n=6, FIG. 34). The EC50 value for the ability of 11F1 to block WT PCSK9-mediated decrease in LDL uptake was 124.2±28.5 nM (n=3, FIG. 35). It should be noted that these EC50 values are a function of the amount of recombinant D374Y PCSK9 or WT PCSK9 used in the cell assay. The EC50 value is lower against D374Y PCSK9 than WT PCSK9 since less D374Y PCSK9 was used in the assay because its binding affinity to the LDLR is 5- to 30-fold greater than that of WT PCSK9 (Cunningham et al, 2007; Fisher et al, 2007; Kwon et al, 2008).

The EC50 values reported here are representative for mean values derived from 3 to 6 separate measurements for 11F1.

Example 35

Efficacy of 11F1 and 8A3 in Blocking Human PCSK9 Expressed Via an Adeno-Associated Virus in a Mouse Model A single intravenous bolus administration of the anti-PCSK9 antibodies 11F1 or 8A3 leads to a significant decrease in serum non-HDL-C and TC in mice expressing human PCSK9 by AAV. This example demonstrates the effectiveness of both anti-PCSK9 antibodies in blocking the function of human PCSK9 in vivo.

Briefly, 120 C57BL/6 mice expressing human PCSK9 were generated by infection with an engineered adeno associated virus (AAV) coding for human PCSK9, resulting in elevated levels of circulating low density lipoprotein cholesterol (LDL-C). Serum cholesterol analysis was performed using the Cobas Integra 400 plus chemistry analyzer (Roche Diagnostics, Indianapolis, Ind.). Animals were randomized into treatment groups with similar levels of non-HDL-C (LDL-C and VLDL-C), HDL-C and TC. On treatment day 0 (T=0) a subset of mice was euthanized and serum collected to establish that day's baseline levels. Remaining mice were then administered 11F1, 8A3 or anti-keyhole limpethemocyanin (KLH) IgG2 control antibody at 30 mg/kg. via tail vein injection. At days 1 through 5 following injection, subsets of mice were euthanized and whole blood was collected from the vena cava and allowed to coagulate for 30 minutes at room temperature. Following centrifugation at 12,000 rpm with a bench top centrifuge for 10 minutes, serum was collected. Serum cholesterol analysis was performed using the Cobas Integra 400 plus chemistry analyzer.

Serum concentrations of PCSK9 were determined using a sandwich ELISA assay. Clear 96 well plates were coated overnight with 2 µg/ml of monoclonal anti-PCSK9 antibody (31H4) diluted in 1×PBS. Plates were washed thoroughly with 1×PBS/0.05% tween and then blocked for 2 hours with 3% BSA/1×PBS. After washing, plates were incubated for 2 hours with serum diluted in general assay diluents (Immunochemistry Technologies, Bloomington, Minn.). Recombinant human PCSK9 (1 ng/ml to 500 ng/ml) was assayed concurrently and used to generate a standard curve on each ELISA plate. A rabbit polyclonal biotinylated anti-PCSK9 antibody (D8773, Amgen Inc, CA) was added at 1 ug/ml (in 1% BSA/PBS), followed by neutravidin-HRP at 200 ng/ml (in 1% BSA/PBS). Bound PCSK9 was detected by incubation with TMB substrate. The reaction was stopped with addition of 1N HCl and the absorbance measured at 450 nm on a Spectra Max Plus 384 Spectrophotometer (Molecular Devices Inc, Sunnyvale, Calif.). The standard curve (4-parameter logistic fit) generated with recombinant human PCSK9 was used to determine the corresponding concentration of PCSK9 in the serum samples.

Serum concentrations of antibody were determined using a sandwich ELISA assay. Polyclonal goat anti-human Fc IgG and an HRP-labeled goat anti-human IgG Fcγ polyclonal reagent (both from Jackson ImmunoResearch Laboratories Inc, West Grove, Pa.) were used as the capture and the detection antibody, respectively. A 3,3',5,5' tetramethylbenzidine (TMB) substrate solution reacted with peroxide, and in the presence of horse radish peroxidase (HRP), created a colorimetric signal that was proportional to the amount of the respective anti-PCSK9 antibody bound by the capture reagent. The intensity of the color (optical density, OD) was measured at 450 nm minus 650 nm using a microplate reader (Spectra Max Plus 384). Data was analyzed using Watson version 7.0.0.01 (Thermo Scientific, Waltham, Mass.) data reduction package with a Logistic (auto-estimate) regression of separately prepared standard curves. The lower limit of quantification (LLOQ) for the assay was ng/mL. 34.4.

Calculation of Pharmacokinetic Parameters in AAV Mice

Non-compartmental analysis (NCA) was performed on serum concentrations using the pre-determined nominal time points for each subject using WinNonlin Enterprise, version 5.1.1 (Pharsight, St. Louis, Mo.). Data points for estimating the terminal elimination rate constants and half-lives were chosen by visual inspection of the concentration-time profiles. NCA parameters reported include: apparent half-life (t½), area under the serum concentration-time curve from time zero to the last measured concentration (AUC0-t), and apparent serum clearance (CL0-t). AUC0-t was determined using the linear log-linear trapezoidal method, and CL0-t was calculated by Dose/AUC0-t. For 11F1, 8A3, and 31H4 antibodies. Post-study dose solution analysis showed actual doses were within 20% of the 30 mg/kg target. However, for the IgG2 control, analysis showed actual dose was only 40% of the intended target. Therefore, a corrected dose of 12 mg/kg was used for CL0-t calculation for IgG2 control. Parameters were reported to three significant figures, except for half-life which was reported to two significant figures.

Statistical Analysis

All cholesterol results were expressed as the mean±standard error of the mean. All pharmacokinetic data were expressed as the mean±standard deviation. The p value of 0.05, determined by 1-way ANOVA was used as a threshold to determine statistical significance between the anti-KLH IgG2 control antibody injected animals and those dosed with anti-PCSK9 antibody at the same time point.

Effect of Anti-PCSK9 Antibodies on Serum Non-HDL-C, HDL-C, and TC

To establish a baseline, a subset of mice expressing human PCSK9 was euthanized prior to injection of antibodies and blood was collected. Non-HDL-C, HDL-C and TC levels in these animals were 33±4, 117±4 and 183±9 mg/dL, respectively (mean±SEM). Levels of PCSK9 in naïve animals were determined to be 4921 ng/mL±2044 ng/mL.

Compared to mice injected with anti-KLH IgG2 control antibody (control animals), injection of 11F1 produced significant lowering of non-HDL-C at days 1, 2, and 4 post-injection (with a maximum of 59%), while TC was significantly lowered at day 4 only (by 22%) (FIG. 36, FIG. 37). No significant lowering of HDL-C was observed at any time point (FIG. 38).

Compared to control animals, injection of 8A3 produced significant lowering of non-HDL-C at days 1, 2, and 4 post-injection (with a maximum of 65%), while TC was significantly lowered at day 2 post-injection (with a maximum of 24%) (FIG. 36, FIG. 37). No significant lowering of HDL-C was observed at any time point (FIG. 38).

Pharmacokinetics

At an intravenous dose of 30 mg/kg, 11F1 and 8A3 had very similar pharmacokinetic behavior (FIG. 39). For these two molecules, AUC0-t exposures, estimated CL0-t, and apparent half-lives were equivalent (Table of FIG. 40). The anti-KLH IgG2 control antibody had an unexpectedly lower AUC0-t exposure than 11F1 and 8A3, but this is likely due to the antibody being administered at a lower dose than intended (12 mg/kg as opposed to 30 mg/kg; dose solution analysis showed antibody concentration to be 40% of target. Anti-KLH IgG2 control antibody CL0-t was similar to that of 11F1 and 8A3, when calculated using the corrected dose, and the apparent half-life of the anti-KLH IgG2 control antibody was estimated at >120 hours. These data suggested that affects of the PCSK9 ligand on antibody disposition are less pronounced for 11F1 and 8A3 when compared to other antibodies dosed in the AAV model because 11F1 and 8A3 CL0-t values are more similar to anti-KLH IgG2 control antibody.

Summary

Expression of human PCSK9 by AAV in mice (approximately 5 ug/mL) resulted in a serum non-HDL-C level of approximately 33 mg/dL. Following a 30 mg/kg injection of 11F1, significant serum non-HDL-C lowering was observed at days 1, 2 and 4 post-injection (with a maximum of 59% as compared to control animals). Significant lowering of TC was seen at day 4 only. Injection of 8A3 resulted in a similar pattern of non-HDL-C lowering with a maximum of 65% as compared to control animals. However, 8A3 administration resulted in significant TC lowering at day 2 only, post-injection, with a maximum of 24%. No significant lowering of HDL-C was observed in animals administered either 11F1 or 8A3. Analysis of serum antibody levels of 11F1 and 8A3 demonstrated a similar profile to anti-KLH IgG2 control antibody.

Example 36

Effect of a Single Subcutaneous Dose of 11F1, 21B12 and 8A3 on Serum Lipids in Cynomolgus Monkeys Single SC administration of 11F1, 8A3 or 21B12 to cynomolgus monkeys leads to the significant lowering of serum LDL-C, and TC. This study demonstrated the ability of anti-PCSK9 antibodies to lower serum cholesterol in non-human primates.

Briefly, naive male cynomolgus monkeys were acclimated to their environment for at least 2 weeks prior to experimentation. Animals were randomized into treatment groups based on a pre-screen of their serum TC, HDL-C, LDL-C, and triglyceride levels, and their body weight. After 1 week, animals were fasted overnight, and bled from the peripheral vasculature (cephalic or saphenous vein), for measurement of baseline serum lipid levels at a time point designated T=0. Animals were then injected SC with either anti-KLH IgG2 control antibody, 11F1, 21B12, or 8A3 (all in 10 mM NaOAc pH 5.2, 9% sucrose) at 0.5 mg/kg (all at 0.4 mL/kg body weight). Fasting blood samples were then collected from animals at designated time points over a 45 day period.

| | | | Experimental Design | | | |
|---|---|---|---|---|---|---|
| Group No. | No Males | Route | Treatment | Dose Level (mg/kg) | Conc. (mg/mL) | Volume (mL/kg) |
| 1 | 5 | SC | Anti-KLH | 0.5 | 1.09 | 0.4 |
| 2 | 5 | SC | 21B12 | 0.5 | 1.19 | 0.4 |
| 3 | 5 | SC | 11F1 | 0.5 | 1.11 | 0.4 |
| 4 | 5 | SC | 8A3 | 0.5 | 1.25 | 0.4 |

At specified time points, blood was collected from animals under overnight fasting conditions from the peripheral vasculature (cephalic or saphenous vein). Whole blood was allowed to coagulate for 30 minutes at room temperature. Following centrifugation at 3,000 rpm for 20 minutes, serum was collected. Direct serum cholesterol analysis was performed using the Cobas Integra 400 analyzer (Roche Diagnostics Inc, Indianapolis, Ind.). Apolipoprotein B serum levels were determined at specified time points (day 0, 3, 6, 15, 24 and 33) by Anilytics, Md., with the following methodology. A 17 µL aliquot of the sample (no preparation) was used for analysis with a Hitachi 717 Analyzer using a 6 points standard curve. If the initial value of the sample was higher than the standard curve linearity, then the sample was diluted and repeated with the result multiplied by the appropriate dilution factor. The reagents for the assay (APO-B Reagent Kit #86071, Antibody Set #86060, Control Set #86103) were obtained from DiaSorin (Stillwater, Minn.).

Antibody concentrations in serum were determined using an enzyme-linked immunosorbent assay (ELISA) with an assay range of 34.4 to 3000 ng/mL (34.4 ng/mL being the lower limit of quantitation [LLOQ]).

Non-compartmental analysis (NCA) was performed on the serum concentrations using the pre-determined nominal time points for each subject using Watson® LIMS, version 7.0.0.01 (Thermo Scientific, Waltham, Mass.). Data points for estimating the terminal elimination rate constants and half-lives were chosen by visual inspection of the concentration-time profile and best linear fit (typically from 360 h until the antibody concentrations dropped below the lower limit of quantitation). NCA parameters reported include: terminal half-life (t½,z), the maximum serum concentration ($C_{max}$), area under the serum concentration-time curve from time zero to infinity (AUC0-inf), and apparent serum clearance (CL/F). AUC0-inf was calculated using the linear log-linear trapezoidal method. All parameters were all reported to three significant figures, except for half-life which was reported to two significant figures.

Statistical Analysis

A statistical model that considers baseline as a covariate and treatment group as a fixed effect was fit to the log transformed response at each time point for LDL-C, HDL-C, TC, and triglycerides. Tukey's multiple comparison correction was applied to adjust the pair wise comparisons at each time point. The statistical significance was evaluated at alpha=0.05 using adjusted p-values.

Effect of 11F1, 21B12, and 8A3 on Serum LDL Cholesterol

Maximal LDL-C lowering for 11F1 was observed 9 days after injection, with a 57% lowering of LDL-C as compared to anti-KLH IgG2 control antibody-treated monkeys (control animals). LDL-C returned to levels similar to those observed in control animals by day 27. Maximal LDL-C lowering for 21B12 was observed 3 days after injection, with a 64% lowering of LDL-C as compared to control animals. LDL-C returned to levels similar to control animals by day 6. Maximal LDL-C lowering for 8A3 was observed 4 days after injection, with a 54% lowering of LDL-C as compared to control animals. LDL-C returned to levels similar to those observed in control animals by day 27 (FIG. 41).

Effect of 11F1, 21B12, and 8A3 on Serum Total Cholesterol

Maximal TC lowering for 11F1 was observed 9 days after injection, with a 27% lowering of TC as compared to anti-KLH IgG2 control antibody-treated monkeys (control animals). TC returned to levels similar to those observed in control animals by day 27. Maximal TC lowering for 21B12 was observed 3 days after injection, with a 20% lowering of TC as compared to control animals. TC transiently returned to levels similar to those observed in vehicle-treated monkeys by day 4, but were significantly lower between days 14 and 18, inclusively. Maximal TC lowering for 8A3 was observed 9 days after injection, with a 22% lowering of TC as compared to control animals. TC returned to levels similar to those observed in control animals by day 30 (FIG. 42).

Effect of 11F1, 21B12, and 8A3 on Serum HDL Cholesterol and Triglycerides

On average and at each time point, HDL-C or triglyceride levels for animals treated with 11F1 or 8A3 were not significantly different (based on an alpha=0.05 significance level) from those observed in anti-KLH IgG2 control antibody-treated monkeys. However, 21B12 did induce a statistically significant change in HDL-C at a single time point (day 18 following injection) (FIG. 43 and FIG. 45).

Effect of 11F1, 21B12, and 8A3 on Apolipoprotein B (ApoB)

Serum ApoB levels were measured at days 3, 6, 15, 24 and 33, post-injection. 11F1 and 8A3 were associated with ApoB lowering at days 3 to 24, as compared to anti-KLH IgG2 control antibody-treated monkeys (FIG. 46). 21B12 was associated with statistically significant lower ApoB levels at day 3 only.

Pharmacokinetic Profiles of 11F1, 21B12, and 8A3

A summary plot of the mean concentration-time profiles by treatment is shown in 748. The estimated mean pharmacokinetic parameters for animals receiving 11F1, 21B12, 8A3, and anti-KLH IgG2 control antibody are displayed in Table of FIG. 47.

Antibody absorption in all groups was consistent and characteristic of subcutaneous antibody administration. 21B12 pharmacokinetic behavior with regard to CL/F, Cmax, and AUC0-inf was consistent with that observed in previous studies where 21B12 was administered at the same dose. Pharmacokinetics of 11F1 and 8A3 differed significantly from 21B12, where lower CL/F was observed (approximately 15% of 21B12 CL/F) and longer half-lives were estimated (approximately 200 h compared to 40 h for 21B12). Notably, pharmacokinetics of 11F1 and 8A3 were indistinguishable both from one another and the anti-KLH IgG2 control antibody. These data suggest that disposition of 11F1 and 8A3 is impacted to a far lesser extent by association with the PCSK9 target than 21B12, given that 11F1 and 8A3 have the same exposure profile as anti-KLH IgG2 control antibody with no affinity for PCSK9.

Summary of Results

Over the course of the 45 day study, statistically significant lowering of TC and LDL-C was observed in animals administered 11F1, 21B12, or 8A3 as compared to anti-KLH IgG2 control antibody. 11F1 was associated with statistically significant LDL-C lowering (vs. anti-KLH IgG2 control antibody) from day 2 to day 24 inclusively. 21B12 demonstrated statistically significant LDL-C lowering (vs anti-KLH IgG2 control antibody) from day 1 to day 4 inclusively. 8A3 demonstrated statistically significant LDL-C lowering (vs anti-KLH IgG2 control antibody) from day 1 to day 24 inclusively. Changes in TC and ApoB mirrored changes observed in LDL-C for all groups. 11F1 achieved a maximal lowering of LDL-C (vs anti-KLH IgG2 control antibody at the same time point) 9 days following injection (−57%). 21B12 achieved a maximal lowering of LDL-C (vs anti-KLH IgG2 control antibody at the same time point) 3 days following injection (−64%). 8A3 achieved a maximal lowering of LDL-C (vs anti-KLH IgG2 control antibody at the same time point) 4 days following injection (−54%). 21B12 lowered HDL-C at a single time point, 18 days after injection. No statistically significant changes were observed in HDL-C levels following 11F1 or 8A3 administration. No statistically significant changes were observed in triglycerides levels following 11F1, 21B12, or 8A3 administration. 5

INCORPORATION BY REFERENCE

All references cited herein, including patents, patent 10 applications, papers, text books, and the like, and the references cited therein, to the extent that they are not already, are hereby incorporated herein by reference in their entirety. To the extent that any of the definitions or terms provided in the references incorporated by reference differ from the terms and discussion provided herein, the present terms and definitions control.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A formulation comprising a monoclonal antibody that specifically binds to PCSK9, wherein PCSK9 comprises the amino acids of SEQ ID NO: 1, the monoclonal antibody in an amount of about 70 mg/ml to about 200 mg/ml, about 10 mM to about 20 mM sodium acetate buffer, a pharmaceutically acceptable surfactant in an amount that is about 0.004% to about 0.1% w/v, and at least one pharmaceutically acceptable stabilizer selected from the group consisting of: proline, arginine, lysine, methionine, benzyl alcohol, and taurine, in an amount of about 1% to about 5%, wherein the formulation has a pH of about 4.8 to about 5.8, wherein the monoclonal antibody comprises the light chain complementarity determining region one (CDRL1) sequence in SEQ ID NO: 23, the CDRL2 sequence in SEQ ID NO: 23, and of the CDRL3 sequence in SEQ ID NO: 23, and the heavy chain complementarity determining region one (CDRH1) sequence in SEQ ID NO: 49, the CDRH2 sequence in SEQ ID NO: 49 and the CDRH3 sequence in SEQ ID NO: 49.

2. The formulation of claim 1, wherein the monoclonal antibody comprises a light chain variable region that comprises an amino acid sequence that is at least 90% identical to that of SEQ ID NO: 23 and a heavy chain variable region that comprises an amino acid sequence that is at least 90% identical to that of SEQ ID NO: 49.

3. The formulation of claim 2 wherein the monoclonal antibody comprises a light chain variable region that comprises the amino acid sequence SEQ ID NO: 23 and a heavy chain variable region comprises the amino acid sequence of SEQ ID NO: 49.

4. The formulation of claim 2 wherein the monoclonal antibody is 21B12.

5. The formulation of claim 2, wherein said pharmaceutically acceptable surfactant is polysorbate 80 or polysorbate 20.

6. The formulation of claim 5, wherein said pharmaceutically acceptable surfactant is polysorbate 80.

7. The formulation of claim 6, wherein said polysorbate 80 is present in an amount of about 0.01%.

8. The formulation of claim 2, wherein the heavy chain comprises: a CDR1 comprising SEQ ID NO: 308, a CDR2 comprising SEQ ID NO: 175, and a CDR3 comprising SEQ ID NO: 180.

9. The formulation of claim 2, wherein the heavy chain comprises: a CDR1 comprising SEQ ID NO: 368, a CDR2 comprising SEQ ID NO: 175, and a CDR3 comprising SEQ ID NO: 180.

10. The formulation of claim 2, wherein the light chain comprises: a CDR1 comprising SEQ ID NO: 158, a CDR2 comprising SEQ ID NO: 162, and a CDR3 comprising SEQ ID NO: 395.

11. The formulation of claim 10, wherein the heavy chain comprises: a CDR1 comprising SEQ ID NO: 308, a CDR2 comprising SEQ ID NO: 175, and a CDR3 comprising SEQ ID NO: 180.

12. The formulation of claim 10, wherein the heavy chain comprises: a CDR1 comprising SEQ ID NO: 368, a CDR2 comprising SEQ ID NO: 175, and a CDR3 comprising SEQ ID NO: 180.

13. The formulation of claim 2, wherein each CDR is defined in accordance with the Kabat definition, the Chothia definition, the combination of the Kabat definition and the Chothia definition, the AbM definition, or the contact definition of CDR.

14. The formulation of claim 13, wherein each CDR is defined in accordance with the CDR definition of Kabat.

15. The formulation of claim 13, wherein each CDR is defined in accordance with the CDR definition of Chothia.

16. A formulation comprising:
(a) a monoclonal antibody in an amount of about 70 mg/ml to about 200 mg/ml, said monoclonal antibody comprising the light chain complementarity determining region one (CDRL1) sequence in SEQ ID NO: 23, the CDRL2 sequence in SEQ ID NO: 23, and the CDRL3 sequence in SEQ ID NO: 23, and the heavy chain complementarity determining region one (CDRH1) sequence in SEQ ID NO: 49, the CDRH2 sequence in SEQ ID NO: 49, and a the CDRH3 sequence in SEQ ID NO:49;
(b) about 10 mM sodium acetate;
(c) about 2.0% to about 3.0% w/v proline;
(d) about 0.01% w/v polysorbate 20 or polysorbate 80, and
(e) a pH of about 5.0.

17. The formulation of claim 1, wherein the monoclonal antibody in an amount of about 100 mg/ml to about 150 mg/ml.

18. A formulation comprising:
(a) a monoclonal antibody in an amount of about 70 mg/ml to about 200 mg/ml, said monoclonal antibody comprising the light chain complementarity determining region one (CDRL1) sequence in SEQ ID NO: 23, the CDRL2 sequence in SEQ ID NO: 23, and the CDRL3 sequence in SEQ ID NO: 23, and the heavy chain complementarity determining region one (CDRH1) of the CDRH1 sequence in SEQ ID NO: 49, the CDRH2 sequence in SEQ ID NO: 49, and of the CDRH3 sequence in SEQ ID NO:49;

(b) about 20 mM sodium acetate;

(c) about 2.0% to about 3.0% w/v proline;

(d) about 0.01% w/v polysorbate 80, and (e) a pH of about 5.0.

19. The formulation of claim 7, wherein the stabilizer is proline.

20. The formulation of claim 19, wherein the proline is present in an amount of about 2% to about 3% w/v.

21. The formulation of claim 20, wherein the formulation has a pH of about 5.0 to about 5.5.

22. The formulation of claim 21, wherein the formulation comprises a viscosity of 30 cP or less at 25° C.

23. The formulation of claim 22, wherein the amount of monoclonal antibody is about 70 mg/ml to about 150 mg/ml and the formulation comprises a viscosity of 12 cP or less at 25°° C.

24. The formulation of claim 23, wherein the formulation remains stable for at least 3 months.

25. The formulation of claim 1, wherein the monoclonal antibody is an IgG2 antibody.

26. The formulation of claim 7, wherein the buffer is present in an amount of about 20 mM.

27. The formulation of claim 26, wherein the stabilizer is proline.

28. The formulation of claim 27, wherein proline is present in an amount of about 2% to about 3% w/v.

29. The formulation of claim 28, wherein the formulation has a pH of about 5.0 to about 5.5.

30. The formulation of claim 29, wherein the formulation comprises a viscosity of 30 cP or less at 25° C.

31. The formulation of claim 29, wherein the amount of monoclonal antibody is about 70 mg/ml to about 150 mg/ml and the formulation comprises a viscosity of 12 cP or less at 25° C.

32. The formulation of claim 29, comprising about 250 mOsmol/kg to about 350 mOsmol/kg.

33. The formulation of claim 29, wherein the formulation remains stable for at least 3 months.

34. The formulation of claim 29, wherein the amount of the monoclonal antibody is about 140 mg/ml.

35. The formulation of claim 29, wherein the amount of the monoclonal antibody is about 120 mg/ml.

36. The formulation of claim 29, wherein the heavy chain comprises: a CDR1 comprising SEQ ID NO: 308, a CDR2 comprising SEQ ID NO: 175, and a CDR3 comprising SEQ ID NO:180, and the light chain comprises: a CDR1 comprising SEQ ID NO: 158, a CDR2 comprising SEQ ID NO: 162, and a CDR3 comprising SEQ ID NO: 395.

37. The formulation of claim 29, wherein the heavy chain comprises: a CDR1 comprising SEQ ID NO: 368, a CDR2 comprising SEQ ID NO: 175, and a CDR3 comprising SEQ ID NO:180, and the light chain comprises: a CDR1 comprising SEQ ID NO: 158, a CDR2 comprising SEQ ID NO: 162, and a CDR3 comprising SEQ ID NO: 395.

38. The formulation of claim 29, wherein the light chain variable region comprises an amino acid sequence that is at least 95% identical to that of SEQ ID NO: 23 and wherein the heavy chain variable region comprises an amino acid sequence that is at least 95% identical to that of SEQ ID NO: 49.

39. The formulation of claim 38, wherein the light chain variable region comprises an amino acid sequence that is at least 97% identical to that of SEQ ID NO: 23 and wherein the heavy chain variable region comprises an amino acid sequence that is at least 97% identical to that of SEQ ID NO: 49.

40. The formulation of claim 39, wherein the light chain variable region comprises an amino acid sequence that is 97-99% identical to that of SEQ ID NO:

23 and wherein the heavy chain variable region comprises an amino acid sequence that is 97-99% identical to that of SEQ ID NO: 49.

41. A formulation comprising:

(a) a monoclonal antibody in an amount of about 120 mg/ml to about 140 mg/ml, said monoclonal antibody comprising:

a light chain variable region comprising an amino acid sequence that is at least 97% identical to that of SEQ ID NO: 23, wherein the light chain variable region comprises:

a complementarity determining region one (CDR1) comprising SEQ ID NO: 158;

a CDR2 comprising SEQ ID NO: 162; and a CDR3 comprising SEQ ID NO: 395;

a heavy chain variable region comprising an amino acid sequence that is at least 97% identical to that of SEQ ID NO: 49, wherein the heavy chain variable region comprises:

a CDR1 comprising SEQ ID NO: 308;

a CDR2 comprising SEQ ID NO: 175; and a CDR3 comprising SEQ ID NO:180;

(b) about 20 mM sodium acetate;

(c) about 2.0% to about 3.0% w/v proline;

(d) about 0.01% w/v polysorbate 80; and (e) a pH of about 5.0.

42. The formulation of claim 41, wherein the formulation exhibits increased aggregation and/or reduced loss of biological activity of not more than 5% when stored at 2-8 degrees C. for 1 month to 2 years when compared with a control formula sample, wherein the control formula sample is the formulation at time zero.

43. The formulation of claim 2, wherein the monoclonal antibody comprises:

a light chain comprising:

the light chain variable region comprising the amino acid sequence of a light chain variable region in SEQ ID NO:297; and a light chain constant region comprising the amino acid sequence of SEQ ID NO: 156; and a heavy chain comprising:

the heavy chain variable region comprising the amino acid sequence of a heavy chain variable region in SEQ ID NO:298; and a heavy chain constant region comprising the amino acid sequence of SEQ ID NO: 154.

44. A formulation comprising:

(a) a monoclonal antibody in an amount of about 120 mg/ml to about 140 mg/ml, said monoclonal antibody comprising:

a light chain comprising:

a light chain variable region comprising-the amino acid sequence of a light chain variable region in SEQ ID NO:297; and a light chain constant region comprising the amino acid sequence of SEQ ID NO: 156; and a heavy chain comprising:

a heavy chain variable region comprising-the amino acid sequence of a heavy chain variable region in SEQ ID NO:298; and a heavy chain constant region comprising the amino
    acid sequence of SEQ ID NO: 154;
(b) about 20 mM sodium acetate;
(c) about 2.0% to about 3.0% w/v proline;
(d) about 0.01% w/v polysorbate 80; and
(e) a pH of about 5.0.

45. The formulation of claim 44, wherein the amount of
the monoclonal antibody is 140 mg/ml.

46. The formulation of claim 44, wherein the amount of
the monoclonal antibody is 120 mg/ml.

47. The formulation of claim 44, comprising:
(a) the monoclonal antibody at 120 to 140 mg/ml;
(b) 20 mM sodium acetate;
(c) 2.0% to 3.0% w/v proline;
(d) 0.01% w/v polysorbate 80; and
(e) a pH of 5.0.

\* \* \* \* \*